US012653139B2

(12) United States Patent
Crawford et al.

(10) Patent No.: US 12,653,139 B2
(45) Date of Patent: Jun. 16, 2026

---

(54) SEEDLESS BLACK RASPBERRY WITH A MUTANT AGAMOUS-CLADE MADS-BOX TRANSCRIPTION FACTOR GENE

(71) Applicant: Pairwise Plants Services, Inc., Durham, NC (US)

(72) Inventors: Brian Charles Wilding Crawford, Cary, NC (US); Thomas J. Poorten, Durham, NC (US)

(73) Assignee: Pairwise Plants Services, Inc., Durham, NC (US)

( * ) Notice: Subject to any disclaimer, the term of this patent is extended or adjusted under 35 U.S.C. 154(b) by 134 days.

(21) Appl. No.: 17/617,635

(22) PCT Filed: Jun. 11, 2020

(86) PCT No.: PCT/US2020/037240
§ 371 (c)(1),
(2) Date: Dec. 9, 2021

(87) PCT Pub. No.: WO2020/252167
PCT Pub. Date: Dec. 17, 2020

(65) Prior Publication Data
US 2022/0243217 A1 Aug. 4, 2022

Related U.S. Application Data

(60) Provisional application No. 62/859,992, filed on Jun. 11, 2019.

(51) Int. Cl.
| | |
|---|---|
| *A01H 6/74* | (2018.01) |
| *C12N 9/22* | (2006.01) |
| *C12N 15/11* | (2006.01) |
| *C12N 15/82* | (2006.01) |

(52) U.S. Cl.
CPC ................. *A01H 6/74* (2018.05); *C12N 9/22* (2013.01); *C12N 15/11* (2013.01); *C12N 15/8213* (2013.01); *C12N 15/8262* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | |
|---|---|---|
| 2015/0024388 A1 | 1/2015 | Singh et al. |
| 2017/0240913 A1 | 8/2017 | Schaffer et al. |

FOREIGN PATENT DOCUMENTS

| | | |
|---|---|---|
| WO | 2018086623 A1 | 5/2018 |

OTHER PUBLICATIONS

Royo et al. The major origin of seedless grapes is associated with a missense mutation in the MADS-box gene VviAGL11. (2018) Plant Physiology; vol. 177; pp. 1234-1253 (Year: 2018).*
Chen et al. Progress in TILLING as a tool for functional genomics and improvement of crops. (2014) Journal of Integrative Plant Biology; vol. 56; pp. 425-443 (Year: 2014).*
Zhang et al. Applications and potential of genome editing in crop improvement. (2018) Genome Biology; vol. 19; pp. 1-11 (Year: 2018).*
Cahn et al. Fruit Quality Evaluation of Raspberries and Blackberries at North Willamette Research and Extension Center (1992) Agriculture Experiment Station, Oregon State University, Corvallis; pp. 1-18 (Year: 1992).*
Vanburen et al. A near complete, chromosome-scale assembly of the black raspberry (*Rubus occidentalis*) genome. (2018) GigaScience; vol. 7; pp. 1-9 (Year: 2018).*
Gaudelli, Nicole M., et al., "Programmable base editing of A•T to G•C in genomic DNA without DNA cleavage", Nature. 551(7681), 2017, pp. 464-471.
Database UniProt. Database accession No. F61457. RecName: Full=Agamous-like MADS-box protein AGL11 {ECO:0000305}, 2019.
Extended European Search Report corresponding to EP Application No. 20822719.9, mailed May 26, 2023, 13 pages.
Ocarez, Nallatt, et al., "Suppression of the D-class MADS-box AGL11 gene triggers seedlessness in fleshy fruits", Plant Cell Reports, Springer Berlin Heidelberg, vol. 35, No. 1, 2015, 239-254.
Royo, Carolina, et al., "The Major Origin of Seedless Grapes Is Associated with a Missense Mutation in the MADS-Box Gene VviAGL11", Plant Physiology vol. 177, No. 3, 2018, 1234-1253.
Singh, Rajinder, et al., "The oil palm SHELL gene controls oil yield and encodes a homologue of SEEDSTICK", Nature, vol. 500, No. 7462, 2013, 340-344.
Carolina Royo et al (2018). The Major Origin of Seedless Grapes Is Associated with a Missense Mutation in the MADS-Box GeneVviAGL11. Plant Physiology, 177(3), 1234-1253.
Database accession No. GU338396, "*Prunus serrulata* var. *lannesiana* cultivar Albo-rosea SEEDSTICK-like protein mRNA, complete cds" Nucleotide, (2010) URL: NCBI 31,33,44.
Honma, T., & Goto, K. (2001). Complexes of MADS-box proteins are sufficient to convert leaves into floral organs. Nature, 409(6819), 525-529.
International Search Report and Written Opinion corresponding to International Patent Application No. PCT/US2020/037240, mailed Nov. 17, 2020, 14 pages.
Jeon et al. "leafy hull sterile1 Is a Homeotic Mutation in a Rice MADS Box Gene Affecting Rice Flower Development" The Plant Cell, 12:871-884 2000.

(Continued)

*Primary Examiner* — Cathy Kingdon
(74) *Attorney, Agent, or Firm* — Myers Bigel, P.A.

(57) ABSTRACT

The present disclosure provides plants or plant parts with an altered fruit development phenotype, particularly a seedless or reduced seediness phenotype. A plant or plant part can include a mutation in a SEEDSTICK (STK) gene. These plants or plant parts can be produced via next generation plant breeding technology utilizing targeted gene editing.

4 Claims, 11 Drawing Sheets

Specification includes a Sequence Listing.

(56) References Cited

OTHER PUBLICATIONS

Mizukami Y, Huang H, Tudor M, Hu Y, Ma H. Functional domains of the floral regulator AGAMOUS: characterization of the DNA binding domain and analysis of dominant negative mutations. The Plant Cell. 1996;8(5):831-845.
Singh R, Leslie Low E-T, Ooi LC-L, et al. The oil palm Shell gene controls oil yield and encodes a homologue of SEEDSTICK. Nature. 2013;500(7462):340-344.

* cited by examiner

FIG. 2

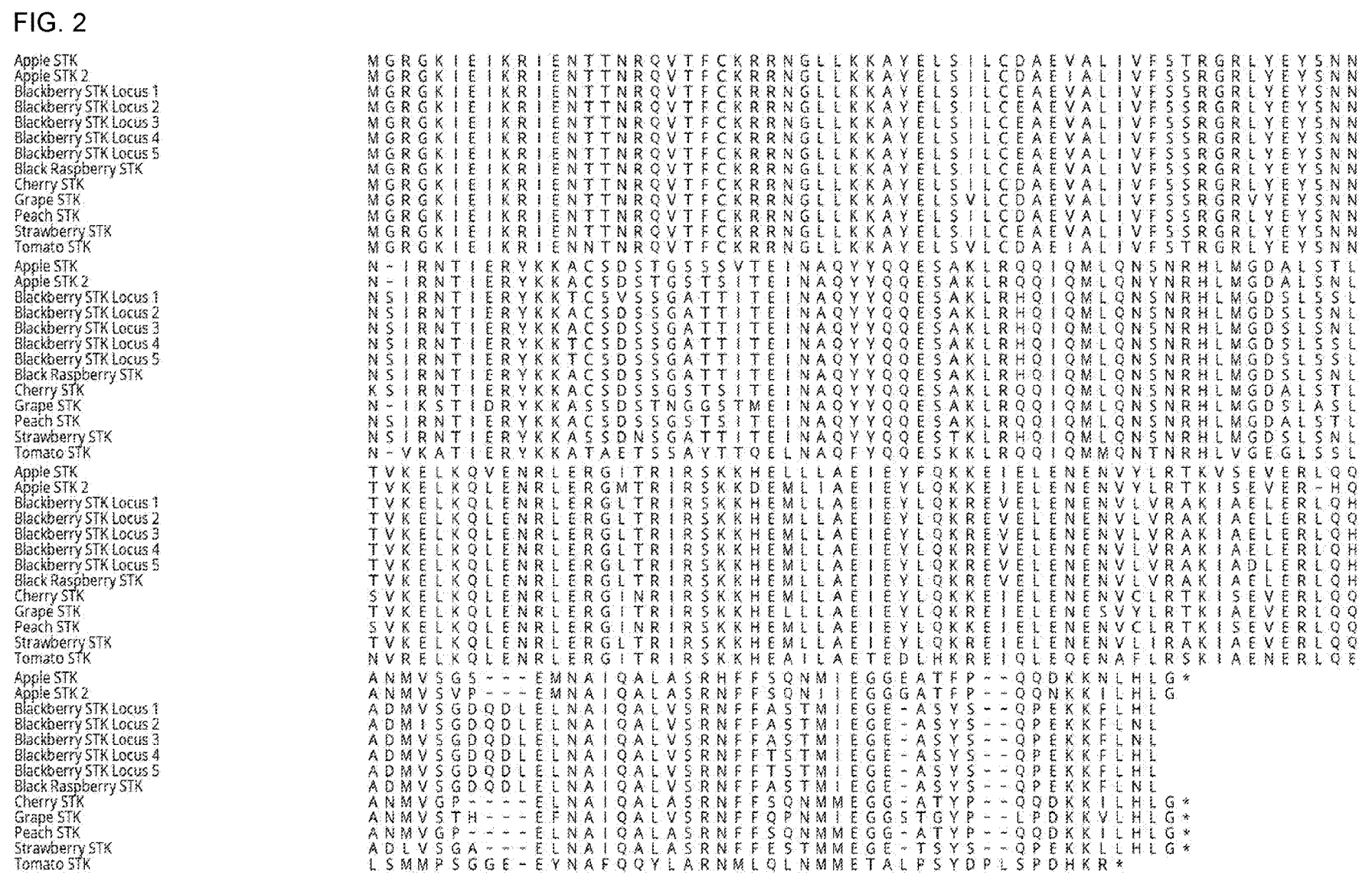

Apple STK
Apple STK 2
Blackberry STK Locus 1
Blackberry STK Locus 2
Blackberry STK Locus 3
Blackberry STK Locus 4
Blackberry STK Locus 5
Black Raspberry STK
Cherry STK
Grape STK
Peach STK
Strawberry STK
Tomato STK Apple STK
Apple STK 2
Blackberry STK Locus 1
Blackberry STK Locus 2
Blackberry STK Locus 3
Blackberry STK Locus 4
Blackberry STK Locus 5
Black Raspberry STK
Cherry STK
Grape STK
Peach STK
Strawberry STK
Tomato STK Apple STK
Apple STK 2
Blackberry STK Locus 1
Blackberry STK Locus 2
Blackberry STK Locus 3
Blackberry STK Locus 4
Blackberry STK Locus 5
Black Raspberry STK
Cherry STK
Grape STK
Peach STK
Strawberry STK
Tomato STK Apple STK
Apple STK 2
Blackberry STK Locus 1
Blackberry STK Locus 2
Blackberry STK Locus 3
Blackberry STK Locus 4
Blackberry STK Locus 5
Black Raspberry STK
Cherry STK
Grape STK
Peach STK
Strawberry STK
Tomato STK

FIG. 3

Almond STK
Cherry STK
Chinese plumSTK
Japanese Cherry STK
Peach STK
Sour Cherry STK
Sweet Cherry STK

SEEDLESS BLACK RASPBERRY WITH A MUTANT AGAMOUS-CLADE MADS-BOX TRANSCRIPTION FACTOR GENE

STATEMENT OF PRIORITY

This application claims the benefit, under 35 U.S.C. § 119(e), of U.S. Provisional Application No. 62/859,992, filed on Jun. 11, 2019, the entire contents of which is incorporated by reference herein.

FIELD

The present disclosure relates to the field of agriculture, particularly consumer crops, including methods for generating plants that produce fruits with an altered fruit development phenotype, such as a seedless or reduced seediness phenotype.

DESCRIPTION OF THE TEXT FILE SUBMITTED ELECTRONICALLY

A Sequence Listing in ASCII text format, submitted under 37 C.F.R. § 1.821, entitled 1499-38_ST25.txt, 400,143 bytes in size, generated on Jan. 15, 2024, is provided in lieu of a paper copy. This Sequence Listing is hereby incorporated herein by reference into the specification for its disclosures.

BACKGROUND

Fruit development normally depends on fertilization and the subsequent formation of the seed. Fruit can have hard seeds such as grapes or watermelons, or be drupes such as cherries, peaches or black raspberries. A drupe (or stone fruit) is an indehiscent fruit in which an outer fleshy part (exocarp, or skin; and mesocarp, or flesh) surrounds a single shell (the pit, stone, or pyrene) of hardened endocarp with a seed (kernel) inside. The endocarp is comprised of lignin to protect the seed. The endocarp develops from the innermost layer of the ovary.

Seedless fruits can develop in one of two ways: parthenocarpy and stenospermocarpy. In parthenocarpy, the fruit develops without pollination or fertilization and is desirable in fruit crops that may be difficult to pollinate or fertilize, such as fig, tomato, and summer squash. In stenospermocarpy, pollination or fertilization triggers fruit development, but the ovules or embryos abort without producing mature seeds.

The present invention provides new approaches to altering plant fruit development and seed production.

SUMMARY

The present disclosure provides a next generation plant breeding method for producing plants with an altered fruit development phenotype. The breeding method is capable of producing plants that exhibit altered fruit development (e.g., a seedless phenotype and/or plants with a reduced level of endocarp formation). An aspect of the next generation plant breeding method, is the inventors discovery of a genomic target that is highly conserved across a host of plant taxa and is correlated with the production of fruit; consequently, when said genomic target is edited in the taught manner, it is possible to produce a plant with, for example, a seedless phenotype and/or a plant with a reduced level of endocarp formation.

In one aspect, the invention provides a plant or plant part thereof comprising at least one non-natural mutation in an endogenous gene encoding an AGAMOUS clade MADS-box transcription factor.

In another aspect, a plant cell is provided, the plant cell comprising a base editing system comprising: (a) a CRISPR-associated effector protein; (b) a cytidine deaminase or adenosine deaminase; and (c) a guide nucleic acid (gRNA) having a spacer sequence with complementarity to an endogenous target gene encoding an AG clade MADS-box transcription factor.

In a further aspect, a plant or part thereof (e.g., a plant cell) is provided, comprising at least one non-natural mutation in an endogenous AG clade MADS-box transcription factor gene that prevents or reduces seed formation, wherein the at least one mutation is a substitution, insertion or a deletion that is introduced using an editing system that comprises a nucleic acid binding domain that binds to a target site in the AG clade MADS-box transcription factor gene, wherein the AG clade MADS-box transcription factor gene is a SEEDSTICK (STK) gene, the STK gene (a) comprising at least 80% sequence identity to any one of the nucleotide sequences of SEQ ID NOs: 153, 155, 157, 159, 161, 163, or 165, or a region having at least 90% sequence identity to any one of the nucleotide sequence of SEQ ID NOs: 172-174; or (b) encoding a AG clade MADS-box transcription factor having at least 80% sequence identity to any one of the amino acid sequences of SEQ ID NOs: 13, 29, 53, 66, 78, 97, 128, 150, 152, 154, 156, 158, 159, 160, 162, 164 or 166-171 or comprising a region having at least 80% sequence identity to any one of the amino acid sequences of SEQ ID NOs: 177-183, 187, 188, or 189.

In another aspect, a plant or part thereof comprising a mutated endogenous AG clade MADS-box transcription factor gene, wherein the mutated endogenous AG clade MADS-box transcription factor gene is a SEEDSTICK (STK) gene that (a) comprises a sequence having at least 80% identity to the nucleotide sequence of SEQ ID NOs: 153, 155, 157, 159, 161, 163, or 165, or sequence comprising a region having at least 80% sequence identity to any one of the nucleotide sequence of SEQ ID NOs: 172-174; or (b) encodes a sequence having at least 80% sequence identity to any one of the amino acid sequences of SEQ ID NOs: 13, 29, 53, 66, 78, 97, 128, 150, 152, 154, 156, 158, 159, 160, 162, 164 or 166-171 or a sequence comprising a region having at least 80% sequence identity to any one of the amino acid sequences of SEQ ID NOs: 177-183, 187, 188, or 189.

Further provided is a method of producing/breeding a transgene-free base-edited plant, comprising: (a) crossing a plant of the invention with a transgene free plant, thereby introducing the at least one mutation, the mutation, or the modification into the plant that is transgene-free; and (b) selecting a progeny plant that comprises the at least one single nucleotide substitution but is transgene-free, thereby producing a transgene free base-edited plant.

In another aspect, a method of providing a plurality of plants exhibiting an altered fruit development phenotype (e.g., reduced or no seed production) is provided, the method comprising planting two or more plants of the invention in a growing area (e.g., a field (e.g., a cultivated field, an agricultural field), a growth chamber, a greenhouse, a recreational area, a lawn, and/or a roadside and the like), thereby providing a plurality of plants exhibiting altered fruit development as compared to a plurality of control plants not comprising the mutation.

In a further aspect, a method for editing a specific site in the genome of a plant cell is provided, the method comprising: cleaving, in a site specific manner, a target site within an endogenous AG clade MADS-box transcription factor gene in the plant cell, the endogenous AG clade MADS-box transcription factor gene being a SEEDSTICK (STK) gene (a) comprising at least 80% sequence identity to any one of the nucleotide sequences of SEQ ID NOs: 153, 155, 157, 159, 161, 163, or 165, or a region having at least 80% sequence identity to any one of the nucleotide sequence of SEQ ID NOs: 172-174; or (b) encoding a AG clade MADS-box transcription factor having at least 80% sequence identity to any one of the amino acid sequences of SEQ ID NOs: 13, 29, 53, 66, 78, 97, 128, 150, 152, 154, 156, 158, 159, 160, 162, 164 or 166-171 or comprising a region having at least 80% sequence identity to any one of the amino acid sequences of SEQ ID NOs: 177-183, 187, 188, or 189, thereby generating an edit in the endogenous AG clade MADS-box transcription factor gene of the plant cell.

An additional aspect provides a method for making a plant, comprising: (a) contacting a population of plant cells comprising a DNA sequence that encodes a wild-type endogenous SEEDSTICK (STK) gene with a nuclease linked to a nucleic acid binding domain (e.g., editing system) that binds to a sequence: (a) having at least 80% sequence identity to any one of the nucleotide sequences of SEQ ID NOs: 153, 155, 157, 159, 161, 163, or 165, or comprising a region having at least 80% sequence identity to any one of the nucleotide sequence of SEQ ID NOs: 172-174; or (b) encoding a SEEDSTICK (STK) transcription factor (i) having at least 80% sequence identity to any one of the amino acid sequences SEQ ID NOs: 13, 29, 53, 66, 78, 97, 128, 150, 152, 154, 156, 158, 160, 162, 164, or 166-171 or (ii) comprising a region having at least 80% sequence identity to any one of the amino acid sequences of SEQ ID NOs: 177-183, 187, 188, or 189; (b) selecting a plant cell from said population in which at least one DNA sequence encoding the STK transcription factor has been mutated, wherein the mutation comprises a substitution of at least one nucleotide in the at least one DNA sequence; and (c) growing the selected plant cell into a plant.

Further provided is a method for producing a plant or part thereof comprising at least one cell in which an endogenous AG clade MADS-box transcription factor gene is mutated, the method comprising contacting a target site in the AG clade MADS-box transcription factor gene in the plant or plant part with a nuclease linked to a nucleic acid binding domain (e.g., editing system) that binds to the target site, wherein the AG clade MADS-box transcription factor gene is a SEEDSTICK (STK) gene (a) comprising a sequence having at least 80% sequence identity to any one of the nucleotide sequences of SEQ ID NOs: 153, 155, 157, 159, 161, 163, or 165 or comprising a region having at least 80% sequence identity to any one of the nucleotide sequence of SEQ ID NOs: 172-174, or (b) encoding a SEEDSTICK (STK) transcription factor having at least 80% sequence identity to any one of the amino acid sequences of SEQ ID NOs: 13, 29, 53, 66, 78, 97, 128, 150, 152, 154, 156, 158, 160, 162, 164, or 166-171, or comprising a region having at least 80% identity to any one of the amino acid sequences of SEQ ID NOs: 177-183, 187, 188, or 189, thereby producing a plant or part thereof comprising at least one cell having a mutation in the endogenous AG clade MADS-box transcription factor gene.

In an additional aspect, a method for producing a plant having an altered fruit development phenotype is provided, comprising (a) contacting a plant cell comprising a wild type endogenous AG clade MADS-box transcription factor gene with a nuclease targeting the wild type endogenous AG clade MADS-box transcription factor gene, wherein the nuclease is linked to a DNA binding domain that binds to a target site in the wild type endogenous AG clade MADS-box transcription factor gene, wherein the wild type endogenous AG clade MADS-box transcription factor gene is a SEEDSTICK (STK) gene that (i) comprises a sequence having at least 80% sequence identity to any one of the nucleotide sequences of SEQ ID NOs: 153, 155, 157, 159, 161, 163, or 165 or comprises a region having at least 80% sequence identity to any one of the nucleotide sequence of SEQ ID NOs: 172-174 and/or (ii) encodes a sequence having at least 80% sequence identity to any one of the amino acid sequences of a sequence having at least 80% sequence identity to any one of the amino acid sequences of SEQ ID NOs: 13, 29, 53, 66, 78, 97, 128, 150, 152, 154, 156, 158, 160, 162, 164, or 166-171, or a sequence comprising a region having at least 90% sequence identity to any one of the amino acid sequences of SEQ ID NOs: 177-183, 187, 188, or 189; (b) growing the plant cell into a plant, thereby producing a plant having an altered fruit phenotype.

In a further aspect, a method for producing a plant or part thereof comprising at least one cell having a mutated endogenous AG clade MADS-box transcription factor gene, the method comprising contacting a target site in an endogenous AG clade MADS-box transcription factor gene in the plant or plant part with a nuclease comprising a cleavage domain and a DNA-binding domain, wherein the DNA binding domain binds to a target site in the endogenous AG clade MADS-box transcription factor gene, wherein the endogenous AG clade MADS-box transcription factor gene is a SEEDSTICK (STK) gene that (a) encodes (i) a sequence having at least 80% sequence identity to any one of the amino acid sequences of SEQ ID NOs: 13, 29, 53, 66, 78, 97, 128, 150, 152, 154, 156, 158, 160, 162, 164, or 166-171 or (ii) a sequence comprising a region having at least 90% sequence identity to any one of the amino acid sequences of SEQ ID NOs: 177-183, 187, 188, or 189; and/or (b) comprises a sequence having at least 80% sequence identity to the nucleotide sequence of any one of SEQ ID NOs: 153, 155, 157, 159, 161, 163, or 165 or a region having at least 80% sequence identity to any one of the nucleotide sequence of SEQ ID NOs: 172-174, thereby producing the plant or part thereof comprising at least one cell having a mutated endogenous AG clade MADS-box transcription factor gene.

Additionally provided is a method of producing a plant or part thereof comprising a mutated endogenous AG clade MADS-box transcription factor gene and having altered fruit development, the method comprising contacting a target site in an endogenous AG clade MADS-box transcription factor gene with a nuclease comprising a cleavage domain and a DNA-binding domain (e.g., editing system) comprising a nucleic acid binding domain that binds to the target site in the AG clade MADS-box transcription factor gene, wherein the AG clade MADS-box transcription factor gene is a SEEDSTICK (STK) gene (a) comprising a sequence having at least 80% sequence identity to any one of the nucleotide sequences of SEQ ID NOs: 153, 155, 157, 159, 161, 163, or 165 or comprising a region having at least 80% sequence identity to any one of the nucleotide sequence of SEQ ID NOs: 172-174, or (b) encoding a SEEDSTICK (STK) transcription factor having at least 80% sequence identity to any one of the amino acid sequences of SEQ ID NOs: 13, 29, 53, 66, 78, 97, 128, 150, 152, 154, 156, 158, 160, 162, 164, or 166-171, or comprising a region having at least 80% identity to any one of the amino acid sequences of SEQ ID NOs: 177-183, 187, 188, or 189, thereby producing a plant or part thereof comprising a mutated endogenous AG clade MADS-box transcription factor gene and having altered fruit development.

In a further aspect, the invention provides a guide nucleic acid (e.g., gRNA, gDNA, crRNA, crDNA) that binds to a target site in a AG clade MADS-box transcription factor gene, wherein the endogenous AG clade MADS-box transcription factor gene is a SEEDSTICK (STK) gene (a) comprising a sequence having at least 80% sequence identity to any one of the nucleotide sequences of SEQ ID NOs: 153, 155, 157, 159, 161, 163, or 165 or comprising a region having at least 80% sequence identity to any one of the nucleotide sequence of SEQ ID NOs: 172-174, or (b) encoding a SEEDSTICK (STK) transcription factor having at least 80% sequence identity to any one of the amino acid sequences of SEQ ID NOs: 13, 29, 53, 66, 78, 97, 128, 150, 152, 154, 156, 158, 160, 162, 164, or 166-171, or a region having at least 80% identity to any one of the amino acid sequences of SEQ ID NOs: 177-183, 187, 188, or 189.

Additionally provided is a system comprising a guide nucleic acid of the invention and a CRISPR-Cas effector protein that associates with the guide nucleic acid.

Further provided is a gene editing system comprising a CRISPR-Cas effector protein in association with a guide nucleic acid, wherein the guide nucleic acid comprises a spacer sequence that binds to a AG clade MADS-box transcription factor gene.

In a further aspect, a complex comprising a CRISPR-Cas effector protein comprising a cleavage domain and a guide nucleic acid is provided, wherein the guide nucleic acid binds to a target site in a AG clade MADS-box transcription factor gene, wherein the AG clade MADS-box transcription factor gene is a SEEDSTICK (STK) gene (a) comprising at least 80% sequence identity to the nucleotide sequence of any one of SEQ ID NOs: 153, 155, 157, 159, 161, 163, or 165 or comprising a region having at least 80% sequence identity to any one of the nucleotide sequence of SEQ ID NOs: 172-174, and/or (b) encoding (i) a sequence having at least 80% sequence identity to any one of the amino acid sequences of SEQ ID NOs: 13, 29, 53, 66, 78, 97, 128 or 150, or (ii) a sequence comprising a region having at least 80% sequence identity to any one of the amino acid sequences of SEQ ID NOs: 13, 29, 53, 66, 78, 97, 128, 150, 152, 154, 156, 158, 160, 162, 164, or 166-171, or a region having at least 80% identity to any one of the amino acid sequences of SEQ ID NOs: 177-183, 187, 188, or 189, wherein the cleavage domain cleaves a target strand in the AG clade MADS-box transcription factor gene.

In an additional aspect, an expression cassette is provided comprising a (a) polynucleotide encoding CRISPR-Cas effector protein comprising a cleavage domain and (b) a guide nucleic acid that binds to a target site in a AG clade MADS-box transcription factor gene, wherein theAG clade MADS-box transcription factor gene is a SEEDSTICK gene and the guide nucleic acid comprises a spacer sequence that is complementary to and binds to a sequence having at least 80% sequence identity to at least a portion of a sequence having at least 80% sequence identity to the nucleotide sequence of any one of SEQ ID NOs: 153, 155, 157, 159, 161, 163, or 165 or a portion of a sequence comprising a region having at least 80% sequence identity to any one of the nucleotide sequence of SEQ ID NOs: 172-174; or a sequence encoding (i) a polypeptide having at least 80% sequence identity to any one of the amino acid sequences of SEQ ID NOs: 13, 29, 53, 66, 78, 97, 128, 150, 152, 154, 156, 158, 160, 162, 164, or 166-171, or (ii) a polypeptide comprising a region having at least 80% sequence identity to any one of the amino acid sequences of SEQ ID NOs: 177-183, 187, 188, or 189, optionally wherein a portion is about 2 to about 22 consecutive nucleotides in length.

Additionally provided is nucleic acid encoding a dominant-negative allele, semi-dominant allele, weak loss of function allele, or a hypomorphic mutation of an AG clade MADS-box transcription factor, optionally wherein the AG clade MADS-box transcription factor is AGAMOUS (AG), SHATTERPROOF 1 (SHP1), SHATTERPROOF 2 (SHP2), and/or SEEDSTICK (STK).

Further provided are plants comprising in their genome one or more mutated AG clade MADS-box transcription factor genes produced by the methods of the invention as well as polypeptides, polynucleotides, nucleic acid constructs, expression cassettes and vectors for making a plant of this invention.

These and other aspects of the invention are set forth in more detail in the description of the invention below.

BRIEF DESCRIPTION OF THE FIGURES

Figure 3:
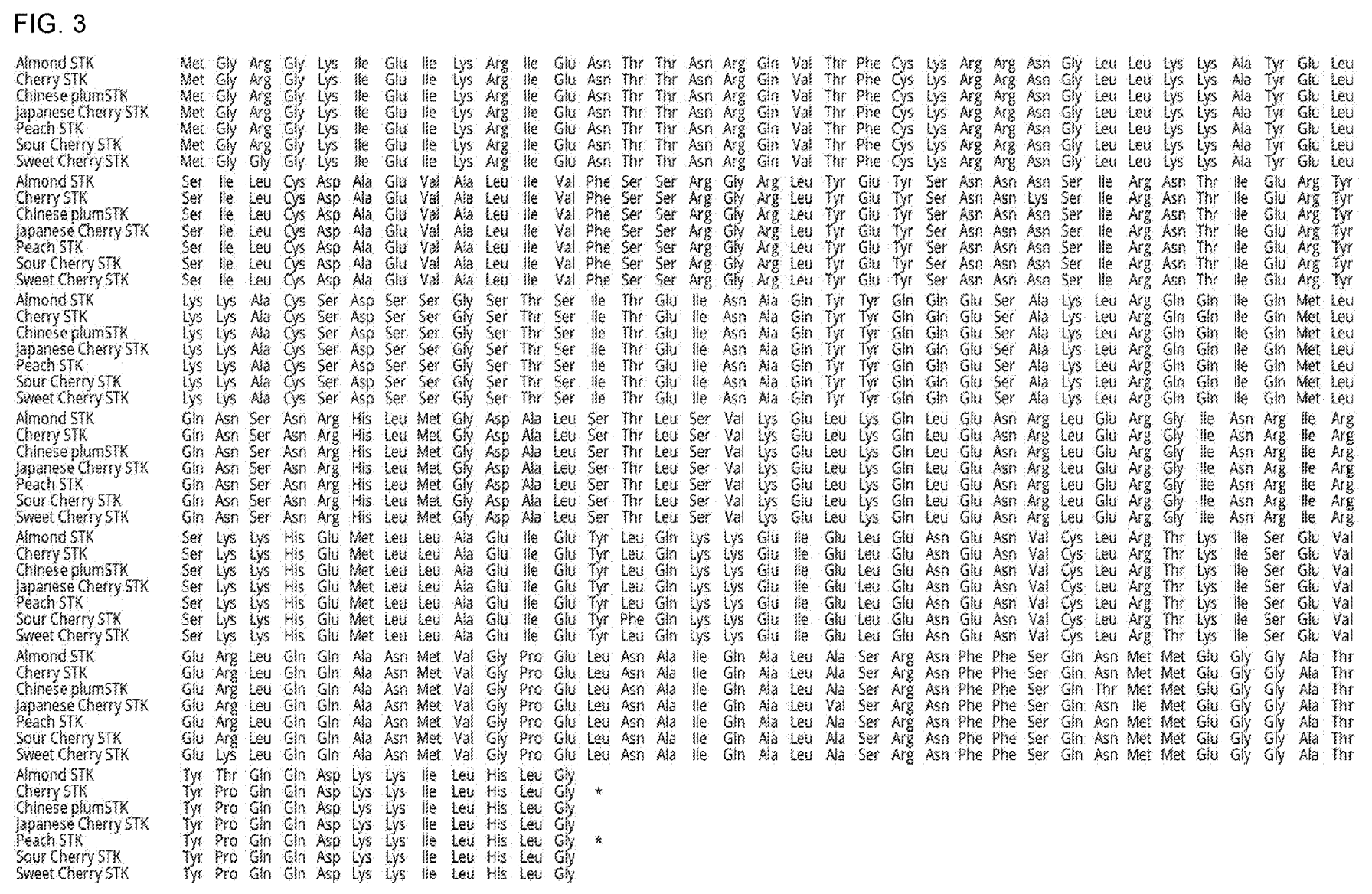

FIG. 3 represents a graphical comparison of the "seediness" of soy, red raspberry, black raspberry, and blackberry, based upon the μg lignin/mg protein free cell wall.

FIG. 2 provides an alignment between SEEDSTICK polypeptide sequences. From top to bottom SEQ ID NO:53, SEQ ID NO:66, SEQ ID NO:160, SEQ ID NO:158, SEQ ID NO:156, SEQ ID NO:154, SEQ ID NO:152, SEQ ID NO:156, SEQ ID NO:166, SEQ ID NO:150, SEQ ID NO: 78, SEQ ID NO:29, SEQ ID NO:128.

FIG. 3 provides an alignment between SEEDSTICK polypeptide sequences. From top to bottom SEQ ID NO:171, SEQ ID NO:166, SEQ ID NO:170, SEQ ID NO:169, SEQ ID NO:78, SEQ ID NO:168, SEQ ID NO:167.

FIG. 4 illustrate example modifications of a wild type blackberry SEEDSTICK sequence (portion (SEQ ID NO:253) of amino acid sequence SEQ ID NO:204; portion (SEQ ID NO:254) of nucleotide sequence SEQ ID NO:205). Example mutated nucleic acid sequences and corresponding amino acid sequences, from top to bottom SEQ ID NO:219, SEQ ID NO:220, SEQ ID NO:221, SEQ ID NO:222, SEQ ID NO:223, SEQ ID NO: 224, SEQ ID NO: 225, SEQ ID NO:226, SEQ ID NO: 227, SEQ ID NO:228, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO: 238, SEQ ID NO:239, SEQ ID NO:240, SEQ ID NO:241, SEQ ID NO:242, SEQ ID NO:243, SEQ ID NO:244, SEQ ID NO:245, SEQ ID NO:246, SEQ ID NO:247, SEQ ID NO:248, SEQ ID NO: 249, SEQ ID NO:250, SEQ ID NO:251, and SEQ ID NO:252.

FIG. 12A depicts two wild-type SEPALLATA transcription factors and two wild-type STK transcription factors interacting in Luciferase assay and FIG. 12B depicts two wild-type SEPALLATA transcription factors, one mutated STK transcription factor (darker shade) and one wild-type STK transcription factor interacting in Luciferase assay.

FIG. 13 shows an alignment of wild-type Strawberry (*Fragaria vesca*) STK (nucleotide sequence of SEQ ID NO:215, protein sequence of SEQ ID NO:216) with mutant STK (nucleotide sequence of SEQ ID NO:217, protein sequence of SEQ ID NO:218) generated through use of a cutting vector as described in Example 4.

DETAILED DESCRIPTION

Figure 1:
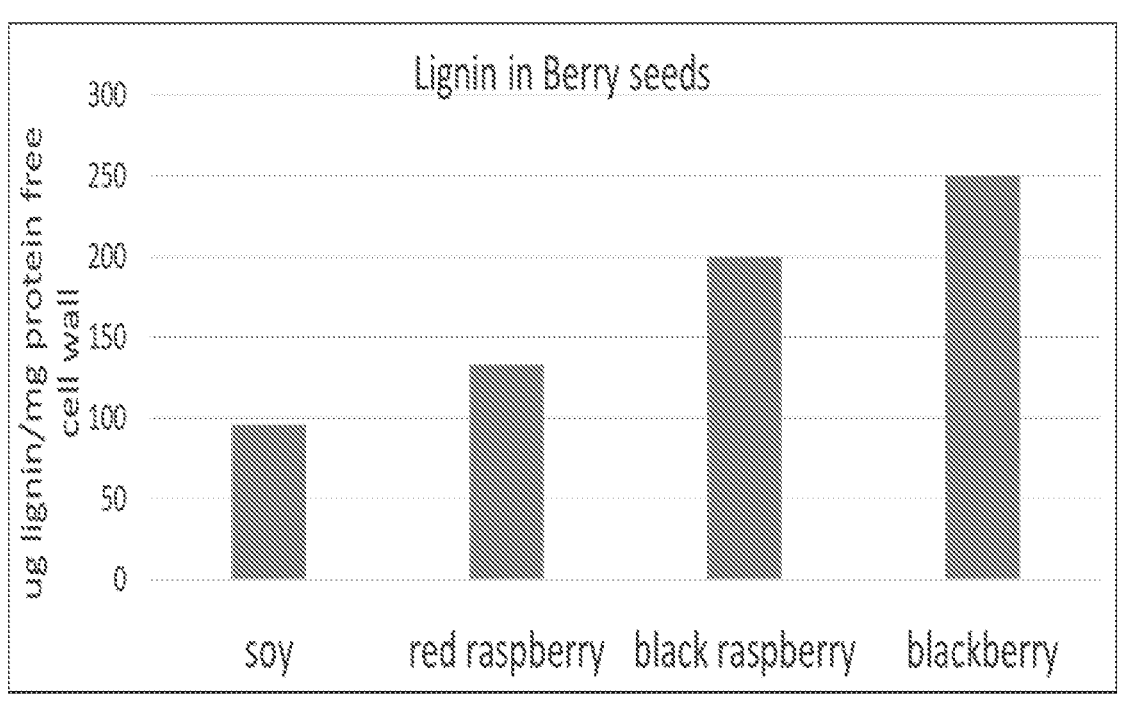
FIG. 1 illustrates one embodiment of a metric that can be utilized to define an altered fruit development phenotype, for example, reduced seediness. That is, in aspects of the disclosure, reduced seediness can be described as reduced lignin content as compared to wild type (lignin/milligram protein-free cell wall in endocarp and/or seed coat).

The present disclosure provides methods for generating plants that produce fruits with an altered fruit development phenotype. In some aspects, the methods provide for the production of seedless fruits or fruits with reduced seediness. Seedless and/or reduced seediness fruit is defined as a fruit that does not have a seed or a pit/drupe (drupeless) or, seeded fruits wherein the seed is altered compared to a wild type fruit of the same plant species due to reduced seed size or reduced seed lignin content or reduced endocarp formation. Reduced seediness is defined as the following: reduced lignin content as compared to wild type (lignin/milligram protein-free cell wall in endocarp and/or seed coat; reduced seed size as compared to wild type (volume of seed and/or drupe); and/or smoother seed/drupe surface as compared to wild type (seed/drupe surface area/volume).

The disclosure provides a method to create seedless fruits (where a seedless fruit is defined as not having a seed or a pit) or, seeded fruits where the seed can be eaten because of a softening of the seed or pit, via a combination of: bioinformatic analysis, evolutionary analysis, gene editing, and phenotypic screening. First, bioinformatic analysis is used to determine which genes are expressed in developing seeds by examining gene expression data (RNASeq, Microarray). Genes that are only expressed in the developing seed and not in other parts of the plant are selected for the second step, evolutionary analysis. In this step, amino acid alignments are used to diagnose residues under positive purifying selection—a strong indication of a critical role in seed development. In the third step, the codons encoding these selected residues are edited to affect non-conservative change in the amino acid, resulting in variation in protein function. These possible candidate edits are then screened phenotypically to select for a seedless phenotype.

Consumers value seedless crops because of the convenience and ease of preparation and consumption. For example, seedless watermelon allows you to eat a watermelon without spitting the seeds out, likewise for grapes, oranges, bananas, etc. There is also ease preparation; bananas would require seed removal prior to eating. Even where seeds are currently edible, such as with blackberries, the substantial seed content is unacceptable to some consumers. These benefits are enjoyed in a very limited number of crops because to date the seedless phenotype has relied on the capture of variation arising in wild and breeding populations or complicated triploid production that only works in some crops. The methods of the present invention allow the development of the seedless phenotype in many if not all plant species.

In addition to producing plants with a seedless phenotype, reducing "seediness" through targeting seed size or the thickness of the endocarp is also desirable. The reason for the low level of seediness in some cultivars of blackberries is due to a perception, apparently due to seed shape and endocarp thickness. The endocarp thickness trait is a reported major factor contributing to seediness, as experienced by a consumer.

The underlying genetic mechanisms and genomic architecture giving rise to the seedless, or reduced seediness phenotype, is not well understood. Therefore, there is a great need in the art for a method of creating a seedless phenotype, in many, if not all, plant species. Such a method would enable consumers to have a choice of consuming fruits or vegetables that are seedless, or which have a reduced perception of seeds when eaten.

The present disclosure provides compositions, methods, and products related to the modification of plant cells to induce seedlessness and/or reduced seed size in the context of improved agronomic traits. In some embodiments, plant cells are modified by the methods of the present disclosure to edit a single nucleotide of one or more endogenous target genes, or to trigger a point mutation in which a single nucleotide changes such as C to T (or G to A), which results in a codon that codes for a different amino acid. In some embodiments, plant cells are modified by the methods of the present disclosure to provide a truncated polypeptide, e.g., a C-terminal truncation in an AG clade MADS-box transcription factor polypeptide. In some embodiments, the plant cells are modified using gene editing techniques, including but not limited by CRISPR-Cas systems and/or base editors associated with a CRISPR-Cas complex. In some embodiments, the present disclosure provides compositions, methods, and products (i.e. gene-edited plants) for modifying plant cells using precisely targeted base-editing techniques of the present disclosure. In some embodiments, the present disclosure provides methods of performing targeted gene/genome editing within a plant cell and producing a gene-edited plant, part and cell thereof, comprising components for targeted gene/genome engineering described herein. In other embodiments, the gene-edited plant is transgene-free. In the disclosure, when the phrase "single nucleotide substitution" is used, it is understood that multiple single nucleotide substitutions can be made utilizing the methods described herein. The methods taught herein are able to make targeted substitutions or deletions of one or more nucleotides The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

The term "a" or "an" refers to one or more of that entity, i.e., can refer to a plural referent. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used in this specification, the term "and/or" is used in this disclosure to mean either "and" or "or" unless indicated otherwise and encompasses any and all possible combinations of one or more of the associated listed items, as well as the lack of combinations when interpreted in the alternative ("or").

Throughout this specification, unless the context requires otherwise, the words "comprise", or variations such as "comprises" or "comprising", will be understood to imply the inclusion of a stated element or integer or group of elements or integers but not the exclusion of any other element or integer or group of elements or integers.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Thus, the term "about," as used herein when referring to a measurable value such as an amount or concentration and the like, is meant to encompass variations of $\pm 10\%$, $\pm 5\%$, $\pm 1\%$, $\pm 0.5\%$, or even $\pm 0.1\%$ of the specified value as well as the specified value. For example, "about X" where X is the measurable value, is meant to include X as well as variations of $\pm 10\%$, $\pm 5\%$, $\pm 1\%$, $\pm 0.5\%$, or even $\pm 0.1\%$ of X. A range provided herein for a measurable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

Recitation of ranges of values herein are merely intended to serve as a shorthand method of referring individually to each separate value falling within the range, unless otherwise indicated herein, and each separate value is incorporated into the specification as if it were individually recited herein. For example, if the range 10 to 15 is disclosed, then 11, 12, 13, and 14 are also disclosed.

As used herein, the terms "increase," "increasing," "increased," "enhance," "enhanced," "enhancing," and "enhancement" (and grammatical variations thereof) describe an elevation of at least about 5%, 10%, 15%, 20%, 25%, 50%, 75%, 100%, 150%, 200%, 300%, 400%, 500% or more as compared to a control.

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 96%, 97%, 98%, 99%, 99.5%, 99.6%, 99.7%, 99.8%, 99.9%, or 100% as compared to a control. In particular embodiments, the reduction can result in no or essentially no (i.e., an insignificant amount, e.g., less than about 10% or even 5%) detectable activity or amount. For example, a plant comprising a mutation in an AG clade MADS-box transcription factor gene as described herein can exhibit reduced seed production (seedlessness) or reduced seediness that is reduced by about 5% to about 75%, about 5% to about 80%, about 5% to about 85%, about 5% to about 90%, about 5% to about 95%, about 15% to about 80%, about 15% to about 85%, about 25% to about 75%, about 25% to about 80%, about 25% to about 85%, about 25% to about 90%, about 25% to about 95%, about 50% to about 80%, about 50% to about 85%, about 75% to about 80%, about 75% to about 85%, about 75% to about 90%, about 75% to about 95%, about 80% to about 85%, about 80% to about 95%, or any range or value therein, as compared to a control plant not comprising the same mutation.

As used herein, the terms "express," "expresses," "expressed" or "expression," and the like, with respect to a nucleic acid molecule and/or a nucleotide sequence (e.g., RNA or DNA) indicates that the nucleic acid molecule and/or a nucleotide sequence is transcribed and, optionally, translated. Thus, a nucleic acid molecule and/or a nucleotide sequence may express a polypeptide of interest or, for example, a functional untranslated RNA.

The terms "genetically engineered host cell," "recombinant host cell," and "recombinant strain" are used interchangeably herein and refer to host cells that have been genetically engineered by the methods of the present disclosure. Thus, the terms include a host cell (e.g., bacteria, yeast cell, fungal cell, CHO, human cell, plant cell, protoplast derived from plant, callus, etc.) that has been genetically altered, modified, or engineered, such that it exhibits an altered, modified, or different genotype and/or phenotype (e.g., when the genetic modification affects coding nucleic acid sequences), as compared to the naturally-occurring host cell from which it was derived. It is understood that the terms refer not only to the particular recombinant host cell in question, but also to the progeny or potential progeny of such a host cell.

The term "genetically engineered" may refer to any manipulation of a host cell's genome (e.g. by insertion or deletion of nucleic acids).

The term "next generation plant breeding" refers to a host of plant breeding tools and methodologies that are available to today's breeder. A key distinguishing feature of next generation plant breeding is that the breeder is no longer confined to relying upon observed phenotypic variation, in order to infer underlying genetic causes for a given trait. Rather, next generation plant breeding may include the utilization of molecular markers and marker assisted selection (MAS), such that the breeder can directly observe movement of alleles and genetic elements of interest from one plant in the breeding population to another, and is not confined to merely observing phenotype. Further, next generation plant breeding methods are not confined to utilizing natural genetic variation found within a plant population. Rather, the breeder utilizing next generation plant breeding methodology can access a host of modern genetic engineering tools that directly alter/change/edit the plant's underlying genetic architecture in a targeted manner, in order to bring about a phenotypic trait of interest. In aspects, the plants bred with a next generation plant breeding methodology are indistinguishable from a plant that was bred in a traditional manner, as the resulting end product plant could theoretically be developed by either method. In particular aspects, a next generation plant breeding methodology may result in a plant that comprises: a genetic modification that is a deletion of any size (e.g., resulting in a truncation); a genetic modification that is a single base pair substitution; a genetic modification that is an introduction of nucleic acid sequences from within the plant's natural gene pool (e.g. any plant that could be crossed or bred with a plant of interest) or from editing of nucleic acid sequences in a plant to correspond to a sequence known to occur in the plant's natural gene pool; and offspring of said plants.

The term "traditional plant breeding" refers to the utilization of natural variation found within a plant population as a source for alleles and genetic variants that impart a trait of a interest to a given plant. Traditional breeding methods make use of crossing procedures that rely largely upon observed phenotypic variation to infer causative allele association. That is, traditional plant breeding relies upon observations of expressed phenotype of a given plant to infer underlying genetic cause. These observations are utilized to inform the breeding procedure in order to move allelic variation into germplasm of interest. Further, traditional plant breeding has also been characterized as comprising random mutagenesis techniques, which can be used to introduce genetic variation into a given germplasm. These random mutagenesis techniques may include chemical and/or radiation-based mutagenesis procedures. Consequently, one key feature of traditional plant breeding, is that the breeder does not utilize a genetic engineering tool that directly alters/changes/edits the plant's underlying genetic architecture in a targeted manner, in order to introduce genetic diversity and bring about a phenotypic trait of interest.

The terms "polynucleotide," "nucleic acid," and "nucleotide sequence," used interchangeably herein, refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. This term includes, but is not limited to, single-, double-, or multistranded DNA or RNA, genomic DNA, cDNA, DNA-RNA hybrids, or a polymer comprising purine and pyrimidine bases or other natural, chemically or biochemically modified, non-natural, or derivatized nucleotide bases. It also includes modified nucleic acids such as methylated and/or capped nucleic acids, nucleic acids containing modified bases, backbone modifications, and the like. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as "oligomers" or "oligos" and may be isolated from genes, or chemically synthesized by methods known in the art. The terms "polynucleotide" "nucleic acid," and "nucleotide sequence" should be understood to include, as applicable to the embodiments being described, single-stranded (such as sense or antisense) and double-stranded polynucleotides.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

A "heterologous" or a "recombinant" nucleotide sequence is a nucleotide sequence not naturally associated with a host cell into which it is introduced, including non-naturally occurring multiple copies of a naturally occurring nucleotide sequence.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type endogenous AG clade MADS-box transcription factor gene" is an AG clade MADS-box transcription factor gene that is naturally occurring in or endogenous to the reference organism, e.g., a *Rubus* plant, a *Prunis* plant and the like.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "allele" refers to one of two or more different nucleotides or nucleotide sequences that occur at a specific locus.

A "null allele" is a nonfunctional allele caused by a genetic mutation that results in a complete lack of production of the corresponding protein or produces a protein that is non-functional.

A "dominant negative mutation" is a mutation that produces an altered gene product (e.g., having an aberrant function relative to wild type), which gene product adversely affects the function of the wild-type allele or gene product. For example, a "dominant negative mutation" may block a function of the wild type gene product. A dominant negative mutation may also be referred to as an "antimorphic mutation."

A "semi-dominant mutation" refers to a mutation in which the penetrance of the phenotype in a heterozygous organism is less than that observed for a homozygous organism.

A "weak loss-of-function mutation" is a mutation that results in a gene product having partial function or reduced function (partially inactivated) as compared to the wildtype gene product.

A "hypomorphic mutation" is a mutation that results in a partial loss of gene function, which may occur through reduced expression (e.g., reduced protein and/or reduced RNA) or reduced functional performance (e.g., reduced activity), but not a complete loss of function/activity. A "hypomorphic" allele is a semi-functional allele caused by a genetic mutation that results in production of the corresponding protein that functions at anywhere between 1% and 99% of normal efficiency.

As used herein, the terms "desired allele," "target allele" and/or "allele of interest" are used interchangeably to refer to an allele associated with a desired trait. In some embodiments, a desired allele may be associated with either an increase or a decrease (relative to a control) of or in a given trait, depending on the nature of the desired phenotype.

A marker is "associated with" a trait when said trait is linked to it and when the presence of the marker is an indicator of whether and/or to what extent the desired trait or trait form will occur in a plant/germplasm comprising the marker. Similarly, a marker is "associated with" an allele or chromosome interval when it is linked to it and when the presence of the marker is an indicator of whether the allele or chromosome interval is present in a plant/germplasm comprising the marker.

As used herein, the terms "backcross" and "backcrossing" refer to the process whereby a progeny plant is crossed back to one of its parents one or more times (e.g., 1, 2, 3, 4, 5, 6, 7, 8, etc.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, in TECHNIQUES ET UTILISATIONS DES MARQUEURS MOLECULAIRES LES COLLOQUES, Vol. 72, pp. 45-56 (1995); and Openshaw et al., *Marker-assisted Selection in Backcross Breeding*, in PROCEEDINGS OF THE SYMPOSIUM "ANALYSIS OF MOLECULAR MARKER DATA," pp. 41-43 (1994). The initial cross gives rise to the FI generation. The term "BC1" refers to the second use of the recurrent parent, "BC2" refers to the third use of the recurrent parent, and so on.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be backcrossed one or more times (e.g., 1, 2, 3, 4, or more times) to a line having a desired genetic background, selecting for the desired allele, with the result being that the desired allele becomes fixed in the desired genetic background. For example, a marker associated with increased yield under non-water stress conditions may be introgressed from a donor into a recurrent parent that does not comprise the marker and does not exhibit increased yield under non-water stress conditions. The resulting offspring could then be backcrossed one or more times and selected until the progeny possess the genetic marker(s) associated with increased yield under non-water stress conditions in the recurrent parent background.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific genetic makeup that provides a foundation for some or all of the hereditary qualities of an organism or cell culture. As used herein, germplasm includes cells, seed or tissues from which new plants may be grown, as well as plant parts that can be cultured into a whole plant (e.g., leaves, stems, buds, roots, pollen, cells, etc.).

As used herein, the terms "cultivar" and "variety" refer to a group of similar plants that by structural or genetic features and/or performance can be distinguished from other varieties within the same species.

As used herein, the term "at least a portion" or "fragment" of a nucleic acid or polypeptide means a portion having the minimal size characteristics of such sequences, or any larger fragment of the full length molecule, up to and including the full length molecule. A fragment of a polynucleotide of the disclosure may encode a biologically active portion of a genetic regulatory element. A biologically active portion of a genetic regulatory element can be prepared by isolating a portion of one of the polynucleotides of the disclosure that comprises the genetic regulatory element and assessing activity as described herein. In some embodiments, a "portion" may encode a targeted region for producing a desired phenotype (e.g., altered fruit development; e.g., seedlessness or reduced seediness). Thus, with respect to nucleic acids, the term "fragment" or "portion" refers to a nucleic acid that is reduced in length relative (e.g., reduced by 1, 2, 3, 4, 5, 6, 7, 8, 9, 10, 11, 12, 13, 14, 15, 16, 17, 18, 19, 20, 20, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 400, 450, 500, 550, 600, 650, 660, 670, 680, 690 or 700 or more nucleotides or any range or value therein) to a reference nucleic acid and that comprises, consists essentially of and/or consists of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to a corresponding portion of the reference nucleic acid. Such a nucleic acid fragment may be, where appropriate, included in a larger polynucleotide of which it is a constituent. As an example, a repeat sequence of guide nucleic acid of this invention may comprise a "portion" of a wild type CRISPR-Cas repeat sequence (e.g., a wild Type CRISR-Cas repeat; e.g., a repeat from the CRISPR Cas system of, for example, a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or a Cas14c, and the like). In some embodiments, a nucleic acid fragment may comprise, consist essentially of or consist of about 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 300, 350, 400, 450, 500, 550, 600, or 650 or more consecutive nucleotides or any range or value therein of a nucleic acid encoding a SEEDSTICK (STK) transcription factor, optionally a fragment STK nucleic acid may be about 50 nucleotides to about 300 nucleotides in length, about 50 nucleotides to about 350 nucleotides in length, about 50 nucleotides to about 400 nucleotides in length, about 50 nucleotides to about 450 nucleotides in length, about 50 nucleotides to about 500 nucleotides in length, about 50 nucleotides to about 600 nucleotides in length, about 100 nucleotides to about 300 nucleotides in length, about 100 nucleotides to about 350 nucleotides in length, about 100 nucleotides to about 400 nucleotides in length, about 100 nucleotides to about 450 nucleotides in length, about 100 nucleotides to about 500 nucleotides in length, or about 100 nucleotides to about 600 nucleotides in length, or any range or value therein.

In some embodiments, a nucleic acid fragment of a STK gene may be the result of a deletion of nucleotides from the 3' end, the 5' end, and/or from within a gene encoding a STK protein. In some embodiments, a deletion of a portion of a gene encoding a STK protein may comprise a deletion of a portion of consecutive nucleotides from the 5' end, the 3' end, or from within, for example, a nucleotide sequence having at least 80% sequence identity to the nucleotide sequence of any one of SEQ ID NOs: 153, 155, 157, 159, 161, 163, or 165. In some embodiments, a deletion of a portion of a STK gene may comprise deletion of a portion of consecutive nucleotides from the 3' end of a nucleotide sequence having at least 80% sequence identity to the nucleotide sequence of any one of SEQ ID NOs: 153, 155, 157, 159, 161, 163, or 165. In some embodiments, a deletion of a portion of a STK gene may comprise a deletion of a portion of consecutive nucleotides from the 3' end of a nucleotide sequence having at least 80% sequence identity to the nucleotide sequence of any one of SEQ ID NOs: 153, 155, 157, 159, 161, 163, or 165 of from about 1 nucleotide to about 300 consecutive nucleotides or more (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 130, 140, 150, 175, 200, 225, 250, or 300 or more consecutive nucleotides, or any range or value therein, optionally about 4 consecutive nucleotides to about 150 consecutive nucleotides). In some embodiments, such a deletion may result in a null allele, which when comprised in a plant can result in a phenotype of altered fruit development. In some embodiments, such a deletion may be a dominant-negative allele, semi-dominant allele, weak loss of function allele, a null allele, or a hypomorphic mutation, which when comprised in a plant can result in in a phenotype of altered fruit development in the plant, wherein the altered fruit development results in, for example, seedlessness or reduced seediness.

Similarly, a portion of a polypeptide may be 4 amino acids, 5 amino acids, 6 amino acids, 7 amino acids, and so on, going up to the full-length polypeptide. The length of the portion to be used will depend on the particular application. A portion of a polypeptide useful as an epitope may be as short as 4 amino acids. A portion of a polypeptide that performs the function of the full-length polypeptide would generally be longer than 4 amino acids. In some embodiments, a fragment of a polypeptide or polynucleotide comprises at least 10%, 20%, 30%, 40%, 50%, 60%, 70%, 80%, 90%, 95%, 96%, 97%, 98%, or 99% of the entire length of the reference polypeptide or polynucleotide.

Further, with respect to polypeptides, the term "fragment" or "portion" may refer to a polypeptide that is reduced in length relative to a reference polypeptide and that comprises, consists essentially of and/or consists of an amino acid sequence of contiguous amino acids identical or almost identical (e.g., 90%, 91%, 92%, 93%, 94%, 95%, 96%, 97%, 98%, 99% identical) to a corresponding portion of the reference polypeptide. Such a polypeptide fragment may be, where appropriate, included in a larger polypeptide of which it is a constituent. In some embodiments, the polypeptide fragment comprises, consists essentially of or consists of at least about 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 300, 350, 400 or more consecutive amino acids of a reference polypeptide. In some embodiments, a polypeptide fragment may comprise, consist essentially of or consist of about 5, 6, 7, 8, 9, 10, 11, 12, 13, 14, 15, 20, 25, 30, 35, 40, 45, 50, 55, 60, 65, 70, 75, 80, 85, 90, 95, 100, 110, 115, 120, 125, 130, 135, 140, 145, 150, 155, 160, 165, 166, 167, 168, 169, 170, 171, 172 or more consecutive amino acid residues (or any range or value therein) of a for example, STK polypeptide (e.g., a fragment or a portion of a polypeptide having at least 80% sequence identity to any one of SEQ ID NOs: 13, 29, 53, 66, 78, 97, 128, 150, 152, 154, 156, 158, 160, 162, 164, or 166-171).

In some embodiments, a "portion" may be related to the number of amino acids that are deleted from a polypeptide. Thus, for example, a deleted "portion" of, for example, a STK polypeptide may comprise at least one amino acid residue (e.g., at least 1, or at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more consecutive amino acid residues) deleted from a polypeptide having at least 80% sequence identity to any one of SEQ ID NOs: 13, 29, 53, 66, 78, 97, 128, 150, 152, 154, 156, 158, 160, 162, 164, or 166-171, optionally at least one amino acid residue to about 50 consecutive amino acid residues. In some embodiments, a deletion of a portion of a STK protein may comprise a deletion of a portion of consecutive amino acid residues from the N- or C-terminus of or within a polypeptide having at least 80% sequence identity to any one of SEQ ID NOs: 13, 29, 53, 66, 78, 97, 128, 150, 152, 154, 156, 158, 160, 162, 164, or 166-171, optionally a deletion of at least one amino acid residue to about 50 consecutive amino acid residues (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive nucleotides). In some embodiments, such a deletion in a polypeptide may result in a null allele, which when comprised in a plant, the plant exhibits altered fruit development as described herein compared to a plant not comprising said deletion. In some embodiments, such a deletion may be a dominant-negative allele, semi-dominant allele, weak loss of function allele, a null allele, or a hypomorphic mutation, which when comprised in a plant, the plant exhibits altered fruit development compared to a plant not comprising the mutation.

As used herein, the term "gene" refers to any segment of DNA associated with a biological function. Thus, genes include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "endogenous" or "endogenous gene," refers to the naturally occurring gene, in the location in which it is naturally found within the host cell genome.

As used herein, the term "exogenous" refers to a substance coming from some source other than its native source. For example, the terms "exogenous protein," or "exogenous gene" refer to a protein or gene from a non-native source, and that has been artificially supplied to a biological system.

As used herein, the term "exogenous" is used interchangeably with the term "heterologous," and refers to a substance coming from some source other than its native source.

As used herein, the term "heterologous" refers to a substance coming from some source or location other than its native source or location. In some embodiments, the term "heterologous nucleic acid" refers to a nucleic acid sequence that is not naturally found in the particular organism. For example, the term "heterologous promoter" may refer to a promoter that has been taken from one source organism and utilized in another organism, in which the promoter is not naturally found. However, the term "heterologous promoter" may also refer to a promoter that is from within the same source organism, but has merely been moved to a novel location, in which said promoter is not normally located.

Heterologous gene sequences can be introduced into a target cell by using an "expression vector," which can be a eukaryotic expression vector, for example a plant expression vector. Methods used to construct vectors are well known to a person skilled in the art and described in various publications. In particular, techniques for constructing suitable vectors, including a description of the functional components such as promoters, enhancers, termination and poly-adenylation signals, selection markers, origins of replication, and splicing signals, are reviewed in the prior art. Vectors may include but are not limited to plasmid vectors, phagemids, cosmids, artificial/mini-chromosomes (e.g. ACE), or viral vectors such as baculovirus, retrovirus, adenovirus, adeno-associated virus, herpes simplex virus, retroviruses, bacteriophages. The eukaryotic expression vectors will typically contain also prokaryotic sequences that facilitate the propagation of the vector in bacteria such as an origin of replication and antibiotic resistance genes for selection in bacteria. A variety of eukaryotic expression vectors, containing a cloning site into which a polynucleotide can be operatively linked, are well known in the art and some are commercially available from companies such as STRATAGENE™, La Jolla, Calif.; INVITROGEN®, Carls-bad, Calif.; PROMEGA®, Madison, Wis. or BD BIOSCI-ENCES™ CLONETECH®, Palo Alto, Calif. In one embodiment the expression vector comprises at least one nucleic acid sequence which is a regulatory sequence necessary for transcription and translation of nucleotide sequences that encode for a peptide/polypeptide/protein of interest.

As used herein, the term "homologous" or "homolog" or "ortholog" is known in the art and refers to related sequences that share a common ancestor or family member and are determined based on the degree of sequence identity. Homologous sequences are orthologous when they are inferred to be descended from the same ancestral sequence separated by a speciation event: when a species diverges into two separate species, the copies of a single gene in the two resulting species are said to be orthologous. "Orthologs", or "orthologous genes," are genes in different species that originated by vertical descent from a single gene of the last common ancestor. The terms "homology," "homologous," "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant disclosure such as deletion or insertion of one or more nucleotides that do not substantially alter the functional properties of the resulting nucleic acid fragment relative to the initial, unmodified fragment. It is therefore understood, as those skilled in the art will appreciate, that the disclosure encompasses more than the specific exemplary sequences. These terms describe the relationship between a gene found in one species, subspecies, variety, cultivar or strain and the corresponding or equivalent gene in another species, subspecies, variety, cultivar or strain. For purposes of this disclosure, homologous sequences are compared. "Homologous sequences" or "homologs" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. Homology can be determined using software programs readily available in the art, such as those discussed in Current Protocols in Molecular Biology (F. M. Ausubel et al., eds., 1987) Supplement 30, section 7.718, Table 7.71. Some alignment programs are MACVECTOR™ (OXFORD MOLECULAR LTD.™, Oxford, U.K.), ALIGN™ Plus (Scientific and Educational Software, Pennsylvania) and ALIGNX™ (VECTOR NTI®, INVITROGEN®, Carlsbad, CA). Another alignment program is SEQUENCHER® (GENE CODES®, Ann Arbor, Michigan), using default parameters, and MUSCLE (Multiple Sequence Comparison by Log-Expection; a computer software licensed as public domain).

As used herein, the term "nucleotide change" refers to, e.g., nucleotide substitution, deletion, and/or insertion, as is well understood in the art. For example, mutations contain alterations that produce single nucleotide substitutions, silent substitutions, additions, or deletions, but do not alter the properties or activities of the encoded protein or how the proteins are made. Alternatively, mutations that result in nucleotide substitutions, additions or deletions (e.g., an in-frame deletion, out of frame deletion) may alter the properties or activities of the encoded protein, e.g., result in a non-natural or premature stop codon, a C-terminal and/or N-terminal truncation.

As used herein, the term "protein modification" refers to, e.g., amino acid modification, substitution, deletion, and/or insertion, as is well understood in the art that may result in, for example, a premature stop codon and/or a C-terminal truncation, an N-terminal truncation or other alteration that affects the function of a polypeptide (e.g. a STK modification that affects the ability of the STK polypeptide to interact with other STK polypeptides and/or with one or more SEPALLATA (SEP1, SEP2, SEP3, SEP4) polypeptides).

As used herein, the term "codon optimization" refers to the codon usage of a DNA or RNA that is adapted to that of a cell or organism of interest to improve the transcription rate of said recombinant nucleic acid in the cell or organism of interest. The skilled person is well aware of the fact that a target nucleic acid can be modified at one position due to the codon degeneracy, whereas this modification will still lead to the same amino acid sequence at that position after translation, which is achieved by codon optimization to take into consideration the species-specific codon usage of a target cell or organism. In some embodiments, the polynucleotides, nucleic acid constructs, expression cassettes, and/or vectors of the editing systems of the invention (e.g., comprising/encoding a sequence-specific DNA binding domain (e.g., a sequence-specific DNA binding domain from a polynucleotide-guided endonuclease, a zinc finger nuclease, a transcription activator-like effector nuclease (TALEN), an Argonaute protein, and/or a CRISPR-Cas endonuclease (e.g., CRISPR-Cas effector protein) (e.g., a Type I CRISPR-Cas effector protein, a Type II CRISPR-Cas effector protein, a Type III CRISPR-Cas effector protein, a Type IV CRISPR-Cas effector protein, a Type V CRISPR-Cas effector protein or a Type VI CRISPR-Cas effector protein)), a nuclease (e.g., an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN)), deaminase proteins/domains (e.g., adenine deaminase, cytosine deaminase), a polynucleotide encoding a reverse transcriptase protein or domain, a polynucleotide encoding a 5'-3' exonuclease polypeptide, and/or affinity polypeptides, peptide tags, etc.) may be codon optimized for expression in a plant. In some embodiments, codon optimized nucleic acids, polynucleotides, expression cassettes, and/or vectors of the invention have about 70% to about 99.9% (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9% or 100%) identity or more to the reference nucleic acids, polynucleotides, expression cassettes, and/or vectors that have not been codon optimized.

As used herein, the term "naturally occurring" as applied to a nucleic acid, a polypeptide, a cell, or an organism, refers to a nucleic acid, polypeptide, cell, or organism that is found in nature. The term "naturally occurring" may refer to a gene or sequence derived from a naturally occurring source. Thus, for the purposes of this disclosure, a "non-naturally occurring" sequence is a sequence that has been synthesized, mutated, engineered, edited, or otherwise modified to have a different sequence from known natural sequences. In some embodiments, the modification may be at the protein level (e.g., amino acid modification, e.g., substitutions, additions, deletions). In other embodiments, the modification may be at the DNA level (e.g., nucleotide modifications, e.g., substitutions, additions, deletions). "Non-natural" refers to a nucleic acid, a polypeptide, a cell, or an organism, that is not found in nature (e.g., a non-natural mutation) or not found in nature in the specific combination described.

The term "mutation" refers to point mutations (e.g., missense, or nonsense, or insertions or deletions of single base pairs that result in frame shifts), insertions, deletions, and/or truncations. When the mutation is a substitution of a residue within an amino acid sequence with another residue, or a deletion or insertion of one or more residues within a sequence, the mutations are typically described by identifying the original residue followed by the position of the residue within the sequence and by the identity of the newly substituted residue. A truncation can include a truncation at the C-terminal end of a polypeptide or at the N-terminal end of a polypeptide. A truncation of a polypeptide can be the result of a deletion of the corresponding 5' end or 3' end of the gene encoding the polypeptide. In some embodiments, a C-terminal truncation is the result of a mutation such as a base deletion, addition, or substitution that produces a premature stop codon.

As used herein, the phrases "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the disclosure. The skilled artisan will also recognize that different independent transformation events will result in different levels and patterns of expression (Jones et al., (1985) EMBO J. 4:2411-2418; De Almeida et al., (1989) Mol. Gen. Genetics 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide conjugated DNA or RNA, a liposome-conjugated DNA, or the like, that is not autonomously replicating. As used herein, the term "expression" refers to the production of a functional end product e.g., an mRNA or a protein (precursor or mature).

By "operably linked" or "operably associated" as used herein in reference to polynucleotides, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, nucleic acid sequences can be present between a promoter and the nucleotide sequence, and the promoter can still be considered "operably linked" to the nucleotide sequence.

As used herein, the term "linked," in reference to polypeptides, refers to the attachment of one polypeptide to another. A polypeptide may be linked to another polypeptide (at the N-terminus or the C-terminus) directly (e.g., via a peptide bond) or through a linker.

The term "linker" is art-recognized and refers to a chemical group, or a molecule linking two molecules or moieties, e.g., two domains of a fusion protein, such as, for example, a DNA binding polypeptide or domain and peptide tag and/or a reverse transcriptase and an affinity polypeptide that binds to the peptide tag; or a DNA endonuclease polypeptide or domain and peptide tag and/or a reverse transcriptase and an affinity polypeptide that binds to the peptide tag. A linker may be comprised of a single linking molecule or may comprise more than one linking molecule. In some embodiments, the linker can be an organic molecule, group, polymer, or chemical moiety such as a bivalent organic moiety. In some embodiments, the linker may be an amino acid or it may be a peptide. In some embodiments, the linker is a peptide.

In some embodiments, a peptide linker useful with this invention may be about 2 to about 100 or more amino acids in length, for example, about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 2 to about 40, about 2 to about 50, about 2 to about 60, about 4 to about 40, about 4 to about 50, about 4 to about 60, about 5 to about 40, about 5 to about 50, about 5 to about 60, about 9 to about 40, about 9 to about 50, about 9 to about 60, about 10 to about 40, about 10 to about 50, about 10 to about 60, or about 2, 3, 4, 5, 6, 7, 8, 9, 10, 11, 12, 13, 14, 15, 16, 17, 18, 19, 20, 21, 22, 23, 24, 25 amino acids to about 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 105, 110, 115, 120, 130, 140 150 or more amino acids in length). In some embodiments, a peptide linker may be a GS linker.

As used herein, the term "linked," or "fused" in reference to polynucleotides, refers to the attachment of one polynucleotide to another. In some embodiments, two or more polynucleotide molecules may be linked by a linker that can be an organic molecule, group, polymer, or chemical moiety such as a bivalent organic moiety. A polynucleotide may be linked or fused to another polynucleotide (at the 5' end or the 3' end) via a covalent or non-covenant linkage or binding, including e.g., Watson-Crick base-pairing, or through one or more linking nucleotides. In some embodiments, a polynucleotide motif of a certain structure may be inserted within another polynucleotide sequence (e.g. extension of the hairpin structure in the guide RNA). In some embodiments, the linking nucleotides may be naturally occurring nucleotides. In some embodiments, the linking nucleotides may be non-naturally occurring nucleotides.

Thus, in the context of the sequential arrangement of a promoter polynucleotide according to the disclosure with a further oligo- or polynucleotide (e.g., operably linked) results in transcription of said further polynucleotide. In some embodiments, the promoter sequences of the present disclosure are inserted just prior to 5'UTR a nucleic acid or open reading frame to be expressed. In some embodiments, operably linked promoter sequences and nucleic acid sequences of the present disclosure may be separated by one or more linker nucleotides.

As used herein, a "CRISPR-Cas effector protein" or "CRISPR-associated effector" is a protein or polypeptide or domain thereof that cleaves or cuts a nucleic acid, binds a nucleic acid (e.g., a target nucleic acid and/or a guide nucleic acid), and/or that identifies, recognizes, or binds a guide nucleic acid as defined herein. In some embodiments, a CRISPR-Cas effector protein may be an enzyme (e.g., a nuclease, endonuclease, nickase, etc.) or portion thereof and/or may function as an enzyme. In some embodiments, a CRISPR-Cas effector protein refers to a CRISPR-Cas nuclease polypeptide or domain thereof that comprises nuclease activity or in which the nuclease activity has been reduced or eliminated, and/or comprises nickase activity or in which the nickase has been reduced or eliminated, and/or comprises single stranded DNA cleavage activity (ss DNAse activity) or in which the ss DNAse activity has been reduced or eliminated, and/or comprises self-processing RNAse activity or in which the self-processing RNAse activity has been reduced or eliminated. A CRISPR-Cas effector protein may bind to a target nucleic acid. Thus, a "CRISPR-associated effector" or "CRISPR-Cas effector protein" as used herein can be defined as any nuclease, nickase, or recombinase associated with the CRISPR (Clustered Regularly Interspaced Short Palindromic Repeats), having the capacity to introduce a single- or double-strand cleavage into a genomic target site, or having the capacity to introduce a targeted modification, including a point mutation, an insertion, or a deletion, into a genomic target site of interest. The at least one CRISPR-associated effector can act on its own, or in combination with other molecules as part of a molecular complex. The CRISPR-associated effector can be present as fusion molecule, or as individual molecules associating by or being associated by at least one of a covalent or noncovalent interaction with gRNA and/or target site so that the components of the CRISPR-associated complex are brought into close physical proximity.

In some embodiments, a sequence-specific DNA binding domain may be a CRISPR-Cas effector protein. In some embodiments, a CRISPR-Cas effector protein may be from a Type I CRISPR-Cas system, a Type II CRISPR-Cas system, a Type III CRISPR-Cas system, a Type IV CRISPR-Cas system, Type V CRISPR-Cas system, or a Type VI CRISPR-Cas system. In some embodiments, a CRISPR-Cas effector protein of the invention may be from a Type II CRISPR-Cas system or a Type V CRISPR-Cas system. In some embodiments, a CRISPR-Cas effector protein may be Type II CRISPR-Cas effector protein, for example, a Cas9 effector protein. In some embodiments, a CRISPR-Cas effector protein may be Type V CRISPR-Cas effector protein, for example, a Cas12 effector protein.

In some embodiments, a CRISPR-Cas effector protein may include, but is not limited to, a Cas9, C2c1, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5 nuclease, optionally wherein the CRISPR-Cas effector protein may be a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or Cas14c effector protein.

In some embodiments, a CRISPR-Cas effector protein useful with the invention may comprise a mutation in its nuclease active site (e.g., RuvC, HNH, e.g., RuvC site of a Cas12a nuclease domain; e.g., RuvC site and/or HNH site of a Cas9 nuclease domain). A CRISPR-Cas effector protein having a mutation in its nuclease active site, and therefore, no longer comprising nuclease activity, is commonly referred to as "dead," e.g., dCas. In some embodiments, a CRISPR-Cas effector protein domain or polypeptide having a mutation in its nuclease active site may have impaired activity or reduced activity as compared to the same CRISPR-Cas effector protein without the mutation, e.g., a nickase, e.g, Cas9 nickase, Cas12a nickase.

A CRISPR Cas9 effector protein or CRISPR Cas9 effector domain useful with this invention may be any known or later identified Cas9 nuclease. In some embodiments, a CRISPR Cas9 polypeptide can be a Cas9 polypeptide from, for example, Streptococcus spp. (e.g., S. pyogenes, S. thermophilus), Lactobacillus spp., Bifidobacterium spp., Kandleria spp., Leuconostoc spp., Oenococcus spp., Pediococcus spp., Weissella spp., and/or Olsenella spp.

In some embodiments, the CRISPR-Cas effector protein may be a Cas9 polypeptide derived from Streptococcus pyogenes and recognizes the PAM sequence motif NGG, NAG, NGA (Mali et al, Science 2013; 339 (6121): 823-826). In some embodiments, the CRISPR-Cas effector protein may be a Cas9 polypeptide derived from Streptococcus thermophiles and recognizes the PAM sequence motif NGGNG and/or NNAGAAW (W=A or T) (See, e.g., Horvath et al, Science, 2010; 327 (5962): 167-170, and Deveau et al, J Bacteriol 2008; 190 (4): 1390-1400). In some embodiments, the CRISPR-Cas effector protein may be a Cas9 polypeptide derived from Streptococcus mutans and recognizes the PAM sequence motif NGG and/or NAAR (R=A or G) (See, e.g., Deveau et al, J BACTERIOL 2008; 190 (4): 1390-1400). In some embodiments, the CRISPR-Cas effector protein may be a Cas9 polypeptide derived from Streptococcus aureus and recognizes the PAM sequence motif NNGRR (R=A or G). In some embodiments, the CRISPR-Cas effector protein may be a Cas9 protein derived from S. aureus, which recognizes the PAM sequence motif N GRRT (R=A or G). In some embodiments, the CRISPR-Cas effector protein may be a Cas9 polypeptide derived from S. aureus, which recognizes the PAM sequence motif N GRRV (R=A or G). In some embodiments, the CRISPR-Cas effector protein may be a Cas9 polypeptide that is derived from Neisseria meningitidis and recognizes the PAM sequence motif N GATT or N GCTT (R=A or G, V=A, G or C) (See, e.g., Hou et ah, PNAS 2013, 1-6). In the aforementioned embodiments, N can be any nucleotide residue, e.g., any of A, G, C or T. In some embodiments, the CRISPR-Cas effector protein may be a Cas13a protein derived from Leptotrichia shahii, which recognizes a protospacer flanking sequence (PFS) (or RNA PAM (rPAM)) sequence motif of a single 3' A, U, or C, which may be located within the target nucleic acid.

In some embodiments, the CRISPR-Cas effector protein may be derived from Cas12a, which is a Type V Clustered Regularly Interspaced Short Palindromic Repeats (CRISPR)-Cas nuclease. Cas12a differs in several respects from the more well-known Type II CRISPR Cas9 nuclease. For example, Cas9 recognizes a G-rich protospacer-adjacent motif (PAM) that is 3' to its guide RNA (gRNA, sgRNA, crRNA, crDNA, CRISPR array) binding site (protospacer, target nucleic acid, target DNA) (3'-NGG), while Cas12a recognizes a T-rich PAM that is located 5' to the target nucleic acid (5'-TTN, 5'-TTTN. In fact, the orientations in which Cas9 and Cas12a bind their guide RNAs are very nearly reversed in relation to their N and C termini. Furthermore, Cas12a enzymes use a single guide RNA (gRNA, CRISPR array, crRNA) rather than the dual guide RNA (sgRNA (e.g., crRNA and tracrRNA)) found in natural Cas9 systems, and Cas12a processes its own gRNAs. Additionally, Cas12a nuclease activity produces staggered DNA double stranded breaks instead of blunt ends produced by Cas9 nuclease activity, and Cas12a relies on a single RuvC domain to cleave both DNA strands, whereas Cas9 utilizes an HNH domain and a RuvC domain for cleavage.

A CRISPR Cas12a effector protein/domain useful with this invention may be any known or later identified Cas12a polypeptide (previously known as Cpf1) (see, e.g., U.S. Pat. No. 9,790,490, which is incorporated by reference for its disclosures of Cpf1 (Cas12a) sequences). The term "Cas12a", "Cas12a polypeptide" or "Cas12a domain" refers to an RNA-guided nuclease comprising a Cas12a polypeptide, or a fragment thereof, which comprises the guide nucleic acid binding domain of Cas12a and/or an active, inactive, or partially active DNA cleavage domain of Cas12a. In some embodiments, a Cas12a useful with the invention may comprise a mutation in the nuclease active site (e.g., RuvC site of the Cas12a domain). A Cas12a domain or Cas12a polypeptide having a mutation in its nuclease active site, and therefore, no longer comprising nuclease activity, is commonly referred to as deadCas12a (e.g., dCas12a). In some embodiments, a Cas12a domain or Cas12a polypeptide having a mutation in its nuclease active site may have impaired activity, e.g., may have nickase activity.

A "base editor" as used herein refers to a protein or a fragment thereof having the same catalytic activity as the protein it is derived from, which protein or fragment thereof, alone or when provided as molecular complex, referred to as base editing complex herein, has the capacity to mediate a targeted base modification, i.e., the conversion of a base of interest resulting in a point mutation of interest, which in turn can result in a targeted mutation, if the base conversion does not cause a silent mutation, but rather a conversion of an amino acid encoded by the codon comprising the position to be converted with the base editor. At least one base editor according to the present disclosure temporarily or permanently linked to at least one CRISPR-associated effector, or optionally to a component of at least one CRISPR-associated effector complex.

The term "Cas9 nuclease" and "Cas9" can be used interchangeably herein, which refer to a RNA-guided DNA endonuclease enzyme associated with the CRISPR (Clustered Regularly Interspaced Short Palindromic Repeats), including the Cas9 protein or fragments thereof (such as a protein comprising an active DNA cleavage domain of Cas9 and/or a gRNA binding domain of Cas9). Cas9 is a component of the CRISPR/Cas genome editing system, which targets and cleaves a DNA target sequence to form a DNA double strand breaks (DSB) under the guidance of a guide RNA.

The terms "guide nucleic acid," "guide RNA," "gRNA," "CRISPR," "CRISPR RNA" or "crRNA" refers to the RNA molecule responsible for hybridizing with target DNA sequences, and recruiting CRISPR endonucleases and/or CRISPR-associated effectors. crRNAs may be naturally occurring, or may be synthesized according to any known method of producing RNA. CRISPRs may be introduced in the form of RNA or DNA. CRISPRs comprise at least one spacer sequence (e.g., 1, 2, 3, 4, 5, 6, 7, 8, 9, 10 or more), which is complementary to (and hybridizes to) a target DNA (e.g., protospacer), and at least one repeat sequence (e.g., a repeat of a Type V Cas12a CRISPR-Cas system, or a fragment or portion thereof; a repeat of a Type II Cas9 CRISPR-Cas system, or fragment thereof; a repeat of a Type V C2c1 CRISPR Cas system, or a fragment thereof; a repeat of a CRISPR-Cas system of, for example, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5, or a fragment thereof), wherein the repeat sequence may be linked to the 5' end and/or the 3' end of the spacer sequence. The design of a gRNA of this invention may be based on a Type I, Type II, Type III, Type IV, Type V, or Type VI CRISPR-Cas system.

A CRISPR or guide nucleic acid may comprise more than one repeat sequence-spacer sequence (e.g., 2, 3, 4, 5, 6, 7, 8, 9, 10, or more repeat-spacer sequences) (e.g., repeat-spacer-repeat, e.g., repeat-spacer-repeat-spacer-repeat-spacer-repeat-spacer-repeat-spacer, and the like). The guide nucleic acids of this invention are synthetic, human-made and not found in nature. A gRNA can be quite long and may be used as an aptamer (like in the MS2 recruitment strategy) or other RNA structures hanging off the spacer.

A "repeat sequence" as used herein, refers to, for example, any repeat sequence of a wild-type CRISPR Cas locus (e.g., a Cas9 locus, a Cas12a locus, a C2c1 locus, etc.) or a repeat sequence of a synthetic crRNA that is functional with the CRISPR-Cas effector protein encoded by the nucleic acid constructs of the invention. A repeat sequence useful with this invention can be any known or later identified repeat sequence of a CRISPR-Cas locus (e.g., Type I, Type II, Type III, Type IV, Type V or Type VI) or it can be a synthetic repeat designed to function in a Type I, II, III, IV, V or VI CRISPR-Cas system. A repeat sequence may comprise a hairpin structure and/or a stem loop structure. In some embodiments, a repeat sequence may form a pseudoknot-like structure at its 5' end (i.e., "handle"). Thus, in some embodiments, a repeat sequence can be identical to or substantially identical to a repeat sequence from wild-type Type I CRISPR-Cas loci, Type II, CRISPR-Cas loci, Type III, CRISPR-Cas loci, Type IV CRISPR-Cas loci, Type V CRISPR-Cas loci and/or Type VI CRISPR-Cas loci. A repeat sequence from a wild-type CRISPR-Cas locus may be determined through established algorithms, such as using the CRISPRfinder offered through CRISPRdb (see, Grissa et al. Nucleic Acids Res. 35 (Web Server issue): W52-7). In some embodiments, a repeat sequence or portion thereof is linked at its 3' end to the 5' end of a spacer sequence, thereby forming a repeat-spacer sequence (e.g., guide nucleic acid, guide RNA/DNA, crRNA, crDNA).

In some embodiments, a repeat sequence comprises, consists essentially of, or consists of at least 10 nucleotides depending on the particular repeat and whether the guide nucleic acid comprising the repeat is processed or unprocessed (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 to 100 or more nucleotides, or any range or value therein). In some embodiments, a repeat sequence comprises, consists essentially of, or consists of about 10 to about 20, about 10 to about 30, about 10 to about 45, about 10 to about 50, about 15 to about 30, about 15 to about 40, about 15 to about 45, about 15 to about 50, about 20 to about 30, about 20 to about 40, about 20 to about 50, about 30 to about 40, about 40 to about 80, about 50 to about 100 or more nucleotides.

A repeat sequence linked to the 5' end of a spacer sequence can comprise a portion of a repeat sequence (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more contiguous nucleotides of a wild type repeat sequence). In some embodiments, a portion of a repeat sequence linked to the 5' end of a spacer sequence can be about five to about ten consecutive nucleotides in length (e.g., about 5, 6, 7, 8, 9, 10 nucleotides) and have at least 90% sequence identity (e.g., at least about 90%, 91%, 92%, 93%, 94%, 95%, 96%, 97%, 98%, 99%, or more) to the same region (e.g., 5' end) of a wild type CRISPR Cas repeat nucleotide sequence. In some embodiments, a portion of a repeat sequence may comprises a pseudoknot-like structure at its 5' end (e.g., "handle").

The term "tracrRNA" refers to a small trans-encoded RNA. TracrRNA is complementary to and base pairs with crRNA to form a crRNA/tracrRNA hybrid, capable of recruiting CRISPR endonucleases and/or CRISPR-associated effectors to target sequences.

In some embodiments, a gRNA is composed of crRNA and tracrRNA molecules forming complexes through partial complement, wherein crRNA comprises a sequence that is sufficiently complementary to a target sequence for hybridization and directs the CRISPR complex (i.e. Cas9-crRNA/tracrRNA hybrid) to specifically bind to the target sequence. Also, single guide RNA (sgRNA) can be designed, which comprises the characteristics of both crRNA and tracrRNA. Therefore, as used herein, a guide RNA can be a natural or synthetic crRNA (e.g., for Cpf1), a natural or synthetic crRNA/tracrRNA hybrid (e.g., for Cas9), or a single-guide RNA (sgRNA).

The term "guide sequence" or "spacer sequence" refers to the portion of a crRNA or guide RNA (gRNA) that is responsible for hybridizing with the target DNA.

A "spacer sequence" as used herein is a nucleotide sequence that is complementary to and binds to a target nucleic acid (e.g., target DNA) (e.g, protospacer) (e.g., consecutive nucleotides of a sequence (i) encoding a sequence having at least 80% sequence identity to any one of the amino acid sequences of SEQ ID Nos: 13, 29, 53, 66, 78, 97, 128, 150, 152, 154, 156, 158, 160, 162, 164, or 166-171; (ii) encoding a region or a portion of a sequence having at least 80% sequence identity to any one of the amino acid sequences of SEQ ID NOs: 177-183, 187, 188, or 189; (iii) comprising a portion of a sequence having at least 80% sequence identity to any one of the nucleotide sequences of SEQ ID NOs: 153, 155, 157, 159, 161, 163, or 165; and/or (iv) comprising a sequence having at least 80% sequence identity to any one of the nucleotide sequences of SEQ ID NOs: 172-174. In some embodiments, a spacer sequence may include, but is not limited to, any one of the nucleotide sequences of SEQ ID NOs: 175, 176 or 184-186. A spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a target nucleic acid. Thus, in some embodiments, the spacer sequence can have one, two, three, four, or five mismatches as compared to the target nucleic acid, which mismatches can be contiguous or noncontiguous. In some embodiments, the spacer sequence can have 70% complementarity to a target nucleic acid. In other embodiments, the spacer nucleotide sequence can have 80% complementarity to a target nucleic acid. In still other embodiments, the spacer nucleotide sequence can have 85%, 90%, 95%, 96%, 97%, 98%, 99% or 99.5% complementarity, and the like, to the target nucleic acid (protospacer). In some embodiments, the spacer sequence is 100% complementary to the target nucleic acid. A spacer sequence may have a length from about 15 nucleotides to about 30 nucleotides (e.g., 15, 16, 17, 18, 19, 20, 21, 22, 23, 24, 25, 26, 27, 28, 29, or 30 nucleotides, or any range or value therein). Thus, in some embodiments, a spacer sequence may have complete complementarity or substantial complementarity over a region of a target nucleic acid (e.g., protospacer) that is at least about 15 nucleotides to about 30 nucleotides in length. In some embodiments, the spacer is about 20 nucleotides in length. In some embodiments, the spacer is about 21, 22, or 23 nucleotides in length.

In some embodiments, the 5' region of a spacer sequence of a guide nucleic acid may be identical to a target DNA, while the 3' region of the spacer may be substantially complementary to the target DNA (e.g., Type V CRISPR-Cas), or the 3' region of a spacer sequence of a guide nucleic acid may be identical to a target DNA, while the 5' region of the spacer may be substantially complementary to the target DNA (e.g., Type II CRISPR-Cas), and therefore, the overall complementarity of the spacer sequence to the target DNA may be less than 100%. Thus, for example, in a guide for a Type V CRISPR-Cas system, the first 1, 2, 3, 4, 5, 6, 7, 8, 9, 10 nucleotides in the 5' region (i.e., seed region) of, for example, a 20 nucleotide spacer sequence may be 100% complementary to the target DNA, while the remaining nucleotides in the 3' region of the spacer sequence are substantially complementary (e.g., at least about 70% complementary) to the target DNA. In some embodiments, the first 1 to 8 nucleotides (e.g., the first 1, 2, 3, 4, 5, 6, 7, 8, nucleotides, and any range therein) of the 5' end of the spacer sequence may be 100% complementary to the target DNA, while the remaining nucleotides in the 3' region of the spacer sequence are substantially complementary (e.g., at least about 50% complementary (e.g., 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to the target DNA.

As a further example, in a guide for a Type II CRISPR-Cas system, the first 1, 2, 3, 4, 5, 6, 7, 8, 9, 10 nucleotides in the 3' region (i.e., seed region) of, for example, a 20 nucleotide spacer sequence may be 100% complementary to the target DNA, while the remaining nucleotides in the 5' region of the spacer sequence are substantially complementary (e.g., at least about 70% complementary) to the target DNA. In some embodiments, the first 1 to 10 nucleotides (e.g., the first 1, 2, 3, 4, 5, 6, 7, 8, 9, 10 nucleotides, and any range therein) of the 3' end of the spacer sequence may be 100% complementary to the target DNA, while the remaining nucleotides in the 5' region of the spacer sequence are substantially complementary (e.g., at least about 50% complementary (e.g., at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or any range or value therein)) to the target DNA.

In some embodiments, a seed region of a spacer may be about 8 to about 10 nucleotides in length, about 5 to about 6 nucleotides in length, or about 6 nucleotides in length.

The term "protospacer" refers to the double stranded DNA targeted by a guide sequence of a CRISPR (e.g., crRNA, gRNA). In some embodiments, the protospacer sequence hybridizes (e.g., is fully or substantially complementary as described above) with the spacer sequence of a CRISPR.

The term "seed region" refers to the portion of a crRNA's or guide RNA's guide sequence that is most susceptible to failure to function as a guide due to mismatches with their targets. In some embodiments, a single mismatch in the seed region of a crRNA/gRNA can render a CRISPR complex inactive at that binding site. In some embodiments, the seed regions for Cas9 endonucleases are located along about the last 12 nts of the 3' portion of the guide sequence, which correspond (hybridize) to the portion of the protospacer target sequence that is adjacent to the PAM. In some embodiments, the seed regions for Cpf1 endonucleases are located along about the first 5 nts of the 5' portion of the guide sequence, which correspond (hybridize) to the portion of the protospacer target sequence adjacent to the PAM.

The term "CRISPR landing site," "target nucleic acid", "target DNA," "target nucleotide sequence," "target region," or a "target region in the genome" as used herein, refers to a DNA sequence capable of being targeted by a CRISPR-Cas complex, e.g., a region of a plant's genome that is fully complementary (100% complementary) or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a spacer sequence in a guide nucleic acid of this invention. In some embodiments, a CRISPR landing site comprises a proximately placed protospacer/Protospacer Adjacent Motif combination sequence that is capable of being cleaved by a CRISPR complex. In some embodiments, A target region useful for a CRISPR-Cas system may be located immediately 3' (e.g., Type V CRISPR-Cas system) or immediately 5' (e.g., Type II CRISPR-Cas system) to a PAM sequence in the genome of the organism (e.g., a plant genome). A target region may be selected from any region of at least 15 consecutive nucleotides (e.g., 16, 17, 18, 19, 20, 21, 22, 23, 24, 25, 26, 27, 28, 29, 30 nucleotides, and the like) located immediately adjacent to a PAM sequence.

In the case of Type II CRISPR-Cas (e.g., Cas9) systems, the PAM is located immediately 3' of the target region. The PAM for Type I CRISPR-Cas systems is located 5' of the target strand. There is no known PAM for Type III CRISPR-Cas systems. Makarova et al. describes the nomenclature for all the classes, types and subtypes of CRISPR systems (*Nature Reviews Microbiology* 13:722-736 (2015)). Guide structures and PAMs are described in by R. Barrangou (*Genome Biol.* 16:247 (2015)).

Canonical Cas12a PAMs are T rich. In some embodiments, a canonical Cas12a PAM sequence may be 5'-TTN, 5'-TTTN, or 5'-TTTV. In some embodiments, canonical Cas9 (e.g., *S. pyogenes*) PAMs may be 5'-NGG-3'. In some embodiments, non-canonical PAMs may be used but may be less efficient.

Additional PAM sequences may be determined by those skilled in the art through established experimental and computational approaches. Thus, for example, experimental approaches include targeting a sequence flanked by all possible nucleotide sequences and identifying sequence members that do not undergo targeting, such as through the transformation of target plasmid DNA (Esvelt et al. 2013. *Nat. Methods* 10:1116-1121; Jiang et al. 2013. *Nat. Biotechnol.* 31:233-239). In some aspects, a computational approach can include performing BLAST searches of natural spacers to identify the original target DNA sequences in bacteriophages or plasmids and aligning these sequences to determine conserved sequences adjacent to the target sequence (Briner and Barrangou. 2014. *Appl. Environ. Microbiol.* 80:994-1001; Mojica et al. 2009. *Microbiology* 155:733-740).

The term "CRISPR complex", "CRISPR endonuclease complex", "CRISPR Cas complex", or "CRISPR-gRNA complex" are used interchangeably herein. "CRISPR complex" refers to, for example, a Cas9 nuclease and/or other CRISPR-associated effector (e.g., Cas12a/Cpf1) complexed with a guide RNA (gRNA). The term "CRISPR complex" thus refers to a combination of CRISPR endonuclease and guide RNA (and any other CRISPR nucleotide sequences/polypeptides) capable of inducing a double stranded break at a CRISPR landing site. In some embodiments, "CRISPR complex" of the present disclosure refers to a combination of catalytically dead Cas9 protein and guide RNA capable of targeting a target sequence, but not capable of inducing a double stranded break at a CRISPR landing site because it loses a nuclease activity. In other embodiments, "CRISPR complex" of the present disclosure refers to a combination of Cas9 nickase and guide RNA capable of introducing gRNA-targeted single-strand breaks in DNA instead of the double-strand breaks created by wild type Cas enzymes.

As used herein, the term "directing sequence-specific binding" in the context of CRISPR complexes refers to a guide RNA's ability to recruit a CRISPR endonuclease and/or a CRISPR-associated effectors to a CRISPR landing site or nucleic acid target.

As used herein, the term "deaminase" refers to an enzyme that catalyzes the deamination reaction. In some embodiments of the present disclosure, the deaminase refers to a cytidine deaminase, which catalyzes the deamination of a cytidine or a deoxycytidine to a uracil or a deoxyuridine, respectively. In other embodiments of the present disclosure, the deaminase refers to an adenosine deaminase, which catalyzes the deamination of an adenine to form hypoxanthine (in the form of its nucleoside inosine), which is read as guanine by DNA polymerase.

As used herein, the term "glycosylase" refers to a family of enzymes involved in base excision repair, classified under EC number EC 3.2.2. Base excision repair is the mechanism by which damaged bases in DNA are removed and replaced. DNA glycosylases catalyze the first step of this process. They remove the damaged nitrogenous base while leaving the sugar-phosphate backbone intact, creating an apurinic/apyrimidinic site, commonly referred to as an AP site. This is accomplished by flipping the damaged base out of the double helix followed by cleavage of the N-glycosidic bond. In some embodiments of the present disclosure, in an expectation of affording a mutation introduction tendency different from that of deaminase and the like, a base excision reaction by hydrolysis of N-glycosidic bond of DNA, and then inducing mutation introduction in a repair process of cells is used. In aspects, an enzyme having cytosine-DNA glycosylase (CDG) activity or thymine-DNA glycosylase (TDG) activity is used. In aspects, a mutant of yeast mitochondrial uracil-DNA glycosylase (UNG 1), is used as an enzyme that performs such base excision reaction. Nishida et al., US 2017/0321210 A1, published on Nov. 9, 2017, is incorporated by reference herein.

As used herein the term "targeted" refers to the expectation that one item or molecule will interact with another item or molecule with a degree of specificity, so as to exclude non-targeted items or molecules. For example, a first polynucleotide that is targeted to a second polynucleotide, according to the present disclosure has been designed to hybridize with the second polynucleotide in a sequence specific manner (e.g., via Watson-Crick base pairing). In some embodiments, the selected region of hybridization is designed so as to render the hybridization unique to the one, or more targeted regions. A second polynucleotide can cease to be a target of a first targeting polynucleotide, if its targeting sequence (region of hybridization) is mutated, or is otherwise removed/separated from the second polynucleotide. Furthermore, "targeted" can be interchangeably used with "site-specific" or "site-directed," which refers to an action of molecular biology which uses information on the sequence of a genomic region of interest to be modified, and which further relies on information of the mechanism of action of molecular tools, e.g., nucleases, including CRISPR nucleases and variants thereof, TALENs, ZFNs, meganucleases or recombinases, DNA-modifying enzymes, including base modifying enzymes like cytidine deaminase enzymes, histone modifying enzymes and the like, DNA-binding proteins, cr/tracr RNAs, guide RNAs and the like.

The term "sequence identity" refers to the percentage of bases or amino acids between two polynucleotide or polypeptide sequences that are the same, and in the same relative position. As such one polynucleotide or polypeptide sequence has a certain percentage of sequence identity compared to another polynucleotide or polypeptide sequence. For sequence comparison, typically one sequence acts as a reference sequence, to which test sequences are compared. The term "reference sequence" refers to a molecule to which a test sequence is compared. Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence as compared to a reference polypeptide.

As used herein, the phrase "substantially identical," or "substantial identity" in the context of two nucleic acid molecules, nucleotide sequences, or polypeptide sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% nucleotide or amino acid residue identity, when compared and aligned for maximum correspondence, as measured using one of the following sequence comparison algorithms or by visual inspection. In some embodiments of the invention, the substantial identity exists over a region of consecutive nucleotides of a nucleotide sequence of the invention that is about 10 nucleotides to about 20 nucleotides, about 10 nucleotides to about 25 nucleotides, about 10 nucleotides to about 30 nucleotides, about 15 nucleotides to about 25 nucleotides, about 30 nucleotides to about 40 nucleotides, about 50 nucleotides to about 60 nucleotides, about 70 nucleotides to about 80 nucleotides, about 90 nucleotides to about 100 nucleotides, about 100 nucleotides to about 200 nucleotides, about 100 nucleotides to about 300 nucleotides, about 100 nucleotides to about 400 nucleotides, about 100 nucleotides to about 500 nucleotides, about 100 nucleotides to about 600 nucleotides, about 100 nucleotides to about 800 nucleotides, about 100 nucleotides to about 900 nucleotides, or more in length, or any range therein, up to the full length of the sequence. In some embodiments, nucleotide sequences can be substantially identical over at least about 20 nucleotides (e.g., about 20, 21, 22, 23, 24, 25, 26, 27, 28, 29, 30, 31, 32, 33, 34, 35, 36, 37, 38, 39, 40, 50, 60, 70 or 80 nucleotides or more).

In some embodiments of the invention, the substantial identity exists over a region of consecutive amino acid residues of a polypeptide of the invention that is about 3 amino acid residues to about 20 amino acid residues, about 5 amino acid residues to about 25 amino acid residues, about 7 amino acid residues to about 30 amino acid residues, about 10 amino acid residues to about 25 amino acid residues, about 15 amino acid residues to about 30 amino acid residues, about 20 amino acid residues to about 40 amino acid residues, about 25 amino acid residues to about 40 amino acid residues, about 25 amino acid residues to about 50 amino acid residues, about 30 amino acid residues to about 50 amino acid residues, about 40 amino acid residues to about 50 amino acid residues, about 40 amino acid residues to about 70 amino acid residues, about 50 amino acid residues to about 70 amino acid residues, about 60 amino acid residues to about 80 amino acid residues, about 70 amino acid residues to about 80 amino acid residues, about 90 amino acid residues to about 100 amino acid residues, or more amino acid residues in length, and any range therein, up to the full length of the sequence. In some embodiments, polypeptide sequences can be substantially identical to one another over at least about 8 consecutive amino acid residues (e.g., about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 130, 140, 150, 175, 200, 225, 250, 300, 350 or more amino acids in length or more consecutive amino acid residues). In some embodiments, two or more STL polypeptides may be identical (100%) or substantially identical (e.g., at least 70% to 99.9% identical; e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9% identical or any range or value therein) to one another. In some embodiments, two or more STL proteins may be substantially identical across consecutive amino acid residues 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 to about 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 125, 130, 135, 140, 145, 150, 155, 160, 165, 170, 175, 180, 185, 190, 195, 200, 205, 210, 215, 220, 225, 230, 235, 240, 245, 250, 275, 300, 325, 350, 375, 400, 425, 450, 475, 500, 525, 550, 575, 600, 625, 650, 660, 665 or more of any one of the amino acid sequences of SEQ ID NOs: SEQ ID NOs: 13, 29, 53, 66, 78, 97, 128, 150, 152, 154, 156, 158, 159, 160, 162, 164 or 166-171.

Complementary" or "complementarity," refers to the capacity for pairing, through base stacking and specific hydrogen bonding, between two sequences comprising naturally or non-naturally occurring bases or analogs thereof. For example, if a base at one position of a nucleic acid is capable of hydrogen bonding with a base at the corresponding position of a target, then the bases are considered to be complementary to each other at that position. Nucleic acids can comprise universal bases, or inert abasic spacers that provide no positive or negative contribution to hydrogen bonding. Base pairings may include both canonical Watson-Crick base pairing and non-Watson-Crick base pairing (e.g., Wobble base pairing and Hoogsteen base pairing). It is understood that for complementary base pairings, adenosine-type bases (A) are complementary to thymidine-type bases (T) or uracil-type bases (U), that cytosine-type bases (C) are complementary to guanosine-type bases (G), and that universal bases such as such as 3-nitropyrrole or 5-nitroindole can hybridize to and are considered complementary to any A, C, U, or T. Nichols et al., Nature, 1994; 369:492-493 and Loakes et al., Nucleic Acids Res., 1994; 22:4039-4043. Inosine (I) has also been considered in the art to be a universal base and is considered complementary to any A, C, U, or T. See Watkins and Santa Lucia, Nucl. Acids Research, 2005; 33 (19): 6258-6267.

As referred to herein, a "complementary nucleic acid sequence" is a nucleic acid sequence comprising a sequence of nucleotides that enables it to non-covalently bind to another nucleic acid in a sequence-specific, antiparallel, manner (i.e., a nucleic acid specifically binds to a complementary nucleic acid) under the appropriate in vitro and/or in vivo conditions of temperature and solution ionic strength. Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Complement," as used herein, can mean 100% complementarity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity) to the comparator nucleotide sequence.

Methods of sequence alignment for comparison and determination of percent sequence identity and percent complementarity are well known in the art. Optimal alignment of sequences for comparison can be conducted, e.g., by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, WI), by manual alignment and visual inspection (see, e.g., Brent et al., (2003) Current Protocols in Molecular Biology), by use of algorithms know in the art including the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information. Some alignment programs are MacVector (Oxford Molecular Ltd, Oxford, U.K.), ALIGN Plus (Scientific and Educational Software, Pennsylvania) and AlignX (Vector NTI, Invitrogen, Carlsbad, CA). Another alignment program is Sequencher (Gene Codes, Ann Arbor, Michigan), using default parameters, and MUSCLE (Multiple Sequence Comparision by Log-Expection; a computer software licensed as public domain).

Herein, the term "hybridize" refers to pairing between complementary nucleotide bases (e.g., adenine (A) forms a base pair with thymine (T) in a DNA molecule and with uracil (U) in an RNA molecule, and guanine (G) forms a base pair with cytosine (C) in both DNA and RNA molecules) to form a double-stranded nucleic acid molecule. (See, e.g., Wahl and Berger (1987) Methods Enzymol. 152:399; Kimmel, (1987) Methods Enzymol. 152:507). In addition, it is also known in the art that for hybridization between two RNA molecules (e.g., dsRNA), guanine (G) base pairs with uracil (U). For example, G/U base-pairing is partially responsible for the degeneracy (i.e., redundancy) of the genetic code in the context of tRNA anti-codon base-pairing with codons in mRNA. In the context of this disclosure, a guanine (G) of a protein-binding segment (dsRNA duplex) of a guide RNA molecule is considered complementary to a uracil (U), and vice versa. As such, when a G/U base-pair can be made at a given nucleotide position a protein-binding segment (dsRNA duplex) of a guide RNA molecule, the position is not considered to be noncomplementary, but is instead considered to be complementary. It is understood in the art that the sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted.

The term "modified" refers to a substance or compound (e.g., a cell, a polynucleotide sequence, and/or a polypeptide sequence) that has been altered or changed as compared to the corresponding unmodified substance or compound.

"Isolated" refers to a material that is free to varying degrees from components which normally accompany it as found in its native state.

The term "gene edited plant, part or cell" as used herein refers to a plant, part or cell that comprises one or more endogenous genes that are edited by a gene editing system. The gene editing system of the present disclosure comprises a targeting element and/or an editing element. The targeting element is capable of recognizing a target genomic sequence. The editing element is capable of modifying the target genomic sequence, e.g., by substitution or insertion of one or more nucleotides in the genomic sequence, deletion of one or more nucleotides in the genomic sequence, alteration of genomic sequences to include regulatory sequences, insertion of transgenes at a safe harbor genomic site or other specific location in the genome, or any combination thereof. The targeting element and the editing element can be on the same nucleic acid molecule or different nucleic acid molecules. In some embodiments, the editing element is capable of precise genome editing by substitution of a single nucleotide using a base editor, such cytosine base editor (CBE) and/or adenine base editor (ABE), which is directly or indirectly fused to a CRISPR-associated effector protein.

As used herein, the term "plant" refers to whole plants. The term "plant part" includes differentiated and undifferentiated tissues including, but not limited to: plant organs, plant tissues, roots, stems, shoots, rootstocks, scions, stipules, petals, leaves, flowers, ovules, pollens, bracts, petioles, internodes, bark, pubescence, tillers, rhizomes, fronds, blades, stamens, fruits, seeds, tumor tissue and plant cells (e.g., single cells, protoplasts, embryos, and callus tissue). Plant cells include, without limitation, cells from seeds, suspension cultures, embryos, meristematic regions, callus tissue, leaves, roots, shoots, gametophytes, sporophytes, pollen and microspores. The plant tissue may be in a plant or in a plant organ, tissue or cell culture. Thus, the term "plant part," as used herein, includes but is not limited to reproductive tissues (e.g., petals, sepals, stamens, pistils, receptacles, anthers, pollen, flowers, fruits, flower bud, ovules, seeds, and embryos); vegetative tissues (e.g., petioles, stems, roots, root hairs, root tips, pith, coleoptiles, stalks, shoots, branches, bark, apical meristem, axillary bud, cotyledon, hypocotyls, and leaves); vascular tissues (e.g., phloem and xylem); specialized cells such as epidermal cells, parenchyma cells, collenchyma cells, sclerenchyma cells, stomates, guard cells, cuticle, mesophyll cells; callus tissue; and cuttings. The term "plant part" also includes plant cells, including plant cells that are intact in plants and/or parts of plants, plant protoplasts, plant tissues, plant organs, plant cell tissue cultures, plant calli, plant clumps, and the like. As used herein, "shoot" refers to the above ground parts including the leaves and stems. As used herein, the term "tissue culture" encompasses cultures of tissue, cells, protoplasts and callus. The term "stem" as used herein refers the above ground structural axis of the plant consisting of both nodes (e.g., leaves and flowers) and internodes (e.g., connecting material between nodes).

As used herein, "plant cell" refers to a structural and physiological unit of the plant, which typically comprise a cell wall but also includes protoplasts. A plant cell of the present invention can be in the form of an isolated single cell or can be a cultured cell or can be a part of a higher-organized unit such as, for example, a plant tissue (including callus) or a plant organ. A "protoplast" is an isolated plant cell without a cell wall or with only parts of the cell wall. Thus, in some embodiments of the invention, a transgenic cell comprising a nucleic acid molecule and/or nucleotide sequence of the invention is a cell of any plant or plant part including, but not limited to, a root cell, a leaf cell, a tissue culture cell, a seed cell, a flower cell, a fruit cell, a pollen cell, and the like. In some aspects of the invention, the plant part can be a plant germplasm. In some aspects, a plant cell can be non-propagating plant cell that does not regenerate into a plant.

"Plant cell culture" means cultures of plant units such as, for example, protoplasts, cell culture cells, cells in plant tissues, pollen, pollen tubes, ovules, embryo sacs, zygotes and embryos at various stages of development.

The term "plant organ" refers to plant tissue or a group of tissues that constitute a morphologically and functionally distinct part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, leaves, stems, roots, root tips, anthers, pistils, meristematic cells, axillary buds, ovaries, seed coat, endosperm, hypocotyls, cotyledons and the like. In some embodiments of the invention, a transgenic tissue culture or transgenic plant cell culture is provided, wherein the transgenic tissue or cell culture comprises a nucleic acid molecule/nucleotide sequence of the invention. In some embodiments, transgenes may be eliminated from a plant developed from the transgenic tissue or cell by breeding of the transgenic plant with a non-transgenic plant and selecting among the progeny for the plants comprising the desired gene edit and not the transgenes used in producing the edit.

"Progeny" comprises any subsequent generation of a plant.

The terms "transgene" or "transgenic" as used herein refer to at least one nucleic acid sequence that is taken from the genome of one organism, or produced synthetically, and which is then introduced into a host cell or organism or tissue of interest and which is subsequently integrated into the host's genome by means of "stable" transformation or transfection approaches. In contrast, the term "transient" transformation or transfection or introduction refers to a way of introducing molecular tools including at least one nucleic acid (DNA, RNA, single-stranded or double-stranded or a mixture thereof) and/or at least one amino acid sequence, optionally comprising suitable chemical or biological agents, to achieve a transfer into at least one compartment of interest of a cell, including, but not restricted to, the cytoplasm, an organelle, including the nucleus, a mitochondrion, a vacuole, a chloroplast, or into a membrane, resulting in transcription and/or translation and/or association and/or activity of the at least one molecule introduced without achieving a stable integration or incorporation and thus inheritance of the respective at least one molecule introduced into the genome of a cell. The terms "transgene-free" refers to a condition that transgene is not present or found in the genome of a host cell or tissue or organism of interest.

"Agronomic trait" is a measurable parameter including but not limited to, seedlessness (e.g., reduced or no seed production), reduced seed size, reduced thickness of fruit endocarp, reduced lignification of fruit endocarp, reduced seediness, leaf greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, disease resistance, cold resistance, salt tolerance, and tiller number and so on.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference!

As used herein, "contact," "contacting," "contacted," and grammatical variations thereof, refer to placing the components of a desired reaction together under conditions suitable for carrying out the desired reaction (e.g., transformation, transcriptional control, genome editing, nicking, and/or cleavage). As an example, a target nucleic acid may be contacted with a sequence-specific DNA binding protein (e.g., polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein)) and a deaminase or a nucleic acid construct encoding the same, under conditions whereby the sequence-specific DNA binding protein, the reverse transcriptase and/or the deaminase are expressed and the sequence-specific DNA binding protein binds to the target nucleic acid, and the reverse transcriptase and/or deaminase may be fused to either the sequence-specific DNA binding protein or recruited to the sequence-specific DNA binding protein (via, for example, a peptide tag fused to the sequence-specific DNA binding protein and an affinity tag fused to the reverse transcriptase and/or deaminase) and thus, the deaminase and/or reverse transcriptase is positioned in the vicinity of the target nucleic acid, thereby modifying the target nucleic acid. Other methods for recruiting reverse transcriptase and/or deaminase may be used that take advantage of other protein-protein interactions, and also RNA-protein interactions and chemical interactions may be used for protein-protein and protein-nucleic acid recruitment.

As used herein, "modifying" or "modification" in reference to a target nucleic acid includes editing (e.g., mutating), covalent modification, exchanging/substituting nucleic acids/nucleotide bases, deleting, cleaving, nicking, and/or altering transcriptional control of a target nucleic acid. In some embodiments, a modification may include one or more single base changes (SNPs) of any type.

"Introducing," "introduce," "introduced" (and grammatical variations thereof) in the context of a polynucleotide of interest means presenting a nucleotide sequence of interest (e.g., polynucleotide, RT template, a nucleic acid construct, and/or a guide nucleic acid) to a plant, plant part thereof, or cell thereof, in such a manner that the nucleotide sequence gains access to the interior of a cell.

The terms "transformation" or transfection" may be used interchangeably and as used herein refer to the introduction of a heterologous nucleic acid into a cell. Transformation of a cell may be stable or transient. Thus, in some embodiments, a host cell or host organism (e.g., a plant) may be stably transformed with a polynucleotide/nucleic acid molecule of the invention. In some embodiments, a host cell or host organism may be transiently transformed with a polynucleotide/nucleic acid molecule of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear and the plastid genome, and therefore includes integration of the nucleic acid into, for example, the chloroplast or mitochondrial genome. Stable transformation as used herein can also refer to a transgene that is maintained extrachromasomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a host organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

Accordingly, in some embodiments, nucleotide sequences, polynucleotides, nucleic acid constructs, and/or expression cassettes of the invention may be expressed transiently and/or they can be stably incorporated into the genome of the host organism. Thus, in some embodiments, a nucleic acid construct of the invention (e.g., one or more expression cassettes comprising polynucleotides for editing as described herein) may be transiently introduced into a cell with a guide nucleic acid and as such, no DNA is maintained in the cell.

A nucleic acid construct of the invention may be introduced into a plant cell by any method known to those of skill in the art. Non-limiting examples of transformation methods include transformation via bacterial-mediated nucleic acid delivery (e.g., via Agrobacteria), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. Procedures for transforming both eukaryotic and prokaryotic organisms are well known and routine in the art and are described throughout the literature (See, for example, Jiang et al. 2013. *Nat. Biotechnol.* 31:233-239; Ran et al. *Nature Protocols* 8:2281-2308 (2013)). General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

In some embodiments of the invention, transformation of a cell may comprise nuclear transformation. In other embodiments, transformation of a cell may comprise plastid transformation (e.g., chloroplast transformation). In still further embodiments, nucleic acids of the invention may be introduced into a cell via conventional breeding techniques. In some embodiments, one or more of the polynucleotides, expression cassettes and/or vectors may be introduced into a plant cell via *Agrobacterium* transformation.

A polynucleotide therefore can be introduced into a plant, plant part, plant cell in any number of ways that are well known in the art. The methods of the invention do not depend on a particular method for introducing one or more nucleotide sequences into a plant, only that they gain access to the interior the cell. Where more than polynucleotide is to be introduced, they can be assembled as part of a single nucleic acid construct, or as separate nucleic acid constructs, and can be located on the same or different nucleic acid constructs. Accordingly, the polynucleotide can be introduced into the cell of interest in a single transformation event, or in separate transformation events, or, alternatively, a polynucleotide can be incorporated into a plant as part of a breeding protocol.

As used herein, the term "AGAMOUS Clade Transcription Factor" or "AG clade transcription factor" is a member of the AGAMOUS (AG) subfamily of MIKC-type MADS-box genes. "MIKC-type" proteins represent a class of MADS-domain transcription factors and are defined by a unique domain structure: (1) 'M'—a highly conserved DNA-binding MADS-domain, (2) 'I'—an intervening domain, (3) 'K'—a keratin-like K-domain, and (4) 'C'—a C-terminal domain. In some embodiments, "AGAMOUS Clade Transcription Factor" or "AG clade transcription factor" further comprises an N-terminal region. In further embodiments, "AGAMOUS Clade Transcription Factor" or "AG clade transcription factor" comprises AG, SHP1, SHP2, and STK genes in plants of the present disclosure, each of which has a NN motif in the M domain, a YQQ motif in the K domain, and/or a R/Q (R or Q) in the C domain.

As used herein, the term "a stable and targeted single nucleotide substitution" refers to a non-naturally occurring nucleotide substitution mediated by a base-editing technology (including CBE and/or ABE) that enables direct, irreversible conversion of one base pair to another at a target genomic locus without requiring double-stranded DNA breaks (DSBs), homology-directed repair (HDR) processes, or donor DNA templates. The base-editing technology taught in the present disclosure also is coupled with a CRISPR-Cas system for precise targeting, which allows a stable and targeted single nucleotide substitution. As aforementioned, more than one single nucleotide substitution can be made with the editing systems taught herein, in one or more genes of interest. The stable and targeted single nucleotide substitution is therefore a non-naturally occurring nucleotide substitution that results from the efforts of the plant breeder practicing the next generation plant breeding methods of the disclosure.

Plants useful for modifying as described herein include any plant for which altered fruit development, optionally seedlessness, reduced seediness, is desirable. Such plants can include but are not limited to those in the Rosaceae plant family. As used herein, the term "Rosaceae plant family", "Rosaceae family" or "Rosaceae" refers to a family of flowering plants, including 4,828 known species in 91 genera. The family Rosaceae includes herbs, shrubs, and trees. Many economically important products come from the Rosaceae, including many edible fruits (such as apples, pears, quinces, apricots, plums, cherries, peaches, blackberries, raspberries, black raspberries, loquats, dates, and strawberries), almonds, and ornamental trees and shrubs (such as roses, meadowsweets, photinias, firethorns, rowans, and hawthorns). Non-limiting examples of Rosaceae plants that may be modified as described herein include, but are not limited to, *Rubus* spp. (e.g., blackberry, black raspberry or raspberry, and the like), *Prunus* spp., *Frageria* spp., and/or *Malus* spp. Example *Rubus* plants useful with the invention can include, but are not limited to, *Rubus occidentalis* L., *Rubus pergratus* Blanch., *Rubus oklahomus* L. H. Bailey *Rubus originalis* L. H. Bailey, *Rubus ortivus* (L. H. Bailey) L. H. Bailey, *Rubus parcifrondifer* L. H. Bailey, *Rubus odoratus* L., *Rubus parvifolius* L., *Rubus pedatus* Sm., and *Rubus phoenicolasius* Maxim. Example *Prunus* spp. plants useful with the invention can include, but are not limited to, *P. persica, P. pyrifolia, P. serotina, P. armeniaca, P. spinosa, P. avium,* or *P. dulcis* (e.g., plum, apricot, cherry, nectarine, peach, almond, chokecherry, cherry laurel, and blackthorn). Example *Fragaria* spp. plants useful with the invention can include, but are not limited to, *F. vesca, Fragaria* x *ananassa* Duchesne, or *F. chiloensis*. Example *Malus* spp. plants useful with the invention can include, but are not limited to, *M. domesticus, Pyrus communis, Cydonia oblonga, Crataegus* spp., *Chaenomeles* spp., or *Amelanchier* spp. In some embodiments, a Rosaceae plant or part thereof is a caneberry or stone fruit. In some embodiments, the Rosaceae plant or part thereof is a blackberry, a black raspberry, a cherry, a plum or a peach.

In some embodiments, a plant useful with this invention may include but is not limited to angiosperm and gymnosperm plants such as acacia, alfalfa, amaranth, apple, apricot, artichoke, ash tree, asparagus, avocado, banana, barley, beans, beet, birch, beech, blackberry, black raspberry, blueberry, broccoli, Brussel's sprouts, cabbage, canola, cantaloupe, carrot, cassava, cauliflower, cedar, a cereal, celery, chestnut, cherry, Chinese cabbage, citrus, Clementine, clover, coffee, corn, cotton, cowpea, cucumber, cypress, eggplant, elm, endive, *eucalyptus*, fennel, figs, fir, geranium, grape, grapefruit, groundnuts, ground cherry, gum hemlock, hickory, kale, kiwifruit, kohlrabi, larch, lettuce, leek, lemon, lime, locust, pine, maidenhair, maize, mango, maple, melon, millet, mushroom, mustard, nuts, oak, oats, oil palm (*Elaeis guineensis*), okra, onion, orange, an ornamental plant or flower or tree, *papaya*, palm, parsley, parsnip, pea, peach, peanut, pear, peat, pepper, persimmon, pigeon pea, peach, pine, pineapple, plantain, plum, pomegranate, potato, pumpkin, radicchio, radish, rapeseed, raspberry, rice, rye, sorghum, safflower, sallow, soybean, spinach, spruce, squash, strawberry, sugar beet, sugarcane, sunflower, sweet potato, sweet corn, tangerine, tea, tobacco, tomato, trees, triticale, turf grasses, turnips, vine, walnut, watercress, watermelon, wheat, wild strawberry, yams, yew, and zucchini, optionally wherein the plant is blackberry, raspberry, black raspberry, strawberry, cherry, peach, plum, apricot, apple, pear, quince, loquat, date and almond.

Next Generation Plant Breeding Methodology Utilizing Mutations on AGAMOUS Clade MADS-Box Transcription Factors for Altered Fruit Development A. Identification of AGAMOUS Clade MADS-box Transcription Factors An AGAMOUS clade MADS-box transcription factor, comprises at least the following three conserved amino acid domains: (1) Y {A,S}NN (SEQ ID NO:259) motif at positions 83-86 with respect to *Arabidopsis thaliana* STK (AT4G09960.3); (2) YQQE {A,S} {A,S,N,K,T}KL {R,H} {Q,H,A,N,R}QI (SEQ ID NO:260) motif at positions 116-127 with respect to *Arabidopsis thaliana* STK (AT4G09960.3); and (3) R at position 225 with respect to *Arabidopsis thaliana* STK (AT4G09960.3).

In some alternative embodiments, the AGAMOUS clade MADS-box transcription factor comprises the aforementioned domains at (1) and (2), but has an expanded (3), which includes the R at position 225 with respect to *Arabidopsis thaliana* STK (AT4G09960.3), but with the exception of Grape gene VIT_12s0142g00360.0, which contains a Q at this position. This, "Expanded AGAMOUS clade MADS-box transcription factor" thus includes R and Q corresponding to position 225 of *Arabidopsis thaliana* STK (AT4G09960.3).

In some embodiments, the present disclosure teaches methods developed by the inventors, using bioinformatics and evolutionary analysis of various MADS-box transcription factors to identify AGAMOUS clade MADS-box transcription factors. In some embodiments, MADS-box gene sequences from *Arabidopsis thaliana* are used for bioinformatics such as nucleotide and/or protein Blast searches to identify and collect sequence information on homologues, orthologues and/or paralogues of the *Arabidopsis* MADS-box genes of interest in other plants. In some embodiments, the collected amino acid sequences corresponding to the MADS-box transcription factors are further analyzed for characterization of structural similarity and functional characteristics among the MADS-box transcription factors using multiple sequence alignment (MSA) and phylogenetic analyses.

In some embodiments, the present disclosure teaches species of the AGAMOUS clade MADS-box transcription factors, which can comprise: STK, AG, and SHP1/2 across plants of interest, including: *Arabidopsis*, black raspberry, wild strawberry, peach, apple, tomato, and grape from phylogenetic trees as disclosed in U.S. Provisional Application No. 62/859,992, filed on Jun. 11, 2019. In other embodiments, the present disclosure teaches species of the AGAMOUS clade MADS-box transcription factors, which can comprise: STK, AG, and SHP1/2 across crops of interest including, but not limited to, raspberry, black raspberry, blackberry, wild strawberry, cherry, peach, plum, avocado, apple, tomato, date, and grape. In further embodiments, crops of interest taught in the present disclosure are black raspberry, blackberry, cherry, peach, and avocado.

In some embodiments, the conserved residues, motifs and/or regions of AG clade transcription factors identified from the MSA and phylogenetic analyses, are further analyzed to identify potential target sites to introduce genetic modifications including, but not limited to, base editing, gene-editing, genome-editing technologies for altering fruit development in plants of interest. In further embodiments, the codons encoding these selected residues in the conserved regions are also analyzed for potential edits that could affect a non-conservative change in the amino acid, resulting in variation in protein function.

Figure 4:
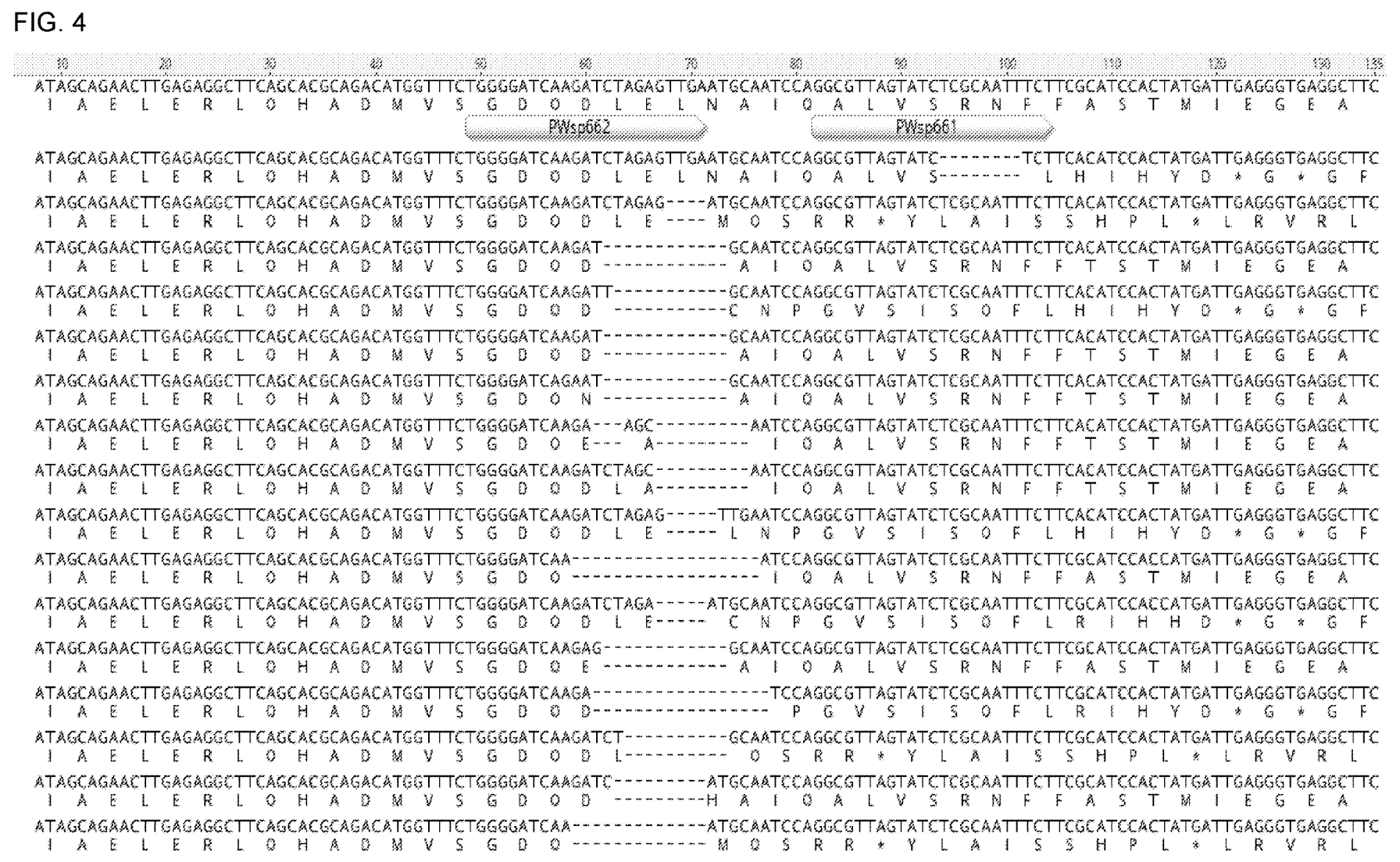

In some embodiments, the target sites for genetic modification of the codons encoding the selected residues are in a nuclear signal peptide of the AG clade transcription factor. In some embodiments, the target sites for genetic modification of the codons encoding the selected residues are in a N-terminal domain of the AG clade transcription factor. In some embodiments, the target sites for genetic modification of the codons encoding the selected residues are in a MADS-box (M) domain of the AG clade transcription factor. In some embodiments, the target sites for genetic modification of the codons encoding the selected residues are in an Intervening (I) domain of the AG clade transcription factor. In some embodiments, the target sites for genetic modification of the codons encoding the selected residues are in a Keratin (K) domain of the AG clade transcription factor. In some embodiments, the target sites for genetic modification of the codons encoding the selected residues are in a C-terminal (C) domain of the AG clade transcription factor, see as an example, FIG. 4. In other embodiments, the target sites for genetic modification of the codons encoding the selected residues are in a NN motif in M domain of the AG clade transcription factor. In other embodiments, the target sites for genetic modification of the codons encoding the selected residues are in a YQQ motif in M domain of the AG clade transcription factor. In other embodiments, the target sites for genetic modification of the codons encoding the selected residues are in a R/Q residue in C domain of the AG clade transcription factor. In further embodiments, the NN motif comprise an extended motif Y[A/S]NN (SEQ ID NO:259) as target sites for genetic modification. In some embodiments, the motif may be YQQE (SEQ ID NO:177). In some embodiments, the YQQ motif or YQQE (SEQ ID NO:177) may comprise an extended motif, YQQE[A/S][A/S/N/K/T]KL[R/H][Q/H/A/N/R]QI (SEQ ID NO:260) as target sites for genetic modification (see, e.g., SEQ ID NO:178, 179, 180, 181, or 182). In some embodiments, a target site for modification of a STK transcription factor is a conserved arginine (conserved R) located at position 225 with reference amino acid position numbering of SEQ ID NO:13; position 196 with reference amino acid position numbering of SEQ ID NO:66; position 197 with reference amino acid position numbering of SEQ ID NOs: 53, 78, 150, 166-171; position 198 with reference amino acid position numbering of SEQ ID NO:29; position 199 with reference amino acid position numbering of SEQ ID NO:128; or position 201 with reference amino acid position numbering of SEQ ID NOs: 97, 152, 154, 156, 158, 160, 162, 164). In some embodiments, a domain in a STK polypeptide that may be targeted for modification maybe a domain comprising a conserved R including but not limited to NVLVRAKIADLER-LQHADMVSGDQDLELNAIQALVSRNFFTS (SEQ ID NO:183) or a domains having any one of the amino acid sequences of SEQ ID NOs: 187, 188, or 189, wherein the modification may be a deletion of one or more amino acids, optionally wherein the deletion results in a C-terminal truncation of the STK polypeptide. In some embodiments, at a minimum, a C-terminal truncation useful for this invention removes at least the conserved arginine located at position 225 of SEQ ID NO:13 (AtSTK), 196 of SEQ ID NO:66; position 197 of SEQ ID NOs: 53, 78, 150, 166-171; 198 of SEQ ID NO:29; 199 of SEQ ID NO:128 or 201 of SEQ ID NO:97 (RoSTK)) or SEQ ID NOs: 152, 154, 156, 158, 160, 162, 164). Example mutations that produce a C-terminal truncation are provided in FIG. 5. The present disclosure teaches that SEQ ID NO:13 is AT4G09960.3, also known as AGAMOUS-LIKE 11 (AGL11) or SEEDSTICK (STK), which is a MADS box transcription factor expressed in the carpel and ovules. AtSTK (a.k.a. AtAGL11) and its orthologues in other plants (see, e.g., SEQ ID NOs: 13, 29, 53, 66, 78, 97, 128, 150, 152, 154, 156, 158, 159, 160, 162, 164 or 166-171) play a maternal role in fertilization and seed development and control the structure and mechanical properties of the seed coat.

In some embodiments, SEQ ID NO:13 is AT4G09960.3 (*Arabidopsis* STK Protein) including an N-terminal region (1-26 amino acids of AT4G09960.3 Protein Sequence) as a reference sequence to identify homologs, orthologs and/or paralogs in other plant species. In further embodiments, the *Arabidopsis* STK protein comprises: an 'NN' motif at positions 85-86 of SEQ ID NO:13, a 'YQQ' motif at positions 116-118 of SEQ ID NO:13 and an "R (Arginine)" at position 225 of SEQ ID NO: 13, as presented in Table 1 and Table 1B (motifs are bolded and underlined).

The present disclosure teaches that SEQ ID NO:97 is a black raspberry STK protein (Ro05_G22454) without an N-terminal region. When compared to *Arabidopsis* STK sequence (SEQ ID NO: 13), black raspberry STK sequence does not contain a N-terminal region corresponding to 1-26 of SEQ ID NO:13 (26 amino acids from start codon). In other embodiments, the black raspberry STK protein comprises: an 'NN' motif at positions 59-60 corresponding to 85-86 of SEQ ID NO:13, a 'YQQ' motif at positions 91-93 corresponding to 116-118 of SEQ ID NO:13 and an "R (Arginine)" at position 201 position corresponding to 225 of SEQ ID NO:13 as presented in Table 1 and Table 1B (motifs are bolded and underlined).

The present disclosure teaches that SEQ ID NO:29 is woodland or wild strawberry STK protein (FvH4_5g32540.1) without an N-terminal region. When compared to *Arabidopsis* STK sequence (SEQ ID NO:13), black raspberry STK sequence does not contain a N-terminal region corresponding to 1-26 of SEQ ID NO:13 (26 amino acids from start codon). In other embodiments, the black raspberry STK protein comprises: an 'NN' motif at positions 59-60 corresponding to 8586 of SEQ ID NO:13, a 'YQQ' motif at positions 91-93 corresponding to 116-118 of SEQ ID NO:13 and an "R (Arginine)" at position 198 position corresponding to 225 of SEQ ID NO:13 as presented in Table 1 and Table 1B (motifs are bolded and underlined).

The species' proteomes were queried with the protein-coding sequence for *Arabidopsis* STK from the *A. thaliana* genome (protein ID AT4G09960.3 in assembly version TAIR10) using Blast (blastp Ver. 2.5.0; parameters: '-seg no-max_hsps 1-max_target_seqs 40-use_sw_tback') and extracted protein sequence Blast hits with passing the E value <1e-10 cutoff. A second iteration of the Blast search were performed using the all passing Blast hits as query sequences, in order to generate reciprocal E value scores, which were used in clustering. Clustering was performed with the program hcluster_sg (Li 2006; Ver. 0.5.1, parameters: "-m 750-w 0-s 0.34"). Sequences were aligned using the multiple sequence alignment program T-Coffee with default parameter settings (Notredame et al. 2000; Version_11.00.8cbe486). For phylogenetic tree reconstruction, we used ModelFinder for substitution model selection (Kalyaanamoorthy et al. 2017) and IQ-Tree for tree inference and branch support estimation with ultrafast bootstrap approximation (Hoang et al. 2018, Nguyen et al. 2015; IQ-Tree Ver. 1.5.5; parameters: "-bb 1000") using DNA coding sequences after back translation with the tranalign software tool from the EMBOSS package (Rice et al. 2000. Ver. 6.6.0.0). Evidence for orthology was found by examining the tree topology for clustering of genes from multiple species for which the most common ancestor node is a speciation event. The multiple sequence alignment for the cluster containing *Arabidopsis* STK was investigated for conserved amino acid motifs in the Agamous MADS-box gene sub-family (*References added below existing reference section)

TABLE 1

Sequence Information of SEQ ID NO: 13, SEQ ID NO: 97 and SEQ ID NO: 29

| SEQ ID NO | Amino Acid Sequence |
|---|---|
| SEQ ID NO: 13 (AT4G09960.3) | MLFPHERKKEKERSQGFYLVTRLRIRMGRGKIEIKRIENSTNRQ VTFCKRRNGLLKKAYELSVLCDAEVALIVFSTRGRLYEYANNN IRSTIERYKKACSDSTNTSTVQEINAAYYQQESAKLRQQIQTIQ NSNRNLMGDSLSSLSVKELKQVENRLEKAISRIRSKKHELLLVE IENAQKREIELDNENIYLRTKVAEVERYQQHHHQMVSGSEINAI EALASRNYFAHSIMTAGSGSGNGGSYSDPDKKILHLG |
| SEQ ID NO: 97 (Ro05_G22454) | MGRGKIEIKRIENTTNRQVTFCKRRNGLLKKAYELSILCEAEVA LIVFSSRGRLYEYSNNNSIRNTIERYKKACSDSSGATTITEINAQ YYQQESAKLRHQIQMLQNSNRHLMGDSLSNLTVKELKQLENR LERGLTRIRSKKHEMLLAEIEYLQKREVELENENVLVRAKIAEL ERLQHADMVSGDQDLELNAIQALVSRNFFASTMIEGEASYSQP EKKFLNLGAGKGLVKQGKTSSSFGYVL |
| SEQ ID NO: 29 (FvH4_5g32540.1) | MGRGKIEIKRIENTTNRQVTFCKRRNGLLKKAYELSILCEAEVA LIVFSSRGRLYEYSNNNSIRNTIERYKKASSDNSGATTITEINAQ YYQQESTKLRHQIQMLQNSNRHLMGDSLSNLTVKELKQLENR LERGLTRIRSKKHEMLLAEIEYLQKREIELENENVLIRAKIAEVE RLQQADLVSGAELNAIQALASRNFFESTMMEGETSYSQPEKKL LHLG |

TABLE 1B

Annotation table for SEQ ID NO: 13, SEQ ID NO: 97, and SEQ ID NO: 29

| Sequence ID | Description | AA Start | AA End | AA Length |
|---|---|---|---|---|
| SEQ ID NO: 13 (AT4G09960) | Ag-specific domain extended | 83 | 86 | 4 |
| SEQ ID NO: 13 (AT4G09960) | Ag-specific domain extended | 116 | 127 | 12 |
| SEQ ID NO: 13 (AT4G09960) | Ag-specific domain extended | 225 | 225 | 1 |
| SEQ ID NO: 13 (AT4G09960) | Ag-specific motif | 85 | 86 | 2 |
| SEQ ID NO: 13 (AT4G09960) | Ag-specific motif | 98 | 98 | 1 |
| SEQ ID NO: 13 (AT4G09960) | Ag-specific motif | 101 | 101 | 1 |
| SEQ ID NO: 13 (AT4G09960) | Ag-specific motif | 116 | 118 | 3 |
| SEQ ID NO: 13 (AT4G09960) | Ag-specific motif | 124 | 124 | 1 |
| SEQ ID NO: 13 (AT4G09960) | Ag-specific motif | 126 | 126 | 1 |
| SEQ ID NO: 13 (AT4G09960) | Ag-specific motif | 131 | 131 | 1 |
| SEQ ID NO: 13 (AT4G09960) | Ag-specific motif | 182 | 182 | 1 |
| SEQ ID NO: 13 (AT4G09960) | Ag-specific motif | 225 | 225 | 1 |
| SEQ ID NO: 13 (AT4G09960) | C-terminal | 197 | 256 | 60 |
| SEQ ID NO: 13 (AT4G09960) | Intervening Domain | 103 | 109 | 7 |

TABLE 1B-continued

Annotation table for SEQ ID NO: 13, SEQ ID NO: 97, and SEQ ID NO: 29

| Sequence ID | Description | AA Start | AA End | AA Length |
|---|---|---|---|---|
| SEQ ID NO: 13 (AT4G09960) | K-box | 110 | 196 | 87 |
| SEQ ID NO: 13 (AT4G09960) | MADS MEF2 like | 27 | 102 | 76 |
| SEQ ID NO: 13 (AT4G09960) | N-terminal | 1 | 26 | 26 |
| SEQ ID NO: 97 (Ro05_G22454) | Ag-specific domain extended | 57 | 60 | 4 |
| SEQ ID NO: 97 (Ro05_G22454) | Ag-specific domain extended | 91 | 102 | 12 |
| SEQ ID NO: 97 (Ro05_G22454) | Ag-specific domain extended | 201 | 201 | 1 |
| SEQ ID NO: 97 (Ro05_G22454) | Ag-specific motif | 73 | 73 | 1 |
| SEQ ID NO: 97 (Ro05_G22454) | Ag-specific motif | 76 | 76 | 1 |
| SEQ ID NO: 97 (Ro05_G22454) | Ag-specific motif | 91 | 93 | 3 |
| SEQ ID NO: 97 (Ro05_G22454) | Ag-specific motif | 99 | 99 | 1 |
| SEQ ID NO: 97 (Ro05_G22454) | Ag-specific motif | 101 | 101 | 1 |
| SEQ ID NO: 97 (Ro05_G22454) | Ag-specific motif | 106 | 106 | 1 |
| SEQ ID NO: 97 (Ro05_G22454) | Ag-specific motif | 157 | 157 | 1 |
| SEQ ID NO: 97 (Ro05_G22454) | Ag-specific motif | 201 | 201 | 1 |
| SEQ ID NO: 29 (FvH4_5g32540.1) | Ag-specific domain extended | 57 | 60 | 4 |
| SEQ ID NO: 29 (FvH4_5g32540.1) | Ag-specific domain extended | 91 | 102 | 12 |
| SEQ ID NO: 29 (FvH4_5g32540.1) | Ag-specific domain extended | 198 | 198 | 1 |
| SEQ ID NO: 29 (FvH4_5g32540.1) | Ag-specific motif | 73 | 73 | 1 |
| SEQ ID NO: 29 (FvH4_5g32540.1) | Ag-specific motif | 76 | 76 | 1 |
| SEQ ID NO: 29 (FvH4_5g32540.1) | Ag-specific motif | 91 | 93 | 3 |
| SEQ ID NO: 29 (FvH4_5g32540.1) | Ag-specific motif | 99 | 99 | 1 |
| SEQ ID NO: 29 (FvH4_5g32540.1) | Ag-specific motif | 101 | 101 | 1 |
| SEQ ID NO: 29 (FvH4_5g32540.1) | Ag-specific motif | 106 | 106 | 1 |
| SEQ ID NO: 29 (FvH4_5g32540.1) | Ag-specific motif | 157 | 157 | 1 |
| SEQ ID NO: 29 (FvH4_5g32540.1) | Ag-specific motif | 198 | 198 | 1 |

B. Generating Mutant Alleles in AGAMOUS Clade MADS-Box Transcription Factors to Create Altered Fruit Development Phenotypes Provided herein are methods for generating modifications in in AGAMOUS clade MADS-box transcription factors, which are key for seed and fruit development. Such modification include but are not limited to those that generate dominant negative alleles, semi-dominant alleles, weak loss of function alleles, or hypomorphic mutations. In the present disclosure, the mutated gene product can still interact with other elements within the cell as the wild type gene product would, but some functions of the gene product have been changed or reduced or blocked entirely. For example, a mutation in a transcription factor, such as a MADS-box transcription factor, could eliminate the activation domain but maintain the DNA binding domain. This altered product can still bind to the DNA site, competing with the wild type transcription factor and thus leading to reduced levels of target gene activation. Consequently, an altered fruit development phenotype results from reduced activity of the target genes due to the dominant negative alleles, semi-dominant alleles, weak loss of function alleles, or hypomorphic mutations generated in the AGAMOUS clade MADS-box transcription factors.

C. HTP In Vivo Screen to Identify Modified Alleles in Candidate AGAMOUS Clade MADS-Box Transcription Factors In some embodiments, the candidate target sites are mutated and then screened by an in vivo luciferase assay in a heterologous system such as tobacco, yeast or human cells to select for effective edits that affect transcription. The selected edits are then made in plants to screen phenotypically for an altered fruit development phenotype, particularly a seedless or reduced seediness phenotype. In some embodiments, an in vivo assay system for analyzing transient luciferase expression in HEK293T cells transfected with reporter and MADS-box transcription factor protein expression constructs is used to screen target sites suitable for mutating AGAMOUS clade MADS-box transcription factors, in order to eventually produce seedless or reduced seed size in fruits of the plants of interest. In some embodiments, the present disclosure teaches methods for generating dual luciferase expression constructs by inserting seven repeats of the MADS protein binding sequence (7× CArG sequence) upstream of a minimal promoter (7× CArG box promoter), which is used to allow for the MADS-box transcription factors to bind multiple CArG boxes. In other embodiments, the 7×CArG::LUC dual luciferase system allows expression of both (i) the 7×CArG box promoter controlling expression of the firefly luciferase (LUC) reporter gene and (ii) a control promoter (CMV) regulating expression of the Renilla luciferase (REN) reporter gene. In other embodiments, the AG-clade co-factor SEPALLATA3 is expressed in the same cell as the 7×CArG::LUC dual luciferase system. The SEPALLATA protein is a required co-factor for AG-clade transcription factor to form a complex to bind the 7×CArG box. The LUC reporter gene is transcribed and expressed when a MADS-box transcription factor complex targets and binds the 7×CArG box promoter region. Expression level of the LUC reporter gene depends on the transcriptional activation by the MADS-box transcription factor complex of interest. Consequently, the relative effectiveness of different mutation(s) of the AG clade transcription factor in various sites (e.g. N-terminal, M, I, K, or C domain, or three motifs described in Example 2) are determined in changing expression of a LUC reporter gene sequence controlled by the 7×CArG box promoter in comparison to the constitutive expression of the REN reporter gene.

In some embodiments, the non-mutated AG clade TF construct is co-transfected with the 7× CArG box-fused dual luciferase constructs. In some embodiments, the mutated AG clade TF construct and the non-mutated AG clade TF construct is co-transfected with the 7×CArG box-fused dual luciferase constructs. In further embodiments, the LUC: REN ratio with the co-transfection of the mutated version and non-mutated version of the AG clade TFs is compared with the LUC:REN ratio with the co-transfection of the non-mutated version. If the LUC:REN ratio in the mutated version and non-mutated version is lower than the non-mutated version alone of the AG clade TFs of interest, the mutation site will be a target of interest for in vivo study by creating a stable plant line with a specific mutation introduced by a stable, but targeted single base-editing technique taught in the present disclosure.

The present disclosure teaches that there is reduction in transactivation when the mutated version of the AG clade TF is co-transfected with the dual luciferase assay system, because the function of the mutated AG clade TF(s) will be negatively affected by the mutations. Thus, the transactivation will be reduced in the mutated version of the AG clade TF compared to the nonmutated version. In some embodiments, the mutation(s) inducing the reduction of the LUC: REN ratio compared to the non-mutated wild type version is selected for genetically modifying plant cells of interest.

Thus, the aforementioned methodology provides for a rapid and HTP in vivo screen, in a model organism, for candidate mutations in AGAMOUS clade MADS-box transcription factors. If there is a reduction in transcription factor mediated activation evident in the screen, i.e. an indication that a mutation could serve as a dominant negative allele, semi-dominant allele, weak loss of function allele, or hypomorphic mutation, then said mutation is then targeted in a plant of interest, which is eventually phenotyped to confirm the positive "hit" from the screen and identify a mutation of interest associated with altered fruit development.

Modified Plant Cells

In some embodiments, the present disclosure provides modified plant cells. Herein, the term "modified plant cells" encompasses plant cells comprising one or more genomic modifications resulting in the altered function of one or more endogenous target genes as well as plant cells comprising a targeted base-editing system capable of modifying a DNA base within a nucleic acid sequence of one or more endogenous target genes and altering the function of a protein encoded by one or more base-edited target genes. Herein, an "un-modified plant cell" or "control plant cell" refers to a cell or population of cells derived from a plant wherein the genomes have not been modified and that does not comprise a gene-editing system or comprises a control gene editing system (e.g., an empty vector control, a non-targeting gRNA, a scrambled siRNA, etc.), In some embodiments, a modified plant cell is a gene-edited plant cell targeted by the editing techniques of the present disclosure.

The present disclosure provides plant cells, which in some aspects refers to cells derived from angiosperm plants, including but not limited to, the Rosaceae plant family. The Rosaceae plant family comprises a fruit-bearing plant such as: blackberries, black raspberries, raspberries, strawberries, cherries, peaches, plums, apricots, apples, pears, quinces, dates, loquats and almonds. In some embodiments, the present disclosure provides plant cells from black raspberry, blackberry, raspberry, cherry, apricot, apple, pear, quince, date, peach, avocado, wild strawberry, loquat, and plum for targeted base-editing. In some embodiments, the present disclosure provides plant cells from black raspberry, blackberry, raspberry, cherry, apricot, apple, pear, quince, date, peach, avocado, wild strawberry, loquat, and plum for gene-editing techniques.

In some embodiments, the plant cell is a black raspberry cell that has been isolated from a black raspberry plant or part thereof (*Rubus occidentalis*). In some embodiments, the plant cell is a wild strawberry cell that has been isolated from a wild strawberry plant or part thereof (*Fragaria vesca*). In some embodiments, the plant cell is a plum cell that has been isolated from a plum plant or part thereof (*Prunus domestica*). In some embodiments, the plant cell is a peach cell that has been isolated from a peach plant or part thereof (*Prunus persica*). In some embodiments, the plant cell is a apple cell that has been isolated from a apple (*Malus domestica*). In some embodiments, the plant cell is a tomato cell that has been isolated from a tomato plant or part thereof (*Solanum lycopersicum*). In some embodiments, the plant cell is a Chinese plum cell that has been isolated from a Chinese plum plant or part thereof (*Prunus mume*). In some embodiments, the plant cell is an almond cell that has been isolated from an almond plant or part thereof (*Prunus dulcis*). In some embodiments, the plant cell is a Japanese cherry cell that has been isolated from a Japanese cherry plant or part thereof (*Prunus serrulata*). In some embodiments, the plant cell is a cherry cell that has been isolated from a cherry plant or part thereof (including many species in *Prunus* genus; e.g., Prinis). In some embodiments, the plant cell is a cherry cell or sweet cherry cell that has been isolated from a cherry plant or sweet cherry plant, or part thereof (*Prunus avium*). In some embodiments, the plant cell is a sour cherry cell that has been isolated from a sour cherry plant or part thereof (*Prunus cerasus*). In some embodiments, the plant cell is a red raspberry cell that has been isolated from a red raspberry plant or part thereof (*Rubus idaeus*). In some embodiments, the plant cell is a wild raspberry cell that has been isolated from a wild raspberry plant or part thereof (*Rubus ulmifolius*). In some embodiments, the plant cell is a blackberry cell that has been isolated from a blackberry plant or part thereof (including many species in *Rubus* genus, e.g., *Rubus* sp.). In some embodiments, the plant cell is an avocado cell that has been isolated from an avocado plant or part thereof (*Persea americana*). In some embodiments, the plant cell is an apple cell that has been isolated from an apple (*Malus pumila*). In some embodiments, the plant cell is a grape cell that has been isolated from a grape plant or part thereof (*Vitis vinifera*). In some embodiments, the plant cell is a tomato cell that has been isolated from a tomato (*Solanum lycoperisicum*). In some embodiments, the plant cell is an *Arabidopsis* cell that has been isolated from an *Arabidopsis* (*Arabidopsis thaliana*).

In some embodiments, the modified plant cells comprise one or more modifications (e.g., insertions, deletions, or mutations of one or more nucleic acids) in the genomic DNA sequence of an endogenous target gene resulting in the altered function the endogenous gene, thereby inducing seedlessness (e.g., no or reduced seed production), reduced seediness, reduced thickness of fruit endocarp and/or reduced lignification of fruit endocarp. In such embodiments, the modified plant cells comprise a "modified endogenous target gene." In some embodiments, the modifications in the genomic DNA sequence cause missense mutation and/or nonsense mutation, thereby altering the function of protein such as dominant negative mutation, a semi-dominant mutation, weak loss of function mutation, or a hypomorphic mutation. In some embodiments, the modifications in the genomic DNA sequence results in amino acid substitutions, thereby altering the normal function of the encoded protein. In some embodiments, the modifications in the genomic DNA sequence encode a modified endogenous protein with reduced, upregulated or altered function compared to the unmodified (i.e., wild type) version of the endogenous protein (e.g., a dominant negative mutant, semi-dominant mutant, weak loss of function mutant or hypomorphic mutant).

In some embodiments, the modified plant cells described herein comprise one or more modified endogenous target genes, wherein the one or more modifications result in an altered function of a gene product (i.e., a protein) encoded by the endogenous target gene compared to an unmodified plant cell. For example, in some embodiments, a modified plant cell demonstrates a downregulated expression of a protein or an upregulated expression of a protein. In some embodiments, the expression of the gene product in a modified plant cell is reduced by at least 5% compared to the expression of the gene product in an unmodified plant cell. In other embodiments, the expression of the gene product in a modified plant cell is reduced by at least 10%, 20%, 30%, 40%, 50%, 60%, 70%, 80%, 90%, or more compared to the expression of the gene product in an unmodified plant cell. In some embodiments, the modified plant cells described herein demonstrate reduced expression and/or function of gene products encoded by a plurality (e.g., two or more) of endogenous target genes compared to the expression of the gene products in an unmodified plant cell. For example, in some embodiments, a modified plant cell demonstrates reduced expression and/or function of gene products from 2, 3, 4, 5, 6, 7, 8, 9, 10, or more endogenous target genes compared to the expression of the gene products in an unmodified plant cell.

In other embodiments, the expression of the gene product in a modified plant cell is upregulated by at least 5% compared to the expression of the gene product in an unmodified plant cell. In other embodiments, the expression of the gene product in a modified plant cell is upregulated by at least 10%, 20%, 30%, 40%, 50%, 60%, 70%, 80%, 90%, or more compared to the expression of the gene product in an unmodified plant cell. In some embodiments, the modified plant cells described herein demonstrate upregulated expression and/or function of gene products encoded by a plurality (e.g., two or more) of endogenous target genes compared to the expression of the gene products in an unmodified plant cell. For example, in some embodiments, a modified plant cell demonstrates upregulated expression and/or function of gene products from 2, 3, 4, 5, 6, 7, 8, 9, 10, or more endogenous target genes compared to the expression of the gene products in an unmodified plant cell.

In some embodiments, the present disclosure provides a modified plant cell wherein a single nucleotide of one or more endogenous target genes, or a portion thereof, is substituted (e.g., "C>T (C to T substitution)" or "G>A (G to A substitution" in the complementary DNA strand) or "A>G (A to G substitution)" or "T>C (T to C substitution" in the complementary DNA strand) such that the modified plant cells express the protein in which one amino acid is substituted, which can trigger missense mutation or nonsense mutation. In some embodiments, a modified plant cell comprises nucleotide substitution of a plurality of endogenous target genes, or portions thereof. In some embodiments, a modified plant cell comprises nucleotide substitution of 2, 3, 4, 5, 6, 7, 8, 9, 10, or more endogenous target genes.

In some embodiments, the modified plant cells described herein comprise one or more modified endogenous target genes, wherein the one or more modifications to the target DNA sequence results in expression of a protein with reduced or altered function (e.g., a "modified endogenous protein") compared to the function of the corresponding protein expressed in an unmodified plant cell (e.g., a "unmodified endogenous protein"). In some embodiments, the modified plant cells described herein comprise 2, 3, 4, 5, 6, 7, 8, 9, 10, or more modified endogenous target genes encoding 2, 3, 4, 5, 6, 7, 8, 9, 10, or more modified endogenous proteins. In some embodiments, the modified endogenous protein demonstrates reduced or altered binding affinity for another protein expressed by the modified plant cell or expressed by another cell; reduced or altered signaling capacity; reduced or altered enzymatic activity; reduced or altered DNA-binding activity; or reduced or altered ability to function as a scaffolding protein.

In some embodiments, the modified endogenous target gene comprises one or more dominant negative mutations. As used herein, a "dominant negative mutation" refers to a substitution, deletion, or insertion of one or more nucleotides of a target gene such that the encoded protein acts antagonistically to the protein encoded by the unmodified target gene. The mutation is dominant negative because the allele produces a phenotype despite the presence of the corresponding unmodified gene. A gene comprising one or more dominant negative mutations and the protein encoded thereby are referred to as a "dominant negative mutants", e.g. dominant negative genes and dominant negative proteins. In some embodiments, the dominant negative mutant protein is encoded in a modified plant cell in which one or more nucleotides of endogenous target genes are edited by a gene editing system of the present disclosure.

Various mechanisms for dominant negativity are known. Typically, the gene product of a dominant negative mutant retains some functions of the unmodified gene product but lacks one or more crucial other functions of the unmodified gene product. This causes the dominant negative mutant to antagonize the unmodified gene product. For example, as one illustrative embodiment, a dominant negative mutant of a transcription factor may lack a functional activation domain but retain a functional DNA binding domain. In this example, the dominant negative transcription factor cannot activate transcription of the DNA as the unmodified transcription factor does, but the dominant negative transcription factor can indirectly inhibit gene expression by preventing the unmodified transcription factor from binding to the transcription-factor binding site. As another illustrative embodiment, are dominant negative mutations of proteins that function as dimers or multimers. For example, dominant negative mutants of such dimeric proteins may retain the ability to dimerize with unmodified protein but be unable to function otherwise. The dominant negative monomers, by dimerizing with unmodified monomers to form heterodimers, prevent formation of functional homodimers of the unmodified monomers. Dominant negative mutations of the *Arabidopsis* AG gene, rice leafy hull sterile 1 gene, and lilly LMADS1 gene are known in the art (See e.g., Mizukami et al., 1996, Jeon et al, 2000, and Tzeng and Yang, 2001). In addition to dominant negative mutation, a plant of this invention may also be generated that comprise in addition or instead of a dominant negative mutation, one or more semi-dominant mutations, weak loss of function mutations or hypomorphic mutations.

In some embodiments, the modified plant cells comprise a targeted base-editing system capable of modifying a DNA base within a nucleic acid sequence of one or more endogenous target genes. The targeted base-editing system can alter the expression and/or function of the endogenous target genes modifications by a variety of mechanisms including by modifying the genomic DNA sequence of the endogenous target gene (e.g., by insertion, deletion, or mutation of one or more nucleic acids in the genomic DNA sequence).

In some embodiment, the present disclosure teaches a modification of the DNA sequence of the endogenous target gene by nucleotide substitution of one or more nucleic acids in the genomic DNA sequence.

The present disclosure teaches that the modified plant cells described herein comprise a targeted base-editing system (e.g., a combination protein/nucleic acid-based gene-regulating system). In some embodiments, the targeted base-editing system comprised in the modified plant cell is capable of modifying one or more endogenous target genes. In some embodiments, the modified plant cells described herein comprise a targeted base-editing system comprising: (1) one or more guide RNAs (gRNAs) capable of binding to a target DNA sequence in an endogenous gene; (2) one or more polynucleotides encoding one or more gRNAs capable of binding to a target DNA sequence in an endogenous gene; (3) one or more site-directed modifying polypeptides capable of interacting with a gRNA and modifying a target DNA sequence in an endogenous gene; (4) one or more polynucleotides encoding a site-directed modifying polypeptide capable of interacting with a gRNA and modifying a target DNA sequence in an endogenous gene; (5) one or more polynucleotides encoding a base-editing polypeptide capable of substituting C with T (or G with A); and/or (6) one or more polynucleotides encoding a base-editing polypeptide capable of substituting A with G (or T with C).

In some embodiments, one or more polynucleotides encoding the targeted base-editing system are inserted into the genome of the plant cell. In some embodiments, one or more polynucleotides encoding the targeted base-editing system are expressed episomally and are not inserted into the genome of the plant cell.

Regulation of Endogenous Target Genes

In some embodiments, the modified plant cells described herein demonstrate an altered expression or function of one or more endogenous target genes. In some embodiments, the one or more endogenous target genes are related to, or associated with, endocarp determination, differentiation, or lignification. In some embodiments, the one or more endogenous target genes are MADS-box genes. In some embodiments, the target gene is an AGAMOUS (AG) clade transcription factor. In other embodiments, the target gene is a MADS-box gene selected from an AGAMOUS clade taught in the present disclosure. In further embodiments, the target gene is AG, SHP1, SHP2, or STK in plants of the present disclosure. In some embodiments, the target gene is an AGAMOUS clade MADS-box transcription factor.

In some embodiments, the expression of an endogenous target gene in a particular pathway is reduced in the modified plant cells. In some embodiments, the expression of a plurality (e.g., two or more) of endogenous target genes in a particular pathway are reduced in the modified plant cells. For example, the expression of 2, 3, 4, 5, 6, 7, 8, 9, 10, or more endogenous target genes in a particular pathway may be reduced. In some embodiments, the expression of an endogenous target gene in one pathway and the expression of an endogenous target genes in another pathway is reduced in the modified plant cells. In some embodiments, the expression of a plurality of endogenous target genes in one pathway and the expression of a plurality of endogenous target genes in another pathway are reduced in the modified plant cells. For example, the expression of 2, 3, 4, 5, 6, 7, 8, 9, 10, or more endogenous target genes in one pathway may be reduced and the expression of 2, 3, 4, 5, 6, 7, 8, 9, 10, or more endogenous target genes in another particular pathway may be reduced. In some embodiments, the expression of a plurality of endogenous target genes in a plurality of pathways is reduced. For example, the expression of one endogenous gene from each of a plurality of pathways (e.g., 2, 3, 4, 5, 6, 7, 8, 9, 10, or more pathways) may be reduced. In additional aspects, the expression of a plurality of endogenous genes (e.g., 2, 3, 4, 5, 6, 7, 8, 9, 10, or more genes) from each of a plurality of pathways (e.g., 2, 3, 4, 5, 6, 7, 8, 9, 10, or more pathways) may be reduced.

In some embodiments, the function of a protein encoded by an endogenous target gene in a particular pathway is altered in the modified plant cells. In some embodiments, the functions of proteins encoded by a plurality (e.g., two or more) of endogenous target genes in a particular pathway are altered in the modified plant cells. For example, the function of proteins encoded by 2, 3, 4, 5, 6, 7, 8, 9, 10, or more endogenous target genes in a particular pathway may be altered. In some embodiments, the function of a protein encoded by an endogenous target gene in one pathway and the function of an endogenous target genes in another pathway is altered in the modified plant cells. In some embodiments, the functions of proteins encoded by a plurality of endogenous target genes in one pathway and the function of proteins encoded by a plurality of endogenous target genes in another pathway are altered in the modified plant cells. For example, the function of proteins encoded by 2, 3, 4, 5, 6, 7, 8, 9, 10, or more endogenous target genes in one pathway may be altered and the function of proteins encoded by 2, 3, 4, 5, 6, 7, 8, 9, 10, or more endogenous target genes in another particular pathway may be altered. In some embodiments, the functions of proteins encoded by a plurality of endogenous target genes in a plurality of pathways are altered. For example, the function of a protein encoded by one endogenous gene from each of a plurality of pathways (e.g., 2, 3, 4, 5, 6, 7, 8, 9, 10, or more pathways) may be altered. In additional aspects, the function of proteins encoded by a plurality of endogenous genes (e.g., 2, 3, 4, 5, 6, 7, 8, 9, 10, or more genes) from each of a plurality of pathways (e.g., 2, 3, 4, 5, 6, 7, 8, 9, 10, or more pathways) may be altered.

In some embodiments, the modified plant cells described herein comprise a mutated gene in an AGAMOUS clade. In some embodiments, the modified plant cells described herein comprise altered function of a transcription factor encoded by MADS-box gene from an AGAMOUS clade comprising AG, SHP1, SHP2, and STK in plants of the present disclosure. In some embodiments, the modified plant cells described herein comprise a mutated AGAMOUS (AG) clade transcription factor. In other embodiments, the modified plant cells described herein comprise a mutated MADS-box gene from an AGAMOUS clade as described in the present disclosure. In further embodiments, the modified plant cells described herein comprise a mutated AG, SHP1, SHP2, and/or STK in plants of the present disclosure.

Molecular Function of MADS-Box Genes Related to Seed Formation

The MADS-box family of transcription factors is present in all eukaryotic genomes analyzed so far, although with higher number of gene members in plant genomes than in other kingdoms. This family of transcription factors is defined by the presence of a conserved domain, the MADS-box, in the N-terminal region, involved in DNA binding and dimerization with other MADS-box proteins. Ancestral MADS-box gene duplication predating divergence of plants and animals separated the two main lineages, type I and type II (Alvarez-Buylla et al., 2000 and Bodt et al., 2003). Type II group genes include MEF2-like genes of animals and yeast and MIKC-type genes only found in plants. MIKC-type genes received this name because, apart from the MADS (M) domain, they contain three additional conserved domains, the weakly conserved Intervening (I) domain, the conserved Keratin-like (K) domain and the highly variable C-terminal (C) domain where the latter usually contains conserved subfamily-specific sequence motifs (Theissen et al, 1996 and Kaufmann et al., 2005). The I domain is responsible for specificity in the formation of DNA-binding dimers, the K domain mediates dimerization and the C domain functions in transcriptional activation and formation of higher order protein complexes. On the other hand, Type I group genes show a simpler gene structure. They are shorter, generally encoding a single exon and lack the K domain. MADS transcription factors in plants encode key developmental regulators of vegetative and reproductive development.

The majority of the plant MADS proteins share a stereotypical MIKC structure. It comprises (from N- to C-terminal) an N-terminal domain, which is, however, present only in a minority of proteins; a MADS domain (PDOC00302, IPR002100), which is the major determinant of DNA-binding but which also performs dimerization and accessory factor binding functions; a weakly conserved intervening (I) domain, which constitutes a key molecular determinant for the selective formation of DNA-binding dimers; a keratin-like (K) domain, which promotes protein dimerization; and a C-terminal (C) domain, which is involved in transcriptional activation or in the formation of ternary or quaternary protein complexes.

MIKC-type genes were initially identified as floral organ identity genes in *Antirrhinum majus* and *Arabidopsis thaliana*. Further genetic and molecular analyses grouped their biological functions in flower organogenesis into five classes: A, B, C, D and E, which are required, in different combinations, to specify the identity of sepals (A+E), petals (A+B+E), stamens (B+C+E), carpels (C+E) and ovules (D+E). In *Arabidopsis*, genes belonging to these functional classes were APETALA1 (AP1) in class A, PISTILATA (PI) and APETALA3 (AP3) in class B, AGAMOUS (AG) in class C, SEEDSTICK/AGAMOUS-LIKE 11 (STK/AGL11) and SHATTERPROOF (SHP) in class D and SEPALLATA (SEP1, SEP2, SEP3, SEP4) genes in class E (Bowman et al, 1991, Colombo et al., 1995, and Theissen et al, 2001). MIKC genes in the AG and APETALA1/FRUITFULL (AP1/FUL) subfamilies also participate in fruit and seed development (Immink et al., 2003, Rijpkema et al., 2006, and Smaczniak et al., 2012).

SEEDSTICK (STK, also known as AGAMOUS-LIKE 11)—AT4G09960.3, a MADS-box transcription factor is known to control ovule identity and seed development in *Arabidopsis*. STK forms a closely related clade with three other transcription factors in *Arabidopsis*: AGAMOUS (AG) —AT4G18960.1, SHATTERPROOF1 (SHP1)— AT3G58780.4 and SHATTERPROOF2 (SHP2)— AT2G42830.2. Researchers have disclosed that AG controls organ identity and floral meristem determinacy. AG specifies carpel and anther identity within the developing flower. The AG protein is a MADS-box transcription factor. Also, another MADS-box transcription factor, STK in the same clade acts redundantly with two other MADSBOX genes, SHP1 and SHP2 in controlling ovule identity. In tomato, SHP homologues control fleshy fruit expansion, while in peaches, which are drupes, homologues of both genes have been implicated in lignified split-pit formation. AG, SHP1, SHP2, and STK are involved with organ identity such as ovule and floral meristem determinacy for seed development, as well as, associated with endocarp determination, differentiation or lignification. In some embodiments, AG, SHP1, SHP2, and STK genes and their orthologues in plants are target MADS-box genes for gene editing, for example, precise base editing. In other embodiments, AG, SHP1, SHP2, and STK genes and their orthologues in plants of the present disclosure share a stereotypical MIKC structure, which gives functional similarity involved with seed and/or endocarp formation and lignification of fruit endocarp Ectopic expression of AG cDNAs with intact MIKC structure including C-terminal regions results transformation of the petals into stamens, which is also known as an "*apetala*" phenotype. Removal of the C-terminal region from the AG protein, that is AG with only MIK domains (AG-MIK), however, does not allow AG-MIK transgenic plants to produce an "*apetala*" phenotype, indicating that this region is required for AG function in specifying stamen and carpel identities in the outer floral whorls. Furthermore, the transgenic plants carrying a construct for constitutively expressing AG-MIK (by 35S: AG-MIK construct) produce flowers similar to agamous (ag) mutant flowers, with indeterminacy and organ conversion in the inner whorls, suggesting that the AG protein lacking its C-terminal region inhibits the function of endogenous AG protein and works as a dominant negative mutation of the endogenous AG protein. Thus, the failure of the overexpression of AG-MIK for converting the outer whorl organs to reproductive organs as well as the inhibition of AG-MIK to normal AG functions indicate that the C-terminal region of the AG protein may be an essential role for organ identity and floral meristem determinacy. The present disclosure teaches that STK protein sharing similar MIKC structure with the AG protein is expected to have a same function of the AG.

As described above, removal of the C-terminal domain in 35S::AG-MIK transgenic plants shows the strongest loss-of-function ag mutant. The C-terminal can be removed in at least two ways as taught herein. One can introduce a stop codon via base editing. Alternatively, one could cut the C-terminal via a CRISPR directed nuclease. Thus, the C-terminal can be deleted at least by the methodology of base editing or by cutting enzymes.

As aforementioned, the present disclosure teaches deletion of the C-terminal domain of STK protein in plants using a targeted base editing system with CRISPR/Cas complex fused with base deaminase domain, thereby resulting in a strong dominant negative STK allele, or alternatively a CRISPR/Cas endonuclease. In some embodiments, a C-terminal deletion of the invention may be introduced by CRISPR directed nuclease that cuts the STK polynucleotide. In some embodiments, strong stk loss-of-function mutant alleles result in infertility. In some embodiments, plant cells of the present disclosure in which the target STK gene is base edited using the targeted base editing system described herein, induce seedlessness by reducing STK function (e.g., missense mutation by amino acid substitution). In some embodiments, plant cells of the present disclosure in which the target STK gene is base edited using the targeted base editing system described herein, induce seedlessness by abolishing STK function (i.e., nonsense mutation by amino acid substitution).

A mutation in STK is the causative gene for the seedless SEED DEVELOPMENT INHIBITOR (SDI) locus in commercial grapes (Royo et al, 2018, incorporated by reference herein). This naturally-occurring mutation is associated with a stenospermocarpic trait, in which fertilization takes place but the seeds do not develop correctly and are essentially unnoticeable. The stk$^{sdi}$ mutation in grape is a missense mutation involving a conversion of G>T at position. This leads to a non-conservative amino acid substitution of Arginine to Leucine in the 'C-terminal region' of STK. The stk$^{sdi}$ mutation causes a dominant negative effect as the heterozygotes have a reduced seed size. In contrast to the strong dominant negative phenotypic effect of 35S::AG-MIK in *Arabidopsis*, the stk$^{sdi}$ mutation in grape has a hypomorphic dominant negative effect. In some embodiments, mutating specific residues of the 'C-terminal' domain using precise base editing system can make hypomorphic dominant negative alleles in plants such as the Rosaceae plant family comprises a fruit-bearing plant, for example, blackberries, black raspberries, raspberries, strawberries, cherries, peaches, plums, apricots, apples, pears, quinces, loquats, dates, and almonds.

STK is also involved in a key event in the domestication and breeding of Palm Oil as well as the loss of the thick coconut-like shell surrounding the kernel oil palm (*Elaeis guineensis*). Modern Oil palm has three fruit forms, dura (thick-shelled; DeliDura), *pisifera* (shell-less: AVROS and MPOB) and *tenera* (thin-shelled), a hybrid between dura and *pisifera*. The *pisifera* palm is usually femalesterile. The *tenera* yields far more oil than dura, and is the basis for commercial palm oil production in all of Southeast Asia. A nucleotide substitution in the 'MADS-box domain' of STK causes two alleles that both lead to the *pisifera* phenotype: i) a nucleotide substitution in stkMPOB results in a leucine to proline amino acid change in the conserved DNA binding and dimerization domain, while ii) a substitution in stkAV-ROS results in a lysine to asparagine amino acid change in the same domain, only two amino acids carboxy-terminal to the stkMPOB. In related proteins, this highly conserved lysine residue is involved in nuclear localization, and direct DNA binding, whereas the substitution by a proline only two amino acid residues amino-terminal to this position would disrupt the alpha-helix that is involved in MADS dimerization and DNA binding. In some embodiments, both mutations of stkMPOB and stkAVROS are found in the 'MADS-box domain' of STK that is involved in nuclear localization, MADS dimerization and DNA binding.

The present disclosure teaches that mutant alleles of a target gene can induce seedlessness in plants, including but not limited to black raspberry, blackberry, raspberry, cherry, avocado, wild strawberry, apple, plum, grape, tomato, date, loquat, and peach. In some embodiments, the target gene is a MADS-box gene from an AGAMOUS clade comprising AG, SHP1, SHP2, and STK. In some embodiments, the target gene is an AGAMOUS (AG) clade transcription factor. In other embodiments, the target gene is a MADS-box gene from an AGAMOUS clade taught in the present disclosure. In further embodiments, the target gene is AG, SHP1, SHP2, or STK in plants of the present disclosure.

In some embodiments, gRNAs are designed for targeting the NLS (Nuclear Localization Sequence) of the target gene. Mutating the NLS using the targeted base editing system of the present disclosure may prevent the transcription factor being transported to the nucleus, thereby resulting in seedlessness, reduced seed size and/or reduced fruit endocarp in a gene-edited plant. In some embodiments, gRNAs are designed for targeting the MADS-box domain of the target gene. Mutating the MADS-box domain using the targeted base editing system of the present disclosure may prevent the transcription factor from DNA binding, and/or dimerization, thereby resulting in seedlessness, reduced seediness, reduced seed size and/or reduced fruit endocarp in a gene-edited plant.

In some embodiments, gRNAs are designed for targeting an NN motif in the MADS-box domain of the target gene. Mutating the NN motif of MADS-box domain using the targeted base editing system of the present disclosure may prevent the transcription factor from DNA binding, and/or dimerization, thereby resulting in seedlessness, reduced seediness, reduced seed size and/or reduced fruit endocarp in a gene-edited plant. In other embodiments, the NN motif comprise an extended motif Y [A/S]NN (SEQ ID NO:259).

In some embodiments, gRNAs are designed to target the K domain of the target gene that is involved with protein dimerization. Mutating the K domain using the targeted base editing system of the present disclosure may give rise to a malfunction of the MADS-box transcription in dimerization, thereby resulting in seedlessness, reduced seed size and/or reduced fruit endocarp in a gene-edited plant.

In some embodiments, gRNAs are designed to target an YQQ motif (or YQQE (SEQ ID NO: 177) motif) of the K domain of the target gene that is involved with protein dimerization. Mutating the YQQ motif of K domain using the targeted base editing system of the present disclosure may give rise to a malfunction of the MADS-box transcription in dimerization, thereby resulting in seedlessness, reduced seed size and/or reduced fruit endocarp in a gene-edited plant. In other embodiments, the YQQ motif comprise an extended motif, YQQE[A/S][A/S/N/K/T]KL[R/H][Q/H/A/N/R]QI (SEQ ID NO:260) (see e.g., SEQ ID NOs.178-182).

In some embodiments, gRNAs are designed for targeting the C-terminal domain of the target gene. Mutating the C-terminal domain using the targeted base editing system of the present disclosure may negatively affect transcriptional activation or in the formation of ternary or quaternary protein complexes, thereby resulting in seedlessness, reduced seediness, reduced seed size and/or reduced fruit endocarp in a gene-edited plant. The C-terminal domain can be truncated using various gene editing methods.

In some embodiments, gRNAs are designed for targeting the R at position corresponding to 225 of SEQ ID NO:13 or 201 of SEQ ID NO:97 in the ortholog gene of plants of the present disclosure. In some embodiments, the conserved arginine is residue 196 with reference amino acid position numbering of SEQ ID NO:66; residue 197 with reference amino acid position numbering of SEQ ID NOs: 53, 78, 150, 166-171; residue 198 with reference amino acid position numbering of SEQ ID NO:29; residue 199 with reference amino acid position numbering of SEQ ID NO:128; or residue 201 with reference amino acid position numbering of SEQ ID NOs: 152, 154, 156, 158, 160, 162, 164. Mutating the R position using the targeted base editing system of the present disclosure may negatively affect transcriptional activation or in the formation of ternary or quaternary protein complexes, thereby resulting in seedlessness, reduced seed size and/or reduced fruit endocarp in a gene-edited plant.

In some embodiments, the present disclosure teaches a targeted base-editing system using a CRSIPR/CAS system and base editor such as Cytosine base editor (CBE) or Adenine base editor (ABE). In some embodiments, the targeted base-editing system comprises a CRISPR-associated effector domain and a cytidine deaminase domain. This base editing system with a gRNA is to target a C>T (or G>T in the complementary strand) nucleotide base pair change, which would lead to an amino acid substitution at a targeted sequence.

In other embodiments, the targeted base-editing system comprises a CRISPR-associated effector domain and an adenosine deaminase domain. This base editing system with a gRNA is to target a A>G (or T>C in the complementary strand) nucleotide base pair change, which would lead to an amino acid substitution at a targeted sequence.

The present disclosure teaches a targeted base editing system to make dominant negative, semi-dominant, weak loss of function or hypomorphic mutations by targeting conserved amino acids in different MIKC domains of the target gene (i.e., STK, SHP1/SHP2, or AG). In some embodiments, there are amino acid sequences that are well conserved between STK orthologs among plants including, but not limited to the Rosaceae plant family. These plants may comprise a fruit-bearing plant including, but not limited to, blackberries, black raspberries, raspberries, strawberries, cherries, peaches, plums, apricots, apples, pears, quinces, dates, loquats and almonds.

In some embodiments, the well-conserved amino acid sequence found in MIKC domains of the target protein (i.e., STK) is substituted and/or mutated in the plants, parts, and cells of the present disclosure by the targeted base-editing system. In other embodiments, 2, 3, 4, 5, 6, 7, 8, 9, 10, or more well conserved amino acid sequences found in MIKC domains of the target protein (i.e., STK, SHP1/SHP2, or AG) may be substituted and/or mutated in the plants, parts, and cells of the present disclosure by the targeted base-editing system.

There are other well-conserved amino acid sequences such as NN, A, D, YYQ, R, Q, N, R, R, which are conserved at over 95% in the AG-clade transcription factors (e.g. STK) across the plant kingdom as shown in, for example, Tables 1, 1B and 3. Such amino acid substitutions can generate dominant negative, semi-dominant, weak loss of function, or hypomorphic mutations in the modified plant cells, parts, and plants, which may give rise to seedlessness, reduced seediness, a reduction in seed size or a reduction in the endocarp tissue in fruits. The present disclosure teaches that introduction of STK mutation for a specific change in nucleotide at a targeted location can alter molecular function of STK to obtain the desired phenotype such as seedlessness, reduced seediness, a reduction in seed size or a reduction in the endocarp tissue in fruits. In other embodiments, the present disclosure provide a method of generating a specific allele with a single base pair change in planta and performing a targeted base editing to induce seedlessness in fruits of many different plant species.

The present disclosure teaches that an NN motif, a YQQ motif (e.g., YQQE (SEQ ID NO: 177) motif at position 91-94 of SEQ ID NOs: 29, 78, 97, 53, 66, 128, 150, 152, 154, 156, 158, 159, 160, 162, 164, 166-171; or position 116-119 of SEQ ID NO:13), or an R position (225 of SEQ ID NO: 13; position 196 of SEQ ID NO:66; position 197 of SEQ ID NOs: 53, 78, 150, 166-171; position 198 of SEQ ID NO:29; position 199 of SEQ ID NO:128; or position 201 of SEQ ID NOs: 97, 152, 154, 156, 158, 160, 162, 164) have at least 90%, 91%, 92%, 93%, 94%, 95% or more sequence identity in MIKC domains among STK homologues and/or orthologs across the plant kingdom (see e.g., FIGS. 2-5). In some embodiments, an NN motif, a YQQ motif, or an R position is targeted for one or more amino acid substitutions by nucleotide base-editing coding for the corresponding amino acid. In some embodiments, an NN motif is targeted for one or more amino acid substitutions in MADS-box domain of the target protein (i.e., STK, SHP1/SHP2, or AG). In other embodiments, an Y [A/S]NN (SEQ ID NO:259) motif is targeted for one or more amino acid substitutions in MADS-box domain of the target protein (i.e., STK, SHP1/SHP2, or AG) (e.g., position 57 of SEQ ID NOs: 152, 154, 156, 158, 160, 162, 164, or 166-171).

In some embodiments, a YQQ motif is targeted for one or more amino acid substitutions in K domain of the target protein (i.e., STK, SHP1/SHP2, or AG). In other embodi-ments, a YQQE[A/S][A/S/N/K/T]KL[R/H][Q/H/A/N/R]QI (SEQ ID NO:260) motif is targeted for one or more amino acid substitutions in K domain of the target protein (i.e., STK, SHP1/SHP2, or AG).

In some embodiments, an R position (225 of SEQ ID NO:13; position 196 of SEQ ID NO:66; position 197 of SEQ ID NOs: 53, 78, 150, 166-171; position 198 of SEQ ID NO:29; position 199 of SEQ ID NO:128; or position 201 of SEQ ID NOs: 97, 152, 154, 156, 158, 160, 162, 164) is targeted for amino acid substitution in C domain of the target protein (i.e., STK, SHP1/SHP2, or AG). In some embodi-ments, an amino acid substitution may be an R>H or R>L. In some embodiments, a Q position that corresponding to 225 of SEQ ID NO:13 or 201 of SEQ ID NO:97 is found in the SHP transcription factor of grape (VIT_12s0142g00360.0) and similarly, may be targeted for amino acid substitution in C domain of the target SHP protein.

Such amino acid substitutions make dominant negative mutations in the modified plant cells, parts, and plants, which may give rise to seedlessness, reduced seediness, a reduction in seed size or a reduction in the endocarp tissue in fruits. The present disclosure teaches that introduction of a mutation in a STK for a specific change in nucleotide at a targeted location can alter molecular function of STK to obtain the desired phenotype such as seedlessness, reduced seediness, a reduction in seed size or a reduction in the endocarp tissue in fruits. In other embodiments, the present disclosure provide a method of generating a specific allele with a single base pair change in planta and performing a targeted base editing to induce seedlessness in fruits of many different plant species.

Amino acid sequences conservation between distantly related plants suggests selective pressure to maintain func-tion. In some embodiments, mutations that cause reduced seed size or induce seedlessness would be a strong selective pressure. In some embodiments, such mutations are mis-sense mutation and/or nonsense mutation caused by the targeted base editing system of the present disclosure. As the well-conserved amino acids are in the C domain of the target protein, the present disclosure provides candidates for muta-tion to mimic the molecular function of the stk$^{sdi}$ mutant allele described above. In some embodiments, a mutation introduced by the targeted base editing system in plants of the present disclosure gives phenotypes similar to the stk$^{sdi}$ allele in the C-terminal domain of grape STK gene. This type of mutation may not completely remove STK function and not produce infertility.

Gene-Editing Systems

Gene editing generally refers to the process of modifying the nucleotide sequence of a genome, preferably in a precise or pre-determined manner. Examples of methods of gene editing described herein include methods of using site-directed nucleases to cut deoxyribonucleic acid (DNA) at precise target locations in the genome, thereby creating single-strand or double-strand DNA breaks at particular locations within the genome. Such breaks can be and regu-larly are repaired by natural, endogenous cellular processes, such as homology-directed repair (HDR) and non-homolo-gous end joining (NHEJ). These two main DNA repair processes consist of a family of alternative pathways. NHEJ directly joins the DNA ends resulting from a double-strand break, sometimes with the loss or addition of nucleotide sequence, which may disrupt or enhance gene expression. HDR utilizes a homologous sequence, or donor sequence, as a template for inserting a defined DNA sequence at the break point. The homologous sequence can be in the endogenous genome, such as a sister chromatid. Alternatively, the donor can be an exogenous nucleic acid, such as a plasmid, a single-strand oligonucleotide, a double-stranded oligonucleotide, a duplex oligonucleotide or a virus, that has regions of high homology with the nuclease-cleaved locus, but which can also contain additional sequence or sequence changes including deletions that can be incorporated into the cleaved target locus. A third repair mechanism can be microhomology-mediated end joining (MMEJ), also referred to as "Alternative NHEJ," in which the genetic outcome is similar to NHEJ in that small deletions and insertions can occur at the cleavage site. MMEJ can make use of homologous sequences of a few base-pairs flanking the DNA break site to drive a more favored DNA end joining repair outcome, and recent reports have further elucidated the molecular mechanism of this process; see, e.g., Cho and Greenberg, Nature 518, 174-76 (2015); Kent et al., Nature Structural and Molecular Biology, Adv. Online doi: 10.1038/nsmb.2961 (2015); Mateos-Gomez et al., Nature 518, 254-57 (2015); Ceccaldi et al., Nature 528, 258-62 (2015). In some instances, it may be possible to predict likely repair outcomes based on analysis of potential microhomologies at the site of the DNA break.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair (HDR) mechanisms. This process requires nucleotide sequence homology, uses a "donor" molecule as a template to repair a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or synthesis-dependent strand annealing, in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

Gene editing methods contemplated in various embodiments comprise engineered nucleases, designed to bind and cleave a target DNA sequence in a gene of interest, such as AG clade transcription factor genes described herein. The engineered nucleases contemplated in particular embodiments, can be used to introduce a double-strand break in a target polynucleotide sequence, which may be repaired (i) by non-homologous end joining (NHEJ) in the absence of a polynucleotide template, e.g., a donor repair template, or (ii) by homology directed repair (HDR), i.e., homologous recombination, in the presence of a donor repair template. Engineered nucleases contemplated in certain embodiments, can also be engineered as nickases, which generate single-stranded DNA breaks that can be repaired using the cell's base-excision-repair (BER) machinery or homologous recombination in the presence of a donor repair template.

Gene editing via sequence-specific nucleases is known in the art. See references (1) Carroll, D. (2011) Genome engineering with zinc-finger nucleases. Genetics, 188, 773-82; (2) Wood, A. J. et al. (2011) Targeted gene editing across species using ZFNs and TALENs. Science (New York, N.Y.), 333, 307; (3) Perez-Pinera, P. et al. (2012) Advances in targeted gene editing. Current opinion in chemical biology, 16, 268-77, each of which is hereby incorporated by reference in their entireties.

A nuclease-mediated double-stranded DNA (dsDNA) break in the genome can be repaired by two main mechanisms: Non-Homologous End Joining (NHEJ), which frequently results in the introduction of non-specific insertions and deletions (indels), or homology directed repair (HDR), which incorporates a homologous strand as a repair template. See Symington, L. S. and Gautier, J. (2011) Double-strand break end resection and repair pathway choice. Annual review of genetics, 45, 247-71, which is hereby incorporated by reference in its entirety.

When a sequence-specific nuclease is delivered along with a homologous donor DNA construct containing the desired mutations, gene targeting efficiencies are increased by 1000-fold compared to just the donor construct alone. See Urnov et al. (2005) Highly efficient endogenous human gene correction using designed zinc-finger nucleases. Nature, 435, 646-51, which is hereby incorporated by reference in its entirety.

In some embodiments, the gene editing techniques of the present disclosure are used for plants that are modified using any gene editing tool, including, but not limited to: ZFNs, TALENS, CRISPR, and Mega nuclease technologies. In some embodiments, the gene editing tools of the present disclosure comprise proteins or polynucleotides which have been custom designed to target and cut at specific deoxyribonucleic acid (DNA) sequences. In some embodiments, gene editing proteins are capable of directly recognizing and binding to selected DNA sequences. In other embodiments, the gene editing tools of the present disclosure form complexes, wherein nuclease components rely on nucleic acid molecules for binding and recruiting the complex to the target DNA sequence.

In some embodiments, the single component gene editing tools comprise a binding domain capable of recognizing specific DNA sequences in the genome of the plant and a nuclease that cuts double-stranded DNA. The rationale of gene editing technology taught in the present disclosure is the use of a tool that allows the introduction of site-specific mutations in the plant genome or the site-specific integration of genes.

Many methods are available for delivering genes into plant cells, e.g. transfection, electroporation, viral vectors and *Agrobacterium* mediated transfer. Genes can be expressed transiently from a plasmid vector. Once expressed, the genes generate the targeted mutation that will be stably inherited, even after the degradation of the plasmid containing the gene.

Customizable nucleases can be used to make targeted double-stranded breaks (DSB) in living cells, the repair of which can be exploited to induce desired sequence changes. Two competing pathways effect repairs in most cells, including plant cells. Repair of a nuclease-induced DSB by non-homologous end joining (NHEJ) leads to the introduction of insertion/deletion mutations (indels) with high frequencies. By contrast, DSB repair by homology directed repair (HDR) with a user-supplied "donor template" DNA can lead to the introduction of specific alterations (e.g., point mutations and insertions) or the correction of mutant sequences back to wild-type.

Nucleases

In some embodiments, a plant cell of interest is generated by gene editing accomplished with engineered nucleases targeting one or more loci that contributes to MADS box transcription factor. Without wishing to be bound to any particular theory, it is contemplated that engineered nucleases are designed to precisely disrupt one or more MADS box transcription factors through gene editing and, once nuclease activity and specificity are validated, lead to pre-dictable disruption of MADS box transcription factor expression and/or function, thereby offering altered fruit development, such as a seedless, reduced seediness, reduced seediness phenotype and/or a reduced endocarp in fruits of the plants.

The engineered nucleases described herein generate single-stranded DNA nicks or double-stranded DNA breaks (DSB) in a target sequence. Furthermore, a DSB can be achieved in the target DNA by the use of two nucleases generating single-stranded micks (nickases). Each nickase cleaves one strand of the DNA and the use of two or more nickases can create a double strand break (e.g., a staggered double-stranded break) in a target DNA sequence. In other embodiments, the nucleases are used in combination with a donor repair template, which is introduced into the target sequence at the DNA break-site via homologous recombi-nation at a DSB.

Engineered nucleases described herein that are suitable for gene editing comprise one or more DNA binding domains and one or more DNA cleavage domains (e.g., one or more endonuclease and/or exonuclease domains), and optionally, one or more linkers contemplated herein. An "engineered nuclease" refers to a nuclease comprising one or more DNA binding domains and one or more DNA cleavage domains, wherein the nuclease has been designed and/or modified to bind a DNA binding target sequence adjacent to a DNA cleavage target sequence. The engineered nuclease may be designed and/or modified from a naturally occurring nuclease or from a previously engineered nucle-ase.

Illustrative examples of nucleases that may be engineered to bind and cleave a target sequence include, but are not limited to homing endonucleases (meganucleases), mega-TALs, transcription activator-like effector nucleases (TAL-ENs), zinc finger nucleases (ZFNs), and clustered regularly-interspaced short palindromic repeats (CRISPR)/Cas nuclease systems. In some embodiments, the nucleases contemplated herein comprise one or more heterologous DNA-binding and cleavage domains (e.g., ZFNs, TALENs, megaTALs), (Boissel et al., 2014; Christian et al., 2010). In other embodiments, the DNA-binding domain of a naturally occurring nuclease may be altered to bind to a selected target site (e.g., a meganuclease that has been engineered to bind to site different than the cognate binding site). For example, meganucleases have been designed to bind target sites different from their cognate binding sites (Boissel et al., 2014). In particular embodiments, a nuclease requires a nucleic acid sequence to target the nuclease to a target site (e.g., CRISPR/Cas).

(i) TALEN

Transcription activator-like effector nucleases (TALENs) comprise a nonspecific DNA-cleaving nuclease (e.g., a Fok I cleavage domain) fused to a DNA-binding domain that can be easily engineered so that TALENs can target essentially any sequence (See, e.g., Joung and Sander, Nature Reviews Molecular Cell Biology 14:49-55 (2013)). Methods for generating engineered TALENs are known in the art, see, e.g., the fast ligation-based automatable solid-phase hight-hroughput (FLASH) system described in U.S. Ser. No. 61/610,212, and Reyon et al., Nature Biotechnology 30,460-465 (2012); as well as the methods described in Bogdanove & Voytas, Science 333, 1843-1846 (2011); Bogdanove et al., Curr Opin Plant Biol 13, 394-401 (2010); Scholze & Boch, J. Curr Opin Microbiol (2011); Boch et al., Science 326, 1509-1512 (2009); Moscou & Bogdanove, Science 326, 1501 (2009); Miller et al., Nat Biotechnol 29, 143-148 (2011); Morbitzer et al., T. Proc Natl Acad Sci USA 107, 21617-21622 (2010); Morbitzer et al., Nucleic Acids Res 39, 5790-5799 (2011); Zhang et al., Nat Biotechnol 29, 149-153 (2011); Geissler et al., PLOS ONE 6, e19509 (2011); Weber et al., PLOS ONE 6, e19722 (2011); Christian et al., Genetics 186, 757-761 (2010); Li et al., Nucleic Acids Res 39, 359-372 (2011); Mahfouz et al., Proc Natl Acad Sci USA 108, 2623-2628 (2011); Mussolino et al., Nucleic Acids Res (2011); Li et al., Nucleic Acids Res 39, 6315-6325 (2011); Cermak et al., Nucleic Acids Res 39, e82 (2011); Wood et al., Science 333, 307 (2011); Hockemeye et al. Nat Bio-technol 29, 731-734 (2011); Tesson et al., Nat Biotechnol 29, 695-696 (2011); Sander et al., Nat Biotechnol 29, 697698 (2011); Huang et al., Nat Biotechnol 29, 699-700 (2011); and Zhang et al., Nat Biotechnol 29, 149-153 (2011); all of which are incorporated herein by reference in their entirety.

In some embodiments, a TALEN that binds to and cleaves a target region of a locus that contributes to MADS box transcription factor. A "TALEN" refers to an engineered nuclease comprising an engineered TALE DNA binding domain contemplated elsewhere herein and an endonuclease domain (or endonuclease half-domain thereof), and option-ally comprise one or more linkers and/or additional func-tional domains, e.g., an end-processing enzymatic domain of an end-processing enzyme that exhibits 5-3' exonuclease, 5-3' alkaline exonuclease, 3-5'exonuclease (e.g., Trex2), 5' flap endonuclease, helicase or template-independent DNA polymerases activity.

In some embodiments, plants of interest are modified through Transcription activator-like (TAL) effector nucle-ases (TALENs). TALENS are polypeptides with repeat polypeptide arms capable of recognizing and binding to specific nucleic acid regions. By engineering the polypep-tide arms to recognize selected target sequences, the TAL nucleases can be use to direct double stranded DNA breaks to specific genomic regions. These breaks can then be repaired via recombination to edit, delete, insert, or other-wise modify the DNA of a host organism. In some embodi-ments, TALENSs are used alone for gene editing (e.g., for the deletion or disruption of a gene). In other embodiments, TALs are used in conjunction with donor sequences and/or other recombination factor proteins that will assist in the Non-homologous end joining (NHEJ) process to replace the targeted DNA region. For more information on the TAL-mediated gene editing compositions and methods of the present disclosure, see U.S. Pat. Nos. 8,440,432; 8,440,432; 8,450,471; 8,586,526; 8,586,363; 8,592,645; 8,697,853; 8,704,041; 8,921,112; and 8,912,138, each of which is hereby incorporated in its entirety for all purposes.

(ii) MegaTALs

Various illustrative embodiments contemplate a mega-TAL nuclease that binds to and cleaves a target region of a locus that contributes to MADS box transcription factor. A "megaTAL" refers to an engineered nuclease comprising an engineered TALE DNA binding domain and an engineered meganuclease, and optionally comprise one or more linkers and/or additional functional domains, e.g., an end-process-ing enzymatic domain of an end-processing enzyme that exhibits 5-3' exonuclease, 5-3' alkaline exonuclease, 3-5'exonuclease, 5' flap endonuclease, helicase or template-independent DNA polymerases activity.

A "TALE DNA binding domain" is the DNA binding portion of transcription activator-like effectors (TALE or TAL-effectors), which mimics plant transcriptional activators to manipulate the plant transcriptome (see e.g., Kay et al., 2007. *Science* 318:648-651). TALE DNA binding domains contemplated in particular embodiments are engineered de novo or from naturally occurring TALEs. Illustrative examples of TALE proteins for deriving and designing DNA binding domains are disclosed in U.S. Pat. No. 9,017,967, and references cited therein, all of which are incorporated herein by reference in their entireties.

In some embodiments, plants of interest are modified through megaTALs. In some embodiments, megaTALs are engineered endonucleases capable of targeting selected DNA sequences and inducing DNA breaks.

(iii) Meganucleases/Homing Endonucleases (HE)

Meganucleases are sequence-specific endonucleases originating from a variety of organisms such as bacteria, yeast, algae and plant organelles. A number of Meganucleases are known in the art, see, e.g., WO 2012010976 (Meganuclease variants cleaving DNA target sequences of the TERT gene); U.S. Pat. Nos. 8,021,867; 8,119,361 and 8,119,381 (I-CreI meganucleases); U.S. Pat. No. 7,897,372 (I-CreI Meganuclease Variants with Modified Specificity).

In some embodiments, a homing endonuclease or meganuclease is engineered to bind to, and to introduce single-stranded nicks or double-strand breaks (DSBs) in, one or more loci that contribute to MADS box transcription factor. "Homing endonuclease" and "meganuclease" are used interchangeably and refer to naturally-occurring nucleases or engineered meganucleases that-recognize 12-45 base-pair cleavage sites and are commonly grouped into five families based on sequence and structure motifs: LAGLIDADG (SEQ ID NO:261), GIY-YIG, HNH, His-Cys box, and PD-(D/E) XK.

Engineered HEs do not exist in nature and can be obtained by recombinant DNA technology or by random mutagenesis. Engineered HEs may be obtained by making one or more amino acid alterations, e.g., mutating, substituting, adding, or deleting one or more amino acids, in a naturally occurring HE or previously engineered HE. In particular embodiments, an engineered HE comprises one or more amino acid alterations to the DNA recognition interface. Engineered HEs contemplated in particular embodiments may further comprise one or more linkers and/or additional functional domains, e.g., an end-processing enzymatic domain of an end-processing enzyme that exhibits 5-3' exonuclease, 5-3' alkaline exonuclease, 3-5'exonuclease, 5' flap endonuclease, helicase or template-independent DNA polymerases activity.

In some embodiments, plants of interest are modified through meganucleases. In some embodiments, meganucleases are engineered endonucleases capable of targeting selected DNA sequences and inducing DNA breaks. In some embodiments, new meganucleases targeting specific regions are developed through recombinant techniques which combine the DNA binding motifs from various other identified nucleases. In other embodiments, new meganucleases are created through semi-rational mutational analysis, which attempts to modify the structure of existing binding domains to obtain specificity for additional sequences. For more information on the use of meganucleases for genome editing, see Silva et al., 2011 Current Gene Therapy 11 pg 11-27; and Stoddard et al., 2014 Mobile DNA 5 pg 7, each of which is hereby incorporated in its entirety for all purposes.

(iv) ZFN

Zinc-finger nucleases (ZFNs) are composed of programmable, sequence-specific zinc finger DNA-binding modules (see above) linked to a nonspecific DNA cleavage domain, e.g., a Fok I cleavage domain. Methods for making and using ZFNs are known in the art, see, e.g., (Maeder et al., 2008, Mol. Cell, 31:294-301; Joung et al., 2010, Nat. Methods, 7:91-92; Isalan et al., 2001, Nat. Biotechnol., 19:656-660; Sander et al., Nat Methods. 8 (1): 67-9, 2011; Bhakta et al., Genome Res. 23 (3): 530-8, 2013). In some embodiments, the ZFNs are described in, or are generated as described in, WO 2011/017293 or WO 2004/099366. Additional suitable ZFNs are described in U.S. Pat. Nos. 6,511, 808, 6,013,453, 6,007,988, and 6,503,717 and U.S. patent application 2002/0160940.

In some embodiments, a zinc finger nuclease (ZFN) that binds to and cleaves a target region of a locus that contributes to MADS box transcription factor. A "ZFN" refers to an engineered nuclease comprising one or more zinc finger DNA binding domains and an endonuclease domain (or endonuclease half-domain thereof), and optionally comprise one or more linkers and/or additional functional domains, e.g., an end-processing enzymatic domain of an end-processing enzyme that exhibits 5-3' exonuclease, 5-3' alkaline exonuclease, 3-5'exonuclease, 5' flap endonuclease, helicase or template-independent DNA polymerases activity.

In one embodiment, targeted double-stranded cleavage is achieved using two ZFNs, each comprising an endonuclease half-domain can be used to reconstitute a catalytically active cleavage domain. In another embodiment, targeted double-stranded cleavage is achieved with a single polypeptide comprising one or more zinc finger DNA binding domains and two endonuclease half domains.

In one embodiment, a ZFN comprises a TALE DNA binding domain contemplated elsewhere herein, a zinc finger DNA binding domain, and an endonuclease domain (or endonuclease half-domain) contemplated elsewhere herein.

In one embodiment, a ZFN comprises a zinc finger DNA binding domain, and a meganuclease contemplated elsewhere herein.

In particular embodiments, the ZFN comprises a zinger finger DNA binding domain that has one, two, three, four, five, six, seven, or eight or more zinger finger motifs and an endonuclease domain (or endonuclease half-domain). Typically, a single zinc finger motif is about 30 amino acids in length. Zinc fingers motifs include both canonical $C_2H_2$ zinc fingers, and non-canonical zinc fingers such as, for example, $C_3H$ zinc fingers and $C_4$ zinc fingers.

Zinc finger binding domains can be engineered to bind any DNA sequence. Candidate zinc finger DNA binding domains for a given 3 bp DNA target sequence have been identified and modular assembly strategies have been devised for linking a plurality of the domains into a multi-finger peptide targeted to the corresponding composite DNA target sequence. Other suitable methods known in the art can also be used to design and construct nucleic acids encoding zinc finger DNA binding domains, e.g., phage display, random mutagenesis, combinatorial libraries, computer/rational design, affinity selection, PCR, cloning from cDNA or genomic libraries, synthetic construction and the like. (See, e.g., U.S. Pat. No. 5,786,538; Wu et al., *PNAS* 92:344348 (1995); Jamieson et al., *Biochemistry* 33:5689-5695 (1994); Rebar & Pabo, *Science* 263:671673 (1994); Choo & Klug, *PNAS* 91:11163-11167 (1994); Choo & Klug, *PNAS* 91:11168-11172 (1994); Desjarlais & Berg, *PNAS* 90:2256-2260 (1993); Desjarlais & Berg, *PNAS* 89:7345-7349 (1992); Pomerantz et al., *Science* 267:93-96 (1995); Pomerantz et al., *PNAS* 92:9752-9756 (1995); Liu et al., *PNAS*

94:5525-5530 (1997); Griesman & Pabo, Science 275:657-661 (1997); Desjarlais & Berg, *PNAS* 91:11-99-11103 (1994)).

Individual zinc finger motifs bind to a three or four nucleotide sequence. The length of a sequence to which a zinc finger binding domain is engineered to bind (e.g., a target sequence) will determine the number of zinc finger motifs in an engineered zinc finger binding domain. For example, for ZFNs in which the zinc finger motifs do not bind to overlapping subsites, a six-nucleotide target sequence is bound by a two-finger binding domain; a nine-nucleotide target sequence is bound by a three-finger binding domain, etc. In particular embodiments, DNA binding sites for individual zinc fingers motifs in a target site need not be contiguous, but can be separated by one or several nucleotides, depending on the length and nature of the linker sequences between the zinc finger motifs in a multi-finger binding domain.

In some embodiments, plants of interest are modified through Zinc Finger Nucleases. Three variants of the ZFN technology are recognized in plant genome engineering (with applications ranging from producing single mutations or short deletions/insertions in the case of ZFN-1 and -2 techniques up to targeted introduction of new genes in the case of the ZFN-3 technique):

ZFN-1: Genes encoding ZFNs are delivered to plant cells without a repair template. The ZFNs bind to the plant DNA and generate site specific double-strand breaks (DSBs). The natural DNA-repair process (which occurs through nonhomologous end-joining, NHEJ) leads to site specific mutations, in one or only a few base pairs, or to short deletions or insertions.

ZFN-2: Genes encoding ZFNs are delivered to plant cells along with a repair template homologous to the targeted area, spanning a few kilo base pairs. The ZFNs bind to the plant DNA and generate site-specific DSBs. Natural gene repair mechanisms generate site-specific point mutations e.g. changes to one or a few base pairs through homologous recombination and the copying of the repair template.

ZFN-3: Genes encoding ZFNs are delivered to plant cells along with a stretch of DNA which can be several kilo base pairs long and the ends of which are homologous to the DNA sequences flanking the cleavage site. As a result, the DNA stretch is inserted into the plant genome in a site specific manner.

(v) FokI

FokI is a type IIs restriction endonuclease that includes a DNA recognition domain and a catalytic (endonuclease) domain. The fusion proteins described herein can include all of FokI or just the catalytic endonuclease domain, e.g., amino acids 388-583 or 408-583 of GenBank Acc. No. AAA24927.1, e.g., as described in WO95/09233, Li et al., Nucleic Acids Res. 39 (1): 359-372 (2011); Cathomen and Joung, Mol. Ther. 16:1200-1207 (2008), or a mutated form of FokI as described in Miller et al. Nat Biotechnol 25:778-785 (2007); Szczepek et al., Nat Biotechnol 25:786-793 (2007); or Bitinaite et al., Proc. Natl. Acad. Sci. USA. 95:10570-10575 (1998). See also Tsai et al., Nat Biotechnol. 2014 June; 32 (6): 569-76.

In some embodiments, plants of interest are modified through FokI endonucleases.

Targeted CRISPR-Cas Systems

Herein, the term "targeted base-editing system" refers to a protein, nucleic acid, or combination thereof that is capable of substituting a single nucleotide at a target site and modifying an endogenous target DNA sequence when introduced into a cell, thereby causing one or more amino acid substitutions. Numerous gene editing systems suitable for use in the methods of the present disclosure, include, but are not limited to, zinc-finger nuclease systems, TALEN systems, and CRISPR/Cas systems.

In some embodiments, a nuclease-inactivated CRISPR/Cas system having a base deaminase activity is utilized for a targeted base-editing. In other aspects, a nickase is used.

In some embodiments, the targeted base-editing system can mediate a change in the sequence of the endogenous target gene, for example, by introducing one or more point mutations into the endogenous target sequence, such as by substituting C with T (or G with A) or A with G (or T with C) in the endogenous target sequence In some embodiments, the targeted base-editing system may mediate a change in the expression of the protein encoded by the endogenous target gene. In such embodiments, the targeted base-editing system may regulate the expression of the encoded protein by modifications of the endogenous target DNA sequence, or by acting on the mRNA product encoded by the DNA sequence. In some embodiments, the targeted base-editing system may result in the expression of a modified endogenous protein. In some embodiments, the modifications to the endogenous DNA sequence mediated by the targeted base-editing system result in an altered function of the modified endogenous protein as compared to the corresponding endogenous protein in an unmodified plant cell. In such embodiments, the expression level of the modified endogenous protein may be increased, decreased or may be the same, or substantially similar to, the expression level of the corresponding endogenous protein in an unmodified plant cell.

The present disclosure provides a targeted base-editing system to edit a target nucleotide sequence in the genome of a plant, comprising at least one of the followings; i) a base editing fusion protein, and a guide RNA; ii) an expression construct comprising a nucleotide sequence encoding a base editing fusion protein, and a guide RNA; iii) a base editing fusion protein, and an expression construction comprising a nucleotide sequence encoding a guide RNA; iv) an expression construct comprising a nucleotide sequence encoding a base editing fusion protein, and an expression construct comprising a nucleotide sequence encoding a guide RNA; v) an expression construct comprising a nucleotide sequence encoding base editing fusion protein and a nucleotide sequence encoding guide RNA; wherein said base editing fusion protein contains a CRISPR associated effector domain and a deaminase domain, said guide RNA can target said base editing fusion protein to the target sequence in the plant genome. In some embodiments, a targeted base-editing fusion protein comprises a nuclease-inactivated CRISPR-associated effector domain and a cytidine deaminase domain. In some embodiments, a targeted base-editing fusion protein comprises a nuclease-inactivated CRISPR-associated effector domain and an adenosine deaminase domain.

Fusion proteins of the invention may comprise sequence-specific DNA binding domains, CRISPR-Cas polypeptides, and/or deaminase domains fused to peptide tags or affinity polypeptides that interact with the peptide tags, as known in the art, for use in recruiting the deaminase to the target nucleic acid. Methods of recruiting may also comprise guide nucleic acids linked to RNA recruiting motifs and deaminases fused to affinity polypeptides capable of interacting with RNA recruiting motifs, thereby recruiting the deaminase to the target nucleic acid. Alternatively, chemical interactions may be used to recruit polypeptides (e.g., deaminases) to a target nucleic acid.

A peptide tag (e.g., epitope) useful with this invention may include, but is not limited to, a GCN4 peptide tag (e.g., Sun-Tag), a c-Myc affinity tag, an HA affinity tag, a His affinity tag, an S affinity tag, a methionine-His affinity tag, an RGD-His affinity tag, a FLAG octapeptide, a strep tag or strep tag II, a V5 tag, and/or a VSV-G epitope. Any epitope that may be linked to a polypeptide and for which there is a corresponding affinity polypeptide that may be linked to another polypeptide may be used with this invention as a peptide tag. In some embodiments, a peptide tag may comprise 1 or 2 or more copies of a peptide tag (e.g., repeat unit, multimerized epitope (e.g., tandem repeats)) (e.g., 1, 2, 3, 4, 5, 6, 7, 8, 9, 10, 11, 12, 13, 14, 15, 16, 17, 18, 19, 20, 21, 22, 23, 24, 25 or more repeat units. In some embodiments, an affinity polypeptide that interacts with/binds to a peptide tag may be an antibody. In some embodiments, the antibody may be a scFv antibody. In some embodiments, an affinity polypeptide that binds to a peptide tag may be synthetic (e.g., evolved for affinity interaction) including, but not limited to, an affibody, an anticalin, a monobody and/or a DARPin (see, e.g., Sha et al., *Protein Sci.* 26 (5): 910-924 (2017)); Gilbreth (*Curr Opin Struc Biol* 22 (4): 413-420 (2013)), U.S. Pat. No. 9,982,053, each of which are incorporated by reference in their entireties for the teachings relevant to affibodies, anticalins, monobodies and/or DARPins.

In some embodiments, a guide nucleic acid may be linked to an RNA recruiting motif, and a polypeptide to be recruited (e.g., a deaminase) may be fused to an affinity polypeptide that binds to the RNA recruiting motif, wherein the guide binds to the target nucleic acid and the RNA recruiting motif binds to the affinity polypeptide, thereby recruiting the polypeptide to the guide and contacting the target nucleic acid with the polypeptide (e.g., deaminase). In some embodiments, two or more polypeptides may be recruited to a guide nucleic acid, thereby contacting the target nucleic acid with two or more polypeptides (e.g., deaminases).

In some embodiments, a polypeptide fused to an affinity polypeptide may be a reverse transcriptase and the guide nucleic acid may be an extended guide nucleic acid linked to an RNA recruiting motif. In some embodiments, an RNA recruiting motif may be located on the 3' end of the extended portion of an extended guide nucleic acid (e.g., 5'-3', repeat-spacer-extended portion (RT template-primer binding site)-RNA recruiting motif). In some embodiments, an RNA recruiting motif may be embedded in the extended portion.

In some embodiments of the invention, an extended guide RNA and/or guide RNA may be linked to one or to two or more RNA recruiting motifs (e.g., 1, 2, 3, 4, 5, 6, 7, 8, 9, 10 or more motifs; e.g., at least 10 to about 25 motifs), optionally wherein the two or more RNA recruiting motifs may be the same RNA recruiting motif or different RNA recruiting motifs. In some embodiments, an RNA recruiting motif and corresponding affinity polypeptide may include, but is not limited, to a telomerase Ku binding motif (e.g., Ku binding hairpin) and the corresponding affinity polypeptide Ku (e.g., Ku heterodimer), a telomerase Sm7 binding motif and the corresponding affinity polypeptide Sm7, an MS2 phage operator stem-loop and the corresponding affinity polypeptide MS2 Coat Protein (MCP), a PP7 phage operator stem-loop and the corresponding affinity polypeptide PP7 Coat Protein (PCP), an SfMu phage Com stem-loop and the corresponding affinity polypeptide Com RNA binding protein, a PUF binding site (PBS) and the affinity polypeptide *Pumilio*/fem-3 mRNA binding factor (PUF), and/or a synthetic RNA-aptamer and the aptamer ligand as the corresponding affinity polypeptide. In some embodiments, the RNA recruiting motif and corresponding affinity polypeptide may be an MS2 phage operator stem-loop and the affinity polypeptide MS2 Coat Protein (MCP). In some embodiments, the RNA recruiting motif and corresponding affinity polypeptide may be a PUF binding site (PBS) and the affinity polypeptide *Pumilio*/fem-3 mRNA binding factor (PUF).

In some embodiments, the components for recruiting polypeptides and nucleic acids may those that function through chemical interactions that may include, but are not limited to, rapamycin-inducible dimerization of FRB-FKBP; Biotin-streptavidin; SNAP tag; Halo tag; CLIP tag; DmrA-DmrC heterodimer induced by a compound; bifunctional ligand (e.g., fusion of two protein-binding chemicals together; e.g. dihyrofolate reductase (DHFR).

In some embodiments, the targeted base-editing system described herein contains CRISPR (Clustered Regularly Interspaced Short Palindromic Repeats)/Cas (CRISPR Associated) nuclease system as a CRISPR-associated effector domain. In some embodiments, the CRISPR/Cas system is a Class 2 system. Class 2 CRISPR/Cas systems are divided into three types: Type II, Type V, and Type VI systems. In some embodiments, the CRISPR/Cas system is a Class 2 Type II system, utilizing the Cas9 protein. In such embodiments, the site-directed modifying polypeptide is a Cas9 DNA endonuclease (or variant thereof) and the nucleic acid guide molecule is a guide RNA (gRNA). In some embodiments, the CRISPR/Cas system is a Class 2 Type V system, utilizing the Cas12 proteins (e.g., Cas12a (also known as Cpf1), Cas12b (also known as C2c1), Cas12c (also known as C2c3), Cas12d (also known as CasY), and Cas12e (also known as CasX)). In some embodiments, the site-directed modifying polypeptide is a Cas12 DNA endonuclease (or variant thereof) and the nucleic acid guide molecule is a gRNA. In some embodiments, the CRISPR/Cas system is a Class 2 and Type VI system, utilizing the Cas13 proteins (e.g., Cas13a (also known as C2c2), Cas13b, and Cas13c). (See, Pyzocha et al., ACS Chemical Biology, 13 (2), 347-356). In some embodiments, the site-directed modifying polypeptide is a Cas13 RNA riboendonuclease and the nucleic acid guide molecule is a gRNA.

A Cas polypeptide refers to a polypeptide that can interact with a gRNA molecule and, in concert with the gRNA molecule, home or localize to a target DNA or target RNA sequence. Cas polypeptides include naturally occurring Cas proteins and engineered, altered, or otherwise modified Cas proteins that differ by one or more amino acid residues from a naturally-occurring Cas sequence.

A guide RNA (gRNA) comprises two segments, a DNA-binding segment and a protein binding segment. In some embodiments, the protein-binding segment of a gRNA is comprised in one RNA molecule and the DNA-binding segment is comprised in another separate RNA molecule. Such embodiments are referred to herein as "double-molecule gRNAs" or "two molecule gRNA" or "dual gRNAs." In some embodiments, the gRNA is a single RNA molecule and is referred to herein as a "single-guide RNA" or an "sgRNA." The term "guide RNA" or "gRNA" is inclusive, referring both to two-molecule guide RNAs and sgRNAs.

The protein-binding segment of a gRNA comprises, in part, two complementary stretches of nucleotides that hybridize to one another to form a double stranded RNA duplex (dsRNA duplex), which facilitates binding to the Cas protein. The nucleic acid-binding segment (or "nucleic acid-binding sequence") of a gRNA comprises a nucleotide sequence that is complementary to and capable of binding to a specific target nucleic acid sequence. The protein binding segment of the gRNA interacts with a Cas polypeptide and the interaction of the gRNA molecule and site-directed modifying polypeptide results in Cas binding to the endogenous nucleic acid sequence and produces one or more modifications within or around the target nucleic acid sequence. The precise location of the target modification site is determined by both (i) base-pairing complementarity between the gRNA and the target nucleic acid sequence; and (ii) the location of a short motif, referred to as the proto-spacer adjacent motif (PAM), in the target DNA sequence (referred to as a protospacer flanking sequence (PFS) in target RNA sequences). The PAM/PFS sequence is required for Cas binding to the target nucleic acid sequence. A variety of PAM/PFS sequences are known in the art and are suitable for use with a particular Cas endonuclease (e.g., a Cas9 endonuclease) (See e.g., Nat Methods. 2013 November; 10 (11): 1116-1121 and Sci Rep. 2014; 4:5405). In some embodiments, the PAM sequence is located within 50 base pairs of the target modification site in a target DNA sequence. In some embodiments, the PAM sequence is located within 10 base pairs of the target modification site in a target DNA sequence. The DNA sequences that can be targeted by this method are limited only by the relative distance of the PAM sequence to the target modification site and the presence of a unique 20 base pair sequence to mediate sequence-specific, gRNA-mediated Cas binding. In some embodiments, the PFS sequence is located at the 3' end of the target RNA sequence. In some embodiments, the target modification site is located at the 5' terminus of the target locus. In some embodiments, the target modification site is located at the 3' end of the target locus. In some embodiments, the target modification site is located within an intron or an exon of the target locus.

In some embodiments, the present disclosure provides a polynucleotide encoding a gRNA. In some embodiments, a gRNA-encoding nucleic acid is comprised in an expression vector, e.g., a recombinant expression vector. In some embodiments, the present disclosure provides a polynucleotide encoding a site-directed modifying polypeptide. In some embodiments, the polynucleotide encoding a site-directed modifying polypeptide is comprised in an expression vector, e.g., a recombinant expression vector.

1. Cas Proteins

In some embodiments, the targeted base-editing system comprises a Cas protein as a CRISPR-associated effector domain. Cas molecules of a variety of species can be used in the methods and compositions described herein, including Cas molecules derived from *S. pyogenes, S. aureus, N. meningitidis, S. thermophiles, Acidovorax avenae, Actinobacillus pleuropneumoniae, Actinobacillus succinogenes, Actinobacillus suis, Actinomyces* sp., *Cycliphilusdenitrificans, Aminomonas paucivorans, Bacillus cereus, Bacillus smithii, Bacillus thuringiensis, Bacteroides* sp., *Blastopirellula marina, Bradyrhizobium* sp., *Brevibacillus laterospoxus, Campylobacter coli, Campylobacter jejuni, Campylobacter lari, Candidatus puniceispirillum, Clostridium cellulolyticum, Clostridium perfringens, Corynebacterium accolens, Corynebacterium diphtheria, Corynebacterium matruchotii, Dinoroseobacter shibae, Eubacterium dolichum, Gammaproteobacterium, Gluconacetobacter diazotrophicus, Haemophilus parainfluenzae, Haemophilus sputomm, Helicobacter canadensis, Helicobacter cinaedi, Helicobacter mustelae, Ilyobacter polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cinerea, Neisseria flavescens,*

*Neisseria lactamica, Neisseria meningitidis, Neisseria* sp., *Neisseria wadsworthii, Nitrosomonas* sp., *Parvibaculum lavamentivorans, Pasteurella multocida, Phascolarctobacterium succinatutens, Ralstonia syzygii, Rhodopseudomonas palustris, Rhodovulum* sp., *Simonsiella muelleri, Sphingomonas* sp., *Sporolactobacillus vineae, Staphylococcus aureus, Staphylococcus lugdunensis, Streptococcus* sp., *Subdoligranulum* sp., *Tistrella mobilis, Treponema* sp., or *Verminephrobacter eiseniae.*

In some embodiments, the Cas protein is a naturally-occurring Cas protein. In other embodiments, the Cas protein is an engineered Cas protein. In some embodiments, the Cas endonuclease includes, but is not limited to, C2C1, C2C3, Cpf1 (also referred to as Cas12a), Cas12b, Cas12c, Cas12d, Cas12e, Cas13a, Cas13b, Cas13c, Cas13d, Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4.

In some embodiments, the Cas protein is an endoribonuclease such as a Cas13 protein. In some embodiments, the Cas13 protein is a Cas13a (Abudayyeh et al., Nature 550 (2017), 280284), Cas13b (Cox et al., Science (2017) 358: 6336, 1019-1027), Cas13c (Cox et al., Science (2017) 358:6336, 1019-1027), or Cas13d (Zhang et al., Cell 175 (2018), 212-223) protein In some embodiments, the Cas protein is a wild type or naturally occurring Cas9 protein or a Cas9 ortholog. Wild type Cas9 is a multi-domain enzyme that uses an HNH nuclease domain to cleave the target strand of DNA and a RuvC-like domain to cleave the non-target strand. Binding of WT Cas9 to DNA based on gRNA specificity results in double-stranded DNA breaks that can be repaired by non-homologous end joining (NHEJ) or homology-directed repair (HDR).

In some embodiments, a naturally occurring Cas9 polypeptide can include, but is not limited to, SpCas9, SpCas9-HF1, SpCas9-HF2, SpCas9-HF3, SpCas9-HF4, SaCas9, FnCpf, FnCas9, eSpCas9, and NmeCas9. In some embodiments, the Cas9 protein comprises an amino acid sequence having at least 60%, 65%, 70%, 75%, 80%, 85%, 90%, 95%, 96%, 97%, 98%, 99%, or 100% sequence identity to a Cas9 amino acid sequence described in Chylinski et al., RNA Biology 2013 10:5, 727-737; Hou et al., PNAS Early Edition 2013, 1-6).

In some embodiments, a Cas polypeptide comprises one or more of the following activities: (a) a nickase activity, i.e., the ability to cleave a single strand, e.g., the noncomplementary strand or the complementary strand, of a nucleic acid molecule; (b) a double stranded nuclease activity, i.e., the ability to cleave both strands of a double stranded nucleic acid and create a double stranded break, which in an embodiment is the presence of two nickase activities; (c) an endonuclease activity; (d) an exonuclease activity; and/or (e) a helicase activity, i.e., the ability to unwind the helical structure of a double stranded nucleic acid. In other embodiments, the Cas protein may be dead or inactive (e.g. dCas).

In some embodiments, the Cas polypeptide is fused to a heterologous polypeptide/protein that has, for example, base deaminase activity.

In some embodiments, different Cas proteins (i.e., Cas proteins from various species) may be advantageous to use in the various provided methods in order to capitalize on various enzymatic characteristics of the different Cas proteins (e.g., for different PAM sequence preferences; for increased or decreased enzymatic activity; for an increased or decreased level of cellular toxicity; to change the balance between NHEJ, homology-directed repair, single strand breaks, double strand breaks, etc.).

In some embodiments, the Cas protein is a Cas9 protein derived from S. pyogenes and recognizes the PAM sequence motif NGG, NAG, NGA (Mali et al, Science 2013; 339 (6121): 823826). In some embodiments, the Cas protein is a Cas9 protein derived from S. thermophiles and recognizes the PAM sequence motif NGGNG and/or NNAGAAW (W=A or T) (See, e.g., Horvath et al, Science, 2010; 327 (5962): 167-170, and Deveau et al, J Bacteriol 2008; 190 (4): 1390-1400). In some embodiments, the Cas protein is a Cas9 protein derived from S. mutans and recognizes the PAM sequence motif NGG and/or NAAR (R=A or G) (See, e.g., Deveau et al, J BACTERIOL 2008; 190 (4): 1390-1400). In some embodiments, the Cas protein is a Cas9 protein derived from S. aureus and recognizes the PAM sequence motif NNGRR (R=A or G). In some embodiments, the Cas protein is a Cas9 protein derived from S. aureus and recognizes the PAM sequence motif N GRRT (R=A or G). In some embodiments, the Cas protein is a Cas9 protein derived from S. aureus and recognizes the PAM sequence motif N GRRV (R=A or G). In some embodiments, the Cas protein is a Cas9 protein derived from N. meningitidis and recognizes the PAM sequence motif N GATT or N GCTT (R=A or G, V=A, G or C) (See, e.g., Hou et ah, PNAS 2013, 1-6). In the aforementioned embodiments, N can be any nucleotide residue, e.g., any of A, G, C or T. In some embodiments, the Cas protein is a Cas13a protein derived from Leptotrichia shahii and recognizes the PFS sequence motif of a single 3' A, U, or C.

In embodiments, a Cas protein as a CRISPR-associated effector domain is codon optimized based on plant genome to be targeted.

In some embodiments, the at least one CRISPR-associated effector is a nuclease, e.g., a CRISPR nuclease, including, but not limited to, Cas9 or Cpf1 (Cas12a) nucleases.

In some embodiments, the at least one CRISPR-associated effector is a Cas polypeptide, wherein the Cas polypeptide comprises a site-specific DNA binding domain linked to at least one base editor. The CRISPR-associated effector or the nucleic acid sequence encoding the same includes, but is not limited to, (i) Cas9, including SpCas9, SaCas9, SaKKH-Cas9, VQRCas9, StlCas9, (ii) Cpf1, including AsCpf1, LbCpf1, FnCpf1, (iii) CasX, or (iv) CasY, or any variant or derivative of the aforementioned CRISPR-associated effector, preferably wherein the at least one CRISPR-associated effector comprises a mutation in comparison to the respective wild type sequence so that the resulting CRISPR-associated effector is converted to a single-strand specific DNA nickase, or to a DNA binding effector lacking all DNA cleavage ability, as described below. Therefore, according to the present disclosure, artificially modified CRISPR nucleases are envisaged, which might indeed not be any "nucleases" in the sense of double-strand cleaving enzymes, but which are nickases or nuclease-dead variants, which still have inherent DNA recognition and thus binding ability.

2. Cas Mutants/Variants

In some embodiments, the Cas protein described above can be engineered to alter one or more properties of the Cas polypeptide. For example, in some embodiments, the Cas polypeptide comprises altered enzymatic properties, e.g., altered nuclease activity, (as compared with a naturally occurring or other reference Cas molecule) or altered helicase activity. In some embodiments, an engineered Cas polypeptide can have an alteration that alters its size, e.g., a deletion of amino acid sequence that reduces its size without significant effect on another property of the Cas polypeptide. In some embodiments, an engineered Cas polypeptide comprises an alteration that affects PAM recognition. For example, an engineered Cas polypeptide can be altered to recognize a PAM sequence other than the PAM sequence recognized by the corresponding wild type Cas protein. In some embodiments, the targeted base-editing system comprises a Cas protein as a CRISPR-associated effector domain.

Cas polypeptides with desired properties can be made in a number of ways, including alteration of a naturally occurring Cas polypeptide or parental Cas polypeptide, to provide a mutant or altered Cas polypeptide having a desired property. For example, one or more mutations can be introduced into the sequence of a parental Cas polypeptide (e.g., a naturally occurring or engineered Cas polypeptide). Such mutations and differences may comprise substitutions (e.g., conservative substitutions or substitutions of non-essential amino acids); insertions; or deletions. In some embodiments, a mutant Cas polypeptide comprises one or more mutations (e.g., at least 1, 2, 3, 4, 5, 10, 15, 20, 30, 40 or 50 mutations) relative to a parental Cas polypeptide.

In an embodiment, a mutant Cas polypeptide comprises a cleavage property that differs from a naturally occurring Cas polypeptide. In some embodiments, the Cas is a deactivated Cas (dCas) mutant, which is catalytically dead. In such embodiments, the Cas polypeptide does not comprise any intrinsic enzymatic activity and is unable to mediate target nucleic acid cleavage. In such embodiments, the dCas is fused with a heterologous protein that is capable of modifying the target nucleic acid in a non-cleavage based manner. In some embodiments, the targeted base-editing system comprises a Cas protein as a CRISPR-associated effector domain.

In some embodiments, the dCas is a dCas9 mutant. In some embodiments, a dCas protein is fused to base deaminase domains (e.g., cytidine deaminase, or adenosine deaminase). In some such cases, the dCas fusion protein is targeted by the gRNA to a specific location (i.e., sequence) in the target nucleic acid and exerts locus-specific modification such as replacing C with T (or G with A) if the fusion protein has cytidine deaminase activity) or replacing A with G (or T with C) if the fusion protein has adenosine deaminase activity.

In some embodiments, the dCas is a dCas13 mutant (Konermann et al., Cell 173 (2018), 665-676). These dCas13 mutants can then be fused to enzymes that modify RNA, including adenosine deaminases (e.g., ADAR1 and ADAR2). Adenosine deaminases convert adenine to inosine, which the translational machinery treats like guanine, thereby creating a functional A to G change in the target sequence.

In some embodiments, the CRISPR-associated effector protein is Cas9 endonuclease. In some embodiments, the CRISPR-associated effector protein is a CRISPR-Cas variant, which is dCas9 mutant or nCas9 nickase mutant. The Cas9 endonuclease has a DNA cleavage domain containing two subdomains: i) the RuvC subdomain cleaving the non-complementary single-stranded chain and ii) the HNH nuclease subdomain cleaving the chain that is complementary to gRNA. Mutations in these subdomains can inactivate Cas9 endonuclease to form deactivated Cas9 (dCas9), which is interchangeably used with "catalytically dead Cas9". The nuclease-inactivated Cas9 retains DNA binding capacity directed by gRNA. Thus, in principle, when fused with an additional protein, the dCas9 can simply target said additional protein to almost any DNA sequence through co-expression with appropriate guide RNA. For example, catalytically dead Cas9 (dCas9) which contains Asp10Ala (D10A) and His840Ala (H840A) mutations that inactivate its nuclease activity, retains its ability to bind DNA in a guide RNA-programmed manner, but does not cleave the DNA backbone (Komor et al., nature (2016), Vol 533:420-424). In some embodiments, conjugation of dCas9 with an enzymatic or chemical catalyst that mediates the direct conversion of one base to another could enable RNA-programmed DNA base editing.

In some embodiments, the mutant Cas9 is a Cas9 nickase (nCas9) mutant. Cas9 nickase mutants comprise only one catalytically active domain (either the RuvC domain (D10A) or the HNH domain (H840A)). The Cas9 nickase mutants retain DNA binding based on gRNA specificity, but are capable of cutting only one strand of DNA resulting in a single-strand break (e.g. a "nick"). In some embodiments, two complementary Cas9 nickase mutants (e.g., one Cas9 nickase mutant with an inactivated RuvC domain, and one Cas9 nickase mutant with an inactivated HNH domain) are expressed in the same cell with two gRNAs corresponding to two respective target sequences; one target sequence on the sense DNA strand, and one on the antisense DNA strand. This dual-nickase system results in staggered double stranded breaks and can increase target specificity, as it is unlikely that two off-target nicks will be generated close enough to generate a double stranded break. In some embodiments, a Cas9 nickase mutant is co-expressed with a nucleic acid repair template to facilitate the incorporation of an exogenous nucleic acid sequence by homology-directed repair.

The dCas9 of the present disclosure can be derived from Cas9 of different species, for example, derived from *S. pyogenes* Cas9 (SpCas9). Mutations in both the RuvC subdomain and the HNH nuclease subdomain of the SpCas9 (includes, for example, D10A and H840A mutations) inactivate *S. pyogenes* Cas9 nuclease, resulting in a nuclease-dead/catalytically dead Cas9 (dCas9). In some embodiments of the present disclosure, the nuclease-inactivated Cas9 comprises the dCas9. In some preferred embodiments, the nuclease-inactivated Cas9 comprises.

Inactivation of one of the subdomains by mutation allows Cas9 to gain nickase activity, i.e., resulting in a Cas9 nickase (nCas9), for example, nCas9 with a D10A mutation only.

In some embodiments, the nuclease-inactivated Cas9 comprises amino acid substitutions D10A and/or H840A relative to wild type Cas9. In some embodiments, the nuclease-inactivated Cas9 of the present disclosure loses nuclease activity completely, which is catalytically dead. In such embodiments, the nuclease-inactivated Cas9 is the dCas9 with D10A and H840A. Therefore, the term "nuclease-inactivated Cas9" refers to dCas9 and/or nCas9.

In some embodiments, the nuclease-inactivated Cas9 of the present disclosure has nickase activity. In some embodiments, the nuclease-inactivated Cas9 is a Cas9 nickase that retains the cleavage activity of the HNH subdomain of Cas9, whereas the cleavage activity of the RuvC subdomain is inactivated. For example, the nuclease-inactivated Cas9 contains an amino acid substitution D10A relative to wild type Cas9. In such embodiments, the nuclease-inactivated Cas9 is the nCas9 with D10A only. In some embodiments of the present disclosure, the nuclease-inactivated Cas9 comprises the nCas9.

In some embodiments, the Cas polypeptides described herein can be engineered to alter the PAM/PFS specificity of the Cas polypeptide. In some embodiments, a mutant Cas polypeptide has a PAM/PFS specificity that is different from the PAM/PFS specificity of the parental Cas polypeptide. For example, a naturally occurring Cas protein can be modified to alter the PAM/PFS sequence that the mutant Cas polypeptide recognizes to decrease off target sites, improve specificity, or eliminate a PAM/PFS recognition requirement. In some embodiments, a Cas protein can be modified to increase the length of the PAM/PFS recognition sequence. In some embodiments, the length of the PAM recognition sequence is at least 4, 5, 6, 7, 8, 9, 10 or 15 amino acids in length. Cas polypeptides that recognize different PAM/PFS sequences and/or have reduced off-target activity can be generated using directed evolution. Exemplary methods and systems that can be used for directed evolution of Cas polypeptides are described, e.g., in Esvelt et al. Nature 2011, 472 (7344): 499-503. Exemplary Cas mutants are described in International PCT Publication No. WO 2015/161276 and Konermann et al., Cell 173 (2018), 665-676, which are incorporated herein by reference in their entireties.

3. Base Editors

In some embodiments, the deaminase domain is fused to the N-terminus of the nuclease inactivated Cas9 domain. In some embodiments, the deaminase domain is fused to the C-terminus of the nuclease-inactivated Cas9 domain. In some embodiments, the deaminase domain and the nuclease inactivated Cas9 domain are fused through a linker. The linker can be a non-functional amino acid sequence having no secondary or higher structure, N-terminus and one or more NLSs at the C-terminus. Where there are more than one NLS, each NLS may be selected as independent from other NLSs. In some embodiments, the targeted base-editing fusion protein comprises two NLSs, for example, the two NLSs are located at the N-terminus and the C-terminus, respectively.

In some embodiment, a targeted base modification is a conversion of any nucleotide C, A, T, or G, to any other nucleotide. Any one of a C, A, T or G nucleotide can be exchanged in a site-directed way as mediated by a base editor, or a catalytically active fragment thereof, to another nucleotide. A base editing complex can comprise any base editor, or a base editor domain or catalytically active fragment thereof, which can convert a nucleotide of interest into any other nucleotide of interest in a targeted way.

A base editing domain according to the present disclosure can comprise at least one cytidine deaminase, or a catalytically active fragment thereof. The at least one base editing complex can comprise the cytidine deaminase, or a domain thereof in the form of a catalytically active fragment, as base editor.

(i) Cytidine Deaminase

The term "cytidine deaminase" or "cytidine deaminase protein" as used herein refers to a protein, a polypeptide, or one or more functional domain(s) of a protein or a polypeptide that is capable of catalyzing a hydrolytic deamination reaction that converts an cytosine (or an cytosine moiety of a molecule) to an uracil (or a uracil moiety of a molecule), as shown below. In some embodiments, the cytosine-containing molecule is an cytidine (C), and the uracil-containing molecule is an uridine (U). The cytosine-containing molecule can be deoxyribonucleic acid (DNA) or ribonucleic acid (RNA).

According to the present disclosure, cytidine deaminases that can be used in connection with the present disclosure include, but are not limited to, members of the enzyme family known as apolipoprotein B mRNA-editing complex (APOBEC) family deaminase, an activation-induced deaminase (AID), or a cytidine deaminase 1 (CDA1). In particular embodiments, the deaminase in an APOBEC1 deaminase, an APOBEC2 deaminase, an APOBEC3A deaminase, an APOBEC3B deaminase, an APOBEC3C deaminase, and APOBEC3D deaminase, an APOBEC3E deaminase, an APOBEC3F deaminase an APOBEC3G deaminase, an APOBEC3H deaminase, or an APOBEC4 deaminase.

Cytidine deaminase is capable of targeting Cytosine in a DNA single strand. In certain example embodiments, a cytodine deaminase may edit on a single strand present outside of the binding component e.g. bound Cas9 and/or Cas13. In other example embodiments, a cytodine deaminase may edit at a localized bubble, such as a localized bubble formed by a mismatch at the target edit site but the guide sequence.

In some embodiments, the cytidine deaminase protein recognizes and converts one or more target cytosine residue(s) in a single-stranded bubble of a DNA-RNA heteroduplex into uracil residues(s). In some embodiments, the cytidine deaminase protein recognizes a binding window on the single-stranded bubble of a DNA-RNA heteroduplex. In some embodiments, the binding window contains at least one target cytosine residue(s). In some embodiments, the binding window is in the range of about 3 bp to about 100 bp. In some embodiments, the binding window is in the range of about 5 bp to about 50 bp. In some embodiments, the binding window is in the range of about 10 bp to about 30 bp. In some embodiments, the binding window is about 1 bp, 2 bp, 3 bp, 5 bp, 7 bp, 10 bp, 15 bp, 20 bp, 25 bp, 30 bp, 40 bp, 45 bp, 50 bp, 55 bp, 60 bp, 65 bp, 70 bp, 75 bp, 80 bp, 85 bp, 90 bp, 95 bp, or 100 bp.

In some embodiments, the cytidine deaminase protein comprises one or more deaminase domains. Not intended to be bound by theory, it is contemplated that the deaminase domain functions to recognize and convert one or more target cytosine (C) residue(s) contained in a single-stranded bubble of a DNA-RNA heteroduplex into (an) uracil (U) residue(s). In some embodiments, the deaminase domain comprises an active center. In some embodiments, the active center comprises a zinc ion. In some embodiments, amino acid residues in or near the active center interact with one or more nucleotide(s) 5' to a target cytosine residue. In some embodiments, amino acid residues in or near the active center interact with one or more nucleotide(s) 3' to a target cytosine residue.

In some embodiments, a cytosine deaminase useful with the invention may be an apolipoprotein B mRNA-editing complex (APOBEC) family deaminase. In some embodiments, the cytosine deaminase may be an APOBEC1 deaminase, an APOBEC2 deaminase, an APOBEC3A deaminase, an APOBEC3B deaminase, an APOBEC3C deaminase, an APOBEC3D deaminase, an APOBEC3F deaminase, an APOBEC3G deaminase, an APOBEC3H deaminase, an APOBEC4 deaminase, a human activation induced deaminase (hAID), an rAPOBEC1, FERNY, and/or a CDA1, optionally a pmCDAI, an atCDAl (e.g., At2g19570), and evolved versions of the same. In some embodiments, the cytidine deaminase comprises human APOBEC1 full protein (hAPOBECl) or the deaminase domain thereof (hAPOBECl-D) or a C-terminally truncated version thereof (hAPOBEC-T). In some embodiments, the cytidine deaminase is an APOBEC family member that is homologous to hAPOBECl, hAPOBEC-D or hAPOBEC-T. In some embodiments, the cytidine deaminase comprises human AID1 full protein (hAID) or the deaminase domain thereof (hAID-D) or a C-terminally truncated version thereof (hAID-T). In some embodiments, the cytidine deaminase is an AID family member that is homologous to hAID, hAID-D or hAID-T. In some embodiments, the hAIDT is a hAID which is C-terminally truncated by about 20 amino acids. In some embodiments, the cytosine deaminase may be an APOBEC1 deaminase. In some embodiments, the cytosine deaminase may be an APOBEC3A deaminase. In some embodiments, the cytosine deaminase may be an CDA1 deaminase. In some embodiments, the cytosine deaminase may be a FERNY deaminase.

In some embodiments, the cytidine deaminase comprises the wild type amino acid sequence of a cytosine deaminase. In some embodiments, the cytidine deaminase comprises one or more mutations in the cytosine deaminase sequence, such that the editing efficiency, and/or substrate editing preference of the cytosine deaminase is changed according to specific needs.

Certain mutations of APOBEC 1 and APOBEC3 proteins have been described in Kim et al., Nature Biotechnology (2017) 35 (4): 371-377 and Harris et al. Mol. Cell (2002) 10:1247-1253, each of which is incorporated herein by reference in its entirety. Additional embodiments of the cytidine deaminase are disclosed in WO2017/070632 and WO2018/213726, each of which is incorporated herein by reference in its entirety.

In some embodiments, at least one CRISPR-associated effector is temporarily or permanently linked to at least one base editor to form a targeted base editing complex, which is a base editing fusion protein, wherein the base editing complex mediates the at least one targeted base modification. The at least one CRISPR-associated effector can be non-covalently (temporarily) or covalently (permanently) be attached to at least one base editor. Any component of the at least one base editor can be temporarily or permanently linked to the at least one CRISPR-associated effector.

(ii) Adenosine Deaminase

The term "adenosine deaminase" or "adenosine deaminase protein" as used herein refers to a protein, a polypeptide, or one or more functional domain(s) of a protein or a polypeptide that is capable of catalyzing a hydrolytic deamination reaction that converts an adenine (or an adenine moiety of a molecule) to a hypoxanthine (or a hypoxanthine moiety of a molecule), as shown below. In some embodiments, the adenine-containing molecule is an adenosine (A), and the hypoxanthine-containing molecule is an inosine (I). The adenine-containing molecule can be deoxyribonucleic acid (DNA) or ribonucleic acid (RNA).

Adenosine deaminases (e.g. engineered adenosine deaminases, evolved adenosine deaminases) may be from any organism, such as a bacterium. In some embodiments, the deaminase or deaminase domain is a variant of a naturally-occurring deaminase from an organism. In some embodiments, the deaminase or deaminase domain does not occur in nature. For example, in some embodiments, the deaminase or deaminase domain is at least 50%, at least 55%, at least 60%, at least 65%, at least 70%, at least 75% at least 80%, at least 85%, at least 90%, at least 95%, at least 96%, at least 97%, at least 98%, at least 99%, or at least 99.5% identical to a naturally-occurring deaminase. In some embodiments, the adenosine deaminase is from a bacterium, such as, *E. coli, S. aureus, S. typhi, S. putrefaciens, H. influenzae,* or *C. crescentus.*

In some embodiments, an adenine deaminase domain may be a wild type tRNA-specific adenosine deaminase domain, e.g., a tRNA-specific adenosine deaminase (TadA) and/or a mutated/evolved adenosine deaminase domain, e.g., mutated/evolved tRNA-specific adenosine deaminase domain (TadA*). In some embodiments, a TadA domain may be from *E. coli*. In some embodiments, the TadA may be modified, e.g., truncated, missing one or more N-terminal and/or C-terminal amino acids relative to a full-length TadA (e.g., 1, 2, 3, 4, 5, 6, 7, 8, 9, 10, 11, 12, 13, 14, 15, 6, 17, 18, 19, or 20 N-terminal and/or C terminal amino acid residues may be missing relative to a full length TadA. In some embodiments, a TadA polypeptide or TadA domain does not comprise an N-terminal methionine. In some embodiments, the adenosine deaminase is a TadA deaminase. In some embodiments, the TadA deaminase is an *E. coli* TadA deaminase (ecTadA). In some embodiments, the TadA deaminase is a truncated *E. coli* TadA deaminase. For example, the truncated ecTadA may be missing one or more N-terminal amino acids relative to a full-length ecTadA. In some embodiments, an adenosine deaminase is as described in Gaudelli et al. (Directed evolution of adenine base editors with increased activity and therapeutic application. Nat Biotechnol (2020) (doi.org/10.1038/s41587-020-0491-6)) and Richter et al. (Phage-assisted evolution of an adenine base editor with improved Cas domain compatibility and activity. Nat Biotechnol (2020) (doi.org/10.1038/s41587-020-0453-z)). In some embodiments, the truncated ecTadA may be missing 1, 2, 3, 4, 5, 6, 7, 8, 9, 10, 11, 12, 13, 14, 15, 6, 17, 18, 19, or 20 N-terminal amino acid residues relative to the full length ecTadA. In some embodiments, the truncated ecTadA may be missing 1, 2, 3, 4, 5, 6, 7, 8, 9, 10, 11, 12, 13, 14, 15, 6, 17, 18, 19, or 20 C-terminal amino acid residues relative to the full length ecTadA. In some embodiments, the ecTadA deaminase does not comprise an N-terminal methionine. In some embodiments, a polynucleotide encoding a TadA/TadA* may be codon optimized for expression in a plant.

Some aspects of the disclosure utilize adenosine deaminases. In some embodiments, the adenosine deaminases provided herein are capable of deaminating adenine. In some embodiments, the adenosine deaminases provided herein are capable of deaminating adenine in a deoxyadenosine residue of DNA. The adenosine deaminase may be derived from any suitable organism (e.g., *E. coli*). In some embodiments, the adenine deaminase is a naturally-occurring adenosine deaminase that includes one or more mutations corresponding to any of the mutations provided herein (e.g., mutations in ecTadA). One of skill in the art will be able to identify the corresponding residue in any homologous protein and in the respective encoding nucleic acid by methods well known in the art, e.g., by sequence alignment and determination of homologous residues. Accordingly, one of skill in the art would be able to generate mutations in any naturally-occurring adenosine deaminase (e.g., having homology to ecTadA) that corresponds to any of the mutations described herein, e.g., any of the mutations identified in ecTadA. In some embodiments, the adenosine deaminase is from a prokaryote. In some embodiments, the adenosine deaminase is from a bacterium. In some embodiments, the adenosine deaminase is from *Escherichia coli, Staphylococcus aureus, Salmonella typhi, Shewanella putrefaciens, Haemophilus influenzae, Caulobacter crescentus*, or *Bacillus subtilis*. In some embodiments, the adenosine deaminase is from *E. coli*.

In other embodiments, adenosine deaminases that can be used that include, but are not limited to, members of the enzyme family known as adenosine deaminases that act on RNA (ADARs), members of the enzyme family known as adenosine deaminases that act on tRNA (ADATs), and other adenosine deaminase domain-containing (ADAD) family members. According to the present disclosure, the adenosine deaminase is capable of targeting adenine in a RNA/DNA heteroduplex. Indeed, Zheng et al. (Nucleic Acids Res. 2017, 45 (6): 3369-3377) has demonstrated that ADARs can carry out adenosine to inosine editing reactions on RNA/DNA heteroduplexes. In particular embodiments, the adenosine deaminase has been modified to increase its ability to edit DNA in a RNA/DNA heteroduplex as detailed herein below.

In some embodiments, the adenosine deaminase is derived from one or more metazoa species, including but not limited to, mammals, birds, frogs, squids, fish, flies and worms. In some embodiments, the adenosine deaminase is a human, squid or *Drosophila* adenosine deaminase. In some embodiments, the adenosine deaminase is a human ADAR, including hADAR1, hADAR2, hADAR3. In some embodiments, the adenosine deaminase is a *Caenorhabditis elegans* ADAR protein, including ADR-1 and ADR-2. In some embodiments, the adenosine deaminase is a *Drosophila* ADAR protein, including dAdar. In some embodiments, the adenosine deaminase is a squid *Loligo pealeii* ADAR protein, including sqADAR2a and sqADAR2b. In some embodiments, the adenosine deaminase is a human ADAT protein. In some embodiments, the adenosine deaminase is a *Drosophila* ADAT protein. In some embodiments, the adenosine deaminase is a human ADAD protein, including TE R (hADAD1) and TE RL (hADAD2).

In some embodiments, the adenosine deaminase is a TadA protein such as *E. coli* TadA. See Kim et al., Biochemistry 45:6407-6416 (2006); Wolf et al., EMBO J. 21:3841-3851 (2002), each of which is incorporated herein by reference in its entirety. In some embodiments, the adenosine deaminase is mouse ADA (See Grunebaum et al., Curr. Opin. Allergy Clin. Immunol. 13:630-638 (2013)) or human ADAT2 (See Fukui et al., J. Nucleic Acids 2010:260512 (2010)), each of which is incorporated herein by reference in its entirety. Additional embodiments of the adenosine deaminase are disclosed in U.S. Pat. No. 10,113,163 and WO2018/213708, each of which is incorporated herein by reference in its entirety In some embodiments, at least one CRISPR-Cas-associated effector is temporarily or permanently linked to at least one base editor to form a targeted base editing complex, which is a base editing fusion protein, wherein the base editing complex mediates the at least one targeted base modification. The at least one CRISPR-associated effector can be non-covalently (temporarily) or covalently (permanently) be attached to at least one base editor. Any component of the at least one base editor can be temporarily or permanently linked to the at least one CRISPR-Cas associated effector.

In one aspect, the present disclosure provides methods for targeted deamination of adenine in a DNA, more particularly in a locus of interest. The disclosure teaches the adenosine deaminase (AD) protein is recruited specifically to the relevant Adenine in the locus of interest by a CRISPR Cas complex which can specifically bind to a target sequence. In order to achieve this, the adenosine deaminase protein can either be covalently linked to the CRISPR-Cas enzyme or be provided as a separate protein, but adapted so as to ensure recruitment thereof to the CRISPR-Cas complex.

In some embodiments, recruitment of the adenosine deaminase to the target locus is ensured by fusing the adenosine deaminase or catalytic domain thereof to the CRISPR-Cas protein, which is a Cas or Cpf1 protein. Methods of generating a fusion protein from two separate proteins are known in the art and typically involve the use of spacers or linkers. The CRISPR-Cas protein can be fused to the adenosine deaminase protein or catalytic domain thereof on either the N- or C-terminal end thereof. In particular embodiments, the CRISPR-Cas protein is a Cas or Cpf1 protein and is linked to the N-terminus of the deaminase protein or its catalytic domain.

4. Linker

In the present disclosure, linker refers to a molecule which joins the proteins to form a fusion protein. Generally, such molecules have no specific biological activity other than to join or to preserve some minimum distance or other spatial relationship between the proteins. However, in some embodiments, the linker may be selected to influence some property of the linker and/or the fusion protein such as the folding, net charge, or hydrophobicity of the linker.

Suitable linkers for use in the methods of the present disclosure are well known to those of skill in the art and include, but are not limited to, straight or branched-chain carbon linkers, heterocyclic carbon linkers, or peptide linkers. However, as used herein the linker may also be a covalent bond (carbon-carbon bond or carbon-heteroatom bond). In particular embodiments, the linker is used to separate the CRISPR-Cas protein and the cytidine deaminase by a distance sufficient to ensure that each protein retains its required functional property. Preferred peptide linker sequences adopt a flexible extended conformation and do not exhibit a propensity for developing an ordered secondary structure.

In some embodiments, the linker can be a chemical moiety which can be monomeric, dimeric, multimeric or polymeric. Exemplary linkers are disclosed in Maratea et al. (1985), Gene 40:39-46; Murphy et al. (1986) Proc. Nat'l. Acad. Sci. USA 83:8258-62; U.S. Pat. Nos. 4,935,233; and 4,751,180. For example, GlySer linkers GGS, GGGS (SEQ ID NO:262) or GSG can be used. GGS, GSG, GGGS (SEQ ID NO:262) or GGGGS (SEQ ID NO:263) linkers can be used in repeats of 3 such as (GGS) 3 (SEQ ID NO:264). In other embodiments, 1, 2, 3, 4, 5, 6, 7, 8, 9, 10, 11, 12 or more of (GGGGS) (SEQ ID NO:263), to provide suitable lengths. In some embodiments, linkers such as (GGGGS): (SEQ ID NO:263), (GGGGS) 2 (SEQ ID NO:265), (GGGGS) 3 (SEQ ID NO: 266), (GGGGS) 4 (SEQ ID NO:267), (GGGGS) s (SEQ ID NO:268), (GGGGS) 6 (SEQ ID NO: 269), (GGGGS) 7 (SEQ ID NO:270), (GGGGS): (SEQ ID NO:271), (GGGGS) 9 (SEQ ID NO: 272), (GGGGS) 10 (SEQ ID NO:273), (GGGGS) 11 (SEQ ID NO:274), or (GGGGS) 12 (SEQ ID NO: 275) may be used. In other embodiments, the linker is XTEN linker. In particular embodiments, the nuclease-inactivated CRISPR-associated effector protein such as dCas9 or nCas9 is linked to the deaminase protein or its catalytic domain by means of an XTEN linker. In some embodiments, the nuclease-inactivated Cas mutant is linked C-terminally to the N-terminus of a deaminase protein or its catalytic domain by means of an XTEN linker. In addition, N- and C-terminal NLSs can also function as linker.

5. gRNAs

The present disclosure provides guide RNAs (gRNAs) that direct a site-directed modifying polypeptide to a specific target nucleic acid sequence. A gRNA comprises a nucleic acid-targeting segment and protein-binding segment. The nucleic acid-targeting segment of a gRNA comprises a nucleotide sequence that is complementary to a sequence in the target nucleic acid sequence. As such, the nucleic acid-targeting segment of a gRNA interacts with a target nucleic acid in a sequence-specific manner via hybridization (i.e., base pairing), and the nucleotide sequence of the nucleic acid-targeting segment determines the location within the target nucleic acid that the gRNA will bind. The nucleic acid-targeting segment of a gRNA can be modified (e.g., by genetic engineering) to hybridize to any desired sequence within a target nucleic acid sequence. The protein-binding segment of a guide RNA interacts with a site-directed modifying polypeptide (e.g. a Cas protein) to form a complex. The guide RNA guides the bound polypeptide to a specific nucleotide sequence within target nucleic acid via the above-described nucleic acid targeting segment. The protein-binding segment of a guide RNA comprises two stretches of nucleotides that are complementary to one another and which form a double stranded RNA duplex.

In some embodiments, a gRNA comprises two separate RNA molecules. In such embodiments, each of the two RNA molecules comprises a stretch of nucleotides that are complementary to one another such that the complementary nucleotides of the two RNA molecules hybridize to form the double-stranded RNA duplex of the protein-binding segment. In some embodiments, a gRNA comprises a single guide RNA molecule (sgRNA).

The specificity of a gRNA for a target loci is mediated by the sequence of the nucleic acid-binding segment (e.g., the spacer), which comprises about 20 nucleotides that are complementary to a target nucleic acid sequence within the target locus. In some embodiments, the corresponding target nucleic acid sequence is approximately 20 nucleotides in length, optionally about 20, 21, 22, 23, 24, or 25 nucleotides in length. In some embodiments, the nucleic acid-binding segments of the gRNA sequences of the present disclosure are at least 90% complementary to a target nucleic acid sequence within a target locus. In some embodiments, the nucleic acid-binding segments of the gRNA sequences of the present disclosure are at least 95%, 96%, 97%, 98%, or 99% complementary to a target nucleic acid sequence within a target locus. In some embodiments, the nucleic acid-binding segments of the gRNA sequences of the present disclosure are 100% complementary to a target nucleic acid sequence within a target locus.

In some embodiments, the target nucleic acid sequence is an RNA target sequence. In some embodiments, the target nucleic acid sequence is a DNA target sequence.

In some embodiments, a targeted editing system (e.g., base-editing system) comprises one or two or more gRNA molecules each comprising a DNA-binding segment, wherein at least one of the nucleic acid binding segments binds to a target DNA sequence of a target gene of an AGAMOUS clade comprising AG, SHP1, SHP2, and STK in plants of the present disclosure. In some embodiments, the guide RNA is a single guide RNA (sgRNA). Methods of constructing suitable sgRNAs according to a given target sequence are known in the art. See e.g., Wang, Y. et al. Simultaneous editing of three homeoalleles in hexaploid bread wheat confers heritable resistance to powdery mildew. Nat. Biotechnol. 32, 947-951 (2014); Shan, Q. et al. Targeted genome modification of crop plants using a CRISPR-Cas system. Nat. Biotechnol. 31, 686-688 (2013); Liang, Z. et al. Targeted mutagenesis in *Zea mays* using TALENs and the CRISPR/Cas system. J Genet Genomics. 41, 63-68 (2014).

6. Base Excision Repair Inhibitor

The addition of a uracil DNA glycosylase (UGI) domain further increased the base-editing efficiency. In some embodiments, the targeted base-editing system further comprises a base excision repair (BER) inhibitor. Cellular DNA-repair response to the presence of a U: G pairing in DNA may be responsible for a decrease in nucleobase editing efficiency in plant cells. Uracil DNA glycosylase catalyzes removal of uracil from DNA in plant cells, which may initiate base excision repair, such that the U: G pair is reversed to C:G. In some embodiments, the BER inhibitor is an uracyl glycosylase inhibitor or an active domain thereof.

In some embodiments, the BER inhibitor is an inhibitor of uracil DNA glycosylase (UDG). In some embodiments, the BER inhibitor is an inhibitor of UDG. In some embodiments, the BER inhibitor is a polypeptide inhibitor. In some embodiments, the BER inhibitor is a protein that binds single-stranded DNA. For example, the BER inhibitor may be a *Erwinia tasmaniensis* single-stranded binding protein. In some embodiments, the BER inhibitor is a protein that binds uracil. In some embodiments, the BER inhibitor is a protein that binds uracil in DNA. In some embodiments, the BER inhibitor is a catalytically inactive UDG or binding domain thereof. In some embodiments, the BER inhibitor is a catalytically inactive UDG or binding domain thereof that does not excise uracil from the DNA. Other proteins that are capable of inhibiting (e.g., sterically blocking) UDG are within the scope of this disclosure. Additionally, any proteins that block or inhibit base-excision repair as also within the scope of this disclosure.

Base excision repair may be inhibited by molecules that bind the edited strand, block the edited base, inhibit uracil DNA glycosylase, inhibit base excision repair, protect the edited base, and/or promote fixing of the non-targeted strand. Accordingly, the use of the BER inhibitor described herein can increase the editing efficiency of a cytidine deaminase that is capable of catalyzing a C to U change.

In some embodiments, the uracil glycosylase inhibitor (UGI) is the uracil DNA glycosylase inhibitor of *Bacillus subtilis* bacteriophage PBS1 or an active fragment thereof, such as an 83 residue protein of *Bacillus subtilis* bacteriophage PBS1.

Suitable UGI protein and nucleotide sequences are provided herein and additional suitable UGI sequences are known to those in the art, and include, for example, those published in Wang et al., Uracil-DNA glycosylase inhibitor gene of bacteriophage PBS2 encodes a binding protein specific for uracil-DNA glycosylase. J. Biol. Chem. 264:1 163-1 171 (1989); Lundquist et al., Site-directed mutagenesis and characterization of uracil-DNA glycosylase inhibitor protein. Role of specific carboxylic amino acids in complex formation with *Escherichia coli* uracil-DNA glycosylase. J. Biol. Chem. 272:21408-21419 (1997); Ravishankar et al., X-ray analysis of a complex of *Escherichia coli* uracil DNA glycosylase (EcUDG) with a proteinaceous inhibitor. The structure elucidation of a prokaryotic UDG. Nucleic Acids Res. 26:4880-4887 (1998); and Putnam et al., Protein mimicry of DNA from crystal structures of the uracil-DNA glycosylase inhibitor protein and its complex with *Escherichia coli* uracil-DNA glycosylase. J. Mol. Biol. 287:331-346 (1999), each of which incorporated herein by reference. Additional embodiments of the uracil glycosylase inhibitor (UGI) are disclosed in WO2018/086623, WO2018/205995, WO2017/70632, and WO2018/213726, each of which is incorporated herein by reference in its entirety.

In some embodiments, the UGI domain comprises a wild type UGI or a UGI. In some embodiments, the UGI proteins provided herein include fragments of UGI and proteins homologous to a UGI or a UGI fragment.

Additional proteins may be uracil glycosylase inhibitors. For example, other proteins that are capable of inhibiting (e.g., sterically blocking) a uracil-DNA glycosylase base-excision repair enzyme are within the scope of this disclosure. Additionally, any proteins that block or inhibit base-excision repair as also within the scope of this disclosure. In some embodiments, a protein that binds DNA is used. In another embodiment, a substitute for UGI is used. In some embodiments, a uracil glycosylase inhibitor is a protein that binds single-stranded DNA. For example, a uracil glycosylase inhibitor may be a *Erwinia tasmaniensis* single-stranded binding protein. In some embodiments, a uracil glycosylase inhibitor is a protein that binds uracil. In some embodiments, a uracil glycosylase inhibitor is a protein that binds uracil in DNA. In some embodiments, a uracil glycosylase inhibitor is a catalytically inactive uracil DNA-glycosylase protein. In some embodiments, a uracil glycosylase inhibitor is a catalytically inactive uracil DNA glycosylase protein that does not excise uracil from the DNA. As another example, a uracil glycosylase inhibitor is a catalytically inactive UDG.

In some embodiments, the base editing system comprises the following domains; i) the CRISPR-Cas protein (dCas9 or nCas9) and ii) the cytidine deaminase, which can be fused to or linked to a BER inhibitor (e.g., an inhibitor of uracil DNA glycosylase).

7. Uracil DNA Glycosylases for Diversification

Uracil-DNA glycosylase (UDG) is an enzyme that reverts mutations in DNA. The most common mutation is the deamination of cytosine to uracil. UDG repairs these mutations and UDG is crucial in DNA repair. Various uracil-DNA glycosylases and related DNA glycosylases (EC) are present such as uracil-DNA glycosylase, thermophilic uracil-DNA glycosylase, G: T/U mismatch-specific DNA glycosylase (Mug), and single-strand selective monofunctional uracil DNA glycosylase (SMUG1).

Uracil DNA glycosylases remove uracil from DNA, which can arise either by spontaneous deamination of cytosine or by the misincorporation of dU opposite dA during DNA replication. The prototypical member of this family is *E. coli* UDG, which was among the first glycosylases discovered. Four different uracil-DNA glycosylase activities have been identified in mammalian cells, including UNG, SMUG1, TDG, and MBD4, which vary in substrate specificity and subcellular localization. SMUG1 prefers single-stranded DNA as substrate, but also removes U from double-stranded DNA. In addition to unmodified uracil, SMUG1 can excise 5-hydroxyuracil, 5-hydroxymethyluracil and 5-formyluracil bearing an oxidized group at ring C5. [13] TDG and MBD4 are strictly specific for double-stranded DNA. TDG can remove thymine glycol when present opposite guanine, as well as derivatives of U with modifications at carbon 5.

TDG and SMUG1 are the major enzymes responsible for the repair of the U:G mispairs caused by spontaneous cytosine deamination, whereas uracil arising in DNA through dU misincorporation is mainly dealt with by UNG. MBD4 is thought to correct T: G mismatches that arise from deamination of 5-methylcytosine to thymine in CpG sites.

Uracil arising in DNA either from misincorporation of dUMP or from deamination of cytosine is actively removed through the multistep base excision repair (BER) pathway. BER of uracil is initiated by a uracil DNA glycosylase (UDG) activity that cleaves the N-glycosidic bond and excises uracil as a free base, generating an abasic (apurinic/apyrimidinic, AP) site in the DNA. Repair is completed through subsequent steps that include incision at the AP site, gap tailoring, repair synthesis, and ligation. In some embodiments, the addition of a Uracil-DNA glycosylase (UDG) such as uracil N-glycosylase (UNG) can induce various mutations at targeted base. In some embodiments, the targeted base-editing system further comprises a Uracil-DNA glycosylase (UDG). Cellular DNA repair response to the presence of a U: G pairing in DNA may be responsible for a decrease in nucleobase editing efficiency in plant cells.

Uracil DNA glycosylase catalyzes removal of uracil from DNA in plant cells, which may initiate base excision repair, such that the U: G pair is reversed to C:G. In other embodiments, removal of uracil from DNA in plant cells are not always reversed to C for C:G paring, but randomized to other bases such as T, A, and G.

In some embodiments, a Uracil-DNA glycosylase (UDG) is fused to the targeted base editing system taught in the present disclosure to introduce a stable and targeted, but randomized single nucleotide substitution in MADS-box transcription factor gene.

The use of the UDG described herein can increase the base randomization in a targeted single nucleotide of a target gene such as a member of MADS box gene family taught in the present disclosure.

In some embodiments, a UDG is provided in cis. In some embodiments, a UDG is provided in trans. In some embodiments, a UDG is fused to a base editor (or a base editing system) described in the present disclosure. Io other embodiments, a UDG trigger a stall DNA replication for base randomization. In other embodiments, a UDG triggers a DNA repair through DNA replication, thereby including base randomization. In further embodiments, naturally occurring UDG variants can be used as a UDG domain. In further embodiments, non-naturally occurring UDG variants can be used as a UDG domain. In further embodiments, a UDG can be genetically engineered to enhance a functional UDG activity.

8. Nuclear Localization Sequences for Targeting to the Nucleus

A nuclear localization signal (NLS), or any other organelle targeting signal, can be further required to ensure proper targeting of the complex. The present disclosure relate to modifying an cytosine in a target locus of interest, whereby the target locus is within a plant cell. In order to improve targeting of the CRISPR-Cas protein and/or the cytidine deaminase protein or catalytic domain thereof used in the methods of the present disclosure to the nucleus, it may be advantageous to provide one or both of these components with one or more nuclear localization sequences (NLSs).

In some embodiments, the NLSs can be heterologous to the proteins. In general, NLS consists of one or more short sequences of positively charged lysine or arginine exposed on the surface of a protein, but other types of NLS are also known in the art.

In some embodiments, the N-terminus of the base editing fusion protein comprises an NLS with an amino acid sequence. In some embodiments, the C-terminus of the base-editing fusion protein comprises an NLS.

A base editing fusion protein may also include other localization sequences, such as cytoplasmic localization sequences, chloroplast localization sequences, mitochondrial localization sequences, and the like, depending on the location of the DNA to be edited. In order to obtain efficient expression in plants, in some embodiments, the nucleotide sequence encoding the base editing fusion protein is codon optimized for the plant to be base edited.

Codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/and these tables can be adapted in a number of ways. See Nakamura, Y., et al. "Codon usage tabulated from the international DNA sequence databases: status for the year 2000" Nucl. Acids Res. 28:292 (2000). In some embodiments, the codon-optimized nucleotide sequence encoding the base editing fusion protein is provided herein. In some embodiments, the guide RNA is a single guide RNA (sgRNA). Methods of constructing suitable sgRNAs according to a given target sequence are known in the art. See e.g., Wang, Y. et al. Simultaneous editing of three homeoalleles in hexaploid bread wheat confers heritable resistance to powdery mildew. *Nat. Biotechnol.* 32, 947951 (2014); Shan, Q. et al. Targeted genome modification of crop plants using a CRISPR-Cas system. *Nat. Biotechnol.* 31, 686-688 (2013); Liang, Z. et al. Targeted mutagenesis in *Zea mays* using TALENs and the CRISPR/Cas system. *J Genet Genomics.* 41, 63-68 (2014).

9. Promoter

In order to ensure appropriate expression in a plant cell, the components of the targeted base-editing system described herein are typically placed under control of a plant promoter, i.e. a promoter operable in plant cells. The use of different types of promoters is envisaged.

A constitutive plant promoter is a promoter that is able to express the open reading frame (ORF) that it controls in all or nearly all of the plant tissues during all or nearly all developmental stages of the plant (referred to as "constitutive expression"). One non-limiting example of a constitutive promoter is the cauliflower mosaic virus 35S promoter. "Regulated promoter" refers to promoters that direct gene expression not constitutively, but in a temporally- and/or spatially-regulated manner, and includes tissue-specific, tissue-preferred and inducible promoters. Different promoters may direct the expression of a gene in different tissues or cell types, or at different stages of development, or in response to different environmental conditions. In particular embodiments, one or more of the components of the targeted base-editing system described herein are expressed under the control of a constitutive promoter, such as the cauliflower mosaic virus 35S promoter. Tissue-preferred promoters can be utilized to target enhanced expression in certain cell types within a particular plant tissue, for instance vascular cells in leaves or roots or in specific cells of the seed. Examples of particular promoters for use of the present disclosure can be found in Kawamata et al., (1997) Plant Cell Physiol 38:792-803; Yamamoto et al., (1997) Plant J 12:25565; Hire et al, (1992) Plant Mol Biol 20:207-18, Kuster et al, (1995) Plant Mol Biol 29:759-72, and Capana et al., (1994) Plant Mol Biol 25:681-91.

Inducible promoters can be of interest to express one or more of the components of the targeted base-editing system described herein under limited circumstances to avoid non-specific activity of the deaminase. In particular embodiments, one or more elements of the targeted base-editing system described herein are expressed under control of an inducible promoter. Examples of promoters that are inducible and that allow for spatiotemporal control of gene editing or gene expression may use a form of energy. The form of energy may include but is not limited to sound energy, electromagnetic radiation, chemical energy and/or thermal energy. Examples of inducible systems include tetracycline inducible promoters (Tet-On or Tet-Off), small molecule two-hybrid transcription activations systems (FKBP, ABA, etc), or light inducible systems (Phytochrome, LOV domains, or cryptochrome)., such as a Light Inducible Transcriptional Effector (LITE) that direct changes in transcriptional activity in a sequence-specific manner. The components of a light inducible system may include a fusion protein of the targeted base-editing system and a light-responsive cytochrome heterodimer (e.g. from *Arabidopsis thaliana*). Further examples of inducible DNA binding proteins and methods for their use are provided in U.S. 61/736,465 and U.S. 61/721,283, which is hereby incorporated by reference in its entirety.

In some embodiments, transient or inducible expression can be achieved by using, for example, chemical-regulated promotors, i.e. whereby the application of an exogenous chemical induces gene expression. Modulating of gene expression can also be obtained by a chemical-repressible promoter, where application of the chemical represses gene expression. Chemical-inducible promoters include, but are not limited to, the maize ln2-2 promoter, activated by benzene sulfonamide herbicide safeners (De Veylder et al., (1997) Plant Cell Physiol 38:568-77), the maize GST promoter (GST-11-27, WO93/01294), activated by hydrophobic electrophilic compounds used as pre-emergent herbicides, and the tobacco PR-1 a promoter (Ono et al., (2004) Biosci Biotechnol Biochem 68:803-7) activated by salicylic acid. Promoters which are regulated by antibiotics, such as tetracycline-inducible and tetracycline-repressible promoters (Gatz et al., (1991) Mol Gen Genet 227:229-37; U.S. Pat. Nos. 5,814,618 and 5,789,156) can also be used herein.

In some embodiments, the nucleotide sequence encoding the base-edited fusion protein and/or the nucleotide sequence encoding the guide RNA is operably linked to a plant expression regulatory element, such as a promoter. Examples of promoters that can be used in the present disclosure include, but are not limited to the cauliflower mosaic virus 35S promoter (Odell et al. (1985) Nature 313:810-812), a maize Ubi-1 promoter, a wheat U6 promoter, a rice U3 promoter, a maize U3 promoter, a rice actin promoter, a TrpPro5 promoter (U.S. patent application Ser. No. 10/377,318; filed on Mar. 16, 2005), a pEMU promoter (Last et al. *Theor. Appl. Genet.* 8 1:581588), a MAS promoter (Velten et al. (1984) EMBO J. 3:2723-2730), a maize H3 histone promoter (Lepetit et al. *Mol. Gen. Genet.* 231: 276-285 and Atanassova et al. (1992) Plant J. 2 (3): 291300), and a *Brassica napus* ALS3 (PCT Application WO 97/41228) promoters. Promoters that can be used in the present disclosure also include the commonly used tissue specific promoters as reviewed in Moore et al. (2006) *Plant J.* 45 (4): 651-683.

Generating a Gene-Edited Plant with Enhanced Agronomic Traits

The present disclosure provides methods for targeted editing in a plant cell, tissue, organ or plant. In one aspect, the present disclosure provides methods for producing a gene-edited plant, comprising introducing a system for performing base editing to a target sequence into a plant genome, and thereby said base editing fusion protein is targeted to the target sequence in said plant genome by the guide RNA, and results in one or more nucleotide substitutions in said target sequence.

In some embodiments, the targeted base-editing system as described herein is used to introduce targeted (e.g., C>T or G>A) mutations, which can cause a nonsense mutation (e.g., premature stop codon) or a missense mutation (e.g., encoding different amino acid residue). This is of interest where the single nucleotide mutations in certain endogenous genes can confer or contribute to a desired trait such as seedlessness, reduced seediness, reduced seed size, reduced endocarp size and/or reduced lignification in endocarp tissue. In some embodiments, the target gene is a MADS-box gene from an AGAMOUS clade.

The methods described herein result in the generation of gene-edited plants that have one or more desirable traits compared to the wild type plant.

In some embodiments, non-transgenic but gene-edited plants, plant parts, or cells are obtained, in that no exogenous DNA sequence is incorporated into the genome of any of the plant cells of the plant. In such embodiments, the gene-edited plants are non-transgenic. Where only the modification of an endogenous gene is ensured and no foreign genes are introduced or maintained in the plant genome, the resulting genetically modified crops contain no foreign genes and can thus basically be considered nontransgenic.

In some embodiments, modification of the target sequence can be accomplished simply by introducing or producing the base editing fusion protein and guide RNA in plant cells, and the modification can be stably inherited without the need of stably transformation of plants with the base editing system.

In other embodiments, the polynucleotides are delivered into the cell by a DNA virus (e.g., a geminivirus) or an RNA virus (e.g., a tobravirus). In other embodiments, the introducing steps include delivering to the plant cell a T-DNA containing one or more polynucleotide sequences encoding the CRISPR-Cas protein, the cytidine deaminase, and the guide RNA, where the delivering is via *Agrobacterium*. The polynucleotide sequence encoding the components of the cytidine deaminase-coupled CRISPR/Cas system can be operably linked to a promoter, such as a constitutive promoter (e.g., a cauliflower mosaic virus 35S promoter), or a cell specific or inducible promoter in a plant cell of interest described herein. In other embodiments, the polynucleotide is introduced by microprojectile bombardment.

In some embodiments, the base editing system can be introduced into plants by any methods known in the art or later developed, including but not limited to particle bombardment, PEG-mediated protoplast transformation, *Agrobacterium*-mediated transformation, plant virus-mediated transformation, pollen tube, and ovary injection.

In some embodiments, introduction of a nucleic acid may be performed in the absence of a selective pressure, thereby avoiding the integration of exogenous nucleotide sequences in the plant genome. In some embodiments, the introduction comprises transforming the base editing system into isolated plant cells or tissues, and then regenerating the transformed plant cells or tissues into an intact plant. Preferably, the regeneration is performed in the absence of a selective pressure, i.e., no selective agent against the selective gene carried on the expression vector is used during the tissue culture. Without the use of a selective agent, the regeneration efficiency of the plant can be increased to obtain a modified plant that does not contain exogenous nucleotide sequences.

An expression cassette of the invention also can include a polynucleotide encoding a selectable marker, which can be used to select a transformed host cell. As used herein, "selectable marker" means a polynucleotide sequence that when expressed imparts a distinct phenotype to the host cell expressing the marker and thus allows such transformed cells to be distinguished from those that do not have the marker. Such a polynucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Many examples of suitable selectable markers are known in the art and can be used in the expression cassettes described herein.

In other embodiments, the base editing system of the present disclosure can be transformed to a particular site on an intact plant, such as leaf, shoot tip, pollen tube, young ear, or hypocotyl. This is particularly suitable for the transformation of plants that are difficult to regenerate by tissue culture. In some embodiments, proteins expressed in vitro and/or RNA molecules transcribed in vitro are directly transformed into the plant. The proteins and/or RNA molecules are capable of achieving base-editing in plant cells, and are subsequently degraded by the cells to avoid the integration of exogenous nucleotide sequences into the plant genome. Plant that can be base-edited by the methods includes monocotyledon and dicotyledon. For example, the plant may be a crop plant such as wheat, rice, maize, soybean, sunflower, sorghum, rape, alfalfa, cotton, barley, millet, sugar cane, tomato, tobacco, cassava, or potato. For another example, the plant may be a fruit crops such as tomato, almond, date, loquat, apple, peach, pear, plum, raspberry, black raspberry, blackberry, cherry, avocado, strawberry, wild strawberry, grape and orange.

In some embodiments, the target sequence is associated with plant traits such as agronomic traits, and thereby the base editing results in the plant having altered traits relative to a wild type plant. In the present disclosure, the target sequence to be modified may be located anywhere in the genome, for example, within a functional gene such as a protein-coding gene or, for example, may be located in a gene expression regulatory region such as a promoter region or an enhancer region, and thereby accomplish the functional modification of said gene or accomplish the modification of a gene expression.

In some embodiments, the method further comprises obtaining progeny of the gene-edited plant. In a further aspect, the disclosure also provides a gene-edited plant or progeny thereof or parts thereof, wherein the plant is obtained by the method described above.

In another aspect, the present disclosure also provides a plant breeding method comprising crossing a first gene-edited plant obtained by the above-mentioned method of the present disclosure with a second plant not containing said genetic modification, thereby introducing said genetic modification into said second plant.

In particular embodiments, the method further includes screening the plant cell after the introducing steps to determine whether the expression of the gene of interest has been modified. In particular embodiments, the methods include the step of regenerating a plant from the plant cell. In further embodiments, the methods include cross breeding the plant to obtain a genetically desired plant lineage.

Transient Delivery of Components of Targeted Editing System to Plant Cell

In some embodiments, the present disclose provides a delivery of one or more components of the targeted base-editing system directly to the plant cell. This is of interest, inter alia, for the generation of non-transgenic plants. In some embodiments, one or more of the components of targeted base-editing system is prepared outside the plant or plant cell and delivered to the cell. In some embodiments, the targeted base-editing fusion protein comprising a nuclease-inactivated CRISPR-Cas domain and cytosine deaminase domain is prepared in vitro prior to introduction to the plant cell. The base-editing fusion protein can be prepared by various methods known by one of skill in the art and include recombinant production. After expression, the CRISPR-Cas protein is isolated, refolded if needed, purified and optionally treated to remove any purification tags if a tag such as a His-tag is present in the fusion protein. Once crude, partially purified, or more completely purified CRISPR-Cas protein is obtained, the protein may be introduced to the plant cell.

In some embodiments, the base-editing fusion protein is mixed with guide RNA targeting the gene of interest to form a pre-assembled ribonucleoprotein. The individual components or pre-assembled ribonucleoprotein can be introduced into the plant cell via electroporation, by bombardment with targeted base-editing system coated particles, by chemical transfection or by some other means of transport across a cell membrane. For instance, transfection of a plant protoplast with a pre-assembled CRISPR-Cas9 ribonucleoprotein has been demonstrated to ensure targeted modification of the plant genome (Woo et al. Nature Biotechnology, 2015; 33 (11): 1162-1164).

In some embodiments, the targeted base-editing system components described herein are introduced into the plant cells using nanoparticles. The components, either as protein or nucleic acid or in a combination thereof, can be uploaded onto or packaged in nanoparticles and applied to the plants (such as for instance described in WO2008/042156 and US2013/0185823). In particular, the disclosure teach nanoparticles uploaded with or packed with DNA molecule(s) encoding the CRISPR-Cas effector protein, DNA molecule(s) encoding cytosine deaminase (which may be fused to the CRISPR-Cas protein or a linker), and DNA molecules encoding the guide RNA and/or isolated guide RNA as described in WO2015/089419.

Further means of introducing one or more components of the targeted base-editing system to the plant cell is by using cell penetrating peptides (CPP). Accordingly, in particular, embodiments the disclosure comprises compositions comprising a cell penetrating peptide linked to the base-editing fusion protein. In particular embodiments, the base-editing fusion protein and/or guide RNA is coupled to one or more CPPs to effectively transport them inside plant protoplasts. Ramakrishna (Genome Res. 2014 June; 24 (6): 1020-7 for Cas9 in human cells). In other embodiments, the base-editing fusion protein and/or guide RNA are encoded by one or more circular or non-circular DNA molecule(s) which are coupled to one or more CPPs for plant protoplast delivery. The plant protoplasts are then regenerated to plant cells and further to plants. CPPs are generally described as short peptides of fewer than 35 amino acids either derived from proteins or from chimeric sequences which are capable of transporting biomolecules across cell membrane in a receptor independent manner. CPP can be cationic peptides, peptides having hydrophobic sequences, amphipathic peptides, peptides having proline-rich and anti-microbial sequence, and chimeric or bipartite peptides (Pooga and Langel 2005). CPPs are able to penetrate biological membranes and as such trigger the movement of various biomolecules across cell membranes into the cytoplasm and to improve their intracellular routing, and hence facilitate interaction of the biomolecule with the target.

In some embodiments, the methods described herein are used to modify endogenous genes or to modify their expression without the permanent introduction of any foreign gene including those encoding CRISPR components into the genome of the plant, so as to avoid the presence of foreign DNA in the genome of the plant. In particular embodiments, this is ensured by transient expression of the targeted base-editing system components. In particular embodiments, one or more of the components are expressed on one or more viral vectors which produce sufficient CRISPR-Cas protein, cytosine deaminase, and guide RNA to consistently steadily ensure modification of a gene of interest according to a method described herein. In particular embodiments, transient expression of the targeted base-editing system constructs is ensured in plant protoplasts and thus not integrated into the genome. The limited window of expression can be sufficient to allow the targeted base-editing system to ensure modification of a target gene as described herein.

In some embodiments, the different components of the targeted base-editing system are introduced in the plant cell, protoplast or plant tissue either separately or in mixture, with the aid of delivering molecules such as nanoparticles or CPP molecules as described herein above. The expression of the targeted base-editing system components can induce targeted modification of the genome, by cytosine deaminase activity. The different strategies described herein above allow CRISPR-mediated targeted genome editing without requiring the introduction of the targeted base-editing system components into the plant genome. Components which are transiently introduced into the plant cell are typically removed upon crossing.

In some embodiments, plant cells which have a modified genome and that are produced or obtained by any of the methods described herein, can be cultured to regenerate a whole plant which possesses the transformed or modified genotype and thus the desired phenotype. Conventional regeneration techniques are well known to those skilled in the art. Particular examples of such regeneration techniques rely on manipulation of certain phytohormones in a tissue culture growth medium, and typically relying on a biocide and/or herbicide marker which has been introduced together with the desired nucleotide sequences. In further particular embodiments, plant regeneration is obtained from cultured protoplasts, plant callus, explants, organs, pollens, embryos or parts thereof (see e.g. Evans et al. (1983), Handbook of Plant Cell Culture, Klee et al (1987) Ann. Rev. of Plant Phys.).

In some embodiments, transformed or improved plants as described herein can be self-pollinated to provide seed for homozygous trait-improved plants of the disclosure, which have a desired trait such as seedlessness, reduced seed size, reduced endocarp tissue, or less lignified endocarp (homozygous for the DNA modification) or crossed with non-transgenic plants or different trait-improved plants to provide seed for heterozygous plants. Where a recombinant DNA was introduced into the plant cell, the resulting plant of such a crossing is a plant which is heterozygous for the recombinant DNA molecule. Both such homozygous and heterozygous plants obtained by crossing from the trait-improved plants and comprising the genetic modification (which can be a recombinant DNA) are referred to herein as "progeny". Alternatively, gene-edited plants can be obtained by one of the methods described herein using the targeted base-editing system whereby no foreign DNA is incorporated into the genome using transient expression/delivery or whereby foreign DNA is incorporated into the genome using stable transformation but removed/segregated away upon crossing. Progeny of such plants, obtained by further breeding may also contain the genetic modification such as nucleotide substitutions. Breedings are performed by any breeding methods that are commonly used for different crops (e.g., Allard, Principles of Plant Breeding, John Wiley & Sons, NY, U. of CA, Davis, CA, 50-98 (1960).

Plants and Plant Parts Having a Modified AG Clade MADS-Box Transcription Factor and Methods of Producing the Same.

In view of the foregoing, additional embodiments of the invention are described herein. Accordingly, in some embodiments, a plant or plant part thereof is provided comprising at least one non-natural mutation in an endogenous gene encoding an AGAMOUS clade MADS-box transcription factor. An AG clade MADS-box transcription factor useful with this invention includes but is not limited to AGAMOUS (AG), SHATTERPROOF 1 (SHP1), SHATTERPROOF 2 (SHP2), and/or SEEDSTICK (STK). In some embodiments, the endogenous gene encoding an AG clade MADS-box transcription factor is an endogenous SEEDSTICK (STK) gene.

A non-natural mutation as described herein includes, but is not limited to, a dominant-negative allele, semi-dominant allele, weak loss of function allele, or a hypomorphic mutation. In some embodiments, the mutation is a dominant-negative allele or a weak loss of function allele. In some embodiments, the mutation is a weak loss of function allele, or a hypomorphic mutation.

In some embodiments, the endogenous gene encoding an AG clade MADS-box transcription factor is capable of regulating seed production. In some embodiments, a plant comprising the at least one non-natural mutation in an endogenous gene encoding an AG clade MADS-box transcription factor exhibits altered fruit development, optionally wherein the endogenous gene encoding an AG clade MADS-box transcription factor is a SEEDSTICK (STK) transcription factor gene. In some embodiments, altered fruit development comprises a phenotype including but not limited to seedlessness (e.g., no seed or a reduced number of seeds), reduced seediness, reduced seed lignin content, reduced seed endocarp formation, or smoother seed surface.

In some embodiments, the endogenous SEEDSTICK (STK) gene encodes a polypeptide having at least 80% identity (e.g., 80, 81, 82, 83, 84, 85, 86, 87, 88, 89, 90, 91, 92, 93, 94, 95, 96, 97, 98, 99, or 100%) to any one of the amino acid sequences of SEQ ID NOs: 13, 29, 53, 66, 78, 97, 128, 150, 152, 154, 156, 158, 160, 162, 164, or 166-171, or encodes a region of a polypeptide having at least 80% identity to any one of the amino acid sequences of SEQ ID NOs: 177-183, 187, 188, or 189; or comprises a nucleotide sequence having at least 80% sequence identity to any one of the nucleotide sequence of SEQ ID NOs: 153, 155, 157, 159, 161, 163, or 165 or comprises a region having at least 80% sequence identity to any one of the nucleotide sequence of SEQ ID NOs: 172-174. Thus, in some embodiments, the motifs/domains described herein may be used to identify a STK gene for modifying a plant or part thereof according to methods of this invention to produce a seedless plant or part thereof or a plant or part thereof having reduced seediness, reduced seed lignin content, reduced seed endocarp formation, or smoother seed surface.

In some embodiments, the at least one non-natural mutation occurs in a region of an AG clade MADS-box transcription factor comprising any one of the nucleotide sequences of SEQ ID NOs: 172-174 or a portion thereof. In some embodiments, the at least one non-natural mutation results in a substitution in an amino acid residue located at any one or more of position 83-86 with reference amino acid position numbering of SEQ ID NO:13 or located at position 57-60 with reference amino acid position numbering of SEQ ID NO:29, 53, 66, 78, 97, 128, 150, 152, 154, 156, 158, 159, 160, 162, 164, or 166-171. In some embodiments, the at least one non-natural mutation results in a substitution in an amino acid residue located at any one or more of position 116-128 with reference amino acid position numbering of SEQ ID NO:13, located at position 91-103 with reference amino acid position numbering of SEQ ID NO:29, SEQ ID NO:78 SEQ ID NO: 97, SEQ ID NO:152, SEQ ID NO:154, SEQ ID NO:156, SEQ ID NO:158, SEQ ID NO: 159, SEQ ID NO:160, SEQ ID NO:162, SEQ ID NO:164 or SEQ ID NOs: 166-171, or located at position 90-102 with reference amino acid position numbering of SEQ ID NO:53, SEQ ID NO: 66, SEQ ID NO:128, or SEQ ID NO:150, optionally located at position 116-119 (YQQE; SEQ ID NO:177) with reference amino acid position numbering of SEQ ID NO:13, position 91-94 with reference amino acid position numbering of SEQ ID NOs: 29, 53, 66, 78, 97, 152, 154, 156, 158, 159, 160, 162, 164, or 166-171, or position 90-93 with reference amino acid position numbering of SEQ ID NOs: 53, 66, 128 or 150.

In some embodiments, the at least one non-natural mutation is a base substitution, a base deletion and/or a base insertion. In some embodiments, a base substitution to an A, a T, a G, or a C. In some embodiments, the at least one non-natural mutation is a substitution of at least one base pair (e.g., 1, 2, 3, 4, or 5 base pairs). In some embodiments, the at least one non-natural mutation results in a deletion of the 3' end of the gene and a polypeptide having a C-terminal truncation or results in a deletion of the 5' end of the gene and a polypeptide having an N-terminal truncation.

In some embodiments, the at least one non-natural mutation is an amino acid substitution at a conserved arginine in a STK gene, wherein the conserved arginine (arg, R) residue is located: at residue 196 with reference amino acid position numbering of SEQ ID NO:66; at residue 197 with reference amino acid position numbering of SEQ ID NOs: 53, 78, 150, 166-171; at residue 198 with reference amino acid position numbering of SEQ ID NO:29; residue 199 with reference amino acid position numbering of SEQ ID NO:128; at residue 201 with reference amino acid position numbering of SEQ ID NOs: 97, 152, 154, 156, 158, 160, 162, 164; or at residue 225 with reference amino acid position numbering of SEQ ID NO:13. In some embodiments, the substitution is R>L or R>H.

In some embodiments, the at least one non-natural mutation is in the C-terminal domain of the polypeptide encoded by the endogenous gene encoding an AG clade MADS-box transcription factor, optionally in the C-terminal domain of a polypeptide encoded by a STK gene. In some embodiments, at least one non-natural mutation in an AG clade MADS-box transcription factor results in a deletion of at least one amino acid or at least two or more consecutive amino acid.

In some embodiments, a deletion is an in-frame deletion or an out-of-frame deletion, optionally wherein the in-frame mutation or the out-of-frame mutation results in a non-natural/premature stop codon and a C-terminal truncation of one amino acid residue or two or more consecutive amino acid. In some embodiments, such a deletion removes the conserved arginine (arg, R) residue located at residue 196 with reference amino acid position numbering of SEQ ID NO: 66; at residue 197 with reference amino acid position numbering of SEQ ID NOs: 53, 78, 150, 166-171; at residue 198 with reference amino acid position numbering of SEQ ID NO:29; residue 199 with reference amino acid position numbering of SEQ ID NO:128; at residue 201 with reference amino acid position numbering of SEQ ID NOs: 97, 152, 154, 156, 158, 160, 162, 164; or at residue 225 with reference amino acid position numbering of SEQ ID NO:13, optionally wherein residues surrounding the conserved arginine are removed.

In some embodiments, the invention provides a plant cell, comprising a base editing system comprising: (a) a CRISPR-associated effector protein; (b) a cytidine deaminase or adenosine deaminase; and (c) a guide nucleic acid (gRNA) having a spacer sequence with complementarity to an endogenous target gene encoding an AG clade MADS-box transcription factor. In some embodiments, the AG clade MADS-box transcription factor is AGAMOUS (AG), SHATTERPROOF 1 (SHP1), SHATTERPROOF 2 (SHP2), and/or SEEDSTICK (STK), optionally the AG clade MADS-box transcription factor is a SEEDSTICK (STK) gene. In some embodiments, the endogenous AG clade MADS-box transcription factor gene encodes a SEED-STICK (STK) transcription factor having at least 80% sequence identity to any one of the amino acid sequences of SEQ ID NOs: 13, 29, 53, 66, 78, 97, 128, 150, 152, 154, 156, 158, 160, 162, 164 or 166-171 or comprises a region having at least 90% sequence identity to any one of the amino acid sequences of SEQ ID NO:SEQ ID NOs: 177-183, 187, 188, or 189. In some embodiments, the SEEDSTICK (STK) transcription factor is encoded by a sequence having at least 80% sequence identity to any one of the nucleotide sequences of SEQ ID NOs: 153, 155, 157, 159, 161, 163, or 165 or is encoded by a sequence having at least 80% sequence identity to any one of the nucleotide sequences of SEQ ID NOs: 172-174. In some embodiments, the gRNA useful with this invention comprises a spacer sequence having at least 80% identity to any one of SEQ ID NOs: 175, 176, 184, 185, or 186.

In some embodiments, a plant or part thereof (e.g., a plant cell) comprising at least one non-natural mutation in an endogenous AG clade MADS-box transcription factor gene that has altered fruit development is provided, wherein the at least one non-natural mutation is a substitution, insertion or a deletion that is introduced using an editing system that comprises a nucleic acid binding domain that binds to a target site in the AG clade MADS-box transcription factor gene, wherein the AG clade MADS-box transcription factor gene is a SEEDSTICK (STK) gene, the STK gene (a) comprising at least 80% sequence identity to any one of the nucleotide sequences of SEQ ID NOs: 153, 155, 157, 159, 161, 163, or 165, or a region having at least 90% sequence identity to any one of the nucleotide sequence of SEQ ID NOs: 172-174; or (b) encoding a AG clade MADS-box transcription factor having at least 80% sequence identity to any one of the amino acid sequences of SEQ ID NOs: 13, 29, 53, 66, 78, 97, 128, 150, 152, 154, 156, 158, 159, 160, 162, 164 or 166-171 or comprising a region having at least 90% sequence identity to any one of the amino acid sequences of SEQ ID NOs: 177-183, 187, 188, or 189. In some embodiments, the nucleic acid binding domain binds to a target site having the nucleotide sequence of any one of the nucleotide sequences of SEQ ID NOs: 172, 173 or 174. Altered fruit development includes, but is not limited to, a phenotype of seedlessness (no or reduced seed production) or reduced seediness as described herein.

In some embodiments, the at least one non-natural mutation is a dominant-negative allele, semi-dominant allele, weak loss of function allele, or a hypomorphic mutation. In some embodiment, the at least one non-natural mutation is at least one (e.g., 1, 2, 3, 4, 5, 6, 7, 8, 9, 10, 11, 12, 13, 14, 15, 16, or more) base substitution, base deletion, or base addition. In some embodiment, the at least one non-natural mutation is a point mutation. In some embodiments, the at least one base substitution comprises a substitution to an A, a T, a G, or a C. In some embodiments, the at least one non-natural mutation is a frameshift mutation (e.g., an in-frame deletion; an out-of-frame deletion). Such deletions can alter the reading frame resulting in premature termination of translation, e.g., a premature stop codon a truncation of the polypeptide. In some embodiments, the at least one non-natural mutation in an endogenous AG clade MADS-box transcription factor gene results in a deletion of at least one amino acid or two or more consecutive amino acids (e.g., 2, 3, 4, 5, 6, 7, 8, 9, 10, 11, 12, 13, 14, 15, 16, 17, 18, 19, or 20 or more), optionally the two or more amino acids are consecutive amino acids.

In some embodiments, at least one non-natural mutation is in the N-terminal domain of the polypeptide encoded by the endogenous gene encoding an AG clade MADS-box transcription factor; optionally an STK polypeptide. In some embodiments, at least one non-natural mutation is in the C-terminal domain of the polypeptide encoded by the endogenous gene encoding an AG clade MADS-box transcription factor; optionally an STK polypeptide.

In some embodiments, the at least one non-natural mutation in the C-terminal domain is a C-terminal truncation, optionally wherein at least the last 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 consecutive amino acids of the C-terminus of an STK polypeptide are truncated. Such a truncation results in the removal of a conserved arginine in the C-terminus of the STK polypeptide, wherein the conserved arginine is residue 196 with reference amino acid position numbering of SEQ ID NO: 66; residue 197 with reference amino acid position numbering of SEQ ID NOs: 53, 78, 150, 166-171; residue 198 with reference amino acid position numbering of SEQ ID NO:29; residue 199 with reference amino acid position numbering of SEQ ID NO:128; residue 201 with reference amino acid position numbering of SEQ ID NOs: 97, 152, 154, 156, 158, 160, 162, 164; or residue 225 with reference amino acid position numbering of SEQ ID NO:13.

In some embodiments, the at least one non-natural mutation is in an endogenous SEEDSTICK (STK) gene and results in a substituted amino acid residue located at position 196 with reference amino acid position numbering of SEQ ID NO:66; at position 197 with reference amino acid position numbering of SEQ ID NOs: 53, 78, 150, 166-171; at position 198 with reference amino acid position numbering of SEQ ID NO:29; at position 199 with reference amino acid position numbering of SEQ ID NO:128; at position 201 with reference amino acid position numbering of SEQ ID NOs: 97, 152, 154, 156, 158, 160, 162, 164; or at position 225 with reference amino acid position numbering of SEQ ID NO:13. In some embodiments, the substitution is arginine to leucine (R>L) or arginine to histidine (R>H).

The invention further provides a plant or part thereof comprising a mutated endogenous AG clade MADS-box transcription factor gene, wherein the mutated endogenous AG clade MADS-box transcription factor gene is a SEED-STICK (STK) gene that (a) comprises a sequence having at least 80% identity to the nucleotide sequence of SEQ ID NOs: 153, 155, 157, 159, 161, 163, or 165, or sequence comprising a region having at least 90% sequence identity to any one of the nucleotide sequence of SEQ ID NOs: 172-174; or (b) encodes a sequence having at least 80% sequence identity to any one of the amino acid sequences of SEQ ID NOs: 13, 29, 53, 66, 78, 97, 128, 150, 152, 154, 156, 158, 159, 160, 162, 164 or 166-171 or a sequence comprising a region having at least 90% sequence identity to any one of the amino acid sequences of SEQ ID NOs: 177-183, 187, 188, or 189, wherein the plant comprising a mutated STK gene exhibits altered fruit development.

Methods for producing a plant or plant part having altered fruit development are provided. In some embodiments, a method of producing/breeding a transgene-free base-edited plant is provided, the method comprising: (a) crossing the plant of the invention with a transgene free plant, thereby introducing the at least one mutation, the mutation, or the modification into the plant that is transgene-free; and (b) selecting a progeny plant that comprises the at least one single nucleotide substitution but is transgene-free, thereby producing a transgene free base-edited plant having altered fruit development.

In some embodiments, a method of producing a plurality of plants exhibiting altered fruit development is provided, the method comprising planting two or more plants of the invention in a growing area (e.g., a field (e.g., a cultivated field, an agricultural field), a growth chamber, a greenhouse, a recreational area, a lawn, and/or a roadside and the like), thereby providing a plurality of plants exhibiting altered fruit development as compared to a plurality of control plants not comprising the mutation.

In some embodiments, a method for editing a specific site in the genome of a plant cell is provided, the method comprising: cleaving, in a site specific manner, a target site within an endogenous AG clade MADS-box transcription factor gene in the plant cell, the endogenous AG clade MADS-box transcription factor gene being a SEEDSTICK (STK) gene (a) comprising at least 80% sequence identity to any one of the nucleotide sequences of SEQ ID NOs: 153, 155, 157, 159, 161, 163, or 165, or a region having at least 90% sequence identity to any one of the nucleotide sequence of SEQ ID NOs: 172-174; or (b) encoding a AG clade MADS-box transcription factor having at least 80% sequence identity to any one of the amino acid sequences of SEQ ID NOs: 13, 29, 53, 66, 78, 97, 128, 150, 152, 154, 156, 158, 159, 160, 162, 164 or 166-171 or comprising a region having at least 90% sequence identity to any one of the amino acid sequences of SEQ ID NOs: 177-183, 187, 188, or 189, thereby generating an edit in the endogenous AG clade MADS-box transcription factor gene of the plant cell. In some embodiment, the method further comprises regenerating a plant from the plant cell comprising an edit in the endogenous STK gene to produce a plant comprising the edit in its endogenous STK gene, wherein the edit results in a non-natural mutation. In some embodiments, a plant comprising the edit in its endogenous STK gene exhibits altered fruit development, optionally wherein altered fruit development is a phenotype of seedlessness and/or reduced seediness. In some embodiments, the non-natural mutation produces a dominant-negative allele, semi-dominant allele, weak loss of function allele, or a hypomorphic mutation. In some embodiments, the non-natural mutation is a substitution, an addition or a deletion. In some embodiments, the non-natural mutation is a deletion of at least 4 consecutive base pairs to about 150 consecutive base pairs from the 3' end of the STK gene, wherein the deletion results in a C-terminal truncation comprising a truncation of at least 1 amino acid residue to about 50 consecutive amino acid residues.

Further provided is a method for making a plant, comprising: (a) contacting a population of plant cells comprising a DNA sequence that encodes a wild-type endogenous SEEDSTICK (STK) gene with a nuclease linked to a nucleic acid binding domain (e.g., editing system) that binds to a sequence: (a) having at least 80% sequence identity to any one of the nucleotide sequences of SEQ ID NOs: 153, 155, 157, 159, 161, 163, or 165, or comprising a region having at least 80% sequence identity to any one of the nucleotide sequence of SEQ ID NOs: 172-174; or (b) encoding a SEEDSTICK (STK) transcription factor (i) having at least 80% sequence identity to any one of the amino acid sequences SEQ ID NOs: 13, 29, 53, 66, 78, 97, 128, 150, 152, 154, 156, 158, 160, 162, 164, or 166-171 or (ii) comprising a region having at least 90% sequence identity to any one of the amino acid sequences of SEQ ID NOs: 177-183, 187, 188, or 189; (b) selecting a plant cell from said population in which at least one DNA sequence encoding the STK transcription factor has been mutated, wherein the mutation comprises a substitution of at least one nucleotide in the at least one DNA sequence; and (c) growing the selected plant cell into a plant.

In some embodiments, a method for producing a plant or part thereof comprising at least one cell in which an endogenous AG clade MADS-box transcription factor gene is mutated is provided, the method comprising contacting a target site in the AG clade MADS-box transcription factor gene in the plant or plant part with a nuclease linked to a nucleic acid binding domain (e.g., editing system) that binds to the target site, wherein the AG clade MADS-box transcription factor gene is a SEEDSTICK (STK) gene (a) comprising a sequence having at least 80% sequence identity to any one of the nucleotide sequences of SEQ ID NOs: 153, 155, 157, 159, 161, 163, or 165 or comprising a region having at least 80% sequence identity to any one of the nucleotide sequence of SEQ ID NOs: 172-174, or (b) encoding a SEEDSTICK (STK) transcription factor having at least 80% sequence identity to any one of the amino acid sequences of SEQ ID NOs: 13, 29, 53, 66, 78, 97, 128, 150, 152, 154, 156, 158, 160, 162, 164, or 166-171, or comprising a region having at least 80% identity to any one of the amino acid sequences of SEQ ID NOs: 177-183, 187, 188, or 189, thereby producing a plant or part thereof comprising at least one cell having a mutation in the endogenous AG clade MADS-box transcription factor gene.

In some embodiments, a method for producing a plant having an altered fruit development phenotype is provided, comprising (a) contacting a plant cell comprising a wild type endogenous AG clade MADS-box transcription factor gene with a nuclease targeting the wild type endogenous AG clade MADS-box transcription factor gene, wherein the nuclease is linked to a DNA binding domain that binds to a target site in the wild type endogenous AG clade MADS-box transcription factor gene, wherein the wild type endogenous AG clade MADS-box transcription factor gene is a SEEDSTICK (STK) gene that (i) comprises a sequence having at least 80% sequence identity to any one of the nucleotide sequences of SEQ ID NOs: 153, 155, 157, 159, 161, 163, or 165 or comprises a region having at least 80% sequence identity to any one of the nucleotide sequence of SEQ ID NOs: 172-174 and/or (ii) encodes a sequence having at least 80% sequence identity to any one of the amino acid sequences of a sequence having at least 80% sequence identity to any one of the amino acid sequences of SEQ ID NOs: 13, 29, 53, 66, 78, 97, 128, 150, 152, 154, 156, 158, 160, 162, 164, or 166-171, or a sequence comprising a region having at least 90% sequence identity to any one of the amino acid sequences of SEQ ID NOs: 177-183, 187, 188, or 189; (b) growing the plant cell into a plant, thereby producing a plant having an altered fruit phenotype.

In some embodiments, a method for producing a plant or part thereof comprising at least one cell having a mutated endogenous AG clade MADS-box transcription factor gene is provided, the method comprising contacting a target site in an endogenous AG clade MADS-box transcription factor gene in the plant or plant part with a nuclease comprising a cleavage domain and a DNA-binding domain, wherein the DNA binding domain binds to a target site in the endogenous AG clade MADS-box transcription factor gene, wherein the endogenous AG clade MADS-box transcription factor gene is a SEEDSTICK (STK) gene that (a) encodes (i) a sequence having at least 80% sequence identity to any one of the amino acid sequences of SEQ ID NOs: 13, 29, 53, 66, 78, 97, 128, 150, 152, 154, 156, 158, 160, 162, 164, or 166-171 or (ii) a sequence comprising a region having at least 90% sequence identity to any one of the amino acid sequences of SEQ ID NOs: 177-183, 187, 188, or 189; and/or (b) comprises a sequence having at least 80% sequence identity to the nucleotide sequence of any one of SEQ ID NOs: 153, 155, 157, 159, 161, 163, or 165 or a region having at least 80% sequence identity to any one of the nucleotide sequence of SEQ ID NOs: 172-174, thereby producing the plant or part thereof comprising at least one cell having a mutated endogenous AG clade MADS-box transcription factor gene.

In some embodiments, a method of producing a plant or part thereof comprising a mutated endogenous AG clade MADS-box transcription factor gene and having altered fruit development is provided, the method comprising contacting a target site in an endogenous AG clade MADS-box transcription factor gene with a nuclease comprising a cleavage domain and a DNA-binding domain (e.g., editing system) comprising a nucleic acid binding domain that binds to the target site in the AG clade MADS-box transcription factor gene, wherein the AG clade MADS-box transcription factor gene is a SEEDSTICK (STK) gene (a) comprising a sequence having at least 80% sequence identity to any one of the nucleotide sequences of SEQ ID NOs: 153, 155, 157, 159, 161, 163, or 165 or comprising a region having at least 80% sequence identity to any one of the nucleotide sequence of SEQ ID NOs: 172-174, or (b) encoding a SEEDSTICK (STK) transcription factor having at least 80% sequence identity to any one of the amino acid sequences of SEQ ID NOs: 13, 29, 53, 66, 78, 97, 128, 150, 152, 154, 156, 158, 160, 162, 164, or 166-171, or comprising a region having at least 80% identity to any one of the amino acid sequences of SEQ ID NOs: 177-183, 187, 188, or 189, thereby producing a plant or part thereof comprising a mutated endogenous AG clade MADS-box transcription factor gene and having altered fruit development.

In some embodiments, the nuclease (e.g., of an editing system) cleaves the endogenous STK gene and a mutation is introduced into the endogenous STK gene. As described herein, a nuclease includes a zinc finger nuclease, a transcription activator-like effector nucleases (TALEN), an endonuclease (e.g. Fok1) or a CRISPR-Cas effector protein. In some embodiments, a DNA binding domain is a zinc finger, a transcription activator-like DNA binding domain (TAL), an argonaute or a CRISPR-Cas effector DNA binding domain.

In some embodiments, the mutation that is introduced is a non-natural mutation, wherein the non-natural mutation results in altered fruit development in the plant. As described herein, an altered fruit development phenotype includes but is not limited to seedlessness or reduced seediness.

A non-natural mutation useful for the methods of this invention includes but is not limited to a substitution, an insertion and/or a deletion of at least one base (nucleotide) (e.g., 1, 2, 3, 4, 5, 6, 7, 8, 9, 10, 11, 12, 13, 14, 15, 16, or more) or at least one amino acid (e.g., 1, 2, 3, 4, 5, 6, 7, 8, 9, 10, 11, 12, 13, 14, 15, 16, or more). In some embodiment, the at least one non-natural mutation is a point mutation. In some embodiments, the at least one base substitution comprises a substitution to an A, a T, a G, or a C. In some embodiments, the at least one non-natural mutation is a frameshift mutation (e.g., an in-frame deletion; an out-of-frame deletion). Such deletions can alter the reading frame resulting in premature termination of translation, e.g., a premature stop codon a truncation of the polypeptide.

In some embodiments, a deletion may be a deletion at least 4 consecutive base pairs to about 150 consecutive base pairs from the 3' end of the STK gene, which deletion may result in a C-terminal truncation comprising a truncation of at least 1 amino acid residue to about 50 consecutive amino acid residues from the C-terminus of a polypeptide encoded by the STK gene.

Also provided herein are example guide nucleic acids for carrying out the methods of the invention. Based on the guidance of the present invention additional guides may be developed beyond those specifically provided. In some embodiments, a guide nucleic acid (e.g., gRNA, gDNA, crRNA, crDNA) that binds to a target site in a AG clade MADS-box transcription factor gene is provided, wherein the endogenous AG clade MADS-box transcription factor gene is a SEEDSTICK (STK) gene (a) comprising a sequence having at least 80% sequence identity to any one of the nucleotide sequences of SEQ ID NOs: 153, 155, 157, 159, 161, 163, or 165 or comprising a region having at least 80% sequence identity to any one of the nucleotide sequence of SEQ ID NOs: 172-174, or (b) encoding a SEEDSTICK (STK) transcription factor having at least 80% sequence identity to any one of the amino acid sequences of SEQ ID NOs: 13, 29, 53, 66, 78, 97, 128, 150, 152, 154, 156, 158, 160, 162, 164, or 166-171, or a region having at least 80% identity to any one of the amino acid sequences of SEQ ID NOs: 177-183, 187, 188, or 189. In some embodiments, the guide nucleic acid comprises a spacer having the nucleotide sequence of any one of SEQ ID NOs: 175, 176, 184, 185, or 186.

In some embodiments, a system is provided comprising a guide nucleic acid of the invention and a CRISPR-Cas effector protein that associates with the guide nucleic acid. In some embodiments, the system further comprises a tracr nucleic acid that associates with the guide nucleic acid and a CRISPR-Cas effector protein, optionally wherein the tracr nucleic acid and the guide nucleic acid are covalently linked.

In some embodiments, a gene editing system is provided comprising a CRISPR-Cas effector protein in association with a guide nucleic acid, wherein the guide nucleic acid comprises a spacer sequence that binds to a AG clade MADS-box transcription factor gene. In some embodiments, the AG clade MADS-box transcription factor gene is a SEEDSTICK (STK) gene (a) comprising at least 80% sequence identity to the nucleotide sequence of any one of SEQ ID NOs: 153, 155, 157, 159, 161, 163, or 165 or comprising a region having at least 80% sequence identity to any one of the nucleotide sequence of SEQ ID NOs: 172-174, and/or (b) encoding (i) a sequence having at least 80% sequence identity to any one of the amino acid sequences of SEQ ID NOs: 13, 29, 53, 66, 78, 97, 128, 150, 152, 154, 156, 158, 160, 162, 164, or 166-171, or (ii) a sequence comprising a region having at least 90% sequence identity to any one of the amino acid sequences of SEQ ID NOs: 177-183, 187, 188, or 189. In some embodiments, the guide nucleic acid of the gene editing system comprises a spacer sequence having the nucleotide sequence of any one of SEQ ID NOs: 175, 176, 184, 185, or 186. In some embodiments, the gene editing system may further comprise a tracr nucleic acid that associates with the guide nucleic acid and a CRISPR-Cas effector protein, optionally wherein the tracr nucleic acid and the guide nucleic acid are covalently linked.

In some embodiments, a complex comprising a CRISPR-Cas effector protein comprising a cleavage domain and a guide nucleic acid is provided, wherein the guide nucleic acid binds to a target site in a AG clade MADS-box transcription factor gene, wherein the AG clade MADS-box transcription factor gene is a SEEDSTICK (STK) gene (a) comprising at least 80% sequence identity to the nucleotide sequence of any one of SEQ ID NOs: 153, 155, 157, 159, 161, 163, or 165 or comprising a region having at least 80% sequence identity to any one of the nucleotide sequence of SEQ ID NOs: 172-174, and/or (b) encoding (i) a sequence having at least 80% sequence identity to any one of the amino acid sequences of SEQ ID NOs: 13, 29, 53, 66, 78, 97, 128 or 150, or (ii) a sequence comprising a region having at least 80% sequence identity to any one of the amino acid sequences of SEQ ID NOs: 13, 29, 53, 66, 78, 97, 128, 150, 152, 154, 156, 158, 160, 162, 164, or 166-171, or a region having at least 80% identity to any one of the amino acid sequences of SEQ ID NOs: 177-183, 187, 188, or 189, wherein the cleavage domain cleaves a target strand in the AG clade MADS-box transcription factor gene.

In some embodiments, an expression cassette is provided, the expression cassetted comprising a (a) polynucleotide encoding CRISPR-Cas effector protein comprising a cleavage domain and (b) a guide nucleic acid that binds to a target site in a AG clade MADS-box transcription factor gene, wherein the AG clade MADS-box transcription factor gene is a SEEDSTICK gene and the guide nucleic acid comprises a spacer sequence that is complementary to and binds to a sequence having at least 80% sequence identity to at least a portion of a sequence having at least 80% sequence identity to the nucleotide sequence of any one of SEQ ID NOs: 153, 155, 157, 159, 161, 163, or 165 or a portion of a sequence comprising a region having at least 80% sequence identity to any one of the nucleotide sequence of SEQ ID NOs: 172-174; or a sequence encoding (i) a polypeptide having at least 80% sequence identity to any one of the amino acid sequences of SEQ ID NOs: 13, 29, 53, 66, 78, 97, 128, 150, 152, 154, 156, 158, 160, 162, 164, or 166-171, or (ii) a polypeptide comprising a region having at least 90% sequence identity to any one of the amino acid sequences of SEQ ID NOs: 177-183, 187, 188, or 189, optionally wherein a portion is about 2 to about 22 consecutive nucleotides in length.

In some embodiments, a nucleic acid is provided, the nucleic acid encoding a dominant-negative allele, semi-dominant allele, weak loss of function allele, or a hypomorphic mutation of an AG clade MADS-box transcription factor, optionally wherein the AG clade MADS-box transcription factor is AGAMOUS (AG), SHATTERPROOF 1 (SHP1), SHATTERPROOF 2 (SHP2), and/or SEEDSTICK (STK). In some embodiments, the endogenous gene encoding an AG clade MADS-box transcription factor is an endogenous SEEDSTICK (STK) gene as described herein. Also provided is a plant or part thereof comprising the nucleic acid of the invention, wherein the plant or part thereof exhibits altered fruit development.

Plants or parts thereof are as described herein and can include any plant or part thereof for which seedlessness, reduced seediness, reduced seed lignin content, reduced seed endocarp formation, or smoother seed surface is desirable. Thus, a plant or part thereof may be a dicot or a monocot, for example, and can include but is not limited to raspberry, black raspberry, blackberry, cherry, peach, avocado, strawberry, wild strawberry, apple, tomato, grape, peach, plum, apricot, pear, quince, loquat, date or almond. When an AG clade MADS-box transcription factor of a plant part, including a plant cell, is modified, the plant part may be regenerated into a plant. Methods for regenerating plants are known and can be readily used with the plant parts of this invention.

EXAMPLES

The following examples are given for the purpose of illustrating various embodiments of the disclosure and are not meant to limit the present disclosure in any fashion. Changes therein and other uses which are encompassed within the spirit of the disclosure, as defined by the scope of the claims, will occur to those skilled in the art.

Example 1: Identification of Agamous Clade Mads-Box Transcription Factors

AGAMOUS clade MADS-box transcription factors were defined and described in § II "Next Generation Plant Breeding Methodology Utilizing Mutations on AGAMOUS Clade MADS-box Transcription Factors for Altered Fruit Development." The contours of the genus and definition of such is provided in that section. The current Example 1 describes how this clade was discovered as a potential target gene for mutation, in order to test for altered fruit development phenotypes.

Bioinformatics and molecular evolutionary analyses were performed on the genome database of seven plant species, including: *Arabidopsis* (*Arabidopsis thaliana*), Apple (*Malus pumila*), Black Raspberry (*Rubus occidentalis*), Grape (*Vitis vinifera*), Peach (*Prunus persica*), Tomato (*Solanum lycoperisicum*), and Wild Strawberry (*Fragaria vesca*). Using analytic techniques derived from molecular evolutionary biology, MADS-box gene sequences from *Arabidopsis thaliana* were searched on the genome database of other plant species of interest to obtain homologues, orthologues, and/or paralogues of the *Arabidopsis* MADS-box genes of interest. Consequently, each amino acid sequence of the MADS-box transcription factors was collected from the genome database of each species (Table 2) and followed by multiple sequence alignment (MSA) analyses.

TABLE 2

| SEQ ID NO: | Sequence Type | Common Name | Scientific Name |
|---|---|---|---|
| 1 | Amino Acid | *Arabidopsis* | *Arabidopsis thaliana* |
| 2 | Amino Acid | *Arabidopsis* | *Arabidopsis thaliana* |
| 3 | Amino Acid | *Arabidopsis* | *Arabidopsis thaliana* |
| 4 | Amino Acid | *Arabidopsis* | *Arabidopsis thaliana* |
| 5 | Amino Acid | *Arabidopsis* | *Arabidopsis thaliana* |

TABLE 2-continued

| SEQ ID NO: | Sequence Type | Common Name | Scientific Name |
|---|---|---|---|
| 6 | Amino Acid | *Arabidopsis* | *Arabidopsis thaliana* |
| 7 | Amino Acid | *Arabidopsis* | *Arabidopsis thaliana* |
| 8 | Amino Acid | *Arabidopsis* | *Arabidopsis thaliana* |
| 9 | Amino Acid | *Arabidopsis* | *Arabidopsis thaliana* |
| 10 | Amino Acid | *Arabidopsis* | *Arabidopsis thaliana* |
| 11 | Amino Acid | *Arabidopsis* | *Arabidopsis thaliana* |
| 12 | Amino Acid | *Arabidopsis* | *Arabidopsis thaliana* |
| 13 | Amino Acid | *Arabidopsis* | *Arabidopsis thaliana* |
| 14 | Amino Acid | *Arabidopsis* | *Arabidopsis thaliana* |
| 15 | Amino Acid | *Arabidopsis* | *Arabidopsis thaliana* |
| 16 | Amino Acid | *Arabidopsis* | *Arabidopsis thaliana* |
| 17 | Amino Acid | *Arabidopsis* | *Arabidopsis thaliana* |
| 18 | Amino Acid | *Arabidopsis* | *Arabidopsis thaliana* |
| 19 | Amino Acid | *Arabidopsis* | *Arabidopsis thaliana* |
| 20 | Amino Acid | *Arabidopsis* | *Arabidopsis thaliana* |
| 21 | Amino Acid | *Arabidopsis* | *Arabidopsis thaliana* |
| 22 | Amino Acid | Strawberry (Wild) | *Fragaria vesca* |
| 23 | Amino Acid | Strawberry (Wild) | *Fragaria vesca* |
| 24 | Amino Acid | Strawberry (Wild) | *Fragaria vesca* |
| 25 | Amino Acid | Strawberry (Wild) | *Fragaria vesca* |
| 26 | Amino Acid | Strawberry (Wild) | *Fragaria vesca* |
| 27 | Amino Acid | Strawberry (Wild) | *Fragaria vesca* |
| 28 | Amino Acid | Strawberry (Wild) | *Fragaria vesca* |
| 29 | Amino Acid | Strawberry (Wild) | *Fragaria vesca* |
| 30 | Amino Acid | Strawberry (Wild) | *Fragaria vesca* |
| 31 | Amino Acid | Strawberry (Wild) | *Fragaria vesca* |
| 32 | Amino Acid | Strawberry (Wild) | *Fragaria vesca* |
| 33 | Amino Acid | Strawberry (Wild) | *Fragaria vesca* |
| 34 | Amino Acid | Strawberry (Wild) | *Fragaria vesca* |
| 35 | Amino Acid | Strawberry (Wild) | *Fragaria vesca* |
| 36 | Amino Acid | Strawberry (Wild) | *Fragaria vesca* |
| 37 | Amino Acid | Apple | *Malus domestica* |
| 38 | Amino Acid | Apple | *Malus domestica* |
| 39 | Amino Acid | Apple | *Malus domestica* |
| 40 | Amino Acid | Apple | *Malus domestica* |
| 41 | Amino Acid | Apple | *Malus domestica* |
| 42 | Amino Acid | Apple | *Malus domestica* |
| 43 | Amino Acid | Apple | *Malus domestica* |

TABLE 2-continued

| SEQ ID NO: | Sequence Type | Common Name | Scientific Name |
|---|---|---|---|
| 44 | Amino Acid | Apple | *Malus domestica* |
| 45 | Amino Acid | Apple | *Malus domestica* |
| 46 | Amino Acid | Apple | *Malus domestica* |
| 47 | Amino Acid | Apple | *Malus domestica* |
| 48 | Amino Acid | Apple | *Malus domestica* |
| 49 | Amino Acid | Apple | *Malus domestica* |
| 50 | Amino Acid | Apple | *Malus domestica* |
| 51 | Amino Acid | Apple | *Malus domestica* |
| 52 | Amino Acid | Apple | *Malus domestica* |
| 53 | Amino Acid | Apple | *Malus domestica* |
| 54 | Amino Acid | Apple | *Malus domestica* |
| 55 | Amino Acid | Apple | *Malus domestica* |
| 56 | Amino Acid | Apple | *Malus domestica* |
| 57 | Amino Acid | Apple | *Malus domestica* |
| 58 | Amino Acid | Apple | *Malus domestica* |
| 59 | Amino Acid | Apple | *Malus domestica* |
| 60 | Amino Acid | Apple | *Malus domestica* |
| 61 | Amino Acid | Apple | *Malus domestica* |
| 62 | Amino Acid | Apple | *Malus domestica* |
| 63 | Amino Acid | Apple | *Malus domestica* |
| 65 | Amino Acid | Apple | *Malus domestica* |
| 65 | Amino Acid | Apple | *Malus domestica* |
| 66 | Amino Acid | Apple | *Malus domestica* |
| 67 | Amino Acid | Apple | *Malus domestica* |
| 68 | Amino Acid | Apple | *Malus domestica* |
| 69 | Amino Acid | Apple | *Malus domestica* |
| 70 | Amino Acid | Apple | *Malus domestica* |
| 71 | Amino Acid | Apple | *Malus domestica* |
| 72 | Amino Acid | Apple | *Malus domestica* |
| 73 | Amino Acid | Peach | *Prunus persica* |
| 74 | Amino Acid | Peach | *Prunus persica* |
| 75 | Amino Acid | Peach | *Prunus persica* |
| 76 | Amino Acid | Peach | *Prunus persica* |
| 77 | Amino Acid | Peach | *Prunus persica* |
| 78 | Amino Acid | Peach | *Prunus persica* |
| 79 | Amino Acid | Peach | *Prunus persica* |
| 80 | Amino Acid | Peach | *Prunus persica* |
| 81 | Amino Acid | Peach | *Prunus persica* |

TABLE 2-continued

| SEQ ID NO: | Sequence Type | Common Name | Scientific Name |
|---|---|---|---|
| 82 | Amino Acid | Peach | *Prunus persica* |
| 83 | Amino Acid | Peach | *Prunus persica* |
| 84 | Amino Acid | Peach | *Prunus persica* |
| 85 | Amino Acid | Peach | *Prunus persica* |
| 86 | Amino Acid | Peach | *Prunus persica* |
| 87 | Amino Acid | Peach | *Prunus persica* |
| 88 | Amino Acid | Peach | *Prunus persica* |
| 89 | Amino Acid | Peach | *Prunus persica* |
| 90 | Amino Acid | Black Raspberry | *Rubus occidentalis* |
| 91 | Amino Acid | Black Raspberry | *Rubus occidentalis* |
| 92 | Amino Acid | Black Raspberry | *Rubus occidentalis* |
| 93 | Amino Acid | Black Raspberry | *Rubus occidentalis* |
| 94 | Amino Acid | Black Raspberry | *Rubus occidentalis* |
| 95 | Amino Acid | Black Raspberry | *Rubus occidentalis* |
| 96 | Amino Acid | Black Raspberry | *Rubus occidentalis* |
| 97 | Amino Acid | Black Raspberry | *Rubus occidentalis* |
| 98 | Amino Acid | Black Raspberry | *Rubus occidentalis* |
| 99 | Amino Acid | Black Raspberry | *Rubus occidentalis* |
| 100 | Amino Acid | Black Raspberry | *Rubus occidentalis* |
| 101 | Amino Acid | Black Raspberry | *Rubus occidentalis* |
| 102 | Amino Acid | Black Raspberry | *Rubus occidentalis* |
| 103 | Amino Acid | Black Raspberry | *Rubus occidentalis* |
| 104 | Amino Acid | Black Raspberry | *Rubus occidentalis* |
| 105 | Amino Acid | Black Raspberry | *Rubus occidentalis* |
| 106 | Amino Acid | Black Raspberry | *Rubus occidentalis* |
| 107 | Amino Acid | Black Raspberry | *Rubus occidentalis* |
| 108 | Amino Acid | Tomato | *Solanum lycopersicum* |
| 109 | Amino Acid | Tomato | *Solanum lycopersicum* |
| 110 | Amino Acid | Tomato | *Solanum lycopersicum* |
| 111 | Amino Acid | Tomato | *Solanum lycopersicum* |
| 112 | Amino Acid | Tomato | *Solanum lycopersicum* |
| 113 | Amino Acid | Tomato | *Solanum lycopersicum* |
| 114 | Amino Acid | Tomato | *Solanum lycopersicum* |
| 115 | Amino Acid | Tomato | *Solanum lycopersicum* |
| 116 | Amino Acid | Tomato | *Solanum lycopersicum* |
| 117 | Amino Acid | Tomato | *Solanum lycopersicum* |
| 118 | Amino Acid | Tomato | *Solanum lycopersicum* |
| 119 | Amino Acid | Tomato | *Solanum lycopersicum* |

TABLE 2-continued

| SEQ ID NO: | Sequence Type | Common Name | Scientific Name |
|---|---|---|---|
| 120 | Amino Acid | Tomato | *Solanum lycopersicum* |
| 121 | Amino Acid | Tomato | *Solanum lycopersicum* |
| 122 | Amino Acid | Tomato | *Solanum lycopersicum* |
| 123 | Amino Acid | Tomato | *Solanum lycopersicum* |
| 124 | Amino Acid | Tomato | *Solanum lycopersicum* |
| 125 | Amino Acid | Tomato | *Solanum lycopersicum* |
| 126 | Amino Acid | Tomato | *Solanum lycopersicum* |
| 127 | Amino Acid | Tomato | *Solanum lycopersicum* |
| 128 | Amino Acid | Tomato | *Solanum lycopersicum* |
| 129 | Amino Acid | Tomato | *Solanum lycopersicum* |
| 130 | Amino Acid | Tomato | *Solanum lycopersicum* |
| 131 | Amino Acid | Tomato | *Solanum lycopersicum* |
| 132 | Amino Acid | Tomato | *Solanum lycopersicum* |
| 133 | Amino Acid | Grape | *Vitis vinifera* |
| 134 | Amino Acid | Grape | *Vitis vinifera* |
| 135 | Amino Acid | Grape | *Vitis vinifera* |
| 136 | Amino Acid | Grape | *Vitis vinifera* |
| 137 | Amino Acid | Grape | *Vitis vinifera* |
| 138 | Amino Acid | Grape | *Vitis vinifera* |
| 139 | Amino Acid | Grape | *Vitis vinifera* |
| 140 | Amino Acid | Grape | *Vitis vinifera* |
| 141 | Amino Acid | Grape | *Vitis vinifera* |
| 142 | Amino Acid | Grape | *Vitis vinifera* |
| 143 | Amino Acid | Grape | *Vitis vinifera* |
| 144 | Amino Acid | Grape | *Vitis vinifera* |
| 145 | Amino Acid | Grape | *Vitis vinifera* |
| 146 | Amino Acid | Grape | *Vitis vinifera* |
| 147 | Amino Acid | Grape | *Vitis vinifera* |
| 148 | Amino Acid | Grape | *Vitis vinifera* |
| 149 | Amino Acid | Grape | *Vitis vinifera* |
| 150 | Amino Acid | Grape | *Vitis vinifera* |
| 151 | Amino Acid | Grape | *Vitis vinifera* |

As one example to identify homologues, orthologues, and/or paralogues of the *Arabidopsis* MADS-box genes of interest, the protein-coding sequence for AtSTK/AtAGL11 was obtained from the *A. thaliana* genome (gene ID AT4G09960 in assembly version TAIR10) and Blast searches were conducted using the *Arabidopsis* STK/AGL11 protein-coding sequence as a query against genomes of the flowering plants. From the blast searches, the coding sequences underlying each blast hit were extracted for subsequent multiple sequence alignment and phylogenetic analysis. The same methodology was applied to other MADS-box genes, in order to identify and collect sequence information on homologues, orthologues, and/or paralogues of the *Arabidopsis* MADS-box genes of interest.

In order to identify an expanded number of MADS-box gene orthologs from disparate species, the Plant Comparative Genomics portal of the Department of Energy's Joint Genome Institute, also known as Phytozome, which hosts 93 assembled and annotated genomes from 82 plant species, was utilized. The amino acid sequences of the MADS-box gene orthologs identified from 7 plant species were aligned with MUSCLE. From this analysis, the amino acid residues of the MADS-box transcription factors that are conserved across the plant kingdom were identified. As aforementioned, the AGAMOUS clade MADS-box transcription factors as defined herein, comprise at least the following three conserved domains: (1) Y{A,S}NN motif (SEQ ID NO:259) at positions 83-86 with respect to *Arabidopsis thaliana* STK (AT4G09960.3); (2) YQQE{A,S} {A,S,N,K,T}KL{R,H}{Q,H,A,N,R}QI (SEQ ID NO:260) motif at positions 116-127 with respect to *Arabidopsis thaliana* STK (AT4G09960.3); and (3) R at position 225 with respect to *Arabidopsis thaliana* STK (AT4G09960.3).

For phylogenetic tree reconstruction, ModelFinder was used for substitution model selection and IQ-Tree for tree inference and branch support estimation with ultrafast bootstrap approximation. Evidence for orthology was found by examining the tree topology for clustering of genes from multiple species to the exclusion of paralogs from the focal species.

At first, the proteins possessing the three motifs characterized above from *Arabidopsis*, black raspberry and wild strawberry were analyzed. The AG clade transcription factors were clustered into the same clade, named herein 'AGAMOUS clade' or 'AG clade' MADS-box transcription factors. This AG clade comprises at least four species, including: MADS box genes, Agamous (AG), Seedstick (STK), and Shatterproof 1 and 2 (SHP1/2). Another phylogenetic analysis was done with the proteins sharing the three motifs described above from seven plant species; *Arabidopsis* (*Arabidopsis thaliana*), apple (*Malus pumila*), black raspberry (*Rubus occidentalis*), grape (*Vitis vinifera*), peach (*Prunus persica*), tomato (*Solanum lycoperisicum*) and wild strawberry (*Fragaria vesca*). From the MSA and phylogenetic analyses, the AG clade MADS-box transcription factors were identified as potential targets for creating altered fruit development phenotypes. These phenotypes will be created by introducing genetic modifications into the targets.

Furthermore, a well-supported cluster with genes that all came from separate species would be indicative of a set of orthologous genes. The result of phylogenetic analyses show that the black raspberry STK gene (i.e. Ro05_G22454), the wild strawberry STK gene (i.e. FvH4_5g32540), are the peach STK gene (i.e. Prupe.1G549600) are in the same cluster with AtSTK/AtAGL11 gene (i.e. AT4G09960). Also, *Arabidopsis* AG, SHP1, and SHP2 genes are clustered close to the STK gene cluster, indicating that STK orthologues are a closely related clade with three other transcription factors AG, SHP1 and SHP2, all of which are categorized under one upper clade named the AG clade MADS-box transcription factor taught in the present disclosure. Additionally, a synteny analysis was conducted between the predicted orthologs using the GEvo tool on the comparative genomics web-based platform CoGe provided on the publically available website, genomevolution.org/coge. 400 kb of flanking chromosomal region surrounding the focal genes were analyzed and the gene neighborhood was assessed for presence of sequence alignments. The synteny analysis between the *Arabidopsis* STK gene (AT4G09960) (Chromosome 4:6236473-6240681 bp) and black raspberry STK gene (Ro05_G22454) (Chromosome 5:34530529-34523413, which includes flanking chromosomal regions of each gene showed that orthologous genes are likely to part of the same neighborhood of genes, in order, in the respective genomes.

Example 2: Identification of Target Sites for Mutations on AGAMOUS Clade MADS-Box Transcription Factors for Altered Fruit Development To identify target sites for mutations on each of the AG clade MADS-box transcription factors characterized in Example 1, the MSA and phylogenetic results were further analyzed. Among the AG clade MADS-box transcription factors, SEEDSTICK (STK) is closely clustered with other transcription factors in *Arabidopsis*: AGAMOUS (AG), SHATTERPROOF1 (SHP1) and SHATTERPROOF2 (SHP2). These four genes are acknowledged in the art to share redundant functions in controlling ovule growth, floral meristem determinacy, and seed abscission in *Arabidopsis thaliana*, and to be required for specifying the identity of ovules. These four targets are species within the larger defined genus. Thus, the inventors proposed that introduction of mutation(s) in the AG clade transcription factors (e.g. the aforementioned four target species from within the genus) disturbs their normal functions, which can give rise to altered fruit development.

Figure 5:
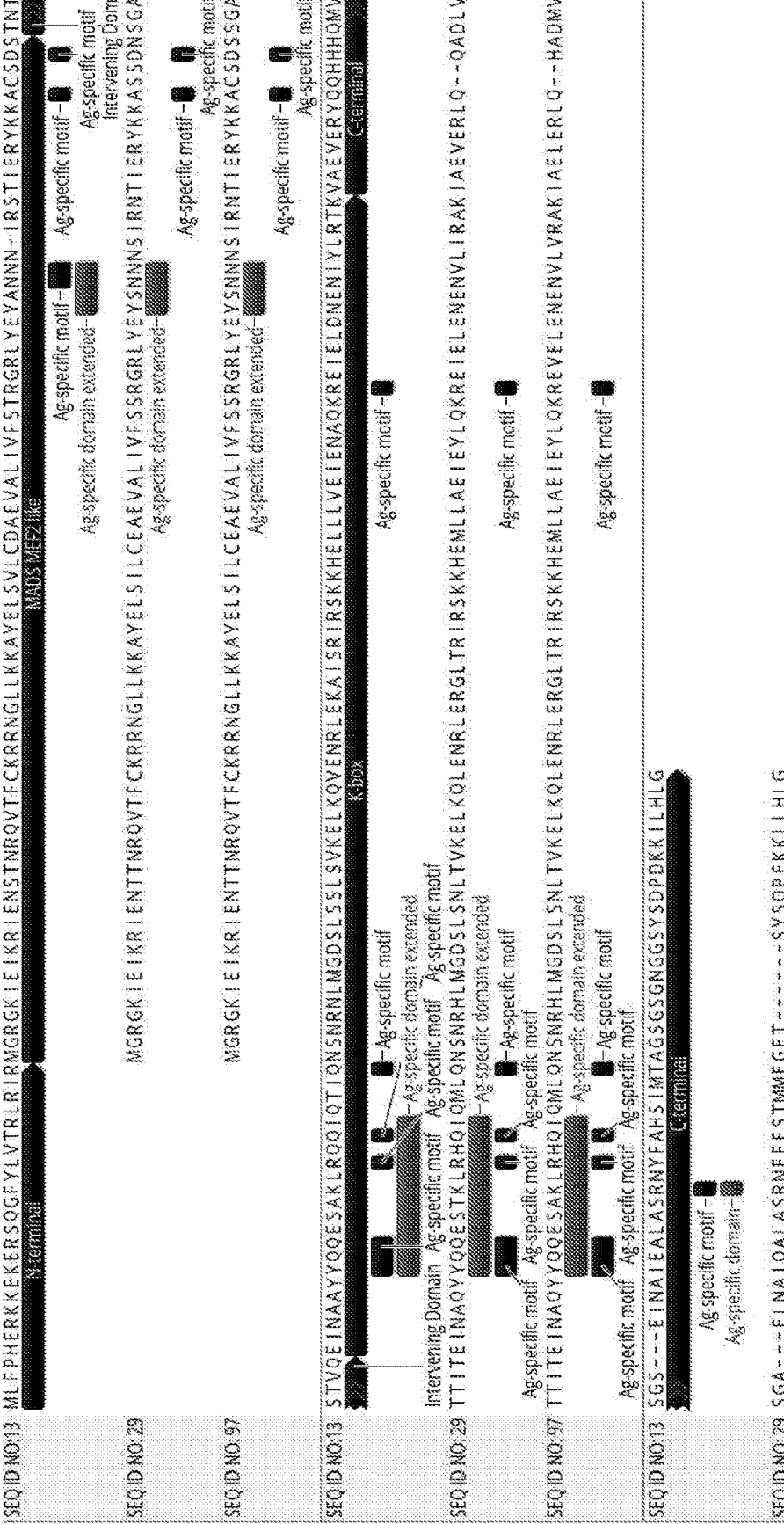
FIG. 5 illustrates a comparison of the putative amino acid sequences of STK orthologs from Arabidopsis (SEQ ID NO:13), wild strawberry (SEQ ID NO:29), and black raspberry (SEQ ID NO: 97). The aligned amino acid sequences demonstrate that protein sequences of three STK orthologs have the typical MIKC-type domain structure comprising a MADS-box/MADS MEF2 like (M) domain, an Intervening (I) domain, a Keratin-like (K-box) domain and a C-terminal (C) domain. Also, Ag-specific motifs, which distinguish AG-clade transcription factor orthologs from other MADS box gene, are illustrated by either a rectangle (e.g. multiple residues) or square (e.g. single residue) box under the corresponding amino acid reside(s).

As one example, amino acid sequences of STK orthologs collected from 4 plant species, *Arabidopsis thaliana, Rubus occidentalis* (blackberry), and *Fragaria vesca* (wild strawberry) were further aligned to identify the conserved residues among MADS box domains as shown in FIG. 5 with four MIKC domains; a MADS (M), an Intervening (I), a Keratin (K), and a C-terminal (C) Domain. In this example, the M domain, I domain, K domain, and C domain are targets of interest for genetic modification(s) such as substitution, addition, or deletion by genetic engineering techniques taught in the present disclosure, including a base-editing system described below. Also, the AG clade transcription factor has the N-terminal region in front of the MIKC domains, which is another target for genetic modification(s) described herein. Furthermore, among highly conserved motifs of the selected AG clade transcription factors, the NN motif (for example, 85-86 of SEQ ID NO:13 (AtSTK) or 59-60 of SEQ ID NO:97 (RoSTK), YQQ motif (e.g., 116-118 of SEQ ID NO:13 (AtSTK) or 91-93 of SEQ ID NO:97 (RoSTK)), or SEQ ID NOs: 29, 78, 97, 53, 66, 128, 150, 152, 154, 156, 158, 159, 160, 162, 164, 166-171), or a conserved R position (e.g., 225 of SEQ ID NO:13; position 196 of SEQ ID NO:66; position 197 of SEQ ID NOs: 53, 78, 150, 166-171; position 198 of SEQ ID NO:29; position 199 of SEQ ID NO:128; or position 201 of SEQ ID NOs: 97, 152, 154, 156, 158, 160, 162, 164) are selected as targets of interest for introduction of mutations taught in the present disclosure using the genetic engineering techniques of the present disclosure.

In some embodiments, the present invention provides the introduction of a C-terminal truncation of an STK polypeptide. A C-terminal truncation may be introduced, for example, by targeting the final exon of an STK polynucleotide as described herein. A targeted mutation, including, for example, one or more deletions or substitutions can produce a premature stop codon that produces a C-terminal truncation. In some aspects, at a minimum, a C-terminal truncation useful for this invention removes at least the conserved arginine located at position 225 of SEQ ID NO: 13 (AtSTK), 196 of SEQ ID NO:66; position 197 of SEQ ID NOs: 53, 78, 150, 166-171; 198 of SEQ ID NO:29; 199 of SEQ ID NO:128 or 201 of SEQ ID NO:97 (RoSTK)) or SEQ ID NOs: 152, 154, 156, 158, 160, 162, 164). Example mutations that produce a C-terminal truncation are provided in FIG. 5.

The codons encoding the residues selected for targeting were analyzed for potential edits, including C-terminal truncations, that could affect a non-conservative change in the amino acid, resulting in variation in protein function. The extended NN motif, Y[A/S]NN (SEQ ID NO:259), and another extended YQQ motif, YQQE[A/S][A/S/N/K/T]KL [R/H][Q/H/A/N/R]QI (SEQ ID NO: 260) were also identified as potential targets to edit one or more amino acids for altered fruit development in plants of interest. There are other well-conserved amino acid sequences such as NN, A, D, YYQ, R, Q, N, R, R, which are conserved at over 95% in the AG-clade transcription factors (e.g. STK) across the plant kingdom as shown in FIG. 5 and Tables 1, 1B, 3. Sequence conservation between distantly related plants suggests selective pressure to maintain function. Mutations that cause reduced seed size or induce seedlessness would be a strong selective pressure. For example, as these amino acids are in the C-terminal domain, and are conserved, these sequences are candidates for mutation to investigate the molecular function of the STK allele in plants of interest. By using genetic tools to induce mutations to effect these residues, gRNAs will be designed, as described below, to introduce single amino acid variation, which cause conformational change of STK protein induced by single amino acid substitution and/or truncation. Table 3 presents location of AG-specific and MADS-box conserved of SEQ ID NO:97.

TABLE 3

| Position of Motifs Identified in SEQ ID 97 | | | |
|---|---|---|---|
| Name | AA start | AA end | Length |
| Ag specific | 115 | 117 | 3 |
| Ag specific | 85 | 86 | 2 |
| Ag specific | 98 | 98 | 1 |
| Ag specific | 124 | 124 | 1 |
| Ag specific | 126 | 126 | 1 |
| Ag specific | 132 | 132 | 1 |
| Ag specific | 182 | 182 | 1 |
| Ag specific | 225 | 225 | 1 |
| Ag specific | 101 | 101 | 1 |
| MADS-box conserved | 43 | 47 | 5 |
| MADS-box conserved | 49 | 51 | 3 |
| MADS-box conserved | 56 | 58 | 3 |
| MADS-box conserved | 29 | 30 | 2 |
| MADS-box conserved | 53 | 54 | 2 |
| MADS-box conserved | 64 | 65 | 2 |
| MADS-box conserved | 74 | 75 | 2 |
| MADS-box conserved | 37 | 37 | 1 |
| MADS-box conserved | 39 | 39 | 1 |
| MADS-box conserved | 60 | 60 | 1 |
| MADS-box conserved | 62 | 62 | 1 |
| MADS-box conserved | 67 | 67 | 1 |
| MADS-box conserved | 78 | 78 | 1 |
| MADS-box conserved | 150 | 150 | 1 |

These identified candidate edits/mutations are then screened in a HTP in vivo assay described below to select for edits that affect transcription. The selected edits, which are documented as "hits" in the screen, are then introduced into plants of interest, in order to screen phenotypically for an altered fruit development phenotype, particularly a seedless or reduced seediness phenotype.

Example 3: HTP Screening and Selection of Effective Mutations in AGAMOUS Clade MADS-box Transcription Factors P An in vivo assay system for analyzing transient luciferase expression in HEK293T cells is used to screen target sites suitable for mutating AG clade transcription factors, in order to eventually produce seedless or reduced seed size in fruits of the plants of interest.

In general, the MADS-box transcription factors are well known to target a particular promoter binding site, which is the CArG box (Honma and Goto, 2001, Nature 409:525-529). For example, MADS-box transcription factors can bind a synthetic CArG box promoter (7×CArG::LUC) that has seven repeats of MADS protein binding consensus sequence (5'-GGGGTGGCTTTCCTTTTTTGGTAAAT-TTTGGATCC-3' (SEQ ID NO:276), CArG box is underlined), upstream of the a minimal promoter. The construct having seven repeats of the MADS protein binding consensus sequence was used to allow for the MADS-box transcription factors tetramer to bind multiple CArG boxes.

At first, 7×CArG box promoter is inserted upstream of the firefly luciferase (LUC) reporter gene in the vector used for a dual luciferase system. The 7×CArG::LUC dual luciferase system allows expression of both (i) the 7×CArG box promoter controlling expression of the firefly luciferase (LUC) reporter gene and (ii) a control promoter (CMV) regulating expression of the *Renilla* luciferase (REN) reporter gene. From this experiment, the LUC reporter gene is transcribed and expressed when a MADS-box transcription factor targets and binds the 7×CArG box promoter region. Expression level of the LUC reporter gene depends on the degree of the binding and capacity of the MADS-box transcription factor of interest to modulate transcription. Thus, the relative effectiveness of different mutation(s) of the AG clade transcription factor in various sites (e.g. N-terminal, M, I, K, or C domain, or three motifs described in Example 2) is determined in stimulating expression of a LUC reporter gene sequence controlled by the 7×CArG box promoter (Hellens et al. 2005, Plant Methods 1:13) in comparison to the constitutive expression of the REN reporter gene.

In the absence of MADS-box transcription factors (TFs), the LUC to REN ratio is low. This background level of activity presumably represents basal levels of MADS-box TFs present in HEK293T cells. The addition of a AG clade TF such as non-mutated STK, AG, or SHP1/2 to a transfection mixture for luciferase expression in HEK293T cells increases the relative level of LUC activity compared with the background promoter activity in the absence of plasmid containing the AG clade TF in the infiltration mixture. Different mutations introduced into the AG clade TFs (e.g. STK, AG, and/or SHP1/2) are predicted to give different relative level of LUC activity compared with the background REN promoter activity.

Then, the effect of mutations in the AG clade TF protein are quantified by the LUC:REN ratio. This assay is performed in HEK293T cells. Once expression vectors capable of overexpressing the mutated candidate AG clade TF genes (e.g. mutations in N-terminal region, M domain, I domain, K domain, C domain, the extended NN motif, the extended YQQ motif, or R/Q residue in C-terminal) are constructed along with the 7×CArG::LUC dual luciferase system prepared above, HEK293T cells are co-transfected with the vectors; (1) an expression vector possessing the mutated candidate AG clade TF genes (e.g. dominant negative mutation) under the control of the CMV promoter, along with (2) the vector for the 7×CArG::LUC dual-luciferase assay system. The 7×CArG box promoter sequences activated by the presence of the AG clade transcription factor are fused to firefly LUCIFERASE (LUC) and transactivation of the LUC gene measured relative to CMV: *RENILLA* luciferase (REN) by measurement of luminescence after expression in HEK239T cells. Luminescence is analyzed two days after transfection. Plate-based assays are conducted using the luminometer function of a SPECTRAMAX™ ID3™ multimode microplate reader (MOLECULAR DEVICES®) according to the manufacturer's specifications for the dual luciferase assay, using the DUAL-GLO® assay reagents (PROMEGA®) for firefly luciferase and *Renilla* luciferase. Luminescence was calculated using SOFTMAX® Pro GxP Software (MOLECULAR DEVICES®). The results are expected as follows, in light of the data from Espley et al. 2009 Plant Cell 21:168-183. The 7×CArG box promoter will show little difference in activity, as determined by the ratio of luminescence produced by the 7×CArG box promoter-LUC to CMV-REN without co-transfection of the AG clade TF. When the AG clade TF is co-transfected with the 7×CArG box promoter-LUC constructs, it will transactivate the promoters. When the mutated AG clade TF construct is cotransfected with the 7×CArG box-fused dual luciferase constructs, there will be reduction in transactivation because binding affinity or MADS-box complex transactivation with the mutated AG clade TF(s) will be negatively affected by the mutations to some degree. Thus, the transactivation will be reduced in the mutated version of the AG clade TF compared to the non-mutated version. The LUC:REN ratio with the cotransfections of the mutated version of the AG clade TFs will be lower than the non-mutated version. If the LUC:REN ratio in the mutated version is lower than the non-mutated version of the AG clade TFs of interest, the mutation site will be a target of interest (i.e. a "hit") for in vivo study by creating a stable plant line with a specific mutation introduced by a stable but targeted single base editing technique taught in the present disclosure.

Thus, the aforementioned methodology provides for a rapid and HTP in vivo screen, in a model organism, for candidate mutations in AGAMOUS clade MADS-box transcription factors. If there is a reduction in transcription factor binding evident in the screen, i.e. an indication that a mutation could serve as a dominant negative allele, then said mutation is then targeted in a plant of interest, which is eventually phenotyped to confirm the positive "hit" from the screen and identify a dominant negative allele associated with altered fruit development.

The above assay was carried out for SEEDSTICK as described in Example 8 and FIGS. 7-11.

Example 4: Construction of Base Editing Vectors

Once target sites for site-specific mutation(s) in the candidate AG clade TFs (e.g. STK, AG, and SHP1/2) are screened and verified by the in vivo, luciferase-based *Agrobacterium* infiltration assay described in Example 3, base editing vectors for the targeted mutation(s) in the candidate genes (e.g STK, AG, and SHP1/2) found in plants of interest will be constructed for the transformation of the base-editing vectors into the plant of interest including, but not limited to: black raspberry, blackberry, cherry, peach, avocado, strawberry, wild strawberry, *Arabidopsis*, apple, tomato, grape, and peach.

Cytosine Base Editor (CBE) expression vectors and Adenine Base Editor (ABE) expression vectors will be generated to introduce into candidate gene(s) (e.g. AG clade transcription factor genes and their orthologs in plants) mutations that cause altered fruit development such as reduced seed size or reduced seediness, based on the information provided in Example 3. By using genetic tools to introduce mutations to effect these residues as described in Example 3, gRNAs will be designed accordingly to introduce single amino acid variation, which cause conformational change of the AG clade TF protein induced by single amino acid substitution and/or truncation. The genetic modification introduced by the base-editing techniques will results in amino acid substitution, addition, deletion, and/or truncation. Truncation will take place at the C-terminal region once the codon sequence become a stop codon. Then, all the peptide sequence downstream of the newly-introduced stop codon will be deleted/truncated accordingly.

Targeting Cutter Vectors to Make a C-Terminal Truncation/Deletion

Cas12a expression vectors will be generated to introduce into candidate gene(s) (e.g. AG clade transcription factor genes and their orthologs in plants) mutations that cause altered fruit development such as reduced seed size or reduced seediness, based on the information provided in Example 3. By using genetic tools to introduce mutations to effect these residues as described in Example 3, gRNAs will be designed accordingly to introduce base pair deletions, which cause conformational change of the AG clade TF protein induced by truncation or in-frame deletions. The genetic modification introduced by the base pair deletions will result in amino acid deletion and/or truncation. Truncation will take place at the C-terminal region once the deletion causes a frameshift in the coding sequence and this causes the codon to sequence become a stop codon. Then, all the peptide sequence downstream of the newly-introduced stop codon will be deleted/truncated accordingly 1. Construction of Cytosine Base Editor (CBE) Expression Vector Cytosine deaminases (CDs) typically deaminate cytosines at specific sites in single stranded DNA so that the deamination of cytosine (C) is catalyzed by cytidine deaminases and results in uracil (U), which has the base-pairing properties of thymine (T). In this example, CD is fused to nuclease-deficient type II CRISPR/Cas9 to achieve RNA-guided cytosine deamination on genomic DNA and CD edits a non-targeted DNA strand displaced by the binding of a Cas9-guide RNA complex to a targeted DNA strand. To induce single-nucleotide substitution, either catalytically dead/deficient Cas9 (dCas9) whose nuclease activity is lost or Cas9 variant having nickase activity (nCas9) is used for Cas9-CD fusion protein. While dCas9 or nCas9 is bound to its target via guide RNA and form the bubble between the guide RNA and its complementary DNA, the CD enzyme will then act on the cytosine in the accessible single stranded DNA in the mismatching bubble. When nCas9 is utilized, the Cas9 nickase will nick the non-targeted DNA strand and facilitate subsequent conversion of the corresponding guanine to Adenine on the nontargeted DNA strand.

In one embodiment, other CRISPR nuclease-deficient system such as Cpf1 nickase, nuclease-deficient C2c1 or nuclease-deficient Cms1 can be used to nick the non-targeted DNA strand for its need. In this example, Cas9, CasX, CasY, Cpf1, C2c1, C2c2, C2c3 or Cms1, each of which is nuclease deficient, can be used for single base substitution along with base-editing enzymes cytidine deaminase and/or adenosine deaminase. For the CBE expression vector construction, the APOBEC1, XTEN, nCas9 (D10A) or dCas9 (D10A and H840A), and UGI sequences will be codon-optimized for plants of interest. A uracil glycosylase inhibitor (UGI) can be fused to the nCas9 or dCas9 to inhibit uracil-DNA glycosylase base-excision repair enzyme and increase the efficiency of base editing. Designs for the CBE Expression Vector:

nCas9, dCas9, Cpf1 nickase, nuclease-deficient C2c1 or nuclease-deficient Cms1 is fused to CD on either the N- or C-terminal end.

Nuclear Localization Sequence (NLS) can be tagged to nCas9, nCas9, dCas9, Cpf1 nickase, nuclease-deficient C2c1 or nuclease-deficient Cms1.

A variety of linkers are used including flexible linkers such as XTEN or less flexible linkers.

A uracil glycosylase inhibitor (UGI) can be linked to the nCas9, dCas9, Cpf1 nickase, nuclease-deficient C2c1 or nuclease-deficient Cms1.

The guide RNA scaffold can be inserted in the CBE expression vector or be expressed in a separate guide RNA expression vector.

2. Construction of Adenine Base Editor (ABE) Expression Vector

Adenosine deaminases (ADs) typically deaminate adenine in a deoxyadenosine residue of DNA at specific sites in single stranded DNA so that the deamination of adenosine (A) is catalyzed by adenosine deaminases and results in Inosine, which base pairs like guanine (G) in the context of DNA and has the base-pairing properties of Guanine (G). In this example, AD is fused to nuclease-deficient type II CRISPR/Cas9 to achieve RNA-guided cytosine deamination on genomic DNA and AD edits a non-targeted DNA strand displaced by the binding of a Cas9-guide RNA complex to a targeted DNA strand. To induce single-nucleotide substitution, either catalytically dead/deficient Cas9 (dCas9) whose nuclease activity is lost or Cas9 variant having nickase activity (nCas9) is used for Cas9-AD fusion protein. While dCas9 or nCas9 is bound to its target via guide RNA and form the bubble between the guide RNA and its complementary DNA, the AD enzyme will then act on the adenosine in the accessible single stranded DNA in the mismatching bubble. When nCas9 is utilized, the Cas9 nickase will nick the non-targeted DNA strand and facilitate subsequent conversion of the corresponding Thymine to Cytosine on the nontargeted DNA strand.

In some embodiments, other CRISPR nuclease-deficient systems such as Cpf1 nickase, nuclease-deficient C2c1 or nuclease-deficient Cms1 can be used to nick the non-targeted DNA strand. In this example, Cas9, CasX, CasY, Cpf1, C2c1, C2c2, C2c3 or Cms1, each of which is nuclease deficient, can be used for single base substitution along with base-editing enzymes cytidine deaminase and/or adenosine deaminase.

For the ABE expression vector construction, the E. coli TadA (ecTadA) including truncations/mutations of adenosine deaminase, human ADAR including hADAR1, hADAR2, hADAR3 and mutated versions thereof, XTEN, nCas9 (D10A) or dCas9 (D10A and H840A), and UGI sequences will be codon-optimized for plants of interest. A uracil glycosylase inhibitor (UGI) can be fused to the nCas9 or dCas9 to inhibit uracil-DNA glycosylase base-excision repair enzyme and increase the efficiency of base editing. Designs for the ABE Expression Vector:

nCas9, dCas9, Cpf1 nickase, nuclease-deficient C2c1, C2c2, C2c3 or nuclease-deficient Cms1 is fused to CD on either the N- or C-terminal end.

Nuclear Localization Sequence (NLS) can be tagged to nCas9, nCas9, dCas9, Cpf1 nickase, nuclease-deficient C2c1 or nuclease-deficient Cms1.

A variety of linkers are used including flexible linkers such as XTEN or less flexible linkers.

A uracil glycosylase inhibitor (UGI) can be linked to the nCas9, dCas9, Cpf1 nickase, nuclease-deficient C2c1, C2c1, C2c2, C2c3or nuclease-deficient Cms1.

The guide RNA scaffold can be inserted in the CBE expression vector or be expressed in a separate guide RNA expression vector.

3. Designs for gRNA Scaffold

The guide system will depend upon the CRISPR system utilized. If Cpf1, it is a natural "single" guide, but with Cas9 it can be single, or dual/native with separate crRNA tracrRNA. Base editing vectors targeting AG clade TF gene will be further constructed by inserting single guide RNA fragments that contain one target single site for Nuclear Localization Signal (NLS) sequence of the MADS-box domain, MADS box domain, Intervening domain, K-box domain, C-terminal domain, and/or three motifs (e.g. the extended NN motif, the extended YQQ motif, R/Q residue in C-terminal). Once the guide RNA leads the Cas/CD fusion protein to the target sites in the MADS box domain of the AG clade TF, cytosine located in the base-editing window, which is 4-8 nt distal to PAM will be deaminated and converted into Uracil, that is the base-pairing properties of Thymine in CBE system. On the other hand, once the guide RNA leads the Cas9/AD fusion protein to the target sites in the MADS box domain of the AG clade TF, Adenine located in the base-editing window, which is 4-8 nt distal to PAM will be deaminated and converted into Inosine that is ready as Guanine by polymerase in ABE system.

(i) The gRNA that targets N-terminal region including NLS will guide Cas/CD fusion protein to the NLS site for a C>T or G>A single nucleotide substitution. The gRNA that targets N-terminal region including NLS will guide Cas9/AD fusion protein to the NLS site for a A>G or T>C single nucleotide substitution. Mutating the NLS will prevent the MADS-box transcription factor from being transported to the nucleus, which results in misregulating other organ identity genes in the downstream and defects in specification of floral meristem identity and organ formation.

(ii) The gRNAs that targets the MADS-box domain will guide Cas/CD fusion protein to the M domain site for a C>T or G>A single nucleotide substitution. The gRNAs that targets the MADS-box domain will guide Cas/AD fusion protein to the M domain site for a A>G or T>C single nucleotide substitution. The MADS-box domain is involved in DNA binding, and may also be involved in dimerization, whose function will be disturbed by these modifications.

(iii) The gRNAs that targets the I domain will guide Cas/CD fusion protein to the I domain site for a C>T or G>A single nucleotide substitution. The gRNAs that targets the I domain will guide Cas/AD fusion protein to the I domain site for a A>G or T>C single nucleotide substitution.

(iv) The gRNAs that targets the K-box domain will guide Cas/CD fusion protein to the K domain site for a C>T or G>A single nucleotide substitution. The gRNAs that targets the K-box domain will guide Cas/AD fusion protein to the K domain site for a A>Gor T>C single nucleotide substitution. K-box domain is involved with protein dimerization, whose function will be disturbed by these modifications.

(v) The gRNAs that targets the C-terminal domain will guide Cas/CD fusion protein to the C domain site for a C>T or G>A single nucleotide substitution. The gRNAs that targets the Cterminal domain will guide Cas/AD fusion protein to the C domain site for a A>G or T>C single nucleotide substitution. C-terminal domain functions as a transcriptional activation domain, whose function will be disturbed by these modifications.

Figure 6:
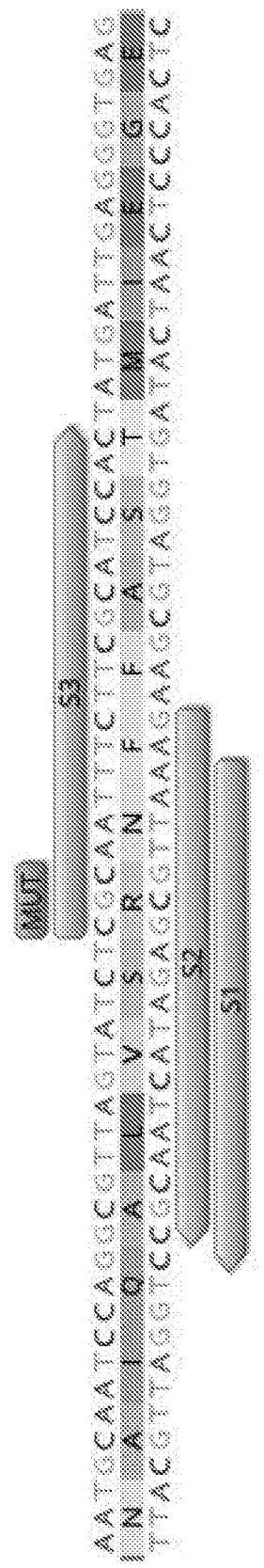
FIG. 6 illustrates three examples of guide RNAs designed to target the conserved Arginine (R) codon (SEQ ID NOs: 255 and 257) in the C-terminal domain of STK protein (SEQ ID NO:256). S1 and S2 guide RNAs can trigger, for example, Arginine (R) to Histidine (H) amino acid substitution by C to T (or G to A) nucleotide change by cytosine base editor. S3 guide RNA may induce, for example, Arginine (R) to Cysteine (C) substitution by C to T (or G to, A) nucleotide change by cytosine base editor.
Figure 7:
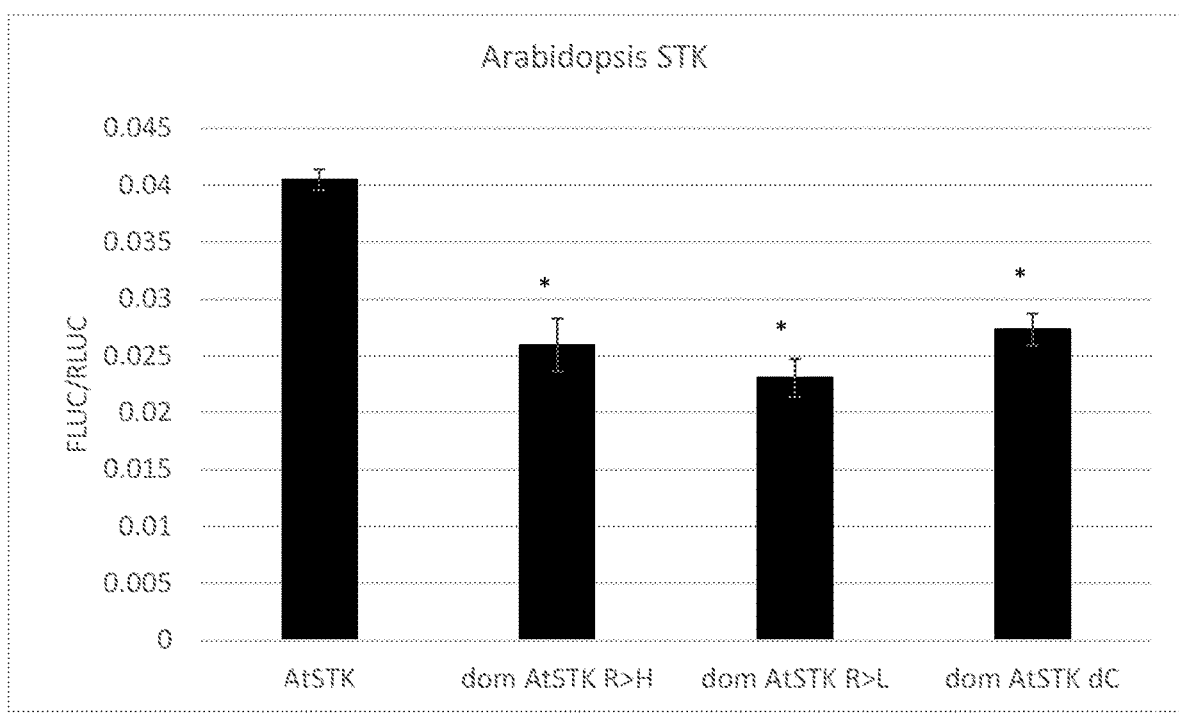
FIG. 7 provides the results of an assay for dominant negative activity of three different mutations in *Arabidopsis thaliana* Seedstick (STK) genes. The assay is carried out as described in Example 3. R>H, R>L is edit of the conserved R to an H or L; dC is a C terminal deletion.
Figure 8:
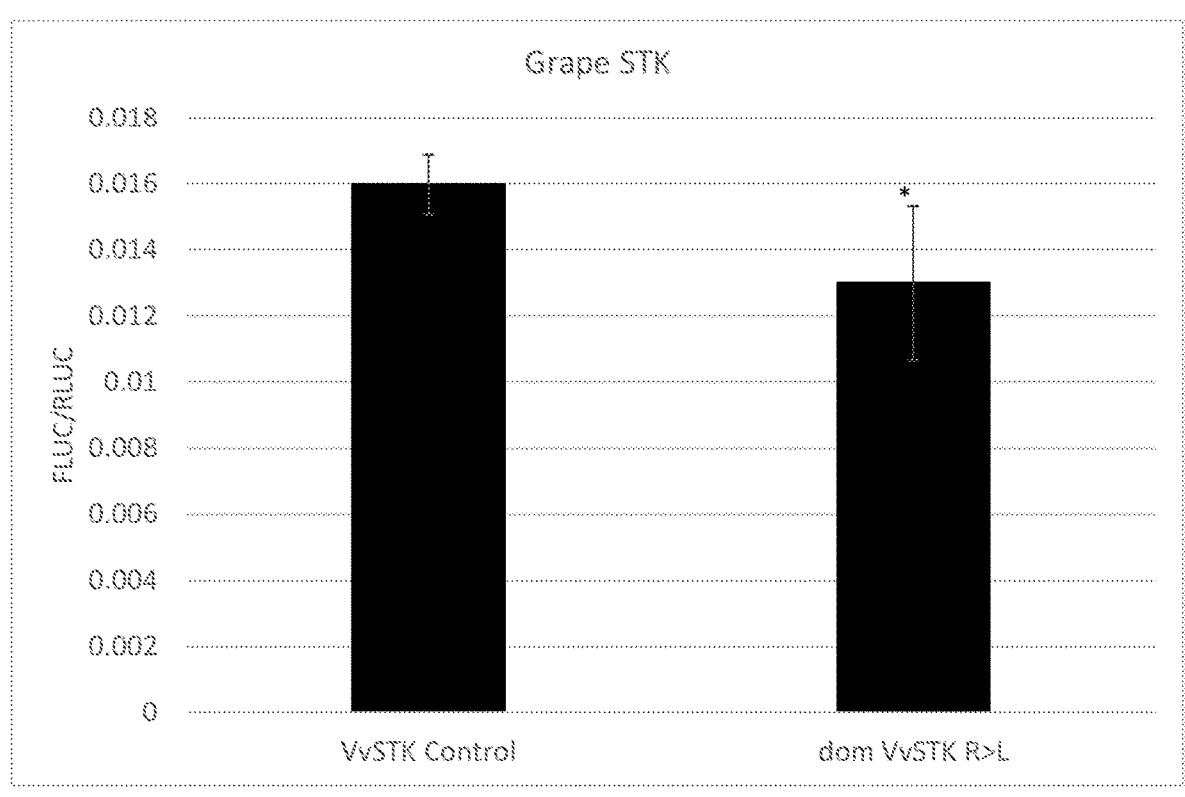
FIG. 8 provides the results of an assay for dominant negative activity of a mutation in a grape (*Vitis vinifera*) STK gene. The assay is carried out as described in Example 3. R>L is edit of the conserved R to an L.
Figure 9:
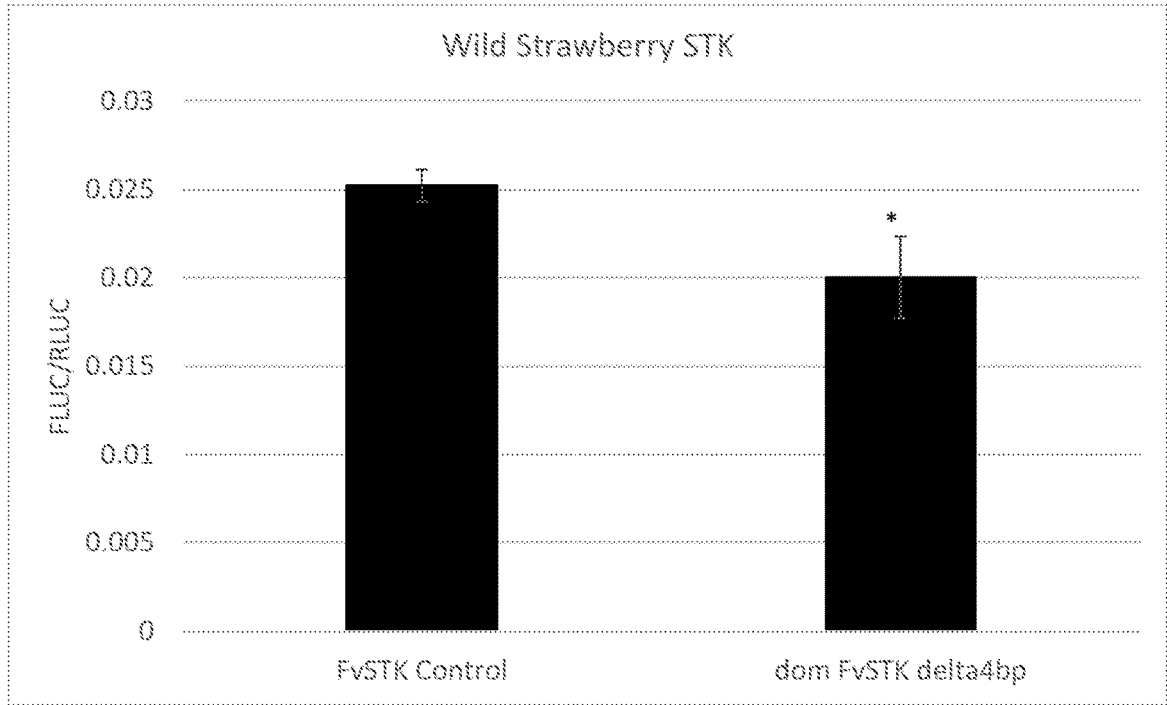
FIG. 9 provides the results of an assay for dominant negative activity of a mutation in a wild strawberry (*Fragaria vesca*) STK gene. The assay is carried out as described in Example 3.
Figure 10:
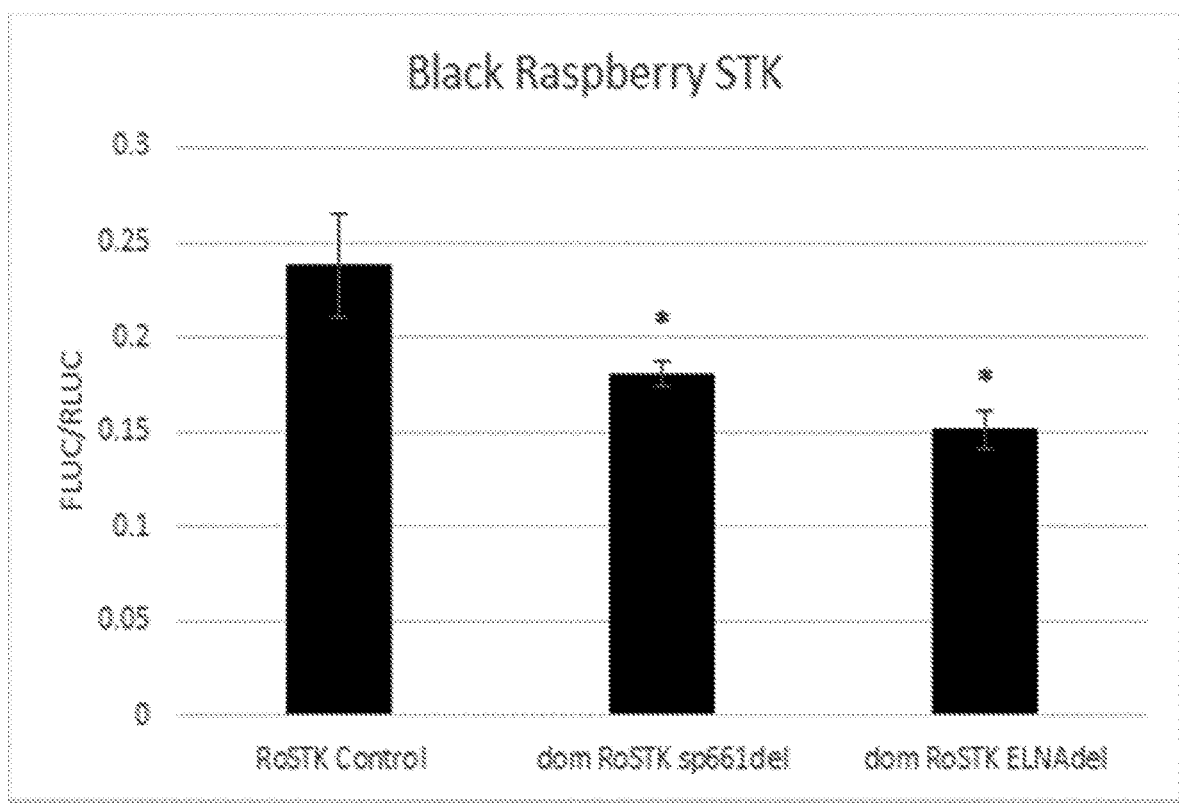
FIG. 10 provides the results of an assay for dominant negative activity (dom) of two mutations in a blackberry (*Rubus occidentalis*) STK gene. The assay is carried out as described in Example 3. ELNAdel=deletion of consecutive residues of ELNA (SEQ ID NO:258); sp661 refers to a mutation generated by spacer 661 (sp661) as shown in FIG. 4.
Figure 11:
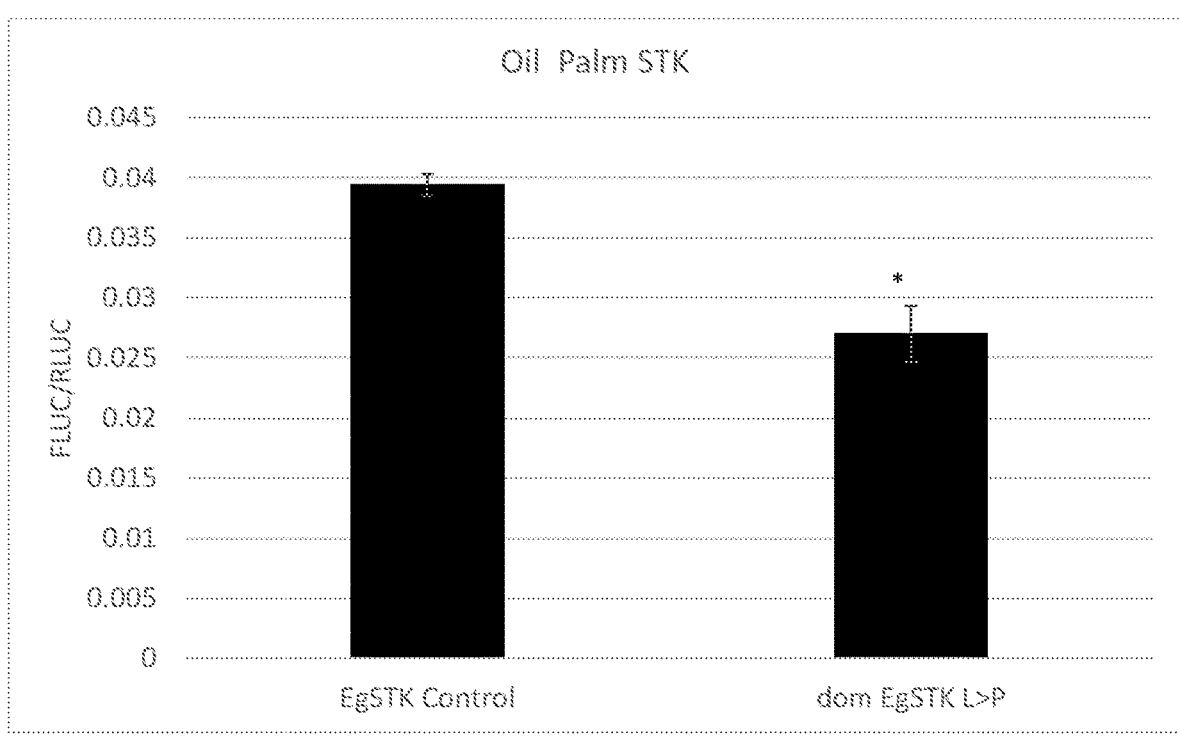
FIG. 11 provides the results of an assay for dominant negative activity of a mutation in an oil palm (*Elaeis guineensis*) STK gene. The assay is carried out as described in Example 3.

FIG. 6 illustrates three example guide RNAs (S1 [CCGCAATCATAGAGCGTTAA SEQ ID NO: 184], S2 [CGCAATCATAGAGCGTTAAAG SEQ ID NO:185], and S3 [CGCAATTTCTTCACATCCAC SEQ ID NO:186]) designed to target the Arginine (R) codon in the C-terminal domain of black raspberry STK (RoSTK) protein. S1 and S2 guide RNAs can, for example, trigger Arginine (R) to Histidine (H) amino acid substitution by C to T (or G to A) nucleotide change by cytosine base editor. S3 guide RNA may induce Arginine (R) to Cysteine (C) substitution by C to T (or G to A) nucleotide change by cytosine base editor. (1) Arginine to Histidine using S1/S2 gRNAs by a G to A nucleotide base pair change or (2) Arginine to Cysteine using S3 gRNA by a C to A nucleotide base pair change. Additional spacers for black raspberry STK include SEQ ID NOs: 175-176 or 184-186.

Appropriate PAM sequence is used for gRNA design and depend on the Cas system used. The source/type of Cas9 protein as Cas9 variants have different PAM requirement for target recognition. PAM sites in a gene of interest can be determined. As an example, the PAM site recognized by Cas9 is NGG, Cpf1 (Cas12a) recognizes TTTN and C2c1/Cms1 recognizes TTN.

In some embodiments, the length of RNA guide (17-24nt) is designed to target the genomic locus of interest. In this example, RoSTK is a target gene of Cas-CD or Cas-AD fusion protein/gRNA complex. RNA guide with longer than canonical length may be used to form heteroduplexes outside of the protein-guide RNA-target DNA complex.

Example 5: Transformation with Base-Editing Vectors into Plants of Interest

The base-editing vectors disclosed in Example 4 will be transformed into plants of interest such as: black raspberry, blackberry, cherry, peach, avocado, strawberry, wild strawberry, *Arabidopsis*, apple, tomato, grape, and peach. The disclosure teaches all types of transformation methods, including using *agrobacterium*-mediated protocols that are known in the art and/or developed by the inventors, as well as biolistic transformation methods. Tissue culture and regeneration of transformed plants will be performed accordingly.

Example 6: Molecular Analysis for Transformed Plants

In this example, the activity of the base-editing vectors disclosed in Example 4 is examined on the transformed plants of interest including *Arabidopsis*, black raspberry, blackberry, cherry, avocado, strawberry, wild strawberry, peach, grape, apple, and/or tomato. As a control for the induction of indel, a construct expressing wild type Cas9 is also be used in this experiment. Base-editing at a target site is examined in all transformed plants. The deamination window encompasses positions 4-8 nt of the protospacer sequence distal to PAM. The frequency of a single base substitution is studied by PCR amplification and subsequent sanger sequencing and/or high-throughput deep sequencing. Also, the amino acid substitution(s) caused by the introduced single base editing technique to the target genome region is analyzed by protein sequencing with mass spectrometry.

Example 7: Observing/Scoring Phenotypic Traits of Transformed Plants

The transformed plants obtained from Example 6 are grown in the controlled green house and/or field conditions. The transformed plants, verified with amino acid substitution of interest, are observed for altered fruit development, such as a seedless or reduced seediness phenotype and/or a reduced endocarp in fruits of the plants. For instance, the assay/metric described above is utilized to define an altered fruit development phenotype.

Figure 12A:
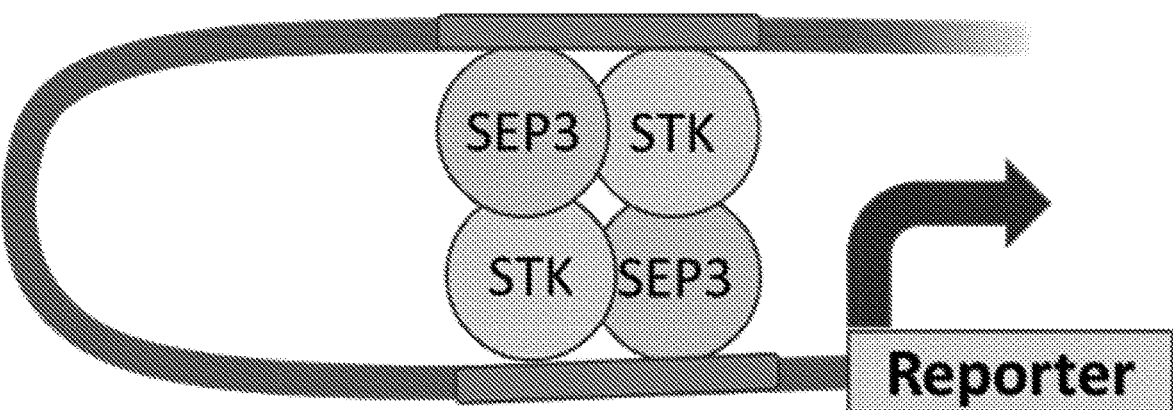
FIGS. 12A-12B.
Figure 12B:
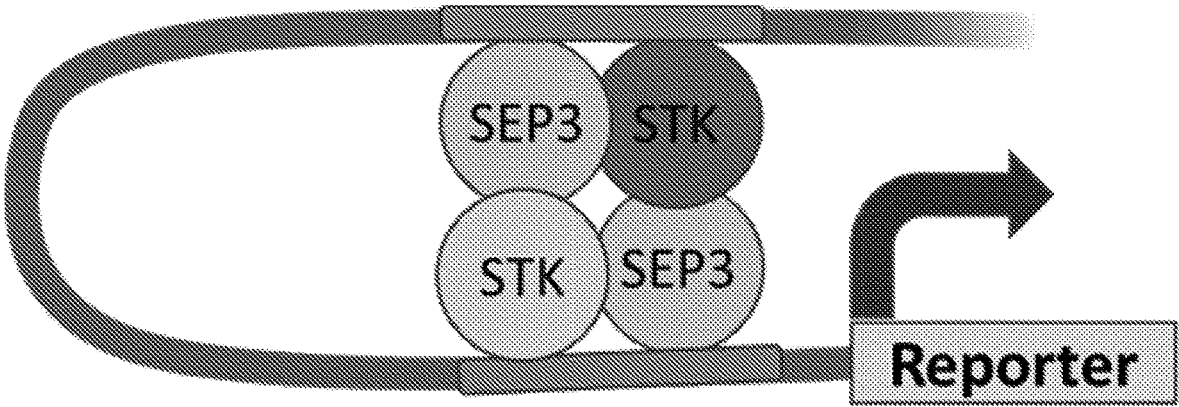

Example 8: Assays for Dominant Negative Activity of Mutated SEEDSTICK (STK) Genes Using the technique described in Example 3, assays were carried out to evaluate the dominant negative activity of SEEDSTICK (STK) genes in several different plant species. The genes were codon optimized for expression in the human cells (HO). The results are shown in FIGS. 7-11. In each case, the control comprises two wild type SEPALLATA genes and two wild type STK genes (see, e.g., (FIG. 12A) The evaluated mutations were dominant negative C-terminal mutations and truncations (labeled "dom" in FIGS. 7-11) in combination with the wild type SEPALLATA genes and a wild type STK gene (see, e.g., FIG. 12B) As shown in FIGS. 7-11, introduction of the mutated STK gene reduces the activity of the SEP3-STK complex and reduces expression of the reporter. This data confirms that the mutated STK alleles are still able to bind to and form a complex with SEP3 and wild-type STK but that the expression caused by the complex is reduced.

Example 9. Modification of STK Genes in Wild Strawberry

Wild-type Strawberry (*Fragaria vesca*) STK gene (encoding the polypeptide of SEQ ID NO: 29) was modified through use of a cutting vector as described in Example 4. FIG. 13 shows an alignment of wild-type Strawberry (*Fragaria vesca*) STK with the mutant STK that were generated.

Achenes were hand dissected from wild type and FvSTKdelta4 bp-heterozygous-mutant fruit 4-5 days after pollination. The seed were excised from achene and compared under a dissecting microscope. The FvSTKdelta4 bp-heterozygous-mutant seed had a darker appearance when compared to wild-type seed. The darker appearance of the seed may correspond to the abortion of the embryo due to the presence of the FvSTKdelta4 bp-heterozygous mutation. Fertilization and seed abortion is a feature of the grape seedless SEEDSTICK mutation in grape.

Additionally, the darker appearance occurs in the heterozygous state suggesting the FvSTKdelta4 bp mutation is a dominant mutation.

FURTHER NUMBERED EMBODIMENTS OF THE DISCLOSURE

Other subject matter contemplated by the present disclosure is set out in the following numbered embodiments:

1. A plant cell, comprising: a. a base editing system capable of modifying an endogenous target gene encoding an AGAMOUS clade MADS-box transcription factor and introducing a stable and targeted single nucleotide substitution in said gene, the base editing system comprising: (i) a base editing fusion protein, comprising: a CRISPR-associated effector protein and a cytidine deaminase or adenosine deaminase; and (ii) a guide RNA (gRNA) capable of targeting the fusion protein to the endogenous target gene encoding an AGAMOUS clade MADS-box transcription factor.

2. The plant cell of embodiment 1 wherein the base editing system introduces a stable and targeted C>T or G>A or A>G or T>C single nucleotide substitution in the endogenous target gene encoding an AGAMOUS clade MADS-box transcription factor.

3. The plant cell of any one of embodiments 1-2, wherein the endogenous target gene encodes an AGAMOUS clade MADS-box transcription factor involved with fruit formation.

4. The plant cell of any one of embodiments 1-3, wherein the endogenous target gene encodes an AGAMOUS clade MADS-box transcription factor involved with endocarp formation.

5. The plant cell of any one of embodiments 1-4, wherein the AGAMOUS clade MADS-box transcription factor is selected from the group consisting of: AG, SHP1, SHP2, and STK.

6. The plant cell of any one of embodiments 1-5, wherein the AGAMOUS clade MADS-box transcription factor is STK.

7. The plant cell of any one of embodiments 1-6, wherein the gRNA comprises a guide sequence that binds to an endogenous target gene encoding an AGAMOUS clade MADS-box transcription factor sharing at least 90% sequence identity to SEQ ID NO:13.

8. The plant cell of any one of embodiments 1-7, wherein the base editing system is adapted to create a stable and targeted C>T or G>A or A>G or T>C single nucleotide substitution in the region of the endogenous target gene encoding for the C-terminal region of the AGAMOUS clade MADS-box transcription factor.

9. The plant cell of any one of embodiments 1-8, wherein the base editing system is adapted to create a stable and targeted C>T or G>A or A>G or T>C single nucleotide substitution in the region of the endogenous target gene encoding for the C-terminal region of the AGAMOUS clade MADS-box transcription factor, wherein upon expression of the gene the resulting AGAMOUS clade MADS-box transcription factor has altered expression and/or function.

10. The plant cell of any one of embodiments 1-9, wherein the plant cell is from the Rosaceae family.

11. The plant cell of any one of embodiments 1-10, wherein the plant cell is from a plant selected from the group consisting of: raspberry, black raspberry, blackberry, cherry, peach, avocado, strawberry, wild strawberry, apple, tomato, grape, peach, plum, apricot, pear, quince, loquat, and almond.

12. The plant cell of any one of embodiments 1-11, wherein the plant cell is from *Rubus occidentalis*.

13. A plant cell with a modified endogenous target gene encoding an AGAMOUS clade MADSbox transcription factor, comprising: a stable and targeted single nucleotide substitution in an endogenous target gene encoding an AGAMOUS clade MADS-box transcription factor.

14. The plant cell of embodiment 13, comprising a stable and targeted C>T or G>A or A>G or T>C single nucleotide substitution in the endogenous target gene encoding an AGAMOUS clade MADS-box transcription factor.

15. The plant cell of any one of embodiments 13-14, wherein the endogenous target gene encodes an AGA-MOUS clade MADS-box transcription factor involved with fruit formation.

16. The plant cell of any one of embodiments 13-15, wherein the endogenous target gene encodes an AGA-MOUS clade MADS-box transcription factor involved with endocarp formation.

17. The plant cell of any one of embodiments 13-16, wherein the AGAMOUS clade MADS-box transcription factor is selected from the group consisting of: AG, SHP1, SHP2, and STK.

18. The plant cell of any one of embodiments 13-17, wherein the AGAMOUS clade MADS-box transcription factor is STK.

19. The plant cell of any one of embodiments 13-18, comprising a stable and targeted C>T or G>A or A>G or T>C single nucleotide substitution in the region of the endogenous target gene encoding for the C-terminal region of the AGAMOUS clade MADS-box transcription factor.

20. The plant cell of any one of embodiments 13-19, comprising a stable and targeted C>T or G>A or A>G or T>C single nucleotide substitution in the region of the endogenous target gene encoding for the C-terminal region of the AGAMOUS clade MADS-box transcription factor, wherein upon expression of the gene the resulting AGAMOUS clade MADS-box transcription factor has altered expression and/or function.

21. The plant cell of any one of embodiments 13-20, wherein the plant cell is from the Rosaceae family.

22. The plant cell of any one of embodiments 13-21, wherein the plant cell is from a plant selected from the group consisting of: raspberry, black raspberry, blackberry, cherry, peach, avocado, strawberry, wild strawberry, apple, tomato, grape, peach, plum, apricot, pear, quince, loquat, and almond.

23. The plant cell of any one of embodiments 13-22, wherein the plant cell is from *Rubus occidentalis*.

24. A method for producing a base-edited plant expressing an altered AGAMOUS clade MADSbox transcription factor, comprising: (a) introducing into the plant a base editing system capable of modifying an endogenous target gene encoding an AGAMOUS clade MADS-box transcription factor and introducing a stable and targeted single nucleotide substitution in said gene, the base editing system comprising: (i) a base editing fusion protein, comprising: a CRISPR-associated effector protein and a cytidine deaminase or adenosine deaminase; and (ii) a guide RNA (gRNA) capable of targeting the fusion protein to an endogenous target gene encoding an AGAMOUS clade MADS-box transcription factor; and (b) expressing the base editing system in the plant such that the gRNA binds to the endogenous target gene and the base editing fusion protein contacts the endogenous target gene and deaminates a nucleotide base resulting in a stable and targeted single nucleotide substitution in the endogenous target gene.

25. The method of embodiment 24, wherein the base editing system introduces a stable and targeted C>T or G>A or A>G or T>C single nucleotide substitution in the endogenous target gene encoding an AGAMOUS clade MADS-box transcription factor.

26. The method of any one of embodiments 24-25, wherein the endogenous target gene encodes an AGA-MOUS clade MADS-box transcription factor involved with fruit formation.

27. The method of any one of embodiments 24-26, wherein the endogenous target gene encodes an AGA-MOUS clade MADS-box transcription factor involved with endocarp formation.

28. The method of any one of embodiments 24-27, wherein the AGAMOUS clade MADS-box transcription factor is selected from the group consisting of: AG, SHP1, SHP2, and STK.

29. The method of any one of embodiments 24-28, wherein the AGAMOUS clade MADS-box transcription factor is STK.

30. The method of any one of embodiments 24-29, wherein the gRNA comprises a guide sequence that binds to an endogenous target gene encoding an AGA-MOUS clade MADS-box transcription factor sharing at least 90% sequence identity to SEQ ID NO:13.

31. The method of any one of embodiments 24-30, wherein the base editing system is adapted to create a stable and targeted C>T or G>A or A>G or T>C single nucleotide substitution in the region of the endogenous target gene encoding for the C-terminal region of the AGAMOUS clade MADS-box transcription factor.

32. The method of any one of embodiments 24-31, wherein the base editing system is adapted to create a stable and targeted C>T or G>A or A>G or T>C single nucleotide substitution in the region of the endogenous target gene encoding for the C-terminal region of the AGAMOUS clade MADS-box transcription factor, wherein upon expression of the gene the resulting AGAMOUS clade MADS-box transcription factor has altered expression and/or function.

33. The method of any one of embodiments 24-32, wherein the plant is a Rosaceae.

34. The method of any one of embodiments 24-33, wherein the plant is selected from the group consisting of: raspberry, black raspberry, blackberry, cherry, peach, avocado, strawberry, wild strawberry, apple, tomato, grape, peach, plum, apricot, pear, quince, loquat, and almond.

35. The method of any one of embodiments 24-34, wherein the plant is *Rubus occidentalis*.

36. A method for producing a dominant negative allele in an AGAMOUS clade MADS-box transcription factor to create an altered fruit development phenotype in a plant, comprising: introducing a stable and targeted single nucleotide substitution in an endogenous target gene encoding an AGAMOUS clade MADS-box transcription factor, wherein the plant has an altered fruit development phenotype when compared to a wild type plant without said single nucleotide substitution.

37. The method of embodiment 36, wherein the stable and targeted single nucleotide substitution is a C>T or G>A or A>G or T>C single nucleotide substitution in the endogenous target gene encoding an AGAMOUS clade MADS-box transcription factor.

38. The method of any one of embodiments 36-37, wherein the endogenous target gene encodes an AGA-MOUS clade MADS-box transcription factor involved with fruit formation.

39. The method of any one of embodiments 36-38, wherein the endogenous target gene encodes an AGA-MOUS clade MADS-box transcription factor involved with endocarp formation.

40. The method of any one of embodiments 36-39, wherein the AGAMOUS clade MADS-box transcription factor is selected from the group consisting of: AG, SHP1, SHP2, and STK.

41. The method of any one of embodiments 36-40, wherein the AGAMOUS clade MADS-box transcription factor is STK.

42. The method of any one of embodiments 36-41, wherein the stable and targeted single nucleotide substitution is introduced in the region of the endogenous target gene encoding for the C-terminal region of the AGAMOUS clade MADS-box transcription factor.

43. The method of any one of embodiments 36-42, wherein the stable and targeted single nucleotide substitution is introduced in the region of the endogenous target gene encoding for the C-terminal region of the AGAMOUS clade MADS-box transcription factor, wherein upon expression of the gene the resulting AGAMOUS clade MADS-box transcription factor has altered expression and/or function.

44. The method of any one of embodiments 36-43, wherein the plant is a Rosaceae.

45. The method of any one of embodiments 36-44, wherein the plant is selected from the group consisting of: raspberry, black raspberry, blackberry, cherry, peach, avocado, strawberry, wild strawberry, apple, tomato, grape, peach, plum, apricot, pear, quince, loquat, and almond.

46. The method of any one of embodiments 36-45, wherein the plant is *Rubus occidentalis*.

47. The method of any one of embodiments 36-46, wherein an altered fruit development phenotype is seedless and/or reduced seediness fruit.

48. The method of any one of embodiments 36-47, wherein an altered fruit development phenotype is at least one of: reduced seed size, reduced seed lignin content, reduced seed endocarp formation, or smoother seed surface.

49. A gene-edited plant, comprising: one or more single nucleotide base modifications in an AGAMOUS clade MADS-box transcription factor gene, wherein the gene-edited plant has an altered fruit development phenotype when compared to a wild type plant without said single nucleotide base modifications.

50. The gene-edited plant of embodiment 49, wherein the one or more single nucleotide base modifications comprise a C>T or G>A or A>G or T>C substitution in the AGAMOUS clade MADS-box transcription factor gene.

51. The gene-edited plant of any one of embodiments 49-50, wherein the AGAMOUS clade MADS-box transcription factor gene is involved with fruit formation.

52. The gene-edited plant of any one of embodiments 49-51, wherein AGAMOUS clade MADSbox transcription factor gene is involved with endocarp formation.

53. The gene-edited plant of any one of embodiments 49-52, wherein the AGAMOUS clade MADS-box transcription factor is selected from the group consisting of: AG, SHP1, SHP2, and STK.

54. The gene-edited plant of any one of embodiments 49-53, wherein the AGAMOUS clade MADS-box transcription factor is STK.

55. The gene-edited plant of any one of embodiments 49-54, wherein the one or more single nucleotide base modifications is in the region of the gene encoding for the C-terminal region of the AGAMOUS clade MADS-box transcription factor.

56. The gene-edited plant of any one of embodiments 49-55, wherein the one or more single nucleotide base modifications is in the region of the gene encoding for the C-terminal region of the AGAMOUS clade MADS-box transcription factor, wherein upon expression of the gene the resulting AGAMOUS clade MADS-box transcription factor has altered expression and/or function.

57. The gene-edited plant of any one of embodiments 49-56, wherein the plant is a Rosaceae.

58. The gene-edited plant of any one of embodiments 49-57, wherein the plant is selected from the group consisting of: raspberry, black raspberry, blackberry, cherry, peach, avocado, strawberry, wild strawberry, apple, tomato, grape, peach, plum, apricot, pear, quince, loquat, and almond.

59. The gene-edited plant of any one of embodiments 49-58, wherein the plant is *Rubus occidentalis*.

60. The gene-edited plant of any one of embodiments 49-59, wherein an altered fruit development phenotype is seedless and/or reduced seediness fruit.

61. The gene-edited plant of any one of embodiments 49-60, wherein an altered fruit development phenotype is at least one of: reduced seed size, reduced seed lignin content, reduced seed endocarp formation, or smoother seed surface.

62. A plant with a modified AGAMOUS clade MADS-box transcription factor proteome, comprising: an introduced amino acid substitution in an AGAMOUS clade MADS-box transcription factor amino acid sequence, wherein the plant has an altered fruit development phenotype when compared to a wild type plant without said introduced amino acid substitution.

63. The plant of embodiment 62, wherein the introduced amino acid substitution is in the N-terminal, MADS-box, K-box, and/or C-terminal amino acid sequence region of said AGAMOUS clade MADS-box transcription factor.

64. The plant of any one of embodiments 62-63, wherein the introduced amino acid substitution causes altered expression and/or function of the AGAMOUS clade MADS-box transcription factor.

65. The plant of any one of embodiments 62-64, wherein the AGAMOUS clade MADS-box transcription factor is involved with fruit formation.

66. The plant of any one of embodiments 62-65, wherein AGAMOUS clade MADS-box transcription factor is involved with endocarp formation.

67. The plant of any one of embodiments 62-66, wherein the AGAMOUS clade MADS-box transcription factor is selected from the group consisting of: AG, SHP1, SHP2, and STK.

68. The plant of any one of embodiments 62-67, wherein the AGAMOUS clade MADS-box transcription factor is STK.

69. The plant of any one of embodiments 62-68, wherein the plant is a Rosaceae.

70. The plant of any one of embodiments 62-69, wherein the plant is selected from the group consisting of: raspberry, black raspberry, blackberry, cherry, peach, avocado, strawberry, wild strawberry, apple, tomato, grape, peach, plum, apricot, pear, quince, loquat, and almond.

71. The plant of any one of embodiments 62-70, wherein the plant is *Rubus occidentalis*.

72. The plant of any one of embodiments 62-71, wherein an altered fruit development phenotype is seedless and/or reduced seediness fruit.

73. The plant of any one of embodiments 62-72, wherein an altered fruit development phenotype is at least one of: reduced seed size, reduced seed lignin content, reduced seed endocarp formation, or smoother seed surface.

74. A *Rubus occidentalis* plant with an altered fruit development phenotype, comprising: one or more targeted single nucleotide substitutions in a gene encoding an AGAMOUS clade MADS-box transcription factor, wherein the *Rubus occidentalis* plant has an altered fruit development phenotype compared to a wild type *Rubus occidentalis* plant without said single nucleotide substitution.

75. A method of generating a base-edited plant with an altered fruit development phenotype, comprising: (a) providing a cell or tissue of the plant for transformation; (b) transforming said cell or tissue with a base editing system capable of modifying an endogenous target gene encoding an AGAMOUS clade MADS-box transcription factor and introducing a stable and targeted single nucleotide substitution in said gene; (c) expressing the base editing system in the transformed cell or tissue, wherein the base editing system deaminates a nucleotide base resulting in a stable and targeted single nucleotide substitution in the endogenous target gene; (d) regenerating plants from said transformed cell or tissue; and (e) identifying a plant having an altered fruit development phenotype.

76. A method of breeding a base-edited plant to produce a transgene-free plant, comprising: (a) making a cross between a first base-edited plant produced from embodiment 75 with a second plant, to introduce the single nucleotide substitution into the second plant; and (b) selecting a progeny plant that has the single nucleotide substitution, but is transgene-free.

77. A plant cell, comprising: a gene editing system capable of modifying an endogenous target gene encoding an AGAMOUS clade MADS-box transcription factor and introducing a mutation in a targeted region of said gene by a nuclease-mediated double-stranded DNA break.

78. The plant cell of embodiment 77, wherein the nuclease-mediated double-stranded DNA break is repaired by Non-Homologous End Joining (NHEJ) or Homology Directed Repair (HDR).

79. The plant cell of any one of embodiments 77-78, wherein the nuclease capable of introducing the mutation by said double-stranded DNA break is selected from the group consisting of: a TALEN, a MegaTAL, a Homing Endonuclease, a ZFN, a FokI endonuclease, and a CRISPR/Cas endonuclease.

80. The plant cell of any one of embodiments 77-79, wherein the gene editing system is introduced into the plant cell for the expression and function of a gene-editing molecule.

81. The plant cell of any one of embodiments 77-80, wherein the plant cell comprises a deletion or insertion of one or more nucleotides in the endogenous target gene encoding an AGAMOUS clade MADS-box transcription factor; wherein the deletion or insertion is introduced by the gene-editing molecule; and wherein the gene editing system is not present in the plant cell.

82. A method for producing a plant expressing an altered AGAMOUS clade MADS-box transcription factor, comprising: (a) introducing into the plant a gene editing system capable of modifying an endogenous target gene encoding an AGAMOUS clade MADS-box transcription factor and introducing a mutation in a targeted region of said gene by a nuclease-mediated double-stranded DNA break; and (b) expressing the gene editing system in the plant such that the expressed gene editing molecule binds to the endogenous target gene and introduces a deletion or insertion of one or more nucleotides in the endogenous target gene.

83. The method of embodiment 82, wherein the nuclease-mediated double-stranded DNA break is repaired by Non-Homologous End Joining (NHEJ) or Homology Directed Repair (HDR).

84. The method of any one of embodiments 82-83, wherein the nuclease capable of introducing the mutation by said double-stranded DNA break is selected from the group consisting of a TALEN, a MegaTAL, a Homing Endonuclease, a ZFN, a FokI endonuclease, and a CRISPR/Cas endonuclease.

85. The method of any one of embodiments 82-84, wherein the gene editing system is introduced into the plant cell for the expression and function of a gene-editing molecule.

86. The method of any one of embodiments 82-85, wherein the plant cell comprises a deletion or insertion of one or more nucleotides in the endogenous target gene encoding an AGAMOUS clade MADS-box transcription factor; wherein the deletion or insertion is introduced by the gene-editing molecule; and wherein the gene editing system is not present in the plant cell.

87. A method for producing a dominant negative allele in an AGAMOUS clade MADS-box transcription factor to create an altered fruit development phenotype in a plant, comprising: introducing a deletion or insertion of one or more nucleotides in an endogenous target gene encoding an AGAMOUS clade MADS-box transcription factor, wherein the plant has an altered fruit development phenotype when compared to a wild type plant without said deletion or insertion.

REFERENCES

U.S. Pat. No. 6,603,061

U.S. Pat. No. 7,868,149

US Patent Application Publication 2009/0100536 A1

Belhaj, K., Chaparro-Garcia, A., Kamoun, S., Nekrasov, V. (2013). Plant genome editing made easy: targeted mutagenesis in model and crop plants using the CRISPR/Cas system. *Plant Methods*, 9 (1): 39.

Blast reference: https://blast.ncbi.nlm.nih.gov/

Brooks, C., Nekrasov, V., Lippman, Z. B., Van Eck, J. (2014). Efficient Gene Editing in Tomato in the First Generation Using the Clustered Regularly Interspaced Short Palindromic Repeats/CRISPR-Associated9 System. *Plant Physiology*, 166 (3), 1292-1297.

Caliando, B. J., Voigt, C. A. (2015). Targeted DNA degradation using a CRISPR device stably carried in the host genome. *Nature Communications*, 6:6989:1-10.

Carolina Royo, Rafael Torres-Pérez, Nuria Mauri, Nieves Diestro, José Antonio Cabezas, Cécile Marchal, Thierry Lacombe, Javier Ibáñez, Manuel Tornel, Juan Carreño, José Miguel Martínez-Zapater, Pablo Carbonell-Bejerano (2018). The Major Origin of Seedless Grapes Is Associated with a Missense Mutation in the MADS-Box GeneV-viAGL11. *Plant Physiology,* 177 (3), 1234-1253.

Espley, R. V., Brendolise, C., Chagne, D., Kutty-Amma, S., Green, S., Volz, R., . . . . Allan, A. C. (2009). Multiple Repeats of a Promoter Segment Causes Transcription Factor Autoregulation in Red Apples. THE PLANT CELL ONLINE, 21 (1), 168-183. doi: 10.1105/tpc.108.059329.

Feng, Z., Zhang, B., Ding, W., Liu, X., Yang, D.-L., Wei, P., Cao F., Zhu S., Zhang F., Mao Y., Zhu, J.-K. (2013). Efficient genome editing in plants using a CRISPR/Cas system. *Cell Research,* 23 (10): 1229-1232.

Hellens, R., Allan, A., Friel, E., Bolitho, K., Grafton, K., Templeton, M., Laing, W. (2005). *Plant Methods,* 1 (1), 13. doi: 10.1186/1746-4811-1-13.

Hoang D. T., Chernomor O., von Haeseler A., Minh B. Q., and L. S. Vinh (2018) UFBoot2: Improving the ultrafast bootstrap approximation. Mol. Biol. Evol., 35:518-522.

Honma, T., & Goto, K. (2001). Complexes of MADS-box proteins are sufficient to convert leaves into floral organs. Nature, 409 (6819), 525-529.

Kalyaanamoorthy S., Minh B. Q., Wong T. K. F, von Haeseler A., and L. S. Jermiin (2017) ModelFinder: Fast model selection for accurate phylogenetic estimates. Nat. Methods, 14:587589.

Li H. Constructing the TreeFam database. PhD thesis, Chinese Academy of Sciences Beijing. 2006.

Morrell, P. L., Buckler, E. S., Ross-Ibarra, J. (2011). Crop genomics: advances and applications. *Nature Reviews Genetics,* 13 (2): 85-96.

Nguyen L.-T., Schmidt H. A., von Haeseler A., and B. Q. Minh (2015) IQ-TREE: A fast and effective stochastic algorithm for estimating maximum likelihood phylogenies. Mol. Biol. Evol., 32:268-274.

Notredame, Higgins, Heringa. 2000. T-Coffee: A novel method for multiple sequence alignments. JMB,302 (205-217) DOI: 10.1006/jmbi.2000.4042.

Rice, P. Longden, I. and Bleasby, A. EMBOSS: The European Molecular Biology Open Software Suite. (2000). Trends in Genetics 16, (6) pp 276-277.

Shan, Q., Wang, Y., Li, J., Zhang, Y., Chen, K., Liang, Z., Liu J., Xi J. J., Qiu J. L., Gao, C. (2013). Targeted genome modification of crop plants using a CRISPR-Cas system. *Nature Biotechnology,* 31 (8): 686-688.

Xie, K., Yang, Y. (2013). RNA-Guided Genome Editing in Plants Using a CRISPR-Cas System. *Molecular Plant,* 6 (6): 1975-1983.

Xu, R., Li, H., Qin, R., Wang, L., Li, L., Wei, P., Yang, J. (2014). Gene targeting using the *Agrobacterium tumefaciens*-mediated CRISPR-Cas system in rice. *Rice,* 7 (1): 5.

Zhou, X., Jacobs, T. B., Xue, L.-J., Harding, S. A., Tsai, C.-J. (2015). Exploiting SNPs for biallelic CRISPR mutations in the outcrossing woody perennial *Populus* reveals 4coumarate: CoA ligase specificity and redundancy. *New Phytologist,* 208 (2): 298-301.

What is claimed is:

1. A plant or plant part thereof comprising a mutated SEEDSTICK (STK) gene, wherein the plant or plant part thereof is black raspberry, wherein the mutated STK gene comprises a mutation relative to an endogenous STK gene, the mutated STK gene encoding a mutated STK protein comprising a deletion of residues ELNA at positions 191-194 with reference to the amino acid sequence of SEQ ID NO:97, wherein the mutated STK gene results in the plant or plant part thereof exhibiting a phenotype of altered fruit development when compared to a control plant or control plant part thereof that is devoid of the mutation in the endogenous STK gene, the altered fruit development comprising seedlessness and/or reduced seediness when compared to the control plant or control plant part thereof that is devoid of the mutation in the endogenous STK gene.

2. A method for editing a specific site in the genome of a plant cell, the method comprising: cleaving, in a site specific manner, a target site within an endogenous AG clade MADS-box transcription factor gene in the plant cell, the endogenous AG clade MADS-box transcription factor gene being a SEEDSTICK (STK) gene encoding the amino acid sequence of SEQ ID NO:97, thereby generating an edit in the endogenous AG clade MADS-box transcription factor gene of the plant cell and providing a mutated STK gene, wherein the plant cell is a black raspberry plant cell, wherein the mutated STK gene encodes a mutated STK protein comprising a deletion of residues ELNA at positions 191-194 with reference to the amino acid sequence of SEQ ID NO: 97, and wherein a black raspberry plant comprising the plant cell exhibits altered fruit development, wherein the altered fruit development is a phenotype of seedlessness and/or reduced seediness when compared to a control black raspberry plant that is devoid of the edit in the endogenous AG clade MADS-box transcription factor gene.

3. A method of producing a plant or plant part thereof comprising a mutation in an endogenous SEEDSTICK (STK) gene and having altered fruit development, the method comprising:

contacting a target site in the endogenous STK gene with a nuclease comprising a cleavage domain and a nucleic acid binding domain that binds to the target site in the endogenous STK gene, wherein the endogenous STK gene encodes the amino acid sequence of SEQ ID NO:97, wherein the nuclease cleaves the endogenous STK gene and a mutation is introduced into the endogenous STK gene, thereby producing a plant or plant part thereof comprising a mutated endogenous STK gene and having altered fruit development, wherein the plant or plant part thereof is black raspberry, wherein the altered fruit development comprises seedlessness and/or reduced seediness when compared to a control plant or control plant part thereof that is devoid of the mutation in the endogenous STK gene, and wherein the mutated endogenous STK gene encodes a mutated STK protein comprising a deletion of residues ELNA at positions 191-194 with reference to the amino acid sequence of SEQ ID NO:97.

4. The plant or plant part thereof of claim 1, wherein the mutated STK gene encodes the polypeptide having the amino acid sequence of SEQ ID NO:206.

* * * * *

SEQUENCE LISTING

```
<160> NUMBER OF SEQ ID NOS: 276

<210> SEQ ID NO 1
<211> LENGTH: 251
<212> TYPE: PRT
<213> ORGANISM: Arabidopsis thaliana

<400> SEQUENCE: 1

Met Gly Arg Gly Arg Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
            20                  25                  30

Tyr Glu Leu Ser Val Leu Cys Asp Ala Glu Val Ala Leu Ile Ile Phe
        35                  40                  45

Ser Asn Arg Gly Lys Leu Tyr Glu Phe Cys Ser Ser Ser Ser Met Leu
    50                  55                  60

Arg Thr Leu Glu Arg Tyr Gln Lys Cys Asn Tyr Gly Ala Pro Glu Pro
65                  70                  75                  80

Asn Val Pro Ser Arg Glu Ala Leu Ala Val Glu Leu Ser Ser Gln Gln
                85                  90                  95

Glu Tyr Leu Lys Leu Lys Glu Arg Tyr Asp Ala Leu Gln Arg Thr Gln
            100                 105                 110

Arg Asn Leu Leu Gly Glu Asp Leu Gly Pro Leu Ser Thr Lys Glu Leu
        115                 120                 125

Glu Ser Leu Glu Arg Gln Leu Asp Ser Ser Leu Lys Gln Ile Arg Ala
    130                 135                 140

Leu Arg Thr Gln Phe Met Leu Asp Gln Leu Asn Asp Leu Gln Ser Lys
145                 150                 155                 160

Glu Arg Met Leu Thr Glu Thr Asn Lys Thr Leu Arg Leu Arg Leu Ala
            165                 170                 175

Asp Gly Tyr Gln Met Pro Leu Gln Leu Asn Pro Asn Gln Glu Glu Val
```

-continued
_____

```
              180               185               190

Asp His Tyr Gly Arg His His His Gln Gln Gln Gln His Ser Gln Ala
             195               200               205

Phe Phe Gln Pro Leu Glu Cys Glu Pro Ile Leu Gln Ile Gly Tyr Gln
        210               215               220

Gly Gln Gln Asp Gly Met Gly Ala Gly Pro Ser Val Asn Asn Tyr Met
225               230               235               240

Leu Gly Trp Leu Pro Tyr Asp Thr Asn Ser Ile
                  245               250

<210> SEQ ID NO 2
<211> LENGTH: 255
<212> TYPE: PRT
<213> ORGANISM: Arabidopsis thaliana

<400> SEQUENCE: 2

Met Gly Arg Gly Arg Val Glu Leu Lys Arg Ile Glu Asn Lys Ile Asn
1               5                 10                15

Arg Gln Val Thr Phe Ser Lys Arg Arg Thr Gly Leu Leu Lys Lys Ala
             20                25                30

Gln Glu Ile Ser Val Leu Cys Asp Ala Glu Val Ser Leu Ile Val Phe
        35                40                45

Ser His Lys Gly Lys Leu Phe Glu Tyr Ser Ser Glu Ser Cys Met Glu
        50                55                60

Lys Val Leu Glu Arg Tyr Glu Arg Tyr Ser Tyr Ala Glu Arg Gln Leu
65                70                75                80

Ile Ala Pro Asp Ser His Val Asn Ala Gln Thr Asn Trp Ser Met Glu
                  85                90                95

Tyr Ser Arg Leu Lys Ala Lys Ile Glu Leu Leu Glu Arg Asn Gln Arg
             100               105               110

His Tyr Leu Gly Glu Glu Leu Glu Pro Met Ser Leu Lys Asp Leu Gln
        115               120               125

Asn Leu Glu Gln Gln Leu Glu Thr Ala Leu Lys His Ile Arg Ser Arg
        130               135               140

Lys Asn Gln Leu Met Asn Glu Ser Leu Asn His Leu Gln Arg Lys Glu
145               150               155               160

Lys Glu Ile Gln Glu Glu Asn Ser Met Leu Thr Lys Gln Ile Lys Glu
                  165               170               175

Arg Glu Asn Ile Leu Arg Thr Lys Gln Thr Gln Cys Glu Gln Leu Asn
             180               185               190

Arg Ser Val Asp Asp Val Pro Gln Pro Gln Pro Phe Gln His Pro His
        195               200               205

Leu Tyr Met Ile Ala His Gln Thr Ser Pro Phe Leu Asn Met Gly Gly
        210               215               220

Leu Tyr Gln Glu Glu Asp Gln Thr Ala Met Arg Arg Asn Asn Leu Asp
225               230               235               240

Leu Thr Leu Glu Pro Ile Tyr Asn Tyr Leu Gly Cys Tyr Ala Ala
                  245               250               255

<210> SEQ ID NO 3
<211> LENGTH: 256
<212> TYPE: PRT
<213> ORGANISM: Arabidopsis thaliana

<400> SEQUENCE: 3

Met Gly Arg Gly Arg Val Gln Leu Lys Arg Ile Glu Asn Lys Ile Asn
```

-continued

```
1               5                    10                   15

Arg Gln Val Thr Phe Ser Lys Arg Arg Ala Gly Leu Leu Lys Lys Ala
            20                  25                  30

His Glu Ile Ser Val Leu Cys Asp Ala Glu Val Ala Leu Val Val Phe
            35                  40                  45

Ser His Lys Gly Lys Leu Phe Glu Tyr Ser Thr Asp Ser Cys Met Glu
    50                  55                  60

Lys Ile Leu Glu Arg Tyr Glu Arg Tyr Ser Tyr Ala Glu Arg Gln Leu
65                  70                  75                  80

Ile Ala Pro Glu Ser Asp Val Asn Thr Asn Trp Ser Met Glu Tyr Asn
                85                  90                  95

Arg Leu Lys Ala Lys Ile Glu Leu Leu Glu Arg Asn Gln Arg His Tyr
            100                 105                 110

Leu Gly Glu Asp Leu Gln Ala Met Ser Pro Lys Glu Leu Gln Asn Leu
            115                 120                 125

Glu Gln Gln Leu Asp Thr Ala Leu Lys His Ile Arg Thr Arg Lys Asn
    130                 135                 140

Gln Leu Met Tyr Glu Ser Ile Asn Glu Leu Gln Lys Lys Glu Lys Ala
145                 150                 155                 160

Ile Gln Glu Gln Asn Ser Met Leu Ser Lys Gln Ile Lys Glu Arg Glu
                165                 170                 175

Lys Ile Leu Arg Ala Gln Gln Glu Gln Trp Asp Gln Gln Asn Gln Gly
            180                 185                 190

His Asn Met Pro Pro Pro Leu Pro Pro Gln Gln His Gln Ile Gln His
            195                 200                 205

Pro Tyr Met Leu Ser His Gln Pro Ser Pro Phe Leu Asn Met Gly Gly
    210                 215                 220

Leu Tyr Gln Glu Asp Asp Pro Met Ala Met Arg Arg Asn Asp Leu Glu
225                 230                 235                 240

Leu Thr Leu Glu Pro Val Tyr Asn Cys Asn Leu Gly Cys Phe Ala Ala
                245                 250                 255
```

<210> SEQ ID NO 4
<211> LENGTH: 211
<212> TYPE: PRT
<213> ORGANISM: Arabidopsis thaliana

<400> SEQUENCE: 4

```
Met Ala Arg Gly Lys Ile Gln Leu Lys Arg Ile Glu Asn Pro Val His
1               5                    10                   15

Arg Gln Val Thr Phe Cys Lys Arg Arg Thr Gly Leu Leu Lys Lys Ala
            20                  25                  30

Lys Glu Leu Ser Val Leu Cys Asp Ala Glu Ile Gly Val Val Ile Phe
            35                  40                  45

Ser Pro Gln Gly Lys Leu Phe Glu Leu Ala Thr Lys Gly Thr Met Glu
    50                  55                  60

Gly Met Ile Asp Lys Tyr Met Lys Cys Thr Gly Gly Arg Gly Ser
65                  70                  75                  80

Ser Ser Ala Thr Phe Thr Ala Gln Glu Gln Leu Gln Pro Pro Asn Leu
                85                  90                  95

Asp Pro Lys Asp Glu Ile Asn Val Leu Lys Gln Glu Ile Glu Met Leu
            100                 105                 110

Gln Lys Gly Ile Ser Tyr Met Phe Gly Gly Gly Asp Gly Ala Met Asn
            115                 120                 125
```

-continued

```
Leu Glu Glu Leu Leu Leu Leu Glu Lys His Leu Glu Tyr Trp Ile Ser
    130                 135                 140

Gln Ile Arg Ser Ala Lys Met Asp Val Met Leu Gln Glu Ile Gln Ser
145                 150                 155                 160

Leu Arg Asn Lys Glu Gly Val Leu Lys Asn Thr Asn Lys Tyr Leu Leu
                165                 170                 175

Glu Lys Ile Glu Glu Asn Asn Asn Ser Ile Leu Asp Ala Asn Phe Ala
                180                 185                 190

Val Met Glu Thr Asn Tyr Ser Tyr Pro Leu Thr Met Pro Ser Glu Ile
            195                 200                 205

Phe Gln Phe
    210
```

```
<210> SEQ ID NO 5
<211> LENGTH: 258
<212> TYPE: PRT
<213> ORGANISM: Arabidopsis thaliana

<400> SEQUENCE: 5
```

```
Met Gly Arg Gly Lys Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
            20                  25                  30

Tyr Glu Leu Ser Val Leu Cys Asp Ala Glu Ile Ala Leu Leu Ile Phe
            35                  40                  45

Ser Asn Arg Gly Lys Leu Tyr Glu Phe Cys Ser Ser Pro Ser Gly Met
    50                  55                  60

Ala Arg Thr Val Asp Lys Tyr Arg Lys His Ser Tyr Ala Thr Met Asp
65                  70                  75                  80

Pro Asn Gln Ser Ala Lys Asp Leu Gln Asp Lys Tyr Gln Asp Tyr Leu
                85                  90                  95

Lys Leu Lys Ser Arg Val Glu Ile Leu Gln His Ser Gln Arg His Leu
            100                 105                 110

Leu Gly Glu Glu Leu Ser Glu Met Asp Val Asn Glu Leu Glu His Leu
            115                 120                 125

Glu Arg Gln Val Asp Ala Ser Leu Arg Gln Ile Arg Ser Thr Lys Ala
    130                 135                 140

Arg Ser Met Leu Asp Gln Leu Ser Asp Leu Lys Thr Lys Glu Glu Met
145                 150                 155                 160

Leu Leu Glu Thr Asn Arg Asp Leu Arg Arg Lys Leu Glu Asp Ser Asp
                165                 170                 175

Ala Ala Leu Thr Gln Ser Phe Trp Gly Ser Ser Ala Ala Glu Gln Gln
            180                 185                 190

Gln Gln His Gln Gln Gln Gln Gly Met Ser Ser Tyr Gln Ser Asn
            195                 200                 205

Pro Pro Ile Gln Glu Ala Gly Phe Phe Lys Pro Leu Gln Gly Asn Val
    210                 215                 220

Ala Leu Gln Met Ser Ser His Tyr Asn His Asn Pro Ala Asn Ala Thr
225                 230                 235                 240

Asn Ser Ala Thr Thr Ser Gln Asn Val Asn Gly Phe Phe Pro Gly Trp
                245                 250                 255

Met Val
```

```
<210> SEQ ID NO 6
<211> LENGTH: 248
```

```
<212> TYPE: PRT
<213> ORGANISM: Arabidopsis thaliana

<400> SEQUENCE: 6

Met Glu Gly Gly Ala Ser Asn Glu Val Ala Glu Ser Ser Lys Lys Ile
1               5                   10                  15

Gly Arg Gly Lys Ile Glu Ile Lys Arg Ile Glu Asn Thr Thr Asn Arg
            20                  25                  30

Gln Val Thr Phe Cys Lys Arg Arg Asn Gly Leu Leu Lys Lys Ala Tyr
        35                  40                  45

Glu Leu Ser Val Leu Cys Asp Ala Glu Val Ala Leu Val Ile Phe Ser
    50                  55                  60

Thr Arg Gly Arg Leu Tyr Glu Tyr Ala Asn Asn Ser Val Arg Gly Thr
65                  70                  75                  80

Ile Glu Arg Tyr Lys Lys Ala Cys Ser Asp Ala Val Asn Pro Pro Thr
                85                  90                  95

Ile Thr Glu Ala Asn Thr Gln Tyr Tyr Gln Gln Glu Ala Ser Lys Leu
            100                 105                 110

Arg Arg Gln Ile Arg Asp Ile Gln Asn Leu Asn Arg His Ile Leu Gly
        115                 120                 125

Glu Ser Leu Gly Ser Leu Asn Phe Lys Glu Leu Lys Asn Leu Glu Ser
    130                 135                 140

Arg Leu Glu Lys Gly Ile Ser Arg Val Arg Ser Lys Lys His Glu Met
145                 150                 155                 160

Leu Val Ala Glu Ile Glu Tyr Met Gln Lys Arg Val Lys Glu Ile Glu
                165                 170                 175

Leu Gln Asn Asp Asn Met Tyr Leu Arg Ser Lys Ile Thr Glu Arg Thr
            180                 185                 190

Gly Leu Gln Gln Gln Glu Ser Ser Val Ile His Gln Gly Thr Val Tyr
        195                 200                 205

Glu Ser Gly Val Thr Ser Ser His Gln Ser Gly Gln Tyr Asn Arg Asn
    210                 215                 220

Tyr Ile Ala Val Asn Leu Leu Glu Pro Asn Gln Asn Ser Ser Asn Gln
225                 230                 235                 240

Asp Gln Pro Pro Leu Gln Leu Val
                245

<210> SEQ ID NO 7
<211> LENGTH: 252
<212> TYPE: PRT
<213> ORGANISM: Arabidopsis thaliana

<400> SEQUENCE: 7

Met Gly Arg Gly Arg Val Glu Met Lys Arg Ile Glu Asn Lys Ile Asn
1               5                   10                  15

Arg Gln Val Thr Phe Ser Lys Arg Arg Asn Gly Leu Leu Lys Lys Ala
            20                  25                  30

Tyr Glu Leu Ser Val Leu Cys Asp Ala Glu Val Ala Leu Ile Ile Phe
        35                  40                  45

Ser Ser Arg Gly Lys Leu Tyr Glu Phe Gly Ser Val Gly Ile Glu Ser
    50                  55                  60

Thr Ile Glu Arg Tyr Asn Arg Cys Tyr Asn Cys Ser Leu Ser Asn Asn
65                  70                  75                  80

Lys Pro Glu Glu Thr Thr Gln Ser Trp Cys Gln Glu Val Thr Lys Leu
                85                  90                  95
```

```
Lys Ser Lys Tyr Glu Ser Leu Val Arg Thr Asn Arg Asn Leu Leu Gly
            100                 105                 110

Glu Asp Leu Gly Glu Met Gly Val Lys Glu Leu Gln Ala Leu Glu Arg
        115                 120                 125

Gln Leu Glu Ala Ala Leu Thr Ala Thr Arg Gln Arg Lys Thr Gln Val
    130                 135                 140

Met Met Glu Glu Met Glu Asp Leu Arg Lys Lys Glu Arg Gln Leu Gly
145                 150                 155                 160

Asp Ile Asn Lys Gln Leu Lys Ile Lys Phe Glu Thr Glu Gly His Ala
                165                 170                 175

Phe Lys Thr Phe Gln Asp Leu Trp Ala Asn Ser Ala Ala Ser Val Ala
            180                 185                 190

Gly Asp Pro Asn Asn Ser Glu Phe Pro Val Glu Pro Ser His Pro Asn
        195                 200                 205

Val Leu Asp Cys Asn Thr Glu Pro Phe Leu Gln Ile Gly Phe Gln Gln
    210                 215                 220

His Tyr Tyr Val Gln Gly Glu Gly Ser Ser Val Ser Lys Ser Asn Val
225                 230                 235                 240

Ala Gly Glu Thr Asn Phe Val Gln Gly Trp Val Leu
            245                 250
```

```
<210> SEQ ID NO 8
<211> LENGTH: 214
<212> TYPE: PRT
<213> ORGANISM: Arabidopsis thaliana

<400> SEQUENCE: 8

Met Val Arg Gly Lys Thr Gln Met Lys Arg Ile Glu Asn Ala Thr Ser
1               5                   10                  15

Arg Gln Val Thr Phe Ser Lys Arg Arg Asn Gly Leu Leu Lys Lys Ala
            20                  25                  30

Phe Glu Leu Ser Val Leu Cys Asp Ala Glu Val Ser Leu Ile Ile Phe
        35                  40                  45

Ser Pro Lys Gly Lys Leu Tyr Glu Phe Ala Ser Ser Asn Met Gln Asp
    50                  55                  60

Thr Ile Asp Arg Tyr Leu Arg His Thr Lys Asp Arg Val Ser Thr Lys
65                  70                  75                  80

Pro Val Ser Glu Glu Asn Met Gln His Leu Lys Tyr Glu Ala Ala Asn
                85                  90                  95

Met Met Lys Lys Ile Glu Gln Leu Glu Ala Ser Lys Arg Lys Leu Leu
            100                 105                 110

Gly Glu Gly Ile Gly Thr Cys Ser Ile Glu Glu Leu Gln Gln Ile Glu
        115                 120                 125

Gln Gln Leu Glu Lys Ser Val Lys Cys Ile Arg Ala Arg Lys Thr Gln
    130                 135                 140

Val Phe Lys Glu Gln Ile Glu Gln Leu Lys Gln Lys Glu Lys Ala Leu
145                 150                 155                 160

Ala Ala Glu Asn Glu Lys Leu Ser Glu Lys Trp Gly Ser His Glu Ser
                165                 170                 175

Glu Val Trp Ser Asn Lys Asn Gln Glu Ser Thr Gly Arg Gly Asp Glu
            180                 185                 190

Glu Ser Ser Pro Ser Ser Glu Val Glu Thr Gln Leu Phe Ile Gly Leu
        195                 200                 205

Pro Cys Ser Ser Arg Lys
    210
```

```
<210> SEQ ID NO 9
<211> LENGTH: 250
<212> TYPE: PRT
<213> ORGANISM: Arabidopsis thaliana

<400> SEQUENCE: 9

Met Gly Arg Gly Arg Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
                20                  25                  30

Tyr Glu Leu Ser Val Leu Cys Asp Ala Glu Val Ser Leu Ile Val Phe
            35                  40                  45

Ser Asn Arg Gly Lys Leu Tyr Glu Phe Cys Ser Thr Ser Asn Met Leu
        50                  55                  60

Lys Thr Leu Glu Arg Tyr Gln Lys Cys Ser Tyr Gly Ser Ile Glu Val
65                  70                  75                  80

Asn Asn Lys Pro Ala Lys Glu Leu Glu Asn Ser Tyr Arg Glu Tyr Leu
                85                  90                  95

Lys Leu Lys Gly Arg Tyr Glu Asn Leu Gln Arg Gln Gln Arg Asn Leu
            100                 105                 110

Leu Gly Glu Asp Leu Gly Pro Leu Asn Ser Lys Glu Leu Glu Gln Leu
        115                 120                 125

Glu Arg Gln Leu Asp Gly Ser Leu Lys Gln Val Arg Cys Ile Lys Thr
    130                 135                 140

Gln Tyr Met Leu Asp Gln Leu Ser Asp Leu Gln Gly Lys Glu His Ile
145                 150                 155                 160

Leu Leu Asp Ala Asn Arg Ala Leu Ser Met Lys Leu Glu Asp Met Ile
                165                 170                 175

Gly Val Arg His His His Ile Gly Gly Gly Trp Glu Gly Gly Asp Gln
            180                 185                 190

Gln Asn Ile Ala Tyr Gly His Pro Gln Ala His Ser Gln Gly Leu Tyr
            195                 200                 205

Gln Ser Leu Glu Cys Asp Pro Thr Leu Gln Ile Gly Tyr Ser His Pro
        210                 215                 220

Val Cys Ser Glu Gln Met Ala Val Thr Val Gln Gly Gln Ser Gln Gln
225                 230                 235                 240

Gly Asn Gly Tyr Ile Pro Gly Trp Met Leu
                245                 250

<210> SEQ ID NO 10
<211> LENGTH: 249
<212> TYPE: PRT
<213> ORGANISM: Arabidopsis thaliana

<400> SEQUENCE: 10

Met Gly Arg Gly Arg Val Gln Leu Arg Arg Ile Glu Asn Lys Ile Arg
1               5                   10                  15

Arg Gln Val Thr Phe Ser Lys Arg Arg Thr Gly Leu Val Lys Lys Ala
                20                  25                  30

Gln Glu Ile Ser Val Leu Cys Asp Ala Glu Val Ala Leu Ile Val Phe
            35                  40                  45

Ser Pro Lys Gly Lys Leu Phe Glu Tyr Ser Ala Gly Ser Ser Met Glu
        50                  55                  60

Arg Ile Leu Asp Arg Tyr Glu Arg Ser Ala Tyr Ala Gly Gln Asp Ile
65                  70                  75                  80
```

-continued

```
Pro Thr Pro Asn Leu Asp Ser Gln Gly Glu Cys Ser Thr Glu Cys Ser
                85              90                  95

Lys Leu Leu Arg Met Ile Asp Val Leu Gln Arg Ser Leu Arg His Leu
            100             105                 110

Arg Gly Glu Glu Val Asp Gly Leu Ser Ile Arg Asp Leu Gln Gly Val
            115             120                 125

Glu Met Gln Leu Asp Thr Ala Leu Lys Lys Thr Arg Ser Arg Lys Asn
    130             135                 140

Gln Leu Met Val Glu Ser Ile Ala Gln Leu Gln Lys Lys Glu Lys Glu
145             150                 155                 160

Leu Lys Glu Leu Lys Lys Gln Leu Thr Lys Lys Ala Gly Glu Arg Glu
            165             170                 175

Asp Phe Gln Thr Gln Asn Leu Ser His Asp Leu Ala Ser Leu Ala Thr
            180             185                 190

Pro Pro Phe Glu Ser Pro His Glu Leu Arg Arg Thr Ile Ser Pro Pro
            195             200                 205

Pro Pro Pro Leu Ser Ser Gly Asp Thr Ser Gln Arg Asp Gly Val Gly
    210             215                 220

Glu Val Ala Ala Gly Thr Leu Ile Arg Arg Thr Asn Ala Thr Leu Pro
225             230                 235                 240

His Trp Met Pro Gln Leu Thr Gly Glu
                245
```

<210> SEQ ID NO 11
<211> LENGTH: 281
<212> TYPE: PRT
<213> ORGANISM: Arabidopsis thaliana

<400> SEQUENCE: 11

```
Met Glu Glu Gly Gly Ser Ser His Asp Ala Glu Ser Ser Lys Lys Leu
1               5                   10                  15

Gly Arg Gly Lys Ile Glu Ile Lys Arg Ile Glu Asn Thr Thr Asn Arg
            20                  25                  30

Gln Val Thr Phe Cys Lys Arg Arg Asn Gly Leu Leu Lys Lys Ala Tyr
            35                  40                  45

Glu Leu Ser Val Leu Cys Asp Ala Glu Val Ala Leu Val Ile Phe Ser
    50                  55                  60

Thr Arg Gly Arg Leu Tyr Glu Tyr Ala Asn Asn Ser Val Arg Gly Thr
65                  70                  75                  80

Ile Glu Arg Tyr Lys Lys Ala Cys Ser Asp Ala Val Asn Pro Pro Ser
                85                  90                  95

Val Thr Glu Ala Asn Thr Gln Tyr Tyr Gln Gln Glu Ala Ser Lys Leu
            100             105                 110

Arg Arg Gln Ile Arg Asp Ile Gln Asn Ser Asn Arg His Ile Val Gly
            115             120                 125

Glu Ser Leu Gly Ser Leu Asn Phe Lys Glu Leu Lys Asn Leu Glu Gly
    130             135                 140

Arg Leu Glu Lys Gly Ile Ser Arg Val Arg Ser Lys Lys Val Lys Ser
145             150                 155                 160

Thr Leu Leu Ser Leu Cys Val Ser Val Ser Leu Ser Ile Tyr Ser Pro
            165             170                 175

Leu Val Tyr Ile Val His His Pro Phe Val Arg Ile Leu Gln Asn Glu
            180             185                 190

Leu Leu Val Ala Glu Ile Glu Tyr Met Gln Lys Arg Glu Met Glu Leu
```

-continued

```
         195                 200                 205

Gln His Asn Asn Met Tyr Leu Arg Ala Lys Ile Ala Glu Gly Ala Arg
    210                 215                 220

Leu Asn Pro Asp Gln Gln Glu Ser Ser Val Ile Gln Gly Thr Thr Val
225                 230                 235                 240

Tyr Glu Ser Gly Val Ser Ser His Asp Gln Ser Gln His Tyr Asn Arg
                245                 250                 255

Asn Tyr Ile Pro Val Asn Leu Leu Glu Pro Asn Gln Gln Phe Ser Gly
                260                 265                 270

Gln Asp Gln Pro Pro Leu Gln Leu Val
        275                 280
```

```
<210> SEQ ID NO 12
<211> LENGTH: 244
<212> TYPE: PRT
<213> ORGANISM: Arabidopsis thaliana

<400> SEQUENCE: 12

Met Gly Arg Gly Lys Val Glu Val Lys Arg Ile Glu Asn Lys Ile Thr
1               5                   10                  15

Arg Gln Val Thr Phe Ser Lys Arg Lys Ser Gly Leu Leu Lys Lys Ala
                20                  25                  30

Tyr Glu Leu Ser Val Leu Cys Asp Ala Glu Val Ser Leu Ile Ile Phe
            35                  40                  45

Ser Thr Gly Gly Lys Leu Tyr Glu Phe Ser Asn Val Gly Val Gly Arg
    50                  55                  60

Thr Ile Glu Arg Tyr Tyr Arg Cys Lys Asp Asn Leu Leu Asp Asn Asp
65                  70                  75                  80

Thr Leu Glu Asp Thr Gln Gly Leu Arg Gln Glu Val Thr Lys Leu Lys
                85                  90                  95

Cys Lys Tyr Glu Ser Leu Leu Arg Thr His Arg Asn Leu Val Gly Glu
            100                 105                 110

Asp Leu Glu Gly Met Ser Ile Lys Glu Leu Gln Thr Leu Glu Arg Gln
            115                 120                 125

Leu Glu Gly Ala Leu Ser Ala Thr Arg Lys Gln Lys Thr Gln Val Met
        130                 135                 140

Met Glu Gln Met Glu Glu Leu Arg Arg Lys Glu Arg Glu Leu Gly Asp
145                 150                 155                 160

Ile Asn Asn Lys Leu Lys Leu Glu Thr Glu Asp His Asp Phe Lys Gly
                165                 170                 175

Phe Gln Asp Leu Leu Leu Asn Pro Val Leu Thr Ala Gly Cys Ser Thr
            180                 185                 190

Asp Phe Ser Leu Gln Ser Thr His Gln Asn Tyr Ile Ser Asp Cys Asn
            195                 200                 205

Leu Gly Tyr Phe Leu Gln Ile Gly Phe Gln Gln His Tyr Glu Gln Gly
        210                 215                 220

Glu Gly Ser Ser Val Thr Lys Ser Asn Ala Arg Ser Asp Ala Glu Thr
225                 230                 235                 240

Asn Phe Val Gln
```

```
<210> SEQ ID NO 13
<211> LENGTH: 256
<212> TYPE: PRT
<213> ORGANISM: Arabidopsis thaliana

<400> SEQUENCE: 13
```

```
Met Leu Phe Pro His Glu Arg Lys Lys Glu Lys Glu Arg Ser Gln Gly
1               5                   10                  15

Phe Tyr Leu Val Thr Arg Leu Arg Ile Arg Met Gly Arg Gly Lys Ile
            20                  25                  30

Glu Ile Lys Arg Ile Glu Asn Ser Thr Asn Arg Gln Val Thr Phe Cys
        35                  40                  45

Lys Arg Arg Asn Gly Leu Leu Lys Lys Ala Tyr Glu Leu Ser Val Leu
    50                  55                  60

Cys Asp Ala Glu Val Ala Leu Ile Val Phe Ser Thr Arg Gly Arg Leu
65                  70                  75                  80

Tyr Glu Tyr Ala Asn Asn Asn Ile Arg Ser Thr Ile Glu Arg Tyr Lys
                85                  90                  95

Lys Ala Cys Ser Asp Ser Thr Asn Thr Ser Thr Val Gln Glu Ile Asn
            100                 105                 110

Ala Ala Tyr Tyr Gln Gln Glu Ser Ala Lys Leu Arg Gln Gln Ile Gln
            115                 120                 125

Thr Ile Gln Asn Ser Asn Arg Asn Leu Met Gly Asp Ser Leu Ser Ser
    130                 135                 140

Leu Ser Val Lys Glu Leu Lys Gln Val Glu Asn Arg Leu Glu Lys Ala
145                 150                 155                 160

Ile Ser Arg Ile Arg Ser Lys Lys His Glu Leu Leu Leu Val Glu Ile
            165                 170                 175

Glu Asn Ala Gln Lys Arg Glu Ile Glu Leu Asp Asn Glu Asn Ile Tyr
            180                 185                 190

Leu Arg Thr Lys Val Ala Glu Val Glu Arg Tyr Gln Gln His His His
            195                 200                 205

Gln Met Val Ser Gly Ser Glu Ile Asn Ala Ile Glu Ala Leu Ala Ser
    210                 215                 220

Arg Asn Tyr Phe Ala His Ser Ile Met Thr Ala Gly Ser Gly Ser Gly
225                 230                 235                 240

Asn Gly Gly Ser Tyr Ser Asp Pro Asp Lys Lys Ile Leu His Leu Gly
                245                 250                 255
```

<210> SEQ ID NO 14
<211> LENGTH: 221
<212> TYPE: PRT
<213> ORGANISM: Arabidopsis thaliana

<400> SEQUENCE: 14

```
Met Val Arg Gly Lys Thr Glu Met Lys Arg Ile Glu Asn Ala Thr Ser
1               5                   10                  15

Arg Gln Val Thr Phe Ser Lys Arg Arg Asn Gly Leu Leu Lys Lys Ala
            20                  25                  30

Phe Glu Leu Ser Val Leu Cys Asp Ala Glu Val Ala Leu Ile Ile Phe
        35                  40                  45

Ser Pro Arg Gly Lys Leu Tyr Glu Phe Ser Ser Ser Ser Ile Pro
    50                  55                  60

Lys Thr Val Glu Arg Tyr Gln Lys Arg Ile Gln Asp Leu Gly Ser Asn
65                  70                  75                  80

His Lys Arg Asn Asp Asn Ser Gln Gln Ser Lys Asp Glu Thr Tyr Gly
                85                  90                  95

Leu Ala Arg Lys Ile Glu His Leu Glu Ile Ser Thr Arg Lys Met Met
            100                 105                 110

Gly Glu Gly Leu Asp Ala Ser Ser Ile Glu Glu Leu Gln Gln Leu Glu
```

-continued

```
                 115                 120                 125
Asn Gln Leu Asp Arg Ser Leu Met Lys Ile Arg Ala Lys Lys Tyr Gln
    130                 135                 140

Leu Leu Arg Glu Glu Thr Glu Lys Leu Lys Glu Lys Glu Arg Asn Leu
145                 150                 155                 160

Ile Ala Glu Asn Lys Met Leu Met Glu Lys Cys Glu Met Gln Gly Arg
                165                 170                 175

Gly Ile Ile Gly Arg Ile Ser Ser Ser Ser Thr Ser Glu Leu Asp
                180                 185                 190

Ile Asp Asp Asn Glu Met Glu Val Val Thr Asp Leu Phe Ile Gly Pro
                195                 200                 205

Pro Glu Thr Arg His Phe Lys Lys Phe Pro Pro Ser Asn
    210                 215                 220
```

```
<210> SEQ ID NO 15
<211> LENGTH: 252
<212> TYPE: PRT
<213> ORGANISM: Arabidopsis thaliana

<400> SEQUENCE: 15
```

```
Thr Ala Tyr Gln Ser Glu Leu Gly Gly Asp Ser Ser Pro Leu Arg Lys
1               5                   10                  15

Ser Gly Arg Gly Lys Ile Glu Ile Lys Arg Ile Glu Asn Thr Thr Asn
                20                  25                  30

Arg Gln Val Thr Phe Cys Lys Arg Arg Asn Gly Leu Leu Lys Lys Ala
            35                  40                  45

Tyr Glu Leu Ser Val Leu Cys Asp Ala Glu Val Ala Leu Ile Val Phe
    50                  55                  60

Ser Ser Arg Gly Arg Leu Tyr Glu Tyr Ser Asn Asn Ser Val Lys Gly
65                  70                  75                  80

Thr Ile Glu Arg Tyr Lys Lys Ala Ile Ser Asp Asn Ser Asn Thr Gly
                85                  90                  95

Ser Val Ala Glu Ile Asn Ala Gln Tyr Tyr Gln Gln Glu Ser Ala Lys
            100                 105                 110

Leu Arg Gln Gln Ile Ile Ser Ile Gln Asn Ser Asn Arg Gln Leu Met
            115                 120                 125

Gly Glu Thr Ile Gly Ser Met Ser Pro Lys Glu Leu Arg Asn Leu Glu
    130                 135                 140

Gly Arg Leu Glu Arg Ser Ile Thr Arg Ile Arg Ser Lys Lys Asn Glu
145                 150                 155                 160

Leu Leu Phe Ser Glu Ile Asp Tyr Met Gln Lys Arg Glu Val Asp Leu
                165                 170                 175

His Asn Asp Asn Gln Ile Leu Arg Ala Lys Ile Ala Glu Asn Glu Arg
            180                 185                 190

Asn Asn Pro Ser Ile Ser Leu Met Pro Gly Gly Ser Asn Tyr Glu Gln
            195                 200                 205

Leu Met Pro Pro Pro Gln Thr Gln Ser Gln Pro Phe Asp Ser Arg Asn
    210                 215                 220

Tyr Phe Gln Val Ala Ala Leu Gln Pro Asn Asn His His Tyr Ser Ser
225                 230                 235                 240

Ala Gly Arg Gln Asp Gln Thr Ala Leu Gln Leu Val
                245                 250
```

```
<210> SEQ ID NO 16
<211> LENGTH: 219
```

<212> TYPE: PRT
<213> ORGANISM: Arabidopsis thaliana

<400> SEQUENCE: 16

```
Met Val Arg Gly Lys Thr Glu Met Lys Arg Ile Glu Asn Ala Thr Ser
1               5                   10                  15

Arg Gln Val Thr Phe Ser Lys Arg Arg Asn Gly Leu Leu Lys Lys Ala
                20                  25                  30

Phe Glu Leu Ser Val Leu Cys Asp Ala Glu Val Ala Leu Val Ile Phe
            35                  40                  45

Ser Pro Arg Ser Lys Leu Tyr Glu Phe Ser Ser Ser Ile Ala Ala
        50                  55                  60

Thr Ile Glu Arg Tyr Gln Arg Ile Lys Glu Ile Gly Asn Asn His
65                  70                  75                  80

Lys Arg Asn Asp Asn Ser Gln Gln Ala Arg Asp Glu Thr Ser Gly Leu
                85                  90                  95

Thr Lys Lys Ile Glu Gln Leu Glu Ile Ser Lys Arg Lys Leu Leu Gly
            100                 105                 110

Glu Gly Ile Asp Ala Cys Ser Ile Glu Glu Leu Gln Gln Leu Glu Asn
        115                 120                 125

Gln Leu Asp Arg Ser Leu Ser Arg Ile Arg Ala Lys Lys Tyr Gln Leu
    130                 135                 140

Leu Arg Glu Glu Ile Glu Lys Leu Lys Ala Glu Glu Arg Asn Leu Val
145                 150                 155                 160

Lys Glu Asn Lys Asp Leu Lys Glu Lys Trp Leu Gly Met Gly Thr Ala
                165                 170                 175

Thr Ile Ala Ser Ser Gln Ser Thr Leu Ser Ser Ser Glu Val Asn Ile
            180                 185                 190

Asp Asp Asn Met Glu Val Glu Thr Gly Leu Phe Ile Gly Pro Pro Glu
        195                 200                 205

Thr Arg Gln Ser Lys Lys Phe Pro Pro Gln Asn
    210                 215
```

<210> SEQ ID NO 17
<211> LENGTH: 262
<212> TYPE: PRT
<213> ORGANISM: Arabidopsis thaliana

<400> SEQUENCE: 17

```
Met Gly Arg Gly Arg Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
                20                  25                  30

Tyr Glu Leu Ser Val Leu Cys Asp Ala Glu Val Ala Leu Ile Ile Phe
            35                  40                  45

Ser Asn Arg Gly Lys Leu Tyr Glu Phe Cys Ser Ser Ser Asn Met Leu
        50                  55                  60

Lys Thr Leu Asp Arg Tyr Gln Lys Cys Ser Tyr Gly Ser Ile Glu Val
65                  70                  75                  80

Asn Asn Lys Pro Ala Lys Glu Leu Glu Asn Ser Tyr Arg Glu Tyr Leu
                85                  90                  95

Lys Leu Lys Gly Arg Tyr Glu Asn Leu Gln Arg Gln Arg Asn Leu
            100                 105                 110

Leu Gly Glu Asp Leu Gly Pro Leu Asn Ser Lys Glu Leu Glu Gln Leu
        115                 120                 125
```

-continued

```
Glu Arg Gln Leu Asp Gly Ser Leu Lys Gln Val Arg Ser Ile Lys Thr
    130             135             140

Gln Tyr Met Leu Asp Gln Leu Ser Asp Leu Gln Asn Lys Glu Gln Met
145             150             155             160

Leu Leu Glu Thr Asn Arg Ala Leu Ala Met Lys Leu Asp Asp Met Ile
            165             170             175

Gly Val Arg Ser His His Met Gly Gly Gly Gly Trp Glu Gly Gly
            180             185             190

Glu Gln Asn Val Thr Tyr Ala His His Gln Ala Gln Ser Gln Gly Leu
            195             200             205

Tyr Gln Pro Leu Glu Cys Asn Pro Thr Leu Gln Met Gly Cys Cys Phe
    210             215             220

Gly Asp Asp Asp Asp Asp Asp Arg Tyr Asp Asn Pro Val Cys Ser Glu
225             230             235             240

Gln Ile Thr Ala Thr Thr Gln Ala Gln Ala Gln Gln Gly Asn Gly Tyr
            245             250             255

Ile Pro Gly Trp Met Leu
            260
```

<210> SEQ ID NO 18
<211> LENGTH: 211
<212> TYPE: PRT
<213> ORGANISM: Arabidopsis thaliana

<400> SEQUENCE: 18

```
Met Val Arg Gly Lys Ile Glu Ile Lys Lys Ile Glu Asn Val Thr Ser
1               5               10              15

Arg Gln Val Thr Phe Ser Lys Arg Arg Ser Gly Leu Phe Lys Lys Ala
            20              25              30

His Glu Leu Ser Val Leu Cys Asp Ala Gln Val Ala Ala Met Ile Phe
            35              40              45

Ser Gln Lys Gly Arg Leu Tyr Glu Phe Ala Ser Ser Asp Ile Arg Asn
    50              55              60

Thr Ile Lys Arg Tyr Ala Glu Tyr Lys Arg Glu Tyr Phe Val Ala Glu
65              70              75              80

Thr His Pro Ile Glu Gln Tyr Val Gln Gly Leu Lys Lys Glu Met Val
            85              90              95

Thr Met Val Lys Lys Ile Glu Val Leu Glu Val His Asn Arg Lys Met
            100             105             110

Met Gly Gln Ser Leu Asp Ser Cys Ser Val Lys Glu Leu Ser Glu Ile
            115             120             125

Ala Thr Gln Ile Glu Lys Ser Leu His Met Val Arg Leu Arg Lys Ala
    130             135             140

Lys Leu Tyr Glu Asp Glu Leu Gln Lys Leu Lys Ala Lys Glu Arg Glu
145             150             155             160

Leu Lys Asp Glu Arg Val Arg Leu Ser Leu Lys Lys Thr Ile Tyr Thr
            165             170             175

His Leu Cys Gln Val Gly Glu Arg Pro Met Gly Met Pro Ser Gly Ser
            180             185             190

Lys Glu Lys Glu Asp Val Glu Thr Asp Leu Phe Ile Gly Phe Leu Lys
            195             200             205

Asn Arg Pro
    210
```

<210> SEQ ID NO 19

-continued

```
<211> LENGTH: 229
<212> TYPE: PRT
<213> ORGANISM: Arabidopsis thaliana

<400> SEQUENCE: 19

Met Asn Leu Gly Met Asn Ile Ala Gly Thr Met Val Arg Gly Lys Ile
1               5                   10                  15

Glu Ile Lys Lys Ile Glu Asn Val Thr Ser Arg Gln Val Thr Phe Ser
                20                  25                  30

Lys Arg Arg Ser Gly Leu Phe Lys Lys Ala His Glu Leu Ser Val Leu
            35                  40                  45

Cys Asp Ala Gln Val Ala Ala Ile Val Phe Ser Gln Ser Gly Arg Leu
        50                  55                  60

His Glu Tyr Ser Ser Ser Gln Met Glu Lys Ile Ile Asp Arg Tyr Gly
65                  70                  75                  80

Lys Phe Ser Asn Ala Phe Tyr Val Ala Glu Arg Pro Gln Val Glu Arg
                85                  90                  95

Tyr Leu Gln Glu Leu Lys Met Glu Ile Asp Arg Met Val Lys Lys Ile
            100                 105                 110

Asp Leu Leu Glu Val His His Arg Lys Leu Leu Gly Gln Gly Leu Asp
            115                 120                 125

Ser Cys Ser Val Thr Glu Leu Gln Glu Ile Asp Thr Gln Ile Glu Lys
        130                 135                 140

Ser Leu Arg Ile Val Arg Ser Arg Lys Ala Glu Leu Tyr Ala Asp Gln
145                 150                 155                 160

Leu Lys Lys Leu Lys Glu Lys Glu Arg Glu Leu Leu Asn Glu Arg Lys
                165                 170                 175

Arg Leu Leu Glu Glu Gln Asn Arg Glu Arg Leu Met Arg Pro Val Val
            180                 185                 190

Pro Ala Thr Leu Gln Ile Cys Asp Lys Gly Asn Thr Glu Gly Gly His
            195                 200                 205

Arg Thr Lys His Ser Ser Glu Val Glu Thr Asp Leu Phe Ile Gly Leu
        210                 215                 220

Pro Val Thr Arg Leu
225

<210> SEQ ID NO 20
<211> LENGTH: 242
<212> TYPE: PRT
<213> ORGANISM: Arabidopsis thaliana

<400> SEQUENCE: 20

Met Gly Arg Gly Arg Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
                20                  25                  30

His Glu Ile Ser Val Leu Cys Asp Ala Glu Val Ala Leu Ile Val Phe
            35                  40                  45

Ser Ser Lys Gly Lys Leu Phe Glu Tyr Ser Thr Asp Ser Cys Met Glu
        50                  55                  60

Arg Ile Leu Glu Arg Tyr Asp Arg Tyr Leu Tyr Ser Asp Lys Gln Leu
65                  70                  75                  80

Val Gly Arg Asp Val Ser Gln Ser Glu Asn Trp Val Leu Glu His Ala
                85                  90                  95

Lys Leu Lys Ala Arg Val Glu Val Leu Glu Lys Asn Lys Arg Asn Phe
            100                 105                 110
```

```
Met Gly Glu Asp Leu Asp Ser Leu Ser Leu Lys Glu Leu Gln Ser Leu
        115                 120                 125

Glu His Gln Leu Asp Ala Ala Ile Lys Ser Ile Arg Ser Arg Lys Asn
    130                 135                 140

Gln Ala Met Phe Glu Ser Ile Ser Ala Leu Gln Lys Lys Asp Lys Ala
145                 150                 155                 160

Leu Gln Asp His Asn Asn Ser Leu Leu Lys Lys Ile Lys Glu Arg Glu
                165                 170                 175

Lys Lys Thr Gly Gln Gln Glu Gly Gln Leu Val Gln Cys Ser Asn Ser
                180                 185                 190

Ser Ser Val Leu Leu Pro Gln Tyr Cys Val Thr Ser Ser Arg Asp Gly
                195                 200                 205

Phe Val Glu Arg Val Gly Gly Glu Asn Gly Gly Ala Ser Ser Leu Thr
    210                 215                 220

Glu Pro Asn Ser Leu Leu Pro Ala Trp Met Leu Arg Pro Thr Thr Thr
225                 230                 235                 240

Asn Glu

<210> SEQ ID NO 21
<211> LENGTH: 210
<212> TYPE: PRT
<213> ORGANISM: Arabidopsis thaliana

<400> SEQUENCE: 21

Met Val Arg Gly Lys Ile Glu Met Lys Lys Ile Glu Asn Ala Thr Ser
1               5                   10                  15

Arg Gln Val Thr Phe Ser Lys Arg Arg Asn Gly Leu Leu Lys Lys Ala
                20                  25                  30

Tyr Glu Leu Ser Val Leu Cys Asp Ala Gln Leu Ser Leu Ile Ile Phe
            35                  40                  45

Ser Gln Arg Gly Arg Leu Tyr Glu Phe Ser Ser Ser Asp Met Gln Lys
        50                  55                  60

Thr Ile Glu Arg Tyr Arg Lys Tyr Thr Lys Asp His Glu Thr Ser Asn
65                  70                  75                  80

His Asp Ser Gln Ile His Leu Gln Gln Leu Lys Gln Glu Ala Ser His
                85                  90                  95

Met Ile Thr Lys Ile Glu Leu Leu Glu Phe His Lys Arg Lys Leu Leu
            100                 105                 110

Gly Gln Gly Ile Ala Ser Cys Ser Leu Glu Glu Leu Gln Glu Ile Asp
        115                 120                 125

Ser Gln Leu Gln Arg Ser Leu Gly Lys Val Arg Glu Arg Lys Ala Gln
    130                 135                 140

Leu Phe Lys Glu Gln Leu Glu Lys Leu Lys Ala Lys Glu Lys Gln Leu
145                 150                 155                 160

Leu Glu Glu Asn Val Lys Leu His Gln Lys Asn Val Ile Asn Pro Trp
                165                 170                 175

Arg Gly Ser Ser Thr Asp Gln Gln Gln Glu Lys Tyr Lys Val Ile Asp
                180                 185                 190

Leu Asn Leu Glu Val Glu Thr Asp Leu Phe Ile Gly Leu Pro Asn Arg
                195                 200                 205

Asn Cys
    210

<210> SEQ ID NO 22
```

<211> LENGTH: 251
<212> TYPE: PRT
<213> ORGANISM: Fragaria vesca

<400> SEQUENCE: 22

```
Met Ala Tyr Glu Asn Lys Pro Asn Thr Asp Leu Asp Ala Asp Ala Gln
1               5                   10                  15

Arg Arg Leu Gly Arg Gly Lys Ile Glu Ile Lys Arg Ile Glu Asn Thr
                20                  25                  30

Thr Asn Arg Gln Val Thr Phe Cys Lys Arg Arg Asn Gly Leu Leu Lys
            35                  40                  45

Lys Ala Tyr Glu Leu Ser Val Leu Cys Asp Ala Glu Val Ala Leu Ile
        50                  55                  60

Val Phe Ser Asn Arg Gly Arg Leu Tyr Glu Tyr Ser Asn Asn Ser Ser
65                  70                  75                  80

Val Arg Glu Thr Ile Glu Arg Tyr Lys Lys Ala Cys Ala Asp Thr Ser
                85                  90                  95

Thr Asn Gly Ser Ala Ser Glu Ala Thr Ala Gln Tyr Tyr Gln Gln Glu
            100                 105                 110

Ala Ala Lys Leu Arg Asn Gln Ile Asn Ala Leu Gln Asn Ser Asn Arg
        115                 120                 125

Gly Tyr Met Ala Glu Gly Leu Ser Asn Met Asn Ile Lys Glu Leu Lys
    130                 135                 140

Gly Met Glu Ser Lys Leu Glu Lys Ala Ile Thr Arg Ile Arg Ser Lys
145                 150                 155                 160

Lys Asn Glu Leu Leu Phe Ala Glu Ile Glu Tyr Met Gln Lys Arg Glu
                165                 170                 175

Leu Asp Leu His Asn Asn Asn Gln Leu Leu Arg Ala Lys Gly Gln Ile
            180                 185                 190

Ala Glu Asn Glu Arg Gln Gln Gln Ser Ile Asn Ala Ile Ala Gly Gly
        195                 200                 205

His Gly Ser Tyr Glu Ile Val Gln Pro Thr Gln Pro Phe His Glu Ala
    210                 215                 220

Arg Asn Tyr Phe Gln Val Asn Ala Leu Gln Pro Asn Ile His Gln Tyr
225                 230                 235                 240

Ser Arg His Asp Gln Val Ser Leu Gln Leu Val
                245                 250
```

<210> SEQ ID NO 23
<211> LENGTH: 242
<212> TYPE: PRT
<213> ORGANISM: Fragaria vesca

<400> SEQUENCE: 23

```
Met Gly Arg Gly Arg Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
                20                  25                  30

Tyr Glu Leu Ser Val Leu Cys Asp Ala Glu Val Ala Leu Ile Ile Phe
            35                  40                  45

Ser Asn Arg Gly Lys Leu Tyr Glu Phe Cys Ser Ser Ser Ser Met Leu
        50                  55                  60

Lys Thr Leu Glu Arg Tyr Gln Lys Cys Asn Tyr Gly Ala Pro Glu Thr
65                  70                  75                  80

Asn Val Ser Thr Arg Glu Ala Leu Glu Leu Ser Ser Gln Gln Glu Tyr
                85                  90                  95
```

```
Leu Lys Leu Lys Ala Arg Tyr Glu Ala Leu Gln Arg Asn Gln Arg Asn
        100             105             110

Leu Leu Gly Glu Asp Leu Gly Pro Leu Ser Ser Lys Glu Leu Glu Ser
        115             120             125

Leu Glu Arg Gln Leu Asp Met Ser Leu Lys Gln Ile Arg Ser Thr Arg
        130             135             140

Thr Gln Cys Met Leu Asp Gln Leu Thr Asp Leu Gln Arg Lys Glu His
145             150             155             160

Leu Leu Asn Glu Ala Asn Arg Thr Leu Lys Gln Arg Leu Phe Glu Gly
                165             170             175

Tyr His His Gln Leu Gln Leu Asn Ala Asn Ala Glu Glu Val Ala Tyr
                180             185             190

Gly Arg Gln Glu Ala His Gln Pro Gln Gly Asp Gly Phe Phe Gln Ala
                195             200             205

Leu Glu Cys Glu Pro Thr Leu Gln Ile Gly Tyr His Gln Asn Asp Pro
        210             215             220

Ile Gln Val Val Thr Ala Gly Pro Ser Val Asn Tyr Met Gly Gly Trp
225             230             235             240

Leu Pro

<210> SEQ ID NO 24
<211> LENGTH: 231
<212> TYPE: PRT
<213> ORGANISM: Fragaria vesca

<400> SEQUENCE: 24

Met Gly Arg Gly Arg Val Gln Leu Lys Arg Ile Glu Asn Lys Ile Asn
1               5               10              15

Arg Gln Val Thr Phe Ser Lys Arg Arg Thr Gly Leu Leu Lys Lys Ala
                20              25              30

His Glu Ile Ser Val Met Cys Asp Ala Gln Val Ala Leu Ile Val Phe
        35              40              45

Ser Asn Lys Gly Lys Leu Phe Glu Tyr Ala Thr Asp Ser Cys Met Glu
        50              55              60

Asp Ile Leu Glu Arg Tyr Glu Arg Tyr Ser Tyr Ala Glu Arg Gln Leu
65              70              75              80

Val Glu Pro Asp Phe Asp Ser Gln Gly Asn Trp Pro Phe Glu His Ala
                85              90              95

Arg Leu Lys Val Lys Val Glu Leu Leu Gln Arg Asn Leu Arg His Tyr
        100             105             110

Leu Gly Glu Asp Leu Asp Ser Leu Ser Ile Lys Glu Ile Gln Ser Leu
        115             120             125

Glu Gln Gln Leu Glu Thr Ala Leu Lys Gln Ile Arg Ser Arg Lys Glu
        130             135             140

Lys Ala Ile Lys Glu Gln Asn Asn Leu Leu Ser Lys Lys Ile Lys Glu
145             150             155             160

His Glu Lys Asn Val Ala Glu Ala Gln Glu Val His Asp Trp Glu Gln
                165             170             175

Gln Gln Gln Asn His Gly Leu Asn Leu Leu Ala Gln Gly Pro Ile Pro
                180             185             190

Cys Leu Asn Met Gly Gly Thr Gln Gln Asn Asp Gln Phe Leu Gln Val
        195             200             205

Arg Arg Asn Gln Leu Asp Leu Thr Leu Glu Pro Ser Leu Tyr Ser Cys
        210             215             220
```

-continued

---

His Leu Gly Cys Phe Ala Ser
225                 230

<210> SEQ ID NO 25
<211> LENGTH: 90
<212> TYPE: PRT
<213> ORGANISM: Fragaria vesca

<400> SEQUENCE: 25

Met Gly Arg Gly Lys Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
            20                  25                  30

Cys Glu Leu Ser Ile Leu Cys Asp Ala Glu Val Ala Leu Ile Ile Phe
        35                  40                  45

Ser Ser Arg Gly Lys Leu Tyr Glu Phe Cys Ser Gly Pro Ser Met Glu
    50                  55                  60

Lys Thr Ile Glu Lys Tyr Gln Arg Tyr Thr Tyr Ala Glu Leu Glu Ala
65                  70                  75                  80

Ala Gln Pro Ala Gln Asp Thr Gln Val Asn
                85                  90

<210> SEQ ID NO 26
<211> LENGTH: 225
<212> TYPE: PRT
<213> ORGANISM: Fragaria vesca

<400> SEQUENCE: 26

Met Val Arg Gly Lys Thr Gln Met Lys Arg Ile Glu Asn Ala Ala Ser
1               5                   10                  15

Arg Gln Val Thr Phe Ser Lys Arg Arg Ser Gly Leu Leu Lys Lys Ala
            20                  25                  30

Phe Glu Leu Ser Val Leu Cys Asp Ala Glu Val Ala Leu Ile Ile Phe
        35                  40                  45

Ser Asn Arg Gly Lys Leu Phe Glu Phe Ser Ser Cys Ser Ser Leu Asn
    50                  55                  60

Lys Thr Ile Asp Arg Phe Gln Lys Arg Ala Lys Asp Gln Gly Leu Ser
65                  70                  75                  80

Gly Lys Ala Ala Arg Asp His Asp His Met Glu Leu Ala Asn Glu Asp
                85                  90                  95

Thr Ser Ser Met Ala Met Arg Ile Glu Leu Ile Glu Ser Ser Lys Arg
                100                 105                 110

Lys Leu Leu Gly Asp Gly Leu Glu Ser Cys Ser Ile Asp Glu Leu His
        115                 120                 125

Gln Leu Glu Lys Asp Leu Glu Arg Ser Leu Ala Lys Ile Arg Asp Gln
    130                 135                 140

Lys Asn Leu Met Leu Arg Glu Gln Ile Gln Gln Leu Lys Glu Lys Glu
145                 150                 155                 160

Ile Ser Leu Leu Glu Glu Asn Ala Glu Leu Met Glu Lys Cys Gly Met
                165                 170                 175

Gln Gln Ile Gly Pro Pro Ser Asn Gly Glu Gln Tyr Gly Val Glu Asp
                180                 185                 190

Asp Asp Val Glu Thr Glu Ser Asp Ser Gln Asn Met Glu Val Glu Thr
        195                 200                 205

Glu Leu Phe Ile Gly Pro Pro Lys Arg Gln Arg Ser Ala Lys Lys Ile
    210                 215                 220

-continued

```
Pro
225

<210> SEQ ID NO 27
<211> LENGTH: 290
<212> TYPE: PRT
<213> ORGANISM: Fragaria vesca

<400> SEQUENCE: 27

Met Gly Arg Gly Arg Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Ala Leu Ile Val Phe
        35                  40                  45

Ser Thr Lys Gly Lys Leu Phe Glu Tyr Ser Thr Asp Ser Ser Tyr Ser
    50                  55                  60

Phe Ile Asp Ser Met Glu Arg Ile Leu Glu Arg Tyr Glu Arg Tyr Ser
65                  70                  75                  80

Tyr Ala Glu Arg Gln Leu Leu Gly Asn Asn His Glu Gln Gln Asp Gln
                85                  90                  95

Asp Gln Ser Asn Gly Asn Trp Thr Leu Glu His Ala Lys Leu Lys Ala
            100                 105                 110

Arg Val Glu Val Leu Gln Lys Asn Gln Ser His Phe Met Gly Glu Asp
            115                 120                 125

Leu Gln Ser Leu Ser Met Lys Gln Leu Gln Asn Leu Glu Gln Gln Leu
    130                 135                 140

Asp Ser Ala Leu Lys His Val Arg Ser Arg Lys Asn Gln Leu Met Tyr
145                 150                 155                 160

Glu Ser Ile Ser Thr Leu Gln Lys Lys Asp Lys Ala Leu Gln Glu Gln
                165                 170                 175

Asn Asn Leu Leu Thr Lys Lys Val Lys Glu Lys Glu Lys Ala Val Ala
            180                 185                 190

Gly Ser Ala Pro Gln Ser Gln Ala Gln Ala Gln Val Arg Gly Gln Ala
            195                 200                 205

Gln Ala Gln Val Gln Ala Gln Ala Gln Ala Gln Ala Gln Ala Gln Ser
    210                 215                 220

Gln Trp Glu Gln Met Gln Arg Gln Ser Phe Asp Ser Ser Thr Ser Ala
225                 230                 235                 240

Leu Leu Pro Gln Ala Leu Pro Ser Met Asn Phe Gly Gly Ser Ser Gly
            245                 250                 255

Gly Tyr Asp Gln Asp Glu Glu Ile Pro Pro Pro Gln His Gln Ala
            260                 265                 270

Ala Ala Asn Ser Asn Thr Leu Leu Pro Pro Trp Met Leu Arg His Leu
        275                 280                 285

Asn Glu
    290

<210> SEQ ID NO 28
<211> LENGTH: 255
<212> TYPE: PRT
<213> ORGANISM: Fragaria vesca

<400> SEQUENCE: 28

Met Gly Arg Gly Arg Val Glu Leu Lys Arg Ile Glu Asn Lys Ile Asn
1               5                   10                  15
```

```
Arg Gln Val Thr Phe Ala Lys Arg Arg Asn Gly Leu Leu Lys Lys Ala
            20                  25                  30

Tyr Glu Leu Ser Val Leu Cys Asp Ala Glu Val Ala Leu Ile Ile Phe
            35                  40                  45

Ser Gly Arg Gly Lys Leu Tyr Glu Phe Cys Ser Ser Leu Ser Met Met
    50                  55                  60

Lys Thr Leu Glu Lys Tyr Gln Arg Cys Ser Tyr Gly Ala Leu Glu Ala
65                  70                  75                  80

Asn Gln Pro Val Asn Glu Thr Gln Asn Ser Tyr Gln Glu Tyr Leu Arg
                85                  90                  95

Leu Lys Ala Arg Val Glu Val Leu Gln Arg Ser Gln Arg Asn Leu Leu
                100                 105                 110

Gly Glu Asp Leu Gly Pro Leu Asn Thr Lys Glu Leu Glu Gln Leu Glu
                115                 120                 125

His Gln Leu Glu Ser Ser Leu Lys His Ile Arg Ser Thr Lys Thr Gln
    130                 135                 140

Phe Met Leu Asp Glu Leu Ser Asp Leu Gln Asn Arg Glu Gln Met Leu
145                 150                 155                 160

Val Glu Thr Asn Lys Ser Leu Arg Arg Lys Leu Glu Glu Thr Asn Leu
                165                 170                 175

Gln Gly Ala Pro Leu His Leu Ala Trp Asp Gly Gly Tyr Gly Gln Asn
                180                 185                 190

Asn Ile His Glu His Asn Ser Arg Phe Pro Pro Gln Ser Gln Gly Phe
            195                 200                 205

Phe Gln Gln Leu Gln Gly Asn Asn Asn Ser Ala Met Gln Met Gly Tyr
    210                 215                 220

Thr Pro Leu Gly Ser Asp His His His His Gln Gln Met Asn Ala Gly
225                 230                 235                 240

Asn Pro Gly Gln Asn Val Asn Gly Phe Ile Pro Gly Trp Met Leu
                245                 250                 255
```

```
<210> SEQ ID NO 29
<211> LENGTH: 223
<212> TYPE: PRT
<213> ORGANISM: Fragaria vesca

<400> SEQUENCE: 29
```

```
Met Gly Arg Gly Lys Ile Glu Ile Lys Arg Ile Glu Asn Thr Thr Asn
1               5                   10                  15

Arg Gln Val Thr Phe Cys Lys Arg Arg Asn Gly Leu Leu Lys Lys Ala
            20                  25                  30

Tyr Glu Leu Ser Ile Leu Cys Glu Ala Glu Val Ala Leu Ile Val Phe
            35                  40                  45

Ser Ser Arg Gly Arg Leu Tyr Glu Tyr Ser Asn Asn Asn Ser Ile Arg
    50                  55                  60

Asn Thr Ile Glu Arg Tyr Lys Lys Ala Ser Ser Asp Asn Ser Gly Ala
65                  70                  75                  80

Thr Thr Ile Thr Glu Ile Asn Ala Gln Tyr Tyr Gln Gln Glu Ser Thr
                85                  90                  95

Lys Leu Arg His Gln Ile Gln Met Leu Gln Asn Ser Asn Arg His Leu
                100                 105                 110

Met Gly Asp Ser Leu Ser Asn Leu Thr Val Lys Glu Leu Lys Gln Leu
            115                 120                 125

Glu Asn Arg Leu Glu Arg Gly Leu Thr Arg Ile Arg Ser Lys Lys His
```

-continued

```
            130                 135                 140

Glu Met Leu Leu Ala Glu Ile Glu Tyr Leu Gln Lys Arg Glu Ile Glu
145                 150                 155                 160

Leu Glu Asn Glu Asn Val Leu Ile Arg Ala Lys Ile Ala Glu Val Glu
                165                 170                 175

Arg Leu Gln Gln Ala Asp Leu Val Ser Gly Ala Glu Leu Asn Ala Ile
                180                 185                 190

Gln Ala Leu Ala Ser Arg Asn Phe Phe Glu Ser Thr Met Met Glu Gly
            195                 200                 205

Glu Thr Ser Tyr Ser Gln Pro Glu Lys Lys Leu Leu His Leu Gly
    210                 215                 220

<210> SEQ ID NO 30
<211> LENGTH: 210
<212> TYPE: PRT
<213> ORGANISM: Fragaria vesca

<400> SEQUENCE: 30

Met Ala Arg Gly Lys Val Gln Met Lys Lys Ile Glu Asn Pro Val His
1               5                   10                  15

Arg Gln Val Thr Phe Cys Lys Arg Arg Ala Gly Leu Leu Lys Lys Ala
                20                  25                  30

Lys Glu Leu Ser Val Leu Cys Asp Ala Asp Ile Gly Val Leu Ile Tyr
            35                  40                  45

Ser Ser His Gly Lys Leu Phe Glu Leu Ala Thr Lys Gly Ser Met Gln
    50                  55                  60

Gly Leu Ile Glu Arg Tyr Met Lys Thr Lys Pro Ala Arg Val Pro Gln
65                  70                  75                  80

Ala Glu Pro Val Met Glu Thr Gln Thr Leu Asp Ala Lys Lys Glu Cys
                85                  90                  95

Asn Leu Leu Lys Gln Glu Ile Glu Ile Leu Gln Lys Gly Leu Arg Tyr
                100                 105                 110

Met Phe Gly Gly Gly Ala Gly Thr Met Ser Leu Asp Glu Leu Gln Val
            115                 120                 125

Leu Glu Lys His Leu Glu Leu Trp Ile Tyr His Val Arg Ser Ala Lys
        130                 135                 140

Met Asp Ile Leu Leu Gln Glu Ile Gln Leu Leu Arg Asn Ser Glu Gly
145                 150                 155                 160

Ile Leu Thr Ala Ala Asn Lys Tyr Leu Gln Asp Lys Ile Glu Glu Asn
                165                 170                 175

Ser Gly Val Thr Asn Leu Met Pro Val Ala Thr Asp Thr Pro Tyr Pro
                180                 185                 190

Leu Thr Ile Pro Asn Asp Asp Ile Ile Ser Leu Leu Gly Ser Asn Phe
            195                 200                 205

Gly Phe
    210

<210> SEQ ID NO 31
<211> LENGTH: 249
<212> TYPE: PRT
<213> ORGANISM: Fragaria vesca

<400> SEQUENCE: 31

Met Glu Ile Pro Lys Gln Ile Thr Pro Ala Asp Asp Pro Glu Ser Ser
1               5                   10                  15

Ser Gln Lys Lys Leu Gly Arg Gly Lys Ile Glu Ile Lys Arg Ile Glu
```

-continued

```
                20              25              30

Asn Thr Thr Asn Arg Gln Val Thr Phe Cys Lys Arg Arg Asn Gly Leu
        35              40              45

Leu Lys Lys Ala Tyr Glu Leu Ser Val Leu Cys Asp Ala Glu Val Ala
    50              55              60

Leu Ile Val Phe Ser Thr Arg Gly Arg Leu Tyr Glu Tyr Ala Asn Asn
65              70              75              80

Ser Val Arg Ala Thr Ile Glu Arg Tyr Lys Lys Ala Cys Asp Ser Ser
                85              90              95

Asn Thr Gly Ser Val Thr Glu Ala Asn Val Gln Phe Tyr Gln Gln Glu
            100             105             110

Ala Ser Lys Leu Arg Arg Gln Ile Arg Glu Ile Gln Asn Ser Asn Arg
        115             120             125

His Ile Leu Gly Glu Ala Leu Ser Thr Leu Asn Val Lys Glu Leu Lys
    130             135             140

Asn Leu Glu Gly Arg Leu Glu Lys Gly Ile Ser Arg Ile Arg Ser Lys
145             150             155             160

Lys Asn Glu Met Leu Phe Ala Glu Ile Glu Tyr Met Gln Lys Arg Glu
            165             170             175

Ile Glu Leu Gln Asn His Asn Asn Phe Leu Arg Ala Lys Ile Ala Glu
            180             185             190

Asn Asp Arg Ala Gln Gln Gln Ala Asn Met Leu Pro Gly Thr Ser
            195             200             205

Ser Ala Tyr Glu Gln Pro Met Pro Pro Pro Gln Ser Tyr Asp Arg Ser
    210             215             220

Phe Leu Pro Val Ile Ile Glu Ser Asn His Asn Tyr Asn Arg Gln Gly
225             230             235             240

Gln Asn Leu Thr Pro Leu Gln Leu Val
            245
```

```
<210> SEQ ID NO 32
<211> LENGTH: 257
<212> TYPE: PRT
<213> ORGANISM: Fragaria vesca

<400> SEQUENCE: 32

Met Gly Arg Gly Lys Val Gln Leu Lys Arg Ile Glu Asn Lys Ile Ser
1               5               10              15

Arg Gln Val Thr Phe Ser Lys Arg Arg Thr Gly Leu Ile Lys Lys Ala
            20              25              30

His Glu Ile Ser Val Leu Cys Asp Ala Asp Val Ala Leu Ile Val Phe
        35              40              45

Ser Thr Lys Gly Lys Leu Phe Glu Tyr Ala Thr Asp Ser Ser Met Asp
    50              55              60

Ala Ile Leu Glu Arg Tyr Glu Gln Tyr Ser Tyr Ala Glu Arg Gln Ser
65              70              75              80

Thr Gly Ile Pro Asp Ser Gln Pro Gln Gly Ser Trp Phe Met Glu Phe
            85              90              95

Pro Lys Leu Ala Ala Arg Ile Glu Ile Leu Gln Arg Lys Ile Arg Asn
            100             105             110

Tyr Thr Gly Glu Asp Leu Asp Pro Leu Ser Leu Arg Glu Leu Gln Asn
        115             120             125

Leu Glu Gln Gln Ile Asp Thr Ala Leu Lys Arg Val Arg Ala Arg Lys
    130             135             140
```

Asn Gln Ala Val His Glu Ser Leu Ser Glu Met His Lys Lys Gln Arg
145                 150                 155                 160

Thr Leu Gln Glu Gln Asn Asn Ser Leu Ala Lys Lys Leu Lys Glu Asn
                165                 170                 175

Glu Lys Leu Leu Gln Glu Glu Pro Asn Asp Asn Gln Gln Pro Asn Pro
                180                 185                 190

Ser Thr Leu Val Leu Met Pro Thr Gln Gln Ala Pro Lys Ser Pro Ala
                195                 200                 205

Leu Leu Ser Ser Leu Thr Ile Gly Gly Asp Phe Gln Gly Arg Arg Asp
                210                 215                 220

Ala Met Asp Glu Asp Val Arg Asp Tyr Gln Gly Arg Ala Glu Thr Gln
225                 230                 235                 240

Pro Ala Ser Ser Thr Val Met Pro Pro Trp Met Val Arg His Leu Asn
                245                 250                 255

Gln

<210> SEQ ID NO 33
<211> LENGTH: 249
<212> TYPE: PRT
<213> ORGANISM: Fragaria vesca

<400> SEQUENCE: 33

Met Gly Arg Gly Arg Val Glu Leu Lys Arg Ile Glu Asn Lys Ile Asn
1                   5                   10                  15

Arg Gln Val Thr Phe Ala Lys Arg Arg Asn Gly Leu Leu Lys Lys Ala
                20                  25                  30

Tyr Glu Leu Ser Ile Leu Cys Asp Ala Glu Val Ala Leu Ile Ile Phe
                35                  40                  45

Ser Asn Arg Gly Lys Leu Tyr Glu Phe Cys Ser Ser Ser Ser Met Leu
                50                  55                  60

Lys Thr Leu Glu Arg Tyr Gln Lys Cys Ser Tyr Gly Ala Met Glu Val
65                  70                  75                  80

Gln Lys Pro Ala Lys Glu Leu Glu Glu Ser Ser Tyr Arg Glu Tyr Leu
                85                  90                  95

Lys Leu Lys Thr Arg Cys Glu Ser Leu Gln Gln Thr Gln Arg Asn Leu
                100                 105                 110

Leu Gly Glu Asp Leu Gly Pro Leu Asn Thr Lys Glu Leu Glu Gln Leu
                115                 120                 125

Glu Arg Gln Leu Glu Ser Ser Leu Lys His Val Arg Ser Thr Lys Thr
                130                 135                 140

Gln His Met Ile Asp Leu Leu Ser Asp Leu Gln Ser Lys Glu His Met
145                 150                 155                 160

Leu Ile Glu Ala Asn Arg Asp Leu Lys Thr Lys Leu Asp Glu Ile Asp
                165                 170                 175

Ser Arg Thr Gln Leu Arg Gln Thr Trp Glu His Gly His Asp His Gln
                180                 185                 190

Thr Met Leu Tyr Gly Thr Gln His Ala Gln Thr Gln Gly Leu Met Phe
                195                 200                 205

Gln Pro Leu Asp Cys Asn Pro Thr Leu Gln Ile Gly Tyr Asn Ala Val
                210                 215                 220

Val Ser Gln Glu Met Pro Ala Ala Thr Pro Ala His Ala Gln Pro Val
225                 230                 235                 240

Asn Gly Phe Ile Pro Gly Trp Met Leu
                245

<210> SEQ ID NO 34
<211> LENGTH: 245
<212> TYPE: PRT
<213> ORGANISM: Fragaria vesca

<400> SEQUENCE: 34

Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Leu Leu Lys Lys Ala
                20                  25                  30

Tyr Glu Leu Ser Val Leu Cys Asp Ala Glu Val Ala Leu Ile Ile Phe
            35                  40                  45

Ser Ser Arg Gly Lys Leu Tyr Glu Phe Ser Ser Ala Gly Met Thr Gln
        50                  55                  60

Thr Leu Glu Arg Tyr Gln Arg Ser Ser Tyr Thr Pro His Asp Asn Pro
65                  70                  75                  80

Ile Lys Gln Glu Thr Glu Cys Trp Tyr Glu Glu Val Ser Lys Leu Arg
                85                  90                  95

Ala Lys His Asp Ser Leu Leu Arg Thr Gln Arg His Leu Leu Gly Glu
            100                 105                 110

Asp Leu Gly Pro Leu Ser Val Lys Glu Leu Gln Asn Leu Glu Lys Gln
            115                 120                 125

Leu Glu Gly Ala Leu Thr Leu Ala Arg Gln Arg Lys Thr Gln Ile Met
        130                 135                 140

Ile Glu Gln Leu Glu His Leu Arg Lys Lys Glu Arg Gln Leu Gly Asp
145                 150                 155                 160

Leu Asn Leu Gln Leu Arg Asp Lys Leu Gln Lys Glu Gly Glu Asn Leu
                165                 170                 175

Lys Ala Ile Gln Asp Phe Trp Ser Ser Asn Thr Val Gln Ala Gly Asn
            180                 185                 190

Asn Asn Phe Leu His Ser Ser Gln Ala Gly His Ile Asp Pro Pro Pro
            195                 200                 205

Glu Pro Ile Leu Gln Ile Gly Tyr Gln His Tyr Val Ala Ala Glu Ser
        210                 215                 220

Ala Tyr Val Pro Lys Thr Met Ala Met Ala Ala Glu Thr Asn Phe Ile
225                 230                 235                 240

Gln Gly Trp Val Leu
                245

<210> SEQ ID NO 35
<211> LENGTH: 215
<212> TYPE: PRT
<213> ORGANISM: Fragaria vesca

<400> SEQUENCE: 35

Met Val Arg Gly Lys Thr Gln Met Arg Arg Ile Glu Asn Ala Thr Ser
1               5                   10                  15

Arg Gln Val Thr Phe Ser Lys Arg Arg Ser Gly Leu Leu Lys Lys Ala
                20                  25                  30

Phe Glu Leu Ser Ile Leu Cys Asp Ala Glu Val Ala Leu Ile Ile Phe
            35                  40                  45

Ser Pro Arg Gly Lys Leu Tyr Glu Phe Ala Ser Ser Ser Met Gln Glu
        50                  55                  60

Thr Ile Glu Arg Tyr Glu Lys His Thr Arg Asp Asn Gln Ala Asn Asn
65                  70                  75                  80

-continued

```
Lys Val Ala Ile Ser Glu Gln Asn Val Gln Gln Leu Lys His Glu Ala
                85              90              95

Thr Ser Met Met Lys Gln Ile Glu His Leu Glu Val Ser Lys Arg Lys
            100             105             110

Leu Leu Gly Glu Ser Leu Gly Leu Cys Thr Ile Glu Glu Leu Gln Glu
        115             120             125

Val Glu Gln Gln Leu Glu Arg Ser Val Asn Thr Ile Arg Ala Arg Lys
    130             135             140

Ala Gln Val Phe Lys Glu Gln Ile Glu Gln Leu Lys Glu Lys Glu Arg
145             150             155             160

Ile Leu Thr Ala Glu Asn Glu Arg Leu Thr Glu Lys Cys Asp Ala Leu
            165             170             175

Gln Gln Arg Gln Pro Val Ile Glu Gln Arg Glu His Leu Ala Tyr Asn
            180             185             190

Glu Ser Ser Thr Ser Ser Asp Val Glu Thr Glu Leu Phe Ile Gly Leu
        195             200             205

Pro Glu Arg Arg Ser Lys His
    210             215

<210> SEQ ID NO 36
<211> LENGTH: 229
<212> TYPE: PRT
<213> ORGANISM: Fragaria vesca

<400> SEQUENCE: 36

Met Val Arg Gly Lys Ile Glu Met Lys Arg Ile Glu Asn Ala Thr Ser
1               5               10              15

Arg Gln Val Thr Phe Ser Lys Arg Arg Asn Gly Leu Leu Lys Lys Ala
            20              25              30

Tyr Glu Leu Ser Val Leu Cys Asp Ala Glu Val Ala Val Ile Val Phe
            35              40              45

Ser Gln Lys Gly Arg Leu Tyr Glu Phe Ser Ser Ser Asp Met Gln Lys
    50              55              60

Thr Ile Lys Arg Tyr His Lys His Ala Lys Gly Ala Gln Thr Asn Thr
65              70              75              80

Thr Glu Val Glu Gln Tyr Met Gln Gln Leu Lys His Glu Ser Ala Asp
            85              90              95

Met Ala Lys Lys Ile Glu Ile Leu Glu Ala Ser Gln Arg Phe Met Thr
            100             105             110

Trp Arg Leu Leu Gly His Asp Leu Asp Ser Cys Ser Ala Gln Glu Leu
            115             120             125

Asn Gln Ile Ser Ser Gln Leu Glu Arg Ser Ile Arg Ile Val Arg Asp
    130             135             140

Arg Lys Gly Gln Leu Phe Met Glu Gln Ile Glu Arg Leu Gln Ala Lys
145             150             155             160

Glu Arg Ile Leu Leu Glu Glu Asn Thr Lys Leu His Ile Ala Cys Gly
            165             170             175

Ala Arg Pro Trp Gln Gln His Ile Val Gln Glu Lys Glu Val Gly Ala
            180             185             190

Ala Thr Tyr Asn Trp Met Asn Ser Ser Gln Ser Ser Ser Ser Gln Thr
            195             200             205

Ile Ser Asn Ser Asp Gln Val Glu Thr Gly Leu Phe Ile Gly Pro Pro
    210             215             220

Ala Met Arg Cys Glu
225
```

<210> SEQ ID NO 37
<211> LENGTH: 141
<212> TYPE: PRT
<213> ORGANISM: Malus domestica

<400> SEQUENCE: 37

Met Trp His Ile Phe Thr Asn Phe Tyr Lys Ile Ile Phe Leu Tyr Tyr
1               5                   10                  15

Tyr Leu Trp Trp Trp Met Met Ile Arg Gln Ser Glu Asp Met Val Arg
            20                  25                  30

Gly Lys Ile Glu Ile Lys Arg Ile Glu Asn Asp Thr Ser Arg Gln Val
        35                  40                  45

Thr Phe Ser Lys Arg Arg Asn Gly Leu Phe Lys Lys Ala Phe Glu Leu
    50                  55                  60

Ser Val Leu Cys Asp Ala Glu Val Ala Val Ile Thr Phe Ser Gln Lys
65                  70                  75                  80

Gly Arg Ile Tyr Glu Phe Ser Ser Ser Asp Met His Gln Thr Ile Glu
                85                  90                  95

Arg Tyr Leu Lys His Glu Asn Gly Gly Glu Thr Asn Met Val Glu Ala
            100                 105                 110

Glu Gln Tyr Val Gln Val Arg Ser Ser Ile Phe Glu Phe Glu Asn Pro
            115                 120                 125

Ser Leu Ile Ser Glu Phe Ile Ile Lys Leu Thr Val Ser
        130                 135                 140

<210> SEQ ID NO 38
<211> LENGTH: 228
<212> TYPE: PRT
<213> ORGANISM: Malus domestica

<400> SEQUENCE: 38

Met Lys Arg Ile Glu Asn Asn Thr Ser Arg Gln Val Thr Phe Ser Lys
1               5                   10                  15

Arg Arg Lys Gly Leu Leu Lys Lys Ala Tyr Glu Leu Ser Val Leu Cys
            20                  25                  30

Asp Ala Glu Val Ala Val Ile Val Phe Ser Gln Lys Gly Arg Ile Tyr
        35                  40                  45

Glu Phe Ser Ser Ser Asp Met Gln Arg Thr Ile Asn Arg Tyr His Lys
    50                  55                  60

His Glu Asn Gly Ser Gly Pro Thr Asn Lys Val Glu Val Glu Gln Tyr
65                  70                  75                  80

Val Gln His Leu Lys His Glu Ser Ala Ile Ile Ala Lys Lys Ile Glu
                85                  90                  95

Ile Leu Glu Ala Ser Gln Arg Lys Leu Leu Gly Asn Asp Leu Asp Ser
            100                 105                 110

Cys Pro Val Glu Glu Leu Gln Glu Ile Ser Ser Gln Leu Glu Arg Ser
            115                 120                 125

Leu Arg Ser Ile Ser Glu Arg Lys Ala Gln Leu Tyr Thr Glu Gln Met
        130                 135                 140

Glu Gln His Lys Ala Arg Glu Arg Phe Leu Leu Gln Glu Asn Ala Gln
145                 150                 155                 160

Leu Arg Glu Glu Cys Cys Ala Lys Pro Trp Met Glu Phe Ser Pro Gln
                165                 170                 175

Glu Lys Arg Ala Ser Ala Ser Val Ser Asn Glu Lys Ala Gly Ala Ser
            180                 185                 190

-continued

```
Ala Ser Ala Pro Ile Asn Tyr Arg Ser Gln Ser Ser Met Ser Ser Glu
        195                 200                 205

Val Asp Thr Asp Leu Leu Ile Gly Gln Pro Met Val Arg Ala Val Asp
    210                 215                 220

Arg Ile Ala Val
225

<210> SEQ ID NO 39
<211> LENGTH: 247
<212> TYPE: PRT
<213> ORGANISM: Malus domestica

<400> SEQUENCE: 39

Met Lys Arg Ile Glu Asn Ala Thr Ser Arg Gln Val Thr Phe Thr Lys
1               5                   10                  15

Arg Arg Asn Gly Leu Leu Lys Lys Ala Tyr Glu Leu Ser Val Leu Cys
            20                  25                  30

Asp Ala Glu Val Ala Val Ile Ile Phe Ser Gln Lys Asp Lys Leu Tyr
        35                  40                  45

Glu Phe Cys Ser Ser Asp Met Gln Glu Thr Leu Thr Arg Tyr His Asn
    50                  55                  60

Tyr Ala Lys Asp Glu Gln Thr Asn Lys Val Glu Val Glu Gln His Val
65                  70                  75                  80

Gln His Leu Lys His Glu Ser Ala Ile Met Thr Lys Lys Ile Glu Ile
                85                  90                  95

Leu Glu Ala Ser Gln Arg Lys Leu Leu Gly Asn Asp Leu Asp Ser Cys
            100                 105                 110

Phe Val Glu Glu Leu Gln Glu Ile Ser Ser Gln Leu Glu Arg Ser Leu
        115                 120                 125

Arg Ser Ile Arg Glu Arg Lys Ala Gln Leu Phe Met Glu Gln Met Glu
    130                 135                 140

Asn Leu Lys Ala Lys Glu Thr Leu Leu Leu Gln Glu Asn Ala Lys Leu
145                 150                 155                 160

Arg Glu Glu Ser Gly Ala Lys Leu Leu Met Glu His Ser Ala Gln Glu
                165                 170                 175

Lys Arg Ala Ser Ala Ser Val Ser Tyr Glu Lys Ala Gly Ala Ser Ala
            180                 185                 190

Ser Ala Ser Val Asn Tyr Trp Ser Gln Ser Ile Met Ser Ser Glu Val
        195                 200                 205

Glu Thr Glu Leu Leu Ile Gly Pro Pro Ile Met Arg Ala Val Asp Arg
    210                 215                 220

Ile Ala Val Leu Ser Asn Ile His Gln Ile Asn Asn Asn Ala Cys Gln
225                 230                 235                 240

Ser Ser Leu Lys Thr Ile Pro
                245

<210> SEQ ID NO 40
<211> LENGTH: 231
<212> TYPE: PRT
<213> ORGANISM: Malus domestica

<400> SEQUENCE: 40

Met Lys Arg Ile Glu Asn Ala Thr Ser Arg Gln Val Thr Phe Ser Lys
1               5                   10                  15

Arg Arg Asn Gly Leu Leu Lys Lys Ala Tyr Glu Leu Ser Val Leu Cys
            20                  25                  30
```

-continued

```
Asp Ala Glu Val Ala Val Ile Ile Phe Ser Gln Lys Asp Arg Leu Tyr
        35                  40                  45

Glu Phe Ser Ser Ser Asp Met Arg Glu Thr Leu Thr Arg Tyr Arg Lys
    50                  55                  60

Tyr Ala Lys Asp His Glu Gln Thr Asn Lys Val Glu Val Glu Gln His
65                  70                  75                  80

Val Gln His Leu Lys His Glu Ser Ala Ile Met Ala Lys Lys Ile Glu
                85                  90                  95

Ile Leu Glu Ala Thr Gln Arg Lys Leu Leu Gly Asn Asp Leu Asp Ser
                100                 105                 110

Cys Tyr Val Glu Glu Leu Gln Glu Leu Ser Ser Gln Leu Glu Arg Ser
                115                 120                 125

Leu Arg Ser Ile Arg Glu Arg Lys Ala Gln Leu Phe Met Glu Gln Met
        130                 135                 140

Glu Gln Leu Lys Ala Lys Glu Thr Leu Leu Leu Gln Glu Asn Ala Lys
145                 150                 155                 160

Leu Arg Glu Gln Ser Gly Ala Lys Leu Trp Met Glu His Ser Val Gln
                165                 170                 175

Ala Lys Arg Ala Ser Thr Leu Ser Tyr Glu Lys Ala Gly Val Ser Ala
        180                 185                 190

Ser Val Asn Tyr Arg Ser Gln Gly Ser Met Ser Ser Glu Val Glu Thr
                195                 200                 205

Glu Leu Phe Ile Gly Pro Pro Ile Met Arg Ala Val Asp Ala Ser Gln
        210                 215                 220

Pro Glu Ser Thr Tyr Ile Arg
225                 230

<210> SEQ ID NO 41
<211> LENGTH: 211
<212> TYPE: PRT
<213> ORGANISM: Malus domestica

<400> SEQUENCE: 41

Met Val Arg Gly Lys Thr Gln Met Arg Arg Ile Glu Asn Thr Thr Ser
1               5                   10                  15

Arg Gln Val Thr Phe Ser Lys Arg Arg Ser Gly Leu Leu Lys Lys Ala
                20                  25                  30

Phe Glu Leu Ser Val Leu Cys Asp Ala Glu Val Ser Leu Ile Ile Phe
        35                  40                  45

Ser Pro Arg Gly Lys Leu Tyr Glu Phe Ala Ser Ser Ser Met Gln Gly
    50                  55                  60

Thr Ile Glu Arg Tyr Gln Lys His Ala Lys Asp Asn Gln Thr Asn Asp
65                  70                  75                  80

Lys Ser Ser Ser Ser Glu Gln Asn His Leu Lys Gln Glu Ala Thr Ser
                85                  90                  95

Met Met Lys Gln Ile Glu Leu Leu Glu Val Ser Lys Arg Lys Leu Leu
                100                 105                 110

Gly Glu Gly Leu Gly Ser Cys Thr Leu Ala Glu Leu Gln Glu Ile Glu
                115                 120                 125

Asp Gln Leu Glu Lys Ser Val Tyr Asn Val Arg Ala Arg Lys Ser Gln
        130                 135                 140

Val Phe Lys Glu Gln Ile Glu Gln Leu Arg Glu Lys Glu Lys Leu Leu
145                 150                 155                 160

Thr Ala Glu Asn Thr Arg Leu Val Glu Lys Tyr Gly Ser Phe Lys Lys
```

-continued

```
                 165                 170                 175
Thr Leu His Glu Arg Arg Glu Lys Thr Pro Tyr Asn Glu Ser Ser Thr
            180                 185                 190

Ser Ser Asp Val Glu Thr Glu Leu Phe Ile Gly Leu Pro Glu Ser Arg
        195                 200                 205

Ala Arg Arg
    210

<210> SEQ ID NO 42
<211> LENGTH: 243
<212> TYPE: PRT
<213> ORGANISM: Malus domestica

<400> SEQUENCE: 42

Met Gly Arg Gly Arg Val Glu Leu Lys Arg Ile Glu Asn Lys Ile Asn
1               5                  10                  15

Arg Gln Val Thr Phe Ser Lys Arg Arg Asn Gly Leu Leu Lys Lys Ala
            20                  25                  30

Tyr Glu Leu Ser Val Leu Cys Asp Ala Glu Val Gly Leu Ile Ile Phe
        35                  40                  45

Ser Ser Arg Gly Lys Leu Tyr Glu Phe Ala Ser Ala Gly Met Ser Lys
    50                  55                  60

Thr Leu Glu Arg Tyr Gln Arg Cys Ser Phe Thr Pro Pro Glu Asn Ser
65                  70                  75                  80

Ile Glu Arg Glu Thr Gln Ser Trp Tyr Gln Glu Val Thr Lys Leu Lys
                85                  90                  95

Ala Lys Tyr Glu Ser Leu Gln Arg Thr Gln Arg His Leu Leu Gly Glu
            100                 105                 110

Asp Leu Gly Pro Leu Ser Val Lys Glu Leu Gln Asn Leu Glu Lys Gln
        115                 120                 125

Leu Glu Gly Ala Leu Ala Gln Thr Arg Gln Arg Lys Thr Gln Leu Met
    130                 135                 140

Ile Glu Gln Met Glu Asp Leu Arg Lys Lys Glu Arg His Leu Gly Asp
145                 150                 155                 160

Leu Asn Lys Gln Leu Arg Val Lys Leu Glu Ala Glu Gly Gln Asn Leu
                165                 170                 175

Asn Val Ile Gln Asn Met Trp Ser Ser Asp Ala Ala Ala Gly Ser Ser
            180                 185                 190

Asn Phe Ser Leu His Ser Ser Gln Thr Asn Pro Met Asp Cys Thr Pro
        195                 200                 205

Glu Pro Val Ile Gln Met Gly Tyr His Pro Tyr His Pro Ala Glu Gly
    210                 215                 220

Ser Ser Ile Pro Arg Ser Leu Thr Gly Glu Thr Asn Phe Ile Gln Gly
225                 230                 235                 240

Trp Val Leu

<210> SEQ ID NO 43
<211> LENGTH: 219
<212> TYPE: PRT
<213> ORGANISM: Malus domestica

<400> SEQUENCE: 43

Met Val Arg Gly Lys Thr Gln Met Lys Arg Ile Glu Asn Ala Ala Ser
1               5                  10                  15

Arg Gln Val Thr Phe Ser Lys Arg Arg Asn Gly Leu Leu Lys Lys Ala
            20                  25                  30
```

-continued

```
Phe Glu Leu Ser Val Leu Cys Asp Ala Glu Val Ala Leu Val Ile Phe
        35                  40                  45

Ser Ala Arg Gly Lys Leu Tyr Glu Phe Ser Ser Thr Ser Ile Arg Ser
        50                  55                  60

Thr Ile Asp Arg Tyr Gln Met Arg Val Lys Asp Gln Gly Gln Leu Thr
65                  70                  75                  80

Thr Lys Ala Phe Gln Glu Asp Met Glu His Glu Thr Asn Asp Thr Gln
                    85                  90                  95

Thr Leu Ala Lys Lys Ile Glu Ser Ile Glu Ala Ser Lys Arg Lys Leu
                    100                 105                 110

Leu Gly Asn Asp Leu Glu Ser Cys Ser Met Glu Glu Leu His Gln Thr
                    115                 120                 125

Glu Asn Gln Leu Glu Arg Ser Leu Lys Lys Ile Arg Ala Lys Lys His
        130                 135                 140

Gln Leu Leu Arg Glu Gln Ile Asp Lys Leu Lys Glu Glu Glu Lys Asn
145                 150                 155                 160

Leu Leu Glu Gln Asn Ala Lys Leu Arg Glu Met Cys Gly Met Gln Gln
                    165                 170                 175

Leu Gly Pro Ser Arg Lys Ser Lys His Gly Asp Asp Arg Glu Val Phe
                    180                 185                 190

Gln Pro Gln Thr Pro Asn Val Asp Val Glu Thr Asp Leu Phe Ile Gly
        195                 200                 205

Pro Pro Lys Arg Gln Gln Ser Gly Arg Lys Pro
        210                 215

<210> SEQ ID NO 44
<211> LENGTH: 242
<212> TYPE: PRT
<213> ORGANISM: Malus domestica

<400> SEQUENCE: 44

Met Gly Arg Gly Lys Val Gln Leu Lys Arg Ile Asp Asp Lys Ile Arg
1                   5                   10                  15

Arg Gln Val Thr Phe Ser Lys Arg Arg Thr Gly Leu Ile Lys Lys Ala
                    20                  25                  30

Arg Glu Leu Ser Val Leu Cys Gly Val Asp Val Gly Leu Val Ile Phe
        35                  40                  45

Ser Pro Lys Gly Arg Leu Tyr Glu Phe Cys Ser Gly Glu Ser Phe Gly
        50                  55                  60

Lys Leu Val Glu Arg Tyr Gln Ile His Asn Asp Glu Glu Ile Gly Thr
65                  70                  75                  80

Ser Lys Asp Ala Gly Gly Thr Asp Lys Lys Asn Asn Ser Glu Gly Ser
                    85                  90                  95

Gly Leu Arg Thr Gly Ala Asn Gln Ser Leu Lys Met Ile Gln Ser Asp
                    100                 105                 110

Met Glu Ala Gln Asp Ile Glu Asn Leu Asp Ile Pro Glu Leu Thr Gln
        115                 120                 125

Leu Glu Glu Glu Leu Asp Ala Val Leu Arg Arg Thr Arg Ser Arg Lys
        130                 135                 140

Thr Gln Leu Met Thr Glu Thr Cys Thr Ala Leu Ile Glu Thr Glu Lys
145                 150                 155                 160

Gln Leu Lys Glu Glu Lys Leu Leu Leu Glu Asn Glu Ile Ala Ala Leu
                    165                 170                 175

Lys Leu Lys Gln Gln Gln Ser Lys Asp Arg Ala Ala Asp Glu Glu Pro
```

-continued

```
                  180              185              190
```

Asp Gln Gln Ser Thr Phe Ala Ala Asn Asn Thr Thr Thr Thr Thr Thr
        195                  200                  205

Asn Ser Cys Cys Ser Asp Asp Asn Val Pro Ala Ile Lys Leu His Leu
    210                  215                  220

Phe Leu Ser Glu Lys Arg Lys His Asn Ala Asp Thr Asp Thr Asp Gln
225                  230                  235                  240

Thr Asn

<210> SEQ ID NO 45
<211> LENGTH: 120
<212> TYPE: PRT
<213> ORGANISM: Malus domestica

<400> SEQUENCE: 45

Met Gly Arg Gly Lys Ile Val Ile Arg Arg Ile Asp Asn Ser Thr Ser
1               5                   10                  15

Arg Gln Val Thr Phe Ser Lys Arg Arg Asn Gly Leu Leu Lys Lys Ala
            20                  25                  30

Lys Glu Leu Ser Ile Leu Cys Asp Ala Glu Val Gly Leu Ile Val Phe
        35                  40                  45

Ser Ser Thr Gly Arg Leu Tyr Asp Tyr Ala Ser Thr Arg Lys Cys Ser
    50                  55                  60

Phe Leu Gly Thr Tyr Glu Gly Gly Cys Met Met Gly Lys Ala Glu Phe
65                  70                  75                  80

Leu Asp Val Arg Ile Leu Tyr Leu Gln Val Leu Thr Gln Leu His Lys
                85                  90                  95

Tyr Ile Tyr Arg Gly Arg Phe Cys Gly Asp Ile Lys Lys Thr Asn Phe
            100                 105                 110

Glu Thr Val Arg Phe Val His Phe
            115                 120

<210> SEQ ID NO 46
<211> LENGTH: 245
<212> TYPE: PRT
<213> ORGANISM: Malus domestica

<400> SEQUENCE: 46

Met Ala Asn Glu Asn Lys Ser Leu Ser Ile Asp Ser Pro Gln Arg Lys
1               5                   10                  15

Leu Gly Arg Gly Lys Ile Glu Ile Lys Arg Ile Glu Asn Thr Thr Asn
            20                  25                  30

Arg Gln Val Thr Phe Cys Lys Arg Arg Asn Gly Leu Leu Lys Lys Ala
        35                  40                  45

Tyr Glu Leu Ser Val Leu Cys Asp Ala Glu Val Ala Leu Ile Val Phe
    50                  55                  60

Ser Asn Arg Gly Arg Leu Tyr Glu Tyr Ala Asn Asn Ser Val Lys Ala
65                  70                  75                  80

Thr Val Glu Arg Tyr Lys Lys Thr Cys Ala Asp Ser Ser Asn Thr Gly
                85                  90                  95

Ser Val Ser Glu Ala Ser Thr Gln Tyr Tyr Gln Gln Glu Ser Ala Lys
            100                 105                 110

Leu Arg Ala Gln Ile Gly Asn Leu Gln Asn Ala Asn Arg Asn Met Met
            115                 120                 125

Gly Asp Ala Leu Ser Ser Met Pro Ile Lys Asp Leu Lys Ser Leu Glu
            130                 135                 140
```

Ser Lys Leu Glu Lys Gly Ile Ser Arg Ile Arg Ser Lys Lys Asn Glu
145                 150                 155                 160

Leu Leu Phe Ala Glu Ile Glu Tyr Met Gln Lys Arg Glu Leu Asp Leu
                165                 170                 175

His Asn Asn Asn Gln Leu Leu Arg Ala Lys Ile Ala Glu Asn Glu Arg
            180                 185                 190

Gly Gln Gln Asn Ile Asn Val Met Ala Gly Gly Thr Ser Ser Tyr
        195                 200                 205

Asp Ile Leu Gln Ser Gln Pro Tyr Asp Ser Arg Asn Tyr Phe Gln Val
    210                 215                 220

Asn Ala Leu Gln Pro Asn His Gln Tyr Asn Pro Arg His Asp Gln Ile
225                 230                 235                 240

Ser Leu Gln Leu Val
            245

<210> SEQ ID NO 47
<211> LENGTH: 223
<212> TYPE: PRT
<213> ORGANISM: Malus domestica

<400> SEQUENCE: 47

Met Asp Lys Tyr Asn Lys Val Leu Val Lys Met Gly Arg Gly Lys Val
1               5                   10                  15

Glu Leu Lys Arg Ile Asp Asn Pro Thr Ser Arg His Val Thr Phe Ser
                20                  25                  30

Lys Arg Arg Asn Gly Leu Leu Lys Lys Ala Phe Glu Leu Ser Ile Leu
            35                  40                  45

Cys Asp Ala Glu Val Ala Val Ile Val Phe Ser His Ser Gly Lys Ala
    50                  55                  60

Tyr Glu Phe Ala Ser His Asp Ile Asn Arg Thr Ile Ala Met Tyr Arg
65                  70                  75                  80

Arg Glu Val Gly Leu Pro Glu Pro Asn Asn Ser Thr Phe Arg Arg Ala
                85                  90                  95

Arg Thr Met Glu Tyr Trp Arg Asn Glu Thr Glu Glu Leu Arg Arg Ser
                100                 105                 110

Ile Gln Asn Leu Glu Met Arg Leu Lys His Leu Ala Gly Glu Glu Leu
            115                 120                 125

Ser Thr Leu Gly Met Gln Glu Leu Lys Gln Leu Glu Arg Gln Leu Lys
        130                 135                 140

Thr Gly Val Glu Arg Ile Arg Ser Lys Ser Ile Ile Ser Glu Asn Val
145                 150                 155                 160

Asn Leu Leu Lys Arg Lys His Lys Glu Leu Arg Glu Glu Asn Lys Arg
                165                 170                 175

Leu Gln Lys Arg Val Lys Leu Gln Glu Phe His Phe Ala Asp Val Thr
            180                 185                 190

Ser Ser Thr Ser Thr Thr Thr Leu Gly Ala Asn Ala Cys Met Ser Ala
        195                 200                 205

Phe Pro Arg Val Met Phe Ser Gln Gln His Gln Leu Leu Pro Asn
    210                 215                 220

<210> SEQ ID NO 48
<211> LENGTH: 234
<212> TYPE: PRT
<213> ORGANISM: Malus domestica

<400> SEQUENCE: 48

-continued

```
Met Gly Arg Gly Lys Val Glu Leu Lys Arg Ile Glu Asn Lys Ser Asn
1               5                   10                  15

Arg Gln Val Thr Phe Ser Lys Arg Arg Asn Gly Leu Leu Lys Lys Ala
            20                  25                  30

Phe Glu Leu Ser Val Leu Cys Asp Ala Glu Val Ala Leu Ile Ile Phe
        35                  40                  45

Ser Gly Arg Gly Lys Leu Tyr Glu Phe Ser Ser Ser Leu Ser Met Met
    50                  55                  60

Lys Thr Leu Glu Lys Tyr Gln Arg Cys Ser Tyr Ser Ser Leu Asp Ala
65                  70                  75                  80

Asn Arg Pro Ala Lys Glu Thr Gln Gln Asn Ser Tyr Gln Glu Tyr Leu
                85                  90                  95

Gln Leu Glu Thr Arg Val Asp Val Leu Gln Gln Ser Gln Arg Asn Leu
            100                 105                 110

Leu Gly Glu Asp Leu Ala Thr Leu Asn Thr Lys Glu Leu Glu Glu Leu
        115                 120                 125

Glu His Gln Leu Glu Thr Ser Leu Asn Lys Ile Arg Ser Thr Lys Thr
    130                 135                 140

Gln Phe Met Leu Asp Gln Leu Ser Asp Leu Gln Asn Thr Glu Gln Met
145                 150                 155                 160

Leu Val Glu Ala Asn Lys Ala Leu Arg Arg Lys Leu Glu Glu Thr Ser
                165                 170                 175

Val Gln Ala Pro Gln Phe Met Ala Arg Glu Ala Ala Gly His Gly His
            180                 185                 190

Asn Asn Gly Gln Gln Thr Trp Leu Pro Ser Asn Ser Glu Ala Phe Phe
            195                 200                 205

His Pro Leu Gly Gly Asn Asn Ser Thr Tyr Gln Ile Gly Gly Tyr Ala
    210                 215                 220

Asp Thr Leu Met His Pro Phe Gly Phe Thr
225                 230
```

<210> SEQ ID NO 49
<211> LENGTH: 249
<212> TYPE: PRT
<213> ORGANISM: Malus domestica

<400> SEQUENCE: 49

```
Met Gly Arg Gly Lys Val Glu Leu Lys Arg Ile Glu Asn Lys Ser Asn
1               5                   10                  15

Arg Gln Val Thr Phe Ser Lys Arg Arg Asn Gly Leu Leu Lys Lys Ala
            20                  25                  30

Phe Glu Leu Ser Val Leu Cys Asp Ala Glu Val Ala Leu Ile Ile Phe
        35                  40                  45

Ser Gly Arg Gly Lys Leu Tyr Glu Phe Ser Ser Ser Leu Ser Met Met
    50                  55                  60

Lys Thr Leu Glu Arg Tyr Gln Arg Cys Ser Tyr Ser Ser Leu Asp Ala
65                  70                  75                  80

Asn Arg Pro Ala Asn Glu Thr Gln Gln Asn Ser Tyr Gln Glu Tyr Leu
                85                  90                  95

Gln Leu Glu Thr Arg Val Glu Ala Leu Gln Gln Ser Gln Arg Asn Leu
            100                 105                 110

Leu Gly Glu Asp Leu Ala Thr Leu Asn Thr Lys Lys Leu Glu Glu Leu
        115                 120                 125

Glu His Gln Leu Glu Thr Ser Leu Asn Lys Ile Arg Ser Thr Lys Thr
```

-continued

```
        130                 135                 140

Gln Phe Met Leu Asp Gln Leu Ser Asp Leu Gln Asn Arg Glu Gln Met
145                 150                 155                 160

Leu Ile Glu Ala Asn Lys Ala Leu Arg Arg Lys Leu Glu Glu Thr Ser
                165                 170                 175

Val Gln Ala Pro Gln Phe Met Ala Trp Glu Ala Ala Gly Asp Gly His
                180                 185                 190

Asn Asn Ile Gln Gln Thr Trp Leu Pro Ser Asn Ser Glu Ala Phe Phe
                195                 200                 205

His Pro Leu Gly Gly Asn Asn Ser Thr Ser Gln Ile Gly Tyr Ala His
        210                 215                 220

Leu Gly Ser His Asn Gly Met Asp Val Gly Asn Pro Gly Gln His Val
225                 230                 235                 240

Asn Gly Tyr Ile Pro Gly Trp Met Leu
                245

<210> SEQ ID NO 50
<211> LENGTH: 234
<212> TYPE: PRT
<213> ORGANISM: Malus domestica

<400> SEQUENCE: 50

Met Gly Arg Gly Arg Val Gln Leu Lys Arg Ile Glu Asn Lys Ile Asn
1               5                   10                  15

Arg Gln Val Thr Phe Ser Lys Arg Thr Ser Gly Leu Leu Lys Lys Ala
                20                  25                  30

His Glu Ile Ser Val Leu Cys Asp Ala Glu Val Ala Leu Ile Val Phe
                35                  40                  45

Ser Thr Lys Gly Lys Leu Phe Glu Tyr Ser Thr Asp Ser Cys Met Glu
        50                  55                  60

Arg Ile Leu Glu Arg Tyr Glu Arg Tyr Ser His Ala Glu Arg Gln Leu
65                  70                  75                  80

Leu Ala Asn Asp Asn Glu Ser Thr Gly Asn Trp Thr Leu Glu His Ala
                85                  90                  95

Lys Leu Lys Ala Arg Val Glu Val Leu Gln Arg Asn Gln Ser His Tyr
                100                 105                 110

Met Gly Glu Asp Leu Gln Ile Leu Ser Phe Gln Glu Leu Gln Asn Leu
                115                 120                 125

Glu Gln Gln Leu Asp Ser Ala Leu Arg Arg Ile Arg Ser Arg Lys Asn
        130                 135                 140

Gln Val Met Tyr Glu Ser Ile Ser Glu Leu Gln Lys Lys Asp Lys Ala
145                 150                 155                 160

Leu Gln Glu Gln Asn Asn Leu Leu Ala Lys Asn Val Lys Glu Lys Glu
                165                 170                 175

Lys Ala Val Thr Ser Gln Ala Gln Leu Glu His Ala Gln Lys Gln Ser
                180                 185                 190

Leu Asp Ser Ser Ser Thr Leu Leu Pro Gln Glu Leu Gln Tyr Leu Asn
                195                 200                 205

Phe Arg Trp Arg Glu Asn Ile Trp Glu Lys Arg Gly Met Lys Asp Asp
        210                 215                 220

Trp Lys Val Val Gly Gly Arg Arg Lys Lys
225                 230

<210> SEQ ID NO 51
<211> LENGTH: 215
```

<212> TYPE: PRT
<213> ORGANISM: Malus domestica

<400> SEQUENCE: 51

```
Met Val Arg Gly Lys Thr Gln Met Arg Arg Ile Glu Asn Ala Thr Ser
1               5                   10                  15

Arg Gln Val Thr Phe Ser Lys Arg Arg Ser Gly Leu Leu Lys Lys Ala
            20                  25                  30

Phe Glu Leu Ser Val Leu Cys Asp Ala Glu Val Ser Leu Ile Ile Phe
        35                  40                  45

Ser Pro Arg Gly Lys Leu Phe Glu Phe Ala Ser Ser Ser Met Gln Gly
    50                  55                  60

Thr Ile Glu Arg Tyr Gln Lys His Ala Lys Gly Asn Gln Thr Gly Asn
65                  70                  75                  80

Lys Ser Ser Ser Asn Glu Gln Asn Met Gln His Leu Lys Gln Lys Ala
                85                  90                  95

Thr Ser Met Met Lys Gln Leu Glu Leu Leu Glu Val Ser Lys Arg Lys
            100                 105                 110

Leu Leu Gly Glu Gly Leu Gly Ser Cys Thr Leu Ala Glu Leu Gln Glu
            115                 120                 125

Ile Glu His Gln Leu Glu Lys Ser Val Asn Asn Val Arg Ala Arg Lys
        130                 135                 140

Ser Gln Val Phe Lys Glu Gln Ile Glu Gln Leu Arg Glu Lys Glu Lys
145                 150                 155                 160

Leu Leu Lys Ala Glu Thr Ala Arg Leu Val Glu Lys Cys Gly Ser Phe
                165                 170                 175

Gln Pro Arg Lys Thr Leu Asp Glu Arg Arg Gln Asn Thr Thr Tyr Thr
            180                 185                 190

Asp Ser Ser Thr Ser Ser Asp Val Glu Thr Glu Leu Phe Ile Gly Leu
            195                 200                 205

Pro Glu Ser Arg Ala Arg Arg
    210                 215
```

<210> SEQ ID NO 52
<211> LENGTH: 202
<212> TYPE: PRT
<213> ORGANISM: Malus domestica

<400> SEQUENCE: 52

```
Met Ala Arg Gly Lys Val Gln Met Lys Arg Ile Glu Asn Met Val His
1               5                   10                  15

Arg Gln Val Thr Phe Cys Lys Arg Arg Ala Gly Leu Leu Lys Lys Ala
            20                  25                  30

Lys Glu Leu Ser Val Leu Cys Asp Ala Glu Ile Gly Val Phe Ile Phe
        35                  40                  45

Ser Ser His Gly Lys Leu Phe Glu Leu Ala Thr Lys Gly Ser Met Gln
    50                  55                  60

Gly Leu Ile Glu Arg Tyr Met Lys Met Lys Ser Thr Arg Ala Pro Gln
65                  70                  75                  80

Thr Glu Gln Thr Met Glu Thr Gln Thr Leu Asp Ala Lys Lys Glu Ile
            85                  90                  95

Asn Trp Met Lys Gln Glu Ile Glu Ile Leu Gln Lys Gly Leu Arg Tyr
            100                 105                 110

Met Phe Asp Gly Gly Ala Gly Thr Met Thr Leu Asp Glu Leu Gln Val
            115                 120                 125
```

```
Leu Glu Lys His Leu Glu Thr Trp Ile Tyr His Val Arg Ser Ala Lys
    130                 135                 140

Met Asp Ile Leu Phe Gln Glu Ile Gln Leu Leu Arg Asn Ser Glu Gly
145                 150                 155                 160

Ile Leu Ala Ala Ala Asn Lys Phe Leu Gln Asp Lys Ile Glu Val Asn
                165                 170                 175

Thr Gly Pro Asn Asp Phe Met Pro Ile Ala Thr Asp Asn Thr Tyr Pro
                180                 185                 190

Leu Thr Ile Pro Asn Gly Ile Tyr Glu Phe
                195                 200

<210> SEQ ID NO 53
<211> LENGTH: 223
<212> TYPE: PRT
<213> ORGANISM: Malus domestica

<400> SEQUENCE: 53

Met Gly Arg Gly Lys Ile Glu Ile Lys Arg Ile Glu Asn Thr Thr Asn
1                   5                   10                  15

Arg Gln Val Thr Phe Cys Lys Arg Arg Asn Gly Leu Leu Lys Lys Ala
                20                  25                  30

Tyr Glu Leu Ser Ile Leu Cys Asp Ala Glu Val Ala Leu Ile Val Phe
            35                  40                  45

Ser Thr Arg Gly Arg Leu Tyr Glu Tyr Ser Asn Asn Asn Ile Arg Asn
    50                  55                  60

Thr Ile Glu Arg Tyr Lys Lys Ala Cys Ser Asp Ser Thr Gly Ser Ser
65                  70                  75                  80

Ser Val Thr Glu Ile Asn Ala Gln Tyr Tyr Gln Gln Glu Ser Ala Lys
                85                  90                  95

Leu Arg Gln Gln Ile Gln Met Leu Gln Asn Ser Asn Arg His Leu Met
                100                 105                 110

Gly Asp Ala Leu Ser Thr Leu Thr Val Lys Glu Leu Lys Gln Val Glu
            115                 120                 125

Asn Arg Leu Glu Arg Gly Ile Thr Arg Ile Arg Ser Lys Lys His Glu
    130                 135                 140

Leu Leu Leu Ala Glu Ile Glu Tyr Phe Gln Lys Lys Glu Ile Glu Leu
145                 150                 155                 160

Glu Asn Glu Asn Val Tyr Leu Arg Thr Lys Val Ser Glu Val Glu Arg
                165                 170                 175

Leu Gln Gln Ala Asn Met Val Ser Gly Ser Glu Met Asn Ala Ile Gln
            180                 185                 190

Ala Leu Ala Ser Arg His Phe Phe Ser Gln Asn Met Ile Glu Gly Gly
            195                 200                 205

Glu Ala Thr Phe Pro Gln Gln Asp Lys Lys Asn Leu His Leu Gly
    210                 215                 220

<210> SEQ ID NO 54
<211> LENGTH: 246
<212> TYPE: PRT
<213> ORGANISM: Malus domestica

<400> SEQUENCE: 54

Met Gly Arg Gly Arg Val Glu Leu Lys Arg Ile Glu Asn Lys Ile Asn
1                   5                   10                  15

Arg Gln Val Thr Phe Ala Lys Arg Arg Asn Gly Leu Leu Lys Lys Ala
                20                  25                  30
```

-continued

```
Tyr Glu Leu Ser Val Leu Cys Asp Ala Glu Val Ala Leu Ile Val Phe
    35                  40                  45

Ser Asn Arg Gly Lys Leu Tyr Glu Phe Cys Ser Ser Pro Ser Ile Leu
    50                  55                  60

Gln Thr Val Asp Arg Tyr Gln Lys Cys Ser Tyr Gly Ala Val Asp Gln
65                  70                  75                  80

Val Asn Ile Pro Ala Lys Glu Leu Glu Ser Ser Tyr Arg Glu Tyr Met
                85                  90                  95

Lys Leu Lys Gly Arg Cys Glu Ser Leu Gln Arg Thr Gln Arg Asn Leu
                100                 105                 110

Leu Gly Glu Glu Leu Gly Pro Leu Asn Thr Lys Glu Leu Glu Gln Leu
                115                 120                 125

Glu Arg Gln Leu Glu Ala Ser Leu Lys Gln Val Arg Ser Thr Lys Thr
    130                 135                 140

Gln Tyr Met Leu Asp Gln Leu Ser Ala Leu Gln Asn Lys Glu Gln Leu
145                 150                 155                 160

Leu Ile Glu Ala Asn Arg Asp Leu Thr Met Lys Leu Asp Glu Ile Gly
                165                 170                 175

Ser Arg Asn Gln Leu Arg Gln Ser Trp Glu Gly Gly Asp Gln Gly Met
                180                 185                 190

Ala Tyr Gly Thr Gln His His His Ala Gln Ser Gln Gly Phe Phe Gln
                195                 200                 205

Pro Leu Asp Cys Asn Pro Thr Leu Gln Ile Gly Tyr Pro Ala Glu Gly
    210                 215                 220

Ser Glu Gln Met Gly Ala Thr Thr His Ala Gln Gln Val Asn Cys Phe
225                 230                 235                 240

Ile Pro Gly Trp Met Leu
                245

<210> SEQ ID NO 55
<211> LENGTH: 242
<212> TYPE: PRT
<213> ORGANISM: Malus domestica

<400> SEQUENCE: 55

Met Glu Phe Ala Asn Gln Ala Pro Glu Ser Ser Thr Gln Lys Lys Leu
1               5                   10                  15

Gly Arg Gly Lys Ile Glu Ile Lys Arg Ile Glu Asn Thr Thr Asn Arg
                20                  25                  30

Gln Val Thr Phe Cys Lys Arg Arg Asn Gly Leu Leu Lys Lys Ala Tyr
            35                  40                  45

Glu Leu Ser Val Leu Cys Asp Ala Glu Val Ala Leu Ile Val Phe Ser
    50                  55                  60

Thr Arg Gly Arg Leu Tyr Glu Tyr Ala Asn Asn Ser Val Arg Ala Thr
65                  70                  75                  80

Ile Asp Arg Tyr Lys Lys Ala Cys Ala Asp Ser Thr Asp Gly Gly Ser
                85                  90                  95

Val Ser Glu Ala Asn Thr Gln Phe Tyr Gln Gln Glu Ala Ser Lys Leu
                100                 105                 110

Arg Arg Gln Ile Arg Glu Ile Gln Asn Ser Asn Arg His Ile Leu Gly
            115                 120                 125

Glu Ser Leu Ser Thr Leu Lys Val Lys Glu Leu Lys Asn Leu Glu Gly
    130                 135                 140

Arg Leu Glu Lys Gly Ile Ser Arg Ile Arg Ser Lys Lys Asn Glu Ile
145                 150                 155                 160
```

```
Leu Phe Ser Glu Ile Glu Phe Met Gln Lys Arg Glu Thr Glu Leu Gln
                165             170             175

His His Asn Asn Phe Leu Arg Ala Lys Ile Ala Glu Ser Glu Arg Glu
            180             185             190

Gln Gln Gln Gln Gln Thr His Met Met Pro Gly Thr Ser Tyr Asp Pro
        195             200             205

Ser Met Pro Ser Asn Ser Tyr Asp Arg Asn Phe Phe Pro Val Ile Leu
    210             215             220

Glu Ser Asn Asn Asn His Tyr Pro Arg Gln Gly Gln Thr Ala Leu Gln
225             230             235             240

Leu Val
```

```
<210> SEQ ID NO 56
<211> LENGTH: 201
<212> TYPE: PRT
<213> ORGANISM: Malus domestica

<400> SEQUENCE: 56

Met Gly Arg Gly Lys Val Glu Leu Lys Leu Ile Asp Asp Lys Leu Arg
1               5               10              15

Arg Gln Val Thr Phe Ser Lys Arg Arg Ser Gly Leu Ile Lys Lys Ala
            20              25              30

Arg Glu Leu Ser Val Leu Cys Gly Val Glu Val Gly Leu Val Ile Phe
        35              40              45

Ser Ala Lys Gly Arg Leu Tyr Glu Phe Cys Ser Gly Glu Ser Leu Gly
    50              55              60

Lys Leu Leu Glu Arg Tyr Gln Met His Ser Glu Glu Glu Ile Gly Ala
65              70              75              80

Ser Lys Asn Ala Gly Gly Thr Asp Lys Lys His Asn Ser Glu Cys Ser
            85              90              95

Asp Leu Arg Ala Gly Ala Asn Arg Ser Pro Lys Met Ile Gln Ser Gly
        100             105             110

Arg Glu Ala Gln Asp Leu Glu Asn Leu Asp Val Pro Glu Leu Thr Gln
        115             120             125

Leu Glu Glu Glu Leu Asp Ala Leu Leu Arg Gln Thr Arg Ser Arg Lys
    130             135             140

Thr Gln Leu Met Met Glu Asn Leu Thr Ala Leu Ile Glu Thr Glu Lys
145             150             155             160

Gln Leu Lys Glu Glu Lys Arg Leu Ile Glu Asn Glu Ile Ala Ala Leu
            165             170             175

Lys Leu Lys Glu Gln Ala Glu Gln Gly Leu Ser Cys Arg Arg Gly Thr
            180             185             190

Gly Ser Ala Glu His Phe Leu Arg Leu
        195             200
```

```
<210> SEQ ID NO 57
<211> LENGTH: 65
<212> TYPE: PRT
<213> ORGANISM: Malus domestica

<400> SEQUENCE: 57

Met Gly Arg Gly Lys Val Val Ile Arg Arg Ile Asp Asn Leu Thr Ser
1               5               10              15

Arg Gln Val Thr Phe Ser Lys Arg Arg Asn Gly Leu Leu Lys Lys Ala
            20              25              30
```

-continued

```
Lys Glu Leu Ser Ile Leu Cys Asp Ala Glu Val Gly Leu Ile Ile Phe
        35                  40                  45

Ser Ser Thr Gly Arg Leu Tyr Asp Tyr Ala Ser Thr Ser Leu His Trp
    50                  55                  60

Asn
65

<210> SEQ ID NO 58
<211> LENGTH: 234
<212> TYPE: PRT
<213> ORGANISM: Malus domestica

<400> SEQUENCE: 58

Met Asp Ser Pro Gln Arg Lys Leu Gly Arg Gly Lys Ile Glu Ile Lys
1               5                   10                  15

Arg Ile Glu Asn Thr Thr Asn Arg Gln Val Thr Phe Cys Lys Arg Arg
                20                  25                  30

Asn Gly Leu Leu Lys Lys Ala Tyr Glu Leu Ser Val Leu Cys Asp Ala
        35                  40                  45

Glu Val Ala Leu Ile Val Phe Ser Asn Arg Gly Arg Leu Tyr Glu Tyr
    50                  55                  60

Ala Asn Asn Ser Val Lys Gly Thr Ile Glu Arg Tyr Lys Lys Ala Ser
65                  70                  75                  80

Ala Asp Ser Ser Asn Thr Gly Ser Val Ser Glu Ala Ser Thr Gln Tyr
                85                  90                  95

Tyr Gln Gln Glu Ala Ala Lys Leu Arg Ala Gln Ile Val Lys Leu Gln
                100                 105                 110

Asn Asp Asn Arg Asn Met Met Gly Asp Ala Leu Ser Ser Met Ser Val
        115                 120                 125

Lys Asp Leu Lys Ser Leu Glu Asn Lys Leu Glu Lys Ala Ile Ser Arg
    130                 135                 140

Ile Arg Ser Lys Lys Asn Glu Leu Leu Phe Ala Glu Ile Glu Tyr Met
145                 150                 155                 160

Gln Lys Arg Glu Leu Asp Leu His Asn Asn Asn Gln Leu Leu Arg Ala
                165                 170                 175

Lys Ile Ala Glu Asn Glu Arg Gly Gln Gln Asn Ile Asn Val Met Ala
            180                 185                 190

Gly Gly Gly Ser Tyr Glu Ile Leu Gln Ser Gln Pro Tyr Asp Ser Arg
        195                 200                 205

Asp Tyr Phe Gln Val Asn Val Leu Gln Pro Asn His His Asn Pro
    210                 215                 220

Arg His Asp Gln Ile Ser Leu Gln Leu Val
225                 230

<210> SEQ ID NO 59
<211> LENGTH: 239
<212> TYPE: PRT
<213> ORGANISM: Malus domestica

<400> SEQUENCE: 59

Met Gly Arg Gly Arg Val Gln Leu Lys Arg Ile Glu Asn Lys Ile Asn
1               5                   10                  15

Arg Gln Val Thr Phe Ser Lys Arg Ser Thr Gly Leu Leu Lys Lys Ala
                20                  25                  30

His Glu Ile Ser Val Leu Cys Asp Ala Gln Val Ala Leu Ile Val Phe
        35                  40                  45
```

-continued

```
Ser Asn Lys Gly Lys Leu Leu Glu Tyr Ala Thr Asp Ser Cys Met Glu
    50              55                  60

Gln Ile Leu Glu Arg Tyr Glu Arg Tyr Ser Tyr Ala Glu Arg Gln Leu
65              70                  75                  80

Val Glu Pro Asp Phe Glu Ser Gln Gly Asn Trp Thr Phe Glu Tyr Ser
                85                  90                  95

Arg Leu Lys Ala Lys Val Glu Val Leu Gln Arg Asn His Arg His Tyr
            100                 105                 110

Leu Gly Glu Asp Leu Asp Ser Leu Thr Leu Lys Asp Ile Gln Ser Leu
            115                 120                 125

Glu Gln Gln Leu Asp Thr Ala His Lys Gln Ile Arg Leu Arg Lys Asn
    130                 135                 140

Gln Leu Met His Glu Ser Ile Thr Glu Leu Gln Arg Lys Glu Lys Ala
145                 150                 155                 160

Ile Gln Glu Gln Asn Asn Leu Leu Ala Lys Lys Ile Lys Glu Lys Glu
                165                 170                 175

Lys Ala Ala Ala Gln Pro Gln Val Gln Asn Trp Glu Gln Gln Asn His
            180                 185                 190

Asp Leu Asp Leu Leu Pro Gln Pro Leu Pro Cys Leu Asn Ile Gly Gly
            195                 200                 205

Thr Gln Gln Asp Glu Phe Leu Gln Val Arg Arg Asn Gln Leu Asp Leu
    210                 215                 220

Thr Leu Glu Pro Phe Tyr Ser Cys His Leu Gly Cys Phe Ala Ala
225                 230                 235
```

<210> SEQ ID NO 60
<211> LENGTH: 235
<212> TYPE: PRT
<213> ORGANISM: Malus domestica

<400> SEQUENCE: 60

```
Met Gly Arg Gly Lys Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
            20                  25                  30

Tyr Glu Leu Ser Val Leu Cys Asp Ala Glu Val Ala Leu Ile Val Phe
            35                  40                  45

Ser Thr Ser Gly Lys Leu Tyr Glu Phe Cys Ser Gly Pro Ser Ile Ala
    50              55                  60

Lys Thr Leu Glu Arg His Gln Arg Cys Thr Tyr Gly Glu Leu Gly Ala
65              70                  75                  80

Ser Gln Ser Ala Glu Asp Glu Gln Ser Arg Tyr Gln Glu Tyr Leu Lys
                85                  90                  95

Leu Lys Thr Lys Val Glu Ala Leu Gln Arg Thr Gln Arg His Leu Leu
            100                 105                 110

Gly Glu Asp Leu Val His Leu Gly Thr Lys Glu Leu Gln Gln Leu Glu
            115                 120                 125

Asn Gln Leu Asp Val Ser Met Lys Lys Ile Arg Ser Thr Lys Thr Gln
    130                 135                 140

Phe Met His Val Gln Ile Ser Glu Leu Gln Arg Lys Glu Glu Met Leu
145                 150                 155                 160

Leu Glu Ala Asn Thr Gly Leu Arg Arg Lys Leu Glu Glu Ile Thr Ala
                165                 170                 175

Gly His Gln Arg Ser Trp Asn Gly Asn His Gln Ala Ala Gln Leu Glu
            180                 185                 190
```

```
Gly Phe Pro Glu His Leu Gln Tyr Asn Asn Ala Leu Gln Ile Gly Thr
        195                 200                 205

Pro Val Val Thr Asn Asp Glu Ala Asn Val Ala Thr Ser Ser Ala Gln
        210                 215                 220

Asn Gly Thr Gly Phe Phe Pro Gly Trp Met Leu
225                 230                 235
```

```
<210> SEQ ID NO 61
<211> LENGTH: 239
<212> TYPE: PRT
<213> ORGANISM: Malus domestica

<400> SEQUENCE: 61
```

```
Met Gly Arg Gly Arg Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
        20                  25                  30

Tyr Glu Leu Ser Val Leu Cys Asp Ala Glu Val Ala Leu Ile Ile Phe
        35                  40                  45

Ser Asn Arg Gly Lys Leu Tyr Glu Phe Cys Ser Ser Ser Ser Thr Leu
        50                  55                  60

Lys Thr Leu Glu Arg Tyr Gln Lys Cys Asn Tyr Gly Ala Pro Glu Thr
65                  70                  75                  80

Asn Ile Ser Thr Arg Glu Ala Leu Glu Leu Ser Ser Gln Gln Glu Tyr
                85                  90                  95

Leu Lys Leu Lys Ala Arg Phe Glu Ala Leu Gln Arg Asn Gln Arg Asn
        100                 105                 110

Leu Leu Gly Glu Asp Leu Gly Pro Leu Ser Ser Lys Asp Leu Glu Ser
        115                 120                 125

Leu Glu Arg Gln Leu Asp Met Ser Leu Lys Gln Ile Arg Ser Thr Arg
        130                 135                 140

Thr Gln Cys Met Leu Asp Gln Leu Thr Asp Leu Gln Arg Lys Glu His
145                 150                 155                 160

Met Leu Asn Glu Ala Asn Lys Thr Leu Lys Glu Arg Leu Phe Glu Gly
                165                 170                 175

Tyr His Ala Leu Gln Leu Asn Ala Asn Ala Asp Glu Tyr Gly Arg Gln
                180                 185                 190

Gln Ala Gln Ala Ala Gln Gly Asp Val Phe Phe His Pro Leu Asp Cys
        195                 200                 205

Glu Pro Thr Leu Gln Ile Gly Tyr Gln Asn Asp Pro Ile Ser Val Val
        210                 215                 220

Thr Ala Gly Pro Ser Val Ser Asn Tyr Met Gly Gly Trp Leu Pro
225                 230                 235
```

```
<210> SEQ ID NO 62
<211> LENGTH: 204
<212> TYPE: PRT
<213> ORGANISM: Malus domestica

<400> SEQUENCE: 62
```

```
Met Gly Arg Gly Lys Val Glu Leu Lys Arg Ile Asp Asn Pro Thr Ser
1               5                   10                  15

Arg Gln Val Thr Phe Ser Lys Arg Arg Asn Gly Leu Leu Lys Lys Ala
        20                  25                  30

Phe Glu Leu Ser Ile Leu Cys Asp Ala Glu Val Ala Leu Ile Ile Phe
        35                  40                  45
```

-continued

```
Ser Pro Ser Gly Lys Ala Tyr Gln Phe Ala Ser His Asp Ile Thr Arg
    50              55              60

Thr Ile Ser Met Tyr Arg Arg Glu Val Gly Leu Pro Glu Ser Asn Asn
65              70              75              80

Ser Ser Phe Leu Arg Ala Arg Thr Met Glu Tyr Trp Arg Asn Glu Asn
            85              90              95

Glu Glu Leu Arg Arg Ser Ile Gly Asn Leu Glu Met Arg Leu Met Asn
            100             105             110

Leu Ala Gly Glu Glu Leu Ser Thr Leu Gly Val Gln Glu Leu Lys Gln
            115             120             125

Leu Glu Arg Gln Leu Lys Thr Gly Val Glu Arg Ile Arg Ser Lys Met
    130             135             140

Arg Arg Ile Ile Ser Glu Asn Val Ser Leu Leu Lys Arg Lys His Lys
145             150             155             160

Ala Ser Gln Glu Glu Asn Thr His Leu Leu Lys Arg Ile Lys Leu His
            165             170             175

Glu Leu Asn Val Ala Asp Ala Ser Cys Ser Thr Thr Val Gly Ala
            180             185             190

Asn Ala Arg Ile Ser Ala Phe Pro Ser Glu Leu Ile
            195             200
```

<210> SEQ ID NO 63
<211> LENGTH: 249
<212> TYPE: PRT
<213> ORGANISM: Malus domestica

<400> SEQUENCE: 63

```
Met Gly Arg Gly Arg Val Glu Leu Lys Arg Ile Glu Asn Lys Ile Asn
1               5               10              15

Arg Gln Val Thr Phe Ala Lys Arg Arg Asn Gly Leu Leu Lys Lys Ala
            20              25              30

Tyr Glu Leu Ser Val Leu Cys Asp Ala Glu Val Ala Leu Ile Ile Phe
            35              40              45

Ser Ser Arg Gly Lys Leu Tyr Glu Phe Cys Ser Ser Phe Ser Met Met
    50              55              60

Lys Thr Leu Glu Lys Tyr Gln Ser Cys Ser Tyr Gly Ser Leu Glu Ala
65              70              75              80

Asn Leu Pro Ala Asn Glu Thr Gln Gln Asn Ser Tyr Gln Asp Tyr Leu
            85              90              95

Met Leu Lys Ala Arg Val Glu Val Leu Gln Gln Ser Gln Arg Asn Leu
            100             105             110

Leu Gly Glu Asp Leu Ser His Leu Asn Thr Lys Glu Leu Glu His Leu
            115             120             125

Glu His Gln Leu Glu Thr Ser Leu Lys Gln Ile Arg Ser Arg Lys Thr
    130             135             140

Gln Phe Ile Leu Asp Gln Leu Ser Asp Leu Gln Asn Arg Glu Gln Met
145             150             155             160

Leu Val Glu Ala Asn Lys Ala Leu Lys Arg Lys Leu Glu Glu Thr Ser
            165             170             175

Val Gln Ala Pro Glu Gly Met Ala Trp Glu Ala Ala Gly His Gly Pro
            180             185             190

Asn Asn Ile Gln Gln Thr Arg Leu Pro Ser His Ser Glu Ala Phe Phe
            195             200             205

His Pro Leu Glu Gly Asn Asn Ser Ser Ser Gln Ile Gly Tyr Thr His
```

-continued

```
            210                 215                 220

Met Gly Ser Asp Asn Glu Met Asn Val Gly Asn Pro Gly Gln Tyr Val
225                 230                 235                 240

Asn Gly Tyr Ile Pro Gly Trp Met Leu
                245

<210> SEQ ID NO 64
<211> LENGTH: 255
<212> TYPE: PRT
<213> ORGANISM: Malus domestica

<400> SEQUENCE: 64

Met Gly Arg Gly Arg Val Gln Leu Lys Arg Ile Glu Asn Lys Ile Asn
1               5                   10                  15

Arg Gln Val Thr Phe Ser Lys Arg Arg Ser Gly Leu Met Lys Lys Ala
                20                  25                  30

His Glu Ile Ser Val Leu Cys Asp Ala Glu Val Ala Leu Ile Ile Phe
            35                  40                  45

Ser Thr Lys Gly Lys Leu Phe Glu Tyr Ser Asn Asp Ser Cys Met Glu
    50                  55                  60

Arg Ile Leu Glu Arg Tyr Glu Arg Tyr Ser Tyr Thr Glu Arg Gln Leu
65                  70                  75                  80

Leu Ala Asn Asp Asn Glu Ser Thr Gly Ser Trp Thr Leu Glu His Ala
                85                  90                  95

Lys Leu Lys Ala Arg Val Glu Val Leu Gln Arg Asn Gln Arg His Tyr
                100                 105                 110

Met Gly Glu Asp Leu Gln Ser Leu Ser Leu Lys Glu Leu Gln Asn Leu
            115                 120                 125

Glu Gln Gln Leu Asp Ser Ala Leu Lys His Ile Arg Ser Arg Lys Asn
    130                 135                 140

Gln Val Met Tyr Glu Ser Ile Ser Glu Leu Gln Lys Lys Asp Lys Ala
145                 150                 155                 160

Leu Gln Glu Gln Asn Asn Leu Leu Ala Lys Lys Val Lys Glu Lys Glu
                165                 170                 175

Asn Ala Val Ala Gln Gln Ala Gln Leu Glu His Val Gln Glu Gln Arg
            180                 185                 190

Leu Asn Ser Ser Ser Ser Leu Leu Pro Arg Ala Leu Gln Ser Leu Asn
            195                 200                 205

Phe Gly Ser Gly Ser Asn Tyr Gln Ala Ile Arg Ser Ser Glu Gly Ile
    210                 215                 220

Pro Gly Asp Asn Gln Gln Tyr Gly Asp Glu Thr Pro Thr Pro His Arg
225                 230                 235                 240

Pro Asn Met Leu Leu Pro Ala Trp Met Leu Arg His Leu Asn Glu
                245                 250                 255

<210> SEQ ID NO 65
<211> LENGTH: 202
<212> TYPE: PRT
<213> ORGANISM: Malus domestica

<400> SEQUENCE: 65

Met Ala Arg Gly Lys Val Gln Met Lys Arg Ile Glu Asn Pro Val His
1               5                   10                  15

Arg Gln Val Thr Phe Cys Lys Arg Arg Val Gly Leu Leu Lys Lys Ala
                20                  25                  30

Lys Glu Leu Ser Val Leu Cys Asp Ala Glu Ile Gly Val Phe Ile Phe
```

```
          35                    40                    45
Ser Ser His Gly Lys Leu Phe Glu Leu Ala Thr Lys Gly Ser Met Gln
    50                    55                    60

Gly Leu Ile Glu Arg Tyr Met Lys Met Lys Pro Thr Arg Val Ser Gln
65                    70                    75                    80

Val Glu Gln Thr Val Glu Thr Gln Thr Leu Asp Ala Lys Lys Glu Ile
                  85                    90                    95

Asn Leu Leu Lys Gln Glu Ile Glu Ile Leu Gln Lys Gly Leu Arg Tyr
              100                   105                   110

Met Phe Asp Gly Gly Ala Gly Thr Met Thr Leu Asp Glu Leu Gln Val
              115                   120                   125

Leu Glu Lys Asn Leu Glu Ile Trp Ile Tyr His Val Arg Ser Ala Lys
          130                   135                   140

Met Asp Ile Leu Phe Gln Glu Ile Gln Leu Leu Arg Asn Ser Glu Gly
145                   150                   155                   160

Val Leu Thr Ala Ala Asn Lys Tyr Leu Gln Asp Lys Ile Glu Glu Asn
                  165                   170                   175

Thr Gly Val Thr Asn Phe Ile Pro Met Ala Thr Asp Asn Thr Tyr Pro
              180                   185                   190

Phe Thr Ile Pro Asp Asp Ile Phe Glu Cys
          195                   200

<210> SEQ ID NO 66
<211> LENGTH: 222
<212> TYPE: PRT
<213> ORGANISM: Malus domestica

<400> SEQUENCE: 66

Met Gly Arg Gly Lys Ile Glu Ile Lys Arg Ile Glu Asn Thr Thr Asn
1                 5                     10                    15

Arg Gln Val Thr Phe Cys Lys Arg Arg Asn Gly Leu Leu Lys Lys Ala
                  20                    25                    30

Tyr Glu Leu Ser Ile Leu Cys Asp Ala Glu Ile Ala Leu Ile Val Phe
              35                    40                    45

Ser Ser Arg Gly Arg Leu Tyr Glu Tyr Ser Asn Asn Asn Ile Arg Asn
    50                    55                    60

Thr Ile Glu Arg Tyr Lys Lys Ala Cys Ser Asp Ser Thr Gly Ser Thr
65                    70                    75                    80

Ser Ile Thr Glu Ile Asn Ala Gln Tyr Gln Gln Glu Ser Ala Lys
                  85                    90                    95

Leu Arg Gln Gln Ile Gln Met Leu Gln Asn Tyr Asn Arg His Leu Met
              100                   105                   110

Gly Asp Ala Leu Ser Asn Leu Thr Val Lys Glu Leu Lys Gln Leu Glu
              115                   120                   125

Asn Arg Leu Glu Arg Gly Met Thr Arg Ile Arg Ser Lys Lys Asp Glu
          130                   135                   140

Met Leu Ile Ala Glu Ile Glu Tyr Leu Gln Lys Lys Glu Ile Glu Leu
145                   150                   155                   160

Glu Asn Glu Asn Val Tyr Leu Arg Thr Lys Ile Ser Glu Val Glu Arg
                  165                   170                   175

His Gln Ala Asn Met Val Ser Val Pro Glu Met Asn Ala Ile Gln Ala
              180                   185                   190

Leu Ala Ser Arg Asn Phe Phe Ser Gln Asn Ile Ile Glu Gly Gly Gly
          195                   200                   205
```

-continued

```
Ala Thr Phe Pro Gln Gln Asn Lys Lys Ile Leu His Leu Gly
    210             215             220
```

```
<210> SEQ ID NO 67
<211> LENGTH: 239
<212> TYPE: PRT
<213> ORGANISM: Malus domestica

<400> SEQUENCE: 67
```

```
Met Gly Arg Gly Arg Val Gln Leu Lys Arg Ile Glu Asn Lys Ile Asn
1               5               10              15
```

```
Arg Gln Val Thr Phe Ser Lys Arg Arg Thr Gly Leu Leu Lys Lys Ala
            20              25              30
```

```
His Glu Ile Ser Val Leu Cys Asp Ala Gln Val Ala Leu Ile Val Phe
        35              40              45
```

```
Ser Asn Lys Gly Lys Leu Phe Glu Tyr Ala Thr Asp Ser Cys Met Glu
    50              55              60
```

```
Gln Ile Leu Glu Arg Tyr Glu Arg Tyr Ser Tyr Ala Glu Arg Gln Leu
65              70              75              80
```

```
Val Glu Pro Asp Phe Glu Ser Gln Gly Asn Trp Thr Phe Glu Tyr Ser
            85              90              95
```

```
Arg Leu Lys Ala Lys Ala Glu Val Leu Gln Arg Asn His Arg His Tyr
            100             105             110
```

```
Leu Gly Glu Asp Leu Asp Ser Leu Thr Leu Lys Glu Ile Gln Asn Leu
            115             120             125
```

```
Glu Gln Gln Leu Asp Thr Ala Leu Lys Gln Ile Arg Leu Arg Lys Asn
    130             135             140
```

```
Gln Leu Met Asn Glu Ser Ile Ser Glu Leu Gln Arg Lys Arg Lys Ala
145             150             155             160
```

```
Ile Gln Glu Glu Asn Asn Leu Leu Ala Lys Lys Ile Lys Glu Lys Glu
            165             170             175
```

```
Lys Ala Ala Ala Gln Pro Gln Val Gln Asn Trp Glu Gln Gln Asn His
            180             185             190
```

```
Gly Leu Asp Leu Leu Pro Gln Pro Leu Pro Cys Leu Asn Asn Gly Gly
            195             200             205
```

```
Thr Gln Gln Asp Glu Phe Leu Gln Val Arg Arg Asn Gln Leu Asp Leu
    210             215             220
```

```
Thr Leu Glu Pro Leu Tyr Glu Cys His Leu Gly Cys Phe Ala Ala
225             230             235
```

```
<210> SEQ ID NO 68
<211> LENGTH: 237
<212> TYPE: PRT
<213> ORGANISM: Malus domestica

<400> SEQUENCE: 68
```

```
Met Gly Arg Gly Lys Val Glu Leu Lys Arg Ile Glu Asn Lys Ile Asn
1               5               10              15
```

```
Arg Gln Val Thr Phe Ala Lys Arg Arg Lys Gly Leu Leu Lys Lys Ala
            20              25              30
```

```
Tyr Glu Leu Ser Val Leu Cys Asp Ala Glu Val Ala Leu Ile Val Phe
        35              40              45
```

```
Ser Thr Arg Gly Lys Leu Ser Glu Phe Ser Ser Gly Pro Ser Met Ala
    50              55              60
```

```
Lys Thr Leu Glu Arg Tyr Gln Arg Cys Thr Tyr Gly Glu Leu Gly Ala
65              70              75              80
```

-continued

```
Ser Gln Ser Ala Glu Asp Glu Gln Ser Arg Tyr Gln Asp Tyr Leu Lys
                85              90              95

Leu Lys Thr Lys Val Glu Ala Leu Gln Arg Thr Gln Arg His Phe Leu
            100             105             110

Gly Glu Asp Leu Val His Leu Gly Met Thr Glu Leu Gln Gln Leu Glu
            115             120             125

Asn Gln Leu Asp Met Ser Leu Lys Lys Ile Arg Ser Thr Lys Thr Gln
    130             135             140

Phe Met His Val Gln Ile Ser Glu Leu Gln Arg Lys Glu Glu Met Leu
145             150             155             160

Leu Glu Ala Asn Thr Gly Leu Arg Arg Lys Leu Glu Glu Ser Thr Ala
                165             170             175

Asp Leu Gln Arg Ser Trp Asn Ser His His Gln Ala Ala Gln Leu Glu
            180             185             190

Gly Phe Pro Glu His Leu Gln Phe Asn Asn Thr Leu Gln Ile Gly Tyr
            195             200             205

Ser Thr Pro Ala Val Thr Asn Asp Glu Val Asn Val Ala Thr Ser Ser
    210             215             220

Glu Gln Ser Arg Arg Gly Phe Ile Pro Gly Trp Met Leu
225             230             235

<210> SEQ ID NO 69
<211> LENGTH: 202
<212> TYPE: PRT
<213> ORGANISM: Malus domestica

<400> SEQUENCE: 69

Met Gly Arg Gly Arg Val Glu Leu Lys Arg Ile Glu Asn Lys Ile Asn
1               5               10              15

Arg Gln Val Thr Phe Ala Lys Arg Arg Asn Gly Leu Leu Lys Lys Ala
            20              25              30

Tyr Glu Leu Ser Val Leu Cys Asp Ala Glu Val Ala Leu Ile Ile Phe
            35              40              45

Ser Asn Arg Gly Lys Leu Tyr Glu Phe Cys Ser Ser Ser Arg Leu Ser
    50              55              60

Val Ser Ala Ser Ala Leu Leu Leu Asp Leu Gln Gln Glu Ile Lys Ile
65              70              75              80

Asn Pro Ile Lys Arg Arg Ser Leu Ile Ser His His Ser Ser Leu Thr
                85              90              95

Val Phe Phe His Asn Ser Pro Ser Val Ser Ala Gly Ser His Leu Cys
            100             105             110

Ser Tyr Thr Glu Asn Leu Gly Arg Glu Phe Phe Ser Ile Phe Leu Lys
            115             120             125

Ile Lys Leu Ser Phe Leu Glu Ile Leu Ile Gln Lys Gln Glu Leu Asn
    130             135             140

Tyr Pro Val Phe Pro Val Pro His Leu Gly Leu Asn Ile Phe Ser Tyr
145             150             155             160

Thr Val Leu Ile Ile Ser Ser Leu Phe Lys Phe Asn Phe Tyr Glu Ile
                165             170             175

Gly Leu Ile Leu Ser Phe Phe Ser Ile Phe Val Phe Arg Phe Leu Val
            180             185             190

Ser Gln Met His Gly Asn Val Lys Lys Phe
            195             200

<210> SEQ ID NO 70
```

```
<211> LENGTH: 225
<212> TYPE: PRT
<213> ORGANISM: Malus domestica

<400> SEQUENCE: 70

Met Gly Arg Gly Lys Val Gln Leu Lys Arg Ile Asp Asp Lys Ile Arg
1               5                   10                  15

Arg Gln Val Thr Phe Ser Lys Arg Arg Ser Gly Leu Ile Lys Lys Ala
            20                  25                  30

Arg Glu Leu Ser Val Leu Cys Gly Val Glu Val Gly Leu Val Ile Phe
            35                  40                  45

Ser Thr Lys Gly Arg Leu Tyr Glu Phe Cys Ser Gly Ser Ser Phe Ala
        50                  55                  60

Lys Leu Leu Glu Arg Tyr Gln Gln His Asn Ala Glu Glu Ile Ala Ala
65                  70                  75                  80

Ser Lys Asn Ala Gly Asp Thr Asp Lys Lys His Asn Leu Glu Cys Ser
                85                  90                  95

Gly Leu Arg Thr Gly Ala Ser Arg Ser Leu Lys Met Ile Gln Ser Asp
            100                 105                 110

Ile Glu Ala Gln Asp Leu Asp Asn Leu Asp Val Pro Glu Leu Thr Lys
            115                 120                 125

Leu Glu Glu Glu Leu Asp Ala Val Leu Arg Gln Thr Arg Ser Arg Lys
        130                 135                 140

Thr Gln Leu Met Met Glu Thr Leu Thr Ala Leu Ile Glu Gln Glu Lys
145                 150                 155                 160

Gln Leu Lys Glu Glu Lys Leu Leu Leu Glu Asn Glu Ile Ala Ala Lys
                165                 170                 175

Glu Gln Gln Ile Arg Asp Arg Ala Ala Asp Glu Glu Pro Val Gln Gln
            180                 185                 190

Asn Thr Ser Ala Ala Asn His Thr Thr Thr Thr Thr Ser Asn Asn Asn
        195                 200                 205

Asn Asn Cys Ser Ser Asp Asp Asp Val Pro Ala Thr Ile Leu Arg Leu
        210                 215                 220

Phe
225

<210> SEQ ID NO 71
<211> LENGTH: 246
<212> TYPE: PRT
<213> ORGANISM: Malus domestica

<400> SEQUENCE: 71

Met Gly Arg Gly Arg Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
            20                  25                  30

Tyr Glu Leu Ser Val Leu Cys Asp Ala Glu Val Ala Leu Ile Ile Phe
            35                  40                  45

Ser Asn Arg Gly Lys Leu Tyr Glu Phe Cys Ser Ser Ser Ser Ile Leu
        50                  55                  60

Lys Thr Leu Asp Arg Tyr Gln Lys Cys Ser Tyr Gly Ala Val Asp Gln
65                  70                  75                  80

Val Asn Arg Pro Ala Lys Glu Leu Glu Ser Ser Tyr Arg Glu Tyr Met
                85                  90                  95

Lys Leu Lys Gly Arg Tyr Glu Ser Leu Gln Arg Thr Gln Arg Asn Leu
            100                 105                 110
```

```
Leu Gly Glu Asp Leu Gly Pro Leu Asn Thr Lys Glu Leu Glu Gln Leu
        115                 120                 125

Glu Arg Gln Leu Glu Gly Ser Leu Lys Gln Val Arg Ser Thr Lys Thr
    130                 135                 140

Gln Tyr Met Leu Asp Gln Leu Ser Asp Leu Gln Asn Lys Glu Gln Leu
145                 150                 155                 160

Leu Ile Glu Ala Asn Arg Asp Leu Thr Met Lys Leu Asp Glu Ile Ser
                165                 170                 175

Ser Arg Asn Gln Leu Arg Gln Ser Trp Glu Gly Gly Asp Gln Gly Met
                180                 185                 190

Ala Tyr Ala Thr Gln His His His Ala Gln Ser Gln Gly Phe Phe Gln
                195                 200                 205

Pro Leu Asp Cys Asn Pro Thr Leu Gln Met Gly Tyr Ser Ala Val Gly
    210                 215                 220

Ser Glu Gln Met Ser Ala Thr Thr Asn Ala Gln Gln Val Asn Cys Phe
225                 230                 235                 240

Ile Pro Gly Trp Met Leu
                245

<210> SEQ ID NO 72
<211> LENGTH: 262
<212> TYPE: PRT
<213> ORGANISM: Malus domestica

<400> SEQUENCE: 72

Met Gly Arg Gly Lys Val Gln Leu Lys Arg Ile Glu Asn Thr Ile Ser
1               5                   10                  15

Arg Gln Val Thr Phe Ser Lys Arg Arg Thr Gly Leu Leu Lys Lys Ala
                20                  25                  30

His Glu Ile Ser Val Leu Cys Asp Ala Asp Val Ala Leu Ile Val Phe
            35                  40                  45

Ser Thr Lys Gly Lys Leu Phe Glu Tyr Ser Thr Asp Ser Ser Met Glu
    50                  55                  60

Arg Ile Leu Asp Arg Tyr Glu Gln Tyr Thr Val Ala Glu Arg Gln Leu
65                  70                  75                  80

Asn Gly Thr Asn Ser Glu Ser Gln Glu Asn Trp Cys Val Glu Tyr Pro
                85                  90                  95

Lys Leu Ala Ala Arg Ile Glu Val Ile Gln Arg Lys Leu Arg Asn Phe
                100                 105                 110

Thr Gly Glu Asp Leu Gly Pro Leu Ser Leu Arg Glu Leu Gln Asn Leu
        115                 120                 125

Glu Gln Gln Leu Asp Thr Ala Leu Lys Arg Ile Arg Thr Arg Lys Asn
    130                 135                 140

Gln Leu Met His Glu Ser Ile Ser Glu Met His Lys Lys Gln Lys Ala
145                 150                 155                 160

Leu Arg Glu Leu Asn Asn Ser Leu Ala Lys Gln Val Lys Glu Asn Gly
                165                 170                 175

Lys Met Leu Glu Glu Glu His Asp Gln Val Gln Val Val Gly Arg Gln
                180                 185                 190

Gln Gln Thr Asn Gln Gly Arg His Asn Ser Ser Thr Leu Met Leu Met
                195                 200                 205

Pro Pro Pro Gln Pro Pro Ser Thr Pro Ser Leu Pro Thr Ser Arg Ser
    210                 215                 220

Thr Ser Gly Gly Phe Gln Ala Arg Gly Ala Thr Asp Gly Asp Tyr Glu
```

```
225                 230                 235                 240

Gly Arg Pro Arg Pro Pro Ala Ala Lys Asn Thr His Met Pro Leu Trp
                245                 250                 255

Met Leu Ser Pro Phe Gly
            260

<210> SEQ ID NO 73
<211> LENGTH: 240
<212> TYPE: PRT
<213> ORGANISM: Prunus persica

<400> SEQUENCE: 73

Met Gly Arg Gly Arg Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
            20                  25                  30

Tyr Glu Leu Ser Val Leu Cys Glu Ala Glu Val Ala Leu Ile Ile Phe
        35                  40                  45

Ser Asn Arg Gly Lys Leu Tyr Glu Phe Cys Ser Ser Ser Met Leu
    50                  55                  60

Lys Thr Leu Glu Arg Tyr Gln Lys Cys Asn Tyr Gly Ala Pro Glu Thr
65                  70                  75                  80

Asn Val Ser Ala Arg Glu Ala Leu Glu Leu Ser Ser Gln Gln Glu Tyr
                85                  90                  95

Leu Lys Leu Lys Ala Arg Tyr Glu Ala Leu Gln Arg Asn Gln Arg Asn
            100                 105                 110

Leu Leu Gly Glu Asp Leu Gly Pro Leu Ser Ser Lys Glu Leu Glu Ser
            115                 120                 125

Leu Glu Arg Gln Leu Asp Met Ser Leu Lys Gln Ile Arg Ser Thr Arg
        130                 135                 140

Thr Gln Cys Met Leu Asp Gln Leu Thr Asp Leu Gln Arg Lys Glu His
145                 150                 155                 160

Met Leu Asn Glu Ala Asn Lys Thr Leu Lys Gln Arg Leu Phe Glu Gly
                165                 170                 175

Tyr His Val Asn Ser Leu Gln Met Asn Pro Asn Ala Asp Glu Tyr Gly
            180                 185                 190

Arg Gln Gln Thr Gln Ala His Gly Asp Gly Phe Phe His Pro Leu Asp
        195                 200                 205

Cys Glu Pro Thr Leu Gln Ile Gly Tyr Gln Asn Asp Pro Ile Ser Val
    210                 215                 220

Val Thr Ala Gly Pro Ser Val Ser Asn Tyr Met Ala Gly Trp Leu Pro
225                 230                 235                 240

<210> SEQ ID NO 74
<211> LENGTH: 249
<212> TYPE: PRT
<213> ORGANISM: Prunus persica

<400> SEQUENCE: 74

Met Gly Arg Gly Lys Val Glu Leu Lys Arg Ile Glu Asn Lys Ile Asn
1               5                   10                  15

Gln Gln Val Thr Phe Ala Lys Arg Arg Asn Gly Leu Leu Lys Lys Ala
            20                  25                  30

Tyr Glu Leu Ser Val Leu Cys Asp Ala Glu Val Ala Leu Ile Val Phe
        35                  40                  45

Ser Thr Arg Gly Lys Leu Tyr Glu Phe Cys Ser Gly Ser Ser Met Glu
```

-continued

```
              50                  55                  60

Lys Thr Leu Glu Arg Tyr Gln Arg Cys Ser Tyr Ser Ala Leu Glu Ala
65                  70                  75                  80

Ser Gln Pro Ala Gln Asp Ser Gln Ser Arg Tyr Gln Asp Tyr Leu Asn
                85                  90                  95

Leu Lys Ala Lys Val Glu Val Leu Gln Arg Thr Gln Arg Asn Phe Leu
                100                 105                 110

Gly Glu Asp Leu Gly His Leu Gly Thr Lys Glu Leu Gln Gln Leu Glu
            115                 120                 125

Asn Gln Leu Asp Met Ser Leu Arg Gln Ile Arg Ser Thr Lys Thr Gln
        130                 135                 140

Val Met His Gly Gln Ile Ser Asp Leu Leu Arg Lys Glu Gln Met Leu
145                 150                 155                 160

Leu Glu Ala Asn His Glu Leu Arg Arg Lys Leu Glu Glu Cys Asp Ala
                165                 170                 175

Thr Ile Glu Arg Tyr Ser Arg Thr Thr Lys Glu Gln Asn Gln Asn Val
                180                 185                 190

Pro Asn Ser Ser His His Gln Ala Ala Gln Phe Glu Gly Val Leu Asp
            195                 200                 205

His Ser Gln Cys Asn Asn Thr Leu Gln Ile Gly Tyr Asn Pro Pro Glu
        210                 215                 220

Val Thr Asp His His Gly Leu Gln Ser Ser Thr Gln Ser His Ser Gly
225                 230                 235                 240

Leu Phe Val Pro Gly Thr Trp Val Leu
                245

<210> SEQ ID NO 75
<211> LENGTH: 238
<212> TYPE: PRT
<213> ORGANISM: Prunus persica

<400> SEQUENCE: 75

Met Gly Arg Gly Arg Val Gln Leu Lys Arg Ile Glu Asn Lys Ile Asn
1               5                   10                  15

Arg Gln Val Thr Phe Ser Lys Arg Arg Thr Gly Leu Leu Lys Lys Ala
                20                  25                  30

His Glu Ile Ser Val Leu Cys Asp Ala Gln Val Ala Leu Val Val Phe
            35                  40                  45

Ser Asn Lys Gly Lys Leu Cys Glu Tyr Ala Thr Asp Ser Cys Met Asp
        50                  55                  60

Gln Ile Leu Asp Arg Tyr Glu Arg Tyr Ser Tyr Ala Glu Arg Gln Leu
65                  70                  75                  80

Val Glu Pro Asp Ile Glu Ser Gln Cys Asn Trp Thr Phe Glu Tyr Ser
                85                  90                  95

Arg Leu Lys Ala Lys Val Glu Leu Leu Gln Arg Asn Gln Arg His Tyr
                100                 105                 110

Leu Gly Glu Asp Leu Asp Ser Leu Thr Leu Lys Glu Ile Gln Ser Leu
            115                 120                 125

Glu His Gln Leu Glu Thr Ala Leu Lys Gln Ile Arg Ser Arg Lys Asn
        130                 135                 140

Gln Leu Met His Glu Ser Ile Ser Glu Leu Gln Arg Lys Glu Arg Ala
145                 150                 155                 160

Met Gln Glu Gln Asn Asn Leu Leu Ala Lys Lys Ile Lys Glu Lys Glu
                165                 170                 175
```

-continued

```
Lys Ala Ala Ala Glu Glu Val His Asn Trp Glu Gln Gln Asn Asn Gly
            180                 185                 190

Leu Asn Leu Leu Pro Gln Pro Leu Pro Cys Leu Asn Met Gly Gly Thr
        195                 200                 205

Gln Gln Asp Glu Phe Leu Gln Val Arg Arg Asn Gln Leu Asp Leu Thr
    210                 215                 220

Leu Glu Pro Leu Tyr Ser Cys Asn Leu Gly Cys Phe Ala Ala
225                 230                 235

<210> SEQ ID NO 76
<211> LENGTH: 70
<212> TYPE: PRT
<213> ORGANISM: Prunus persica

<400> SEQUENCE: 76

Met Gly Arg Gly Lys Ile Val Ile Arg Arg Ile Asp Asn Ser Thr Ser
1               5                   10                  15

Arg Gln Val Thr Phe Ser Lys Arg Arg Asn Gly Leu Leu Lys Lys Ala
            20                  25                  30

Lys Glu Leu Ala Ile Leu Cys Asp Ala Glu Val Gly Val Met Ile Phe
        35                  40                  45

Ser Ser Thr Gly Lys Leu Tyr Asp Phe Ala Ser Thr Arg Phe Arg Phe
    50                  55                  60

Ile Ala Ile Trp Thr Ala
65                  70

<210> SEQ ID NO 77
<211> LENGTH: 204
<212> TYPE: PRT
<213> ORGANISM: Prunus persica

<400> SEQUENCE: 77

Met Ala Arg Gly Lys Val Gln Met Lys Lys Ile Glu Asn Pro Val His
1               5                   10                  15

Arg Gln Val Thr Phe Cys Lys Arg Arg Ala Gly Leu Leu Lys Lys Ala
            20                  25                  30

Lys Glu Leu Ser Val Leu Cys Asp Ala Asp Ile Gly Ile Leu Ile Phe
        35                  40                  45

Ser Ser His Gly Lys Leu Phe Glu Leu Ala Thr Lys Gly Asn Met Gln
    50                  55                  60

Gly Leu Ile Glu Lys Tyr Met Lys Met Lys Pro Pro Arg Val Ser Gln
65                  70                  75                  80

Ala Asp Gln Ala Ile Glu Thr Gln Thr Leu Asp Ala Lys Lys Glu Ile
                85                  90                  95

Asn Leu Leu Lys Gln Glu Ile Glu Ile Leu Gln Lys Gly Leu Arg Tyr
            100                 105                 110

Met Phe Gly Gly Gly Ala Gly Thr Met Thr Leu Asp Glu Leu Gln Val
        115                 120                 125

Leu Glu Lys His Leu Glu Val Trp Ile Tyr His Val Arg Ser Ala Lys
    130                 135                 140

Met Asp Val Leu Phe Gln Glu Ile Gln Leu Leu Arg Asn Ser Glu Gly
145                 150                 155                 160

Ile Leu Thr Ala Ala Asn Lys Tyr Leu Gln Asp Lys Ile Val Glu Glu
                165                 170                 175

Asn Ile Gly Val Thr Asn Ile Thr Pro Met Ala Ser Asp Asn Pro Tyr
            180                 185                 190
```

```
Pro Leu Thr Ile Pro Asp Asp Asp Ile Phe Gln Ile
        195                 200

<210> SEQ ID NO 78
<211> LENGTH: 222
<212> TYPE: PRT
<213> ORGANISM: Prunus persica

<400> SEQUENCE: 78

Met Gly Arg Gly Lys Ile Glu Ile Lys Arg Ile Glu Asn Thr Thr Asn
1               5                   10                  15

Arg Gln Val Thr Phe Cys Lys Arg Arg Asn Gly Leu Leu Lys Lys Ala
            20                  25                  30

Tyr Glu Leu Ser Ile Leu Cys Asp Ala Glu Val Ala Leu Ile Val Phe
        35                  40                  45

Ser Ser Arg Gly Arg Leu Tyr Glu Tyr Ser Asn Asn Asn Ser Ile Arg
    50                  55                  60

Asn Thr Ile Glu Arg Tyr Lys Lys Ala Cys Ser Asp Ser Ser Gly Ser
65                  70                  75                  80

Thr Ser Ile Thr Glu Ile Asn Ala Gln Tyr Tyr Gln Gln Glu Ser Ala
            85                  90                  95

Lys Leu Arg Gln Gln Ile Gln Met Leu Gln Asn Ser Asn Arg His Leu
            100                 105                 110

Met Gly Asp Ala Leu Ser Thr Leu Ser Val Lys Glu Leu Lys Gln Leu
            115                 120                 125

Glu Asn Arg Leu Glu Arg Gly Ile Asn Arg Ile Arg Ser Lys Lys His
    130                 135                 140

Glu Met Leu Leu Ala Glu Ile Glu Tyr Leu Gln Lys Lys Glu Ile Glu
145                 150                 155                 160

Leu Glu Asn Glu Asn Val Cys Leu Arg Thr Lys Ile Ser Glu Val Glu
            165                 170                 175

Arg Leu Gln Gln Ala Asn Met Val Gly Pro Glu Leu Asn Ala Ile Gln
            180                 185                 190

Ala Leu Ala Ser Arg Asn Phe Phe Ser Gln Asn Met Met Glu Gly Gly
        195                 200                 205

Ala Thr Tyr Pro Gln Gln Asp Lys Lys Ile Leu His Leu Gly
    210                 215                 220

<210> SEQ ID NO 79
<211> LENGTH: 244
<212> TYPE: PRT
<213> ORGANISM: Prunus persica

<400> SEQUENCE: 79

Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Leu Leu Lys Lys Ala
            20                  25                  30

Tyr Glu Leu Ser Val Leu Cys Asp Ala Glu Val Ala Leu Ile Ile Phe
        35                  40                  45

Ser Ser Arg Gly Lys Leu His Glu Phe Gly Ser Ala Gly Met Thr Lys
    50                  55                  60

Thr Leu Glu Arg Tyr Gln His Ser Cys Phe Asn Pro Glu Glu Asn Ser
65                  70                  75                  80

Thr Glu Arg Glu Ala Gln Ser Trp Tyr Gln Glu Val Thr Lys Leu Lys
            85                  90                  95
```

-continued

```
Ala Lys Tyr Glu Ser Leu Leu Arg Thr Gln Arg Gln Leu Leu Gly Glu
            100                 105                 110

Asp Leu Gly Pro Leu Asn Val Lys Glu Leu Gln Asn Leu Glu Lys Gln
            115                 120                 125

Leu Glu Gly Ala Leu Ala Gln Ala Arg Gln Arg Lys Thr Gln Leu Met
        130                 135                 140

Ile Glu Gln Met Glu Asp Leu Arg Lys Lys Glu Arg His Leu Gly Asp
145                 150                 155                 160

Leu Asn Lys Gln Leu Arg Val Lys Leu Glu Thr Glu Gly Gln Asn Leu
                165                 170                 175

Lys Ala Ile Gln Asn Met Trp Ser Ser Asn Ala Ala Ala Gly Ser Ser
            180                 185                 190

Ser Phe Ser Phe His Ser Ser Gln Thr Asn Pro Met Asp Cys Gln Pro
            195                 200                 205

His Glu Pro Val Leu Gln Ile Gly Tyr His Gln Tyr Leu Pro Ala Glu
        210                 215                 220

Gly Pro Ser Ile Ser Lys Ser Met Ala Cys Glu Thr Asn Phe Ile Gln
225                 230                 235                 240

Gly Trp Val Leu

<210> SEQ ID NO 80
<211> LENGTH: 215
<212> TYPE: PRT
<213> ORGANISM: Prunus persica

<400> SEQUENCE: 80

Met Val Arg Gly Lys Thr Gln Met Arg Arg Ile Glu Asn Ala Thr Ser
1               5                   10                  15

Arg Gln Val Thr Phe Ser Lys Arg Arg Ser Gly Leu Leu Lys Lys Ala
            20                  25                  30

Phe Glu Leu Ser Val Leu Cys Asp Ala Glu Val Ala Leu Ile Ile Phe
            35                  40                  45

Ser Pro Arg Gly Lys Leu Tyr Glu Phe Ala Ser Ser Ser Met Gln Thr
        50                  55                  60

Thr Ile Glu Arg Tyr Gln Lys His Thr Lys Asp Asn His Thr Ser Asn
65                  70                  75                  80

Lys Ser Val Ser Thr Asp Gln Asn Met Gln His Leu Lys Gln Glu Ser
                85                  90                  95

Ser Ser Met Met Lys Gln Ile Glu Leu Leu Glu Val Ser Lys Arg Lys
            100                 105                 110

Leu Leu Gly Glu Gly Leu Gly Ser Cys Thr Ile Glu Glu Leu Gln Glu
            115                 120                 125

Ile Glu Gln Gln Leu Glu Arg Ser Val Ser Asn Val Arg Ala Arg Lys
        130                 135                 140

Thr Gln Val Phe Lys Glu Gln Ile Asp Gln Leu Arg Glu Lys Gly Lys
145                 150                 155                 160

Ala Leu Ala Ala Glu Asn Glu Arg Leu Ile Glu Lys Cys Gly Lys Ile
                165                 170                 175

Gln Pro Arg Lys Ala Ser Asn Glu Gln Arg Glu Asn Leu Ala Tyr Thr
            180                 185                 190

Glu Ser Ser Pro Ser Ser Asp Val Glu Thr Glu Leu Phe Ile Gly Leu
            195                 200                 205

Pro Glu Arg Arg Met Lys Arg
        210                 215
```

-continued

<210> SEQ ID NO 81
<211> LENGTH: 217
<212> TYPE: PRT
<213> ORGANISM: Prunus persica

<400> SEQUENCE: 81

Met Val Arg Gly Lys Ile Glu Met Lys Arg Ile Glu Asn Ala Thr Ser
1               5                   10                  15

Arg Gln Val Thr Phe Ser Lys Arg Arg Asn Gly Leu Leu Lys Lys Ala
            20                  25                  30

Phe Glu Leu Ser Val Leu Cys Asp Ala Gln Val Ser Val Ile Ile Phe
        35                  40                  45

Ser Gln Lys Gly Arg Leu Tyr Glu Phe Ser Ser Ser Asp Met Gln Asp
    50                  55                  60

Thr Ile Lys Arg Tyr His Lys His Ala Lys Ala Gly Gln Thr Asn Lys
65                  70                  75                  80

Ile Glu Val Glu Glu Tyr Val Glu Gln Leu Lys His Glu Ser Thr Ala
                85                  90                  95

Met Ala Lys Lys Ile Glu Asn Leu Glu Ala Ser Gln Arg Lys Leu Leu
            100                 105                 110

Gly His Gly Leu Asp Ser Cys Ser Val Glu Glu Leu Gln Glu Ile Thr
        115                 120                 125

Gly Gln Leu Glu Arg Ser Val Arg Lys Ile Arg Glu Arg Lys Ala His
    130                 135                 140

Leu Phe Ala Glu Gln Met Glu Gln Leu Arg Ala Lys Glu Arg Leu Leu
145                 150                 155                 160

Ile Glu Glu Asn Ala Lys Leu Ser Glu Glu Phe Gly Ala Gln Pro Arg
                165                 170                 175

Gln Leu Leu Leu Gln Gln Gln Leu Ser Val Glu Glu Lys Gly Ala Val
            180                 185                 190

Ser Tyr Trp Ser Gln Ser Ser Leu Ser Ser Glu Val Glu Thr Glu Leu
            195                 200                 205

Phe Ile Gly Pro Pro Val Thr Arg Cys
    210                 215

<210> SEQ ID NO 82
<211> LENGTH: 244
<212> TYPE: PRT
<213> ORGANISM: Prunus persica

<400> SEQUENCE: 82

Met Glu Phe Pro Asn Gln Ala Pro Glu Ser Ser Ser Gln Arg Lys Ile
1               5                   10                  15

Gly Arg Gly Lys Ile Glu Ile Lys Arg Ile Glu Asn Thr Thr Asn Arg
            20                  25                  30

Gln Val Thr Phe Cys Lys Arg Arg Asn Gly Leu Leu Lys Lys Ala Tyr
        35                  40                  45

Glu Leu Ser Val Leu Cys Asp Ala Glu Val Ala Leu Ile Val Phe Ser
    50                  55                  60

Thr Arg Gly Arg Leu Tyr Glu Tyr Ala Asn Asn Ser Val Arg Ala Thr
65                  70                  75                  80

Ile Asp Arg Tyr Lys Lys Ala Cys Thr Asp Ser Thr Asn Gly Gly Ser
                85                  90                  95

Val Ser Glu Ala Asn Thr Gln Phe Tyr Gln Gln Glu Ser Ser Lys Leu
            100                 105                 110

-continued

```
Arg Arg Gln Ile Arg Glu Ile Gln Asn Ser Asn Arg His Ile Leu Gly
        115                 120                 125

Glu Ala Leu Ser Thr Leu Asn Ile Lys Glu Leu Lys Asn Leu Glu Gly
        130                 135                 140

Arg Leu Glu Lys Gly Ile Ser Arg Ile Arg Ser Lys Lys Asn Glu Met
145                 150                 155                 160

Leu Phe Ala Glu Ile Glu Phe Met Gln Lys Arg Glu Met Glu Leu Gln
                165                 170                 175

Asn His Asn Asn Tyr Leu Arg Ala Lys Ile Ala Glu Asn Glu Arg Ala
                180                 185                 190

Gln Gln Gln Gln Thr Asn Met Ile Gln Gly Thr Ser Tyr Asp Gln Ser
        195                 200                 205

Met Pro Ser Gln Ser Tyr Asp Arg Asn Phe Leu Pro Val Ile Leu Glu
        210                 215                 220

Ala Asn Asn Asn Asn Asn Asn His Tyr Ser Arg His Asp Gln Thr Ala
225                 230                 235                 240

Leu Gln Leu Val

<210> SEQ ID NO 83
<211> LENGTH: 321
<212> TYPE: PRT
<213> ORGANISM: Prunus persica

<400> SEQUENCE: 83

Met Gly Arg Gly Lys Val Gln Leu Lys Arg Ile Glu Asn Lys Ile Ser
1               5                   10                  15

Arg Gln Val Thr Phe Ser Lys Arg Arg Ala Gly Leu Leu Lys Lys Ala
            20                  25                  30

His Glu Ile Ser Val Leu Cys Asp Ala Asp Val Ala Leu Ile Val Phe
        35                  40                  45

Ser Thr Lys Gly Lys Leu Phe Glu Tyr Ser Ser Asp Ser Ser Met Glu
        50                  55                  60

Ser Ile Leu Glu Arg Tyr Asp Gln Tyr Ser Tyr Ala Glu Gln Gln Leu
65                  70                  75                  80

Thr Thr Asp Ser Glu Pro Gln Gly Ser Cys Trp Ser Leu Glu Tyr Pro
                85                  90                  95

Lys Leu Ala Ala Arg Ile Glu Val Leu Gln Arg Lys Leu Arg His Phe
            100                 105                 110

Thr Gly Glu Asp Leu Glu Ser Leu Ser Leu Arg Glu Leu Gln Asn Leu
        115                 120                 125

Glu Leu Gln Leu Glu Thr Ala Leu Lys Arg Ile Arg Thr Arg Lys Asn
        130                 135                 140

Gln Leu Met His Glu Ser Ile Ser Glu Leu His Lys Lys Gln Lys Ala
145                 150                 155                 160

Leu Gln Glu Gln Asn Asn Ser Leu Ala Lys Lys Leu Lys Leu Lys Glu
                165                 170                 175

Asn Glu Asn Met Leu Glu Val Glu His Asp Gly Gln Gly Arg Gln Val
                180                 185                 190

Glu Gln His Gln Ser Asn Gln Ala Ala His Asn Ser Ser Thr Leu Leu
        195                 200                 205

Leu Met Pro Pro Pro Pro Gln Pro Pro Ser Thr Pro Ala Leu Leu
        210                 215                 220

Ala Ser Leu Thr Ile Gly Phe Ser Leu Ser Leu Ser Leu Ser Leu Ser
225                 230                 235                 240
```

-continued

```
Leu Leu Met Ile Gln Leu Thr Asn Ile Trp Val Thr Cys Lys Lys Lys
            245             250             255

Ala Ser Ile Leu Arg Leu Tyr Ala Asn Ile Asp Ala Val Gly Glu Ser
            260             265             270

Arg Gln Glu Glu Gly Trp Lys Met Val Met Ile Met Thr Glu Glu Leu
            275             280             285

Lys Leu Gly Arg Pro Leu Leu Leu Thr His Ser Cys Gln Cys Gly Cys
        290             295             300

Ile Ala Ile Ser Thr Asn Asn Gly Leu Ala Gly Arg Pro Ala Ile Leu
305             310             315             320

Lys

<210> SEQ ID NO 84
<211> LENGTH: 246
<212> TYPE: PRT
<213> ORGANISM: Prunus persica

<400> SEQUENCE: 84

Met Gly Arg Gly Arg Val Glu Leu Lys Arg Ile Glu Asn Lys Ile Asn
1               5               10              15

Arg Gln Val Thr Phe Ala Lys Arg Arg Asn Gly Leu Leu Lys Lys Ala
            20              25              30

Tyr Glu Leu Ser Ile Leu Cys Asp Ala Glu Val Ala Leu Ile Ile Phe
            35              40              45

Ser Asn Arg Gly Lys Leu Tyr Glu Phe Cys Ser Ser Ser Ser Ser Ile
        50              55              60

Leu Lys Thr Leu Glu Arg Tyr Gln Lys Cys Ser Tyr Gly Gln Val Glu
65              70              75              80

Val Asn Lys Pro Ala Lys Glu Leu Glu Gln Ser Ser Tyr Arg Glu Tyr
            85              90              95

Leu Lys Leu Lys Gly Arg Phe Glu Ser Leu Gln Arg Thr Gln Arg Asn
            100             105             110

Leu Leu Gly Glu Asp Leu Gly Pro Leu Asn Thr Lys Glu Leu Glu Gln
        115             120             125

Leu Glu Arg Gln Leu Glu Ser Ser Leu Lys Gln Val Arg Ser Thr Lys
        130             135             140

Thr Gln Tyr Met Leu Asp Gln Leu Ser Asp Leu Gln Asn Lys Glu Gln
145             150             155             160

Met Leu Ile Glu Ala Asn Arg Asp Leu Ser Leu Lys Leu Asp Asp Ile
            165             170             175

Ser Ser Arg Asn Gln Ile Arg Gln Ser Trp Glu Gly Gly Asn Gln Gly
            180             185             190

Gly Met Ala Tyr Gly Ser Gln His Ala Gln Ser Gln Gly Phe Phe Gln
            195             200             205

Pro Leu Asp Cys Asn Pro Thr Leu Gln Ile Gly Tyr Ser Asn Val Gly
        210             215             220

Ser Glu Gln Met Ser Ala Thr Thr His Ala Gln Gln Val Asn Gly Phe
225             230             235             240

Ile Pro Gly Trp Met Leu
                245

<210> SEQ ID NO 85
<211> LENGTH: 243
<212> TYPE: PRT
<213> ORGANISM: Prunus persica
```

-continued

```
<400> SEQUENCE: 85

Met Ala Tyr Glu Asn Lys Ser Met Ser Leu Asp Ser Pro Gln Arg Lys
1               5                   10                  15

Leu Gly Arg Gly Lys Ile Glu Ile Lys Arg Ile Glu Asn Thr Thr Asn
                20                  25                  30

Arg Gln Val Thr Phe Cys Lys Arg Arg Asn Gly Leu Leu Lys Lys Ala
                35                  40                  45

Tyr Glu Leu Ser Val Leu Cys Asp Ala Glu Val Ala Leu Ile Val Phe
    50                  55                  60

Ser Asn Arg Gly Arg Leu Tyr Glu Tyr Ala Asn Asn Ser Val Lys Glu
65                  70                  75                  80

Thr Ile Glu Arg Tyr Lys Lys Ala Cys Ala Glu Ser Thr Asn Thr Gly
                85                  90                  95

Ser Val Ser Glu Ala Ser Thr Gln Tyr Tyr Gln Gln Glu Ala Ala Lys
                100                 105                 110

Leu Arg Ala Gln Ile Gly Asn Leu Gln Asn Ser Ser Arg His Met Met
            115                 120                 125

Gly Glu Ser Leu Ser Ser Met Asn Met Lys Asp Leu Lys Asn Leu Glu
    130                 135                 140

Ser Lys Leu Glu Lys Gly Ile Asn Arg Ile Arg Ser Lys Lys Asn Glu
145                 150                 155                 160

Leu Leu Phe Ala Glu Ile Glu Tyr Met Gln Lys Arg Glu Ile Asp Leu
                165                 170                 175

His Asn Asn Asn Gln Leu Leu Arg Ala Lys Ile Ala Glu Asn Glu Arg
                180                 185                 190

Ser Gln Gln Asn Ile Asn Val Met Ala Gly Gly Gly Ser Tyr Glu Ile
            195                 200                 205

Met Gln Ser Gln Pro Tyr Asp Ser Arg Asn Tyr Phe Gln Val Asn Ala
    210                 215                 220

Leu Gln Pro Asn His Gln Tyr Asn Ser Arg Gln Asp Pro Met Ala Leu
225                 230                 235                 240

Gln Leu Val

<210> SEQ ID NO 86
<211> LENGTH: 218
<212> TYPE: PRT
<213> ORGANISM: Prunus persica

<400> SEQUENCE: 86

Met Val Arg Gly Lys Thr Gln Met Lys Arg Ile Glu Asn Ala Ala Ser
1               5                   10                  15

Arg Gln Val Thr Phe Ser Lys Arg Arg Asn Gly Leu Leu Lys Lys Ala
                20                  25                  30

Phe Glu Leu Ser Val Leu Cys Asp Ala Glu Val Ala Leu Ile Ile Phe
            35                  40                  45

Ser Thr Arg Gly Lys Leu Tyr Glu Phe Ser Ser Ser Ser Ile Ser Asn
    50                  55                  60

Thr Leu Asp Arg Tyr Gln Lys Arg Val Gln Asp Gln Gly Leu Gly Ser
65                  70                  75                  80

Lys Ala Val Gln Val Asp Met Glu His Gly Lys Asp Asp Thr Cys Ser
                85                  90                  95

Met Ala Lys Lys Ile Asp Phe Ile Glu Ala Ser Lys Gln Lys Leu Leu
                100                 105                 110

Gly Asn Cys Leu Glu Ser Cys Ser Ile Glu Glu Leu Gln Gln Thr Glu
```

-continued

```
            115                 120                 125

Asn Gln Leu Glu Arg Ser Leu Ser Lys Ile Arg Ala Arg Lys Thr Gln
    130                 135                 140

Leu Leu Arg Glu Gln Ile Glu Lys Leu Lys Glu Glu Glu Lys Asn Leu
145                 150                 155                 160

Phe Glu Gln Asn Ala Lys Leu Arg Glu Lys Cys Gly Met Gln Pro Leu
                165                 170                 175

Gly Pro Pro Ser Lys Ile Lys Asp Gly Glu Asn Arg Ala Val Cys Gln
                180                 185                 190

Pro Gln Thr Pro Asp Met Glu Asp Val Glu Thr Glu Leu Val Ile Gly
            195                 200                 205

Pro Pro Glu Arg Arg Ser Gly Gln Asn Leu
    210                 215

<210> SEQ ID NO 87
<211> LENGTH: 202
<212> TYPE: PRT
<213> ORGANISM: Prunus persica

<400> SEQUENCE: 87

Met Gly Arg Gly Lys Val Glu Leu Lys Arg Ile Glu Asn Pro Thr Ser
1               5                   10                  15

Arg Gln Val Thr Phe Ser Lys Arg Arg Asn Gly Leu Leu Lys Lys Ala
                20                  25                  30

Phe Glu Leu Ser Val Leu Cys Asp Ala Glu Val Ala Ile Ile Ile Leu
            35                  40                  45

Ser Pro Ser Gly Lys Ile Tyr Gln Phe Ala Ser His Asp Ile Asn Arg
    50                  55                  60

Thr Ile Ala Met Tyr Arg Asn Gln Val Gly Leu Pro Glu Ser Asn Asn
65                  70                  75                  80

Ser Ser Phe Arg Arg Asp Arg Thr Met Glu Phe Arg Arg Asn Asn Glu
                85                  90                  95

Asn Glu Glu Leu Arg Arg Ser Ile Ala Asn Leu Glu Met Arg Leu Lys
                100                 105                 110

Asn Leu Ala Gly Glu Glu Leu Asp Ile Leu Gly Met Gln Glu Leu Lys
            115                 120                 125

Gln Leu Glu Arg Gln Leu Lys Thr Gly Val Glu Arg Ile Arg Ser Gln
    130                 135                 140

Ile Gly Arg Val Ile Ser Glu Asn Ile Ser Ser Leu Lys Arg Lys His
145                 150                 155                 160

Lys Ala Met Gln Glu Glu Asn Ser Arg Leu Gln Lys Arg Phe His Glu
                165                 170                 175

Leu His His Tyr Ala Asp His Ala Ser Ser Ser Ile Leu Gly Pro Asn
            180                 185                 190

Ala Tyr Met Gln Phe Phe Pro Ser Glu Phe
            195                 200

<210> SEQ ID NO 88
<211> LENGTH: 251
<212> TYPE: PRT
<213> ORGANISM: Prunus persica

<400> SEQUENCE: 88

Met Gly Arg Gly Arg Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
```

-continued

```
                20               25               30

Tyr Glu Leu Ser Val Leu Cys Asp Ala Glu Val Ala Leu Ile Ile Phe
        35               40               45

Ser Ser Arg Gly Lys Leu Tyr Glu Phe Cys Ser Ser Met Ser Met Leu
    50               55               60

Lys Thr Leu Glu Lys Tyr Gln Arg Cys Ser Tyr Gly Ser Leu Glu Ala
65               70               75               80

Asn Arg Pro Val Asn Glu Thr Gln Asn Ser Tyr Gln Glu Tyr Leu Lys
            85               90               95

Leu Lys Ala Arg Val Glu Val Leu Gln Gln Ser Gln Arg Asn Leu Leu
            100              105              110

Gly Glu Asp Leu Ala Pro Leu Asn Thr Lys Glu Leu Glu Gln Leu Glu
            115              120              125

His Gln Leu Glu Ala Ser Leu Asn Gln Ile Arg Ser Thr Lys Thr Gln
        130              135              140

Phe Met Leu Asp Gln Leu Cys Asp Leu Gln Asn Lys Glu Gln Met Leu
145              150              155              160

Val Glu Ala Asn Lys Ala Leu Arg Arg Lys Leu Glu Glu Thr Ser Gly
            165              170              175

Gln Ala Pro Pro Leu Leu Ala Trp Glu Ala Ala Gly His Gly Asn Asn
            180              185              190

Asn Val Gln His Thr Gly Leu Pro His His Pro His Ser Gln Gly Phe
            195              200              205

Phe His Pro Leu Gly Asn Asn Ser Thr Ser Gln Ile Gly Tyr Thr Pro
        210              215              220

Leu Gly Ser Asp His His Glu Gln Met Asn Val Gly Asn His Gly Gln
225              230              235              240

His Val Asn Gly Phe Ile Pro Gly Trp Met Leu
            245              250

<210> SEQ ID NO 89
<211> LENGTH: 255
<212> TYPE: PRT
<213> ORGANISM: Prunus persica

<400> SEQUENCE: 89

Met Gly Arg Gly Arg Val Gln Leu Lys Arg Ile Glu Asn Lys Ile Asn
1                5               10               15

Arg Gln Val Thr Phe Ser Lys Arg Arg Ser Gly Leu Leu Lys Lys Ala
            20               25               30

Gln Glu Ile Ser Val Leu Cys Asp Ala Glu Val Ala Leu Ile Val Phe
        35               40               45

Ser Thr Lys Gly Lys Leu Phe Glu Tyr Ser Thr Asp Ser Cys Met Glu
    50               55               60

Arg Ile Leu Glu Arg Tyr Glu Arg Tyr Ser Tyr Ser Glu Lys Gln Leu
65               70               75               80

Leu Ala Asn Asp His Glu Ser Thr Gly Ser Trp Thr Leu Glu His Ala
            85               90               95

Lys Leu Lys Ala Arg Val Glu Val Leu Gln Arg Asn Cys Ser His Phe
            100              105              110

Met Gly Glu Asp Leu Gln Ser Leu Ser Leu Lys Glu Leu Gln Asn Leu
            115              120              125

Glu Gln Gln Leu Asp Ser Ala Leu Lys His Ile Arg Ser Arg Lys Asn
        130              135              140
```

-continued

```
Gln Val Met Tyr Glu Ser Ile Ser Glu Leu Gln Lys Lys Asp Lys Ala
145             150                 155                 160

Leu Gln Glu Gln Asn Asn Leu Leu Ala Lys Lys Val Lys Glu Lys Glu
                165                 170                 175

Lys Ala Leu Ala Pro Gln Ala Glu Ser Trp Glu Gln Gln Val Gln Asn
            180                 185                 190

Gln Gly Leu Asp Cys Ser Ser Thr Leu Leu Pro Glu Ala Leu Gln Ser
        195                 200                 205

Leu Asn Phe Gly Ser Gly Ser Asn Tyr Gln Gly Ile Arg Asn Asp Gly
        210                 215                 220

Ser Gly Gly Asp His Glu Asp Glu Asn Glu Thr Pro Thr Ala Asn Arg
225                 230                 235                 240

Pro Asn Thr Leu Leu Pro Pro Trp Met Leu Arg His Leu Asn Glu
                245                 250                 255

<210> SEQ ID NO 90
<211> LENGTH: 257
<212> TYPE: PRT
<213> ORGANISM: Rubus occidentalis

<400> SEQUENCE: 90

Met Ala Tyr Glu Asn Lys Pro Asn Met Ser Leu Asp Ala Asp Val Gln
1               5                   10                  15

Arg Arg Leu Gly Arg Gly Lys Ile Glu Ile Lys Arg Ile Glu Asn Thr
                20                  25                  30

Thr Asn Arg Gln Val Thr Phe Cys Lys Arg Arg Asn Gly Leu Leu Lys
            35                  40                  45

Lys Ala Tyr Glu Leu Ser Val Leu Cys Asp Ala Glu Val Ala Leu Ile
        50                  55                  60

Val Phe Ser Asn Arg Gly Arg Leu Tyr Glu Tyr Ser Asn Asn Asn Ser
65                  70                  75                  80

Val Arg Glu Thr Ile Glu Arg Tyr Lys Lys Ala Cys Ala Asp Ser Ser
                85                  90                  95

Asn Asn Gly Ser Val Ser Glu Ala Thr Thr Gln Tyr Tyr Gln Gln Glu
            100                 105                 110

Ala Asn Lys Leu Arg Ala Gln Ile Thr Ala Leu Gln Asn Ser Asn Arg
        115                 120                 125

Gly Tyr Met Ala Glu Gly Leu Ser Asn Met Ser Ile Lys Asp Leu Arg
        130                 135                 140

Gly Val Glu Ser Lys Leu Glu Lys Ala Ile Ser Arg Ile Arg Ser Lys
145                 150                 155                 160

Lys Asn Glu Leu Leu Phe Ala Glu Ile Glu Tyr Met Gln Lys Arg Glu
                165                 170                 175

Leu Asp Leu His Asn Asn Asn Gln Leu Leu Arg Ala Lys Gly Gln Ile
            180                 185                 190

Ala Glu Asn Glu Arg Gln Gln Gln Ser Ile Asn Ala Ile Ala Gly Ala
        195                 200                 205

Gly His Gly Ser Tyr Glu Ile Met Gln Ser Ser Gln Gln Phe His Glu
        210                 215                 220

Ala Arg Asn Tyr Phe Gln Val Asn Ala Leu Gln Pro Asn Leu Gln Tyr
225                 230                 235                 240

Ser Arg His Asp Gln Ile Ser Leu Gln Leu Gln Tyr Gly Ser Lys Ile
                245                 250                 255

Arg
```

```
<210> SEQ ID NO 91
<211> LENGTH: 243
<212> TYPE: PRT
<213> ORGANISM: Rubus occidentalis

<400> SEQUENCE: 91

Met Gly Arg Gly Lys Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
            20                  25                  30

Tyr Glu Leu Ser Leu Leu Cys Asp Ala Glu Val Ala Leu Ile Val Phe
        35                  40                  45

Ser Ser Arg Gly Lys Leu Tyr Glu Phe Ala Ser Gly Pro Ser Met Glu
    50                  55                  60

Lys Thr Ile Glu Arg Tyr Gln Arg Tyr Thr Tyr Ala Ala Leu Glu Ala
65                  70                  75                  80

Asp Arg Pro Ala Gln Asp Glu Gln Ser Arg His Gln Asp Tyr Val Glu
                85                  90                  95

Leu Lys Ala Lys Val Glu Val Leu Gln Arg Thr Gln Arg His Phe Leu
            100                 105                 110

Gly Glu Glu Leu Asp His Leu Gly Ile Asn Asp Leu Gln Glu Leu Glu
        115                 120                 125

Asn Gln Leu Asp Thr Ser Leu Lys Arg Val Arg Ser Thr Gln Asn Gln
    130                 135                 140

His Met Leu Asp Gln Leu Ser Asp Leu Gln Thr Lys Glu Glu Met Leu
145                 150                 155                 160

Leu Glu Ala Asn Asp Glu Leu Ser Arg Lys Leu Glu Glu Ser Asn Ala
                165                 170                 175

Ala Leu Gln Arg Ser Trp Lys Ala Gln Glu Pro Asn Ile Pro Ile Ser
            180                 185                 190

Leu Gln Ser Ser Thr Ala Gln Ser Asp Gln Gly Phe Phe Val Val Pro
        195                 200                 205

Val Gln Cys Asn Asn Asn Thr Leu Gln Ile Gly His Ser Arg Glu Val
    210                 215                 220

Thr Arg Glu Val Asn Val Ala Thr Ser Thr Gln Thr Arg Ser Ala Phe
225                 230                 235                 240

Val Pro Gly

<210> SEQ ID NO 92
<211> LENGTH: 244
<212> TYPE: PRT
<213> ORGANISM: Rubus occidentalis

<400> SEQUENCE: 92

Met Gly Arg Gly Arg Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
            20                  25                  30

Tyr Glu Leu Ser Val Leu Cys Asp Ala Glu Val Ala Leu Ile Ile Phe
        35                  40                  45

Ser Asn Arg Gly Lys Leu Tyr Glu Phe Cys Ser Ser Ser Met Leu
    50                  55                  60

Lys Thr Leu Glu Arg Tyr Gln Lys Cys Asn Tyr Gly Ala Pro Glu Thr
65                  70                  75                  80

Asn Val Ser Thr Arg Glu Ala Leu Glu Leu Ser Ser Gln Gln Glu Tyr
```

-continued

```
                   85                    90                    95
Ile Lys Leu Lys Ala Arg Tyr Glu Gln Leu Gln Arg Asn Gln Arg Asn
                  100                   105                   110
Leu Leu Gly Glu Asp Leu Gly Pro Leu Ser Ser Lys Glu Leu Glu Ser
                  115                   120                   125
Leu Glu Arg Gln Leu Asp Met Ser Leu Lys Gln Ile Arg Ser Thr Arg
                  130                   135                   140
Thr Gln Cys Met Leu Asp Gln Leu Thr Asp Leu Gln Arg Lys Glu His
145                   150                   155                   160
Met Leu Asn Glu Ala Asn Arg Thr Leu Lys Gln Arg Leu Phe Glu Gly
                  165                   170                   175
Tyr Asn Val Asn Pro Leu Gln Leu Asn Ala Ser Ala Glu Asp Val Gly
                  180                   185                   190
Tyr Gly Arg Gln Gln Ala His Gln Pro His Gly Asp Gly Phe Phe His
                  195                   200                   205
Pro Leu Glu Leu Glu Pro Thr Leu Gln Met Gly Ser Tyr His Gln Asn
                  210                   215                   220
Asp Pro Ile Ser Val Val Thr Ala Gly Pro Ser Val Asn Tyr Met Gly
225                   230                   235                   240
Gly Trp Leu Pro

<210> SEQ ID NO 93
<211> LENGTH: 183
<212> TYPE: PRT
<213> ORGANISM: Rubus occidentalis

<400> SEQUENCE: 93

Met Gly Arg Gly Lys Val Gln Leu Lys Arg Ile Glu Asp Lys Ile Arg
1                   5                    10                    15
Arg Gln Val Thr Phe Ser Lys Arg Arg Ser Gly Leu Ile Lys Lys Ala
                  20                    25                    30
Arg Glu Leu Ser Val Leu Cys Gly Val Glu Val Gly Leu Val Val Phe
                  35                    40                    45
Ser Ala Lys Gly Arg Leu Tyr Glu Phe Cys Ser Gly Asp Ser Leu Gly
                  50                    55                    60
Asn Val Leu Glu Arg Tyr Gln Ile His Asn Glu Glu Glu Val Ala Asn
65                   70                    75                    80
Pro Lys Asn Gly Lys Lys His His Leu Glu Ser Ser Gly Asn Gly Thr
                  85                    90                    95
Gly Ala Asn Lys Ser Leu Lys Met Ile Gln Ser Glu Leu Glu Ala Gln
                  100                   105                   110
Asn Ile Glu Asn Leu Asp Val Thr Glu Leu Thr Glu Leu Glu Thr Gln
                  115                   120                   125
Leu Asp Ala Leu Leu Arg Gln Ile Arg Ser Arg Lys Thr Gln Leu Met
                  130                   135                   140
Met Glu Thr Val Thr Ala Leu Ile Glu Lys Glu Lys Lys Leu Ile Glu
145                   150                   155                   160
Glu Asn Lys Tyr Leu Arg Glu Lys Glu Glu Pro His Cys Ser Thr Phe
                  165                   170                   175
Ile Ser Phe Val Ala Phe Lys
                  180

<210> SEQ ID NO 94
<211> LENGTH: 205
<212> TYPE: PRT
```

<213> ORGANISM: Rubus occidentalis

<400> SEQUENCE: 94

```
Met Gly Arg Gly Lys Val Glu Leu Lys Arg Ile Glu Asn Pro Ala Ser
1               5                   10                  15

Arg Lys Val Thr Phe Ser Lys Arg Arg Asn Gly Leu Leu Lys Lys Ala
            20                  25                  30

Phe Glu Leu Ser Ile Leu Cys Asp Ala Gln Val Ala Leu Ile Ala Phe
        35                  40                  45

Ser Pro Ser Gly Lys Val Tyr Gln Phe Ala Ser His Asp Ile Asn Arg
    50                  55                  60

Thr Ile Ala Met Tyr Arg Arg Glu Val Gly Leu Pro Gln Ser Ser Ile
65                  70                  75                  80

Pro Ala Cys Cys Thr Arg Thr Ala Thr Met Glu Phe Trp Arg Asn Glu
                85                  90                  95

Thr Glu Glu Leu Arg Arg Ser Ile Gln Asn Leu Glu Met Arg Leu Lys
            100                 105                 110

Asn Leu Ala Gly Ala Glu Leu Ser Met Leu Gly Met Gln Glu Leu Lys
        115                 120                 125

Gln Leu Glu Arg Gln Leu Lys Thr Gly Ile Glu Arg Ile His Ser Lys
    130                 135                 140

Met Arg Arg Val Ile Ser Glu Asn His Ser Ser Leu Lys Arg Lys Val
145                 150                 155                 160

Lys Leu Asp Glu Leu Asp Gln Tyr Gly Asp Ala Ser Cys Met Ile Thr
                165                 170                 175

Leu Gly Ala Ser Thr Ala Gly Phe Phe Val Phe Val Arg Ile Asp Ile
            180                 185                 190

Ala Ala Val Met Pro Thr Val Gly Leu Glu Lys Ala Ile
        195                 200                 205
```

<210> SEQ ID NO 95
<211> LENGTH: 294
<212> TYPE: PRT
<213> ORGANISM: Rubus occidentalis

<400> SEQUENCE: 95

```
Met Gly Arg Gly Arg Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
            20                  25                  30

Tyr Glu Leu Ser Val Leu Cys Asp Ala Glu Val Ala Leu Ile Ile Phe
        35                  40                  45

Ser Gly Arg Gly Lys Leu Tyr Glu Phe Cys Ser Ser Leu Ser Met Met
    50                  55                  60

Lys Thr Leu Glu Lys Tyr Gln Arg Cys Ser Tyr Gly Ala Leu Glu Ala
65                  70                  75                  80

Asn Gln Thr Val Ser Glu Thr Gln Asn Ser Tyr Gln Glu Tyr Leu Lys
                85                  90                  95

Leu Lys Ala Arg Val Glu Val Leu Gln Gln Ser Gln Arg Asn Leu Leu
            100                 105                 110

Gly Glu Asp Leu Gly Pro Leu Asn Thr Lys Glu Leu Glu Gln Leu Glu
        115                 120                 125

His Gln Leu Glu Ala Ser Leu Lys His Ile Arg Ser Thr Lys Thr Gln
    130                 135                 140

Phe Met Leu Asp Glu Leu Ser Asp Leu Gln Asn Arg Glu Gln Met Leu
```

-continued

```
145              150              155              160

Ala Glu Thr Asn Lys Ala Leu Arg Arg Lys Leu Glu Glu Thr Ser Leu
             165              170              175

Gln Gly Ala Ala Pro Leu Gln Leu Ala Trp Glu Gly Gly Tyr Gly His
             180              185              190

Lys Ala His Asn Asn Ile Gln Gln His Asn Arg Leu Pro Pro Gln Ser
             195              200              205

Gln Gly Phe Phe Gln Pro Leu His Gly Asn Asn Ser Ser Thr Leu Gln
             210              215              220

Ile Gly Tyr Leu Ser Ile Phe Gln Ile His Ser Thr Gly Leu Arg Ser
225              230              235              240

Ser Ser Ser Pro Asp Glu Leu Gly Lys Ser Arg Pro Lys Cys Glu Trp
             245              250              255

Ile His Ser Trp Val Asp Ala Leu Thr Ala Leu Val Phe Asn Lys Asp
             260              265              270

Ala Trp Asn Asp Val Arg Ala Ser Ser Ser Arg Ile Asn Gln Glu Leu
             275              280              285

Leu Ile Cys Phe Leu Thr
    290

<210> SEQ ID NO 96
<211> LENGTH: 223
<212> TYPE: PRT
<213> ORGANISM: Rubus occidentalis

<400> SEQUENCE: 96

Met Val Arg Gly Lys Thr Gln Met Lys Arg Ile Glu Asn Ala Ala Ser
1               5               10              15

Arg Gln Val Thr Phe Ser Lys Arg Arg Asn Gly Leu Leu Lys Lys Ala
             20              25              30

Phe Glu Leu Ser Val Leu Cys Asp Ala Glu Val Ala Val Ile Ile Phe
             35              40              45

Ser Thr Arg Gly Lys Leu Tyr Glu Phe Ser Ser Cys Ser Ser Leu Asn
    50              55              60

Asn Thr Ile Asp Arg Phe Gln Lys Arg Met Lys Asp Gln Glu Gly Leu
65              70              75              80

Gly Gly Lys Ala Val Arg Asp His Asp His Met Glu His Val Asn Glu
             85              90              95

Asp Asn Gly Ser Ile Ala Lys Arg Ile Glu Phe Ile Glu Ser Ser Lys
             100             105             110

Arg Lys Leu Leu Gly Asp Gly Leu Glu Ser Cys Ser Ile Asp Glu Leu
             115             120             125

His Gln Met Glu Asn Gln Leu Glu Gln Ser Leu Ser Lys Ile Arg Ala
             130             135             140

Arg Lys Met Leu Arg Glu Gln Ile Glu Lys Leu Lys Gly Glu Glu Lys
145             150             155             160

Ser Leu Leu Glu Gln Asn Ala Lys Leu Met Glu Lys Cys Gly Met Gln
             165             170             175

Leu Ile Gly Pro Pro Ser Asn Gly Glu Asp Asp Asp Asp Asn Asp
             180             185             190

Asp Val Glu Cys Glu Ser Pro Thr Glu Thr Met Glu Val Glu Thr Glu
             195             200             205

Leu Phe Ile Gly Pro Pro Lys Arg Arg Ser Ala Lys Lys Thr Pro
    210             215             220
```

-continued

<210> SEQ ID NO 97
<211> LENGTH: 245
<212> TYPE: PRT
<213> ORGANISM: Rubus occidentalis

<400> SEQUENCE: 97

Met Gly Arg Gly Lys Ile Glu Ile Lys Arg Ile Glu Asn Thr Thr Asn
1               5                   10                  15

Arg Gln Val Thr Phe Cys Lys Arg Arg Asn Gly Leu Leu Lys Lys Ala
                20                  25                  30

Tyr Glu Leu Ser Ile Leu Cys Glu Ala Glu Val Ala Leu Ile Val Phe
            35                  40                  45

Ser Ser Arg Gly Arg Leu Tyr Glu Tyr Ser Asn Asn Asn Ser Ile Arg
        50                  55                  60

Asn Thr Ile Glu Arg Tyr Lys Lys Ala Cys Ser Asp Ser Ser Gly Ala
65                  70                  75                  80

Thr Thr Ile Thr Glu Ile Asn Ala Gln Tyr Tyr Gln Gln Glu Ser Ala
                85                  90                  95

Lys Leu Arg His Gln Ile Gln Met Leu Gln Asn Ser Asn Arg His Leu
            100                 105                 110

Met Gly Asp Ser Leu Ser Asn Leu Thr Val Lys Glu Leu Lys Gln Leu
            115                 120                 125

Glu Asn Arg Leu Glu Arg Gly Leu Thr Arg Ile Arg Ser Lys Lys His
    130                 135                 140

Glu Met Leu Leu Ala Glu Ile Glu Tyr Leu Gln Lys Arg Glu Val Glu
145                 150                 155                 160

Leu Glu Asn Glu Asn Val Leu Val Arg Ala Lys Ile Ala Glu Leu Glu
                165                 170                 175

Arg Leu Gln His Ala Asp Met Val Ser Gly Asp Gln Asp Leu Glu Leu
            180                 185                 190

Asn Ala Ile Gln Ala Leu Val Ser Arg Asn Phe Phe Ala Ser Thr Met
            195                 200                 205

Ile Glu Gly Glu Ala Ser Tyr Ser Gln Pro Glu Lys Lys Phe Leu Asn
    210                 215                 220

Leu Gly Ala Gly Lys Gly Leu Val Lys Gln Gly Lys Thr Ser Ser Ser
225                 230                 235                 240

Phe Gly Tyr Val Leu
                245

<210> SEQ ID NO 98
<211> LENGTH: 138
<212> TYPE: PRT
<213> ORGANISM: Rubus occidentalis

<400> SEQUENCE: 98

Met Pro Ser Glu Ala Lys Lys Glu Ile Asn Leu Leu Lys Gln Glu Ile
1               5                   10                  15

Asp Arg Asn Thr Ala Glu Arg Ser Gln Val Tyr Val Trp Thr Arg Leu
                20                  25                  30

Gly Thr Gly Thr Met Ser Trp Asp Glu Leu Gln Val Leu Glu Lys His
            35                  40                  45

Leu Glu Ile Trp Ile Phe Thr Thr Tyr Val Gln Gln Arg Tyr Pro Ile
        50                  55                  60

Trp Leu Ile His Lys Gln Gln Met Asp Ile Leu Leu Gln Glu Ile Gln
65                  70                  75                  80

-continued

Leu Leu Arg Asn Ser Glu Gly Ile Leu Thr Ala Ala Asn Lys Tyr Leu
                85              90              95

Gln Asp Lys Ile Glu Glu Asn Ser Gly Val Thr Asn Leu Ile Pro Met
            100             105             110

Ala Ser Asp Ser Pro Tyr Pro Leu Thr Ile Pro Ser Glu Asp Ile Asn
        115             120             125

Ser Ile Leu Gly Ser Asn Phe Gly Leu Asn
    130             135

<210> SEQ ID NO 99
<211> LENGTH: 211
<212> TYPE: PRT
<213> ORGANISM: Rubus occidentalis

<400> SEQUENCE: 99

Met Ala Arg Gly Lys Val Gln Met Lys Lys Ile Glu Asn Pro Val His
1               5               10              15

Arg Gln Val Thr Phe Cys Lys Arg Arg Ala Gly Leu Leu Lys Lys Ala
            20              25              30

Lys Glu Leu Ser Val Leu Cys Asp Ala Asp Ile Gly Val Leu Ile Tyr
        35              40              45

Ser Ser His Gly Lys Leu Phe Glu Leu Ala Thr Lys Gly Thr Met Gln
    50              55              60

Gly Leu Ile Glu Lys Tyr Met Lys Met Lys Pro Ala Arg Val Pro Gln
65              70              75              80

Ala Glu Thr Ala Met Glu Thr Gln Thr Val Glu Ala Lys Lys Glu Ile
            85              90              95

Asn Leu Leu Lys Gln Glu Ile Glu Ile Leu Gln Lys Gly Leu Arg Tyr
            100             105             110

Met Phe Gly Gly Gly Ala Gly Thr Met Ser Leu Asp Glu Leu Gln Val
            115             120             125

Leu Glu Lys His Leu Glu Ile Trp Ile Tyr His Val Arg Ser Ala Lys
        130             135             140

Met Asp Ile Leu Leu Gln Glu Ile Gln Leu Leu Arg Asn Ser Glu Gly
145             150             155             160

Ile Leu Thr Ala Ala Asn Lys Tyr Leu Gln Asp Lys Ile Glu Glu Asn
            165             170             175

Ser Gly Val Thr Asn Leu Ile Pro Met Ala Ser Asp Ser Pro Tyr Pro
            180             185             190

Leu Thr Ile Pro Ser Asp Asp Ile Asn Ser Ile Leu Gly Asn Asn Phe
        195             200             205

Gly Leu Asn
    210

<210> SEQ ID NO 100
<211> LENGTH: 201
<212> TYPE: PRT
<213> ORGANISM: Rubus occidentalis

<400> SEQUENCE: 100

Met Thr Thr Ala Ile Thr Ile Glu Asn Leu Pro Val Ala Ser Pro Val
1               5               10              15

Thr Phe Ser Lys Arg Arg Arg Gly Leu Phe Lys Lys Ala Arg Glu Leu
            20              25              30

Ser Val His Cys Asp Ala Glu Val Ala Val Val Val Phe Ser Ala Thr
        35              40              45

-continued

```
Gly Lys Pro Tyr Gly Ser Ser Ser Asn Ser Ser Met Glu Asp Val Ile
    50              55                  60

Ala Arg Tyr Lys Leu His Thr Lys Asp Val Glu Lys Leu Asp Gln Gln
65              70                  75                  80

Pro Cys Pro Glu Leu Gln Leu Glu Asn Asn Asp Gly Ile Arg Leu Asn
            85                  90                  95

Lys Glu Leu Ala Asp Ser Ile Arg Glu Leu Arg Gln Met Glu Gly Gln
            100                 105                 110

Asp Leu Glu Glu Leu Asn Ile Asp Glu Leu Gln Lys Leu Glu Asp Ala
            115                 120                 125

Ile Glu Gly Gly Leu Ser Arg Val Leu Lys Thr Lys Asp Glu Arg Ile
    130                 135                 140

Met Ser Gln Ile Met Ala Leu Glu Thr Lys Gly Ala Gly Leu Ile Glu
145                 150                 155                 160

Ala Asn Asn Gln Leu Gln Gln Arg Ile Trp Met Leu Ser Asn Gly Ala
                165                 170                 175

Ser Gly Val Ala Leu Glu Ser Glu Ile Ser Ser Ala Glu Glu Asp His
            180                 185                 190

Gly Asp Tyr Met Asp Asn Thr Lys Asn
        195                 200

<210> SEQ ID NO 101
<211> LENGTH: 290
<212> TYPE: PRT
<213> ORGANISM: Rubus occidentalis

<400> SEQUENCE: 101

Met Asp Ala Val Asn Phe Phe Val Phe Ile Arg Arg Tyr Asp Glu Tyr
1               5                   10                  15

Thr Trp Arg Arg Glu Asp Ala Ser Tyr Ile Leu Asp Met Lys Leu Glu
            20                  25                  30

Glu Gly Leu Asn Leu Gly Arg Glu Gly Glu Arg Glu Arg Glu Arg Glu
        35                  40                  45

Arg Glu Arg Val Arg Gln Asn Ser Gln Leu Arg Val Thr Ala Phe Ile
    50                  55                  60

Thr Thr Ser Glu Ala Arg Val Arg Val Phe Asn Phe Gln Leu Ala Lys
65                  70                  75                  80

Ile Met Gly Arg Gly Lys Val Gln Leu Lys Arg Ile Glu Asp Lys Ile
                85                  90                  95

Arg Arg Gln Val Thr Phe Ser Lys Arg Arg Ser Gly Leu Met Lys Lys
            100                 105                 110

Ala Arg Glu Leu Ser Val Leu Cys Gly Val Glu Val Gly Leu Ile Ile
            115                 120                 125

Phe Ser Ala Lys Gly Arg Leu Tyr Glu Phe Cys Ser Gly Asp Ser Leu
    130                 135                 140

Gly Asn Val Leu Glu Arg Tyr Gln Ile His Asn Glu Glu Glu Val Ala
145                 150                 155                 160

Asn Pro Lys Asn Gly Lys Lys His His Phe Glu Ser Ser Gly Asn Gly
                165                 170                 175

Thr Gly Ala Asn Lys Ser Leu Lys Met Ile Gln Ser Glu Leu Glu Ala
            180                 185                 190

Gln Asn Ile Glu Asn Leu Asp Val Thr Glu Leu Thr Gln Leu Glu Lys
            195                 200                 205

Gln Leu Asp Val Val Leu Arg Gln Thr Arg Ser Arg Lys Thr Gln Leu
    210                 215                 220
```

```
Met Met Glu Thr Ile Thr Gly Leu Ile Glu Lys Glu Lys Lys Leu Gly
225             230             235             240

Glu Glu Lys Asp Leu Met Glu Lys Lys Val Ala Glu Leu Met Arg Glu
                245             250             255

Lys Glu Asn Ser Gln Glu Asp Pro Asp Ala His Ala Asp Glu Glu Val
            260             265             270

Tyr Glu His Ser Ser Ser Cys Val Asn Thr Lys His Pro Val Leu Asn
        275             280             285

Leu Phe
    290

<210> SEQ ID NO 102
<211> LENGTH: 250
<212> TYPE: PRT
<213> ORGANISM: Rubus occidentalis

<400> SEQUENCE: 102

Met Gly Arg Gly Arg Val Glu Leu Lys Arg Ile Glu Asn Lys Ile Asn
1               5               10              15

Arg Gln Val Thr Phe Ala Lys Arg Arg Asn Gly Leu Leu Lys Lys Ala
                20              25              30

Tyr Glu Leu Ser Ile Leu Cys Asp Ala Glu Val Ala Leu Ile Ile Phe
            35              40              45

Ser Asn Arg Gly Lys Leu Tyr Glu Phe Cys Ser Ser Ser Ser Met Leu
        50              55              60

Lys Thr Leu Glu Arg Tyr Gln Lys Cys Ser Tyr Gly Ala Val Glu Ile
65              70              75              80

Asn Asn Pro Ala Lys Glu Leu Glu Ser Ser Tyr Arg Glu Tyr Leu Lys
                85              90              95

Leu Lys Thr Arg Cys Glu Ser Leu Gln Arg Thr Gln Arg Asn Leu Leu
            100             105             110

Gly Glu Glu Leu Asp Pro Leu Asn Thr Lys Glu Leu Glu Gln Leu Glu
            115             120             125

Arg Gln Leu Glu Ser Ser Leu Lys His Val Arg Ser Thr Lys Thr Gln
        130             135             140

Tyr Met Leu Asp Gln Leu Ser Asp Leu Gln Ser Lys Glu His Met Leu
145             150             155             160

Lys Glu Thr Asn Arg Asp Leu Thr Met Lys Leu Asp Glu Ile Asn Ser
                165             170             175

Gly Asn Gln Leu Arg Gln Thr Trp Glu Ser Gly His Asp His Gln Arg
            180             185             190

Met Leu Tyr Glu Thr Gln His Ala Gln Thr Gln Leu Gly Leu Met Phe
            195             200             205

Gln Pro Leu Asp Cys Asn Pro Thr Leu Gln Ile Gly Tyr Asn Val Val
        210             215             220

Gly Ser Gln Gln Gln Met Ala Ala Ala Thr Thr Thr His Ala Gln Gln
225             230             235             240

Val Asn Gly Phe Ile Pro Gly Trp Met Leu
                245             250

<210> SEQ ID NO 103
<211> LENGTH: 257
<212> TYPE: PRT
<213> ORGANISM: Rubus occidentalis

<400> SEQUENCE: 103
```

```
Met Val Glu Ser Thr Met Glu Phe Pro Lys Gln Ile Thr Pro Ala Asp
1               5                   10                  15

Glu Pro Glu Arg Ser Ser Gln Lys Lys Leu Gly Arg Gly Lys Ile Glu
                20                  25                  30

Ile Lys Arg Ile Glu Asn Thr Thr Asn Arg Gln Val Thr Phe Cys Lys
            35                  40                  45

Arg Arg Asn Gly Leu Leu Lys Lys Ala Tyr Glu Leu Ser Val Leu Cys
        50                  55                  60

Asp Ala Glu Val Ala Leu Ile Val Phe Ser Thr Arg Gly Arg Leu Tyr
65                  70                  75                  80

Glu Tyr Ala Asn Asn Ser Val Arg Ala Thr Ile Glu Arg Tyr Lys Lys
                85                  90                  95

Ala Cys Asp Ser Ser Asn Thr Gly Ser Val Ala Glu Ala Asn Val Gln
            100                 105                 110

Phe Tyr Gln Gln Glu Ala Ser Lys Leu Arg Arg Gln Ile Arg Glu Ile
        115                 120                 125

Gln Asn Ser Asn Arg His Ile Leu Gly Glu Ala Leu Ser Thr Leu Asn
    130                 135                 140

Val Lys Asp Leu Lys Asn Leu Glu Gly Arg Leu Glu Lys Gly Ile Ser
145                 150                 155                 160

Arg Ile Arg Ser Lys Lys Asn Glu Met Leu Phe Ala Glu Ile Glu Tyr
                165                 170                 175

Met Gln Lys Arg Glu Ile Glu Leu Gln Asn His Asn Asn Phe Leu Arg
            180                 185                 190

Ala Lys Ile Ala Glu Thr Asp Arg Ala Gln Gln Gln Thr Asn Met
        195                 200                 205

Met Pro Gly Thr Ser Ser Ser Ala Tyr Asp Gln Ser Met Pro Pro Ser
    210                 215                 220

Gln Ser Tyr Asp Arg Ser Phe Leu Pro Val Ile Leu Glu Ser Asn His
225                 230                 235                 240

His Tyr Asn Arg Gln Asp Gln Asn Gln Thr Pro Leu Gln Leu Leu Lys
                245                 250                 255

Cys
```

```
<210> SEQ ID NO 104
<211> LENGTH: 246
<212> TYPE: PRT
<213> ORGANISM: Rubus occidentalis

<400> SEQUENCE: 104
```

```
Met Gly Arg Gly Lys Val Gln Leu Lys Arg Ile Glu Asn Lys Ile Ser
1               5                   10                  15

Arg Gln Val Thr Phe Ser Lys Arg Arg Thr Gly Leu Leu Lys Lys Ala
                20                  25                  30

His Glu Ile Ser Val Leu Cys Asp Ala Glu Val Ala Leu Ile Val Phe
            35                  40                  45

Ser Thr Lys Gly Lys Leu Phe Glu Tyr Ser Thr Asp Ser Arg Gly Ser
        50                  55                  60

Trp Ser Asp Met Asn Asn Ile Leu Met Gln Lys Gly Arg Glu Ser Trp
65                  70                  75                  80

Ser Met Glu Tyr Pro Lys Leu Ala Ala Arg Ile Glu Ile Leu Gln Arg
                85                  90                  95

Lys Ile Arg Asn Tyr Thr Gly Glu Asp Leu Asp Pro Leu Ser Leu Arg
            100                 105                 110
```

-continued

```
Glu Leu Gln Ser Leu Glu Gln Gln Ile Asp Thr Ala Leu Lys Arg Val
        115                 120                 125

Arg Thr Arg Lys Asn Gln Leu Met His Glu Ser Ile Ser Glu Met Gln
    130                 135                 140

Lys Lys His Lys Thr Leu Gln Glu Gln Asn Asn Ser Leu Thr Lys Lys
145                 150                 155                 160

Leu Lys Glu Asn Glu Lys Val Arg Gln Ala Glu Pro Asn Asn Gln Gln
                165                 170                 175

Pro Asn Ala Ser Thr Leu Met Leu Met Pro Pro Leu Arg Pro Pro Ser
                180                 185                 190

Gln Pro Ser Pro Pro Thr Leu Leu Ser Ser Leu Thr Ile Gly Gly Ala
        195                 200                 205

Val Gln Gly Arg Arg Glu Ala Met Asp Glu Asp Gly Glu Asp His Gln
    210                 215                 220

Gly Arg Ala Gln Thr Arg Pro Thr Thr Asn Thr Leu Met Pro Pro Trp
225                 230                 235                 240

Met Val Arg His Leu Asn
                245

<210> SEQ ID NO 105
<211> LENGTH: 234
<212> TYPE: PRT
<213> ORGANISM: Rubus occidentalis

<400> SEQUENCE: 105

Met Val Arg Gly Lys Ile Glu Met Lys Arg Ile Glu Asn Val Thr Ser
1               5                   10                  15

Arg Gln Val Thr Phe Ser Lys Arg Arg Asn Gly Leu Leu Lys Lys Ala
                20                  25                  30

Tyr Glu Leu Ser Val Leu Cys Asp Ala Glu Val Ala Val Ile Ile Phe
            35                  40                  45

Ser Gln Lys Gly Arg Ile His Glu Phe Ser Ser Ser Asp Met Gln Gln
        50                  55                  60

Thr Ile Lys Arg Tyr His Lys His Ala Lys Ala Val Gln Thr Asn Thr
65                  70                  75                  80

Phe Glu Val Glu Lys Tyr Met Gln Val Arg Thr Glu Gln Tyr Thr Gln
                85                  90                  95

Leu Lys Asn Glu Ser Ala Lys Met Ala Lys Gln Ile Glu Ile Leu Glu
                100                 105                 110

Ala Ser Gln Arg Arg Leu Leu Gly His Asp Leu Asp Ser Cys Ser Ala
        115                 120                 125

Gln Glu Leu His Gln Ile Ser Asp Gln Leu Glu Arg Ser Leu Arg Asn
    130                 135                 140

Val Arg Glu Arg Lys Ala His Leu Leu Lys Glu Gln Ile Gln Gln Leu
145                 150                 155                 160

Lys Glu Lys Gly Arg Leu Leu Leu Glu Glu Asn Ala Lys Leu His Ile
                165                 170                 175

Glu Cys Cys Ala Arg Pro Trp Gln Gln His Leu Val Glu Glu Lys Gly
            180                 185                 190

Gly Gly Gly Ala Ala Ala Ser Tyr Ser Arg Met Asn Ser Ser Gln Ser
        195                 200                 205

Ser Ser Ser Gln Thr Ile Ser Asn Ser Asp Gln Leu Glu Thr Arg Leu
    210                 215                 220

Phe Ile Gly Pro Pro Val Met Arg Cys Glu
```

-continued

```
225                     230

<210> SEQ ID NO 106
<211> LENGTH: 247
<212> TYPE: PRT
<213> ORGANISM: Rubus occidentalis

<400> SEQUENCE: 106

Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Leu Leu Lys Lys Ala
                20                  25                  30

Tyr Glu Leu Ser Val Leu Cys Glu Ala Glu Val Ala Leu Ile Ile Phe
            35                  40                  45

Ser Ser Arg Gly Lys Leu Tyr Glu Phe Ser Ser Ala Gly Met Thr Asn
        50                  55                  60

Thr Leu Glu Arg Tyr Gln Arg Ser Ser Phe Ser Pro His Asp Asn Ala
65                  70                  75                  80

Ile Lys Gln Glu Thr Glu Ser Trp Tyr Glu Glu Val Ser Lys Leu Arg
                85                  90                  95

Ala Lys Tyr Glu Ser Leu Leu Arg Thr Gln Arg His Leu Leu Gly Glu
            100                 105                 110

Asp Leu Gly Pro Leu Ser Val Lys Glu Leu Gln Asn Leu Glu Lys Gln
        115                 120                 125

Leu Glu Gly Ala Leu Ala Gln Ala Arg Gln Arg Lys Thr Gln Ile Met
        130                 135                 140

Thr Glu Gln Met Glu Gln Leu Arg Lys Lys Glu Arg Gln Leu Gly Asp
145                 150                 155                 160

Leu Asn Val Gln Leu Arg Val Lys Leu Gln Lys Glu Gly Glu Asn Leu
                165                 170                 175

Lys Ala Ile Gln Asp Phe Trp Ser Ser Asn Asn Ala Ala Ala Gly Asn
            180                 185                 190

Ser Asn Phe Leu His Ser Ser Gln Ala Ser His Met Asp Pro Pro Pro
        195                 200                 205

Glu Pro Ile Leu Gln Ile Gly Tyr His His Tyr Val Ala Ala Glu Glu
        210                 215                 220

Ser Gln Asp Val Pro Lys Ser Met Ala Met Ala Ala Glu Thr Asn Phe
225                 230                 235                 240

Ile Gln Gly Trp Ala Glu Arg
                245

<210> SEQ ID NO 107
<211> LENGTH: 214
<212> TYPE: PRT
<213> ORGANISM: Rubus occidentalis

<400> SEQUENCE: 107

Met Val Arg Gly Lys Thr Gln Met Lys Arg Ile Glu Asn Ala Thr Ser
1               5                   10                  15

Arg Gln Val Thr Phe Ser Lys Arg Arg Ser Gly Leu Leu Lys Lys Ala
                20                  25                  30

Phe Glu Leu Ser Val Leu Cys Asp Ala Glu Val Ala Leu Ile Ile Phe
            35                  40                  45

Ser Pro Arg Gly Lys Leu Tyr Glu Phe Ala Ser Ser Met Gln Gly
        50                  55                  60

Thr Ile Glu Arg Tyr Glu Lys His Thr Lys Asp Asn Gln Ala Asn Lys
```

-continued

```
65                    70              75              80

Lys Ser Val Ser Thr Glu Gln Asn Glu Gln Gln Leu Lys Gln Glu Ala
                85              90              95

Ser Gly Met Met Lys Gln Ile Glu His Leu Glu Val Ser Lys Arg Lys
            100             105             110

Leu Leu Gly Glu Ser Val Gly Leu Cys Thr Ile Glu Glu Leu Gln Glu
            115             120             125

Leu Glu Gln Gln Leu Glu Thr Ser Val His Arg Ile Arg Ala Arg Lys
        130             135             140

Thr Gln Val Phe Lys Glu Gln Ile Glu Gln Leu Arg Glu Lys Glu Arg
145             150             155             160

Val Leu Ala Ala Glu Asn Glu Arg Leu Phe Glu Lys Cys Gly Ala Met
                165             170             175

Gln Gln Arg Glu Pro Glu Thr Glu Gln Arg Glu Asn Leu Ala Ser Asn
            180             185             190

Glu Ser Ser Gln Ser Ser Asp Val Glu Thr Glu Leu Leu His Leu Ala
            195             200             205

Tyr Ile His Met Thr Arg
    210

<210> SEQ ID NO 108
<211> LENGTH: 61
<212> TYPE: PRT
<213> ORGANISM: Solanum lycopersicum

<400> SEQUENCE: 108

Met Val Arg Gly Lys Thr Gln Met Arg Arg Ile Glu Asn Ala Thr Ser
1               5               10              15

Arg Gln Val Thr Phe Ser Lys Arg Arg Asn Gly Leu Leu Lys Lys Ala
            20              25              30

Phe Glu Leu Ser Val Leu Cys Asp Ala Glu Val Gly Leu Ile Ile Phe
        35              40              45

Ser Pro Arg Gly Lys Leu Tyr Glu Phe Ala Ser Ser Arg
    50              55              60

<210> SEQ ID NO 109
<211> LENGTH: 252
<212> TYPE: PRT
<213> ORGANISM: Solanum lycopersicum

<400> SEQUENCE: 109

Met Gly Arg Gly Arg Val Glu Leu Lys Arg Ile Glu Asn Lys Ile Asn
1               5               10              15

Arg Gln Val Thr Phe Ser Lys Arg Arg Asn Gly Leu Leu Lys Lys Ala
            20              25              30

Tyr Glu Leu Ser Val Leu Cys Glu Ala Glu Val Ala Leu Ile Ile Phe
        35              40              45

Ser Ser Arg Gly Lys Leu Tyr Glu Phe Gly Ser Ala Gly Ile Thr Lys
    50              55              60

Thr Leu Glu Arg Tyr Gln Arg Cys Cys Leu Asn Pro Gln Asp Asn Cys
65              70              75              80

Gly Glu Arg Glu Thr Gln Ser Trp Tyr Gln Glu Val Ser Lys Leu Lys
                85              90              95

Ala Lys Phe Glu Ala Leu Gln Arg Thr Gln Arg His Leu Leu Gly Glu
            100             105             110

Asp Leu Gly Ala Leu Ser Val Lys Glu Leu Gln Asn Leu Glu Lys Gln
```

```
          115                120                125

Leu Glu Gly Ala Leu Ala Gln Ala Arg Gln Arg Lys Thr Gln Ile Met
    130                135                140

Met Glu Gln Met Glu Glu Leu Arg Arg Lys Glu Arg His Leu Gly Asp
145                150                155                160

Val Asn Lys Gln Leu Lys Ile Lys Val Ser Leu Glu Leu Ser Ser Phe
                165                170                175

Glu Gly Glu Gly Gln Gly Val Pro Phe Pro Trp Ser Asn Cys Asn Ala
                180                185                190

Ser Leu Asp Glu Ala Gly Ser Ser Thr Phe His Val His His Ser Gln
                195                200                205

Ser Asn His Met Asp Cys Asp Leu Pro Asp Pro Val Leu Gln Ile Gly
    210                215                220

Tyr His Gln Tyr Met Ala Ala Asp Gly Ala Ser Gly Ser Arg Asn Met
225                230                235                240

Ala Val Glu Ser Asn Ile Ile His Gly Trp Gly Leu
                245                250

<210> SEQ ID NO 110
<211> LENGTH: 234
<212> TYPE: PRT
<213> ORGANISM: Solanum lycopersicum

<400> SEQUENCE: 110

Met Gly Arg Gly Arg Val Glu Met Lys Arg Ile Glu Asn Lys Ile Ser
1               5                 10                15

Arg Gln Val Thr Phe Ser Lys Arg Arg Ser Gly Leu Leu Lys Lys Thr
                20                25                30

Asn Glu Ile Ser Val Leu Cys Asp Ala Glu Val Ala Leu Ile Val Phe
                35                40                45

Ser Ser Asn Gly Lys Leu Phe Glu Tyr Ser Thr Gln Ser Ser Met Glu
    50                55                60

Asn Ile Leu Glu Arg Tyr Glu Asn Tyr Ser Tyr Glu Glu Met Asn Leu
65                70                75                80

Asn Thr Thr Tyr Lys Glu Asn Trp Thr Leu Glu Tyr Pro Lys Leu Met
                85                90                95

Ala Arg Val Glu Leu Leu Gln Arg Asn Ile Arg His Phe Met Gly Glu
                100                105                110

Asp Leu Asp Ala Phe Asn Leu Arg Glu Phe Arg Gly Leu Glu Lys Gln
    115                120                125

Leu Asp Thr Ala Leu Lys Arg Val Arg Ser Lys Lys Asn Gln Leu Met
    130                135                140

His Glu Ser Ile Ser Gln Leu Gln Lys Lys Glu Lys Glu Leu Gln Gln
145                150                155                160

Arg Asn Asn Leu Ile Ser Asn Lys Leu Lys Glu Asn Glu Lys Lys Gln
                165                170                175

Ile Val Gln Thr Asn Pro Gly Gln Ser Ser Thr Met Thr Phe Leu Leu
                180                185                190

Gln Ser Pro Thr Val Thr Asn Gln Thr Ile Gly Gly Pro Ser Gln Ala
    195                200                205

Thr Asp Gln Ser Gln Asn Arg Asp Gly Tyr Asn Ser Leu Met Pro Pro
    210                215                220

Trp Met Phe His His Val His Asn Lys Gly
225                230
```

-continued

<210> SEQ ID NO 111
<211> LENGTH: 248
<212> TYPE: PRT
<213> ORGANISM: Solanum lycopersicum

<400> SEQUENCE: 111

Met Asp Phe Gln Ser Asp Leu Thr Arg Glu Ile Ser Pro Gln Arg Lys
1               5                   10                  15

Leu Gly Arg Gly Lys Ile Glu Ile Lys Arg Ile Glu Asn Thr Thr Asn
            20                  25                  30

Arg Gln Val Thr Phe Cys Lys Arg Arg Asn Gly Leu Leu Lys Lys Ala
        35                  40                  45

Tyr Glu Leu Ser Val Leu Cys Asp Ala Glu Val Ala Leu Val Val Phe
    50                  55                  60

Ser Asn Arg Gly Arg Leu Tyr Glu Tyr Ala Asn Asn Ser Val Lys Ala
65                  70                  75                  80

Thr Ile Glu Arg Tyr Lys Lys Ala Cys Ser Asp Ser Ser Asn Thr Gly
                85                  90                  95

Ser Val Ser Glu Ala Asn Ala Gln Tyr Tyr Gln Gln Glu Ala Ser Lys
            100                 105                 110

Leu Arg Ala Gln Ile Gly Asn Leu Met Asn Gln Asn Arg Asn Met Met
        115                 120                 125

Gly Glu Ala Leu Ala Gly Met Lys Leu Lys Glu Leu Lys Asn Leu Glu
    130                 135                 140

Gln Arg Ile Glu Lys Gly Ile Ser Lys Ile Arg Ser Lys Lys Asn Glu
145                 150                 155                 160

Leu Leu Phe Ala Glu Ile Glu Tyr Met Gln Lys Arg Glu Val Asp Leu
                165                 170                 175

His Asn Asn Asn Gln Tyr Leu Arg Ala Lys Ile Ala Glu Thr Glu Arg
            180                 185                 190

Ala Gln His Gln His Gln Gln Met Asn Leu Met Pro Gly Ser Ser Ser
        195                 200                 205

Asn Tyr His Glu Leu Val Pro Pro Gln Gln Phe Asp Thr Arg Asn
    210                 215                 220

Tyr Leu Gln Val Asn Gly Leu Gln Thr Asn Asn His Tyr Pro Arg Gln
225                 230                 235                 240

Asp Gln Pro Pro Ile Gln Leu Val
                245

<210> SEQ ID NO 112
<211> LENGTH: 218
<212> TYPE: PRT
<213> ORGANISM: Solanum lycopersicum

<400> SEQUENCE: 112

Met Gly Arg Gly Arg Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
            20                  25                  30

Tyr Glu Leu Ser Val Leu Cys Asp Ala Glu Val Ala Leu Leu Val Phe
        35                  40                  45

Ser Asn Arg Gly Lys Leu Tyr Glu Phe Cys Ser Thr Asn Asn Met Leu
    50                  55                  60

Lys Thr Leu Asp Arg Tyr Gln Lys Cys Ser Tyr Gly Thr Leu Glu Val
65                  70                  75                  80

-continued

```
Asn Arg Ser Ile Lys Asp Asn Glu Gln Ser Ser Tyr Arg Glu Tyr Leu
            85                  90                  95

Lys Leu Lys Ala Lys Tyr Glu Ser Leu Gln Arg Tyr Gln Arg His Leu
            100                 105                 110

Leu Gly Asp Glu Leu Gly Pro Leu Thr Ile Asp Asp Leu Glu His Leu
            115                 120                 125

Glu Val Gln Leu Asp Thr Ser Leu Lys His Ile Arg Ser Thr Arg Thr
    130                 135                 140

Gln Met Met Leu Asp Gln Leu Ser Asp Leu Gln Thr Lys Glu Lys Leu
145                 150                 155                 160

Trp Asn Glu Ala Asn Lys Val Leu Glu Arg Lys Met Glu Glu Ile Tyr
                165                 170                 175

Ala Glu Asn Asn Met Gln Gln Ala Trp Gly Gly Glu Gln Ser Leu
            180                 185                 190

Asn Tyr Gly Gln Gln Gln His Pro Gln Ser Gln Gly Phe Phe Gln Pro
            195                 200                 205

Leu Glu Cys Asn Ser Ser Leu Gln Ile Gly
    210                 215
```

```
<210> SEQ ID NO 113
<211> LENGTH: 164
<212> TYPE: PRT
<213> ORGANISM: Solanum lycopersicum

<400> SEQUENCE: 113
```

```
Met Gly Arg Gly Arg Val Glu Leu Lys Arg Ile Glu Asn Lys Ile Ser
1               5                   10                  15

Arg Gln Val Thr Phe Ser Lys Arg Arg Ser Gly Leu Leu Lys Lys Ala
            20                  25                  30

Asn Glu Ile Ser Val Leu Cys Asp Ala Asp Val Ala Leu Ile Val Phe
            35                  40                  45

Ser Thr Lys Gly Lys Leu Phe Glu Tyr Ser Ser Asn Asp Ser Arg Cys
    50                  55                  60

Ser Tyr Ala Glu Arg Gln Met Asn Ala Asn Asp Ser Asp Pro Lys Glu
65                  70                  75                  80

Asn Trp Ser Val Glu Tyr Pro Lys Leu Met Ser Arg Ile Glu Leu Leu
                85                  90                  95

Gln Arg Asn Ile Arg His Tyr Met Gly Gln Asp Leu Asp Pro Leu Ser
            100                 105                 110

Leu Arg Glu Leu Gln Ser Ile Glu Gln Gln Ile Asp Thr Ser Leu Lys
            115                 120                 125

Arg Ile Arg Ser Arg Lys Asn Gln Leu Met His Glu Ser Ile Ser Glu
    130                 135                 140

Leu Gln Lys Lys Glu Lys Ala Leu Gln Glu Gln Asn Asn Leu Ile Thr
145                 150                 155                 160

Lys Lys Ile Thr
```

```
<210> SEQ ID NO 114
<211> LENGTH: 229
<212> TYPE: PRT
<213> ORGANISM: Solanum lycopersicum

<400> SEQUENCE: 114
```

```
Met Val Arg Gly Lys Val Glu Met Lys Arg Ile Glu Asn Ser Thr Ser
1               5                   10                  15

Arg Gln Val Thr Phe Ser Lys Arg Arg Asn Gly Leu Thr Lys Lys Ala
```

-continued

```
                20              25              30

Tyr Glu Leu Ser Val Leu Cys Asp Ala Glu Val Ala Phe Ile Ile Phe
            35              40              45

Ser His Lys Gly Arg Leu Tyr Glu Phe Ala Ser Ser Asn Met Gln Lys
        50              55              60

Ile Ile Glu Arg Tyr Arg Gly Arg Ala Arg Glu Thr Thr Thr Val Asp
65                  70              75                  80

Lys Ser Thr Glu Leu Glu His Tyr Met Glu Asn Leu Lys His Glu Thr
                85              90              95

Ala Asn Met Ala Lys Lys Ile Glu Ile Leu Glu Ile Ser Lys Arg Lys
            100             105             110

Leu Met Gly Gln Gly Leu Gly Ser Cys Ser Met Asp Glu Leu Glu Asp
        115             120             125

Ile Asp Ser Gln Leu Glu Arg Thr Leu Lys Ile Ile Arg Ala Arg Lys
    130             135             140

Thr Gln Leu Phe Lys Glu Glu Ile Glu Ser Leu Lys Ala Lys Glu Arg
145             150             155             160

Leu Leu Leu Gln Gln Asn Ala Ser Leu Arg Glu Lys Cys Gly Leu Arg
            165             170             175

Pro Met Leu Ser Glu Ser Ala Ser Ala Pro Glu Pro Ile Pro Ala Pro
            180             185             190

Pro Ser Thr Pro Pro Ala Gln Ser Lys Glu Arg Gly Asn Cys Ser Gln
            195             200             205

Ser Thr Lys Ser Trp Glu Val Glu Thr Glu Leu Phe Ile Gly Leu Pro
        210             215             220

Gln Thr Arg Cys Leu
225

<210> SEQ ID NO 115
<211> LENGTH: 179
<212> TYPE: PRT
<213> ORGANISM: Solanum lycopersicum

<400> SEQUENCE: 115

Met Gly Arg Gly Lys Val Glu Leu Lys Arg Ile Glu Asn Gln Thr Asn
1               5               10              15

Arg Gln Val Thr Phe Ser Lys Arg Arg Asn Gly Leu Leu Lys Lys Ala
            20              25              30

Tyr Glu Leu Ser Ile Leu Cys Asp Ala Glu Val Ala Leu Leu Leu Phe
            35              40              45

Ser Pro Ser Gly Lys Ala Tyr His Phe Ala Ser His Asp Ile Glu Arg
        50              55              60

Thr Ile Leu Arg Tyr Lys Asn Glu Val Gly Leu Ser Lys Asn Ser Asp
65                  70              75                  80

Gln Gly Pro Arg Ala Met Glu Val Trp Arg Thr Lys Ile Asp Asp Met
            85              90              95

Thr Arg Thr Ile His Glu Leu Glu Ala Arg Asp Lys His Phe Ala Gly
            100             105             110

Glu Glu Leu Ser Asn Leu Gly Met Lys Glu Leu Lys Gln Leu Glu Arg
        115             120             125

Gln Leu Arg Val Gly Val Glu Arg Ile Arg Ser Lys Lys His Lys Ile
    130             135             140

Leu His Glu Glu Asn Ile His Leu Gln Lys Gln Val Lys Leu Tyr Glu
145             150             155             160
```

-continued

Val Glu Gly Ser Ser Arg Ile Leu Asp Thr Asn Pro Ser Glu Leu Leu
                165             170             175

Ser Lys Gly

<210> SEQ ID NO 116
<211> LENGTH: 247
<212> TYPE: PRT
<213> ORGANISM: Solanum lycopersicum

<400> SEQUENCE: 116

Met Gly Arg Gly Arg Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
                20                  25                  30

His Glu Ile Ser Val Leu Cys Asp Ala Glu Val Gly Leu Ile Val Phe
            35                  40                  45

Ser Thr Lys Gly Lys Leu Phe Glu Tyr Ser Thr Asp Ser Cys Met Glu
        50                  55                  60

Arg Ile Leu Glu Arg Tyr Glu Arg Tyr Ser Tyr Ala Glu Arg Gln Leu
65                  70                  75                  80

Asn Ala Thr Asp Ile Ile Thr Pro Gly Ser Trp Thr Leu Glu His Ala
                85                  90                  95

Lys Leu Lys Ala Arg Leu Glu Val Leu Gln Arg Asn Gln Lys His Tyr
                100                 105                 110

Ala Gly Glu Glu Leu Asp Thr Leu Ser Met Lys Glu Leu Gln Asn Leu
        115                 120                 125

Glu His Gln Leu Asp Ser Ala Leu Lys His Ile Arg Ser Arg Lys Asn
    130                 135                 140

Gln Leu Met His Glu Ser Ile Ser Glu Leu Gln Lys Lys Asp Lys Ala
145                 150                 155                 160

Leu Gln Glu Gln Asn Asn Asn Leu Ser Lys Gln Val Lys Glu Arg Glu
                165                 170                 175

Lys Glu Met Ala Gln Gln Thr Pro Trp Glu Gln Gln Ser His Asp His
            180                 185                 190

Leu Asn Ser Ser Ser Phe Val Leu Pro His Pro Phe Asn Asn Leu His
        195                 200                 205

Ile Gly Glu Ala Tyr Pro Asn Ala Gly Asp Asn Gly Glu Val Glu Gly
    210                 215                 220

Ser Ser Arg Gln Gln Gln Gln Asn Ser Ala Ser Val Met Pro Pro Trp
225                 230                 235                 240

Met Leu Arg His Leu Asn Gly
                245

<210> SEQ ID NO 117
<211> LENGTH: 246
<212> TYPE: PRT
<213> ORGANISM: Solanum lycopersicum

<400> SEQUENCE: 117

Met Gly Arg Gly Arg Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
                20                  25                  30

Tyr Glu Leu Ser Val Leu Cys Asp Ala Glu Val Ala Leu Ile Ile Phe
            35                  40                  45

Ser Asn Arg Gly Lys Leu Tyr Glu Phe Cys Ser Thr Ser Ser Met Val

-continued

```
            50                    55                    60

Lys Thr Ile Glu Lys Tyr Gln Arg Cys Ser Tyr Ala Thr Leu Glu Ala
65                    70                    75                    80

Asn Gln Ser Val Thr Asp Thr Gln Asn Asn Tyr His Glu Tyr Leu Arg
                      85                    90                    95

Leu Lys Ala Arg Val Glu Leu Leu Gln Arg Ser Gln Arg Asn Phe Leu
                     100                   105                   110

Gly Glu Asp Leu Gly Thr Leu Ser Ser Lys Asp Leu Glu Gln Leu Glu
                 115                   120                   125

Asn Gln Leu Glu Ser Ser Leu Lys Gln Ile Arg Ser Arg Lys Thr Gln
                 130                   135                   140

Phe Met Leu Asp Gln Leu Ala Asp Leu Gln Gln Lys Glu Gln Met Leu
145                   150                   155                   160

Ala Glu Ser Asn Arg Leu Leu Arg Arg Lys Leu Glu Glu Ser Val Ala
                 165                   170                   175

Gly Phe Pro Leu Arg Leu Cys Trp Glu Asp Gly Gly Asp His Gln Leu
                 180                   185                   190

Met His Gln Gln Asn Arg Leu Pro Asn Thr Glu Gly Phe Phe Gln Pro
                 195                   200                   205

Leu Gly Leu His Ser Ser Ser Pro His Phe Gly Tyr Asn Pro Val Asn
                 210                   215                   220

Thr Asp Glu Val Asn Ala Ala Ala Thr Ala His Asn Met Asn Gly Phe
225                   230                   235                   240

Ile His Gly Trp Met Leu
                 245
```

```
<210> SEQ ID NO 118
<211> LENGTH: 238
<212> TYPE: PRT
<213> ORGANISM: Solanum lycopersicum

<400> SEQUENCE: 118

Met Gly Arg Gly Lys Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
                20                  25                  30

Tyr Glu Leu Ser Ile Leu Cys Glu Ala Glu Val Ala Leu Ile Ile Phe
            35                  40                  45

Ser Asn Arg Gly Lys Leu Tyr Glu Phe Cys Ser Thr Ser Ser Met Ser
        50                  55                  60

Asp Thr Leu Glu Arg Tyr His Arg Cys Ser Tyr Gly Asp Leu Glu Thr
65                  70                  75                  80

Gly Gln Ser Ser Lys Asp Ser Gln Asn Asn Tyr Gln Glu Tyr Met Lys
                85                  90                  95

Leu Lys Ala Arg Val Glu Val Leu Gln Gln Ser Gln Arg His Ile Leu
                100                 105                 110

Gly Glu Asp Leu Gly Gln Leu Asn Thr Lys Asp Leu Glu Gln Leu Glu
            115                 120                 125

Arg Gln Leu Asp Ser Ser Leu Arg Leu Ile Arg Ser Arg Arg Thr Gln
        130                 135                 140

Asn Met Leu Asp Gln Leu Ser Asp Leu Gln Gln Lys Glu Gln Ser Leu
145                 150                 155                 160

Leu Glu Ile Asn Arg Ser Leu Lys Thr Lys Leu Glu Glu Asn Ser Val
                165                 170                 175
```

-continued

```
Ala His Trp His Ile Thr Gly Glu Gln Asn Val Gln Phe Arg Gln Gln
            180                 185                 190

Pro Ala Gln Ser Glu Gly Phe Phe Gln Pro Leu Gln Cys Asn Thr Asn
        195                 200                 205

Ile Val Pro Asn Arg Tyr Asn Val Ala Pro Leu Asp Ser Ile Glu Pro
    210                 215                 220

Ser Thr Gln Asn Ala Thr Gly Ile Leu Pro Gly Trp Met Leu
225                 230                 235

<210> SEQ ID NO 119
<211> LENGTH: 242
<212> TYPE: PRT
<213> ORGANISM: Solanum lycopersicum

<400> SEQUENCE: 119

Met Gly Arg Gly Lys Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
            20                  25                  30

Tyr Glu Leu Ser Ile Leu Cys Asp Ala Glu Ile Ala Leu Ile Ile Phe
        35                  40                  45

Ser Ser Arg Gly Lys Leu Tyr Glu Phe Cys Ser Asn Ser Ser Met Ser
    50                  55                  60

Lys Thr Leu Glu Arg Tyr His Arg Tyr Asn Tyr Gly Thr Leu Glu Gly
65                  70                  75                  80

Thr Gln Thr Ser Ser Asp Ser Gln Asn Asn Tyr Gln Glu Tyr Leu Lys
                85                  90                  95

Leu Lys Thr Arg Val Glu Met Leu Gln Gln Ser Gln Arg His Leu Leu
            100                 105                 110

Gly Glu Asp Leu Gly Gln Leu Gly Thr Lys Asp Leu Glu Gln Leu Glu
        115                 120                 125

Arg Gln Leu Asp Ser Ser Leu Arg Gln Ile Arg Ser Thr Lys Thr Gln
    130                 135                 140

His Ile Leu Asp Gln Leu Ala Glu Leu Gln Gln Lys Glu Gln Ser Leu
145                 150                 155                 160

Thr Glu Met Asn Lys Ser Leu Arg Ile Lys Leu Glu Glu Leu Gly Val
                165                 170                 175

Thr Phe Gln Thr Ser Trp His Cys Gly Glu Gln Ser Val Gln Tyr Arg
            180                 185                 190

His Glu Gln Pro Ser His His Glu Gly Phe Phe Gln His Val Asn Cys
        195                 200                 205

Asn Asn Thr Leu Pro Ile Ser Tyr Gly Tyr Asp Asn Val Gln Pro Glu
    210                 215                 220

Asn Ala Ala Pro Ser Thr His Asp Ala Thr Gly Val Val Pro Gly Trp
225                 230                 235                 240

Met Leu

<210> SEQ ID NO 120
<211> LENGTH: 241
<212> TYPE: PRT
<213> ORGANISM: Solanum lycopersicum

<400> SEQUENCE: 120

Met Gly Arg Gly Arg Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
```

-continued

```
                   20              25              30

Tyr Glu Leu Ser Val Leu Cys Asp Ala Glu Val Ala Leu Ile Ile Phe
        35              40              45

Ser Asn Arg Gly Lys Leu Tyr Glu Phe Cys Ser Ser Ser Ser Met Leu
    50              55              60

Lys Thr Leu Glu Arg Tyr Gln Lys Cys Asn Tyr Gly Ala Pro Glu Pro
65              70              75              80

Asn Ile Ser Thr Arg Glu Ala Leu Glu Ile Ser Ser Gln Gln Glu Tyr
            85              90              95

Leu Lys Leu Lys Gly Arg Tyr Glu Ala Leu Gln Arg Ser Gln Arg Asn
        100             105             110

Leu Leu Gly Glu Asp Leu Gly Pro Leu Asn Ser Lys Glu Leu Glu Ser
        115             120             125

Leu Glu Arg Gln Leu Asp Met Ser Leu Lys Gln Ile Arg Ser Thr Arg
        130             135             140

Thr Gln Leu Met Leu Asp Gln Leu Thr Asp Tyr Gln Arg Lys Glu His
145             150             155             160

Ala Leu Asn Glu Ala Asn Arg Thr Leu Lys Gln Arg Leu Met Glu Gly
            165             170             175

Ser Gln Leu Asn Leu Gln Trp Gln Pro Asn Ala Gln Asp Val Gly Tyr
        180             185             190

Gly Arg Gln Thr Thr Gln Thr Gln Gly Asp Gly Phe Phe His Pro Leu
        195             200             205

Asp Cys Glu Pro Thr Leu Gln Ile Gly Tyr Gln Asn Asp Pro Ile Thr
        210             215             220

Val Gly Gly Ala Gly Pro Ser Val Asn Asn Tyr Met Ala Gly Trp Leu
225             230             235             240

Pro
```

```
<210> SEQ ID NO 121
<211> LENGTH: 244
<212> TYPE: PRT
<213> ORGANISM: Solanum lycopersicum

<400> SEQUENCE: 121

Met Gly Arg Gly Lys Val Glu Leu Arg Lys Ile Glu Asn Lys Ile Asn
1               5               10              15

Arg Gln Val Thr Phe Ser Lys Arg Arg Gly Gly Leu Val Lys Lys Ala
            20              25              30

His Glu Ile Ser Val Leu Cys Asp Ala Glu Val Ala Leu Ile Val Phe
        35              40              45

Ser Gln Lys Gly Lys Ile Phe Glu Tyr Ser Ser Asp Ser Cys Met Glu
    50              55              60

Gln Ile Leu Glu Arg Tyr Glu Arg Tyr Ser Tyr Ala Glu Arg Arg Leu
65              70              75              80

Leu Ala Asn Asn Ser Glu Ser Pro Val Gln Glu Asn Trp Ser Leu Glu
            85              90              95

Tyr Thr Lys Leu Lys Ala Arg Ile Asp Leu Leu Gln Arg Asn His Lys
        100             105             110

His Tyr Met Gly Glu Asp Leu Asp Ser Met Ser Leu Lys Asp Leu Gln
        115             120             125

Asn Leu Glu Gln Gln Leu Asp Ser Ala Leu Lys Leu Ile Arg Ser Arg
        130             135             140

Lys Asn Gln Leu Met His Glu Ser Ile Ser Glu Leu Gln Lys Lys Glu
```

-continued

```
145              150              155              160

Arg Ala Ile Leu Glu Glu Asn Asn Met Leu Thr Lys Lys Ile Lys Glu
             165              170              175

Lys Asp Lys Ile Val Glu Gln Gln Gly Glu Trp His Gln Gln Thr Asn
             180              185              190

Gln Val Ser Thr Ser Thr Ser Phe Leu Leu Gln Pro His Gln Cys Leu
             195              200              205

Asn Met Gly Gly Asn Tyr Gln Asp Glu Val Ala Glu Ala Arg Arg Asn
     210              215              220

Asn Glu Leu Asp Leu Asn Leu Asp Ser Leu Tyr Pro Leu Tyr Asn Met
225              230              235              240

Asn Lys His Leu

<210> SEQ ID NO 122
<211> LENGTH: 138
<212> TYPE: PRT
<213> ORGANISM: Solanum lycopersicum

<400> SEQUENCE: 122

Met Val Arg Gly Lys Val Glu Met Lys Arg Ile Glu Asn Ala Thr Ser
1               5                10               15

Arg Gln Val Thr Phe Ser Lys Arg Arg Asn Gly Val Ile Lys Lys Ala
             20               25               30

Tyr Glu Leu Ser Val Leu Cys Asp Ala Gln Val Ala Leu Ile Ile Phe
             35               40               45

Ser Asn Lys Gly Arg Leu Phe Gln Phe Ser Ser Ser Cys Met Gln Lys
     50               55               60

Thr Ile Glu Arg Tyr Arg Glu Tyr Thr Lys Glu Thr Leu Ile Asn Ile
65               70               75               80

Asn Thr Phe Glu Val Glu Gln Gln Met Glu Arg Phe Pro Phe Leu Lys
             85               90               95

Val Cys His Lys Ile Glu Phe Leu Thr Leu Asp Gly Cys Leu Val Cys
             100              105              110

Ile His Leu Gln Thr Lys Val Val Asp Leu Asp Gly Lys Leu Ala Lys
             115              120              125

Leu Leu Val Asn Ile Cys Thr Tyr Ser Ser
     130              135

<210> SEQ ID NO 123
<211> LENGTH: 237
<212> TYPE: PRT
<213> ORGANISM: Solanum lycopersicum

<400> SEQUENCE: 123

Met Met Ile Leu Cys Met Gly Arg Gly Lys Ile Glu Ile Lys Arg Ile
1               5                10               15

Glu Asn Asn Thr Asn Arg Gln Val Thr Phe Cys Lys Arg Arg Asn Gly
             20               25               30

Leu Leu Lys Lys Ala Tyr Glu Leu Ser Val Leu Cys Glu Ala Glu Ile
             35               40               45

Ala Leu Ile Val Phe Ser Thr Arg Gly Arg Val Tyr Glu Tyr Ser Asn
     50               55               60

Asn Asn Ile Lys Ala Thr Ile Glu Arg Tyr Lys Lys Ala Thr Ala Glu
65               70               75               80

Thr Ser Asn Ala Cys Thr Thr Gln Glu Leu Asn Ala Gln Phe Tyr Gln
             85               90               95
```

-continued

```
Gln Glu Ser Lys Lys Leu Arg Gln Gln Ile Gln Met Met Gln Asn Ser
            100                 105                 110

Asn Arg His Leu Val Gly Glu Gly Leu Ser Cys Leu Asn Val Arg Glu
            115                 120                 125

Leu Lys Gln Leu Glu Asn Arg Leu Glu Arg Gly Ile Ser Arg Ile Arg
    130                 135                 140

Ser Lys Lys His Glu Met Ile Leu Ala Glu Thr Glu Asn Leu Gln Lys
145                 150                 155                 160

Arg Glu Ile Leu Leu Glu Gln Glu Asn Ala Phe Leu Arg Ser Lys Ile
                165                 170                 175

Ala Glu Asn Glu Arg Leu Gln Glu Leu Ser Met Met Pro Ala Ala Gly
            180                 185                 190

Gly Gln Asp Tyr Ser Ala Ile Gln Gln Tyr Leu Ala Arg Asn Met Leu
            195                 200                 205

Gln Leu Asn Met Met Glu Gly Gln Gly Val Ser Ser Tyr Asp Pro Leu
    210                 215                 220

Pro Pro Pro His His Asp Lys Lys Ser Leu Glu Leu Gln
225                 230                 235
```

<210> SEQ ID NO 124
<211> LENGTH: 245
<212> TYPE: PRT
<213> ORGANISM: Solanum lycopersicum

<400> SEQUENCE: 124

```
Met Gly Arg Gly Arg Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Gly Leu Ile Val Phe
            35                  40                  45

Ser Thr Lys Gly Lys Leu Phe Glu Tyr Ala Asn Asp Ser Cys Met Glu
    50                  55                  60

Arg Ile Leu Glu Arg Tyr Glu Arg Tyr Ser Phe Ala Glu Lys Gln Leu
65                  70                  75                  80

Val Pro Thr Asp His Thr Ser Pro Val Ser Trp Thr Leu Glu His Ala
                85                  90                  95

Lys Leu Lys Ala Arg Leu Glu Val Leu Gln Arg Asn Gln Lys His Tyr
            100                 105                 110

Val Gly Glu Asp Leu Glu Ser Leu Ser Met Lys Glu Leu Gln Asn Leu
            115                 120                 125

Glu His Gln Leu Asp Ser Ala Leu Lys His Ile Arg Ser Arg Lys Asn
    130                 135                 140

Gln Leu Met His Glu Ser Ile Ser Val Leu Gln Lys Lys Asp Arg Ala
145                 150                 155                 160

Leu Gln Glu Gln Asn Asn Gln Leu Ser Lys Lys Val Lys Glu Arg Glu
                165                 170                 175

Lys Glu Val Ala Gln Gln Asn Gln Trp Glu Ile Asn Ser Ser Ser Phe
            180                 185                 190

Val Leu Pro Gln Gln Leu Asp Ser Pro His Leu Gly Glu Ala Tyr Gln
            195                 200                 205

Ser Thr Asn Val Ile Asp Asn Gly Glu Val Glu Gly Gly Ser Ser Ser
    210                 215                 220

Gln Gln Gln Gly Ala Ala Asn Asn Thr Val Met Pro Gln Trp Met Leu
```

-continued

```
225                 230                 235                 240

Arg His Leu Asn Asn
                245

<210> SEQ ID NO 125
<211> LENGTH: 269
<212> TYPE: PRT
<213> ORGANISM: Solanum lycopersicum

<400> SEQUENCE: 125

Met Val Phe Pro Ile Asn Gln Glu Leu Leu Val Asp Glu Ser Ser Ser
1               5                   10                  15

Gln Leu Arg Lys Thr Ser Gly Gly Thr Gly Gly Gly Arg Gly Lys
            20                  25                  30

Ile Glu Ile Lys Arg Ile Glu Asn Thr Thr Asn Arg Gln Val Thr Phe
            35                  40                  45

Cys Lys Arg Arg Asn Gly Leu Leu Lys Lys Ala Tyr Glu Leu Ser Val
        50                  55                  60

Leu Cys Asp Ala Glu Val Ser Leu Ile Val Phe Ser Ser Arg Gly Arg
65                  70                  75                  80

Leu Tyr Glu Tyr Ala Asn Asn Ser Val Arg Ala Thr Ile Asp Arg Tyr
                85                  90                  95

Lys Lys His His Ala Asp Ser Thr Ser Thr Gly Ser Val Ser Glu Ala
            100                 105                 110

Asn Thr Gln Tyr Tyr Gln Gln Glu Ala Ser Lys Leu Arg Arg Gln Ile
        115                 120                 125

Arg Asp Ile Gln Thr Tyr Asn Arg Gln Ile Val Gly Glu Ala Leu Gly
    130                 135                 140

Ser Leu Ser Pro Arg Asp Leu Lys Asn Leu Glu Gly Lys Leu Glu Lys
145                 150                 155                 160

Ala Ile Gly Arg Val Arg Ser Lys Lys Asn Glu Leu Leu Phe Ser Glu
                165                 170                 175

Ile Glu Leu Met Gln Lys Arg Glu Ile Glu Leu Gln Asn Ala Asn Met
            180                 185                 190

Tyr Leu Arg Ala Lys Ile Ala Glu Val Glu Arg Ala Gln Glu Gln Met
        195                 200                 205

Asn Leu Met Pro Gly Gly Gly Gly Gly Gly Gly Gly Gly Gly Gly
    210                 215                 220

Gly Ser Asp His Gln Tyr His His Gln Pro Asn Tyr Glu Asp Ala Arg
225                 230                 235                 240

Asn Asn Phe Leu Pro Val Asn Leu Leu Glu Pro Asn Pro His Tyr Ser
                245                 250                 255

Arg Arg Asp Asn Gly Asp Gln Thr Pro Leu Gln Leu Val
            260                 265

<210> SEQ ID NO 126
<211> LENGTH: 224
<212> TYPE: PRT
<213> ORGANISM: Solanum lycopersicum

<400> SEQUENCE: 126

Met Val Arg Gly Lys Thr Glu Leu Lys Arg Ile Glu Asn Ala Thr Ser
1               5                   10                  15

Arg Gln Val Thr Phe Ser Lys Arg Arg Ser Gly Leu Leu Lys Lys Ala
            20                  25                  30

Phe Glu Leu Ser Val Leu Cys Asp Ala Glu Val Ala Leu Ile Val Phe
```

-continued

```
            35                  40                  45
Ser Pro Lys Gly Lys Leu Tyr Glu Phe Ser Ser Ser Thr Asn Lys
    50                  55                  60

Thr Ile Glu Arg Tyr Gln Lys Asn Glu Lys Ser Leu Gly Arg Leu Asn
65                  70                  75                  80

Arg Lys Leu Thr Asp Gln Leu Thr Thr Glu His Leu Lys Glu Glu Val
                85                  90                  95

Ala Thr Met Thr Arg Lys Leu Glu Phe Leu Glu Asp Ser Lys Arg Lys
            100                 105                 110

Leu Leu Gly His Gly Leu Glu Ser Ser Thr Phe Asp Glu Leu Gln Lys
            115                 120                 125

Val Glu Glu Gln Leu Glu Lys Ser Leu Ser Asn Ile Arg Ala Arg Lys
        130                 135                 140

Asn Leu Leu Phe Lys Glu Gln Ile Ala Gln Leu Lys Glu Glu Glu Lys
145                 150                 155                 160

Ile Leu Leu Lys Glu Asn Val Asp Leu Lys Lys Lys Cys Gln Val Leu
            165                 170                 175

Pro Leu Thr Leu Thr Pro Val Pro Leu Val Glu Lys Asp Val Glu Arg
            180                 185                 190

Gln Ile Met Glu Val Glu Thr Glu Leu Phe Ile Gly Leu Pro Glu Thr
        195                 200                 205

Arg Lys Ser Ser Tyr Cys Pro Asn Leu Asn Thr Leu Pro Thr Leu Leu
    210                 215                 220
```

<210> SEQ ID NO 127
<211> LENGTH: 61
<212> TYPE: PRT
<213> ORGANISM: Solanum lycopersicum

<400> SEQUENCE: 127

```
Met Val Arg Gly Lys Thr Glu Met Arg Arg Ile Glu Asn Ala Thr Ser
1               5                   10                  15

Arg Gln Val Thr Phe Ser Lys Arg Arg Asn Gly Leu Leu Lys Lys Ala
            20                  25                  30

Phe Glu Leu Ser Val Leu Cys Asp Ala Gln Val Gly Leu Val Ile Leu
        35                  40                  45

Ser Pro Arg Asp Lys Leu Tyr Glu Phe Ser Thr Ser Arg
    50                  55                  60
```

<210> SEQ ID NO 128
<211> LENGTH: 223
<212> TYPE: PRT
<213> ORGANISM: Solanum lycopersicum

<400> SEQUENCE: 128

```
Met Gly Arg Gly Lys Ile Glu Ile Lys Arg Ile Glu Asn Asn Thr Asn
1               5                   10                  15

Arg Gln Val Thr Phe Cys Lys Arg Arg Asn Gly Leu Leu Lys Lys Ala
            20                  25                  30

Tyr Glu Leu Ser Val Leu Cys Asp Ala Glu Ile Ala Leu Ile Val Phe
        35                  40                  45

Ser Thr Arg Gly Arg Leu Tyr Glu Tyr Ser Asn Asn Asn Val Lys Ala
    50                  55                  60

Thr Ile Glu Arg Tyr Lys Lys Ala Thr Ala Glu Thr Ser Ser Ala Tyr
65                  70                  75                  80

Thr Thr Gln Glu Leu Asn Ala Gln Phe Tyr Gln Gln Glu Ser Lys Lys
```

-continued

```
                85                  90                  95

Leu Arg Gln Gln Ile Gln Met Met Gln Asn Thr Asn Arg His Leu Val
            100                 105                 110

Gly Glu Gly Leu Ser Ser Leu Asn Val Arg Glu Leu Lys Gln Leu Glu
            115                 120                 125

Asn Arg Leu Glu Arg Gly Ile Thr Arg Ile Arg Ser Lys Lys His Glu
            130                 135                 140

Ala Ile Leu Ala Glu Thr Glu Asp Leu His Lys Arg Glu Ile Gln Leu
145                 150                 155                 160

Glu Gln Glu Asn Ala Phe Leu Arg Ser Lys Ile Ala Glu Asn Glu Arg
                165                 170                 175

Leu Gln Glu Leu Ser Met Met Pro Ser Gly Gly Glu Glu Tyr Asn Ala
            180                 185                 190

Phe Gln Gln Tyr Leu Ala Arg Asn Met Leu Gln Leu Asn Met Met Glu
            195                 200                 205

Thr Ala Leu Pro Ser Tyr Asp Pro Leu Ser Pro Asp His Lys Arg
    210                 215                 220

<210> SEQ ID NO 129
<211> LENGTH: 201
<212> TYPE: PRT
<213> ORGANISM: Solanum lycopersicum

<400> SEQUENCE: 129

Met Ala Arg Gly Lys Val Gln Met Lys Arg Ile Glu Asn Pro Val His
1               5                   10                  15

Arg Gln Val Thr Phe Cys Lys Arg Arg Ala Gly Leu Leu Lys Lys Ala
            20                  25                  30

Lys Glu Leu Ser Val Leu Cys Asp Ala Glu Ile Gly Leu Phe Ile Phe
            35                  40                  45

Ser Ala His Gly Lys Leu Tyr Glu Leu Ala Thr Lys Gly Ser Met Gln
    50                  55                  60

Gly Leu Ile Glu Arg Tyr Ile Lys Ser Thr Lys Gly Val Glu Val Ala
65                  70                  75                  80

Glu Glu Ala Lys Asp Thr Gln Pro Leu Asp Pro Lys Glu Glu Ile Asn
                85                  90                  95

Met Leu Lys Asn Glu Ile Asp Val Leu Gln Lys Gly Leu Ser Tyr Met
            100                 105                 110

Tyr Gly Gly Gly Ala Gly Thr Met Thr Leu Asp Glu Leu His Ser Leu
            115                 120                 125

Glu Lys Tyr Leu Glu Ile Trp Met Tyr His Ile Arg Ser Ala Lys Met
    130                 135                 140

Asp Ile Met Phe Gln Glu Ile Gln Leu Leu Lys Asn Lys Glu Gly Ile
145                 150                 155                 160

Leu Glu Ala Ala Asn Lys Tyr Leu Gln Asp Lys Ile Asp Glu Gln Tyr
                165                 170                 175

Thr Val Thr Asn Met Thr Gln Asn Leu Thr Asp Phe Gln Cys Pro Leu
            180                 185                 190

Thr Val Gln Asn Glu Ile Phe Gln Phe
        195                 200

<210> SEQ ID NO 130
<211> LENGTH: 250
<212> TYPE: PRT
<213> ORGANISM: Solanum lycopersicum
```

-continued

```
<400> SEQUENCE: 130

Met Gly Arg Gly Arg Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
            20                  25                  30

Tyr Glu Leu Ser Ile Leu Cys Asp Ala Glu Val Ala Leu Ile Ile Phe
        35                  40                  45

Ser Ser Arg Gly Lys Leu Tyr Glu Phe Ser Ser Ala Ser Ser Met Met
    50                  55                  60

Thr Thr Leu Glu Lys Tyr Gln Gln Cys Ser Tyr Ala Ser Leu Asp Pro
65                  70                  75                  80

Met Leu Pro Val Ser Asp Thr Gln Met Asn Tyr Asn Glu Tyr Val Arg
                85                  90                  95

Leu Lys Ala Arg Val Glu Leu Leu Gln Arg Ser Gln Arg His Ile Leu
            100                 105                 110

Gly Glu Asp Leu Gly Thr Leu Asn Ser Lys Glu Leu Glu Gln Leu Glu
            115                 120                 125

His Gln Leu Asp Ala Ser Leu Lys Lys Val Arg Ser Lys Lys Thr Gln
    130                 135                 140

Ser Met Leu Asp Gln Leu Ala Asp Leu Gln Glu Lys Glu Gln Met Leu
145                 150                 155                 160

Glu Glu Ala Asn Lys Gln Leu Lys Asn Lys Leu Glu Glu Ser Ala Ala
            165                 170                 175

Arg Ile Pro Leu Gly Leu Ser Trp Gly Asn Asn Gly Gly Gln Thr Met
            180                 185                 190

Glu Tyr Asn Arg Leu Pro Pro Gln Thr Thr Ala Gln Pro Phe Phe Gln
            195                 200                 205

Pro Leu Arg Leu Asn Ser Ser Ser Pro Gln Phe Gly Tyr Asn Pro Asn
    210                 215                 220

Met Gly Ala Asn Asp His Glu Val Asn Ala Ala Thr Thr Ala His Asn
225                 230                 235                 240

Ile Asn Gly Phe Ile Pro Gly Trp Met Leu
            245                 250

<210> SEQ ID NO 131
<211> LENGTH: 206
<212> TYPE: PRT
<213> ORGANISM: Solanum lycopersicum

<400> SEQUENCE: 131

Met Val Arg Gly Ile Thr Glu Met Lys Arg Ile Glu Asn Thr Thr Ser
1               5                   10                  15

Arg Gln Val Thr Phe Ser Lys Arg Arg Gly Gly Leu Leu Lys Lys Ala
            20                  25                  30

Phe Glu Leu Ser Val Leu Cys Asp Ala Glu Val Ser Leu Ile Ile Phe
        35                  40                  45

Ser Gln Lys Gly Lys Leu Phe Glu Phe Ser Ser Ser Thr Asn Lys
    50                  55                  60

Thr Ile Glu Arg Tyr Gln Lys Asn Asp Lys Asn Leu Gly His Glu Asn
65                  70                  75                  80

Ile Leu Leu Glu Gln Thr Thr Glu His Leu Lys Gly Glu Val Met Ser
            85                  90                  95

Met Thr Arg Asn Leu Glu Val Leu Glu Ile Ser Lys Arg Arg Leu Leu
            100                 105                 110
```

-continued

```
Gly Glu Asp Leu Glu Ser Cys Ser Ile Asp Glu Leu Glu Lys Val Glu
            115                 120                 125

Gly Gln Leu Asp Gln Ser Leu Arg Asn Ile Arg Ala Lys Lys Asn Gln
    130                 135                 140

Leu Phe Lys Glu Gln Ile Ser Leu Leu Lys Asp Glu Glu Lys Val Leu
145                 150                 155                 160

Met Asn Lys Asn Ala Glu Leu Arg Glu Lys Tyr Glu Ala Arg Ser Leu
                165                 170                 175

Pro Leu Phe Ile Asp Arg Arg Glu Asp Glu Ser Pro Gln Thr Gln Asn
                180                 185                 190

Met Glu Val Asp Thr Gln Leu Phe Ile Gly Leu Pro Glu Arg
        195                 200                 205
```

<210> SEQ ID NO 132
<211> LENGTH: 97
<212> TYPE: PRT
<213> ORGANISM: Solanum lycopersicum

<400> SEQUENCE: 132

```
Met Gly Arg Gly Lys Ile Leu Ile Arg Arg Ile Asp Asn Ser Thr Ser
1               5                   10                  15

Arg Gln Val Thr Phe Ser Lys Arg Arg Asn Gly Leu Leu Lys Lys Ala
                20                  25                  30

Lys Glu Leu Ala Ile Leu Cys Asp Ala Glu Val Gly Val Ile Ile Phe
            35                  40                  45

Ser Ser Thr Ser Lys Leu Tyr Asp Tyr Ala Asn Thr Arg Phe Ser Pro
    50                  55                  60

Pro Ile Ser His Thr Phe Phe Ala Cys Gln Met Leu Glu Leu Gln Phe
65                  70                  75                  80

Ile Phe Asn Phe Leu Glu Lys Asn Phe Leu Arg Val Phe Ser Phe Val
                85                  90                  95

Tyr
```

<210> SEQ ID NO 133
<211> LENGTH: 70
<212> TYPE: PRT
<213> ORGANISM: Vitis vinifera

<400> SEQUENCE: 133

```
Met Gly Arg Gly Lys Ile Glu Ile Arg Arg Ile Asp Asn Thr Thr Ser
1               5                   10                  15

Arg Gln Val Thr Phe Ser Lys Arg Arg Lys Gly Leu Leu Lys Lys Ala
                20                  25                  30

Lys Glu Leu Ala Ile Leu Cys Asp Ala Glu Val Gly Leu Ile Ile Phe
            35                  40                  45

Ser Ser Thr Gly Lys Leu Tyr Glu Phe Ala Ser Thr Arg Phe Ala Ala
    50                  55                  60

Ser Tyr His Leu Ile Ile
65                  70
```

<210> SEQ ID NO 134
<211> LENGTH: 221
<212> TYPE: PRT
<213> ORGANISM: Vitis vinifera

<400> SEQUENCE: 134

```
Met Gly Arg Gly Arg Val Glu Leu Lys Arg Ile Glu Asn Lys Ile Asn
1               5                   10                  15
```

-continued

```
Arg Gln Val Thr Phe Ala Lys Arg Arg Asn Gly Leu Leu Lys Lys Ala
             20                  25                  30

Tyr Glu Leu Ser Val Leu Cys Asp Ala Glu Val Ala Leu Ile Ile Phe
         35                  40                  45

Ser Asn Arg Gly Lys Leu Tyr Glu Phe Cys Ser Ser Ser Ser Met Leu
     50                  55                  60

Lys Thr Leu Glu Arg Tyr Gln Lys Cys Asn Tyr Gly Ala Pro Glu Thr
 65                  70                  75                  80

Asn Val Ser Thr Arg Glu Ala Leu Glu Leu Ser Ser Gln Gln Glu Tyr
                 85                  90                  95

Leu Lys Leu Lys Ala Arg Tyr Glu Ala Leu Gln Arg Ser Gln Arg Asn
            100                 105                 110

Leu Leu Gly Glu Asp Leu Gly Pro Leu Ser Thr Lys Glu Leu Glu Ser
            115                 120                 125

Leu Glu Arg Gln Leu Asp Val Ser Leu Lys Gln Ile Arg Ser Thr Arg
    130                 135                 140

Thr Gln Tyr Met Leu Asp Gln Leu Thr Asp Leu Gln Arg Lys Glu His
145                 150                 155                 160

Met Leu Asn Glu Ala Asn Lys Thr Leu Lys Gln Arg Leu Leu Glu Gly
                165                 170                 175

Thr Gln Val Asn Gln Leu Gln Trp Asn Pro Asn Ala Gln Asp Val Gly
                180                 185                 190

Tyr Gly Arg Gln Gln Ala Gln Pro Gln Gly Asp Gly Phe Phe His Pro
            195                 200                 205

Leu Glu Cys Glu Pro Thr Leu Gln Ile Gly Pro Ile Gln
    210                 215                 220
```

<210> SEQ ID NO 135
<211> LENGTH: 241
<212> TYPE: PRT
<213> ORGANISM: Vitis vinifera

<400> SEQUENCE: 135

```
Met Gly Arg Gly Arg Val Gln Leu Lys Arg Ile Glu Asn Lys Ile Asn
1               5                   10                  15

Arg Gln Val Thr Phe Ser Lys Arg Arg Thr Gly Leu Leu Lys Lys Ala
             20                  25                  30

His Glu Ile Ser Val Leu Cys Asp Ala Glu Val Ala Leu Ile Val Phe
         35                  40                  45

Ser Thr Lys Gly Lys Leu Phe Glu Tyr Ser Thr Asp Ser Cys Met Glu
     50                  55                  60

Lys Ile Leu Asp Arg Tyr Glu Arg Tyr Ser Tyr Ala Glu Arg Gln Leu
 65                  70                  75                  80

Thr Ala Thr Asp Pro Glu Ser Gln Gly Asn Trp Ser Leu Glu Tyr Ser
                 85                  90                  95

Lys Leu Lys Ala Lys Ile Glu Leu Leu Gln Arg Ser Gln Arg His Phe
            100                 105                 110

Leu Gly Glu Asp Leu Asp Ser Leu Ser Leu Lys Glu Leu Gln Asn Leu
            115                 120                 125

Glu Gln Gln Leu Asp Thr Ala Leu Lys His Ile Arg Ser Arg Lys Asn
    130                 135                 140

Gln Leu Met Tyr Glu Ser Ile Ser Glu Leu Gln Arg Lys Glu Lys Ala
145                 150                 155                 160

Met Gln Glu Gln Asn Asn Met Leu Ala Lys Glu Ile Lys Glu Lys Glu
```

-continued

```
                165                170                175
Lys Thr Val Ala Gln Gln Thr His Trp Glu Gln Gln Asn His Gly Leu
            180                185                190

Asn Thr Ser Ser Phe Leu Leu Pro Gln Gln Leu Pro Cys Leu Asn Met
        195                200                205

Gly Gly Thr Tyr Gln Gly Glu Ala His Gly Ala Arg Arg Asn Glu Leu
    210                215                220

Asp Leu Thr Leu Glu Pro Ile Tyr Pro Ser His Leu Gly Cys Phe Thr
225                230                235                240

Thr
```

```
<210> SEQ ID NO 136
<211> LENGTH: 243
<212> TYPE: PRT
<213> ORGANISM: Vitis vinifera

<400> SEQUENCE: 136

Met Gly Arg Gly Lys Val Glu Leu Lys Arg Ile Glu Asn Lys Ile Asn
1                5                10                15

Arg Gln Val Thr Phe Ala Lys Arg Arg Asn Gly Leu Leu Lys Lys Ala
            20                25                30

Tyr Glu Leu Ser Val Leu Cys Asp Ala Glu Val Ala Leu Ile Ile Phe
        35                40                45

Ser Asn Arg Gly Lys Leu Tyr Glu Phe Cys Ser Gly Ser Ser Met Pro
    50                55                60

Glu Thr Leu Glu Arg Tyr Gln Arg Cys Ser Tyr Ser Ala Leu Glu Ala
65                70                75                80

Ser Gln Pro Ala Lys Glu Thr Gln Asn Ser Tyr Gln Glu Tyr Leu Lys
                85                90                95

Leu Lys Ser Lys Val Glu Val Leu Gln Arg Thr Gln Arg Asn Phe Leu
            100                105                110

Gly Glu Asp Leu Gly His Leu Gly Thr Lys Glu Leu Glu Gln Leu Glu
        115                120                125

His Gln Leu Asp Lys Ser Leu Lys Gln Ile Arg Ser Thr Lys Thr Gln
    130                135                140

Phe Met Leu Asp Gln Leu Ser Asp Leu Gln Arg Lys Glu Gln Ile Leu
145                150                155                160

Met Glu Ala Asn Asn Ala Leu Arg Arg Lys Leu Gly Glu Ser Ser Ala
                165                170                175

Glu Ser Gly Leu Gly Ser Thr Trp Glu Ala Ala Ala His Asn Leu Pro
            180                185                190

Tyr Asn Arg Glu Pro Val Gln Ser Glu Asp Phe Phe Glu Pro Leu Gln
        195                200                205

Cys Asp Ser Thr Leu Gln Ile Gly Tyr Asn Pro Val Leu Arg Val Glu
    210                215                220

Met Asn Gly Ala Ser Thr Thr Gln Asn Val Asn Gly Phe Ile Pro Gly
225                230                235                240

Trp Met Val
```

```
<210> SEQ ID NO 137
<211> LENGTH: 214
<212> TYPE: PRT
<213> ORGANISM: Vitis vinifera

<400> SEQUENCE: 137
```

```
Met Val Arg Gly Lys Thr Gln Met Lys Arg Ile Glu Asn Ala Ala Ser
1               5                   10                  15

Arg Gln Val Thr Phe Ser Lys Arg Arg Ser Gly Leu Leu Lys Lys Ala
            20                  25                  30

Phe Glu Leu Ser Val Leu Cys Asp Ala Glu Val Ala Leu Ile Ile Phe
            35                  40                  45

Ser Pro Arg Gly Lys Val Phe Glu Phe Ser Ser Ser Ser Ile Asn Lys
    50                  55                  60

Thr Ile Glu Arg Tyr Gln Ser Lys Ala Lys Gly Leu Gly Ile Ser Lys
65                  70                  75                  80

Arg Gly Ala Pro Glu Asn Glu Gln His His Leu Glu Gly Glu Thr Val
                85                  90                  95

Asp Leu Ala Lys Lys Ile Glu Leu Leu Glu Val Ser Lys Arg Arg Leu
            100                 105                 110

Leu Gly Glu Cys Leu Asp Ser Cys Ser Ile Glu Glu Leu Gln Gln Ile
            115                 120                 125

Glu Asn Glu Leu Glu Gln Ser Leu Ser Asn Ile Arg Ile Gln Lys Asn
    130                 135                 140

His Leu Cys Lys Gly His Ile Glu Arg Leu Lys Glu Gln Glu Arg Ile
145                 150                 155                 160

Leu Gly Glu Glu Asn Ala Lys Leu Arg Gly Lys Cys Gly Leu Gln Pro
            165                 170                 175

Leu Gln Pro Ser Thr Lys His Gln Ser Val Pro Tyr Val Glu Ile Ser
            180                 185                 190

Glu Val Glu Thr Glu Leu Phe Ile Gly Pro Pro Glu Arg Arg Thr Val
            195                 200                 205

Arg Tyr Leu Ser Glu Thr
    210
```

```
<210> SEQ ID NO 138
<211> LENGTH: 62
<212> TYPE: PRT
<213> ORGANISM: Vitis vinifera

<400> SEQUENCE: 138

Met Gly Arg Gly Lys Ile Val Ile Arg Arg Ile Asp Asn Ser Thr Ser
1               5                   10                  15

Arg Gln Val Thr Phe Ser Lys Arg Arg Asn Gly Leu Leu Lys Lys Ala
            20                  25                  30

Lys Glu Leu Ser Ile Leu Cys Asp Ala Glu Val Gly Leu Val Ile Phe
            35                  40                  45

Ser Ser Thr Gly Lys Leu Tyr Asp Tyr Ala Asn Thr Arg Lys
    50                  55                  60
```

```
<210> SEQ ID NO 139
<211> LENGTH: 226
<212> TYPE: PRT
<213> ORGANISM: Vitis vinifera

<400> SEQUENCE: 139

Met Gly Arg Gly Lys Ile Glu Ile Lys Arg Ile Glu Asn Thr Thr Asn
1               5                   10                  15

Arg Gln Val Thr Phe Cys Lys Arg Arg Asn Gly Leu Leu Lys Lys Ala
            20                  25                  30

Tyr Glu Leu Ser Val Leu Cys Asp Ala Glu Val Ala Leu Ile Val Phe
            35                  40                  45
```

```
Ser Ser Arg Gly Arg Leu Tyr Glu Tyr Ala Asn Asn Ser Val Lys Ser
    50                  55                  60

Thr Ile Glu Arg Tyr Lys Lys Ala Ser Ala Asp Ser Ser Asn Thr Gly
65                  70                  75                  80

Ser Val Ser Glu Ala Asn Ala Gln Phe Tyr Gln Gln Glu Ser Ser Lys
                85                  90                  95

Leu His Gln Gln Ile Arg Asn Leu Gln Asn Ser Asn Arg His Met Leu
                100                 105                 110

Gly Glu Ser Leu Gly Ser Leu Asn Phe Lys Asp Leu Lys Ser Leu Glu
                115                 120                 125

Ile Arg Leu Glu Lys Gly Ile Ser Arg Ile Arg Ser Arg Lys Asn Glu
    130                 135                 140

Leu Leu Phe Ala Glu Ile Glu Tyr Met Gln Lys Arg Glu Ile Asp Leu
145                 150                 155                 160

His Asn Asp Asn Gln Tyr Leu Arg Ala Arg Ile Ala Glu Asn Glu Arg
                165                 170                 175

Asn Glu Gln Gln Met Ser Leu Met Pro Gly Gly Ala Asn Tyr Glu Leu
                180                 185                 190

Met Pro Ser Gln Gln Phe Asp Ser Arg Asn Tyr Phe Gln Leu Asn Gly
                195                 200                 205

Leu Gln Pro Asn Gln Ser Tyr Ser Arg Gln Asp Gln Pro Ala Leu Gln
    210                 215                 220

Leu Val
225

<210> SEQ ID NO 140
<211> LENGTH: 274
<212> TYPE: PRT
<213> ORGANISM: Vitis vinifera

<400> SEQUENCE: 140

Met Gly Arg Gly Lys Ile Glu Ile Lys Arg Ile Glu Asn Thr Thr Asn
1               5                   10                  15

Arg Gln Val Thr Phe Cys Lys Arg Arg Asn Gly Leu Leu Lys Lys Ala
                20                  25                  30

Tyr Glu Leu Ser Val Leu Cys Asp Ala Glu Val Ala Leu Ile Val Phe
                35                  40                  45

Ser Ser Arg Gly Arg Leu Tyr Glu Tyr Ala Asn Asn Ser Val Arg Thr
    50                  55                  60

Thr Ile Glu Arg Tyr Lys Lys Val Cys Ser Asp Ser Ser Asn Thr Gly
65                  70                  75                  80

Ser Val Ser Glu Ala Asn Ala Gln Phe Tyr Gln Gln Glu Ala Ser Lys
                85                  90                  95

Leu Arg Arg Gln Ile Arg Asp Ile Gln Asn Leu Asn Arg His Ile Leu
                100                 105                 110

Gly Glu Ala Leu Ser Ser Leu Asn Phe Lys Glu Leu Lys Asn Leu Glu
                115                 120                 125

Thr Arg Leu Glu Lys Gly Ile Ser Arg Ile Arg Ser Lys Lys Asn Glu
    130                 135                 140

Leu Leu Phe Ala Glu Ile Glu Tyr Met Gln Lys Arg Glu Ile Glu Leu
145                 150                 155                 160

Gln Asn Ser Asn Leu Phe Leu Arg Ala Gln Ile Ala Glu Asn Glu Arg
                165                 170                 175

Ala Gln Gln Gln Met Asn Leu Met Pro Gly Ser Gln Tyr Glu Ser Val
                180                 185                 190
```

```
Pro Gln Gln Pro Tyr Asp Ser Gln Asn Leu Leu Pro Val Asn Leu Leu
        195             200             205

Asp Pro Asn His His Tyr Ser Arg His Asp Gln Thr Ala Leu Gln Leu
    210             215             220

Val Thr Ile Cys Leu Leu Tyr Leu Tyr Leu Lys Thr Tyr Phe Ser Ser
225             230             235             240

Ile Leu Lys Ile Asn Lys Leu Met Lys Tyr His Phe Ile Val Ala Leu
            245             250             255

Ser Tyr Asn Gly Leu Val Arg Ser Gly Ala Val Phe Val Gly Leu Phe
            260             265             270

Val Glu

<210> SEQ ID NO 141
<211> LENGTH: 247
<212> TYPE: PRT
<213> ORGANISM: Vitis vinifera

<400> SEQUENCE: 141

Met Gly Arg Gly Arg Val Gln Leu Lys Arg Ile Glu Asn Lys Ile Ser
1           5               10              15

Arg Gln Val Thr Phe Ser Lys Arg Arg Ser Gly Leu Leu Lys Lys Ala
        20              25              30

His Glu Ile Ser Val Leu Cys Asp Ala Glu Val Ala Leu Ile Val Phe
        35              40              45

Ser Thr Lys Gly Lys Leu Phe Glu Tyr Ser Ser Asp Ser Ser Met Glu
    50              55              60

Arg Ile Leu Glu Arg Tyr Glu Arg Tyr Ser Leu Ser Glu Arg Gln Leu
65              70              75              80

Leu Ser Thr Asp Pro Asp Pro Gln Gly Asn Trp Ser Met Asp Tyr Pro
            85              90              95

Lys Leu Thr Ala Arg Ile Glu Val Leu Gln Arg Asn Leu Arg His Phe
            100             105             110

Val Gly Glu Asp Leu Asp Pro Leu Ser Leu Arg Glu Leu Gln Asn Leu
            115             120             125

Glu Gln Gln Leu Asp Thr Ala Leu Lys Arg Ile Arg Thr Arg Lys Asn
    130             135             140

Gln Leu Met His Glu Ser Ile Ser Glu Leu Gln Lys Lys Glu Lys Ser
145             150             155             160

Leu Val Glu Gln Asn Asn Ala Leu Ala Lys Lys Val Lys Glu Lys Glu
            165             170             175

Lys Val Glu Gln Asn Asn Arg Ala Gln Trp Glu Gln Gln Asn Asn Ile
            180             185             190

Gly Gln Asn Ser Ser Ala Tyr Val Val Pro Pro Pro Leu Gln Leu
            195             200             205

Pro Ser Leu Thr Ile Gly Gly Ser Phe Val Gly Arg Ala Val Glu Glu
    210             215             220

Asp Gly Ala Glu Ala Arg Pro Ser Pro Asn Thr Leu Met Pro Pro Trp
225             230             235             240

Met Leu Arg His Val Asn Glu
            245

<210> SEQ ID NO 142
<211> LENGTH: 243
<212> TYPE: PRT
<213> ORGANISM: Vitis vinifera
```

<400> SEQUENCE: 142

Met Gly Arg Gly Arg Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
            20                  25                  30

Tyr Glu Leu Ser Val Leu Cys Asp Ala Glu Val Ala Leu Ile Ile Phe
        35                  40                  45

Ser Thr Arg Gly Lys Leu Tyr Glu Phe Cys Ser Ser Ser Met Leu
    50                  55                  60

Lys Thr Leu Glu Arg Tyr Gln Lys Cys Ser Tyr Gly Ala Val Glu Val
65                  70                  75                  80

Ser Arg Pro Ser Lys Glu Leu Glu Ser Ser Tyr Arg Glu Tyr Leu Lys
                85                  90                  95

Leu Lys Ser Lys Phe Glu Ser Leu Gln Arg Thr Gln Arg Asn Leu Leu
            100                 105                 110

Gly Glu Asp Leu Gly Pro Leu Asn Thr Lys Glu Leu Glu Gln Leu Glu
        115                 120                 125

Arg Gln Leu Glu Thr Ser Leu Lys Gln Val Arg Ser Thr Lys Thr Gln
    130                 135                 140

Phe Met Leu Asp Gln Leu Ser Asp Leu Gln Asn Lys Glu Gln Val Leu
145                 150                 155                 160

Val Glu Ser Asn Lys Ala Leu Thr Arg Lys Leu Asp Glu Ile Ser Val
                165                 170                 175

Lys Asn His Leu Gln Leu Ser Trp Glu Ser Gly Glu Gln Ser Met Pro
            180                 185                 190

Tyr Gly His Gln Gln Ala Gln Ser Gln Gly Phe Phe Gln Pro Leu Glu
        195                 200                 205

Cys Asn Pro Thr Leu Gln Ile Gly Tyr Asn Pro Ala Gly Ser Ser Gln
    210                 215                 220

Leu Ser Ala Pro Ser Asn Ala Gln Asn Val Asn Gly Phe Ile Pro Gly
225                 230                 235                 240

Trp Met Leu

<210> SEQ ID NO 143
<211> LENGTH: 61
<212> TYPE: PRT
<213> ORGANISM: Vitis vinifera

<400> SEQUENCE: 143

Met Val Arg Gly Lys Thr Gln Met Arg Arg Ile Glu Asn Ala Thr Ser
1               5                   10                  15

Arg Gln Val Thr Phe Ser Lys Arg Arg Asn Gly Leu Phe Lys Lys Ala
            20                  25                  30

Phe Glu Leu Ser Val Leu Cys Asp Ala Glu Val Ala Leu Ile Ile Phe
        35                  40                  45

Ser Pro Arg Gly Lys Leu Tyr Glu Phe Ser Ser Ser Arg
    50                  55                  60

<210> SEQ ID NO 144
<211> LENGTH: 244
<212> TYPE: PRT
<213> ORGANISM: Vitis vinifera

<400> SEQUENCE: 144

Met Gly Arg Gly Arg Val Glu Leu Lys Arg Ile Glu Asn Lys Ile Asn

-continued

```
1               5                   10                  15

Arg Gln Val Thr Phe Ser Lys Arg Arg Asn Gly Leu Leu Lys Lys Ala
                20                  25                  30

Tyr Glu Leu Ser Val Leu Cys Asp Ala Glu Val Ala Leu Ile Ile Phe
            35                  40                  45

Ser Ser Arg Gly Lys Leu Tyr Glu Phe Gly Ser Ala Gly Thr Thr Lys
        50                  55                  60

Thr Leu Glu Arg Tyr Gln Arg Val Cys Tyr Thr Pro Gln Asp Asn Asn
65                  70                  75                  80

Met Glu Cys Glu Thr Gln Ser Trp Tyr Gln Glu Val Ser Lys Leu Lys
                85                  90                  95

Ala Lys Tyr Glu Ser Leu Gln Arg Thr Gln Arg His Leu Leu Gly Glu
            100                 105                 110

Asp Leu Gly Pro Leu Ser Val Lys Glu Leu Gln Asn Leu Glu Lys Gln
            115                 120                 125

Leu Glu Gly Ala Leu Ala Gln Ala Arg Gln Arg Lys Thr Gln Met Met
        130                 135                 140

Ile Glu Gln Met Glu Asp Leu Arg Arg Lys Glu Arg Gln Leu Gly Asp
145                 150                 155                 160

Leu Asn Lys Gln Leu Lys Leu Lys Leu Glu Ala Glu Gly Gln Ser Leu
                165                 170                 175

Lys Ala Ile Gln Gly Ser Trp Asn Pro Ser Thr Ala Thr Ala Gly Asn
            180                 185                 190

Ser Ser Phe Pro Val His Pro Ser Gln Ser Asn Pro Met Asp Cys Glu
            195                 200                 205

Pro Glu Pro Ile Leu Gln Ile Gly Tyr His His Tyr Val Pro Ala Glu
        210                 215                 220

Gly Pro Ser Val Ser Lys Ser Met Ala Gly Glu Ser Asn Phe Ile Gln
225                 230                 235                 240

Gly Trp Val Leu
```

```
<210> SEQ ID NO 145
<211> LENGTH: 249
<212> TYPE: PRT
<213> ORGANISM: Vitis vinifera

<400> SEQUENCE: 145

Met Gly Arg Gly Arg Val Val Leu Gln Arg Ile Glu Asn Lys Ile Asn
1               5                   10                  15

Arg Gln Val Thr Phe Ser Lys Arg Arg Asn Gly Leu Leu Lys Lys Ala
                20                  25                  30

Tyr Glu Leu Ser Val Leu Cys Asp Ala Glu Val Cys Leu Ile Ile Phe
            35                  40                  45

Ser Ser Arg Gly Lys Leu Phe Glu Phe Gly Ser Ser Gly Met Thr Lys
        50                  55                  60

Thr Ile Glu Arg Tyr Arg Arg Cys Cys Tyr Ala Ser Arg Asp Asn Asn
65                  70                  75                  80

Asp Ala Glu His Asp Arg Gln Ile Gly His Glu Glu Tyr Ser Lys Leu
                85                  90                  95

Lys Ala Lys Tyr Glu Ser Leu Met Asp Ser Gln Arg His Leu Leu Gly
            100                 105                 110

Glu Asp Leu Gly Leu Leu Ser Ile Lys Glu Leu Gln Asn Leu Glu Lys
            115                 120                 125

Met Leu Glu Gly Thr Leu Ser Gln Ala Arg Gln Arg Lys Ala Gln Met
```

-continued

```
          130                135                140

Met Leu Lys Gln Met Asp Glu Leu Lys Lys Glu His Asp Leu Glu
145                150                155                160

Glu Met Asn Lys Gln Leu Thr Ser Lys Leu Glu Glu Leu Glu Glu Cys
                  165                170                175

Val Arg Val Ile Glu Ala Ser Trp Asp Ser Gly Thr Val Ala Gly Asn
                  180                185                190

Asp Ser Leu Asn Met His Ile Ser Gln Pro Asn Gln Ile Gln Pro Gln
          195                200                205

Pro Gln Pro Gln Pro Gln Pro Ser Leu Pro Met Gly Phe His Glu Phe
          210                215                220

Val Pro Pro Glu Gly Ala Ala Ile Ala Arg Asn Val Gly Asn Ala Arg
225                230                235                240

Asn Gly Leu Ala Gln Gly Trp Leu Val
                  245
```

<210> SEQ ID NO 146
<211> LENGTH: 79
<212> TYPE: PRT
<213> ORGANISM: Vitis vinifera

<400> SEQUENCE: 146

```
Met Val Arg Gly Lys Ile Gln Met Arg Arg Ile Glu Asn Ala Thr Ser
1               5               10                15

Arg Gln Val Thr Phe Ser Lys Arg Arg Asn Gly Leu Leu Lys Lys Ala
                  20                25                30

Tyr Glu Leu Ser Val Leu Cys Asp Ala Glu Val Ala Val Ile Ile Phe
          35                40                45

Ser Gln Lys Gly Arg Leu Tyr Glu Phe Ser Ser Ser Lys Trp Arg Ile
          50                55                60

Phe Lys Cys His Ser Arg Ser Ile Gln Gly Gly Ser Asn Trp Pro
65                70                75
```

<210> SEQ ID NO 147
<211> LENGTH: 235
<212> TYPE: PRT
<213> ORGANISM: Vitis vinifera

<400> SEQUENCE: 147

```
Met Gly Arg Gly Lys Val Glu Leu Lys Arg Ile Glu Asn Ser Thr Ser
1               5               10                15

Arg Gln Val Thr Phe Ser Lys Arg Lys Asn Gly Leu Leu Lys Lys Ala
                  20                25                30

Phe Glu Leu Ser Ile Leu Cys Asp Ala Glu Val Ala Leu Leu Ile Phe
          35                40                45

Ser Pro Ser Gly Lys Ala Tyr Gln Phe Ala Ser His Asp Met Asp Arg
          50                55                60

Ser Ile Ala Arg Tyr Arg Asn Glu Val Gly Leu Met Glu Phe Asn Asn
65                70                75                80

Tyr Gln Arg Ser Arg Thr Ile Glu Phe Trp Met Ser Glu Ile Asp Asn
                  85                90                95

Leu Arg Arg Thr Ile Asp Thr Leu Glu Ala Lys His Lys His Leu Ala
                  100                105                110

Gly Glu Asp Leu Ser Thr Leu Gly Met Lys Glu Leu Lys Gln Leu Glu
          115                120                125

Arg Gln Leu Lys Asn Gly Val Glu Arg Ile Arg Ala Lys Lys Arg Arg
```

```
         130              135              140

Ile Ile Ser Glu His Ile Ser Leu Leu Lys Lys Arg Gln Arg Ala Leu
145               150               155               160

Gln Glu Asp Asn Thr Arg Leu Gln Lys Lys Val Lys Leu His Glu Ala
              165               170               175

Asn Leu Asn Thr Arg Ala Phe Gly Ala Glu Glu Cys Asp Ala Phe Gly
              180               185               190

Arg Ala Val Ala Ala Val Val Leu Ala Val His Met Thr Gly Pro Gly
          195               200               205

Tyr Glu Lys Asp Gly Gln Met Gly Ser Lys Ser His His Gln Thr Ala
      210               215               220

Arg Met Leu Ala Asp Gln Asp Gly Gly Asp Pro
225               230               235

<210> SEQ ID NO 148
<211> LENGTH: 243
<212> TYPE: PRT
<213> ORGANISM: Vitis vinifera

<400> SEQUENCE: 148

Met Gly Arg Gly Arg Val Gln Leu Lys Arg Ile Glu Asn Lys Val Asn
1               5               10               15

Arg Gln Val Thr Phe Ser Lys Arg Arg Ser Gly Leu Leu Lys Lys Ala
              20               25               30

His Glu Ile Ser Val Leu Cys Asp Ala Glu Val Ala Leu Ile Val Phe
          35               40               45

Ser Thr Lys Gly Lys Leu Tyr Glu Tyr Ser Thr Asp Ser Cys Met Glu
      50               55               60

Arg Ile Leu Glu Arg Tyr Glu Arg Tyr Ala Tyr Ala Gln Ser Gln Leu
65               70               75               80

Ile Ala Thr Asp Leu Glu Ser Gln Gly Ser Trp Thr Leu Glu Tyr Ala
              85               90               95

Lys Leu Lys Ala Arg Met Glu Val Leu Gln Lys Ser Gln Arg Asn Phe
              100               105               110

Met Gly Glu Asp Leu Asp Ser Leu Ser Leu Lys Glu Leu Gln Asn Leu
          115               120               125

Glu Gln Gln Leu Asp Asn Ser Leu Lys Ser Thr Arg Thr Arg Lys Asn
      130               135               140

Gln Leu Met Tyr Glu Ser Leu Ser Glu Leu His Lys Lys Gly Lys Ala
145               150               155               160

Leu Gln Glu Glu His Asp Leu Leu Thr Ala Lys Val Gln Glu Lys Glu
              165               170               175

Lys Glu Gln Ala Glu Gln Ala Gln Trp Asn Gln Gln Asn Gln Asp Leu
          180               185               190

Asp Ser Pro Ser Phe Leu Leu Gln Gln Pro Leu His Ala Leu Asn Ile
          195               200               205

Ser Gly Asn Cys Leu Ala Arg Asp Ser Gly Asp Asp Gln Gly Ile Pro
      210               215               220

Pro Gln Asn Arg Thr Asn Thr Pro Leu Pro Ala Trp Met Leu Arg His
225               230               235               240

Val Asn Lys

<210> SEQ ID NO 149
<211> LENGTH: 246
<212> TYPE: PRT
```

<213> ORGANISM: Vitis vinifera

<400> SEQUENCE: 149

```
Met Gly Arg Gly Arg Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
                20                  25                  30

Tyr Glu Leu Ser Val Leu Cys Asp Ala Glu Val Ala Leu Ile Val Phe
            35                  40                  45

Ser Ser Arg Gly Lys Leu Tyr Glu Phe Cys Ser Gly Pro Ser Met Ala
        50                  55                  60

Lys Thr Leu Glu Lys Tyr Gln Lys Cys Ser Tyr Gly Ala Leu Glu Ala
65                  70                  75                  80

Ser Gln Pro Val Tyr Glu Leu Thr Gln Ser Ser Tyr Gln Glu Tyr Leu
                85                  90                  95

Lys Leu Lys Thr Arg Val Glu Val Leu Gln Arg Ser Gln Arg His Leu
            100                 105                 110

Leu Gly Glu Asp Leu Asp Pro Leu Asn Thr Lys Glu Leu Glu Gln Leu
        115                 120                 125

Glu His Gln Leu Glu Met Ser Leu Lys Gln Ile Arg Ser Thr Lys Thr
    130                 135                 140

Gln Asn Met Leu Asp Gln Leu Ala Asp Leu Gln Asn Lys Glu His Met
145                 150                 155                 160

Leu Ile Glu Ala Asn Asn Ala Leu Arg Arg Lys Leu Glu Glu Ser Asn
                165                 170                 175

Gly Lys His Pro Leu Gln Gln Ser Trp Glu Ala Ala Gly Asn Ser Ala
            180                 185                 190

Leu Tyr Ser Arg Leu Pro Ala Gln Ser Glu Gly Phe Phe Gln Pro Leu
        195                 200                 205

Glu Arg Asn Ser Thr Leu Glu Met Gly Tyr Asn Ala Ala Gly Ser Asn
    210                 215                 220

Glu Ile Thr Leu Ala Ala Pro Ser Gln Asn Asp Asn Gly Phe Gly Pro
225                 230                 235                 240

Gly Trp Met Leu Trp Ile
                245
```

<210> SEQ ID NO 150
<211> LENGTH: 223
<212> TYPE: PRT
<213> ORGANISM: Vitis vinifera

<400> SEQUENCE: 150

```
Met Gly Arg Gly Lys Ile Glu Ile Lys Arg Ile Glu Asn Thr Thr Asn
1               5                   10                  15

Arg Gln Val Thr Phe Cys Lys Arg Arg Asn Gly Leu Leu Lys Lys Ala
                20                  25                  30

Tyr Glu Leu Ser Val Leu Cys Asp Ala Glu Val Ala Leu Ile Val Phe
            35                  40                  45

Ser Ser Arg Gly Arg Val Tyr Glu Tyr Ser Asn Asn Asn Ile Lys Ser
        50                  55                  60

Thr Ile Asp Arg Tyr Lys Lys Ala Ser Ser Asp Ser Thr Asn Gly Gly
65                  70                  75                  80

Ser Thr Met Glu Ile Asn Ala Gln Tyr Tyr Gln Gln Glu Ser Ala Lys
                85                  90                  95

Leu Arg Gln Gln Ile Gln Met Leu Gln Asn Ser Asn Arg His Leu Met
```

-continued

```
              100              105                 110

Gly Asp Ser Leu Ala Ser Leu Thr Val Lys Glu Leu Lys Gln Leu Glu
         115                 120                 125

Asn Arg Leu Glu Arg Gly Ile Thr Arg Ile Arg Ser Lys Lys His Glu
     130                 135                 140

Leu Leu Leu Ala Glu Ile Glu Tyr Leu Gln Lys Arg Glu Ile Glu Leu
145                 150                 155                 160

Glu Asn Glu Ser Val Tyr Leu Arg Thr Lys Ile Ala Glu Val Glu Arg
                 165                 170                 175

Leu Gln Gln Ala Asn Met Val Ser Thr His Glu Phe Asn Ala Ile Gln
             180                 185                 190

Ala Leu Val Ser Arg Asn Phe Phe Gln Pro Asn Met Ile Glu Gly Gly
             195                 200                 205

Ser Thr Gly Tyr Pro Leu Pro Asp Lys Lys Val Leu His Leu Gly
     210                 215                 220
```

```
<210> SEQ ID NO 151
<211> LENGTH: 198
<212> TYPE: PRT
<213> ORGANISM: Vitis vinifera

<400> SEQUENCE: 151

Met Ala Arg Gly Lys Ile Gln Met Lys Arg Ile Glu Asn Pro Val His
1               5                   10                  15

Arg Gln Val Thr Phe Cys Lys Arg Arg Ala Gly Leu Leu Lys Lys Ala
             20                  25                  30

Lys Glu Leu Ser Val Leu Cys Asp Ala Glu Ile Gly Ile Phe Ile Phe
         35                  40                  45

Ser Ala His Gly Lys Leu Tyr Glu Leu Ala Thr Lys Gly Thr Met Gln
     50                  55                  60

Gly Leu Ile Glu Lys Tyr Met Lys Ser Ser Cys Gly Ser Gln Asp Asp
65                  70                  75                  80

Gln Ala Lys Glu Ala Gln Leu Leu Asp Thr Lys Glu Glu Ile Asn Met
             85                  90                  95

Leu Lys His Glu Ile Glu Leu Leu Gln Lys Gly Leu Arg Tyr Met Leu
             100                 105                 110

Gly Gly Gly Ala Gly Thr Met Thr Leu Asp Glu Leu His Ile Phe Glu
         115                 120                 125

Lys His Leu Glu Ile Trp Ile Tyr Asn Ile Arg Ser Ala Lys Met Glu
     130                 135                 140

Ile Met Phe Gln Glu Ile Gln Leu Leu Lys Asn Lys Glu Gly Ile Leu
145                 150                 155                 160

Lys Ala Ala Asn Asn Tyr Leu Gln Glu Met Ile Asp Asp Gln Thr Gly
             165                 170                 175

Ile Thr Asn Ile Ala Pro Met Ile Asn Pro Tyr Pro Leu Thr Thr Gln
             180                 185                 190

Asn Glu Ile Phe Gln Thr
         195
```

```
<210> SEQ ID NO 152
<211> LENGTH: 225
<212> TYPE: PRT
<213> ORGANISM: Rubus sp.

<400> SEQUENCE: 152

Met Gly Arg Gly Lys Ile Glu Ile Lys Arg Ile Glu Asn Thr Thr Asn
```

```
1                 5                   10                  15
Arg Gln Val Thr Phe Cys Lys Arg Arg Asn Gly Leu Leu Lys Lys Ala
          20                  25                  30

Tyr Glu Leu Ser Ile Leu Cys Glu Ala Glu Val Ala Leu Ile Val Phe
          35                  40                  45

Ser Ser Arg Gly Arg Leu Tyr Glu Tyr Ser Asn Asn Asn Ser Ile Arg
          50                  55                  60

Asn Thr Ile Glu Arg Tyr Lys Lys Thr Cys Ser Asp Ser Ser Gly Ala
65                  70                  75                  80

Thr Thr Ile Thr Glu Ile Asn Ala Gln Tyr Tyr Gln Gln Glu Ser Ala
                  85                  90                  95

Lys Leu Arg His Gln Ile Gln Met Leu Gln Asn Ser Asn Arg His Leu
          100                 105                 110

Met Gly Asp Ser Leu Ser Ser Leu Thr Val Lys Glu Leu Lys Gln Leu
          115                 120                 125

Glu Asn Arg Leu Glu Arg Gly Leu Thr Arg Ile Arg Ser Lys Lys His
          130                 135                 140

Glu Met Leu Leu Ala Glu Ile Glu Tyr Leu Gln Lys Arg Glu Val Glu
145                 150                 155                 160

Leu Glu Asn Glu Asn Val Leu Val Arg Ala Lys Ile Ala Asp Leu Glu
                  165                 170                 175

Arg Leu Gln His Ala Asp Met Val Ser Gly Asp Gln Asp Leu Glu Leu
          180                 185                 190

Asn Ala Ile Gln Ala Leu Val Ser Arg Asn Phe Phe Thr Ser Thr Met
          195                 200                 205

Ile Glu Gly Glu Ala Ser Tyr Ser Gln Pro Glu Lys Lys Phe Leu His
          210                 215                 220

Leu
225
```

<210> SEQ ID NO 153
<211> LENGTH: 677
<212> TYPE: DNA
<213> ORGANISM: Rubus sp.

<400> SEQUENCE: 153

```
atggggagag gaaagattga gataaagagg attgagaaca ccacaaaccg tcaagtgacc        60
ttctgcaaaa gaagaaatgg actgttgaag aaagcttatg agctttccat tctctgtgag       120
gctgaagttg ccctcattgt cttctctagc cgtggccgcc tctacgagta ctctaacaac       180
aacagcataa gaaacacaat agagaggtac aagaagacat gttcagatag ctcaggtgca       240
accactatta cagaaatcaa tgctcaatat taccagcagg aatcggcaaa gctgaggcac       300
caaattcaaa tgctgcagaa ttctaacagg cacttaatgg gagattcctt gagtagtctg       360
actgtgaaag aactaaagca actggagaat aggcttgaac gaggccttac tagaatcagg       420
tccaagaagc atgaaatgtt gcttgctgaa attgaatact tgcagaaaag ggaggttgag       480
ctggaaaacg agaatgtttt agttcgagct aagatagcag accttgagag gcttcagcac       540
gcagacatgg tttctgggga tcaagatcta gagttgaatg caatccaggc gttagtatct       600
cgcaatttct tcacatccac tatgattgag ggtgaggctt catactcaca gccagagaag       660
aaatttctcc atctggg                                                      677
```

<210> SEQ ID NO 154
<211> LENGTH: 225

<212> TYPE: PRT
<213> ORGANISM: Rubus sp.

<400> SEQUENCE: 154

Met Gly Arg Gly Lys Ile Glu Ile Lys Arg Ile Glu Asn Thr Thr Asn
1               5                   10                  15

Arg Gln Val Thr Phe Cys Lys Arg Arg Asn Gly Leu Leu Lys Lys Ala
            20                  25                  30

Tyr Glu Leu Ser Ile Leu Cys Glu Ala Glu Val Ala Leu Ile Val Phe
        35                  40                  45

Ser Ser Arg Gly Arg Leu Tyr Glu Tyr Ser Asn Asn Asn Ser Ile Arg
    50                  55                  60

Asn Thr Ile Glu Arg Tyr Lys Lys Thr Cys Ser Asp Ser Ser Gly Ala
65                  70                  75                  80

Thr Thr Ile Thr Glu Ile Asn Ala Gln Tyr Tyr Gln Gln Glu Ser Ala
                85                  90                  95

Lys Leu Arg His Gln Ile Gln Met Leu Gln Asn Ser Asn Arg His Leu
            100                 105                 110

Met Gly Asp Ser Leu Ser Ser Leu Thr Val Lys Glu Leu Lys Gln Leu
        115                 120                 125

Glu Asn Arg Leu Glu Arg Gly Leu Thr Arg Ile Arg Ser Lys Lys His
    130                 135                 140

Glu Met Leu Leu Ala Glu Ile Glu Tyr Leu Gln Lys Arg Glu Val Glu
145                 150                 155                 160

Leu Glu Asn Glu Asn Val Leu Val Arg Ala Lys Ile Ala Glu Leu Glu
                165                 170                 175

Arg Leu Gln His Ala Asp Met Val Ser Gly Asp Gln Asp Leu Glu Leu
            180                 185                 190

Asn Ala Ile Gln Ala Leu Val Ser Arg Asn Phe Phe Thr Ser Thr Met
        195                 200                 205

Ile Glu Gly Glu Ala Ser Tyr Ser Gln Pro Glu Lys Lys Phe Leu His
    210                 215                 220

Leu
225

<210> SEQ ID NO 155
<211> LENGTH: 677
<212> TYPE: DNA
<213> ORGANISM: Rubus sp.

<400> SEQUENCE: 155
atggggagag gaaagattga dataaagagg attgagaaca ccacaaaccg tcaagtgacc        60
ttctgcaaaa gaagaaatgg actgttgaag aaagcttatg agctttccat tctctgcgag       120
gctgaagttg ccctcattgt cttctctagc cgtggccgcc tctacgagta ctctaacaac       180
aacagcataa gaaacactat agagaggtac aagaagacat gttcagatag ctcaggtgca       240
accactatta cagaaatcaa tgctcaatat taccagcagg aatcggcgaa gctgaggcac       300
caaattcaaa tgctgcagaa ttctaacagg cacttaatgg gagattcctt gagtagtctg       360
actgtgaaag aactaaagca actggagaat agacttgaac gaggccttac tagaatcagg       420
tccaagaagc atgaaatgtt gcttgctgaa attgaatact tgcagaaaag ggaggttgag       480
ctggaaaacg agaatgtttt agttcgagct aagatagcag aacttgagag gcttcagcac       540
gcagacatgg tttctgggga tcaagatcta gagttgaatg caatccaggc gttagtatct       600
cgcaatttct tcacatccac tatgattgag ggtgaggctt catactcaca gccagagaag       660

-continued

```
aaatttctcc atctggg                                                    677

<210> SEQ ID NO 156
<211> LENGTH: 225
<212> TYPE: PRT
<213> ORGANISM: Rubus sp.

<400> SEQUENCE: 156

Met Gly Arg Gly Lys Ile Glu Ile Lys Arg Ile Glu Asn Thr Thr Asn
1               5                   10                  15

Arg Gln Val Thr Phe Cys Lys Arg Arg Asn Gly Leu Leu Lys Lys Ala
                20                  25                  30

Tyr Glu Leu Ser Ile Leu Cys Glu Ala Glu Val Ala Leu Ile Val Phe
            35                  40                  45

Ser Ser Arg Gly Arg Leu Tyr Glu Tyr Ser Asn Asn Asn Ser Ile Arg
        50                  55                  60

Asn Thr Ile Glu Arg Tyr Lys Lys Ala Cys Ser Asp Ser Ser Gly Ala
65                  70                  75                  80

Thr Thr Ile Thr Glu Ile Asn Ala Gln Tyr Tyr Gln Gln Glu Ser Ala
                85                  90                  95

Lys Leu Arg His Gln Ile Gln Met Leu Gln Asn Ser Asn Arg His Leu
            100                 105                 110

Met Gly Asp Ser Leu Ser Asn Leu Thr Val Lys Glu Leu Lys Gln Leu
            115                 120                 125

Glu Asn Arg Leu Glu Arg Gly Leu Thr Arg Ile Arg Ser Lys Lys His
        130                 135                 140

Glu Met Leu Leu Ala Glu Ile Glu Tyr Leu Gln Lys Arg Glu Val Glu
145                 150                 155                 160

Leu Glu Asn Glu Asn Val Leu Val Arg Ala Lys Ile Ala Glu Leu Glu
                165                 170                 175

Arg Leu Gln His Ala Asp Met Val Ser Gly Asp Gln Asp Leu Glu Leu
            180                 185                 190

Asn Ala Ile Gln Ala Leu Val Ser Arg Asn Phe Phe Ala Ser Thr Met
            195                 200                 205

Ile Glu Gly Glu Ala Ser Tyr Ser Gln Pro Glu Lys Lys Phe Leu Asn
        210                 215                 220

Leu
225

<210> SEQ ID NO 157
<211> LENGTH: 677
<212> TYPE: DNA
<213> ORGANISM: Rubus sp.

<400> SEQUENCE: 157
atggggagag gaaagattga gataaagagg attgagaaca ccacaaaccg tcaagtgacc        60
ttctgcaaaa aagaaaatgg actgttgaag aaagcttatg agctttccat tctctgtgag       120
gctgaagttg ccctcattgt cttctctagc cgtggccgcc tctatgagta ctctaacaac       180
aacagcataa gaaacactat agagaggtac aagaaggcat gttcagatag ctcaggtgca       240
acaactatta cagaaatcaa tgctcaatat taccagcagg aatcggcaaa gctgaggcac       300
caaattcaaa tgctgcagaa ttctaacagg cacttaatgg gagattcctt gagtaatctg       360
actgtgaaaa aactgaagca gctggagaat aggcttgaac gaggccttac tagaatcagg       420
tccaagaagc atgaaatgtt gcttgctgaa attgaatact tgcagaaaag ggaggttgag       480
```

-continued

```
ctggaaaacg agaatgtttt agttcgagct aagatagcag aacttgagag gcttcagcac      540
gcagacatgg tttctgggga tcaagatcta gagttgaatg caatccaggc gttagtatct      600
cgcaatttct tcgcatccac tatgattgag ggtgaggctt catactcaca gccagagaag      660
aaatttctca atctggg                                                       677
```

<210> SEQ ID NO 158
<211> LENGTH: 225
<212> TYPE: PRT
<213> ORGANISM: Rubus sp.

<400> SEQUENCE: 158

```
Met Gly Arg Gly Lys Ile Glu Ile Lys Arg Ile Glu Asn Thr Thr Asn
1               5                   10                  15

Arg Gln Val Thr Phe Cys Lys Arg Arg Asn Gly Leu Leu Lys Lys Ala
            20                  25                  30

Tyr Glu Leu Ser Ile Leu Cys Glu Ala Glu Val Ala Leu Ile Val Phe
        35                  40                  45

Ser Ser Arg Gly Arg Leu Tyr Glu Tyr Ser Asn Asn Asn Ser Ile Arg
    50                  55                  60

Asn Thr Ile Glu Arg Tyr Lys Lys Ala Cys Ser Asp Ser Ser Gly Ala
65                  70                  75                  80

Thr Thr Ile Thr Glu Ile Asn Ala Gln Tyr Tyr Gln Gln Glu Ser Ala
                85                  90                  95

Lys Leu Arg His Gln Ile Gln Met Leu Gln Asn Ser Asn Arg His Leu
            100                 105                 110

Met Gly Asp Ser Leu Ser Asn Leu Thr Val Lys Glu Leu Lys Gln Leu
        115                 120                 125

Glu Asn Arg Leu Glu Arg Gly Leu Thr Arg Ile Arg Ser Lys Lys His
    130                 135                 140

Glu Met Leu Leu Ala Glu Ile Glu Tyr Leu Gln Lys Arg Glu Val Glu
145                 150                 155                 160

Leu Glu Asn Glu Asn Val Leu Val Arg Ala Lys Ile Ala Glu Leu Glu
                165                 170                 175

Arg Leu Gln Gln Ala Asp Met Ile Ser Gly Asp Gln Asp Leu Glu Leu
            180                 185                 190

Asn Ala Ile Gln Ala Leu Val Ser Arg Asn Phe Phe Ala Ser Thr Met
        195                 200                 205

Ile Glu Gly Glu Ala Ser Tyr Ser Gln Pro Glu Lys Lys Phe Leu Asn
    210                 215                 220

Leu
225
```

<210> SEQ ID NO 159
<211> LENGTH: 677
<212> TYPE: DNA
<213> ORGANISM: Rubus sp.

<400> SEQUENCE: 159

```
atggggagag gaaagattga gataaagagg attgagaaca ccacaaaccg tcaagtgacc       60
ttctgcaaaa gaagaaatgg actgttgaag aaagcttatg agctttccat tctctgtgag      120
gctgaagttg ccctcattgt cttctctagc cgtggccgcc tctatgagta ctctaacaac      180
aacagcataa gaaacactat agagaggtac aagaaggcat gttcagatag ctcaggtgca      240
acaactatta cagaaatcaa tgctcaatat taccagcagg aatcggcaaa gctgaggcac      300
```

-continued

```
caaattcaaa tgctgcagaa ttctaacagg cacttaatgg gagattcctt gagtaatctg      360
actgtgaaag aactgaagca gctggagaat aggcttgaac gaggccttac tagaatcagg      420
tccaagaagc atgaaatgtt gcttgctgaa attgaatact tgcagaaaag ggaggttgag      480
ctggaaaacg agaatgtttt agttcgagct aagatagcag aacttgagag gcttcagcaa      540
gcagacatga tttctgggga tcaagatcta gagttgaatg caatccaggc gttagtatct      600
cgcaatttct tcgcatccac tatgattgag ggtgaggctt catactcaca gccagagaag      660
aaatttctca atctggg                                                     677
```

<210> SEQ ID NO 160
<211> LENGTH: 225
<212> TYPE: PRT
<213> ORGANISM: Rubus sp.

<400> SEQUENCE: 160

```
Met Gly Arg Gly Lys Ile Glu Ile Lys Arg Ile Glu Asn Thr Thr Asn
1               5                   10                  15

Arg Gln Val Thr Phe Cys Lys Arg Arg Asn Gly Leu Leu Lys Lys Ala
                20                  25                  30

Tyr Glu Leu Ser Ile Leu Cys Glu Ala Glu Val Ala Leu Ile Val Phe
            35                  40                  45

Ser Ser Arg Gly Arg Leu Tyr Glu Tyr Ser Asn Asn Asn Ser Ile Arg
        50                  55                  60

Asn Thr Ile Glu Arg Tyr Lys Lys Thr Cys Ser Val Ser Ser Gly Ala
65                  70                  75                  80

Thr Thr Ile Thr Glu Ile Asn Ala Gln Tyr Tyr Gln Gln Glu Ser Ala
                85                  90                  95

Lys Leu Arg His Gln Ile Gln Met Leu Gln Asn Ser Asn Arg His Leu
            100                 105                 110

Met Gly Asp Ser Leu Ser Ser Leu Thr Val Lys Glu Leu Lys Gln Leu
            115                 120                 125

Glu Asn Arg Leu Glu Arg Gly Leu Thr Arg Ile Arg Ser Lys Lys His
        130                 135                 140

Glu Met Leu Leu Ala Glu Ile Glu Tyr Leu Gln Lys Arg Glu Val Glu
145                 150                 155                 160

Leu Glu Asn Glu Asn Val Leu Val Arg Ala Lys Ile Ala Glu Leu Glu
                165                 170                 175

Arg Leu Gln His Ala Asp Met Val Ser Gly Asp Gln Asp Leu Glu Leu
            180                 185                 190

Asn Ala Ile Gln Ala Leu Val Ser Arg Asn Phe Phe Ala Ser Thr Met
        195                 200                 205

Ile Glu Gly Glu Ala Ser Tyr Ser Gln Pro Glu Lys Lys Phe Leu His
    210                 215                 220

Leu
225
```

<210> SEQ ID NO 161
<211> LENGTH: 677
<212> TYPE: DNA
<213> ORGANISM: Rubus sp.

<400> SEQUENCE: 161

```
atggggagag gaaagattga gataaagagg attgagaaca ccacaaaccg tcaagtgacc       60
ttctgcaaaa gaagaaatgg actgttgaag aaagcttatg agctttccat tctctgtgag      120
```

```
gctgaagttg ccctcattgt cttctctagc cgtggccgcc tctacgagta ctctaacaac    180
aacagcataa gaaacactat agagaggtac aagaagacat gttcagttag ctcaggtgca    240
accactatta cagaaatcaa tgctcaatat taccagcagg aatcggcaaa gctgaggcac    300
caaattcaaa tgctgcagaa ttctaacagg cacttaatgg gagattcctt gagtagtctg    360
actgtgaaag aactaaagca actggagaat aggcttgaac gaggccttac tagaatcagg    420
tccaagaagc atgaaatgtt gcttgctgaa attgaatact tgcagaaaag ggaggttgag    480
ctggaaaacg agaatgtttt agttcgagct aagatagcag aacttgagag gcttcagcac    540
gcagacatgg tttctgggga tcaagatcta gagttgaatg caatccaggc gttagtatct    600
cgcaatttct tcgcatccac catgattgag ggtgaggctt catactcaca gccagagaag    660
aaatttctcc atctggg                                                  677
```

<210> SEQ ID NO 162
<211> LENGTH: 225
<212> TYPE: PRT
<213> ORGANISM: Rubus ulmifolius

<400> SEQUENCE: 162

```
Met Gly Arg Gly Lys Ile Glu Ile Lys Arg Ile Glu Asn Thr Thr Asn
1               5                   10                  15

Arg Gln Val Thr Phe Cys Lys Arg Arg Asn Gly Leu Leu Lys Lys Ala
                20                  25                  30

Tyr Glu Leu Ser Ile Leu Cys Glu Ala Glu Val Ala Leu Ile Val Phe
            35                  40                  45

Ser Ser Arg Gly Arg Leu Tyr Glu Tyr Ser Asn Asn Asn Ser Ile Arg
        50                  55                  60

Asn Thr Ile Glu Arg Tyr Lys Lys Thr Cys Ser Asp Ser Ser Gly Ala
65                  70                  75                  80

Thr Thr Ile Thr Glu Ile Asn Ala Gln Tyr Tyr Gln Gln Glu Ser Ala
                85                  90                  95

Lys Leu Arg His Gln Ile Gln Met Leu Gln Asn Ser Asn Arg His Leu
            100                 105                 110

Met Gly Asp Ser Leu Ser Ser Leu Thr Val Lys Glu Leu Lys Gln Leu
        115                 120                 125

Glu Asn Arg Leu Glu Arg Gly Leu Thr Arg Ile Arg Ser Lys Lys His
    130                 135                 140

Glu Met Leu Leu Ala Glu Ile Glu Tyr Leu Gln Lys Arg Glu Val Glu
145                 150                 155                 160

Leu Glu Asn Glu Asn Val Leu Val Arg Ala Lys Ile Ala Glu Leu Glu
                165                 170                 175

Arg Leu Gln His Ala Asp Met Val Ser Gly Asp Gln Asp Leu Glu Leu
            180                 185                 190

Asn Ala Ile Gln Ala Leu Val Ser Arg Asn Phe Phe Thr Ser Thr Met
        195                 200                 205

Ile Glu Gly Glu Ala Ser Tyr Ser Gln Pro Glu Lys Lys Phe Leu His
    210                 215                 220

Leu
225
```

<210> SEQ ID NO 163
<211> LENGTH: 677
<212> TYPE: DNA
<213> ORGANISM: Rubus ulmifolius -continued

<400> SEQUENCE: 163

```
atggggagag gaaagattga gataaagagg attgagaaca ccacaaaccg tcaagtgacc        60
ttctgcaaaa gaagaaatgg actgttgaag aaagcttatg agctttccat tctctgtgag       120
gctgaagttg ccctcattgt cttctctagc cgtggccgcc tctacgagta ctctaacaac       180
aacagcataa gaaacactat agagaggtac aagaagacat gttcagatag ctcaggtgca       240
accactatta cagaaatcaa tgctcaatat taccagcagg aatcggcaaa gctgaggcac       300
caaattcaaa tgctgcagaa ttctaacagg cacttaatgg gggattcctt gagtagtctg       360
actgtgaaag aactaaagca gctggagaat aggcttgaac gaggccttac tagaatcagg       420
tccaagaagc atgaaatgtt gcttgctgaa attgaatact tgcagaaaag ggaggttgag       480
ctggaaaacg agaatgtttt agttcgagct aagatagcag aacttgagag gcttcagcac       540
gcagacatgg tttctgggga tcaagatcta gagttgaatg caatccaggc gttagtatct       600
cgcaatttct tcacatccac tatgattgag ggtgaggctt catactcaca gccagagaag       660
aaatttctcc atctggg                                                       677
```

<210> SEQ ID NO 164
<211> LENGTH: 225
<212> TYPE: PRT
<213> ORGANISM: Rubus idaeus

<400> SEQUENCE: 164

```
Met Gly Arg Gly Lys Ile Glu Ile Lys Arg Ile Glu Asn Thr Thr Asn
1               5                   10                  15

Arg Gln Val Thr Phe Cys Lys Arg Arg Asn Gly Leu Leu Lys Lys Ala
            20                  25                  30

Tyr Glu Leu Ser Ile Leu Cys Glu Ala Glu Val Ala Leu Ile Val Phe
        35                  40                  45

Ser Ser Arg Gly Arg Leu Tyr Glu Tyr Ser Asn Asn Asn Ser Ile Arg
    50                  55                  60

Asn Thr Ile Glu Arg Tyr Lys Lys Ala Cys Ser Asp Ser Ser Gly Ala
65                  70                  75                  80

Thr Thr Ile Thr Glu Ile Asn Ala Gln Tyr Tyr Gln Gln Glu Ser Ala
                85                  90                  95

Lys Leu Arg His Gln Ile Gln Met Leu Gln Asn Ser Asn Arg His Leu
            100                 105                 110

Met Gly Asp Ser Leu Ser Asn Leu Thr Val Lys Glu Leu Lys Gln Leu
            115                 120                 125

Glu Asn Arg Leu Glu Arg Gly Leu Thr Arg Ile Arg Ser Lys Lys His
        130                 135                 140

Glu Met Leu Leu Ala Glu Ile Glu Tyr Leu Gln Lys Arg Glu Val Glu
145                 150                 155                 160

Leu Glu Asn Glu Asn Val Leu Val Arg Ala Lys Ile Ala Glu Leu Glu
                165                 170                 175

Arg Leu Gln His Ala Asp Met Val Ser Gly Asp Gln Asp Leu Glu Leu
            180                 185                 190

Asn Ala Ile Gln Ala Leu Val Ser Arg Asn Phe Phe Ala Ser Thr Met
        195                 200                 205

Ile Glu Gly Glu Ala Ser Tyr Ser Gln Pro Glu Lys Lys Phe Leu Asn
    210                 215                 220

Leu
225
```

<210> SEQ ID NO 165
<211> LENGTH: 677
<212> TYPE: DNA
<213> ORGANISM: Rubus idaeus

<400> SEQUENCE: 165
atggggagag gaaagattga gataaagagg attgagaaca ccacaaaccg tcaagtgacc      60
ttctgcaaaa gaagaaatgg actgttgaag aaagcttatg agctttccat tctctgtgag     120
gctgaagttg ccctcattgt cttctctagc cgtggccgcc tctatgagta ctctaacaac     180
aacagcataa gaaacactat agagaggtac aagaaggcat gttcagatag ctcaggtgca     240
acaactatta cagaaatcaa tgctcaatat taccagcagg aatcggcaaa gctgaggcac     300
caaattcaaa tgctgcagaa ttctaacagg cacttaatgg gagattcctt gagtaatctg     360
actgtgaaag aactaaagca gctggagaat aggcttgaac gaggccttac tagaatcagg     420
tccaagaagc atgaaatgtt gcttgctgaa attgaatact tgcagaaaag ggaggttgag     480
ctggaaaacg agaatgtttt agttcgagct aagatagcag aacttgagag gcttcagcac     540
gcagacatgt tttctgggga tcaagatcta gagttgaatg caatccaggc gttagtatct     600
cgcaatttct tcgcatccac tatgattgag ggtgaggctt catactcaca gccagagaag     660
aaatttctca atctggg                                                    677

<210> SEQ ID NO 166
<211> LENGTH: 222
<212> TYPE: PRT
<213> ORGANISM: Prunus avium

<400> SEQUENCE: 166

Met Gly Arg Gly Lys Ile Glu Ile Lys Arg Ile Glu Asn Thr Thr Asn
1               5                   10                  15

Arg Gln Val Thr Phe Cys Lys Arg Arg Asn Gly Leu Leu Lys Lys Ala
            20                  25                  30

Tyr Glu Leu Ser Ile Leu Cys Asp Ala Glu Val Ala Leu Ile Val Phe
        35                  40                  45

Ser Ser Arg Gly Arg Leu Tyr Glu Tyr Ser Asn Asn Lys Ser Ile Arg
    50                  55                  60

Asn Thr Ile Glu Arg Tyr Lys Lys Ala Cys Ser Asp Ser Ser Gly Ser
65                  70                  75                  80

Thr Ser Ile Thr Glu Ile Asn Ala Gln Tyr Tyr Gln Gln Glu Ser Ala
                85                  90                  95

Lys Leu Arg Gln Gln Ile Gln Met Leu Gln Asn Ser Asn Arg His Leu
            100                 105                 110

Met Gly Asp Ala Leu Ser Thr Leu Ser Val Lys Glu Leu Lys Gln Leu
            115                 120                 125

Glu Asn Arg Leu Glu Arg Gly Ile Asn Arg Ile Arg Ser Lys Lys His
    130                 135                 140

Glu Met Leu Leu Ala Glu Ile Glu Tyr Leu Gln Lys Lys Glu Ile Glu
145                 150                 155                 160

Leu Glu Asn Glu Asn Val Cys Leu Arg Thr Lys Ile Ser Glu Val Glu
                165                 170                 175

Arg Leu Gln Gln Ala Asn Met Val Gly Pro Glu Leu Asn Ala Ile Gln
            180                 185                 190

Ala Leu Ala Ser Arg Asn Phe Phe Ser Gln Asn Met Met Glu Gly Gly
        195                 200                 205

```
Ala Thr Tyr Pro Gln Gln Asp Lys Lys Ile Leu His Leu Gly
    210             215             220

<210> SEQ ID NO 167
<211> LENGTH: 222
<212> TYPE: PRT
<213> ORGANISM: Prunus avium

<400> SEQUENCE: 167

Met Gly Gly Gly Lys Ile Glu Ile Lys Arg Ile Glu Asn Thr Thr Asn
1               5                   10                  15

Arg Gln Val Thr Phe Cys Lys Arg Arg Asn Gly Leu Leu Lys Lys Ala
            20                  25                  30

Tyr Glu Leu Ser Ile Leu Cys Asp Ala Glu Val Ala Leu Ile Val Phe
        35                  40                  45

Ser Ser Arg Gly Arg Leu Tyr Glu Tyr Ser Asn Asn Asn Ser Ile Arg
    50                  55                  60

Asn Thr Ile Glu Arg Tyr Lys Lys Ala Cys Ser Asp Ser Ser Gly Ser
65                  70                  75                  80

Thr Ser Ile Thr Glu Ile Asn Ala Gln Tyr Tyr Gln Gln Glu Ser Ala
                85                  90                  95

Lys Leu Arg Gln Gln Ile Gln Met Leu Gln Asn Ser Asn Arg His Leu
            100                 105                 110

Met Gly Asp Ala Leu Ser Thr Leu Ser Val Lys Glu Leu Lys Gln Leu
            115                 120                 125

Glu Asn Arg Leu Glu Arg Gly Ile Asn Arg Ile Arg Ser Lys Lys His
    130                 135                 140

Glu Met Leu Leu Ala Glu Ile Glu Tyr Leu Gln Lys Lys Glu Ile Glu
145                 150                 155                 160

Leu Glu Asn Glu Asn Val Cys Leu Arg Thr Lys Ile Ser Glu Val Glu
                165                 170                 175

Lys Leu Gln Gln Ala Asn Met Val Gly Pro Glu Leu Asn Ala Ile Gln
            180                 185                 190

Ala Leu Ala Ser Arg Asn Phe Phe Ser Gln Asn Met Met Glu Gly Gly
        195                 200                 205

Ala Thr Tyr Pro Gln Gln Asp Lys Lys Ile Leu His Leu Gly
    210             215             220

<210> SEQ ID NO 168
<211> LENGTH: 222
<212> TYPE: PRT
<213> ORGANISM: Prunus cerasus

<400> SEQUENCE: 168

Met Gly Arg Gly Lys Ile Glu Ile Lys Arg Ile Glu Asn Thr Thr Asn
1               5                   10                  15

Arg Gln Val Thr Phe Cys Lys Arg Arg Asn Gly Leu Leu Lys Lys Ala
            20                  25                  30

Tyr Glu Leu Ser Ile Leu Cys Asp Ala Glu Val Ala Leu Ile Val Phe
        35                  40                  45

Ser Ser Arg Gly Arg Leu Tyr Glu Tyr Ser Asn Asn Asn Ser Ile Arg
    50                  55                  60

Asn Thr Ile Glu Arg Tyr Lys Lys Ala Cys Ser Asp Ser Ser Gly Ser
65                  70                  75                  80

Thr Ser Ile Thr Glu Ile Asn Ala Gln Tyr Tyr Gln Gln Glu Ser Ala
                85                  90                  95
```

-continued

```
Lys Leu Arg Gln Gln Ile Gln Met Leu Gln Asn Ser Asn Arg His Leu
            100                 105                 110

Met Gly Asp Ala Leu Ser Thr Leu Ser Val Lys Glu Leu Lys Gln Leu
            115                 120                 125

Glu Asn Arg Leu Glu Arg Gly Ile Asn Arg Ile Arg Ser Lys Lys His
        130                 135                 140

Glu Met Leu Leu Ala Glu Ile Glu Tyr Phe Gln Lys Lys Glu Ile Glu
145                 150                 155                 160

Leu Glu Asn Glu Asn Val Cys Leu Arg Thr Lys Ile Ser Glu Val Glu
                165                 170                 175

Arg Leu Gln Gln Ala Asn Met Val Gly Pro Glu Leu Asn Ala Ile Gln
            180                 185                 190

Ala Leu Ala Ser Arg Asn Phe Phe Ser Gln Asn Met Met Glu Gly Gly
        195                 200                 205

Ala Thr Tyr Pro Gln Gln Asp Lys Lys Ile Leu His Leu Gly
    210                 215                 220
```

```
<210> SEQ ID NO 169
<211> LENGTH: 222
<212> TYPE: PRT
<213> ORGANISM: Prunus serrulata

<400> SEQUENCE: 169
```

```
Met Gly Arg Gly Lys Ile Glu Ile Lys Arg Ile Glu Asn Thr Thr Asn
1               5                   10                  15

Arg Gln Val Thr Phe Cys Lys Arg Arg Asn Gly Leu Leu Lys Lys Ala
            20                  25                  30

Tyr Glu Leu Ser Ile Leu Cys Asp Ala Glu Val Ala Leu Ile Val Phe
        35                  40                  45

Ser Ser Arg Gly Arg Leu Tyr Glu Tyr Ser Asn Asn Asn Ser Ile Arg
    50                  55                  60

Asn Thr Ile Glu Arg Tyr Lys Lys Ala Cys Ser Asp Ser Ser Gly Ser
65                  70                  75                  80

Thr Ser Ile Thr Glu Ile Asn Ala Gln Tyr Tyr Gln Gln Glu Ser Ala
                85                  90                  95

Lys Leu Arg Gln Gln Ile Gln Met Leu Gln Asn Ser Asn Arg His Leu
            100                 105                 110

Met Gly Asp Ala Leu Ser Thr Leu Ser Val Lys Glu Leu Lys Gln Leu
            115                 120                 125

Glu Asn Arg Leu Glu Arg Gly Ile Asn Arg Ile Arg Ser Lys Lys His
        130                 135                 140

Glu Met Leu Leu Ala Glu Ile Glu Tyr Leu Gln Lys Lys Glu Ile Glu
145                 150                 155                 160

Leu Glu Asn Glu Asn Val Cys Leu Arg Thr Lys Ile Ser Glu Val Glu
                165                 170                 175

Arg Leu Gln Gln Ala Asn Met Val Gly Pro Glu Leu Asn Ala Ile Gln
            180                 185                 190

Ala Leu Val Ser Arg Asn Phe Phe Ser Gln Asn Ile Met Glu Gly Gly
        195                 200                 205

Ala Thr Tyr Pro Gln Gln Asp Lys Lys Ile Leu His Leu Gly
    210                 215                 220
```

```
<210> SEQ ID NO 170
<211> LENGTH: 222
<212> TYPE: PRT
```

-continued

```
<213> ORGANISM: Prunus mume

<400> SEQUENCE: 170

Met Gly Arg Gly Lys Ile Glu Ile Lys Arg Ile Glu Asn Thr Thr Asn
1               5                   10                  15

Arg Gln Val Thr Phe Cys Lys Arg Arg Asn Gly Leu Leu Lys Lys Ala
            20                  25                  30

Tyr Glu Leu Ser Ile Leu Cys Asp Ala Glu Val Ala Leu Ile Val Phe
        35                  40                  45

Ser Ser Arg Gly Arg Leu Tyr Glu Tyr Ser Asn Asn Asn Ser Ile Arg
    50                  55                  60

Asn Thr Ile Glu Arg Tyr Lys Lys Ala Cys Ser Asp Ser Ser Gly Ser
65                  70                  75                  80

Thr Ser Ile Thr Glu Ile Asn Ala Gln Tyr Tyr Gln Gln Glu Ser Ala
                85                  90                  95

Lys Leu Arg Gln Gln Ile Gln Met Leu Gln Asn Ser Asn Arg His Leu
            100                 105                 110

Met Gly Asp Ala Leu Ser Thr Leu Ser Val Lys Glu Leu Lys Gln Leu
        115                 120                 125

Glu Asn Arg Leu Glu Arg Gly Ile Asn Arg Ile Arg Ser Lys Lys His
    130                 135                 140

Glu Met Leu Leu Ala Glu Ile Glu Tyr Leu Gln Lys Lys Glu Ile Glu
145                 150                 155                 160

Leu Glu Asn Glu Asn Val Cys Leu Arg Thr Lys Ile Ser Glu Val Glu
                165                 170                 175

Arg Leu Gln Gln Ala Asn Met Val Gly Pro Glu Leu Asn Ala Ile Gln
            180                 185                 190

Ala Leu Ala Ser Arg Asn Phe Phe Ser Gln Thr Met Met Glu Gly Gly
        195                 200                 205

Ala Thr Tyr Pro Gln Gln Asp Lys Lys Ile Leu His Leu Gly
    210                 215                 220

<210> SEQ ID NO 171
<211> LENGTH: 222
<212> TYPE: PRT
<213> ORGANISM: Prunus dulcis

<400> SEQUENCE: 171

Met Gly Arg Gly Lys Ile Glu Ile Lys Arg Ile Glu Asn Thr Thr Asn
1               5                   10                  15

Arg Gln Val Thr Phe Cys Lys Arg Arg Asn Gly Leu Leu Lys Lys Ala
            20                  25                  30

Tyr Glu Leu Ser Ile Leu Cys Asp Ala Glu Val Ala Leu Ile Val Phe
        35                  40                  45

Ser Ser Arg Gly Arg Leu Tyr Glu Tyr Ser Asn Asn Asn Ser Ile Arg
    50                  55                  60

Asn Thr Ile Glu Arg Tyr Lys Lys Ala Cys Ser Asp Ser Ser Gly Ser
65                  70                  75                  80

Thr Ser Ile Thr Glu Ile Asn Ala Gln Tyr Tyr Gln Gln Glu Ser Ala
                85                  90                  95

Lys Leu Arg Gln Gln Ile Gln Met Leu Gln Asn Ser Asn Arg His Leu
            100                 105                 110

Met Gly Asp Ala Leu Ser Thr Leu Ser Val Lys Glu Leu Lys Gln Leu
        115                 120                 125

Glu Asn Arg Leu Glu Arg Gly Ile Asn Arg Ile Arg Ser Lys Lys His
```

-continued

```
         130                135                140
Glu Met Leu Leu Ala Glu Ile Glu Tyr Leu Gln Lys Lys Glu Ile Glu
145                150                155                160

Leu Glu Asn Glu Asn Val Cys Leu Arg Thr Lys Ile Ser Glu Val Glu
                165                170                175

Arg Leu Gln Gln Ala Asn Met Val Gly Pro Glu Leu Asn Ala Ile Gln
            180                185                190

Ala Leu Ala Ser Arg Asn Phe Phe Ser Gln Asn Met Met Glu Gly Gly
        195                200                205

Ala Thr Tyr Thr Gln Gln Asp Lys Lys Ile Leu His Leu Gly
    210                215                220
```

<210> SEQ ID NO 172
<211> LENGTH: 56
<212> TYPE: DNA
<213> ORGANISM: Rubus sp.

<400> SEQUENCE: 172
tggggatcaa gatctagagt tgaatgcaat ccaggcgtta gtatctcgca atttct          56

<210> SEQ ID NO 173
<211> LENGTH: 96
<212> TYPE: DNA
<213> ORGANISM: Rubus sp.

<400> SEQUENCE: 173
cagcacgcag acatggtttc tggggatcaa gatctagagt tgaatgcaat ccaggcgtta          60
gtatctcgca atttcttcac atccactatg attgag          96

<210> SEQ ID NO 174
<211> LENGTH: 76
<212> TYPE: DNA
<213> ORGANISM: Rubus sp.

<400> SEQUENCE: 174
acatggtttc tggggatcaa gatctagagt tgaatgcaat ccaggcgtta gtatctcgca          60
atttcttcac atccac          76

<210> SEQ ID NO 175
<211> LENGTH: 23
<212> TYPE: DNA
<213> ORGANISM: Rubus sp.

<400> SEQUENCE: 175
ggcgttagta tctcgcaatt tct          23

<210> SEQ ID NO 176
<211> LENGTH: 23
<212> TYPE: DNA
<213> ORGANISM: Rubus sp.

<400> SEQUENCE: 176
tggggatcaa gatctagagt tga          23

<210> SEQ ID NO 177
<211> LENGTH: 4
<212> TYPE: PRT
<213> ORGANISM: Rubus sp.

<400> SEQUENCE: 177

Tyr Gln Gln Glu
1

<210> SEQ ID NO 178
<211> LENGTH: 13
<212> TYPE: PRT
<213> ORGANISM: Artificial
<220> FEATURE:
<223> OTHER INFORMATION: motif
<220> FEATURE:
<221> NAME/KEY: MISC_FEATURE
<222> LOCATION: (6)..(6)
<223> OTHER INFORMATION: wherein Xaa can be A, K or T
<220> FEATURE:
<221> NAME/KEY: MISC_FEATURE
<222> LOCATION: (10)..(10)
<223> OTHER INFORMATION: wherein Xaa can be Q or H

<400> SEQUENCE: 178

Tyr Gln Gln Glu Ser Xaa Lys Leu Arg Xaa Gln Ile Gln
1               5                   10

<210> SEQ ID NO 179
<211> LENGTH: 13
<212> TYPE: PRT
<213> ORGANISM: Malus domestica

<400> SEQUENCE: 179

Tyr Gln Gln Glu Ser Ala Lys Leu Arg Gln Gln Ile Gln
1               5                   10

<210> SEQ ID NO 180
<211> LENGTH: 13
<212> TYPE: PRT
<213> ORGANISM: Fragaria vesca

<400> SEQUENCE: 180

Tyr Gln Gln Glu Ser Thr Lys Leu Arg His Gln Ile Gln
1               5                   10

<210> SEQ ID NO 181
<211> LENGTH: 13
<212> TYPE: PRT
<213> ORGANISM: Rubus sp.

<400> SEQUENCE: 181

Tyr Gln Gln Glu Ser Ala Lys Leu Arg His Gln Ile Gln
1               5                   10

<210> SEQ ID NO 182
<211> LENGTH: 13
<212> TYPE: PRT
<213> ORGANISM: Solanum lycopersicum

<400> SEQUENCE: 182

Tyr Gln Gln Glu Ser Lys Lys Leu Arg Gln Gln Ile Gln
1               5                   10

<210> SEQ ID NO 183
<211> LENGTH: 42
<212> TYPE: PRT
<213> ORGANISM: Rubus sp.

<400> SEQUENCE: 183

Asn Val Leu Val Arg Ala Lys Ile Ala Asp Leu Glu Arg Leu Gln His
1               5                   10                  15

-continued

```
Ala Asp Met Val Ser Gly Asp Gln Asp Leu Glu Leu Asn Ala Ile Gln
        20                      25                  30

Ala Leu Val Ser Arg Asn Phe Phe Thr Ser
        35                      40

<210> SEQ ID NO 184
<211> LENGTH: 20
<212> TYPE: DNA
<213> ORGANISM: Rubus sp.

<400> SEQUENCE: 184
ccgcaatcat agagcgttaa                                                    20

<210> SEQ ID NO 185
<211> LENGTH: 21
<212> TYPE: DNA
<213> ORGANISM: Rubus sp.

<400> SEQUENCE: 185
cgcaatcata gagcgttaaa g                                                  21

<210> SEQ ID NO 186
<211> LENGTH: 20
<212> TYPE: DNA
<213> ORGANISM: Rubus sp.

<400> SEQUENCE: 186
cgcaatttct tcacatccac                                                    20

<210> SEQ ID NO 187
<211> LENGTH: 49
<212> TYPE: PRT
<213> ORGANISM: Rubus sp.

<400> SEQUENCE: 187

Arg Leu Gln His Ala Asp Met Val Ser Gly Asp Gln Asp Leu Glu Leu
1               5                   10                  15

Asn Ala Ile Gln Ala Leu Val Ser Arg Asn Phe Phe Thr Ser Thr Met
                20                  25                  30

Ile Glu Gly Glu Ala Ser Tyr Ser Gln Pro Glu Lys Lys Phe Leu His
            35                  40                  45

Leu

<210> SEQ ID NO 188
<211> LENGTH: 41
<212> TYPE: PRT
<213> ORGANISM: Rubus sp.

<400> SEQUENCE: 188

Ala Asp Met Val Ser Gly Asp Gln Asp Leu Glu Leu Asn Ala Ile Gln
1               5                   10                  15

Ala Leu Val Ser Arg Asn Phe Phe Thr Ser Thr Met Ile Glu Gly Glu
                20                  25                  30

Ala Ser Tyr Ser Gln Pro Glu Lys Lys
            35                  40

<210> SEQ ID NO 189
<211> LENGTH: 21
<212> TYPE: PRT
<213> ORGANISM: Rubus sp.

<400> SEQUENCE: 189
```

-continued

```
Glu Leu Asn Ala Ile Gln Ala Leu Val Ser Arg Asn Phe Phe Thr Ser
1               5                   10                  15

Thr Met Ile Glu Gly
            20

<210> SEQ ID NO 190
<211> LENGTH: 301
<212> TYPE: DNA
<213> ORGANISM: Artificial
<220> FEATURE:
<223> OTHER INFORMATION: 7x CArG Reporter promoter

<400> SEQUENCE: 190
ggggtggctt tcctttttg gtaaattttg gatccggagt ggcattcctt ttttggtaca      60
tcttggttcc gaggtggcta tcctttttg gtcaattctg gaaccgggct gcctttcctt     120
ttttggtaat tttagcatcc gcggtcgcta tcctttttg gttaatattg gaaccggcgt     180
cgcattcctt ttttggtata ttatggttcc gtggtagctc tccttttttg gttaaatttc     240
gatccggcgt ttactatggg aggtctatat aagcagagct cgtttagtga accgtcagat     300
c                                                                     301

<210> SEQ ID NO 191
<211> LENGTH: 756
<212> TYPE: DNA
<213> ORGANISM: Arabidopsis thaliana

<400> SEQUENCE: 191
atggggcggg gcagggtcga gctgaagcgc attgaaaaca agatcaaccg ccaggttact      60
ttcgctaagc ggcggaatgg cctgttgaaa aaagcttacg agctctccgt cctctgtgac     120
gctgaggtcg ccctcattat cttttccaac cgcggaaagc tctacgaatt ctgttcttcc     180
tcaagtatgc tgcgcaccct ggaaagatac caaaaatgca actatggagc gccagagcct     240
aatgtgccca gcagggaagc attggctgtc gagctgtcta gccaacagga gtatttgaag     300
ttaaaggaga ggtatgacgc cctgcagcgt acacagagga atctcctggg cgaggatctc     360
ggcccactgt caactaagga actggaaagt ctcgagagac agctcgattc ctctctgaag     420
cagatccgtg cactgcgcac acagttcatg ctggaccagc tcaacgacct tcagagtaaa     480
gaaagaatgc tgaccgagac taacaaaact ctcagactgc gcctggccga tggttatcag     540
atgcctctcc agctcaaccc caaccaagaa gaggtcgatc attacggtcg tcaccaccac     600
caacagcagc agcattcaca ggctttcttc caacccctgg agtgtgaacc catcctgcag     660
atcgggtacc aaggtcagca ggacggcatg ggggccggcc ctagcgtgaa taattacatg     720
ctgggctggt tgccgtacga cacaaactca atataa                               756

<210> SEQ ID NO 192
<211> LENGTH: 251
<212> TYPE: PRT
<213> ORGANISM: Arabidopsis thaliana

<400> SEQUENCE: 192

Met Gly Arg Gly Arg Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
            20                  25                  30

Tyr Glu Leu Ser Val Leu Cys Asp Ala Glu Val Ala Leu Ile Ile Phe
        35                  40                  45
```

```
Ser Asn Arg Gly Lys Leu Tyr Glu Phe Cys Ser Ser Ser Met Leu
    50              55              60

Arg Thr Leu Glu Arg Tyr Gln Lys Cys Asn Tyr Gly Ala Pro Glu Pro
65              70              75              80

Asn Val Pro Ser Arg Glu Ala Leu Ala Val Glu Leu Ser Ser Gln Gln
                85              90              95

Glu Tyr Leu Lys Leu Lys Glu Arg Tyr Asp Ala Leu Gln Arg Thr Gln
            100             105             110

Arg Asn Leu Leu Gly Glu Asp Leu Gly Pro Leu Ser Thr Lys Glu Leu
        115             120             125

Glu Ser Leu Glu Arg Gln Leu Asp Ser Ser Leu Lys Gln Ile Arg Ala
    130             135             140

Leu Arg Thr Gln Phe Met Leu Asp Gln Leu Asn Asp Leu Gln Ser Lys
145             150             155             160

Glu Arg Met Leu Thr Glu Thr Asn Lys Thr Leu Arg Leu Arg Leu Ala
            165             170             175

Asp Gly Tyr Gln Met Pro Leu Gln Leu Asn Pro Asn Gln Glu Glu Val
            180             185             190

Asp His Tyr Gly Arg His His His Gln Gln Gln Gln His Ser Gln Ala
        195             200             205

Phe Phe Gln Pro Leu Glu Cys Glu Pro Ile Leu Gln Ile Gly Tyr Gln
    210             215             220

Gly Gln Gln Asp Gly Met Gly Ala Gly Pro Ser Val Asn Asn Tyr Met
225             230             235             240

Leu Gly Trp Leu Pro Tyr Asp Thr Asn Ser Ile
            245             250
```

```
<210> SEQ ID NO 193
<211> LENGTH: 942
<212> TYPE: DNA
<213> ORGANISM: Arabidopsis thaliana

<400> SEQUENCE: 193
atgggtcgag ggagggtcga actcaaacgg atcgagaata aaatcaatag acaggtgaca      60
tttgctaaaa ggagaaacgg cctgctgaag aaggcctacg aactgagtgt gttgtgcgat     120
gccgaagtgg ctctgattat atttagcaac aggggcaaac tgtacgagtt ttgctcatct     180
tcttccatgt tgcgaaccct tgaacgatac cagaaatgta actacggagc tcccgaaccg     240
aatgtgcctt cacgcgaggc actggcagtg gagctttctt ctcagcagga gtatctgaag     300
ttgaaggagc gctatgatgc cctgcagcgc actcaacgta acctgctggg agaggacttg     360
ggtccactga gcactaaaga gctggagtcc ctggagaggc agttggactc cagtttaaag     420
caaatacgcg ccctgcggac ccaatttatg cttgatcaac tcaatgatct ccagtccaaa     480
gagcggatgc tgaccgaaac aaacaagaca cttcgcttac ggttagccga cggctaccag     540
atgccacttc aactgaatcc caatcaggaa gaggtggacc attatggaag gcaccaccac     600
cagcagcagc agcattctca ggctttttc cagcctctgg agtgtgaacc catcctgcag     660
ataggatatc agggccagca agatgggatg ggggctggac ctagcgttaa caactacatg     720
ctgggatggc ttccctatga tacaaatagt atcggatcta gcggtggcag ctcaggggc     780 agctctggtg acgccctgga cgatttcgac ctcgatatgc tcggttccga cgctctggat     840
gattttgatc ttgatatgct ggggtctgac gccctggacg attttgatct cgacatgtta     900
ggttcagatg cactcgatga ctttgacctg gatatgctgt ga                        942
```

-continued

```
<210> SEQ ID NO 194
<211> LENGTH: 313
<212> TYPE: PRT
<213> ORGANISM: Arabidopsis thaliana

<400> SEQUENCE: 194

Met Gly Arg Gly Arg Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
            20                  25                  30

Tyr Glu Leu Ser Val Leu Cys Asp Ala Glu Val Ala Leu Ile Ile Phe
        35                  40                  45

Ser Asn Arg Gly Lys Leu Tyr Glu Phe Cys Ser Ser Ser Ser Met Leu
    50                  55                  60

Arg Thr Leu Glu Arg Tyr Gln Lys Cys Asn Tyr Gly Ala Pro Glu Pro
65                  70                  75                  80

Asn Val Pro Ser Arg Glu Ala Leu Ala Val Glu Leu Ser Ser Gln Gln
                85                  90                  95

Glu Tyr Leu Lys Leu Lys Glu Arg Tyr Asp Ala Leu Gln Arg Thr Gln
            100                 105                 110

Arg Asn Leu Leu Gly Glu Asp Leu Gly Pro Leu Ser Thr Lys Glu Leu
            115                 120                 125

Glu Ser Leu Glu Arg Gln Leu Asp Ser Ser Leu Lys Gln Ile Arg Ala
    130                 135                 140

Leu Arg Thr Gln Phe Met Leu Asp Gln Leu Asn Asp Leu Gln Ser Lys
145                 150                 155                 160

Glu Arg Met Leu Thr Glu Thr Asn Lys Thr Leu Arg Leu Arg Leu Ala
            165                 170                 175

Asp Gly Tyr Gln Met Pro Leu Gln Leu Asn Pro Asn Gln Glu Glu Val
            180                 185                 190

Asp His Tyr Gly Arg His His His Gln Gln Gln Gln His Ser Gln Ala
        195                 200                 205

Phe Phe Gln Pro Leu Glu Cys Glu Pro Ile Leu Gln Ile Gly Tyr Gln
    210                 215                 220

Gly Gln Gln Asp Gly Met Gly Ala Gly Pro Ser Val Asn Asn Tyr Met
225                 230                 235                 240

Leu Gly Trp Leu Pro Tyr Asp Thr Asn Ser Ile Gly Ser Ser Gly Gly
            245                 250                 255

Ser Ser Gly Gly Ser Ser Gly Asp Ala Leu Asp Asp Phe Asp Leu Asp
            260                 265                 270

Met Leu Gly Ser Asp Ala Leu Asp Asp Phe Asp Leu Asp Met Leu Gly
        275                 280                 285

Ser Asp Ala Leu Asp Asp Phe Asp Leu Asp Met Leu Gly Ser Asp Ala
    290                 295                 300

Leu Asp Asp Phe Asp Leu Asp Met Leu
305                 310

<210> SEQ ID NO 195
<211> LENGTH: 771
<212> TYPE: DNA
<213> ORGANISM: Arabidopsis thaliana

<400> SEQUENCE: 195
atgctgttcc ctcacgaaag gaaaaaagaa aaggagcggt ctcaagggtt ttatttggtg        60
```

-continued

```
accaggctcc ggatcagaat gggtcgtggc aagatcgaga ttaaacggat agaaaattcc    120
acgaaccgtc aggtgacatt ctgtaagcgg cgcaacggct tgctcaagaa ggcctatgaa    180
ttgtcagtat tgtgtgacgc cgaagtggca ctgatcgtct ttagcacaag aggacgcctg    240
tatgaatatg ctaacaataa tattcgctcc actatcgaaa gatataaaaa ggcctgcagt    300
gatagcacta acactagtac tgtgcaagag atcaacgccg catattatca acaggagagt    360
gcaaagctgc ggcagcagat ccaaactatt cagaactcca atcggaactt aatgggggac    420
agtctgagca gcttatccgt caaggagctt aagcaggtgg aaaatcgcct cgagaaagcc    480
atctccagaa tccgctctaa gaagcacgaa ctgcttcttg tcgaaattga aaacgcacaa    540
aagagagaaa tcgagctgga caacgagaac atttatctga gaaccaaggt tgctgaagtg    600
gagcgctacc agcagcacca tcaccagatg gttagcggaa gtgagatcaa cgctatcgaa    660
gctctcgctt cccggaatta ttttgcacac agcataatga ccgctgggtc tggatccgga    720
aacggaggat catactccga ccctgataaa aaaatcctgc acttgggata a            771
```

<210> SEQ ID NO 196
<211> LENGTH: 256
<212> TYPE: PRT
<213> ORGANISM: Arabidopsis thaliana

<400> SEQUENCE: 196

```
Met Leu Phe Pro His Glu Arg Lys Lys Glu Lys Glu Arg Ser Gln Gly
1               5                   10                  15

Phe Tyr Leu Val Thr Arg Leu Arg Ile Arg Met Gly Arg Gly Lys Ile
            20                  25                  30

Glu Ile Lys Arg Ile Glu Asn Ser Thr Asn Arg Gln Val Thr Phe Cys
        35                  40                  45

Lys Arg Arg Asn Gly Leu Leu Lys Lys Ala Tyr Glu Leu Ser Val Leu
    50                  55                  60

Cys Asp Ala Glu Val Ala Leu Ile Val Phe Ser Thr Arg Gly Arg Leu
65                  70                  75                  80

Tyr Glu Tyr Ala Asn Asn Asn Ile Arg Ser Thr Ile Glu Arg Tyr Lys
                85                  90                  95

Lys Ala Cys Ser Asp Ser Thr Asn Thr Ser Thr Val Gln Glu Ile Asn
            100                 105                 110

Ala Ala Tyr Tyr Gln Gln Glu Ser Ala Lys Leu Arg Gln Gln Ile Gln
        115                 120                 125

Thr Ile Gln Asn Ser Asn Arg Asn Leu Met Gly Asp Ser Leu Ser Ser
    130                 135                 140

Leu Ser Val Lys Glu Leu Lys Gln Val Glu Asn Arg Leu Glu Lys Ala
145                 150                 155                 160

Ile Ser Arg Ile Arg Ser Lys Lys His Glu Leu Leu Leu Val Glu Ile
                165                 170                 175

Glu Asn Ala Gln Lys Arg Glu Ile Glu Leu Asp Asn Glu Asn Ile Tyr
            180                 185                 190

Leu Arg Thr Lys Val Ala Glu Val Glu Arg Tyr Gln Gln His His His
        195                 200                 205

Gln Met Val Ser Gly Ser Glu Ile Asn Ala Ile Glu Ala Leu Ala Ser
    210                 215                 220

Arg Asn Tyr Phe Ala His Ser Ile Met Thr Ala Gly Ser Gly Ser Gly
225                 230                 235                 240

Asn Gly Gly Ser Tyr Ser Asp Pro Asp Lys Lys Ile Leu His Leu Gly
                245                 250                 255
```

-continued

```
<210> SEQ ID NO 197
<211> LENGTH: 771
<212> TYPE: DNA
<213> ORGANISM: Artificial sequence
<220> FEATURE:
<223> OTHER INFORMATION: Synthetic polynucleotide

<400> SEQUENCE: 197
atgctgttcc ctcacgaaag gaaaaaagaa aaggagcggt ctcaagggtt ttatttggtg       60
accaggctcc ggatcagaat gggtcgtggc aagatcgaga ttaaacggat agaaaattcc      120
acgaaccgtc aggtgacatt ctgtaagcgg cgcaacggct tgctcaagaa ggcctatgaa      180
ttgtcagtat tgtgtgacgc cgaagtggca ctgatcgtct ttagcacaag aggacgcctg      240
tatgaatatg ctaacaataa tattcgctcc actatcgaaa gatataaaaa ggcctgcagt      300
gatagcacta cactagtac tgtgcaagag atcaacgccg catattatca acaggagagt      360
gcaaagctgc ggcagcagat ccaaactatt cagaactcca atcggaactt aatgggggac      420
agtctgagca gcttatccgt caaggagctt aagcaggtgg aaaatcgcct cgagaaagcc      480
atctccagaa tccgctctaa gaagcacgaa ctgcttcttg tcgaaattga aaacgcacaa      540
aagagagaaa tcgagctgga caacgagaac atttatctga aaccaaggt tgctgaagtg      600 gagcgctacc agcagcacca tcaccagatg gttagcggaa gtgagatcaa cgctatcgaa      660
gctctcgctt cccacaatta ttttgcacac agcataatga ccgctgggtc tggatccgga      720
aacggaggat catactccga ccctgataaa aaaatcctgc acttgggata a                771

<210> SEQ ID NO 198
<211> LENGTH: 256
<212> TYPE: PRT
<213> ORGANISM: Artificial sequence
<220> FEATURE:
<223> OTHER INFORMATION: Synthetic polypeptide

<400> SEQUENCE: 198

Met Leu Phe Pro His Glu Arg Lys Lys Glu Lys Glu Arg Ser Gln Gly
1               5                   10                  15

Phe Tyr Leu Val Thr Arg Leu Arg Ile Arg Met Gly Arg Gly Lys Ile
            20                  25                  30

Glu Ile Lys Arg Ile Glu Asn Ser Thr Asn Arg Gln Val Thr Phe Cys
        35                  40                  45

Lys Arg Arg Asn Gly Leu Leu Lys Lys Ala Tyr Glu Leu Ser Val Leu
    50                  55                  60

Cys Asp Ala Glu Val Ala Leu Ile Val Phe Ser Thr Arg Gly Arg Leu
65                  70                  75                  80

Tyr Glu Tyr Ala Asn Asn Asn Ile Arg Ser Thr Ile Glu Arg Tyr Lys
                85                  90                  95

Lys Ala Cys Ser Asp Ser Thr Asn Thr Ser Thr Val Gln Glu Ile Asn
            100                 105                 110

Ala Ala Tyr Tyr Gln Gln Glu Ser Ala Lys Leu Arg Gln Gln Ile Gln
        115                 120                 125

Thr Ile Gln Asn Ser Asn Arg Asn Leu Met Gly Asp Ser Leu Ser Ser
    130                 135                 140

Leu Ser Val Lys Glu Leu Lys Gln Val Glu Asn Arg Leu Glu Lys Ala
145                 150                 155                 160

Ile Ser Arg Ile Arg Ser Lys Lys His Glu Leu Leu Leu Val Glu Ile
                165                 170                 175
```

```
Glu Asn Ala Gln Lys Arg Glu Ile Glu Leu Asp Asn Glu Asn Ile Tyr
            180             185             190

Leu Arg Thr Lys Val Ala Glu Val Glu Arg Tyr Gln Gln His His His
            195             200             205

Gln Met Val Ser Gly Ser Glu Ile Asn Ala Ile Glu Ala Leu Ala Ser
            210             215             220

His Asn Tyr Phe Ala His Ser Ile Met Thr Ala Gly Ser Gly Ser Gly
225             230             235             240

Asn Gly Gly Ser Tyr Ser Asp Pro Asp Lys Lys Ile Leu His Leu Gly
                245             250             255
```

```
<210> SEQ ID NO 199
<211> LENGTH: 771
<212> TYPE: DNA
<213> ORGANISM: Artificial sequence
<220> FEATURE:
<223> OTHER INFORMATION: Synthetic polynucleotide

<400> SEQUENCE: 199
atgctgttcc ctcacgaaag gaaaaaagaa aaggagcggt ctcaagggtt ttatttggtg      60
accaggctcc ggatcagaat gggtcgtggc aagatcgaga ttaaacggat agaaaattcc     120
acgaaccgtc aggtgacatt ctgtaagcgg cgcaacggct tgctcaagaa ggcctatgaa     180
ttgtcagtat tgtgtgacgc cgaagtggca ctgatcgtct ttagcacaag aggacgcctg     240
tatgaatatg ctaacaataa tattcgctcc actatcgaaa gatataaaaa ggcctgcagt     300
gatagcacta cactagtac tgtgcaagag atcaacgccg catattatca acaggagagt     360
gcaaagctgc ggcagcagat ccaaactatt cagaactcca atcggaactt aatgggggac     420
agtctgagca gcttatccgt caaggagctt aagcaggtgg aaaatcgcct cgagaaagcc     480
atctccagaa tccgctctaa gaagcacgaa ctgcttcttg tcgaaattga aaacgcacaa     540
aagagagaaa tcgagctgga caacgagaac atttatctga aaccaaggt tgctgaagtg     600 gagcgctacc agcagcacca tcaccagatg gttagcggaa gtgagatcaa cgctatcgaa     660
gctctcgctt ccctgaatta ttttgcacac agcataatga ccgctgggtc tggatccgga     720
aacggaggat catactccga ccctgataaa aaaatcctgc acttgggata a              771
```

```
<210> SEQ ID NO 200
<211> LENGTH: 256
<212> TYPE: PRT
<213> ORGANISM: Artificial sequence
<220> FEATURE:
<223> OTHER INFORMATION: Synthetic polypeptide

<400> SEQUENCE: 200

Met Leu Phe Pro His Glu Arg Lys Lys Glu Lys Glu Arg Ser Gln Gly
1               5               10              15

Phe Tyr Leu Val Thr Arg Leu Arg Ile Arg Met Gly Arg Gly Lys Ile
            20              25              30

Glu Ile Lys Arg Ile Glu Asn Ser Thr Asn Arg Gln Val Thr Phe Cys
            35              40              45

Lys Arg Arg Asn Gly Leu Leu Lys Lys Ala Tyr Glu Leu Ser Val Leu
            50              55              60

Cys Asp Ala Glu Val Ala Leu Ile Val Phe Ser Thr Arg Gly Arg Leu
65              70              75              80

Tyr Glu Tyr Ala Asn Asn Asn Ile Arg Ser Thr Ile Glu Arg Tyr Lys
                85              90              95
```

-continued

```
Lys Ala Cys Ser Asp Ser Thr Asn Thr Ser Thr Val Gln Glu Ile Asn
            100                 105                 110

Ala Ala Tyr Tyr Gln Gln Glu Ser Ala Lys Leu Arg Gln Gln Ile Gln
            115                 120                 125

Thr Ile Gln Asn Ser Asn Arg Asn Leu Met Gly Asp Ser Leu Ser Ser
    130                 135                 140

Leu Ser Val Lys Glu Leu Lys Gln Val Glu Asn Arg Leu Glu Lys Ala
145                 150                 155                 160

Ile Ser Arg Ile Arg Ser Lys Lys His Glu Leu Leu Leu Val Glu Ile
                165                 170                 175

Glu Asn Ala Gln Lys Arg Glu Ile Glu Leu Asp Asn Glu Asn Ile Tyr
            180                 185                 190

Leu Arg Thr Lys Val Ala Glu Val Glu Arg Tyr Gln Gln His His His
            195                 200                 205

Gln Met Val Ser Gly Ser Glu Ile Asn Ala Ile Glu Ala Leu Ala Ser
    210                 215                 220

Leu Asn Tyr Phe Ala His Ser Ile Met Thr Ala Gly Ser Gly Ser Gly
225                 230                 235                 240

Asn Gly Gly Ser Tyr Ser Asp Pro Asp Lys Lys Ile Leu His Leu Gly
                245                 250                 255
```

<210> SEQ ID NO 201
<211> LENGTH: 591
<212> TYPE: DNA
<213> ORGANISM: Artificial sequence
<220> FEATURE:
<223> OTHER INFORMATION: Synthetic polynucleotide

<400> SEQUENCE: 201

```
atgctgttcc ctcacgaaag gaaaaagaa aaggagcggt ctcaagggtt ttatttggtg      60
accaggctcc ggatcagaat gggtcgtggc aagatcgaga ttaaacggat agaaaattcc     120
acgaaccgtc aggtgacatt ctgtaagcgg cgcaacggct tgctcaagaa ggcctatgaa     180
ttgtcagtat tgtgtgacgc cgaagtggca ctgatcgtct ttagcacaag aggacgcctg     240
tatgaatatg ctaacaataa tattcgctcc actatcgaaa gatataaaaa ggcctgcagt     300
gatagcacta cactagtac tgtgcaagag atcaacgccg catattatca acaggagagt      360
gcaaagctgc ggcagcagat ccaaactatt cagaactcca tcggaactt aatgggggac      420 agtctgagca gcttatccgt caaggagctt aagcaggtgg aaaatcgcct cgagaaagcc     480
atctccagaa tccgctctaa gaagcacgaa ctgcttcttg tcgaaattga aaacgcacaa     540
aagagagaaa tcgagctgga caacgagaac atttatctga gaaccaagta a               591
```

<210> SEQ ID NO 202
<211> LENGTH: 196
<212> TYPE: PRT
<213> ORGANISM: Artificial sequence
<220> FEATURE:
<223> OTHER INFORMATION: Synthetic polypeptide

<400> SEQUENCE: 202

```
Met Leu Phe Pro His Glu Arg Lys Lys Glu Lys Glu Arg Ser Gln Gly
1               5                   10                  15

Phe Tyr Leu Val Thr Arg Leu Arg Ile Arg Met Gly Arg Gly Lys Ile
            20                  25                  30

Glu Ile Lys Arg Ile Glu Asn Ser Thr Asn Arg Gln Val Thr Phe Cys
        35                  40                  45
```

-continued

```
Lys Arg Arg Asn Gly Leu Leu Lys Lys Ala Tyr Glu Leu Ser Val Leu
    50              55              60

Cys Asp Ala Glu Val Ala Leu Ile Val Phe Ser Thr Arg Gly Arg Leu
65              70              75              80

Tyr Glu Tyr Ala Asn Asn Asn Ile Arg Ser Thr Ile Glu Arg Tyr Lys
                85              90              95

Lys Ala Cys Ser Asp Ser Thr Asn Thr Ser Thr Val Gln Glu Ile Asn
            100             105             110

Ala Ala Tyr Tyr Gln Gln Glu Ser Ala Lys Leu Arg Gln Gln Ile Gln
        115             120             125

Thr Ile Gln Asn Ser Asn Arg Asn Leu Met Gly Asp Ser Leu Ser Ser
    130             135             140

Leu Ser Val Lys Glu Leu Lys Gln Val Glu Asn Arg Leu Glu Lys Ala
145             150             155             160

Ile Ser Arg Ile Arg Ser Lys Lys His Glu Leu Leu Leu Val Glu Ile
            165             170             175

Glu Asn Ala Gln Lys Arg Glu Ile Glu Leu Asp Asn Glu Asn Ile Tyr
        180             185             190

Leu Arg Thr Lys
        195
```

```
<210> SEQ ID NO 203
<211> LENGTH: 738
<212> TYPE: DNA
<213> ORGANISM: Rubus occidentalis

<400> SEQUENCE: 203
atgggtagag gcaagattga gatcaagcgc atcgagaaca ccacaaaccg gcaagttact    60
ttctgcaaac ggagaaatgg gctgcttaag aaagcttatg agctttccat actctgtgag   120
gcagaagtgg ccctcattgt cttctctagc cgaggtcggc tgtatgagta ctcaaacaac   180
aacagcatcc gaaacaccat agagaggtac aagaaggcct gtagtgatag ttccggcgca   240
actacaataa cggaaatcaa tgcccaatat taccagcagg aaagtgctaa gctccgacac   300
caaatccaaa tgctgcagaa ttctaaccgg cacctgatgg gcgattccct gtccaatctg   360
actgttaaag aactcaagca gctggagaat cgccttgaac ggggacttac tcgaatccga   420
agtaagaagc atgaaatgct tcttgccgaa attgaatact tgcagaaacg agaggtcgag   480
ctggaaaacg agaatgttct ggttcgggct aagatagctg aactggagcg attgcagcac   540
gctgacatgg tttctgggga tcaagatctc gagctgaatg ctatccaggc tctcgtctct   600
cgtaacttct tcgcatccac catgattgag ggagaggcca gctactccca gccagaaaag   660
aaatttctta atcttggggc tgggaaaggt cttgtgaagc agggcaaaac aagcagctca   720
ttcggatatg tcctttaa                                                 738
```

```
<210> SEQ ID NO 204
<211> LENGTH: 245
<212> TYPE: PRT
<213> ORGANISM: Rubus occidentalis

<400> SEQUENCE: 204

Met Gly Arg Gly Lys Ile Glu Ile Lys Arg Ile Glu Asn Thr Thr Asn
1               5               10              15

Arg Gln Val Thr Phe Cys Lys Arg Arg Asn Gly Leu Leu Lys Lys Ala
            20              25              30
```

-continued

```
Tyr Glu Leu Ser Ile Leu Cys Glu Ala Glu Val Ala Leu Ile Val Phe
        35                  40                  45

Ser Ser Arg Gly Arg Leu Tyr Glu Tyr Ser Asn Asn Asn Ser Ile Arg
    50                  55                  60

Asn Thr Ile Glu Arg Tyr Lys Lys Ala Cys Ser Asp Ser Ser Gly Ala
65                  70                  75                  80

Thr Thr Ile Thr Glu Ile Asn Ala Gln Tyr Tyr Gln Gln Glu Ser Ala
                85                  90                  95

Lys Leu Arg His Gln Ile Gln Met Leu Gln Asn Ser Asn Arg His Leu
            100                 105                 110

Met Gly Asp Ser Leu Ser Asn Leu Thr Val Lys Glu Leu Lys Gln Leu
            115                 120                 125

Glu Asn Arg Leu Glu Arg Gly Leu Thr Arg Ile Arg Ser Lys Lys His
    130                 135                 140

Glu Met Leu Leu Ala Glu Ile Glu Tyr Leu Gln Lys Arg Glu Val Glu
145                 150                 155                 160

Leu Glu Asn Glu Asn Val Leu Val Arg Ala Lys Ile Ala Glu Leu Glu
                165                 170                 175

Arg Leu Gln His Ala Asp Met Val Ser Gly Asp Gln Asp Leu Glu Leu
            180                 185                 190

Asn Ala Ile Gln Ala Leu Val Ser Arg Asn Phe Phe Ala Ser Thr Met
            195                 200                 205

Ile Glu Gly Glu Ala Ser Tyr Ser Gln Pro Glu Lys Lys Phe Leu Asn
        210                 215                 220

Leu Gly Ala Gly Lys Gly Leu Val Lys Gln Gly Lys Thr Ser Ser Ser
225                 230                 235                 240

Phe Gly Tyr Val Leu
                245
```

```
<210> SEQ ID NO 205
<211> LENGTH: 726
<212> TYPE: DNA
<213> ORGANISM: Rubus occidentalis

<400> SEQUENCE: 205
atgggtagag gcaagattga gatcaagcgc atcgagaaca ccacaaaccg gcaagttact      60
ttctgcaaac ggagaaatgg gctgcttaag aaagcttatg agctttccat actctgtgag     120
gcagaagtgg ccctcattgt cttctctagc cgaggtcggc tgtatgagta ctcaaacaac     180
aacagcatcc gaaacaccat agagaggtac aagaaggcct gtagtgatag ttccggcgca     240
actacaataa cggaaatcaa tgcccaatat taccagcagg aaagtgctaa gctccgacac     300
caaatccaaa tgctgcagaa ttctaaccgg cacctgatgg gcgattccct gtccaatctg     360
actgttaaag aactcaagca gctggagaat cgccttgaac ggggacttac tcgaatccga     420
agtaagaagc atgaaatgct tcttgccgaa attgaatact gcagaaacg agaggtcgag      480 ctggaaaacg agaatgttct ggttcgggct aagatagctg aactggagcg attgcagcac     540
gctgacatgg tttctgggga tcaagatctc atccaggctc tcgtctctcg taacttcttc     600
gcatccacca tgattgaggg agaggccagc tactcccagc cagaaaagaa atttcttaat     660 cttgggggctg ggaaaggtct tgtgaagcag ggcaaaacaa gcagctcatt cggatatgtc     720
ctttaa                                                                726
```

```
<210> SEQ ID NO 206
<211> LENGTH: 241
```

```
<212> TYPE: PRT
<213> ORGANISM: Artificial sequence
<220> FEATURE:
<223> OTHER INFORMATION: Synthetic polypeptide

<400> SEQUENCE: 206

Met Gly Arg Gly Lys Ile Glu Ile Lys Arg Ile Glu Asn Thr Thr Asn
1               5                   10                  15

Arg Gln Val Thr Phe Cys Lys Arg Arg Asn Gly Leu Leu Lys Lys Ala
            20                  25                  30

Tyr Glu Leu Ser Ile Leu Cys Glu Ala Glu Val Ala Leu Ile Val Phe
        35                  40                  45

Ser Ser Arg Gly Arg Leu Tyr Glu Tyr Ser Asn Asn Asn Ser Ile Arg
    50                  55                  60

Asn Thr Ile Glu Arg Tyr Lys Lys Ala Cys Ser Asp Ser Ser Gly Ala
65                  70                  75                  80

Thr Thr Ile Thr Glu Ile Asn Ala Gln Tyr Tyr Gln Gln Glu Ser Ala
                85                  90                  95

Lys Leu Arg His Gln Ile Gln Met Leu Gln Asn Ser Asn Arg His Leu
            100                 105                 110

Met Gly Asp Ser Leu Ser Asn Leu Thr Val Lys Glu Leu Lys Gln Leu
        115                 120                 125

Glu Asn Arg Leu Glu Arg Gly Leu Thr Arg Ile Arg Ser Lys Lys His
    130                 135                 140

Glu Met Leu Leu Ala Glu Ile Glu Tyr Leu Gln Lys Arg Glu Val Glu
145                 150                 155                 160

Leu Glu Asn Glu Asn Val Leu Val Arg Ala Lys Ile Ala Glu Leu Glu
                165                 170                 175

Arg Leu Gln His Ala Asp Met Val Ser Gly Asp Gln Asp Leu Ile Gln
            180                 185                 190

Ala Leu Val Ser Arg Asn Phe Phe Ala Ser Thr Met Ile Glu Gly Glu
        195                 200                 205

Ala Ser Tyr Ser Gln Pro Glu Lys Lys Phe Leu Asn Leu Gly Ala Gly
    210                 215                 220

Lys Gly Leu Val Lys Gln Gly Lys Thr Ser Ser Ser Phe Gly Tyr Val
225                 230                 235                 240

Leu

<210> SEQ ID NO 207
<211> LENGTH: 672
<212> TYPE: DNA
<213> ORGANISM: Vitis vinifera

<400> SEQUENCE: 207
atgggccgag gcaaaattga aattaaacgg attgagaata ctacaaatag acaagtgacg        60
ttttgtaaac ggcgaaacgg actcctgaag aaagcctacg agctgagcgt attgtgcgac       120
gccgaggtcg cgctgatagt gtttagctcc cgagggagag tgtacgaata ttctaataat       180
aatatcaagt ccactatcga ccgttataag aaagcatctt ctgacagcac gaacggtgga       240
agtactatgg aaattaacgc acagtattat caacaggagt ccgccaaact ccggcaacag       300
atccaaatgc tccaaaacag caatagacat ttgatgggtg acagccttgc aagccttacc       360
gttaaagaac tgaaacaact ggaaaatcgc ctggagcgtg ggataacccg catacgatcc       420
aagaaacacg aactcttgct ggcggaaata gaatatcttc aaaagagaga gatcgaattg       480
gagaacgaga gtgtctacct gcggacaaag atcgccgagg ttgaacggtt gcaacaggct       540
```

-continued

```
aatatggtct ctacccacga atttaacgcg attcaagcgc tggtcagcag gaacttcttc       600
caaccaaaca tgatcgaagg cggctcaact ggatatcctc tgcccgacaa gaaagtgctg       660
cacctgggct ga                                                           672
```

```
<210> SEQ ID NO 208
<211> LENGTH: 223
<212> TYPE: PRT
<213> ORGANISM: Vitis vinifera

<400> SEQUENCE: 208
```

```
Met Gly Arg Gly Lys Ile Glu Ile Lys Arg Ile Glu Asn Thr Thr Asn
1               5                   10                  15

Arg Gln Val Thr Phe Cys Lys Arg Arg Asn Gly Leu Leu Lys Lys Ala
                20                  25                  30

Tyr Glu Leu Ser Val Leu Cys Asp Ala Glu Val Ala Leu Ile Val Phe
            35                  40                  45

Ser Ser Arg Gly Arg Val Tyr Glu Tyr Ser Asn Asn Asn Ile Lys Ser
        50                  55                  60

Thr Ile Asp Arg Tyr Lys Lys Ala Ser Ser Asp Ser Thr Asn Gly Gly
65                  70                  75                  80

Ser Thr Met Glu Ile Asn Ala Gln Tyr Tyr Gln Gln Glu Ser Ala Lys
                85                  90                  95

Leu Arg Gln Gln Ile Gln Met Leu Gln Asn Ser Asn Arg His Leu Met
            100                 105                 110

Gly Asp Ser Leu Ala Ser Leu Thr Val Lys Glu Leu Lys Gln Leu Glu
        115                 120                 125

Asn Arg Leu Glu Arg Gly Ile Thr Arg Ile Arg Ser Lys Lys His Glu
    130                 135                 140

Leu Leu Leu Ala Glu Ile Glu Tyr Leu Gln Lys Arg Glu Ile Glu Leu
145                 150                 155                 160

Glu Asn Glu Ser Val Tyr Leu Arg Thr Lys Ile Ala Glu Val Glu Arg
                165                 170                 175

Leu Gln Gln Ala Asn Met Val Ser Thr His Glu Phe Asn Ala Ile Gln
            180                 185                 190

Ala Leu Val Ser Arg Asn Phe Phe Gln Pro Asn Met Ile Glu Gly Gly
        195                 200                 205

Ser Thr Gly Tyr Pro Leu Pro Asp Lys Lys Val Leu His Leu Gly
    210                 215                 220
```

```
<210> SEQ ID NO 209
<211> LENGTH: 672
<212> TYPE: DNA
<213> ORGANISM: Artificial sequence
<220> FEATURE:
<223> OTHER INFORMATION: Synthetic polynucleotide

<400> SEQUENCE: 209
```

```
atgggccgag gcaaaattga aattaaacgg attgagaata ctacaaatag acaagtgacg        60
ttttgtaaac ggcgaaacgg actcctgaag aaagcctacg agctgagcgt attgtgcgac       120
gccgaggtcg cgctgatagt gtttagctcc cgagggagtg tgtacgaata ttctaataat       180
aatatcaagt ccactatcga ccgttataag aaagcatctt ctgacagcac gaacggtgga       240
agtactatgg aaattaacgc acagtattat caacaggagt ccgccaaact ccggcaacag       300
atccaaatgc tccaaaacag caatagacat ttgatgggtg acagccttgc aagccttacc       360
```

-continued

```
gttaaagaac tgaaacaact ggaaaatcgc ctggagcgtg ggataacccg catacgatcc      420
aagaaacacg aactcttgct ggcggaaata gaatatcttc aaaagagaga gatcgaattg      480
gagaacgaga gtgtctacct gcggacaaag atcgccgagg ttgaacggtt gcaacaggct      540
aatatggtct ctacccacga atttaacgcg attcaagcgc tggtcagcct gaacttcttc      600
caaccaaaca tgatcgaagg cggctcaact ggatatcctc tgcccgacaa gaaagtgctg      660
cacctgggct ga                                                          672
```

```
<210> SEQ ID NO 210
<211> LENGTH: 223
<212> TYPE: PRT
<213> ORGANISM: Artificial sequence
<220> FEATURE:
<223> OTHER INFORMATION: Synthetic polypeptide

<400> SEQUENCE: 210

Met Gly Arg Gly Lys Ile Glu Ile Lys Arg Ile Glu Asn Thr Thr Asn
1               5                   10                  15

Arg Gln Val Thr Phe Cys Lys Arg Arg Asn Gly Leu Leu Lys Lys Ala
            20                  25                  30

Tyr Glu Leu Ser Val Leu Cys Asp Ala Glu Val Ala Leu Ile Val Phe
        35                  40                  45

Ser Ser Arg Gly Arg Val Tyr Glu Tyr Ser Asn Asn Asn Ile Lys Ser
    50                  55                  60

Thr Ile Asp Arg Tyr Lys Lys Ala Ser Ser Asp Ser Thr Asn Gly Gly
65                  70                  75                  80

Ser Thr Met Glu Ile Asn Ala Gln Tyr Tyr Gln Gln Glu Ser Ala Lys
                85                  90                  95

Leu Arg Gln Gln Ile Gln Met Leu Gln Asn Ser Asn Arg His Leu Met
            100                 105                 110

Gly Asp Ser Leu Ala Ser Leu Thr Val Lys Glu Leu Lys Gln Leu Glu
        115                 120                 125

Asn Arg Leu Glu Arg Gly Ile Thr Arg Ile Arg Ser Lys Lys His Glu
    130                 135                 140

Leu Leu Leu Ala Glu Ile Glu Tyr Leu Gln Lys Arg Glu Ile Glu Leu
145                 150                 155                 160

Glu Asn Glu Ser Val Tyr Leu Arg Thr Lys Ile Ala Glu Val Glu Arg
                165                 170                 175

Leu Gln Gln Ala Asn Met Val Ser Thr His Glu Phe Asn Ala Ile Gln
            180                 185                 190

Ala Leu Val Ser Leu Asn Phe Phe Gln Pro Asn Met Ile Glu Gly Gly
        195                 200                 205

Ser Thr Gly Tyr Pro Leu Pro Asp Lys Lys Val Leu His Leu Gly
    210                 215                 220
```

```
<210> SEQ ID NO 211
<211> LENGTH: 717
<212> TYPE: DNA
<213> ORGANISM: Elaeis guineensis

<400> SEQUENCE: 211
atgggacgtg gcaaaataga aataaaacgc atagagaata caactagtcg gcaagtaaca       60
ttttgcaaga gacgcaacgg gcttctgaag aaggcatatg aattgagcgt cttgtgtgat      120
gccgaggttg cattgatcgt gttcagcagt agaggccgcc tgtatgagta tgctaataac      180
agcatccggt ccactataga cagatacaag aaggcttgcg caaattcctc aaattccggt      240
```

-continued

```
gcaacaatcg agattaatag tcaacaatac tatcagcagg aatccgctaa gcttagacat     300
caaattcaaa tattgcagaa tgccaaccgc cacctcatgg gtgaagcact tagcactctt     360
actgtgaagg aacttaaaca actggagaat cgcctcgaga gaggcatcac aagaattcgc     420
agtaagaaac atgagctctt gtttgcggaa attgagtata tgcagaagcg ggaagtcgaa     480
ttgcaaaacg acaatatgta tctgagagct aaaattgcag aaaatgagcg ggcccaacaa     540
gctgggatag ttccggccgg accagacttc gacgctttgc ctacttttga tacgcgaaac     600
tattatcatg tgaatatgct ggaagctgcg caacattatt ctcaccatca agaccaaacc     660
accctgcacc tggggtatga aatgaaagcc gatcccgcag ctaagaacct gctctga       717
```

```
<210> SEQ ID NO 212
<211> LENGTH: 238
<212> TYPE: PRT
<213> ORGANISM: Elaeis guineensis

<400> SEQUENCE: 212

Met Gly Arg Gly Lys Ile Glu Ile Lys Arg Ile Glu Asn Thr Thr Ser
1               5                   10                  15

Arg Gln Val Thr Phe Cys Lys Arg Arg Asn Gly Leu Leu Lys Lys Ala
            20                  25                  30

Tyr Glu Leu Ser Val Leu Cys Asp Ala Glu Val Ala Leu Ile Val Phe
        35                  40                  45

Ser Ser Arg Gly Arg Leu Tyr Glu Tyr Ala Asn Asn Ser Ile Arg Ser
    50                  55                  60

Thr Ile Asp Arg Tyr Lys Lys Ala Cys Ala Asn Ser Ser Asn Ser Gly
65                  70                  75                  80

Ala Thr Ile Glu Ile Asn Ser Gln Gln Tyr Tyr Gln Gln Glu Ser Ala
                85                  90                  95

Lys Leu Arg His Gln Ile Gln Ile Leu Gln Asn Ala Asn Arg His Leu
            100                 105                 110

Met Gly Glu Ala Leu Ser Thr Leu Thr Val Lys Glu Leu Lys Gln Leu
        115                 120                 125

Glu Asn Arg Leu Glu Arg Gly Ile Thr Arg Ile Arg Ser Lys Lys His
    130                 135                 140

Glu Leu Leu Phe Ala Glu Ile Glu Tyr Met Gln Lys Arg Glu Val Glu
145                 150                 155                 160

Leu Gln Asn Asp Asn Met Tyr Leu Arg Ala Lys Ile Ala Glu Asn Glu
                165                 170                 175

Arg Ala Gln Gln Ala Gly Ile Val Pro Ala Gly Pro Asp Phe Asp Ala
            180                 185                 190

Leu Pro Thr Phe Asp Thr Arg Asn Tyr Tyr His Val Asn Met Leu Glu
        195                 200                 205

Ala Ala Gln His Tyr Ser His His Gln Asp Gln Thr Thr Leu His Leu
    210                 215                 220

Gly Tyr Glu Met Lys Ala Asp Pro Ala Ala Lys Asn Leu Leu
225                 230                 235
```

```
<210> SEQ ID NO 213
<211> LENGTH: 717
<212> TYPE: DNA
<213> ORGANISM: Artificial sequence
<220> FEATURE:
<223> OTHER INFORMATION: Synthetic polynucleotide

<400> SEQUENCE: 213
```

-continued

```
atgggacgtg gcaaaataga aataaaacgc atagagaata caactagtcg gcaagtaaca      60
ttttgcaaga gacgcaacgg gcttcccaag aaggcatatg aattgagcgt cttgtgtgat     120
gccgaggttg cattgatcgt gttcagcagt agaggccgcc tgtatgagta tgctaataac     180
agcatccggt ccactataga cagatacaag aaggcttgcg caaattcctc aaattccggt     240
gcaacaatcg agattaatag tcaacaatac tatcagcagg aatccgctaa gcttagacat     300
caaattcaaa tattgcagaa tgccaaccgc cacctcatgg gtgaagcact tagcactctt     360
actgtgaagg aacttaaaca actggagaat cgcctcgaga gaggcatcac aagaattcgc     420
agtaagaaac atgagctctt gtttgcggaa attgagtata tgcagaagcg ggaagtcgaa     480
ttgcaaaacg acaatatgta tctgagagct aaaattgcag aaaatgagcg ggcccaacaa     540
gctgggatat tccggccgg accagacttc gacgctttgc ctacttttga tacgcgaaac     600
tattatcatg tgaatatgct ggaagctgcg caacattatt ctcaccatca agaccaaacc     660
accctgcacc tggggtatga aatgaaagcc gatcccgcag ctaagaacct gctctga       717
```

```
<210> SEQ ID NO 214
<211> LENGTH: 238
<212> TYPE: PRT
<213> ORGANISM: Artificial sequence
<220> FEATURE:
<223> OTHER INFORMATION: Synthetic polypeptide

<400> SEQUENCE: 214

Met Gly Arg Gly Lys Ile Glu Ile Lys Arg Ile Glu Asn Thr Thr Ser
1               5                   10                  15

Arg Gln Val Thr Phe Cys Lys Arg Arg Asn Gly Leu Pro Lys Lys Ala
            20                  25                  30

Tyr Glu Leu Ser Val Leu Cys Asp Ala Glu Val Ala Leu Ile Val Phe
        35                  40                  45

Ser Ser Arg Gly Arg Leu Tyr Glu Tyr Ala Asn Asn Ser Ile Arg Ser
    50                  55                  60

Thr Ile Asp Arg Tyr Lys Lys Ala Cys Ala Asn Ser Ser Asn Ser Gly
65                  70                  75                  80

Ala Thr Ile Glu Ile Asn Ser Gln Gln Tyr Tyr Gln Gln Glu Ser Ala
                85                  90                  95

Lys Leu Arg His Gln Ile Gln Ile Leu Gln Asn Ala Asn Arg His Leu
            100                 105                 110

Met Gly Glu Ala Leu Ser Thr Leu Thr Val Lys Glu Leu Lys Gln Leu
        115                 120                 125

Glu Asn Arg Leu Glu Arg Gly Ile Thr Arg Ile Arg Ser Lys Lys His
    130                 135                 140

Glu Leu Leu Phe Ala Glu Ile Glu Tyr Met Gln Lys Arg Glu Val Glu
145                 150                 155                 160

Leu Gln Asn Asp Asn Met Tyr Leu Arg Ala Lys Ile Ala Glu Asn Glu
                165                 170                 175

Arg Ala Gln Gln Ala Gly Ile Val Pro Ala Gly Pro Asp Phe Asp Ala
            180                 185                 190

Leu Pro Thr Phe Asp Thr Arg Asn Tyr Tyr His Val Asn Met Leu Glu
        195                 200                 205

Ala Ala Gln His Tyr Ser His His Gln Asp Gln Thr Thr Leu His Leu
    210                 215                 220

Gly Tyr Glu Met Lys Ala Asp Pro Ala Ala Lys Asn Leu Leu
225                 230                 235
```

-continued

```
<210> SEQ ID NO 215
<211> LENGTH: 750
<212> TYPE: DNA
<213> ORGANISM: Fragaria vesca

<400> SEQUENCE: 215
atgggaagag ggaaaataga aatcaaacgg atagaaaata ctactaatcg gcaggtcact        60
ttctgtaaac gaaggaacgg ccttcttaag aaggcatacg aactgagcat cctctgcgaa       120
gccgaggtgg cgctgatcgt atttagctca cgagggcgtt tgtacgaata cagtaataat       180
aattccattc gcaataccat cgaacgttat aagaaagcgt cctcagacaa ctccggcgcg       240
actacaataa ctgagataaa cgcccagtat tatcagcaag agtcaaccaa attgcgccat       300
cagatccaga tgttgcaaaa ctcaaatcgt catctcatgg gtgactccct ctctaacctt       360
acagtaaagg agctgaaaca attggagaac cgactggagc gtggtctcac ccggatacgg       420
tctaagaagg tgaatataga cgagaaggag tgcgagtctt atgagaacgc gtgtatgcac       480
tttaccacca aaacagaaca gcagcagcac gagatgctgc tcgcagagat agaatatctg       540
caaaagcgcg aaatcgaact cgagaatgaa aacgtcttga tacgggccaa aattgccgag       600
gtcgaacggc tgcaacaggc tgatctcgtg agcggagcgg agctcaacgc tattcaagcc       660
ctggccagca ggaacttctt cgaaagcaca atgatggaag cgaaacgag ctattctcaa        720 cctgagaaga agctgctgca ccttggctga                                        750

<210> SEQ ID NO 216
<211> LENGTH: 249
<212> TYPE: PRT
<213> ORGANISM: Fragaria vesca

<400> SEQUENCE: 216

Met Gly Arg Gly Lys Ile Glu Ile Lys Arg Ile Glu Asn Thr Thr Asn
1               5                   10                  15

Arg Gln Val Thr Phe Cys Lys Arg Arg Asn Gly Leu Leu Lys Lys Ala
            20                  25                  30

Tyr Glu Leu Ser Ile Leu Cys Glu Ala Glu Val Ala Leu Ile Val Phe
        35                  40                  45

Ser Ser Arg Gly Arg Leu Tyr Glu Tyr Ser Asn Asn Asn Ser Ile Arg
    50                  55                  60

Asn Thr Ile Glu Arg Tyr Lys Lys Ala Ser Ser Asp Asn Ser Gly Ala
65                  70                  75                  80

Thr Thr Ile Thr Glu Ile Asn Ala Gln Tyr Tyr Gln Gln Glu Ser Thr
                85                  90                  95

Lys Leu Arg His Gln Ile Gln Met Leu Gln Asn Ser Asn Arg His Leu
            100                 105                 110

Met Gly Asp Ser Leu Ser Asn Leu Thr Val Lys Glu Leu Lys Gln Leu
        115                 120                 125

Glu Asn Arg Leu Glu Arg Gly Leu Thr Arg Ile Arg Ser Lys Lys Val
    130                 135                 140

Asn Ile Asp Glu Lys Glu Cys Glu Ser Tyr Glu Asn Ala Cys Met His
145                 150                 155                 160

Phe Thr Thr Lys Thr Glu Gln Gln Gln His Glu Met Leu Leu Ala Glu
                165                 170                 175

Ile Glu Tyr Leu Gln Lys Arg Glu Ile Glu Leu Glu Asn Glu Asn Val
            180                 185                 190
```

```
Leu Ile Arg Ala Lys Ile Ala Glu Val Glu Arg Leu Gln Gln Ala Asp
        195                 200                 205

Leu Val Ser Gly Ala Glu Leu Asn Ala Ile Gln Ala Leu Ala Ser Arg
        210                 215                 220

Asn Phe Phe Glu Ser Thr Met Met Glu Gly Glu Thr Ser Tyr Ser Gln
225                 230                 235                 240

Pro Glu Lys Lys Leu Leu His Leu Gly
                245
```

```
<210> SEQ ID NO 217
<211> LENGTH: 690
<212> TYPE: DNA
<213> ORGANISM: Artificial sequence
<220> FEATURE:
<223> OTHER INFORMATION: Synthetic polynucleotide

<400> SEQUENCE: 217
atgggaagag ggaaaataga aatcaaacgg atagaaaata ctactaatcg gcaggtcact      60
ttctgtaaac gaaggaacgg ccttcttaag aaggcatacg aactgagcat cctctgcgaa     120
gccgaggtgg cgctgatcgt atttagctca cgagggcgtt tgtacgaata cagtaataat     180
aattccattc gcaataccat cgaacgttat aagaaagcgt cctcagacaa ctccggcgcg     240
actacaataa ctgagataaa cgcccagtat tatcagcaag agtcaaccaa attgcgccat     300
cagatccaga tgttgcaaaa ctcaaatcgt catctcatgg gtgactccct ctctaacctt     360
acagtaaagg agctgaaaca attggagaac cgactggagc gtggtctcac ccggatacgg     420
tctaagaagg tgaatataga cgagaaggag tgcgagtctt atgagaacgc gtgtatgcac     480
tttaccacca aaacagaaca gcagcagcac gagatgctgc tcgcagagat agaatatctg     540
caaaagcgcg aaatcgaact cgagaatgaa aacgtcttga tacgggccaa aattgccgag     600
gtcgaacggc tgcaacaggc tgatctcgtg agcggagcgg agctcaactt caagccctgg     660
ccagcaggaa cttcttcgaa agcacaatga                                      690
```

```
<210> SEQ ID NO 218
<211> LENGTH: 229
<212> TYPE: PRT
<213> ORGANISM: Artificial sequence
<220> FEATURE:
<223> OTHER INFORMATION: Synthetic polypeptide

<400> SEQUENCE: 218

Met Gly Arg Gly Lys Ile Glu Ile Lys Arg Ile Glu Asn Thr Thr Asn
1               5                   10                  15

Arg Gln Val Thr Phe Cys Lys Arg Arg Asn Gly Leu Leu Lys Lys Ala
                20                  25                  30

Tyr Glu Leu Ser Ile Leu Cys Glu Ala Glu Val Ala Leu Ile Val Phe
            35                  40                  45

Ser Ser Arg Gly Arg Leu Tyr Glu Tyr Ser Asn Asn Asn Ser Ile Arg
        50                  55                  60

Asn Thr Ile Glu Arg Tyr Lys Lys Ala Ser Ser Asp Asn Ser Gly Ala
65                  70                  75                  80

Thr Thr Ile Thr Glu Ile Asn Ala Gln Tyr Tyr Gln Gln Glu Ser Thr
                85                  90                  95

Lys Leu Arg His Gln Ile Gln Met Leu Gln Asn Ser Asn Arg His Leu
            100                 105                 110

Met Gly Asp Ser Leu Ser Asn Leu Thr Val Lys Glu Leu Lys Gln Leu
            115                 120                 125
```

Glu Asn Arg Leu Glu Arg Gly Leu Thr Arg Ile Arg Ser Lys Lys Val
    130                 135                 140

Asn Ile Asp Glu Lys Glu Cys Glu Ser Tyr Glu Asn Ala Cys Met His
145                 150                 155                 160

Phe Thr Thr Lys Thr Glu Gln Gln Gln His Glu Met Leu Leu Ala Glu
                165                 170                 175

Ile Glu Tyr Leu Gln Lys Arg Glu Ile Glu Leu Glu Asn Glu Asn Val
            180                 185                 190

Leu Ile Arg Ala Lys Ile Ala Glu Val Glu Arg Leu Gln Gln Ala Asp
        195                 200                 205

Leu Val Ser Gly Ala Glu Leu Asn Phe Lys Pro Trp Pro Ala Gly Thr
    210                 215                 220

Ser Ser Lys Ala Gln
225

<210> SEQ ID NO 219
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 219
atagcagaac ttgagaggct tcagcacgca gacatggttt ctggggatca agatctagag      60
ttgaatgcaa tccaggcgtt agtatctctt cgcatccact atgattgagg gtgaggcttc     120

<210> SEQ ID NO 220
<211> LENGTH: 35
<212> TYPE: PRT
<213> ORGANISM: Artificial Sequence
<220> FEATURE:
<223> OTHER INFORMATION: Synthetic polypeptide

<400> SEQUENCE: 220

Ile Ala Glu Leu Glu Arg Leu Gln His Ala Asp Met Val Ser Gly Asp
1               5                   10                  15

Gln Asp Leu Glu Leu Asn Ala Ile Gln Ala Leu Val Ser Leu His Ile
            20                  25                  30

His Tyr Asp
        35

<210> SEQ ID NO 221
<211> LENGTH: 124
<212> TYPE: DNA
<213> ORGANISM: Artificial Sequence
<220> FEATURE:
<223> OTHER INFORMATION: Synthetic polynucleotide

<400> SEQUENCE: 221
atagcagaac ttgagaggct tcagcacgca gacatggttt ctggggatca agatctagag      60
atgcaatcca ggcgttagta tctcgcaatt tcttcgcatc cactatgatt gagggtgagg     120
cttc                                                                  124

<210> SEQ ID NO 222
<211> LENGTH: 25
<212> TYPE: PRT
<213> ORGANISM: Artificial Sequence
<220> FEATURE:
<223> OTHER INFORMATION: Synthetic peptide -continued

```
<400> SEQUENCE: 222

Ile Ala Glu Leu Glu Arg Leu Gln His Ala Asp Met Val Ser Gly Asp
1               5                   10                  15

Gln Asp Leu Glu Met Gln Ser Arg Arg
            20                  25

<210> SEQ ID NO 223
<211> LENGTH: 9
<212> TYPE: PRT
<213> ORGANISM: Artificial Sequence
<220> FEATURE:
<223> OTHER INFORMATION: Synthetic peptide

<400> SEQUENCE: 223

Tyr Leu Ala Ile Ser Ser His Pro Leu
1               5

<210> SEQ ID NO 224
<211> LENGTH: 5
<212> TYPE: PRT
<213> ORGANISM: Artificial Sequence
<220> FEATURE:
<223> OTHER INFORMATION: Synthetic peptide

<400> SEQUENCE: 224

Leu Arg Val Arg Leu
1               5

<210> SEQ ID NO 225
<211> LENGTH: 116
<212> TYPE: DNA
<213> ORGANISM: Artificial Sequence
<220> FEATURE:
<223> OTHER INFORMATION: Synthetic polynucleotide

<400> SEQUENCE: 225
atagcagaac ttgagaggct tcagcacgca gacatggttt ctggggatca agatgcaatc      60
caggcgttag tatctcgcaa tttcttcgca tccactatga ttgagggtga ggcttc        116

<210> SEQ ID NO 226
<211> LENGTH: 36
<212> TYPE: PRT
<213> ORGANISM: Artificial Sequence
<220> FEATURE:
<223> OTHER INFORMATION: Synthetic polypeptide

<400> SEQUENCE: 226

Ile Ala Glu Leu Glu Arg Leu Gln His Ala Asp Met Val Ser Gly Asp
1               5                   10                  15

Ala Ile Gln Ala Leu Val Ser Arg Asn Phe Phe Thr Ser Thr Met Ile
            20                  25                  30

Glu Gly Glu Ala
        35

<210> SEQ ID NO 227
<211> LENGTH: 117
<212> TYPE: DNA
<213> ORGANISM: Artificial Sequence
<220> FEATURE:
<223> OTHER INFORMATION: Synthetic polynucleotide

<400> SEQUENCE: 227
atagcagaac ttgagaggct tcagcacgca gacatggttt ctggggatca agattgcaat      60
```

-continued

```
ccaggcgtta gtatctcgca atttcttcgc atccactatg attgagggtg aggcttc          117
```

```
<210> SEQ ID NO 228
<211> LENGTH: 34
<212> TYPE: PRT
<213> ORGANISM: Artificial Sequence
<220> FEATURE:
<223> OTHER INFORMATION: Synthetic polypeptide

<400> SEQUENCE: 228

Ile Ala Glu Leu Glu Arg Leu Gln His Ala Asp Met Val Ser Gly Asp
1               5                   10                  15

Gln Asp Cys Asn Pro Gly Val Ser Ile Ser Gln Phe Leu His Ile His
            20                  25                  30

Tyr Asp
```

```
<210> SEQ ID NO 229
<211> LENGTH: 116
<212> TYPE: DNA
<213> ORGANISM: Artificial Sequence
<220> FEATURE:
<223> OTHER INFORMATION: Synthetic polynucleotide

<400> SEQUENCE: 229
atagcagaac ttgagaggct tcagcacgca gacatggttt ctggggatca agatgcaatc          60
caggcgttag tatctcgcaa tttcttcgca tccactatga ttgagggtga ggcttc          116
```

```
<210> SEQ ID NO 230
<211> LENGTH: 38
<212> TYPE: PRT
<213> ORGANISM: Artificial Sequence
<220> FEATURE:
<223> OTHER INFORMATION: Synthetic polypeptide

<400> SEQUENCE: 230

Ile Ala Glu Leu Glu Arg Leu Gln His Ala Asp Met Val Ser Gly Asp
1               5                   10                  15

Gln Asp Ala Ile Gln Ala Leu Val Ser Arg Asn Phe Phe Thr Ser Thr
            20                  25                  30

Met Ile Glu Gly Glu Ala
        35
```

```
<210> SEQ ID NO 231
<211> LENGTH: 116
<212> TYPE: DNA
<213> ORGANISM: Artificial Sequence
<220> FEATURE:
<223> OTHER INFORMATION: Synthetic polynucleotide

<400> SEQUENCE: 231
atagcagaac ttgagaggct tcagcacgca gacatggttt ctggggatca gaatgcaatc          60
caggcgttag tatctcgcaa tttcttcgca tccactatga ttgagggtga ggcttc          116
```

```
<210> SEQ ID NO 232
<211> LENGTH: 38
<212> TYPE: PRT
<213> ORGANISM: Artificial Sequence
<220> FEATURE:
<223> OTHER INFORMATION: Synthetic polypeptide

<400> SEQUENCE: 232

Ile Ala Glu Leu Glu Arg Leu Gln His Ala Asp Met Val Ser Gly Asp
1               5                   10                  15
```

-continued

Gln Asn Ala Ile Gln Ala Leu Val Ser Arg Asn Phe Phe Thr Ser Thr
            20                  25                  30

Met Ile Glu Gly Glu Ala
        35

<210> SEQ ID NO 233
<211> LENGTH: 116
<212> TYPE: DNA
<213> ORGANISM: Artificial Sequence
<220> FEATURE:
<223> OTHER INFORMATION: Synthetic polynucleotide

<400> SEQUENCE: 233
atagcagaac ttgagaggct tcagcacgca gacatggttt ctggggatca agaagcaatc      60
caggcgttag tatctcgcaa tttcttcgca tccactatga ttgagggtga ggcttc        116

<210> SEQ ID NO 234
<211> LENGTH: 38
<212> TYPE: PRT
<213> ORGANISM: Artificial Sequence
<220> FEATURE:
<223> OTHER INFORMATION: Synthetic polypeptide

<400> SEQUENCE: 234

Ile Ala Glu Leu Glu Arg Leu Gln His Ala Asp Met Val Ser Gly Asp
1               5                   10                  15

Gln Glu Ala Ile Gln Ala Leu Val Ser Arg Asn Phe Phe Thr Ser Thr
            20                  25                  30

Met Ile Glu Gly Glu Ala
        35

<210> SEQ ID NO 235
<211> LENGTH: 119
<212> TYPE: DNA
<213> ORGANISM: Artificial Sequence
<220> FEATURE:
<223> OTHER INFORMATION: Synthetic polynucleotide

<400> SEQUENCE: 235
atagcagaac ttgagaggct tcagcacgca gacatggttt ctggggatca agatctagca      60
atccaggcgt tagtatctcg caatttcttc gcatccacta tgattgaggg tgaggcttc     119

<210> SEQ ID NO 236
<211> LENGTH: 39
<212> TYPE: PRT
<213> ORGANISM: Artificial Sequence
<220> FEATURE:
<223> OTHER INFORMATION: Synthetic polypeptide

<400> SEQUENCE: 236

Ile Ala Glu Leu Glu Arg Leu Gln His Ala Asp Met Val Ser Gly Asp
1               5                   10                  15

Gln Asp Leu Ala Ile Gln Ala Leu Val Ser Arg Asn Phe Phe Thr Ser
            20                  25                  30

Thr Met Ile Glu Gly Glu Ala
        35

<210> SEQ ID NO 237
<211> LENGTH: 123
<212> TYPE: DNA
<213> ORGANISM: Artificial Sequence
<220> FEATURE:

-continued

```
<223> OTHER INFORMATION: Synthetic polynucleotide

<400> SEQUENCE: 237
atagcagaac ttgagaggct tcagcacgca gacatggttt ctggggatca agatctagag      60
ttgaatccag gcgttagtat ctcgcaattt cttcgcatcc actatgattg agggtgaggc     120
ttc                                                                   123

<210> SEQ ID NO 238
<211> LENGTH: 36
<212> TYPE: PRT
<213> ORGANISM: Artificial Sequence
<220> FEATURE:
<223> OTHER INFORMATION: Synthetic polypeptide

<400> SEQUENCE: 238

Ile Ala Glu Leu Glu Arg Leu Gln His Ala Asp Met Val Ser Gly Asp
1               5                   10                  15

Gln Asp Leu Glu Leu Asn Pro Gly Val Ser Ile Ser Gln Phe Leu His
            20                  25                  30

Ile His Tyr Asp
        35

<210> SEQ ID NO 239
<211> LENGTH: 110
<212> TYPE: DNA
<213> ORGANISM: Artificial Sequence
<220> FEATURE:
<223> OTHER INFORMATION: Synthetic polynucleotide

<400> SEQUENCE: 239
atagcagaac ttgagaggct tcagcacgca gacatggttt ctggggatca aatccaggcg      60
ttagtatctc gcaatttctt cgcatccact atgattgagg gtgaggcttc               110

<210> SEQ ID NO 240
<211> LENGTH: 36
<212> TYPE: PRT
<213> ORGANISM: Artificial Sequence
<220> FEATURE:
<223> OTHER INFORMATION: Synthetic polypeptide

<400> SEQUENCE: 240

Ile Ala Glu Leu Glu Arg Leu Gln His Ala Asp Met Val Ser Gly Asp
1               5                   10                  15

Gln Ile Gln Ala Leu Val Ser Arg Asn Phe Phe Ala Ser Thr Met Ile
            20                  25                  30

Glu Gly Glu Ala
        35

<210> SEQ ID NO 241
<211> LENGTH: 123
<212> TYPE: DNA
<213> ORGANISM: Artificial Sequence
<220> FEATURE:
<223> OTHER INFORMATION: Synthetic polynucleotide

<400> SEQUENCE: 241
atagcagaac ttgagaggct tcagcacgca gacatggttt ctggggatca agatctagaa      60
tgcaatccag gcgttagtat ctcgcaattt cttcgcatcc actatgattg agggtgaggc     120
ttc                                                                   123
```

<210> SEQ ID NO 242
<211> LENGTH: 36
<212> TYPE: PRT
<213> ORGANISM: Artificial Sequence
<220> FEATURE:
<223> OTHER INFORMATION: Synthetic polypeptide

<400> SEQUENCE: 242

Ile Ala Glu Leu Glu Arg Leu Gln His Ala Asp Met Val Ser Gly Asp
1               5                   10                  15

Gln Asp Leu Glu Cys Asn Pro Gly Val Ser Ile Ser Gln Phe Leu Arg
            20                  25                  30

Ile His His Asp
        35

<210> SEQ ID NO 243
<211> LENGTH: 116
<212> TYPE: DNA
<213> ORGANISM: Artificial Sequence
<220> FEATURE:
<223> OTHER INFORMATION: Synthetic polynucleotide

<400> SEQUENCE: 243
atagcagaac ttgagaggct tcagcacgca gacatggttt ctggggatca agaggcaatc      60
caggcgttag tatctcgcaa tttcttcgca tccactatga ttgagggtga ggcttc         116

<210> SEQ ID NO 244
<211> LENGTH: 38
<212> TYPE: PRT
<213> ORGANISM: Artificial Sequence
<220> FEATURE:
<223> OTHER INFORMATION: Synthetic polypeptide

<400> SEQUENCE: 244

Ile Ala Glu Leu Glu Arg Leu Gln His Ala Asp Met Val Ser Gly Asp
1               5                   10                  15

Gln Glu Ala Ile Gln Ala Leu Val Ser Arg Asn Phe Phe Ala Ser Thr
            20                  25                  30

Met Ile Glu Gly Glu Ala
        35

<210> SEQ ID NO 245
<211> LENGTH: 111
<212> TYPE: DNA
<213> ORGANISM: Artificial Sequence
<220> FEATURE:
<223> OTHER INFORMATION: Synthetic polynucleotide

<400> SEQUENCE: 245
atagcagaac ttgagaggct tcagcacgca gacatggttt ctggggatca agatccaggc      60
gttagtatct cgcaatttct cgcatccac tatgattgag ggtgaggctt c              111

<210> SEQ ID NO 246
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 246

Ile Ala Glu Leu Glu Arg Leu Gln His Ala Asp Met Val Ser Gly Asp
1               5                   10                  15

Gln Asp Pro Gly Val Ser Ile Ser Gln Phe Leu Arg Ile His Tyr Asp

```
            20              25              30
```

<210> SEQ ID NO 247
<211> LENGTH: 118
<212> TYPE: DNA
<213> ORGANISM: Artificial Sequence
<220> FEATURE:
<223> OTHER INFORMATION: Synthetic polynucleotide

<400> SEQUENCE: 247
atagcagaac ttgagaggct tcagcacgca gacatggttt ctggggatca agatctgcaa    60
tccaggcgtt agtatctcgc aatttcttcg catccactat gattgagggt gaggcttc    118

<210> SEQ ID NO 248
<211> LENGTH: 23
<212> TYPE: PRT
<213> ORGANISM: Artificial Sequence
<220> FEATURE:
<223> OTHER INFORMATION: Synthetic peptide

<400> SEQUENCE: 248

Ile Ala Glu Leu Glu Arg Leu Gln His Ala Asp Met Val Ser Gly Asp
1               5                   10                  15

Gln Asp Leu Gln Ser Arg Arg
            20

<210> SEQ ID NO 249
<211> LENGTH: 119
<212> TYPE: DNA
<213> ORGANISM: Artificial Sequence
<220> FEATURE:
<223> OTHER INFORMATION: Synthetic polynucleotide

<400> SEQUENCE: 249
atagcagaac ttgagaggct tcagcacgca gacatggttt ctggggatca agatcatgca    60
atccaggcgt tagtatctcg caatttcttc gcatccacta tgattgaggg tgaggcttc    119

<210> SEQ ID NO 250
<211> LENGTH: 39
<212> TYPE: PRT
<213> ORGANISM: Artificial Sequence
<220> FEATURE:
<223> OTHER INFORMATION: Synthetic polypeptide

<400> SEQUENCE: 250

Ile Ala Glu Leu Glu Arg Leu Gln His Ala Asp Met Val Ser Gly Asp
1               5                   10                  15

Gln Asp His Ala Ile Gln Ala Leu Val Ser Arg Asn Phe Phe Ala Ser
            20                  25                  30

Thr Met Ile Glu Gly Glu Ala
        35

<210> SEQ ID NO 251
<211> LENGTH: 115
<212> TYPE: DNA
<213> ORGANISM: Artificial Sequence
<220> FEATURE:
<223> OTHER INFORMATION: Synthetic polynucleotide

<400> SEQUENCE: 251
atagcagaac ttgagaggct tcagcacgca gacatggttt ctggggatca aatgcaatcc    60
aggcgttagt atctcgcaat tcttcgcat ccactatgat tgagggtgag gcttc    115
```

<210> SEQ ID NO 252
<211> LENGTH: 22
<212> TYPE: PRT
<213> ORGANISM: Artificial Sequence
<220> FEATURE:
<223> OTHER INFORMATION: Synthetic peptide

<400> SEQUENCE: 252

Ile Ala Glu Leu Glu Arg Leu Gln His Ala Asp Met Val Ser Gly Asp
1               5                   10                  15

Gln Met Gln Ser Arg Arg
            20

<210> SEQ ID NO 253
<211> LENGTH: 42
<212> TYPE: PRT
<213> ORGANISM: Rubus occidentalis

<400> SEQUENCE: 253

Ile Ala Glu Leu Glu Arg Leu Gln His Ala Asp Met Val Ser Gly Asp
1               5                   10                  15

Gln Asp Leu Glu Leu Asn Ala Ile Gln Ala Leu Val Ser Arg Asn Phe
            20                  25                  30

Phe Ala Ser Thr Met Ile Glu Gly Glu Ala
        35                  40

<210> SEQ ID NO 254
<211> LENGTH: 128
<212> TYPE: DNA
<213> ORGANISM: Rubus occidentalis

<400> SEQUENCE: 254
atagcagaac ttgagaggct tcagcacgca gacatggttt ctggggatca agatctagag      60
ttgaatgcaa tccaggcgtt agtatctcgc aatttcttcg catccactat gattgagggt     120
gaggcttc                                                             128

<210> SEQ ID NO 255
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 255
aatgcaatcc aggcgttagt atctcgcaat ttcttcgcat ccactatgat tgagggtgag      60

<210> SEQ ID NO 256
<211> LENGTH: 20
<212> TYPE: PRT
<213> ORGANISM: Artificial Sequence
<220> FEATURE:
<223> OTHER INFORMATION: Synthetic peptide

<400> SEQUENCE: 256

Asn Ala Ile Gln Ala Leu Val Ser Arg Asn Phe Phe Ala Ser Thr Met
1               5                   10                  15

Ile Glu Gly Glu
            20

<210> SEQ ID NO 257
<211> LENGTH: 60
<212> TYPE: DNA

-continued

```
<213> ORGANISM: Artificial Sequence
<220> FEATURE:
<223> OTHER INFORMATION: Synthetic oligonucleotide

<400> SEQUENCE: 257
ttacgttagg tccgcaatca tagagcgtta aagaagcgta ggtgatacta actcccactc        60

<210> SEQ ID NO 258
<211> LENGTH: 4
<212> TYPE: PRT
<213> ORGANISM: Rubus occidentalis

<400> SEQUENCE: 258

Glu Leu Asn Ala
1

<210> SEQ ID NO 259
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa may be Ala or Ser

<400> SEQUENCE: 259

Tyr Xaa Asn Asn
1

<210> SEQ ID NO 260
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa denotes Ala or Ser
<220> FEATURE:
<221> NAME/KEY: MISC_FEATURE
<222> LOCATION: (6)..(6)
<223> OTHER INFORMATION: Xaa denotes Ala, Ser, Asn, Lys, or Thr
<220> FEATURE:
<221> NAME/KEY: MISC_FEATURE
<222> LOCATION: (9)..(9)
<223> OTHER INFORMATION: Xaa denotes Arg or His
<220> FEATURE:
<221> NAME/KEY: MISC_FEATURE
<222> LOCATION: (10)..(10)
<223> OTHER INFORMATION: Xaa denotes Gln, His, Ala, Asn or Arg

<400> SEQUENCE: 260

Tyr Gln Gln Glu Xaa Xaa Lys Leu Xaa Xaa Gln Ile
1               5                   10

<210> SEQ ID NO 261
<211> LENGTH: 9
<212> TYPE: PRT
<213> ORGANISM: Artificial Sequence
<220> FEATURE:
<223> OTHER INFORMATION: Synthetic peptide

<400> SEQUENCE: 261

Leu Ala Gly Leu Ile Asp Ala Asp Gly
1               5
```

<210> SEQ ID NO 262
<211> LENGTH: 4
<212> TYPE: PRT
<213> ORGANISM: Artificial Sequence
<220> FEATURE:
<223> OTHER INFORMATION: Synthetic peptide

<400> SEQUENCE: 262

Gly Gly Gly Ser
1

<210> SEQ ID NO 263
<211> LENGTH: 5
<212> TYPE: PRT
<213> ORGANISM: Artificial Sequence
<220> FEATURE:
<223> OTHER INFORMATION: Synthetic peptide

<400> SEQUENCE: 263

Gly Gly Gly Gly Ser
1               5

<210> SEQ ID NO 264
<211> LENGTH: 9
<212> TYPE: PRT
<213> ORGANISM: Artificial Sequence
<220> FEATURE:
<223> OTHER INFORMATION: Synthetic peptide

<400> SEQUENCE: 264

Gly Gly Ser Gly Gly Ser Gly Gly Ser
1               5

<210> SEQ ID NO 265
<211> LENGTH: 10
<212> TYPE: PRT
<213> ORGANISM: Artificial Sequence
<220> FEATURE:
<223> OTHER INFORMATION: Synthetic peptide

<400> SEQUENCE: 265

Gly Gly Gly Gly Ser Gly Gly Gly Gly Ser
1               5                   10

<210> SEQ ID NO 266
<211> LENGTH: 15
<212> TYPE: PRT
<213> ORGANISM: Artificial Sequence
<220> FEATURE:
<223> OTHER INFORMATION: Synthetic peptide

<400> SEQUENCE: 266

Gly Gly Gly Gly Ser Gly Gly Gly Gly Ser Gly Gly Gly Gly Ser
1               5                   10                  15

<210> SEQ ID NO 267
<211> LENGTH: 20
<212> TYPE: PRT
<213> ORGANISM: Artificial Sequence
<220> FEATURE:
<223> OTHER INFORMATION: Synthetic peptide

<400> SEQUENCE: 267

Gly Gly Gly Gly Ser Gly Gly Gly Gly Ser Gly Gly Gly Gly Ser Gly
1               5                   10                  15

Gly Gly Gly Ser
            20

-continued

```
<210> SEQ ID NO 268
<211> LENGTH: 25
<212> TYPE: PRT
<213> ORGANISM: Artificial Sequence
<220> FEATURE:
<223> OTHER INFORMATION: Synthetic peptide

<400> SEQUENCE: 268

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 269
<211> LENGTH: 30
<212> TYPE: PRT
<213> ORGANISM: Artificial Sequence
<220> FEATURE:
<223> OTHER INFORMATION: Synthetic peptide

<400> SEQUENCE: 269

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 270
<211> LENGTH: 35
<212> TYPE: PRT
<213> ORGANISM: Artificial Sequence
<220> FEATURE:
<223> OTHER INFORMATION: Synthetic peptide

<400> SEQUENCE: 270

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 271
<211> LENGTH: 40
<212> TYPE: PRT
<213> ORGANISM: Artificial Sequence
<220> FEATURE:
<223> OTHER INFORMATION: Synthetic peptide

<400> SEQUENCE: 271

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40

<210> SEQ ID NO 272
<211> LENGTH: 45
<212> TYPE: PRT
<213> ORGANISM: Artificial Sequence
<220> FEATURE:
<223> OTHER INFORMATION: Synthetic peptide
```

-continued

```
<400> SEQUENCE: 272

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser
        35                  40                  45

<210> SEQ ID NO 273
<211> LENGTH: 50
<212> TYPE: PRT
<213> ORGANISM: Artificial Sequence
<220> FEATURE:
<223> OTHER INFORMATION: Synthetic peptide

<400> SEQUENCE: 273

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 274
<211> LENGTH: 55
<212> TYPE: PRT
<213> ORGANISM: Artificial Sequence
<220> FEATURE:
<223> OTHER INFORMATION: Synthetic peptide

<400> SEQUENCE: 274

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser
    50                  55

<210> SEQ ID NO 275
<211> LENGTH: 60
<212> TYPE: PRT
<213> ORGANISM: Artificial Sequence
<220> FEATURE:
<223> OTHER INFORMATION: Synthetic peptide

<400> SEQUENCE: 275

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser
    50                  55                  60

<210> SEQ ID NO 276
```

-continued

```
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 276
ggggtggctt tccttttttg gtaaattttg gatcc                                    35
```